US008097698B2

(12) United States Patent
Knudsen et al.

(10) Patent No.: US 8,097,698 B2
(45) Date of Patent: *Jan. 17, 2012

(54) DERIVATIVES OF GLP-1 ANALOGS

(75) Inventors: Liselotte Bjerre Knudsen, Valby (DK); Per Olaf Huusfeldt, Copenhagen O (DK); Per Franklin Nielsen, Vaerlose (DK); Niels C. Kaarsholm, Vanlose (DK); Helle Birk Olsen, Allerod (DK); Soren Erik Bjorn, Lyngby (DK); Freddy Zimmerdahl Pedersen, Vaerlose (DK); Kjeld Madsen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 846 days.

This patent is subject to a terminal disclaimer.

(21) Appl. No.: 11/944,757

(22) Filed: Nov. 26, 2007

(65) Prior Publication Data

US 2009/0176700 A1   Jul. 9, 2009

Related U.S. Application Data

(63) Continuation of application No. 11/008,743, filed on Dec. 9, 2004, now abandoned, which is a continuation of application No. 10/285,079, filed on Aug. 19, 2002, now Pat. No. 7,235,627, which is a continuation of application No. 09/398,111, filed on Sep. 16, 1999, now Pat. No. 6,458,924, which is a continuation-in-part of application No. 09/265,141, filed on Mar. 8, 1999, now Pat. No. 6,384,016, and a continuation-in-part of application No. 09/258,750, filed on Feb. 26, 1999, now Pat. No. 6,268,343, which is a continuation-in-part of application No. 09/038,432, filed on Mar. 11, 1998, now abandoned, which is a continuation-in-part of application No. 08/918,810, filed on Aug. 26, 1997, now abandoned, and a continuation-in-part of application No. PCT/DK97/00340, filed on Aug. 22, 1997.

(60) Provisional application No. 60/078,422, filed on Mar. 18, 1998, provisional application No. 60/082,479, filed on Apr. 21, 1998, provisional application No. 60/082,478, filed on Apr. 21, 1998, provisional application No. 60/082,480, filed on Apr. 21, 1998, provisional application No. 60/082,802, filed on Apr. 23, 1998, provisional application No. 60/084,357, filed on May 5, 1998, provisional application No. 60/035,904, filed on Jan. 24, 1997, provisional application No. 60/036,226, filed on Jan. 25, 1997, provisional application No. 60/036,255, filed on Jan. 24, 1997.

(30) Foreign Application Priority Data

Aug. 30, 1996   (DK) .................. 0931/96
Nov. 8, 1996    (DK) .................. 1259/96
Dec. 20, 1996   (DK) .................. 1470/96
Feb. 27, 1998   (DK) .................. 0263/98
Feb. 27, 1998   (DK) .................. 0264/98
Feb. 27, 1998   (DK) .................. 0268/98
Feb. 27, 1998   (DK) .................. 0272/98
Feb. 27, 1998   (DK) .................. 0274/98
Mar. 13, 1998   (EP) .................. 98610006
Apr. 8, 1998    (DK) .................. 0508/98
Apr. 8, 1998    (DK) .................. 0509/98
Apr. 8, 1998    (DK) .................. 1998 00507

(51) Int. Cl.
*A61K 38/16*   (2006.01)
*C07K 14/605*  (2006.01)

(52) U.S. Cl. .......... 530/324; 530/308; 514/21.3
(58) Field of Classification Search .......... 530/399, 530/324, 308; 514/21.3
See application file for complete search history.

(56) References Cited

U.S. PATENT DOCUMENTS

| | | |
|---|---|---|
| 5,118,666 A | 6/1992 | Habener |
| 5,120,712 A | 6/1992 | Habener |
| 5,336,782 A | 8/1994 | Ebashi et al. |
| 5,380,872 A | 1/1995 | Sugg et al. |
| 5,512,549 A | 4/1996 | Chen et al. |
| 5,521,157 A | 5/1996 | Noda et al. |
| 5,545,618 A | 8/1996 | Buckley et al. |
| 5,614,492 A | 3/1997 | Habener |
| 5,869,602 A | 2/1999 | Jonassen |
| 5,912,229 A | 6/1999 | Thim et al. |
| 6,268,343 B1 | 7/2001 | Knudsen et al. |
| 6,458,924 B2 | 10/2002 | Knudsen et al. |
| 6,660,716 B1 | 12/2003 | Yakubu-Madus et al. |
| 2004/0127414 A1 | 7/2004 | Yakubu-Madus et al. |

FOREIGN PATENT DOCUMENTS

| | | |
|---|---|---|
| EP | 0658568 | 6/1995 |
| EP | 0708179 | 12/2004 |
| EP | 0619322 | 12/2005 |
| GB | 1202607 | 8/1970 |
| WO | WO 87/06941 | 11/1987 |
| WO | WO 90/11296 | 10/1990 |
| WO | WO 91/11457 | 8/1991 |
| WO | WO 95/07931 | 3/1995 |

(Continued)

OTHER PUBLICATIONS

Adelhorst K. et al., "Structure Activity Studies of GLP-1", Journal of Biological Chemistry, vol. 269, No. 9, pp. 6275-6278 (1994).
Broderick, Diabetologia (1995), vol. 38, No. Suppl. 1, pp. A171. Meeting Info: 31st Annual Meeting of the European Association for the Study of Diabetes Stockholm, Sweden, Sep. 12-16, 1995.
Deacon C. F. et al., "Both subcutaneously and intravenously administered glucagon-like peptide I are rapidly degraded from the NH2-terminus in type II diabetic patients and in healthy subjects," Diabetes, vol. 44, pp. 1126-1130 (1995).
Deacon C. F. et al., "Degradation of glucagon-like peptide-1 by human plasma in vitro yields an N-terminally truncated peptide that is a major endogenous metabolite in vivo," Journal of Clinical Endocrinology and Metabolism, vol. 80, No. 3, pp. 952-957 (1995).

(Continued)

*Primary Examiner* — David Lukton
(74) *Attorney, Agent, or Firm* — Richard W. Bork

(57) ABSTRACT

The present invention relates to a pharmaceutical composition comprising a GLP-1 derivative having a lipophilic substituent; and a surfactant.

15 Claims, 1 Drawing Sheet

FOREIGN PATENT DOCUMENTS

| | | |
|---|---|---|
| WO | WO 95/31214 | 11/1995 |
| WO | WO 95/32730 | 12/1995 |
| WO | WO 96/29342 | 9/1996 |
| WO | WO 96/29344 | 9/1996 |
| WO | WO 97/31943 | 9/1997 |
| WO | WO 98/08531 | 3/1998 |
| WO | WO 98/08871 | 3/1998 |
| WO | WO 98/08873 | 3/1998 |
| WO | WO 98/19698 | 5/1998 |

OTHER PUBLICATIONS

Kieffer et al., "Degradation of glucose-dependent insulinotropic polypeptide and truncated glucagon-like peptide 1 in vitro and in vivo by dipeptidyl peptidase IV," Endocrinology, vol. 136, No. 8, pp. 3585-3596 (1995).

Knudsen L. B. et al., "Potent Derivatives of Glucagon-like Peptide-1 with Pharmacokinetic Properties Suitable for Once Daily Administration", Journal of Medicinal Chemistry, vol. 43, pp. 1664-1669 (2000).

Knudsen L. B. et al., "GLP-1 derivatives as novel compounds for the treatment of type 2 diabetes: selection of NN-2211 for clinical development," Drugs of the Future, vol. 26, No. 7, pp. 677-685 (2001).

Kurtzhals P. et al., "Albumin binding of insulins acylated with fatty acids: characterization of the ligand-protein interaction and correlation between binding affinity and timing of the insulin effect in vivo," Biochemical Journal, vol. 312, pp. 725-731 (1995).

Kurtzhals P. et al., "Albumin binding and time action of acylated insulins in various species," Journal of Pharmaceutical Sciences, vol. 85, No. 3, pp. 304-308 (1996).

Markussen J. et al., "Soluble, fatty acid acylated insulins bind to albumin and show protracted action in pigs," Diabetologia, vol. 39, pp. 281-288 (1996).

Mentlein et al., "Dipeptidyl-peptidase IV hydrolyses gastric inhibitory polypeptide, glucagon-like peptide-1(7-36)amide, peptide histidine methionine and is responsible for their degradation in human serum," European Journal of Biochemistry, vol. 214, pp. 829-835 (1993).

Mojsov S., "Structural Requirements for Biological Activity of Glucagon-like Peptide-I", International Journal of Peptide and Protein Research, vol. 40, pp. 333-343 (1992).

M. Gutniak et al., "Antidiabetogenic Effect of Glucagon-Like Peptide-1 (7-36) Amide in Normal Subjects and Patients with Diabetes Mellitus" New England Journal of Medicine (1992) vol. 326 No. 20 p. 1316-1322.

M. Navarro et al., "Changes in Food Intake Induced by GLP-1 (7-36) Amide in the Rat", Abstracts of the 15th International Diabetes Federation Congress, Nov. 6-11, 1994 Kobe, poster presentation 11A 5PP1295.

R. Schick et al "Glucagon-like peptide 1—a novel brain peptide involved in feeding regulation" Obesity in Europe 1993, Chapter 53, pp. 363-367.

P.D. Lambert et al., "A Role for GLP-1(7-36)NH$_2$ in the Central Control of Feeding Behaviour" Digestion 1994:vol. 54, pp. 360-361.

"New Appetite Suppresser May Help Cut Pounds", CNN Food and Health Web Site, Jan. 5, 1996.

B. Willms et al., "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients" Journal of Clinical Endocrinology and Metabolism vol. 81 No. 1 (1996) pp. 327-332.

M. Tang-Christensen et al., "Central Administration of GLP-1-(7-36) Amide Inhibits Food and Water Intake in Rats", The American Physiological Society (1996) 271: R848-R856.

Zhili Wang et al., "Glucagon-like Peptide-1 Is a Physiological Incretin in Rat" J. Clin. Invest. The American Society for Clin. Invest, Inc. vol. 95, pp. 417-421, Jan. 1995.

C. Ørskov. "Glucagon-like peptide-1, a new hormone of the entero-insular axis" Diabetologia vol. 35: pp. 701-711, (1992).

Gutzwiller et al., Abstract "Glucagon-like peptide-1 is a physiologic regulator of food intake in human" Gastroenterology, vol. 12(4, Suppl.S):PA:1153 (1997).

Ranganath et al., Attenuated GLP-1 secretion in obesity: cause or consequence?

Gur vol. 38: pp. 916-919 (1996).

Marx J. "Obesity gene discovery may help solve weighty problem" [news]. Science, (Dec. 2, 1994) 266 (5190) 1477-8.

Zhang et al. "Positional cloning of the mouse obese gene and its human homologue". Nature, (Dec. 1, 1994) 372 (6505) 425-32.

Rink T J. "In search of a satiety factor". Nature, (Dec. 1, 1994) 372 (6505) 406.7.

Woods et al. "Signals that regulate food intake and energy homeostasis". Science, 280:1378-1383, May 29, 1998.

Thorens T. "Glucagon-like peptide-1 and control of insulin secretion". Diabete & Metabolisme (Paris). 1995, 21, 311-318.

Henriksen et al. Peptide amidation by chemical protein engineering. A combination of enzymic and photochemical synthesis. J. Am. Chem. Soc. (1992). 114(5). 1876-7.

Wang et al. "Glucagon-like peptide-1 is a physiological incretin in rat". J. Clin. Invest., (Jan. 1995) 95 (1) 417-21.

Bell et al. Exon duplication and divergence in the human preproglucagon gene. Nature, Jul. 28-Aug. 3, 1983.

Wettergren et al. "Truncated GLP-1 (proglucagon 78-107-amide) inhibits gastric and pancreatic functions in man". Digest. Dis. Sci., (Apr. 1993) 38 (4) 665-73.

Suzuki et al. "Comparison of the effects of various C-terminal and N-Terminal fragment peptides of glucagons-like peptide-1 on insulin and glucagons release from the isolated perfused rat pancreas". Endocrinology, (Dec. 1989) 125(6) 3109-14.

Navarro et al., Journal of Neurochemistry, vol. 67, No. 5, pp. 1982-1991 (Nov. 1996).

Turton et al., Nature, vol. 379, pp. 69-72 (Jan. 4, 1996).

C.L. Broderick et al., Abstract 664 "Effect of Sub-Chronic Administration of GLP-1 (7-37) OH on Beta Cell Failure in Zucker Diabetic Rats," Diabetologia (Aug. 1995), vol. 38, Supp 1, p. A171.

Kim et al., (1994) J. of Pharma. Sciences 83(8):1175-1180.

Clodfelter et al., (1998) Pharmaceutical Res. 15(2):254-262.

W.B. Gratzer et al., "Relation Between Conformation and Association State" The Journal of Biological Chemistry, 244, No. 24, Dec. 25, 1969, pp. 6675-6679.

Sasaki et al., "X-Ray Analysis of Glucagon and Its Relationship to Receptor Binding", Nature Vo. 257, Oct. 30, 1975, pp. 751-757.

Wagman et al., "Proton NMR Studies Of The Association And Folding of Glucagon In Solution", Elsevier/North-Holland Biomedical Press, vol. 119, No. 2, Oct. 1980, pp. 265-270.

Epand et al., "Molecular Interactions in the Model Lipoprotein Complex Formed Between Glucagon and Dimyristoylglycerophosphocholine", Biochemistry vol. 16, No. 20, 1977, pp. 4360-4368.

Schneider et al., "Polypeptide Hormone Interaction" (Glucagon Binding To Lysolecithin), The Journal of Biological Chemistry, Vo. 247, No. 16, Aug. 25, 1972, pp. 4986-4991.

Schneider et al., "Polypeptide Hormone Interaction" (Conformational Changes of Glucagon Bound To Lysolecithin), The Journal of Biological Chemistry, vol. 247, No. 16, Aug. 25, 1972, pp. 4992-4995.

Robinson et al., "Lipid-Induced Conformational Changes in Glucagon, Secretin, and Vasoactive Intestinal Peptide", Biopolymers, vol. 21, 1982, pp. 1217-1228.

Hamed et al. "Bahavior of Amphipathic Helices on Analysis Via Matrix Methods, With Application to Glucagon, Secretin, and Vasoactive Intestinal Peptide", Biopolymers, vol. 22, 1983, pp. 1003-1021.

Wu et al., "Helical Conformation of Glucagon in Surfactant Solutions", American Chemical Society, Biochemistry, vol. 19, No. 10, 1980, pp. 2117-2122.

Bösch et al., "Physicochemical Characterization of Glucagon-Containing Lipid Micelles" Biochimic et Biophysica Acta, 603 (1980) pp. 298-312.

Thornton et al., Structure of Glucagon-Like Peptide (7-36) Amide in a Dodecylphosphocholine Micelle as Determined by 2D NMR, Biochemistry 1994, 33, pp. 3532-3539.

SEQUENCE LISTING

```
<160> NUMBER OF SEQ ID NOS: 96

<210> SEQ ID NO 1
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 1

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 4

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly
            20                  25                  30

<210> SEQ ID NO 5
<211> LENGTH: 32
<212> TYPE: PRT
```

<213> ORGANISM: Artificial Sequence
<220> FEATURE:
<223> OTHER INFORMATION: Chemically Synthesized

<400> SEQUENCE: 5

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

<210> SEQ ID NO 6
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 6

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Lys

<210> SEQ ID NO 7
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 7

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Lys

<210> SEQ ID NO 8
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 8

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Lys Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Lys Gly
            20                  25                  30

<210> SEQ ID NO 10
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 10

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly Arg
            20                  25                  30

Lys

<210> SEQ ID NO 11
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 11

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Arg
            20                  25                  30

Arg Lys

<210> SEQ ID NO 12
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 12

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Lys

<210> SEQ ID NO 13
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 13

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Arg Lys

<210> SEQ ID NO 14
<211> LENGTH: 31
<212> TYPE: PRT
<213> ORGANISM: Artificial Sequence
<220> FEATURE:
<223> OTHER INFORMATION: Chemically Synthesized -continued

```
<400> SEQUENCE: 14

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 15

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 16

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Lys Gly
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 17

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly
            20                  25                  30

<210> SEQ ID NO 18
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 18

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Lys

<210> SEQ ID NO 19
<211> LENGTH: 34
<212> TYPE: PRT
<213> ORGANISM: Artificial Sequence
<220> FEATURE:
```

<223> OTHER INFORMATION: Chemically Synthesized

<400> SEQUENCE: 19

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Lys

<210> SEQ ID NO 20
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 20

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Lys Gly
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Chemically Synthesized

<400> SEQUENCE: 21

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Lys Gly
            20                  25                  30

<210> SEQ ID NO 22
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 22

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly Arg
            20                  25                  30

Lys

<210> SEQ ID NO 23
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 23

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Arg
            20                  25                  30

Arg Lys

```
<210> SEQ ID NO 24
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 24
```

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Lys

```
<210> SEQ ID NO 25
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 25
```

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Arg Lys

```
<210> SEQ ID NO 26
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 26
```

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

```
<210> SEQ ID NO 27
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 27
```

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Lys

```
<210> SEQ ID NO 28
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 28
```

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Lys

<210> SEQ ID NO 29
<211> LENGTH: 35
<212> TYPE: PRT
<213> ORGANISM: Artificial Sequence
<220> FEATURE:
<223> OTHER INFORMATION: Chemically Synthesized

<400> SEQUENCE: 29

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Glu Lys
        35

<210> SEQ ID NO 30
<211> LENGTH: 36
<212> TYPE: PRT
<213> ORGANISM: Artificial Sequence
<220> FEATURE:
<223> OTHER INFORMATION: Chemically Synthesized

<400> SEQUENCE: 30

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Glu Phe Lys
        35

<210> SEQ ID NO 31
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 31

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Glu Phe Pro Lys
        35

<210> SEQ ID NO 32
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 32

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Glu Phe Pro Glu Lys
        35

<210> SEQ ID NO 33
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 33

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Arg
            20                  25                  30

Arg Glu Phe Pro Glu Glu Lys
        35

<210> SEQ ID NO 34
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 34

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Lys
        35

<210> SEQ ID NO 35
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 35

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Lys
        35

<210> SEQ ID NO 36
<211> LENGTH: 40
<212> TYPE: PRT
<213> ORGANISM: Artificial Sequence
<220> FEATURE:
<223> OTHER INFORMATION: Chemically Synthesized

<400> SEQUENCE: 36

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Lys
        35                  40

<210> SEQ ID NO 37
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 37

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Arg Glu Lys
        35                  40

<210> SEQ ID NO 38
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 38

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Arg Glu Phe Lys
        35                  40

<210> SEQ ID NO 39
<211> LENGTH: 43
<212> TYPE: PRT
<213> ORGANISM: Artificial Sequence
<220> FEATURE:
<223> OTHER INFORMATION: Chemically Synthesized

<400> SEQUENCE: 39

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Arg Glu Phe Pro Lys
        35                  40

<210> SEQ ID NO 40
<211> LENGTH: 44
<212> TYPE: PRT
<213> ORGANISM: Artificial Sequence
<220> FEATURE:
<223> OTHER INFORMATION: Chemically Synthesized

<400> SEQUENCE: 40

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Arg Glu Phe Pro Glu Lys
        35                  40

<210> SEQ ID NO 41
<211> LENGTH: 45
<212> TYPE: PRT

<213> ORGANISM: Artificial Sequence
<220> FEATURE:
<223> OTHER INFORMATION: Chemically Synthesized

<400> SEQUENCE: 41

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Arg Gly Arg Arg Glu Phe Pro Glu Glu Lys
        35                  40                  45

<210> SEQ ID NO 42
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 42

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Lys
        35

<210> SEQ ID NO 43
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 43

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Lys
        35

<210> SEQ ID NO 44
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 44

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Arg Lys
        35

<210> SEQ ID NO 45
<211> LENGTH: 40
<212> TYPE: PRT
<213> ORGANISM: Artificial Sequence
<220> FEATURE:
<223> OTHER INFORMATION: Chemically Synthesized -continued

```
<400> SEQUENCE: 45

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Glu Lys
        35                  40

<210> SEQ ID NO 46
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 46

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Arg Glu Phe Lys
        35                  40

<210> SEQ ID NO 47
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 47

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Arg Glu Phe Pro Lys
        35                  40

<210> SEQ ID NO 48
<211> LENGTH: 43
<212> TYPE: PRT
<213> ORGANISM: Artificial Sequence
<220> FEATURE:
<223> OTHER INFORMATION: Chemically Synthesized

<400> SEQUENCE: 48

Asp Glu Phe Glu Arg His Ala Glu Gly Thr Phe Thr Ser Asp Val Ser
1               5                   10                  15

Ser Tyr Leu Glu Gly Gln Ala Ala Arg Glu Phe Ile Ala Trp Leu Val
            20                  25                  30

Arg Gly Arg Gly Arg Arg Glu Phe Pro Glu Lys
        35                  40

<210> SEQ ID NO 49
<211> LENGTH: 44
<212> TYPE: PRT
<213> ORGANISM: Artificial Sequence
<220> FEATURE:
<223> OTHER INFORMATION: Chemically Synthesized

<400> SEQUENCE: 49

Asp Glu Phe Glu Arg His Ala Glu Gly Thr Phe Thr Ser Asp Val Ser
1               5                   10                  15
```

```
Ser Tyr Leu Glu Gly Gln Ala Ala Arg Glu Phe Ile Ala Trp Leu Val
            20                  25                  30

Arg Gly Arg Gly Arg Glu Phe Pro Glu Glu Lys
            35                  40

<210> SEQ ID NO 50
<211> LENGTH: 36
<212> TYPE: PRT
<213> ORGANISM: Artificial Sequence
<220> FEATURE:
<223> OTHER INFORMATION: Chemically Synthesized

<400> SEQUENCE: 50

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Lys
            35

<210> SEQ ID NO 51
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 51

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Lys
            35

<210> SEQ ID NO 52
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 52

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Arg Lys
            35

<210> SEQ ID NO 53
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 53

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30
```

Gly Arg Gly Arg Arg Glu Lys
        35

<210> SEQ ID NO 54
<211> LENGTH: 40
<212> TYPE: PRT
<213> ORGANISM: Artificial Sequence
<220> FEATURE:
<223> OTHER INFORMATION: Chemically Synthesized

<400> SEQUENCE: 54

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Arg Glu Phe Lys
        35                  40

<210> SEQ ID NO 55
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 55

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Arg Glu Phe Pro Lys
        35                  40

<210> SEQ ID NO 56
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 56

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Arg Glu Phe Pro Glu Lys
        35                  40

<210> SEQ ID NO 57
<211> LENGTH: 43
<212> TYPE: PRT
<213> ORGANISM: Artificial Sequence
<220> FEATURE:
<223> OTHER INFORMATION: Chemically Synthesized

<400> SEQUENCE: 57

Glu Phe Glu Arg His Ala Glu Gly Thr Phe Thr Ser Asp Val Ser Ser
1               5                   10                  15

Tyr Leu Glu Gly Gln Ala Ala Arg Glu Phe Ile Ala Trp Leu Val Arg
            20                  25                  30

Gly Arg Gly Arg Arg Glu Phe Pro Glu Glu Lys
        35                  40

<210> SEQ ID NO 58
<211> LENGTH: 35
<212> TYPE: PRT
<213> ORGANISM: Artificial Sequence
<220> FEATURE:
<223> OTHER INFORMATION: Chemically Synthesized

<400> SEQUENCE: 58

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Lys
        35

<210> SEQ ID NO 59
<211> LENGTH: 36
<212> TYPE: PRT
<213> ORGANISM: Artificial Sequence
<220> FEATURE:
<223> OTHER INFORMATION: Chemically Synthesized

<400> SEQUENCE: 59

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Lys
        35

<210> SEQ ID NO 60
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 60

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Lys
        35

<210> SEQ ID NO 61
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 61

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Glu Lys
        35

<210> SEQ ID NO 62
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 62

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Glu Phe Lys
        35

<210> SEQ ID NO 63
<211> LENGTH: 40
<212> TYPE: PRT
<213> ORGANISM: Artificial Sequence
<220> FEATURE:
<223> OTHER INFORMATION: Chemically Synthesized

<400> SEQUENCE: 63

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Glu Phe Pro Lys
        35                  40

<210> SEQ ID NO 64
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 64

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Glu Phe Pro Glu Lys
        35                  40

<210> SEQ ID NO 65
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 65

Phe Glu Arg His Ala Glu Gly Thr Phe Thr Ser Asp Val Ser Ser Tyr
1               5                   10                  15

Leu Glu Gly Gln Ala Ala Arg Glu Phe Ile Ala Trp Leu Val Arg Gly
            20                  25                  30

Arg Gly Arg Arg Glu Phe Pro Glu Glu Lys
        35                  40

<210> SEQ ID NO 66
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 66

Glu Arg His Ala Glu Gly Thr Phe Thr Ser Asp Val Ser Ser Tyr Leu
1               5                   10                  15

Glu Gly Gln Ala Ala Arg Glu Phe Ile Ala Trp Leu Val Arg Gly Arg
            20                  25                  30

Gly Lys

<210> SEQ ID NO 67
<211> LENGTH: 35
<212> TYPE: PRT
<213> ORGANISM: Artificial Sequence
<220> FEATURE:
<223> OTHER INFORMATION: Chemically Synthesized

<400> SEQUENCE: 67

Glu Arg His Ala Glu Gly Thr Phe Thr Ser Asp Val Ser Ser Tyr Leu
1               5                   10                  15

Glu Gly Gln Ala Ala Arg Glu Phe Ile Ala Trp Leu Val Arg Gly Arg
            20                  25                  30

Gly Arg Lys
        35

<210> SEQ ID NO 68
<211> LENGTH: 36
<212> TYPE: PRT
<213> ORGANISM: Artificial Sequence
<220> FEATURE:
<223> OTHER INFORMATION: Chemically Synthesized

<400> SEQUENCE: 68

Glu Arg His Ala Glu Gly Thr Phe Thr Ser Asp Val Ser Ser Tyr Leu
1               5                   10                  15

Glu Gly Gln Ala Ala Arg Glu Phe Ile Ala Trp Leu Val Arg Gly Arg
            20                  25                  30

Gly Arg Arg Lys
        35

<210> SEQ ID NO 69
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 69

Glu Arg His Ala Glu Gly Thr Phe Thr Ser Asp Val Ser Ser Tyr Leu
1               5                   10                  15

Glu Gly Gln Ala Ala Arg Glu Phe Ile Ala Trp Leu Val Arg Gly Arg
            20                  25                  30

Gly Arg Arg Glu Lys
        35

<210> SEQ ID NO 70
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 70

Glu Arg His Ala Glu Gly Thr Phe Thr Ser Asp Val Ser Ser Tyr Leu
1               5                   10                  15

Glu Gly Gln Ala Ala Arg Glu Phe Ile Ala Trp Leu Val Arg Gly Arg

-continued

```
                20                  25                  30
Gly Arg Arg Glu Phe Lys
        35

<210> SEQ ID NO 71
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 71

Glu Arg His Ala Glu Gly Thr Phe Thr Ser Asp Val Ser Ser Tyr Leu
1               5                   10                  15
Glu Gly Gln Ala Ala Arg Glu Phe Ile Ala Trp Leu Val Arg Gly Arg
                20                  25                  30
Gly Arg Arg Glu Phe Pro Lys
        35

<210> SEQ ID NO 72
<211> LENGTH: 40
<212> TYPE: PRT
<213> ORGANISM: Artificial Sequence
<220> FEATURE:
<223> OTHER INFORMATION: Chemically Synthesized

<400> SEQUENCE: 72

Glu Arg His Ala Glu Gly Thr Phe Thr Ser Asp Val Ser Ser Tyr Leu
1               5                   10                  15
Glu Gly Gln Ala Ala Arg Glu Phe Ile Ala Trp Leu Val Arg Gly Arg
                20                  25                  30
Gly Arg Arg Glu Phe Pro Glu Lys
        35                  40

<210> SEQ ID NO 73
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 73

Glu Arg His Ala Glu Gly Thr Phe Thr Ser Asp Val Ser Ser Tyr Leu
1               5                   10                  15
Glu Gly Gln Ala Ala Arg Glu Phe Ile Ala Trp Leu Val Arg Gly Arg
                20                  25                  30
Gly Arg Arg Glu Phe Pro Glu Glu Lys
        35                  40

<210> SEQ ID NO 74
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 74

Arg His Ala Glu Gly Thr Phe Thr Ser Asp Val Ser Ser Tyr Leu Glu
1               5                   10                  15
Gly Gln Ala Ala Arg Glu Phe Ile Ala Trp Leu Val Arg Gly Arg Gly
                20                  25                  30
Lys
```

<210> SEQ ID NO 75
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 75

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Lys

<210> SEQ ID NO 76
<211> LENGTH: 35
<212> TYPE: PRT
<213> ORGANISM: Artificial Sequence
<220> FEATURE:
<223> OTHER INFORMATION: Chemically Synthesized

<400> SEQUENCE: 76

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Lys
        35

<210> SEQ ID NO 77
<211> LENGTH: 36
<212> TYPE: PRT
<213> ORGANISM: Artificial Sequence
<220> FEATURE:
<223> OTHER INFORMATION: Chemically Synthesized

<400> SEQUENCE: 77

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Glu Lys
        35

<210> SEQ ID NO 78
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 78

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Glu Phe Lys
        35

<210> SEQ ID NO 79
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 79

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Glu Phe Pro Lys
        35

<210> SEQ ID NO 80
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 80

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Glu Phe Pro Glu Lys
        35

<210> SEQ ID NO 81
<211> LENGTH: 40
<212> TYPE: PRT
<213> ORGANISM: Artificial Sequence
<220> FEATURE:
<223> OTHER INFORMATION: Chemically Synthesized

<400> SEQUENCE: 81

Arg His Ala Glu Gly Thr Phe Thr Ser Asp Val Ser Ser Tyr Leu Glu
1               5                   10                  15

Gly Gln Ala Ala Arg Glu Phe Ile Ala Trp Leu Val Arg Gly Arg Gly
            20                  25                  30

Arg Arg Glu Phe Pro Glu Glu Lys
        35                  40

<210> SEQ ID NO 82
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 82

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Lys Gly Arg Gly Lys
        35

<210> SEQ ID NO 83
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 83

```
His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Arg Gly Arg Gly Lys
            35

<210> SEQ ID NO 84
<211> LENGTH: 38
<212> TYPE: PRT
<213> ORGANISM: Artificial Sequence
<220> FEATURE:
<223> OTHER INFORMATION: Chemically Synthesized

<400> SEQUENCE: 84

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Lys Gly Lys
            35

<210> SEQ ID NO 85
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 85

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly Lys
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 86

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Lys
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 87

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Lys
            20                  25                  30

<210> SEQ ID NO 88
<211> LENGTH: 32
```

<212> TYPE: PRT
<213> ORGANISM: Artificial Sequence
<220> FEATURE:
<223> OTHER INFORMATION: Chemically Synthesized

<400> SEQUENCE: 88

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 89
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 89

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Lys Gly Arg Gly Arg Lys
        35

<210> SEQ ID NO 90
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 90

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Arg Gly Arg Gly Arg Lys
        35

<210> SEQ ID NO 91
<211> LENGTH: 39
<212> TYPE: PRT
<213> ORGANISM: Artificial Sequence
<220> FEATURE:
<223> OTHER INFORMATION: Chemically Synthesized

<400> SEQUENCE: 91

His Asp Glu Phe Glu Arg His Ala Glu Gly Thr Phe Thr Ser Asp Val
1               5                   10                  15

Ser Ser Tyr Leu Glu Gly Gln Ala Ala Arg Glu Phe Ile Ala Trp Leu
            20                  25                  30

Val Arg Gly Lys Gly Arg Lys
        35

<210> SEQ ID NO 92
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 92

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly Arg
            20                  25                  30

Lys

<210> SEQ ID NO 93
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 93

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Arg
            20                  25                  30

Lys

<210> SEQ ID NO 94
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 94

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Lys

<210> SEQ ID NO 95
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 95

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly Lys
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Chemically Synthesized

<400> SEQUENCE: 96

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Lys
            20                  25                  30

DERIVATIVES OF GLP-1 ANALOGS

CROSS-REFERENCE TO RELATED APPLICATIONS

This application is a continuation of U.S. application Ser. No. 11/008,743, filed Dec. 9, 2004, now abandoned which is a continuation of U.S. application Ser. No. 10/285,079, filed Aug. 19, 2002, now U.S. Pat. No. 7,235,627, which is a continuation of U.S. application Ser. No. 09/398,111, filed Sep. 16, 1999, now U.S. Pat. No. 6,458,924, which is a continuation-in-part of U.S. application Ser. No. 09/265,141 filed Mar. 8, 1999, now U.S. Pat. No. 6,384,016, and of U.S. application Ser. No. 09/258,750 filed Feb. 26, 1999, now U.S. Pat. No. 6,268,343, which is a continuation-in-part of U.S. application Ser. No. 09/038,432 filed Mar. 11, 1998, now abandoned, which is a continuation-in-part of U.S. application Ser. No. 08/918,810 filed Aug. 26, 1997, now abandoned, and of PCT Application No. PCT/DK97/00340 filed Aug. 22, 1997, and claims priority of U.S. Provisional Application Nos. 60/035,904, 60/036,226, 60/036,255, 60/078,422, 60/082,478, 60/082,479, 60/082,480, 60/082,802, and 60/084,357 filed Jan. 24, 1997, Jan. 25, 1997, Jan. 24, 1997, Mar. 18, 1998, Apr. 21, 1998, Apr. 21, 1998, Apr. 21, 1998, Apr. 23, 1998, and May 5, 1998, respectively, and of Danish Application Nos. 0931/96, 1259/96, 1470/96, 0263/98, 0264/98, 0268/98, 0272/98, 0274/98, 0508/98, 0509/98 and PA 1998 00507 filed Aug. 30, 1996, Nov. 8, 1996, Dec. 20, 1996, Feb. 27, 1998, Feb. 27, 1998, Feb. 27, 1998, Feb. 27, 1998, Feb. 27, 1998, Apr. 8, 1998, Apr. 8, 1998 and Apr. 8, 1998, respectively, and of European Application No. 98610006.3 filed Mar. 13, 1998, the contents of each of which is fully incorporated herein by reference.

FIELD OF THE INVENTION

The present invention relates to novel derivatives of human glucagon-like peptide-1 (GLP-1) and fragments and/or analogues thereof which have a protracted profile of action and to methods of making and using them.

BACKGROUND OF THE INVENTION

Peptides are widely used in medical practice, and since they can be produced by recombinant DNA technology it can be expected that their importance will increase also in the years to come. When native peptides or analogues thereof are used in therapy it is generally found that they have a high clearance. A high clearance of a therapeutic agent is inconvenient in cases where it is desired to maintain a high blood level thereof over a prolonged period of time since repeated administrations will then be necessary. Examples of peptides which have a high clearance are: ACTH, corticotropin-releasing factor, angiotensin, calcitonin, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease. In some cases it is possible to influence the release profile of peptides by applying suitable pharmaceutical compositions, but this approach has various shortcomings and is not generally applicable.

The hormones regulating insulin secretion belong to the so-called enteroinsular axis, designating a group of hormones, released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1). Because of its insulinotropic effect, GIP, isolated in 1973 (1) immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (IDDM) (2). Furthermore, as an insulinotropic hormone, GIP was found to be almost ineffective in NIDDM (2). The other incretin hormone, GLP-1 is the most potent insulinotropic substance known (3). Unlike GIP, it is surprisingly effective in stimulating insulin secretion in NIDDM patients. In addition, and in contrast to the other insulinotropic hormones (perhaps with the exception of secretin) it also potently inhibits glucagon secretion. Because of these actions it has pronounced blood glucose lowering effects particularly in patients with NIDDM.

GLP-1, a product of the proglucagon (4), is one of the youngest members of the secretin-VIP family of peptides, but is already established as an important gut hormone with regulatory function in glucose metabolism and gastrointestinal secretion and metabolism (5). The glucagon gene is processed differently in the pancreas and in the intestine. In the pancreas (9), the processing leads to the formation and parallel secretion of 1) glucagon itself, occupying positions 33-61 of proglucagon (PG); 2) an N-terminal peptide of 30 amino acids (PG (1-30)) often called glicentin-related pancreatic peptide, GRPP (10, 11); 3) a hexapeptide corresponding to PG (64-69); 4) and, finally, the so-called major proglucagon fragment (PG (72-158)), in which the two glucagon-like sequences are buried (9). Glucagon seems to be the only biologically active product. In contrast, in the intestinal mucosa, it is glucagon that is buried in a larger molecule, while the two glucagon-like peptides are formed separately (8). The following products are formed and secreted in parallel: 1) glicentin, corresponding to PG (1-69), with the glucagon sequence occupying residues Nos. 33-61 (12); 2) GLP-1(7-36)amide (PG (78-107))amide (13), not as originally believed PG (72-107)amide or 108, which is inactive). Small amounts of C-terminally glycine-extended but equally bioactive GLP-1(7-37), (PG (78-108)) are also formed (14); 3) intervening peptide-2 (PG (111-122)amide) (15); and 4) GLP-2 (PG (126-158)) (15, 16). A fraction of glicentin is cleaved further into GRPP (PG (1-30)) and oxyntomodulin (PG (33-69)) (17, 18). Of these peptides, GLP-1, has the most conspicuous biological activities.

Being secreted in parallel with glicentin/enteroglucagon, it follows that the many studies of enteroglucagon secretion (6, 7) to some extent also apply to GLP-1 secretion, but GLP-1 is metabolised more quickly with a plasma half-life in humans of 2 min (19). Carbohydrate or fat-rich meals stimulate secretion (20), presumably as a result of direct interaction of yet unabsorbed nutrients with the microvilli of the open-type L-cells of the gut mucosa. Endocrine or neural mechanisms promoting GLP-1 secretion may exist but have not yet been demonstrated in humans.

The incretin function of GLP-1(29-31) has been clearly illustrated in experiments with the GLP-1 receptor antagonist, exendin 9-39, which dramatically reduces the incretin effect elicited by oral glucose in rats (21, 22). The hormone interacts directly with the β-cells via the GLP-1 receptor (23) which belongs to the glucagon/VIP/calcitonin family of G-protein-coupled 7-transmembrane spanning receptors. The importance of the GLP-1 receptor in regulating insulin secretion was illustrated in recent experiments in which a targeted disruption of the GLP-1 receptor gene was carried out in mice. Animals homozygous for the disruption had greatly deteriorated glucose tolerance and fasting hyperglycaemia, and even heterozygous animals were glucose intolerant (24). The signal transduction mechanism (25) primarily involves activation of adenylate cyclase, but elevations of intracellular $Ca^{2+}$ are also essential (25, 26). The action of the hormone is best described as a potentiation of glucose stimulated insulin release (25), but the mechanism that couples glucose and GLP-1 stimulation is not known. It may involve a calcium-induced calcium release (26, 27). As already mentioned, the insulinotropic action of GLP-1 is preserved in diabetic β-cells. The relation of the latter to its ability to convey "glucose competence" to isolated insulin-secreting cells (26, 28), which respond poorly to glucose or GLP-1 alone, but fully to a combination of the two, is also not known. Equally importantly, however, the hormone also potently inhibits glucagon secretion (29). The mechanism is not known, but seems to be paracrine, via neighbouring insulin or somatostatin cells (25). Also the glucagonostatic action is glucose-dependent, so that the inhibitory effect decreases as blood glucose decreases. Because of this dual effect, if the plasma GLP-1 concentrations increase either by increased secretion or by exogenous infusion the molar ratio of insulin to glucagon in the blood that reaches the liver via the portal circulation is greatly increased, whereby hepatic glucose production decreases (30). As a result blood glucose concentrations decrease. Because of the glucose dependency of the insulinotropic and glucagonostatic actions, the glucose lowering effect is self-limiting, and the hormone, therefore, does not cause hypoglycaemia regardless of dose (31). The effects are preserved in patients with diabetes mellitus (32), in whom infusions of slightly supraphysiological doses of GLP-1 may completely normalise blood glucose values in spite of poor metabolic control and secondary failure to sulphonylurea (33). The importance of the glucagonostatic effect is illustrated by the finding that GLP-1 also lowers blood glucose in type-1 diabetic patients without residual β-cell secretory capacity (34).

In addition to its effects on the pancreatic islets, GLP-1 has powerful actions on the gastrointestinal tract. Infused in physiological amounts, GLP-1 potently inhibits pentagastrin-induced as well as meal-induced gastric acid secretion (35, 36). It also inhibits gastric emptying rate and pancreatic enzyme secretion (36). Similar inhibitory effects on gastric and pancreatic secretion and motility may be elicited in humans upon perfusion of the ileum with carbohydrate- or lipid-containing solutions (37, 38). Concomitantly, GLP-1 secretion is greatly stimulated, and it has been speculated that GLP-1 may be at least partly responsible for this so-called "ileal-brake" effect (38). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (39).

GLP-1 seems to have an effect on food intake. Intraventricular administration of GLP-1 profoundly inhibits food intake in rats (40, 42). This effect seems to be highly specific. Thus, N-terminally extended GLP-1 (PG 72-107)amide is inactive and appropriate doses of the GLP-1 antagonist, exendin 9-39, abolish the effects of GLP-1(41). Acute, peripheral administration of GLP-1 does not inhibit food intake acutely in rats (41, 42). However, it remains possible that GLP-1 secreted from the intestinal L-cells may also act as a satiety signal.

Not only the insulinotropic effects but also the effects of GLP-1 on the gastrointestinal tract are preserved in diabetic patients (43), and may help curtailing meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (44). The peptide is fully active after subcutaneous administration (45), but is rapidly degraded mainly due to degradation by dipeptidyl peptidase IV-like enzymes (46, 47).

The amino acid sequence of GLP-1 is given i.a. by Schmidt et al. (*Diabetologia* 28 704-707 (1985). Human GLP-1 is a 37 amino acid residue peptide originating from preproglucagon which is synthesised, i.a. in the L-cells in the distal ileum, in the pancreas and in the brain. Processing of preproglucagon to GLP-1(7-36)amide, GLP-1(7-37) and GLP-2 occurs mainly in the L-cells. Although the interesting pharmacological properties of GLP-1(7-37) and analogues thereof have attracted much attention in recent years only little is known about the structure of these molecules. The secondary structure of GLP-1 in micelles has been described by Thorton et al. (*Biochemistry* 33 3532-3539 (1994)), but in normal solution, GLP-1 is considered a very flexible molecule. Surprisingly, we found that derivatisation of this relatively small and very flexible molecule resulted in compounds whose plasma profile were highly protracted and still had retained activity.

GLP-1 and analogues of GLP-1 and fragments thereof are useful i.a. in the treatment of Type 1 and Type 2 diabetes and obesity.

WO 87/06941 discloses GLP-1 fragments, including GLP-1(7-37), and functional derivatives thereof and to their use as an insulinotropic agent.

WO 90/11296 discloses GLP-1 fragments, including GLP-1(7-36), and functional derivatives thereof which have an insulinotropic activity which exceeds the insulinotropic activity of GLP-1(1-36) or GLP-1(1-37) and to their use as insulinotropic agents.

The amino acid sequence of GLP-1(7-36) and GLP-1(7-37) is (SEQ ID NO:1):

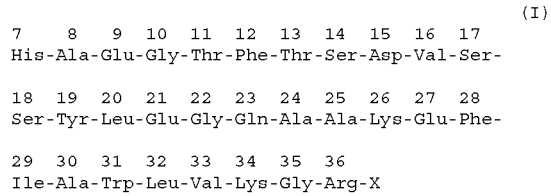

```
                                                            (I)
 7    8    9   10   11   12   13   14   15   16   17
His-Ala-Glu-Gly-Thr-Phe-Thr-Ser-Asp-Val-Ser- 18   19   20   21   22   23   24   25   26   27   28
Ser-Tyr-Leu-Glu-Gly-Gln-Ala-Ala-Lys-Glu-Phe- 29   30   31   32   33   34   35   36
Ile-Ala-Trp-Leu-Val-Lys-Gly-Arg-X
``` wherein X is $NH_2$ for GLP-1(7-36) and X is Gly for GLP-1(7-37).

WO 91/11457 discloses analogues of the active GLP-1 peptides 7-34, 7-35, 7-36, and 7-37 which can also be useful as GLP-1 moieties.

EP 0708179-A2 (Eli Lilly & Co.) discloses GLP-1 analogues and derivatives that include an N-terminal imidazole group and optionally an unbranched $C_6$-$C_{10}$ acyl group in attached to the lysine residue in position 34.

EP 0699686-A2 (Eli Lilly & Co.) discloses certain N-terminal truncated fragments of GLP-1 that are reported to be biologically active.

Unfortunately, the high clearance limits the usefulness of these compounds. Thus there still is a need for improvements in this field.

Accordingly, it is an object of the present invention to provide derivatives of GLP-1 and analogues thereof which have a protracted profile of action relative to GLP-1(7-37).

It is a further object of the invention to provide derivatives of GLP-1 and analogues thereof which have a lower clearance than GLP-1(7-37).

It is a further object of the invention to provide a pharmaceutical composition with improved solubility and stability.

REFERENCES

1. Pederson R A. Gastric Inhibitory Polypeptide. In Walsh J H, Dockray G J (eds) Gut peptides: Biochemistry and Physiology. Raven Press, New York 1994, pp. 217259.
2. Krarup T. Immunoreactive gastric inhibitory polypeptide. Endocr Rev 1988; 9: 122-134.
3. Ørskov C. Glucagon-like peptide-1, a new hormone of the enteroinsular axis. Diabetologia 1992; 35:701-711.
4. Bell G I, Sanchez-Pescador R, Laybourn P J, Najarian R C. Exon duplication and divergence in the human preproglucagon gene. Nature 1983; 304: 368-371.
5. Hoist J J. Glucagon-like peptide-1 (GLP-1)—a newly discovered GI hormone. Gastroenterology 1994; 107: 1848-1855.
6. Hoist J J. Gut glucagon, enteroglucagon, gut GLI, glicentin—current status. Gastroenterology 1983; 84:1602-1613.
7. Hoist J J, Ørskov C. Glucagon and other proglucagon-derived peptides. In Walsh J H, Dockray G J, eds. Gut peptides: Biochemistry and Physiology. Raven Press, New York, pp. 305-340, 1993.
8. Ørskov C, Hoist J J, Knuhtsen S, Baldissera F G A, Poulsen S S, Nielsen O V. Glucagon-like peptides GLP-1 and GLP-2, predicted products of the glucagon gene, are secreted separately from the pig small intestine, but not pancreas. Endocrinology 1986; 119:1467-1475.
9. Hoist J J, Bersani M, Johnsen A H, Kofod H, Hartmann B, Ørskov C. Proglucagon processing in porcine and human pancreas. J Biol Chem, 1994; 269: 18827-1883.
10. Moody A J, Hoist J J, Thim L, Jensen S L. Relationship of glicentin to proglucagon and glucagon in the porcine pancreas. Nature 1981; 289: 514-516.
11. Thim L, Moody A J, Purification and chemical characterisation of a glicentin-related pancreatic peptide (proglucagon fragment) from porcine pancreas. Biochim Biophys Acta 1982; 703:134-141.
12. Thim L, Moody A J. The primary structure of glicentin (proglucagon). Regul Pept 1981; 2:139-151.
13. Ørskov C, Bersani M, Johnsen A H, Højrup P, Holst J J. Complete sequences of glucagon-like peptide-1 (GLP-1) from human and pig small intestine. J. Biol. Chem. 1989; 264:12826-12829.
14. Ørskov C, Rabenhøj L, Kofod H, Wettergren A, Hoist J J. Production and secretion of amidated and glycine-extended glucagon-like peptide-1 (GLP-1) in man. Diabetes 1991; 43: 535-539.
15. Buhl T, Thim L, Kofod H, Ørskov C, Harling H, & Holst J J: Naturally occurring products of proglucagon 111-160 in the porcine and human small intestine. J. Biol. Chem. 1988; 263:8621-8624.
16. Ørskov C, Buhl T, Rabenhøj L, Kofod H, Holst J J: Carboxypeptidase-B-like processing of the C-terminus of glucagon-like peptide-2 in pig and human small intestine. FEBS letters, 1989; 247: 193-106.
17. Hoist J J. Evidence that enteroglucagon (II) is identical with the C-terminal sequence (residues 33-69) of glicentin. Biochem J. 1980; 187:337-343.
18. Bataille D, Tatemoto K, Gespach C, Jörnvall H, Rosselin G, Mutt V. Isolation of glucagon-37 (bioactive enteroglucagon/oxyntomodulin) from porcine jejuno-ileum. Characterisation of the peptide. FEBS Lett 1982; 146:79-86.
19. Ørskov C, Wettergren A, Holst J J. The metabolic rate and the biological effects of GLP-1 7-36 amide and GLP-1 7-37 in healthy volunteers are identical. Diabetes 1993; 42:658-661.
20. Elliott R M, Morgan L M, Tredger J A, Deacon S, Wright J, Marks V. Glucagon-like peptide-1 (7-36)amide and glucose-dependent insulinotropic polypeptide secretion in response to nutrient ingestion in man: acute post-prandial and 24-h secretion patterns. J Endocrinol 1993; 138: 159-166.
21. Kolligs F, Fehmann H C, Göke R, Göke B. Reduction of the incretin effect in rats by the glucagon-like peptide-1 receptor antagonist exendin (9-39)amide. Diabetes 1995; 44: 16-19.
22. Wang Z, Wang R M, Owi A A, Smith D M, Ghatei M, Bloom S R. Glucagon-like peptide-1 is a physiological incretin in rat. J. Clin. Invest. 1995; 95: 417-421.
23. Thorens B. Expression cloning of the pancreatic b cell receptor for the gluco-incretin hormone glucagon-like peptide 1. Proc Natl Acad Sci 1992; 89:8641-4645.
24. Scrocchi L, Auerbach A, Joyner A L, Drucker D J. Diabetes in mice with targeted disruption of the GLP-1 receptor gene. Diabetes 1996; 45: 21A.
25. Fehmann H C, Göke R, Göke B. Cell and molecular biology of the incretin hormones glucagon-like peptide-I (GLP-1) and glucose-dependent insulin releasing polypeptide (GIP). Endocrine Reviews, 1995; 16: 390-410.
26. Gromada J, Dissing S, Bokvist K, Renström E, Frøkjær-Jensen J, Wulff B S, Rorsman P. Glucagon-like peptide I increases cytoplasmic calcium in insulin-secreting bTC3-cells by enhancement of intracellular calcium mobilisation. Diabetes 1995; 44: 767-774.
27. Holz G G, Leech C A, Habener J F. Activation of a cAMP-regulated $Ca^{2+}$-signaling pathway in pancreatic β-cells by the insulinotropic hormone glucagon-like peptide-1. J Biol Chem, 1996; 270: 17749-17759.
28. Holz G G, Kühltreiber W M, Habener J F. Pancreatic beta-cells are rendered glucose competent by the insulinotropic hormone glucagon-like peptide-1(7-37). Nature 1993; 361:362-365.
29. Ørskov C, Holst J J, Nielsen O V: Effect of truncated glucagon-like peptide-1 (proglucagon 78-107 amide) on endocrine secretion from pig pancreas, antrum and stomach. Endocrinology 1988; 123:2009-2013.
30. Hvidberg A, Toft Nielsen M, Hilsted J, Ørskov C, Holst J J. Effect of glucagon-like peptide-1 (proglucagon 78-107amide) on hepatic glucose production in healthy man. Metabolism 1994; 43:104-108.

31. Qualmann C, Nauck M, Holst J J, Ørskov C, Creutzfeldt W. Insulinotropic actions of intravenous glucagon-like peptide-1 [7-36 amide] in the fasting state in healthy subjects. Acta Diabetologica, 1995; 32: 13-16.
32. Nauck M A, Heimesaat M M, Ørskov C, Hoist J J, Ebert R, Creutzfeldt W. Preserved incretin activity of GLP-1(7-36amide) but not of synthetic human GIP in patients with type 2-diabetes mellitus. J Clin Invest 1993; 91:301-307.
33. Nauck M A, Kleine N, Ørskov C, Hoist J J, Willms B, Creutzfeldt W. Normalisation of fasting hyperglycaemia by exogenous GLP-1(7-36amide) in type 2-diabetic patients. Diabetologia 1993; 36:741-744.
34. Creutzfeldt W, Kleine N, Willms B, Ørskov C, Hoist J J, Nauck M A. Glucagonostatic actions and reduction of fasting hyperglycaemia by exogenous glucagon-liem, peptide-1(7-36amide) in type I diabetic patients. Diabetes Care 1996; 19: 580-586.
35. Schjoldager B T G, Mortensen P E, Christiansen J, Ørskov C, Hoist J J. GLP-1 (glucagon-like peptide-1) and truncated GLP-1, fragments of human proglucagon, inhibit gastric acid secretion in man. Dig. Dis. Sci. 1989; 35:703-708.
36. Wettergren A, Schjoldager B, Mortensen P E, Myhre J, Christiansen J, Holst J J. Truncated GLP-1 (proglucagon 72-107 amide) inhibits gastric and pancreatic functions in man. Dig Dis Sci 1993; 38:665-673.
37. Layer P, Holst J J, Grandt D, Goebell H: Ileal release of glucagon-like peptide-1 (GLP-1): association with inhibition of gastric acid in humans. Dig Dis Sci 1995; 40: 1074-1082.
38. Layer P, Holst J J. GLP-1: A humoral mediator of the ileal brake in humans? Digestion 1993; 54: 385-386.
39. Nauck M, Ettler R, Niedereichholz U, Ørskov C, Hoist J J, Schmiegel W. Inhibition of gastric emptying by GLP-1 (7-36 amide) or (7-37): effects on postprandial glycaemia and insulin secretion. Abstract. Gut 1995; 37 (suppl. 2): A124.
40. Schick R R, vorm Walde T, Zimmermann J P, Schusdziarra V, Classen M. Glucagon-like peptide 1—a novel brain peptide involved in feeding regulation. in Ditschuneit H, Gries F A, Hauner H, Schusdziarra V, Wechsler J G (eds.) Obesity in Europe. John Libbey & Company ltd, 1994; pp. 363-367.
41. Tang-Christensen M, Larsen P J, Göke R, Fink-Jensen A, Jessop D S, Møller M, Sheikh S. Brain GLP-1(7-36) amide receptors play a major role in regulation of food and water intake. Am. J. Physiol., 1996, in press.
42. Turton M D, O'Shea D, Gunn I, Beak S A, Edwards C M B, Meeran K, et al. A role for glucagon-like peptide-1 in the regulation of feeding. Nature 1996; 379: 69-72.
43. Willms B, Werner J, Creutzfeldt W, Ørskov C, Hoist J J, Nauck M. Inhibition of gastric emptying by glucagon-like peptide-1 (7-36 amide) in patients with type-2-diabetes mellitus. Diabetologia 1994; 37, suppl: A118.
44. Larsen J, Jallad N, Damsbo P. One-week continuous infusion of GLP-1(7-37) improves glycaemic control in NIDDM. Diabetes 1996; 45, suppl. 2: 233A.
45. Ritzel R, Ørskov C, Hoist J J, Nauck M A. Pharmacokinetic, insulinotropic, and glucagonostatic properties of GLP-1 [7-36 amide] after subcutaneous injection in healthy volunteers. Dose-response relationships. Diabetologia 1995; 38: 720-725.
46. Deacon C F, Johnsen A H, Hoist J J. Degradation of glucagon-like peptide-1 by human plasma in vitro yields an N-terminally truncated peptide that is a major endogenous metabolite in vivo. J Clin Endocrinol Metab 1995; 80: 952-957.
47. Deacon C F, Nauck M A, Toft-Nielsen M, Pridal L, Willms B, Holst J J. 1995. Both subcutaneous and intravenously administered glucagon-like peptide-1 are rapidly degraded from the amino terminus in type II diabetic patients and in healthy subjects. Diabetes 44: 1126-1131.

SUMMARY OF THE INVENTION

The present invention relates to a pharmaceutical composition with improved solubility and stability comprising derivatives of GLP-1(1-45) and analogs and/or fragments thereof. The GLP-1 derivatives of the present invention have interesting pharmacological properties, in particular they have a more protracted profile of action than the parent peptides. The GLP-1 derivatives of the present invention also have insulinotropic activity, ability to decrease glucagon, ability to suppress gastric motility, ability to restore glucose competency to beta-cells, and/or ability to suppress appetite/reduce weight.

DETAILED DESCRIPTION OF THE INVENTION

Figure 1:
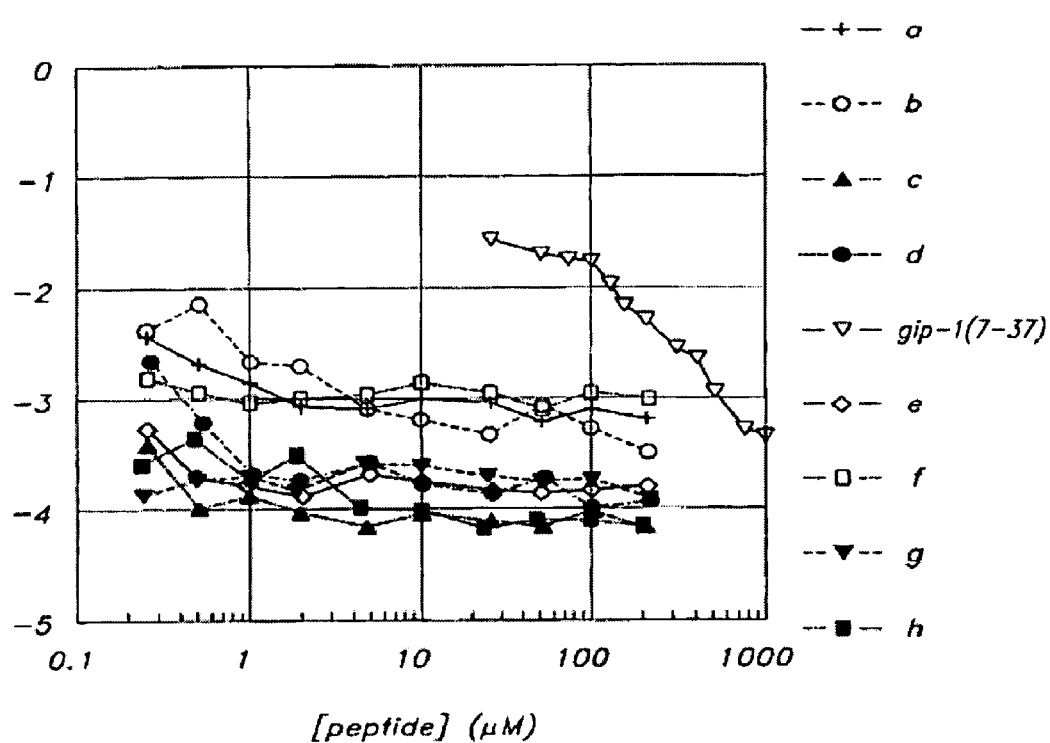
FIG. 1 shows the results of Circular Dichroism (CD) at 222 nm as a function of peptide concentration for native GLP-1 (7-37) and various GLP-1 derivatives of the present invention.

A simple system is used to describe fragments and analogues of GLP-1. For example, $Gly^8$-GLP-1(7-37) designates a peptide which relates to GLP-1 by the deletion of the amino acid residues at positions. 1 to 6 and substituting the naturally occurring amino acid residue in position 8 (Ala) by Gly. Similarly, $Lys^{34}(N^\epsilon$-tetradecanoyl)-GLP-1(7-37) designates GLP-1(7-37) wherein the ε-amino group of the Lys residue in position 34 has been tetradecanoylated. Where reference in this text is made to C-terminally extended GLP-1 analogues, the amino acid residue in position 38 is Arg unless otherwise indicated, the amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

GLP-1 Analogs

The term "an analogue" is defined herein as a peptide wherein one or more amino acid residues of the parent peptide have been substituted by another amino acid residue. In a preferred embodiment, the total number of different amino acids between the GLP-1 derivative and the corresponding native form of GLP-1 is up to fifteen, preferably up to ten amino acid residues, and most preferably up to six amino acid residues.

The total number of different amino acids between the derivative of the GLP-1 analog and the corresponding native form of GLP-1 preferably does not exceed six. Preferably, the number of different amino acids is five. More preferably, the number of different amino acids is four. Even more preferably, the number of different amino acids is three. Even more preferably, the number of different amino acids is two. Most preferably, the number of different amino acids is one. In order to determine the number of different amino acids, one should compare the amino acid sequence of the GLP-1 derivative of the present invention with the corresponding native GLP-1. For example, there are two different amino acids between the derivative $Gly^8Arg^{26}Lys^{34}(N^\epsilon$-(7-deoxychoyl))-GLP-1(7-40) and the corresponding native GLP-1 (i.e., GLP-1(7-40)). The differences are located at positions 8 and 26. Similarly, there is only one different amino acid between the derivative Lys$^{26}$(N$^\epsilon$-(7-deoxycholoyl))Arg$^{34}$-GLP-1(7-40) and the corresponding native GLP-1. The difference is located at position 34.

In a preferred embodiment, the present invention relates to a GLP-1 derivative wherein the parent peptide is GLP-1(1-45) or an analogue thereof. In a further preferred embodiment, the parent peptide is GLP-1(1-35), GLP-1(1-36), GLP-1(1-36)amide, GLP-1(1-37), GLP-1(1-38), GLP-1(1-39), GLP-1(1-40), GLP-1(1-41) or an analogue thereof.

In a preferred embodiment, the present invention relates to derivatives of GLP-1 analogues of formula I (SEQ ID NO:2):

```
          7   8   9  10  11  12  13  14  15  16  17        (I)
         Xaa-Xaa-Xaa-Xaa-Xaa-Xaa-Xaa-Xaa-Xaa-Xaa-Xaa- 18  19  20  21  22  23  24  25  26  27  28
         Xaa-Xaa-Xaa-Xaa-Xaa-Xaa-Xaa-Xaa-Xaa-Xaa-Phe- 29  30  31  32  33  34  35  36  37  38
         Ile-Xaa-Xaa-Xaa-Xaa-Xaa-Xaa-Xaa-Xaa-Xaa 39  40  41  42  43  44  45
         Xaa-Xaa-Xaa-Xaa-Xaa-Xaa-Xaa
``` wherein

Xaa at position 7 is His, a modified amino acid or is deleted,

Xaa at position 8 is Ala, Gly, Ser, Thr, Leu, Ile, Val, Glu, Asp, or Lys, or is deleted, Xaa at position 9 is Glu, Asp, or Lys, or is deleted, Xaa at position 10 is Gly or is deleted, Xaa at position 11 is Thr, Ala, Gly, Ser, Leu, Ile, Val, Glu, Asp, or Lys, or is deleted, Xaa at position 12 is Phe or is deleted, Xaa at position 13 is Thr or is deleted, Xaa at position 14 is Ser, Ala, Gly, Thr, Leu, Ile, Val, Glu, Asp, or Lys, or is deleted, Xaa at position 15 is Asp or is deleted, Xaa at position 16 is Val, Ala, Gly, Ser, Thr, Leu, Ile, Tyr, Glu, Asp, or Lys, or is deleted, Xaa at position 17 is Ser, Ala, Gly, Thr, Leu, Ile, Val, Glu, Asp, or Lys, or is deleted, Xaa at position 18 is Ser, Ala, Gly, Thr, Leu, Ile, Val, Glu, Asp, or Lys, Xaa at position 19 is Tyr, Phe, Trp, Glu, Asp, or Lys, Xaa at position 20 is Leu, Ala, Gly, Ser, Thr, Leu, Ile, Val, Glu, Asp, or Lys, Xaa at position 21 is Glu, Asp, or Lys, Xaa at position 22 is Gly, Ala, Ser, Thr, Leu, Ile, Val, Glu, Asp, or Lys, Xaa at position 23 is Gln, Asn, Arg, Glu, Asp, or Lys, Xaa at position 24 is Ala, Gly, Ser, Thr, Leu, Ile, Val, Arg, Glu, Asp, or Lys, Xaa at position 25 is Ala, Gly, Ser, Thr, Leu, Ile, Val, Glu, Asp, or Lys, Xaa at position 26 is Lys, Arg, Gln, Glu, Asp, or His, Xaa at position 27 is Glu, Asp, or Lys, Xaa at position 30 is Ala, Gly, Ser, Thr, Leu, Ile, Val, Glu, Asp, or Lys, Xaa at position 31 is Trp, Phe, Tyr, Glu, Asp, or Lys, Xaa at position 32 is Leu, Gly, Ala, Ser, Thr, Ile, Val, Glu, Asp, or Lys, Xaa at position 33 is Val, Gly, Ala, Ser, Thr, Leu, Ile, Glu, Asp, or Lys, Xaa at position 34 is Lys, Arg, Glu, Asp, or His, Xaa at position 35 is Gly, Ala, Ser, Thr, Leu, Ile, Val, Glu, Asp, or Lys, Xaa at position 36 is Arg, Lys, Glu, Asp, or His, Xaa at position 37 is Gly, Ala, Ser, Thr, Leu, Ile, Val, Glu, Asp, or Lys, or is deleted, Xaa at position 38 is Arg, Lys, Glu, Asp, or His, or is deleted, Xaa at position 39 is Arg, Lys, Glu, Asp, or His, or is deleted, Xaa at position 40 is Asp, Glu, or Lys, or is deleted, Xaa at position 41 is Phe, Trp, Tyr, Glu, Asp, or Lys, or is deleted, Xaa at position 42 is Pro, Lys, Glu, or Asp, or is deleted, Xaa at position 43 is Glu, Asp, or Lys, or is deleted, Xaa at position 44 is Glu, Asp, or Lys, or is deleted, and Xaa at position 45 is Val, Glu, Asp, or Lys, or is deleted, or (a) a C-1-6-ester thereof, (b) amide, C-1-6-alkylamide, or C-1-6-dialkylamide thereof and/or (c) a pharmaceutically acceptable salt thereof, provided that when the amino acid at position 37, 38, 39, 40, 41, 42, 43 or 44 is deleted, then each amino acid downstream of the amino acid is also deleted and when the amino acid at position 8, 9, 10, 11, 12, 13, 14, 15, 16 or 17 is deleted then each amino acid upstream of the amino acid is also deleted.

The term "modified amino acid" is defined herein as A is:

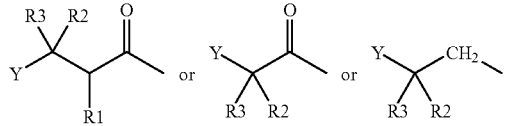

wherein R$^1$, R$^2$ and R$^3$ are independently H, lower alkyl, optionally substituted phenyl, NH$_2$, NH—CO-(lower alkyl), —OH, lower alkoxy, halogen, SO$_2$— (lower alkyl) or CF$_3$, wherein said phenyl is optionally substituted with at least one group selected from NH$_2$, —OH, lower alkyl or lower alkoxy having 1-6 carbon atoms, halogen, SO$_2$— (lower alkyl), NH—CO-(lower alkyl) or CF$_3$, or R$^1$ and R$^2$ may together form a bond; and Y is a five or six membered ring system selected from the group consisting of:

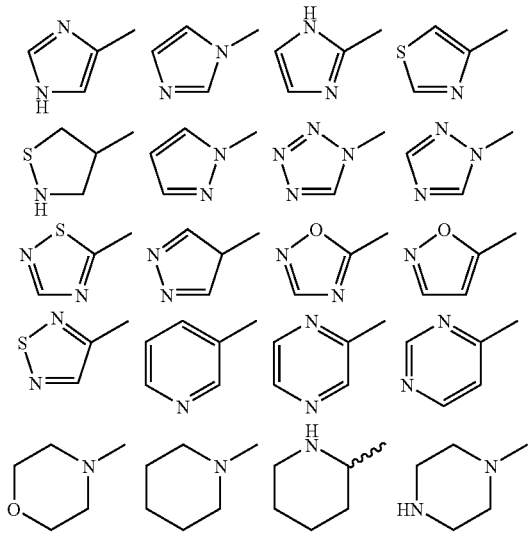

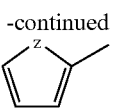

wherein Z is N, O or S, and said ring system is optionally substituted with one or more functional groups selected from the group consisting of $NH_2$, $NO_2$, OH, lower alkyl, lower alkoxy, halogen, $CF_3$ and aryl (i.e., optionally substituted phenyl, as define above), provided that A is not histidine;

The terms "lower alkyl" and "lower alkoxy" refer to an alkyl or alkoxy group, respectively, having 1-6 carbon atoms.

In a preferred embodiment, A is:

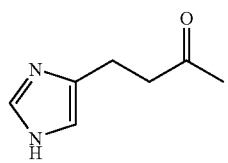

In another preferred embodiment, A is:

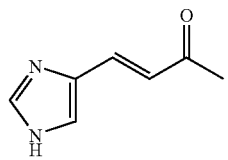

In another preferred embodiment, A is:

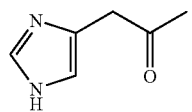

In another preferred embodiment, A is:

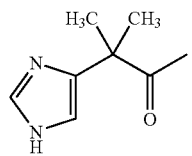

In another preferred embodiment, A is:

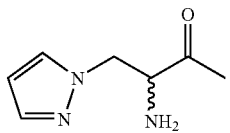

In another preferred embodiment, A is 4-imidazopropionyl.

In another preferred embodiment, A is 4-imidazoacetyl.

In another preferred embodiment, A is 4-imidazo-α,α-dimethyl-acetyl.

The GLP-1 derivatives of the present invention preferably have only one or two Lys wherein the ε-amino group of one or both Lys is substituted with a lipophilic substituent. Preferably, the GLP-1 derivatives of the present invention have only one Lys. In a more preferred embodiment, there is only one Lys which is located at the carboxy terminus of the derivative of the GLP-1 analogs. In an even more preferred embodiment, the GLP-1 derivatives of the present invention have only one Lys and Glu or Asp is adjacent to Lys.

In a preferred embodiment, the amino acids at positions 37-45 are absent.

In another preferred embodiment, the amino acids at positions 38-45 are absent.

In another preferred embodiment, the amino acids at positions 39-45 are absent.

In another preferred embodiment, the amino acid at position 7 is deleted.

In another preferred embodiment, the amino acids at positions 7 and 8 are deleted.

In another preferred embodiment, the amino acids at positions 7-9 are deleted.

In another preferred embodiment, the amino acids at positions 7-10 are deleted.

In another preferred embodiment, the amino acids at positions 7-11 are deleted.

In another preferred embodiment, the amino acids at positions 7-12 are deleted.

In another preferred embodiment, the amino acids at positions 7-13 are deleted.

In another preferred embodiment, the amino acids at positions 7-14 are deleted.

In another preferred embodiment, the amino acids at positions 7-15 are deleted.

In another preferred embodiment, the amino acids at positions 7-16 are deleted.

In another preferred embodiment, the amino acids at positions 7-17 are deleted.

In another preferred embodiment, Xaa at position 7 is His.

In another preferred embodiment, Xaa at position 8 is Ala, Gly, Ser, Thr, or Val.

In another preferred embodiment, Xaa at position 9 is Glu.

In another preferred embodiment, Xaa at position 10 is Gly.

In another preferred embodiment, Xaa at position 11 is Thr.

In another preferred embodiment, Xaa at position 12 is Phe.

In another preferred embodiment, Xaa at position 13 is Thr.

In another preferred embodiment, Xaa at position 14 is Ser.

In another preferred embodiment, Xaa at position 15 is Asp.

In another preferred embodiment, Xaa at position 16 is Val.

In another preferred embodiment, Xaa at position 17 is Ser.

In another preferred embodiment, Xaa at position 18 is Ser, Lys, Glu, or Asp.

In another preferred embodiment, Xaa at position 19 is Tyr, Lys, Glu, or Asp.

In another preferred embodiment, Xaa at position 20 is Leu, Lys, Glu, or Asp.

In another preferred embodiment, Xaa at position 21 is Glu, Lys, or Asp.

In another preferred embodiment, Xaa at position 22 is Gly, Glu, Asp, or Lys.

In another preferred embodiment, Xaa at position 23 is Gln, Glu, Asp, or Lys.

In another preferred embodiment, Xaa at position 24 is Ala, Glu, Asp, or Lys.

In another preferred embodiment, Xaa at position 25 is Ala, Glu, Asp, or Lys.

In another preferred embodiment, Xaa at position 26 is Lys, Glu, Asp, or Arg.

In another preferred embodiment, Xaa at position 27 is Glu, Asp, or Lys.

In another preferred embodiment, Xaa at position 30 is Ala, Glu, Asp, or Lys.

In another preferred embodiment, Xaa at position 31 is Trp, Glu, Asp, or Lys.

In another preferred embodiment, Xaa at position 32 is Leu, Glu, Asp, or Lys.

In another preferred embodiment, Xaa at position 33 is Val, Glu, Asp, or Lys.

In another preferred embodiment, Xaa at position 34 is Lys, Arg, Glu, or Asp.

In another preferred embodiment, Xaa at position 35 is Gly, Glu, Asp, or Lys.

In another preferred embodiment, Xaa at position 36 is Arg, Lys, Glu, or Asp.

In another preferred embodiment, Xaa at position 37 is Gly, Glu, Asp, or Lys.

In another preferred embodiment, Xaa at position 38 is Arg or Lys, or is deleted.

In another preferred embodiment, Xaa at position 39 is deleted.

In another preferred embodiment, Xaa at position 40 is deleted.

In another preferred embodiment, Xaa at position 41 is deleted.

In another preferred embodiment, Xaa at position 42 is deleted.

In another preferred embodiment, Xaa at position 43 is deleted.

In another preferred embodiment, Xaa at position 44 is deleted.

In another preferred embodiment, Xaa at position 45 is deleted.

In another preferred embodiment, Xaa at position 26 is Arg, each of Xaa at positions 37-45 is deleted, and each of the other Xaa is the amino acid in native GLP-1(7-36).

In another preferred embodiment, Xaa at position 26 is Arg, each of Xaa at positions 38-45 is deleted, and each of the other Xaa is the amino acid in native GLP-1(7-37).

In another preferred embodiment, Xaa at position 26 is Arg, each of Xaa at positions 39-45 is deleted, and each of the other Xaa is the amino acid in native GLP-1(7-38).

In another preferred embodiment, Xaa at position 34 is Arg, each of Xaa at positions 37-45 is deleted, and each of the other Xaa is the amino acid in native GLP-1(7-36).

In another preferred embodiment, Xaa at position 34 is Arg, each of Xaa at positions 38-45 is deleted, and each of the other Xaa is the amino acid in native GLP-1(7-37).

In another preferred embodiment, Xaa at position 34 is Arg, each of Xaa at positions 39-45 is deleted, and each of the other Xaa is the amino acid in native GLP-1(7-38).

In another preferred embodiment, Xaa at positions 26 and 34 is Arg, Xaa at position 36 is Lys, each of Xaa at positions 37-45 is deleted, and each of the other Xaa is the amino acid in native GLP-1(7-36).

In another preferred embodiment, Xaa at positions 26 and 34 is Arg, Xaa at position 36 is Lys, each of Xaa at positions 38-45 is deleted, and each of the other Xaa is the amino acid in native GLP-1(7-37).

In another preferred embodiment, Xaa at positions 26 and 34 is Arg, Xaa at position 36 is Lys, each of Xaa at positions 39-45 is deleted, and each of the other Xaa is the amino acid in native GLP-1(7-38).

In another preferred embodiment, Xaa at positions 26 and 34 is Arg, Xaa at position 38 is Lys, each of Xaa at positions 39-45 is deleted, and each of the other Xaa is the amino acid in native GLP-1(7-38).

In another preferred embodiment, Xaa at position 8 is Thr, Ser, Gly or Val, Xaa at position 37 is Asp or Glu, Xaa at position 36 is Lys, each of Xaa at positions 38-45 is deleted, and each of the other Xaa is the amino acid in native GLP-1 (7-37).

In another preferred embodiment, Xaa at position 8 is Thr, Ser, Gly or Val, Xaa at position 37 is Asp or Glu, Xaa at position 36 is Lys, each of Xaa at positions 39-45 is deleted, and each of the other Xaa is the amino acid in native GLP-1 (7-38).

In another preferred embodiment, Xaa at position 8 is Thr, Ser, Gly or Val, Xaa at position 36 is Lys, each of Xaa at positions 37-45 is deleted, and each of the other Xaa is the amino acid in native GLP-1(7-36).

In another preferred embodiment, Xaa at position 8 is Thr, Ser, Gly or Val, Xaa at position 36 is Lys, each of Xaa at positions 38-45 is deleted, and each of the other Xaa is the amino acid in native GLP-1(7-37).

In another preferred embodiment, Xaa at position 8 is Thr, Ser, Gly or Val, Xaa at position 36 is Lys, each of Xaa at positions 39-45 is deleted, and each of the other Xaa is the amino acid in native GLP-1(7-38).

In another preferred embodiment, Xaa at position 8 is Thr, Ser, Gly or Val, Xaa at position 37 is Glu or Asp, Xaa at position 38 is Lys, each of Xaa at positions 39-45 is deleted, and each of the other Xaa is the amino acid in native GLP-1 (7-38).

In another preferred embodiment, Xaa at position 8 is Thr, Ser, Gly or Val, Xaa at position 38 is Lys, each of Xaa at positions 39-45 is deleted, and each of the other Xaa is the amino acid in native GLP-1(7-38).

In another preferred embodiment, Xaa at position 18, 23 or 27 is Lys, and Xaa at positions 26 and 34 is Arg, each of Xaa at positions 37-45 is deleted, and each of the other Xaa is the amino acid in native GLP-1(7-36).

In another preferred embodiment, Xaa at position 18, 23 or 27 is Lys, and Xaa at positions 26 and 34 is Arg, each of Xaa at positions 38-45 is deleted, and each of the other Xaa is the amino acid in native GLP-1(7-37).

In another preferred embodiment, Xaa at position 18, 23 or 27 is Lys, and Xaa at positions 26 and 34 is Arg, each of Xaa at positions 39-45 is deleted, and each of the other Xaa is the amino acid in native GLP-1(7-38).

In another preferred embodiment, Xaa at position 8 is Thr, Ser, Gly, or Val, Xaa at position 18, 23 or 27 is Lys, and Xaa at position 26 and 34 is Arg, each of Xaa at positions 37-45 is deleted, and each of the other Xaa is the amino acid in native GLP-1(7-36).

In another preferred embodiment, Xaa at position 8 is Thr, Ser, Gly, or Val, Xaa at position 18, 23 or 27 is Lys, and Xaa at position 26 and 34 is Arg, each of Xaa at positions 38-45 is deleted, and each of the other Xaa is the amino acid in native GLP-1(7-37).

In another preferred embodiment, Xaa at position 8 is Thr, Ser, Gly, or Val, Xaa at position 18, 23 or 27 is Lys, and Xaa at position 26 and 34 is Arg, each of Xaa at positions 39-45 is deleted, and each of the other Xaa is the amino acid in native GLP-1(7-38).

In another preferred embodiment, Xaa at position 7 is a modified amino acid or is deleted, Xaa at position 26 is Arg, each of Xaa at positions 37-45 is deleted, and each of the other Xaa is the amino acid in native GLP-1(8-36).

In another preferred embodiment, Xaa at position 7 is a modified amino acid or is deleted, Xaa at position 26 is Arg, each of Xaa at positions 38-45 is deleted, and each of the other Xaa is the amino acid in native GLP-1(8-37).

In another preferred embodiment, Xaa at position 7 is a modified amino acid or is deleted, Xaa at position 26 is Arg, each of Xaa at positions 39-45 is deleted, and each of the other Xaa is the amino acid in native GLP-1(8-38).

In another preferred embodiment, Xaa at position 7 is a modified amino acid or is deleted, Xaa at position 34 is Arg, each of Xaa at positions 37-45 is deleted, and each of the other Xaa is the amino acid in native GLP-1(8-36).

In another preferred embodiment, Xaa at position 7 is a modified amino acid or is deleted, Xaa at position 34 is Arg, each of Xaa at positions 38-45 is deleted, and each of the other Xaa is the amino acid in native GLP-1(8-37).

In another preferred embodiment, Xaa at position 7 is a modified amino acid or is deleted, Xaa at position 34 is Arg, each of Xaa at positions 39-45 is deleted, and each of the other Xaa is the amino acid in native GLP-1(8-38).

In another preferred embodiment, Xaa at position 7 is a modified amino acid or is deleted, Xaa at positions 26 and 34 is Arg, Xaa at position 36 is Lys, each of Xaa at positions 37-45 is deleted, and each of the other Xaa is the amino acid in native GLP-1(8-36).

In another preferred embodiment, Xaa at position 7 is a modified amino acid or is deleted, Xaa at positions 26 and 34 is Arg, Xaa at position 36 is Lys, each of Xaa at positions 38-45 is deleted, and each of the other Xaa is the amino acid in native GLP-1(8-37).

In another preferred embodiment, Xaa at position 7 is a modified amino acid or is deleted, Xaa at positions 26 and 34 is Arg, Xaa at position 36 is Lys, each of Xaa at positions 39-45 is deleted, and each of the other Xaa is the amino acid in native GLP-1(8-38).

In another preferred embodiment, Xaa at position 7 is a modified amino acid or is deleted, Xaa at positions 26 and 34 is Arg, Xaa at position 38 is Lys, each of Xaa at positions 39-45 is deleted, and each of the other Xaa is the amino acid in native GLP-1(8-38).

In another preferred embodiment, Xaa at position 7 is a modified amino acid or is deleted, Xaa at position 8 is Thr, Ser, Gly or Val, Xaa at position 37 is Glu, Xaa at position 36 is Lys, each of Xaa at positions 38-45 is deleted, and each of the other Xaa is the amino acid in native GLP-1(8-37).

In another preferred embodiment, Xaa at position 7 is a modified amino acid or is deleted, Xaa at position 8 is Thr, Ser, Gly or Val, Xaa at position 37 is Glu, Xaa at position 36 is Lys, each of Xaa at positions 39-45 is deleted, and each of the other Xaa is the amino acid in native GLP-1(8-38).

In another preferred embodiment, Xaa at position 7 is a modified amino acid or is deleted, Xaa at position 8 is Thr, Ser, Gly or Val, Xaa at position 37 is Glu, Xaa at position 38 is Lys, each of Xaa at positions 39-45 is deleted, and each of the other Xaa is the amino acid in native GLP-1(8-38).

In another preferred embodiment, Xaa at position 7 is a modified amino acid or is deleted, Xaa at position 18, 23 or 27 is Lys, and Xaa at positions 26 and 34 is Arg, each of Xaa at positions 37-45 is deleted, and each of the other Xaa is the amino acid in native GLP-1(8-36).

In another preferred embodiment, Xaa at position 7 is a modified amino acid or is deleted, Xaa at position 18, 23 or 27 is Lys, and Xaa at positions 26 and 34 is Arg, each of Xaa at positions 38-45 is deleted, and each of the other Xaa is the amino acid in native GLP-1(8-37).

In another preferred embodiment, Xaa at position 7 is a modified amino acid or is deleted, Xaa at position 18, 23 or 27 is Lys, and Xaa at positions 26 and 34 is Arg, each of Xaa at positions 39-45 is deleted, and each of the other Xaa is the amino acid in native GLP-1(8-38).

In another preferred embodiment, Xaa at position 7 is a modified amino acid or is deleted, Xaa at position 8 is Thr, Ser, Gly, or Val, Xaa at position 18, 23 or 27 is Lys, and Xaa at position 26 and 34 is Arg, each of Xaa at positions 37-45 is deleted, and each of the other Xaa is the amino acid in native GLP-1(8-36).

In another preferred embodiment, Xaa at position 7 is a modified amino acid or is deleted, Xaa at position 8 is Thr, Ser, Gly, or Val, Xaa at position 18, 23 or 27 is Lys, and Xaa at position 26 and 34 is Arg, each of Xaa at positions 38-45 is deleted, and each of the other Xaa is the amino acid in native GLP-1(8-37).

In another preferred embodiment, Xaa at position 7 is a modified amino acid or is deleted, Xaa at position 8 is Thr, Ser, Gly, or Val, Xaa at position 18, 23 or 27 is Lys, and Xaa at position 26 and 34 is Arg, each of Xaa at positions 39-45 is deleted, and each of the other Xaa is the amino acid in native GLP-1(8-38).

Derivatives

The term "derivative" is defined as a modification of one or more amino acid residues of a peptide by chemical means, either with or without an enzyme, e.g., by alkylation, acylation, ester formation, or amide formation.

Lipophilic Substituents

To obtain a satisfactory protracted profile of action of the GLP-1 derivative, one or more lipophilic substituents are attached to a GLP-1 moiety. The lipophilic substituents preferably comprises 4-40 carbon atoms, in particular 8-25 carbon atoms. The lipophilic substituent may be attached to an amino group of the GLP-1 moiety by means of a carboxyl group of the lipophilic substituent which forms an amide bond with an amino group of the amino acid residue to which it is attached. Preferably, the GLP-1 derivatives have three, more preferably two, and most preferably one lipophilic substituent.

In a preferred embodiment, the present invention relates to a GLP-1 derivative wherein at least one amino acid residue of the parent peptide has a lipophilic substituent attached with the proviso that if only one lipophilic substituent is present and this substituent is attached to the N-terminal or to the C-terminal amino acid residue of the parent peptide then this substituent is an alkyl group or a group which has an ω-carboxylic acid group.

In another preferred embodiment, the present invention relates to a GLP-1 derivative having only one lipophilic substituent which substituent is an alkyl group or a group which has an ω-carboxylic acid group and is attached to the N-terminal amino acid residue of the parent peptide.

In another preferred embodiment, the present invention relates to a GLP-1 derivative having only one lipophilic substituent which substituent is an alkyl group or a group which has an ω-carboxylic acid group and is attached to the C-terminal amino acid residue of the parent peptide.

In another preferred embodiment, the present invention relates to a GLP-1 derivative having only one lipophilic substituent which substituent can be attached to any one amino acid residue which is not the N-terminal or C-terminal amino acid residue of the parent peptide.

In another preferred embodiment, the present invention relates to a GLP-1 derivative wherein two lipophilic substituents are present, one being attached to the N-terminal amino acid residue while the other is attached to the C-terminal amino acid residue.

In another preferred embodiment, the present invention relates to a GLP-1 derivative wherein two lipophilic substituents are present, one being attached to the N-terminal amino acid residue while the other is attached to an amino acid residue which is not N-terminal or the C-terminal amino acid residue.

In another preferred embodiment, the present invention relates to a GLP-1 derivative wherein two lipophilic substituents are present, one being attached to the C-terminal amino acid residue while the other is attached to an amino acid residue which is not the N-terminal or the C-terminal amino acid residue.

A lipophilic substituent may be attached to an amino acid residue in such a way that a carboxyl group of the lipophilic substituent forms an amide bond with an amino group of the amino acid residue. Alternatively, a lipophilic substituent may be attached to an amino acid residue in such a way that an amino group of the lipophilic substituent forms an amide bond with a carboxyl group of the amino acid residue.

In a further preferred embodiment, the present invention relates to a GLP-1 derivative wherein a lipophilic substituent is attached to the parent peptide by means of a spacer. For example, the lipophilic substituent may be attached to the GLP-1 moiety by means of a spacer in such a way that a carboxyl group of the spacer forms an amide bond with an amino group of the GLP-1 moiety.

In a most preferred embodiment, the lipophilic substituent is attached—optionally via a spacer—to the $\epsilon$-amino group of a Lys residue contained in the parent peptide.

In a preferred embodiment, the spacer is an $\alpha,\omega$-amino acid. Examples of suitable spacers are succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the $\epsilon$-amino group of Lys and the lipophilic substituent. In one preferred embodiment, such a further spacer is succinic acid which forms an amide bond with the $\epsilon$-amino group of Lys and with an amino group present in the lipophilic substituent. In another preferred embodiment such a further spacer is Glu or Asp which forms an amide bond with the $\epsilon$-amino group of Lys and another amide bond with a carboxyl group present in the lipophilic substituent, that is, the lipophilic substituent is a $N^\epsilon$-acylated lysine residue. Other preferred spacers are $N^\epsilon$-($\gamma$-L-glutamyl), $N^\epsilon$-($\beta$-L-aspargyl), $N^\epsilon$-glycyl, and $N^\epsilon$-($\alpha$-($\gamma$-aminobutanoyl).

In another preferred embodiment of the present invention, the lipophilic substituent has a group which can be negatively charged. One preferred such group is a carboxylic acid group.

In a further preferred embodiment, the lipophilic substituent comprises from 4 to 40 carbon atoms, more preferred from 8 to 25 carbon atoms.

In a further preferred embodiment, the lipophilic substituent is attached to the parent peptide by means of a spacer which is an unbranched alkane $\alpha,\omega$-dicarboxylic acid group having from 1 to 7 methylene groups, preferably two methylene groups which spacer forms a bridge between an amino group of the parent peptide and an amino group of the lipophilic substituent.

In a further preferred embodiment, the lipophilic substituent is attached to the parent peptide by means of a spacer which is an amino acid residue except Cys, or a dipeptide such as Gly-Lys. The expression "a dipeptide such as Gly-Lys" is defined herein as a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro.

In a further preferred embodiment, the lipophilic substituent is attached to the parent peptide by means of a spacer which is an amino acid residue except Cys, or is a dipeptide such as Gly-Lys and wherein a carboxyl group of the parent peptide forms an amide bond with an amino group of a Lys residue or a dipeptide containing a Lys residue, and the other amino group of the Lys residue or a dipeptide containing a Lys residue forms an amide bond with a carboxyl group of the lipophilic substituent.

In a further preferred embodiment, the lipophilic substituent is attached to the parent peptide by means of a spacer which is an amino acid residue except Cys, or is a dipeptide such as Gly-Lys and wherein an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

In a further preferred embodiment, the lipophilic substituent is attached to the parent peptide by means of a spacer which is an amino acid residue except Cys, or is a dipeptide such as Gly-Lys and wherein a carboxyl group of the parent peptide forms an amide bond with an amino group of the amino acid residue spacer or dipeptide spacer, and the carboxyl group of the amino acid residue spacer or dipeptide spacer forms an amide bond with an amino group of the lipophilic substituent.

In a further preferred embodiment, the lipophilic substituent is attached to the parent peptide by means of a spacer which is an amino acid residue except Cys, or is a dipeptide such as Gly-Lys, and wherein a carboxyl group of the parent peptide forms an amide bond with an amino group of a spacer which is Asp or Glu, or a dipeptide spacer containing an Asp or Glu residue, and a carboxyl group of the spacer forms an amide bond with an amino group of the lipophilic substituent.

In a further preferred embodiment, the lipophilic substituent is a partially or completely hydrogenated cyclopentanophenathrene skeleton.

In a further preferred embodiment, the lipophilic substituent is a straight-chain or branched alkyl group.

In a further preferred embodiment, the lipophilic substituent is the acyl group of a straight-chain or branched fatty acid.

In a further preferred embodiment, the lipophilic substituent is an acyl group of the formula $CH_3(CH_2)_nCO$—, wherein n is an integer from 4 to 38, preferably an integer from 4 to 24, more preferably $CH_3(CH_2)_6CO$—, $CH_3(CH_2)_8CO$—, $CH_3(CH_2)_{10}CO$—, $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— or $CH_3(CH_2)_{22}CO$—.

In a further preferred embodiment, the lipophilic substituent is an acyl group of a straight-chain or branched alkane $\alpha,\omega$-dicarboxylic acid.

In a further preferred embodiment, the lipophilic substituent is an acyl group of the formula $HOOC(CH_2)_mCO$—, wherein m is an integer from 4 to 38, preferably an integer from 4 to 24, more preferably $HOOC(CH_2)_{14}CO$—, $HOOC(CH_2)_{16}CO$—, $HOOC(CH_2)_{18}CO$—, $HOOC(CH_2)_{20}CO$— or $HOOC(CH_2)_{22}CO$—.

In a further preferred embodiment, the lipophilic substituent is a group of the formula $CH_3(CH_2)_p((CH_2)_qCOOH)$ CHNH—CO(CH$_2$)$_2$CO—, wherein p and q are integers and p+q is an integer of from 8 to 33, preferably from 12 to 28.

In a further preferred embodiment, the lipophilic substituent is a group of the formula CH$_3$(CH$_2$)$_r$CO—NHCH(COOH)(CH$_2$)$_2$CO—, wherein r is an integer of from 10 to 24.

In a further preferred embodiment, the lipophilic substituent is a group of the formula CH$_3$(CH$_2$)$_s$CO—NHCH((CH$_2$)$_2$COOH)CO—, wherein s is an integer of from 8 to 24.

In a further preferred embodiment, the lipophilic substituent is a group of the formula COOH(CH$_2$)$_t$CO— wherein t is an integer of from 8 to 24.

In a further preferred embodiment, the lipophilic substituent is a group of the formula —NHCH(COOH)(CH$_2$)$_4$NH—CO(CH$_2$)$_u$CH$_3$, wherein u is an integer of from 8 to 18.

In a further preferred embodiment, the lipophilic substituent is a group of the formula CH$_3$(CH$_2$)$_z$CO—NH—(CH$_2$)$_n$—CO, wherein n is an integer of from 8 to 24 and z is an integer of from 1 to 6.

In a further preferred embodiment, the lipophilic substituent is a group of the formula —NHCH(COOH)(CH$_2$)$_4$NH—COCH((CH$_2$)$_2$COOH)NH—CO(CH$_2$)$_w$CH$_3$, wherein w is an integer of from 10 to 16.

In a further preferred embodiment, the lipophilic substituent is a group of the formula —NHCH(COOH)(CH$_2$)$_4$NH—CO(CH$_2$)$_2$CH(COOH)NH—CO(CH$_2$)$_x$CH$_3$, wherein x is an integer of from 10 to 16.

In a further preferred embodiment, the lipophilic substituent is a group of the formula —NHCH(COOH)(CH$_2$)$_4$NH—CO(CH$_2$)$_2$CH(COOH)NHCO(CH$_2$)$_y$CH$_3$, wherein y is zero or an integer of from 1 to 22.

In a further preferred embodiment, the lipophilic substituent contains a group that can be negatively charged. Such a lipophilic substituent can for example be a substituent which has a carboxyl group.

Other Derivatives

The derivatives of GLP-1 analogues of the present invention may be in the form of one or more of (a) a C-1-6-ester, (b) an amide, C-1-6-alkylamide, or C-1-6-dialkylamide, and (c) a pharmaceutical salt. In a preferred embodiment, the derivatives of GLP-1 analogues are in the form of an acid addition salt or a carboxylate salt, most preferably in the form of an acid addition salt.

Preferred Derivatives of GLP-1 Analogues of the Present Invention

In a preferred embodiment, a parent peptide for a derivative of the invention is
Arg$^{26}$-GLP-1(7-37); Arg$^{34}$-GLP-1(7-37); Lys$^{36}$-GLP-1(7-37); Arg$^{26,34}$Lys$^{36}$-GLP-1(7-37); Arg$^{26,34}$Lys$^{38}$GLP-1(7-38); Arg$^{26,34}$Lys$^{39}$-GLP-1(7-39); Arg$^{26,34}$Lys$^{40}$-GLP-1(7-40); Arg$^{26}$Lys$^{36}$-GLP-1(7-37); Arg$^{34}$Lys$^{36}$-GLP-1(7-37); Arg$^{26}$Lys$^{39}$-GLP-1(7-39); Arg$^{34}$Lys$^{40}$-GLP-1(7-40); Arg$^{26,34}$Lys$^{36,39}$-GLP-1(7-39); Arg$^{26,34}$Lys$^{36,40}$-GLP-1(7-40); Gly$^8$Arg$^{26}$-GLP-1(7-37); Gly$^8$Arg$^{34}$-GLP-1(7-37); Gly$^8$Lys$^{36}$-GLP-1(7-37); Gly$^8$Arg$^{26,34}$Lys$^{36}$-GLP-1(7-37); Gly$^8$Arg$^{26,34}$Lys$^{39}$-GLP-1(7-39); Gly$^8$Arg$^{26,34}$Lys$^{40}$-GLP-1(7-40); Gly$^8$Arg$^{26}$Lys$^{36}$-GLP-1(7-37); Gly$^8$Arg$^{34}$Lys$^{36}$-GLP-1(7-37); Gly$^8$Arg$^{26}$Lys$^{39}$-GLP-1(7-39); Gly$^8$Arg$^{34}$Lys$^{40}$-GLP-1(7-40); Gly$^8$Arg$^{26,34}$Lys$^{36,39}$-GLP-1(7-39); or Gly$^8$Arg$^{26,34}$Lys$^{36,40}$-GLP-1(7-40).

In a further preferred embodiment, the parent peptide is
Arg$^{26,34}$Lys$^{38}$GLP-1(7-38); Arg$^{26,34}$Lys$^{18}$GLP-1(7-39); Arg$^{26,34}$Lys$^{40}$GLP-1(7-40); Arg$^{26,34}$Lys$^{41}$GLP-1(7-41); Arg$^{26,34}$Lys$^{42}$GLP-1(7-42); Arg$^{26,34}$Lys$^{43}$GLP-1(7-43); Arg$^{26,34}$Lys$^{44}$GLP-1(7-44); Arg$^{26,34}$Lys$^{45}$GLP-1(7-45); Arg$^{26,34}$Lys$^{38}$GLP-1(1-38); Arg$^{26,34}$Lys$^{39}$GLP-1(1-39); Arg$^{26,34}$Lys$^{40}$GLP-1(1-40); Arg$^{26,34}$Lys$^{41}$GLP-1(1-41); Arg$^{26,34}$Lys$^{42}$GLP-1(1-42); Arg$^{26,34}$Lys$^{43}$GLP-1(1-43); Arg$^{26,34}$Lys$^{44}$GLP-1(1-44); Arg$^{26,34}$Lys$^{45}$GLP-1(1-45); Arg$^{26,34}$Lys$^{38}$GLP-1(2-38); Arg$^{26,34}$Lys$^{18}$-GLP-1(2-39); Arg$^{26,34}$Lys$^{40}$GLP-1(2-40); Arg$^{26,34}$Lys$^{41}$GLP-1(2-41); Arg$^{26,34}$Lys$^{42}$GLP-1(2-42); Arg$^{26,34}$Lys$^{43}$GLP-1(2-43); Arg$^{26,34}$Lys$^{44}$GLP-1(2-44); Arg$^{26,34}$Lys$^{45}$GLP-1(2-45); Arg$^{26,34}$Lys$^{38}$GLP-1(3-38); Arg$^{26,34}$Lys$^{39}$GLP-1(3-39); Arg$^{26,34}$Lys$^{40}$GLP-1(3-40); Arg$^{26,34}$Lys$^{41}$GLP-1(3-41); Arg$^{26,34}$Lys$^{42}$GLP-1(3-42); Arg$^{26,34}$Lys$^{43}$GLP-1(3-43); Arg$^{26,34}$Lys$^{44}$GLP-1(3-44); Arg$^{26,34}$Lys$^{45}$GLP-1(3-45); Arg$^{26,34}$Lys$^{38}$GLP-1(4-38); Arg$^{26,34}$Lys$^{39}$GLP-1(4-39); Arg$^{26,34}$Lys$^{40}$GLP-1(4-40); Arg$^{26,34}$Lys$^{41}$GLP-1(4-41); Arg$^{26,34}$Lys$^{42}$GLP-1(4-42); Arg$^{26,34}$Lys$^{43}$GLP-1(4-43); Arg$^{26,34}$Lys$^{44}$GLP-1(4-44); Arg$^{26,34}$Lys$^{45}$GLP-1(4-45); Arg$^{26,34}$Lys$^{38}$GLP-1(5-38); Arg$^{26,34}$Lys$^{39}$GLP-1(5-39); Arg$^{26,34}$Lys$^{40}$GLP-1(5-40); Arg$^{26,34}$Lys$^{41}$GLP-1(5-41); Arg$^{26,34}$Lys$^{42}$GLP-1(5-42); Arg$^{26,34}$Lys$^{43}$GLP-1(5-43); Arg$^{26,34}$Lys$^{44}$GLP-1(5-44); Arg$^{26,34}$Lys$^{45}$GLP-1(5-45); Arg$^{26,34}$Lys$^{38}$GLP-1(6-38); Arg$^{26,34}$Lys$^{39}$GLP-1(6-39); Arg$^{26,34}$Lys$^{40}$GLP-1(6-40); Arg$^{26,34}$Lys$^{41}$GLP-1(6-41); Arg$^{26,34}$Lys$^{42}$GLP-1(6-42); Arg$^{26,34}$Lys$^{43}$GLP-1(6-43); Arg$^{26,34}$Lys$^{44}$GLP-1(6-44); Arg$^{26,34}$Lys$^{45}$GLP-1(6-45); Arg$^{26}$Lys$^{38}$GLP-1(1-38); Arg$^{34}$Lys$^{38}$GLP-1(1-38); Arg$^{26,34}$Lys$^{36,38}$GLP-1(1-38); Arg$^{26}$Lys$^{38}$GLP-1(7-38); Arg$^{34}$Lys$^{38}$GLP-1(7-38); Arg$^{26,34}$Lys$^{36,38}$GLP-1(7-38); Arg$^{26,34}$Lys$^{38}$GLP-1(7-38); Arg$^{26}$Lys$^{39}$GLP-1(1-39); Arg$^{34}$Lys$^{39}$GLP-1(1-39); Arg$^{26,34}$Lys$^{36,39}$GLP-1(1-39); Arg$^{26}$Lys$^{39}$GLP-1(7-39); Arg$^{34}$Lys$^{39}$GLP-1(7-39) or Arg$^{26,34}$Lys$^{36,39}$GLP-1(7-39).

In a further preferred embodiment, the present invention relates to a GLP-1 derivative wherein the parent peptide is Arg$^{26}$-GLP-1(7-37), Arg$^{34}$-GLP-1(7-37), Lys$^{36}$-GLP-1(7-37), Arg$^{26,34}$Lys$^{36}$-GLP-1(7-37), Arg$^{26}$Lys$^{36}$-GLP-1(7-37), Arg$^{34}$Lys$^{36}$-GLP-1(7-37), Gly$^8$Arg$^{26}$-GLP-1(7-37), Gly$^8$Arg$^{34}$-GLP-1(7-37), Gly$^8$Lys$^{36}$-GLP-1(7-37), Gly$^8$Arg$^{26,34}$Lys$^{36}$-GLP-1(7-37), Gly$^8$Arg$^{26}$Lys$^{36}$-GLP-1(7-37) or Gly$^8$Arg$^{34}$Lys$^{36}$-GLP-1(7-37).

In a further preferred embodiment, the present invention relates to a GLP-1 derivative wherein the parent peptide is Arg$^{26}$Lys$^{38}$-GLP-1(7-38), Arg$^{26,34}$Lys$^{38}$-GLP-1(7-38), Arg$^{26,34}$Lys$^{36,38}$-GLP-1(7-38), Gly$^8$Arg$^{26}$Lys$^{38}$-GLP-1(7-38) or Gly$^8$Arg$^{26,34}$Lys$^{36,38}$-GLP-1(7-38).

In a further preferred embodiment, the present invention relates to a GLP-1 derivative wherein the parent peptide is Arg$^{26}$Lys$^{39}$-GLP-1(7-39), Arg$^{26,34}$Lys$^{36,39}$-GLP-1(7-39), Gly$^8$Arg$^{26}$Lys$^{39}$-GLP-1(7-39) or Gly$^8$Arg$^{26,34}$Lys$^{36,39}$-GLP-1(7-39).

In a further preferred embodiment, the present invention relates to a GLP-1 derivative wherein the parent peptide is Arg$^{34}$Lys$^{40}$-GLP-1(7-40), Arg$^{26,34}$Lys$^{36,40}$-GLP-1(7-40), Gly$^8$Arg$^{34}$Lys$^{40}$-GLP-1(7-40) or Gly$^8$Arg$^{26,34}$Lys$^{36,40}$-GLP-1(7-40).

In a further preferred embodiment, the present invention relates to a GLP-1 derivative wherein the parent peptide is: Arg$^{26}$-GLP-1(7-36); Arg$^{34}$-GLP-1(7-36); Arg$^{26,34}$Lys$^{36}$-GLP-1(7-36); Arg$^{26}$-GLP-1(7-36)amide; Arg$^{34}$-GLP-1(7-36)amide; Arg$^{26,34}$Lys$^{36}$-GLP-1(7-36)amide; Arg$^{26}$-GLP-1(7-37); Arg$^{34}$-GLP-1(7-37); Arg$^{26,34}$Lys$^{36}$-GLP-1(7-37); Arg$^{26}$-GLP-1(7-38); Arg$^{34}$-GLP-1(7-38); Arg$^{26,34}$Lys$^{38}$GLP-1(7-38); Arg$^{26}$-GLP-1(7-39); Arg$^{34}$-GLP-1(7-39); Arg$^{26,34}$Lys$^{39}$-GLP-1(7-39);
Gly$^8$Arg$^{26}$-GLP-1(7-36); Gly$^8$Arg$^{34}$-GLP-1(7-36); Gly$^8$Arg$^{26,34}$Lys$^{36}$-GLP-1(7-36); Gly$^8$Arg$^{26}$-GLP-1(7-36)amide; Gly$^8$Arg$^{34}$-GLP-1(7-36)amide; Gly$^8$Arg$^{26,34}$Lys$^{36}$-GLP-1(7-36)amide; Gly$^8$Arg$^{26}$-GLP-1(7-37); Gly$^8$Arg$^{34}$-GLP-1(7-37); Gly$^8$Arg$^{26,34}$Lys$^{36}$-GLP-1(7-37); Gly$^8$Arg$^{26}$-GLP-1(7-38); Gly$^8$Arg$^{34}$-GLP-1(7-38); Gly$^8$ Arg$^{26,34}$Lys$^{38}$GLP-1(7-38); Gly$^8$Arg$^{26}$-GLP-1(7-39); Gly$^8$Arg$^{34}$-GLP-1(7-39); Gly$^8$Arg$^{26,34}$Lys$^{39}$-GLP-1(7-39); Val$^8$Arg$^{26}$-GLP-1(7-36); Val$^8$Arg$^{34}$-GLP-1(7-36); Val$^8$Arg$^{26,34}$Lys$^{36}$-GLP-1(7-36); Val$^8$Arg$^{26}$-GLP-1(7-36)amide; Val$^8$Arg$^{34}$-GLP-1(7-36)amide; Val$^8$Arg$^{26,34}$Lys$^{36}$-GLP-1(7-36)amide; Val$^8$Arg$^{26}$-GLP-1(7-37); Val$^8$Arg$^{34}$-GLP-1(7-37); Val$^8$Arg$^{26,34}$Lys$^{36}$-GLP-1(7-37); Val$^8$Arg$^{26}$-GLP-1(7-38); Val$^8$Arg$^{34}$-GLP-1(7-38); Val$^8$Arg$^{26,34}$Lys$^{38}$GLP-1(7-38); Val$^8$Arg$^{26}$-GLP-1(7-39); Val$^8$Arg$^{34}$-GLP-1(7-39); Val$^8$Arg$^{26,34}$Lys$^{39}$-GLP-1(7-39); Ser$^8$Arg$^{26}$-GLP-1(7-36); Ser$^8$Arg$^{34}$-GLP-1(7-36); Ser$^8$Arg$^{26,34}$Lys$^{36}$-GLP-1(7-36); Ser$^8$Arg$^{26}$-GLP-1(7-36)amide; Ser$^8$Arg$^{34}$-GLP-1(7-36)amide; Ser$^8$Arg$^{26,34}$Lys$^{36}$-GLP-1(7-36)amide; Ser$^8$Arg$^{26}$-GLP-1(7-37); Ser$^8$Arg$^{34}$-GLP-1(7-37); Ser$^8$Arg$^{26,34}$Lys$^{36}$-GLP-1(7-37); Ser$^8$Arg$^{26}$-GLP-1(7-38); Ser$^8$Arg$^{34}$-GLP-1(7-38); Ser$^8$Arg$^{26,34}$Lys$^{38}$GLP-1(7-38); Ser$^8$Arg$^{26}$-GLP-1(7-39); Ser$^8$Arg$^{34}$-GLP-1(7-39); Ser$^8$Arg$^{26,34}$Lys$^{39}$-GLP-1(7-39); Thr$^8$Arg$^{26}$-GLP-1(7-36); Thr$^8$Arg$^{34}$-GLP-1(7-36); Thr$^8$Arg$^{26,34}$Lys$^{36}$-GLP-1(7-36); Thr$^8$Arg$^{26}$-GLP-1(7-36)amide; Thr$^8$Arg$^{34}$-GLP-1(7-36)amide; Thr$^8$Arg$^{26,34}$Lys$^{36}$-GLP-1(7-36)amide; Thr$^8$Arg$^{26}$-GLP-1(7-37); Thr$^8$Arg$^{34}$-GLP-1(7-37); Thr$^8$Arg$^{26,34}$Lys$^{36}$-GLP-1(7-37); Thr$^8$Arg$^{26}$-GLP-1(7-38); Thr$^8$Arg$^{34}$-GLP-1(7-38); Thr$^8$Arg$^{26,34}$Lys$^{38}$GLP-1(7-38); Thr$^8$Arg$^{26}$-GLP-1(7-39); Thr$^8$Arg$^{34}$-GLP-1(7-39); Thr$^8$Arg$^{26,34}$Lys$^{39}$-GLP-1(7-39); Val$^8$Glu$^{35}$Arg$^{26,34}$Lys$^{36}$-GLP-1(7-36); Val$^8$Glu$^{35}$Arg$^{26,34}$Lys$^{36}$-GLP-1(7-36)amide; Val$^8$Glu$^{36}$Arg$^{26,34}$Lys$^{37}$GLP-1(7-37); Val$^8$Glu$^{37}$Arg$^{26,34}$Lys$^{38}$GLP-1(7-38); Val$^8$Glu$^{38}$Arg$^{26,34}$Lys$^{39}$-GLP-1(7-39); Val$^8$Glu$^{35}$Arg$^{26,34}$Lys$^{36}$-GLP-1(7-36); Val$^8$Glu$^{35}$Arg$^{26,34}$Lys$^{36}$-GLP-1(7-36)amide; Val$^8$Glu$^{36}$Arg$^{26,34}$Lys$^{37}$GLP-1(7-37); Val$^8$Glu$^{37}$Arg$^{26,34}$Lys$^{38}$GLP-1(7-38); Val$^8$Glu$^{38}$Arg$^{26,34}$Lys$^{39}$-GLP-1(7-39); Val$^8$Asp$^{35}$Arg$^{26,34}$Lys$^{36}$-GLP-1(7-36); Val$^8$Asp$^{35}$Arg$^{26,34}$Lys$^{36}$-GLP-1(7-36)amide; Val$^8$Asp$^{36}$Arg$^{26,34}$Lys$^{37}$GLP-1(7-37); Val$^8$Asp$^{37}$Arg$^{26,34}$Lys$^{38}$GLP-1(7-38); Val$^8$Asp$^{38}$Arg$^{26,34}$Lys$^{39}$-GLP-1(7-39); Val$^8$Asp$^{35}$Arg$^{26,34}$Lys$^{36}$-GLP-1(7-36); Val$^8$Asp$^{35}$Arg$^{26,34}$Lys$^{36}$-GLP-1(7-36)amide; Val$^8$Asp$^{36}$Arg$^{26,34}$Lys$^{37}$GLP-1(7-37); Val$^8$Asp$^{37}$Arg$^{26,34}$Lys$^{38}$GLP-1(7-37); Val$^8$Asp$^{38}$Arg$^{26,34}$Lys$^{39}$-GLP-1(7-39); Ser$^8$Glu$^{35}$Arg$^{26,34}$Lys$^{36}$-GLP-1(7-36); Ser$^8$Glu$^{35}$Arg$^{26,34}$Lys$^{36}$-GLP-1(7-36)amide; Ser$^8$Glu$^{36}$Arg$^{26,34}$Lys$^{37}$GLP-1(7-37); Ser$^8$Glu$^{37}$Arg$^{26,34}$Lys$^{38}$GLP-1(7-38); Ser$^8$Glu$^{38}$Arg$^{26,34}$Lys$^{39}$-GLP-1(7-39); Ser$^8$Glu$^{35}$Arg$^{26,34}$Lys$^{36}$-GLP-1(7-36); Ser$^8$Glu$^{35}$Arg$^{26,34}$Lys$^{36}$-GLP-1(7-36)amide; Ser$^8$Glu$^{36}$Arg$^{26,34}$Lys$^{37}$GLP-1(7-37); Ser$^8$Glu$^{37}$Arg$^{26,34}$Lys$^{38}$GLP-1(7-38); Ser$^8$Glu$^{38}$Arg$^{26,34}$Lys$^{39}$-GLP-1(7-39); Ser$^8$Asp$^{35}$Arg$^{26,34}$Lys$^{36}$-GLP-1(7-36); Ser$^8$Asp$^{35}$Arg$^{26,34}$Lys$^{36}$-GLP-1(7-36)amide; Ser$^8$Asp$^{36}$Arg$^{26,34}$Lys$^{37}$GLP-1(7-37); Ser$^8$Asp$^{37}$Arg$^{26,34}$Lys$^{38}$GLP-1(7-38); Ser$^8$Asp$^{38}$Arg$^{26,34}$Lys$^{39}$-GLP-1(7-39); Ser$^8$Asp$^{35}$Arg$^{26,34}$Lys$^{36}$-GLP-1(7-36); Ser$^8$Asp$^{35}$Arg$^{26,34}$Lys$^{36}$-GLP-1(7-36)amide; Ser$^8$Asp$^{36}$Arg$^{26,34}$Lys$^{37}$GLP-1(7-37); Ser$^8$Asp$^{37}$Arg$^{26,34}$Lys$^{38}$GLP-1(7-38); Ser$^8$Asp$^{38}$Arg$^{26,34}$Lys$^{39}$-GLP-1(7-39); Thr$^8$Glu$^{35}$Arg$^{26,34}$Lys$^{36}$-GLP-1(7-36); Thr$^8$Glu$^{35}$Arg$^{26,34}$Lys$^{36}$-GLP-1(7-36)amide; Thr$^8$Glu$^{36}$Arg$^{26,34}$Lys$^{37}$GLP-1(7-37); Thr$^8$Glu$^{37}$Arg$^{26,34}$Lys$^{38}$GLP-1(7-38); Thr$^8$Glu$^{38}$Arg$^{26,34}$Lys$^{39}$-GLP-1(7-39); Thr$^8$Glu$^{35}$Arg$^{26,34}$Lys$^{36}$-GLP-1(7-36); Thr$^8$Glu$^{35}$Arg$^{26,34}$Lys$^{36}$-GLP-1(7-36)amide; Thr$^8$Glu$^{36}$Arg$^{26,34}$Lys$^{37}$GLP-1(7-37); Thr$^8$Glu$^{37}$Arg$^{26,34}$Lys$^{38}$GLP-1(7-38); Thr$^8$Glu$^{38}$Arg$^{26,34}$Lys$^{39}$-GLP-1(7-39); Thr$^8$Asp$^{35}$Arg$^{26,34}$Lys$^{36}$-GLP-1(7-36); Thr$^8$Asp$^{35}$Arg$^{26,34}$Lys$^{36}$-GLP-1(7-36)amide; Thr$^8$Asp$^{36}$Arg$^{26,34}$Lys$^{37}$GLP-1(7-37); Thr$^8$Asp$^{37}$Arg$^{26,34}$Lys$^{38}$GLP-1(7-38); Thr$^8$Asp$^{38}$Arg$^{26,34}$Lys$^{39}$-GLP-1(7-39); Thr$^8$Asp$^{35}$Arg$^{26,34}$Lys$^{36}$-GLP-1(7-36); Thr$^8$Asp$^{35}$Arg$^{26,34}$Lys$^{36}$-GLP-1(7-36)amide; Thr$^8$Asp$^{36}$Arg$^{26,34}$Lys$^{37}$GLP-1(7-37); Thr$^8$Asp$^{37}$Arg$^{26,34}$Lys$^{38}$GLP-1(7-38); Thr$^8$Asp$^{38}$Arg$^{26,34}$Lys$^{39}$-GLP-1(7-39); Gly$^8$Glu$^{35}$Arg$^{26,34}$Lys$^{36}$-GLP-1(7-36); Gly$^8$Glu$^{35}$Arg$^{26,34}$Lys$^{36}$-GLP-1(7-36)amide; Gly$^8$Glu$^{36}$Arg$^{26,34}$Lys$^{37}$GLP-1(7-37); Gly$^8$Glu$^{37}$Arg$^{26,34}$Lys$^{38}$GLP-1(7-38); Gly$^8$Glu$^{38}$Arg$^{26,34}$Lys$^{39}$-GLP-1(7-39); Gly$^8$Glu$^{35}$Arg$^{26,34}$Lys$^{36}$ GLP-1(7-36); Gly$^8$Glu$^{35}$Arg$^{26,34}$Lys$^{36}$-GLP-1(7-36)amide; Gly$^8$Glu$^{36}$Arg$^{26,34}$Lys$^{37}$GLP-1(7-37); Gly$^8$Glu$^{37}$Arg$^{26,34}$Lys$^{38}$GLP-1(7-38); Gly$^8$Glu$^{38}$Arg$^{26,34}$Lys$^{39}$-GLP-1(7-39); Gly$^8$Asp$^{35}$Arg$^{26,34}$Lys$^{36}$-GLP-1(7-36); Gly$^8$Asp$^{35}$Arg$^{26,34}$Lys$^{36}$-GLP-1(7-36)amide; Gly$^8$Asp$^{36}$Arg$^{26,34}$Lys$^{37}$GLP-1(7-37); Gly$^8$Asp$^{37}$Arg$^{26,34}$Lys$^{38}$GLP-1(7-38); Gly$^8$Asp$^{38}$Arg$^{26,34}$Lys$^{39}$-GLP-1(7-39); Gly$^8$Asp$^{35}$Arg$^{26,34}$Lys$^{36}$-GLP-1(7-36); Gly$^8$Asp$^{35}$Arg$^{26,34}$Lys$^{36}$-GLP-1(7-36)amide; Gly$^8$Asp$^{36}$Arg$^{26,34}$Lys$^{37}$GLP-1(7-37); Gly$^8$Asp$^{37}$Arg$^{26,34}$Lys$^{38}$GLP-1(7-38); Gly$^8$Asp$^{38}$Arg$^{26,34}$Lys$^{39}$-GLP-1(7-39); Arg$^{26,34}$Lys$^{18}$-GLP-1(7-36); Arg$^{26,34}$Lys$^{18}$-GLP-1(7-36)amide; Arg$^{26,34}$Lys$^{18}$-GLP-1(7-37); Arg$^{26,34}$Lys$^{18}$-GLP-1(7-38); Gly$^8$Asp$^{19}$Arg$^{26,34}$Lys$^{18}$-GLP-1(7-36); Gly$^8$Asp$^{17}$Arg$^{26,34}$Lys$^{18}$-GLP-1(7-36); Gly$^8$Asp$^{19}$Arg$^{26,34}$Lys$^{18}$-GLP-1(7-36)amide; Gly$^8$Asp$^{17}$Arg$^{26,34}$Lys$^{18}$-GLP-1(7-36)amide; Gly$^8$Asp$^{19}$Arg$^{26,34}$Lys$^{18}$-GLP-1(7-37); Gly$^8$Asp$^{19}$Arg$^{26,34}$Lys$^{18}$-GLP-1(7-38); Gly$^8$Asp$^{17}$Arg$^{26,34}$Lys$^{18}$-GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$-GLP-1(7-37); Arg$^{26,34}$Lys$^{23}$-GLP-1(7-38); Gly$^8$Asp$^{24}$Arg$^{26,34}$Lys$^{23}$-GLP-1(7-36); Gly$^8$Asp$^{22}$Arg$^{26,34}$Lys$^{23}$-GLP-1(7-36); Gly$^8$Asp$^{24}$Arg$^{26,34}$Lys$^{23}$ GLP-1(7-36)amide; Gly$^8$Asp$^{22}$Arg$^{26,34}$Lys$^{23}$-GLP-1(7-36)amide; Gly$^8$Asp$^{24}$Arg$^{26,34}$Lys$^{23}$GLP-1(7-37); Gly$^8$Asp$^{24}$Arg$^{26,34}$Lys$^{23}$GLP-1(7-38); Gly$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$-GLP-1(7-37); Arg$^{26,34}$Lys$^{27}$GLP-1(7-38); Gly$^8$Asp$^{28}$Arg$^{26,34}$Lys$^{27}$-GLP-1(7-36); Gly$^8$Asp$^{26}$Arg$^{26,34}$Lys$^{27}$-GLP-1(7-36); Gly$^8$Asp$^{28}$Arg$^{26,34}$Lys$^{27}$-GLP-1(7-36)amide; Gly$^8$Asp$^{26}$Arg$^{26,34}$Lys$^{27}$-GLP-1(7-36)amide; Gly$^8$Asp$^{28}$Arg$^{26,34}$Lys$^{27}$-GLP-1(7-37); Gly$^8$Asp$^{28}$Arg$^{26,34}$Lys$^{27}$GLP-1(7-38); Gly$^8$Asp$^{26}$Arg$^{26,34}$Lys$^{27}$GLP-1(7-38); Arg$^{26,34}$Lys$^{18}$-GLP-1(7-36); Arg$^{26,34}$Lys$^{18}$-GLP-1(7-36)amide; Arg$^{26,34}$Lys$^{18}$-GLP-1(7-37); Arg$^{26,34}$Lys$^{18}$-GLP-1(7-38); Val$^8$Asp$^{19}$Arg$^{26,34}$Lys$^{18}$-GLP-1(7-36); Val$^8$Asp$^{17}$Arg$^{26,34}$Lys$^{18}$-GLP-1(7-36); Val$^8$Asp$^{19}$Arg$^{26,34}$Lys$^{18}$-GLP-1(7-36)amide; Val$^8$Asp$^{17}$Arg$^{26,34}$Lys$^{18}$-GLP-1(7-36)amide; Val$^8$Asp$^{19}$Arg$^{26,34}$Lys$^{18}$GLP-1(7-37); Val$^8$Asp$^{19}$Arg$^{26,34}$Lys$^{18}$-GLP-1(7-38); Val$^8$Asp$^{17}$Arg$^{26,34}$Lys$^{18}$GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Val$^8$Asp$^{24}$Arg$^{26,34}$Lys$^{23}$-GLP-1(7-36); Val$^8$Asp$^{22}$Arg$^{26,34}$Lys$^{23}$-GLP-1(7-36); Val$^8$Asp$^{24}$Arg$^{26,34}$Lys$^{23}$ GLP-1(7-36)amide; Val$^8$Asp$^{22}$Arg$^{26,34}$Lys$^{23}$-GLP-1(7-36)amide; Val$^8$Asp$^{24}$Arg$^{26,34}$Lys$^{23}$GLP-1(7-37); Val$^8$Asp$^{24}$Arg$^{26,34}$Lys$^{23}$GLP-1(7-38); Val$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Val$^8$Asp$^{28}$Arg$^{26,34}$Lys$^{27}$-GLP-1(7-36); Val$^8$Asp$^{26}$ Arg$^{26,34}$Lys$^{27}$-GLP-1(7-36); Val$^8$Asp$^{28}$Arg$^{26,34}$Lys$^{27}$ GLP-1 (7-36)amide; Val$^8$Asp$^{26}$Arg$^{26,34}$Lys$^{27}$-GLP-1(7-36)amide; Val$^8$Asp$^{28}$Arg$^{26,34}$Lys$^{27}$GLP-1(7-37); Val$^8$Asp$^{28}$ Arg$^{26,34}$Lys$^{27}$GLP-1(7-38); Val$^8$Asp$^{26}$Arg$^{26,34}$Lys$^{27}$GLP-1(7-38);

Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Ser$^8$Asp$^{19}$Arg$^{26,34}$Lys$^{18}$-GLP-1(7-36); Ser$^8$Asp$^{17}$Arg$^{26,34}$Lys$^{18}$-GLP-1(7-36); Ser$^8$Asp$^{19}$Arg$^{26,34}$Lys$^{18}$-GLP-1(7-36)amide; Ser$^8$Asp$^{17}$Arg$^{26,34}$Lys$^{18}$-GLP-1(7-36)amide; Ser$^8$Asp$^{19}$Arg$^{26,34}$Lys$^{18}$GLP-1(7-37); Ser$^8$Asp$^{19}$Arg$^{26,34}$Lys$^{18}$GLP-1(7-38); Ser$^8$Asp$^{17}$Arg$^{26,34}$Lys$^{18}$GLP-1(7-38);

Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Ser$^8$Asp$^{24}$Arg$^{26,34}$Lys$^{23}$-GLP-1(7-36); Ser$^8$Asp$^{22}$Arg$^{26,34}$Lys$^{23}$-GLP-1(7-36); Ser$^8$Asp$^{24}$Arg$^{26,34}$Lys$^{23}$ GLP-1(7-36)amide; Ser$^8$Asp$^{22}$Arg$^{26,34}$Lys$^{23}$-GLP-1(7-36)amide; Ser$^8$Asp$^{24}$Arg$^{26,34}$Lys$^{23}$GLP-1(7-37); Ser$^8$Asp$^{24}$Arg$^{26,34}$Lys$^{23}$GLP-1(7-38); Ser$^8$Asp$^{22}$Arg$^{26,34}$Lys$^{23}$GLP-1(7-38);

Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Ser$^8$Asp$^{28}$Arg$^{26,34}$Lys$^{27}$-GLP-1(7-36); Ser$^8$Asp$^{26}$Arg$^{26,34}$Lys$^{27}$-GLP-1(7-36); Ser$^8$Asp$^{28}$Arg$^{26,34}$Lys$^{27}$-GLP-1(7-36)amide; Ser$^8$Asp$^{26}$Arg$^{26,34}$Lys$^{27}$-GLP-1(7-36)amide; Ser$^8$Asp$^{28}$Arg$^{26,34}$Lys$^{27}$GLP-1(7-37); Ser$^8$Asp$^{28}$Arg$^{26,34}$Lys$^{27}$GLP-1(7-38); Ser$^8$Asp$^{26}$Arg$^{26,34}$Lys$^{27}$GLP-1(7-38);

Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Thr$^8$Asp$^{19}$Arg$^{26,34}$Lys$^{18}$-GLP-1(7-36); Thr$^8$Asp$^{17}$Arg$^{26,34}$Lys$^{18}$-GLP-1(7-36); Thr$^8$Asp$^{19}$Arg$^{26,34}$Lys$^{18}$-GLP-1(7-36)amide; Thr$^8$Asp$^{17}$Arg$^{26,34}$Lys$^{18}$-GLP-1(7-36)amide; Thr$^8$Asp$^{19}$Arg$^{26,34}$Lys$^{18}$GLP-1(7-37); Thr$^8$Asp$^{19}$Arg$^{26,34}$Lys$^{18}$GLP-1(7-38); Thr$^8$Asp$^{17}$Arg$^{26,34}$Lys$^{18}$GLP-1(7-38);

Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Thr$^8$Asp$^{24}$Arg$^{26,34}$Lys$^{23}$-GLP-1(7-36); Thr$^8$Asp$^{22}$Arg$^{26,34}$Lys$^{23}$-GLP-1(7-36); Thr$^8$Asp$^{24}$Arg$^{26,34}$Lys$^{23}$-GLP-1(7-36)amide; Thr$^8$Asp$^{22}$Arg$^{26,34}$Lys$^{23}$-GLP-1(7-36)amide; Thr$^8$Asp$^{24}$Arg$^{26,34}$Lys$^{23}$GLP-1(7-37); Thr$^8$Asp$^{22}$Arg$^{26,34}$Lys$^{23}$GLP-1(7-38);

Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Thr$^8$Asp$^{28}$Arg$^{26,34}$Lys$^{27}$-GLP-1(7-36); Thr$^8$Asp$^{26}$Arg$^{26,34}$Lys$^{27}$-GLP-1(7-36); Thr$^8$Asp$^{28}$Arg$^{26,34}$Lys$^{27}$-GLP-1(7-36)amide; Thr$^8$Asp$^{26}$Arg$^{26,34}$Lys$^{27}$-GLP-1(7-36)amide; Thr$^8$Asp$^{28}$Arg$^{26,34}$Lys$^{27}$GLP-1(7-37); Thr$^8$Asp$^{28}$Arg$^{26,34}$Lys$^{27}$GLP-1(7-38); or Thr$^8$Asp$^{26}$Arg$^{26,34}$Lys$^{27}$GLP-1(7-38).

In a further preferred embodiment, the present invention relates to a GLP-1 derivative wherein the parent peptide is:
Arg$^{26}$Lys$^{36}$-GLP-1(7-36); Arg$^{34}$Lys$^{36}$-GLP-1(7-36); Arg$^{26}$Lys$^{36}$-GLP-1(7-37); Arg$^{34}$Lys$^{36}$-GLP-1(7-37); Arg$^{26}$Lys$^{37}$-GLP-1(7-37); Arg$^{34}$Lys$^{37}$-GLP-1(7-37); Arg$^{26}$Lys$^{39}$-GLP-1(7-39); Arg$^{34}$Lys$^{39}$-GLP-1(7-39); Arg$^{26,34}$Lys$^{36,39}$-GLP-1(7-39);
Arg$^{26}$Lys$^{18}$-GLP-1(7-36); Arg$^{34}$Lys$^{18}$-GLP-1(7-36); Arg$^{26}$Lys$^{18}$GLP-1(7-37); Arg$^{34}$Lys$^{18}$GLP-1(7-37); Arg$^{26}$Lys$^{18}$GLP-1(7-38); Arg$^{34}$Lys$^{18}$GLP-1(7-38); Arg$^{26}$Lys$^{18}$GLP-1(7-39); Arg$^{34}$Lys$^{18}$GLP-1(7-39);
Arg$^{26}$Lys$^{23}$-GLP-1(7-36); Arg$^{34}$Lys$^{23}$-GLP-1(7-36); Arg$^{26}$Lys$^{23}$GLP-1(7-37); Arg$^{34}$Lys$^{23}$GLP-1(7-37); Arg$^{26}$Lys$^{23}$GLP-1(7-38); Arg$^{34}$Lys$^{23}$GLP-1(7-38); Arg$^{26}$Lys$^{23}$GLP-1(7-39); Arg$^{34}$Lys$^{23}$GLP-1(7-39);
Arg$^{26}$Lys$^{27}$-GLP-1(7-36); Arg$^{34}$Lys$^{27}$-GLP-1(7-36); Arg$^{26}$Lys$^{27}$GLP-1(7-37); Arg$^{34}$Lys$^{27}$GLP-1(7-37); Arg$^{26}$Lys$^{27}$GLP-1(7-38); Arg$^{34}$Lys$^{27}$GLP-1(7-38); Arg$^{26}$Lys$^{27}$GLP-1(7-39); Arg$^{34}$Lys$^{27}$GLP-1(7-39);
Arg$^{26,34}$Lys$^{18,36}$-GLP-1(7-36); Arg$^{26,34}$Lys$^{18}$GLP-1(7-37); Arg$^{26,34}$Lys$^{18,37}$GLP-1(7-37); Arg$^{26,34}$Lys$^{18,38}$-GLP-1(7-38); Arg$^{26,34}$Lys$^{18,39}$GLP-1(7-39); Arg$^{26,34}$Lys$^{23,36}$GLP-1(7-36); Arg$^{26,34}$Lys$^{23}$GLP-1(7-37); Arg$^{26,34}$Lys$^{23,37}$GLP-1(7-37); Arg$^{26,34}$Lys$^{23,38}$GLP-1(7-38); Arg$^{26,34}$Lys$^{23,39}$GLP-1(7-39); Arg$^{26,34}$Lys$^{27,36}$-GLP-1(7-36); Arg$^{26,34}$Lys$^{27}$GLP-1(7-37); Arg$^{26,34}$Lys$^{27,37}$-GLP-1(7-37); Arg$^{26,34}$Lys$^{27,38}$-GLP-1(7-38); Arg$^{26,34}$Lys$^{27,39}$GLP-1(7-39);

Gly$^8$GLP-1(7-36); Gly$^8$GLP-1(7-37); Gly$^8$GLP-1(7-38); Gly$^8$GLP-1(7-39);
Gly$^8$Arg$^{26}$Lys$^{36}$-GLP-1(7-36); Gly$^8$Arg$^{34}$Lys$^{36}$GLP-1(7-3); Gly$^8$Arg$^{26}$Lys$^{36}$-GLP-1(7-37); Gly$^8$Arg$^{34}$Lys$^{36}$-GLP-1(7-37); Gly$^8$Arg$^{26}$Lys$^{37}$-GLP-1(7-37); Gly$^8$Arg$^{34}$Lys$^{37}$-GLP-1(7-37); Gly$^8$Arg$^{26}$Lys$^{39}$-GLP-1(7-39);
Gly$^8$Arg$^{34}$Lys$^{39}$-GLP-1(7-39); Gly$^8$Arg$^{26,34}$Lys$^{36,39}$-GLP-1(7-39);
Gly$^8$Arg$^{26}$Lys$^{18}$-GLP-1(7-36); Gly$^8$Arg$^{34}$Lys$^{18\text{-}GLP\text{-}1}$(7-36); Gly$^8$Arg$^{26}$Lys$^{18}$GLP-1(7-37); Gly$^8$Arg$^{34}$Lys$^{18}$GLP-1(7-37); Gly$^8$Arg$^{26}$Lys$^{18}$GLP-1(7-38); Gly$^8$Arg$^{34}$Lys$^{18}$GLP-1(7-38); Gly$^8$Arg$^{26}$Lys$^{18}$GLP-1(7-39); Gly$^8$Arg$^{34}$Lys$^{18}$GLP-1(7-39);
Gly$^8$Arg$^{26}$Lys$^{23}$-GLP-1(7-36); Gly$^8$Arg$^{34}$Lys$^{23}$-GLP-1(7-36); Gly$^8$Arg$^{26}$Lys$^{23}$GLP-1(7-37); Gly$^8$Arg$^{34}$Lys$^{23}$GLP-1(7-37); Gly$^8$Arg$^{26}$Lys$^{23}$GLP-1(7-38); Gly$^8$Arg$^{34}$Lys$^{23}$GLP-1(7-38); Gly$^8$Arg$^{26}$Lys$^{23}$GLP-1(7-39); Gly$^8$Arg$^{34}$Lys$^{23}$GLP-1(7-39);
Gly$^8$Arg$^{26}$Lys$^{27}$-GLP-1(7-36); Gly$^8$Arg$^{34}$Lys$^{27}$-GLP-1(7-36); Gly$^8$Arg$^{26}$Lys$^{27}$GLP-1(7-37); Gly$^8$Arg$^{34}$Lys$^{27}$GLP-1(7-37); Gly$^8$Arg$^{26}$Lys$^{27}$GLP-1(7-38); Gly$^8$Arg$^{34}$Lys$^{27}$GLP-1(7-38); Gly$^8$Arg$^{26}$Lys$^{27}$GLP-1(7-39); Gly$^8$Arg$^{34}$Lys$^{27}$GLP-1(7-39);
Gly$^8$Arg$^{26,34}$Lys$^{18,36}$-GLP-1(7-36); Gly$^8$Arg$^{26,34}$Lys$^{18}$GLP-1(7-37); Gly$^8$Arg$^{26,34}$Lys$^{18,37}$GLP-1(7-37); Gly$^8$Arg$^{26,34}$Lys$^{18,38}$GLP-1(7-38); Gly$^8$Arg$^{26,34}$Lys$^{18,39}$GLP-1(7-39); Gly$^8$Arg$^{26,34}$Lys$^{23,36}$-GLP-1(7-36); Gly$^8$Arg$^{26,34}$Lys$^{23}$GLP-1(7-37); Gly$^8$Arg$^{26,34}$Lys$^{23,37}$GLP-1(7-37); Gly$^8$Arg$^{26,34}$Lys$^{23,38}$GLP-1(7-38); Gly$^8$Arg$^{26,34}$Lys$^{23,39}$GLP-1(7-39); Gly$^8$Arg$^{26,34}$Lys$^{27,36}$-GLP-1(7-36); Gly$^8$Arg$^{26,34}$Lys$^{27}$GLP-1(7-37); Gly$^8$Arg$^{26,34}$Lys$^{27,37}$GLP-1(7-37); Gly$^8$Arg$^{26,34}$Lys$^{27,38}$GLP-1(7-38); Gly$^8$Arg$^{26,34}$Lys$^{27,39}$GLP-1(7-39);

Val$^8$GLP-1(7-36); Val$^8$GLP-1(7-37); Val$^8$GLP-1(7-38); Val$^8$GLP-1(7-39);
Val$^8$Arg$^{26}$Lys$^{36}$-GLP-1(7-36); Val$^8$Arg$^{34}$Lys$^{36}$-GLP-1(7-36); Val$^8$Arg$^{26}$Lys$^{36}$-GLP-1(7-37); Val$^8$Arg$^{34}$Lys$^{36}$ GLP-1(7-37); Val$^8$Arg$^{26}$Lys$^{37}$-GLP-1(7-37); Val$^8$Arg$^{34}$Lys$^{37}$-GLP-1(7-37); Val$^8$Arg$^{26}$Lys$^{39}$-GLP-1(7-39); Val$^8$Arg$^{34}$Lys$^{39}$-GLP-1(7-39); Val$^8$Arg$^{26,34}$Lys$^{36,39}$-GLP-1(7-39);
Val$^8$Arg$^{26}$Lys$^{18}$-GLP-1(7-36); Val$^8$Arg$^{34}$Lys$^{18}$-GLP-1(7-36); Val$^8$Arg$^{26}$Lys$^{18}$-GLP-1(7-37); Val$^8$Arg$^{34}$Lys$^{18}$-GLP-1(7-37); Val$^8$Arg$^{26}$Lys$^{18}$-GLP-1(7-38); Val$^8$Arg$^{34}$Lys$^{18}$-GLP-1(7-38); Val$^8$Arg$^{26}$Lys$^{18}$-GLP-1(7-39); Val$^8$Arg$^{34}$Lys$^{18}$-GLP-1(7-39);
Val$^8$Arg$^{26}$Lys$^{23}$-GLP-1(7-36); Val$^8$Arg$^{34}$Lys$^{23}$-GLP-1(7-36); Val$^8$Arg$^{26}$Lys$^{23}$-GLP-1(7-37); Val$^8$Arg$^{34}$Lys$^{23}$-GLP-1(7-37); Val$^8$Arg$^{26}$Lys$^{23}$-GLP-1(7-38); Val$^8$Arg$^{34}$Lys$^{23}$-GLP-1(7-38); Val$^8$Arg$^{26}$Lys$^{23}$-GLP-1(7-39); Val$^8$Arg$^{34}$Lys$^{23}$-GLP-1(7-39);
Val$^8$Arg$^{26}$Lys$^{27}$-GLP-1(7-36); Val$^8$Arg$^{34}$Lys$^{27}$-GLP-1(7-36); Val$^8$Arg$^{26}$Lys$^{27}$-GLP-1(7-37); Val$^8$Arg$^{34}$Lys$^{27}$-GLP-1(7-

37); Val$^8$Arg$^{26}$Lys$^{27}$GLP-1(7-38); Val$^8$Arg$^{34}$Lys$^{27}$GLP-1(7-38); Val$^8$Arg$^{26}$Lys$^{27}$GLP-1(7-39); Val$^8$Arg$^{34}$Lys$^{27}$GLP-1(7-39); Val$^8$Arg$^{26,34}$Lys$^{18,36}$-GLP-1(7-36); Val$^8$Arg$^{26,34}$Lys$^{18}$GLP-1(7-37); Val$^8$Arg$^{26,34}$Lys$^{18,37}$GLP-1(7-37); Val$^8$Arg$^{26,34}$Lys$^{18,38}$GLP-1(7-38); Val$^8$Arg$^{26,34}$Lys$^{18,39}$GLP-1(7-39); Val$^8$Arg$^{26,34}$Lys$^{23,36}$-GLP-1(7-36); Val$^8$Arg$^{26,34}$Lys$^{23}$GLP-1(7-37); Val$^8$Arg$^{26,34}$Lys$^{23,37}$GLP-1(7-37); Val$^8$Arg$^{26,34}$Lys$^{23,38}$GLP-1(7-38); Val$^8$Arg$^{26,34}$Lys$^{23,39}$GLP-1(7-39); Val$^8$Arg$^{26,34}$Lys$^{27,36}$-GLP-1(7-36); Val$^8$Arg$^{26,34}$Lys$^{27}$GLP-1(7-37); Val$^8$Arg$^{26,34}$Lys$^{27,37}$GLP-1(7-37); Val$^8$Arg$^{26,34}$Lys$^{27,38}$-GLP-1(7-38); or Val$^8$Arg$^{26,34}$Lys$^{27,39}$-GLP-1(7-39).

In a further preferred embodiment, the parent peptide is: Arg$^{26}$-GLP-1(7-37); Arg$^{34}$-GLP-1(7-37); Lys$^{36}$-GLP-1(7-37); Arg$^{26,34}$Lys$^{36}$-GLP-1(7-37); Arg$^{26,34}$Lys$^{38}$GLP-1(7-38); Arg$^{26,34}$Lys$^{39}$-GLP-1(7-39); Arg$^{26,34}$Lys$^{40}$-GLP-1(7-40); Arg$^{26}$Lys$^{36}$-GLP-1(7-37); Arg$^{34}$Lys$^{36}$-GLP-1(7-37); Arg$^{26}$Lys$^{39}$-GLP-1(7-39); Arg$^{34}$Lys$^{40}$-GLP-1(7-40); Arg$^{26,34}$Lys$^{36,39}$-GLP-1(7-39); Arg$^{26,34}$Lys$^{36,40}$-GLP-1(7-40); Gly$^8$Arg$^{26}$-GLP-1(7-37); Gly$^8$Arg$^{34}$-GLP-1(7-37); Gly$^8$Lys$^{36}$-GLP-1(7-37); Gly$^8$Arg$^{26,34}$Lys$^{36}$-GLP-1(7-37); Gly$^8$Arg$^{26,34}$Lys$^{39}$-GLP-1(7-39); Gly$^8$Arg$^{26,34}$Lys$^{40}$-GLP-1(7-40); Gly$^8$Arg$^{26}$Lys$^{36}$-GLP-1(7-37); Gly$^8$Arg$^{34}$Lys$^{36}$-GLP-1(7-37); Gly$^8$Arg$^{26}$Lys$^{39}$-GLP-1(7-39); Gly$^8$Arg$^{34}$Lys$^{40}$-GLP-1(7-40); Gly$^8$Arg$^{26,34}$Lys$^{36,39}$-GLP-1(7-39); or Gly$^8$Arg$^{26,34}$Lys$^{36,40}$-GLP-1(7-40).

In a further preferred embodiment, the parent peptide is: Arg$^{26,34}$Lys$^{38}$GLP-1(7-38); Arg$^{26,34}$Lys$^{39}$GLP-1(7-39); Arg$^{26,34}$Lys$^{40}$GLP-1(7-40); Arg$^{26,34}$Lys$^{41}$GLP-1(7-41); Arg$^{26,34}$Lys$^{42}$GLP-1(7-42); Arg$^{26,34}$Lys$^{43}$GLP-1(7-43); Arg$^{26,34}$Lys$^{44}$GLP-1(7-44); Arg$^{26,34}$Lys$^{45}$GLP-1(7-45); Arg$^{26}$Lys$^{38}$GLP-1(7-38); Arg$^{34}$Lys$^{38}$GLP-1(7-38); Arg$^{26,34}$Lys$^{36,38}$GLP-1(7-38); Arg$^{26}$Lys$^{38}$GLP-1(7-38); Arg$^{26}$Lys$^{39}$GLP-1(7-39); Arg$^{34}$Lys$^{39}$GLP-1(7-39); or Arg$^{26,34}$Lys$^{36,39}$GLP-1(7-39).

In a further preferred embodiment, the parent peptide is Arg$^{26}$-GLP-1(7-37), Arg$^{34}$-GLP-1(7-37), Lys$^{36}$-GLP-1(7-37), Arg$^{26,34}$Lys$^{36}$-GLP-1(7-37), Arg$^{26}$Lys$^{36}$-GLP-1(7-37), Arg$^{34}$Lys$^{36}$-GLP-1(7-37), Gly$^8$Arg$^{26}$-GLP-1(7-37), Gly$^8$Arg$^{34}$-GLP-1(7-37), Gly$^8$Lys$^{36}$-GLP-1(7-37), Gly$^8$Arg$^{26,34}$Lys$^{36}$-GLP-1(7-37), Gly$^8$Arg$^{26}$Lys$^{36}$-GLP-1(7-37) or Gly$^8$Arg$^{34}$Lys$^{36}$-GLP-1(7-37).

In a further preferred embodiment, the parent peptide is Arg$^{26}$Lys$^{38}$-GLP-1(7-38), Arg$^{26,34}$Lys$^{38}$-GLP-1(7-38), Arg$^{26,34}$Lys$^{36,38}$-GLP-1(7-38), Gly$^8$Arg$^{26}$Lys$^{38}$-GLP-1(7-38) or Gly$^8$Arg$^{26,34}$Lys$^{36,38}$-GLP-1(7-38).

In a further preferred embodiment, the parent peptide is Arg$^{26}$Lys$^{39}$-GLP-1(7-39), Arg$^{26,34}$Lys$^{36,39}$-GLP-1(7-39), Gly$^8$Arg$^{26}$Lys$^{39}$-GLP-1(7-39) or Gly$^8$Arg$^{26,34}$Lys$^{36,39}$-GLP-1(7-39).

In a further preferred embodiment, the parent peptide is Arg$^{34}$Lys$^{40}$-GLP-1(7-40), Arg$^{26,34}$Lys$^{36,40}$-GLP-1(7-40), Gly$^8$Arg$^{34}$Lys$^{40}$-GLP-1(7-40) or Gly$^8$Arg$^{26,34}$Lys$^{36,40}$-GLP-1(7-40).

In a further preferred embodiment, the parent peptide is: Arg$^{26}$-GLP-1(7-36); Arg$^{34}$-GLP-1(7-36); Arg$^{26,34}$Lys$^{36}$-GLP-1(7-36); Arg$^{26}$-GLP-1(7-36)amide; Arg$^{34}$-GLP-1(7-36)amide; Arg$^{26,34}$Lys$^{36}$-GLP-1(7-36)amide; Arg$^{26}$-GLP-1(7-37); Arg$^{34}$-GLP-1(7-37); Arg$^{26,34}$Lys$^{36}$-GLP-1(7-37); Arg$^{26}$-GLP-1(7-38); Arg$^{34}$-GLP-1(7-38); Arg$^{26,34}$Lys$^{38}$-GLP-1(7-38); Arg$^{26}$-GLP-1(7-39); Arg$^{34}$-GLP-1(7-39); Arg$^{26,34}$Lys$^{39}$-GLP-1(7-39); Gly$^8$Arg$^{26}$-GLP-1(7-36); Gly$^8$Arg$^{34}$-GLP-1(7-36); Gly$^8$Arg$^{26,34}$Lys$^{36}$-GLP-1(7-36); Gly$^8$Arg$^{26}$-GLP-1(7-36)amide; Gly$^8$Arg$^{34}$-GLP-1(7-36)amide; Gly$^8$Arg$^{26,34}$Lys$^{36}$-GLP-1(7-36)amide; Gly$^8$Arg$^{26}$-GLP-1(7-37); Gly$^8$Arg$^{34}$-GLP-1(7-37); Gly$^8$Arg$^{26,34}$Lys$^{36}$-GLP-1(7-37); Gly$^8$Arg$^{26}$-GLP-1(7-38); Gly$^8$Arg$^{34}$-GLP-1(7-38); Gly$^8$Arg$^{26,34}$Lys$^{38}$GLP-1(7-38); Gly$^8$Arg$^{26}$-GLP-1(7-39); Gly$^8$Arg$^{34}$-GLP-1(7-39); Gly$^8$Arg$^{26,34}$Lys$^{39}$-GLP-1(7-39); Val$^8$Arg$^{26}$-GLP-1(7-36); Val$^8$Arg$^{34}$-GLP-1(7-36); Val$^8$Arg$^{26,34}$Lys$^{36}$-GLP-1(7-36); Val$^8$Arg$^{26}$-GLP-1(7-36)amide; Val$^8$Arg$^{34}$-GLP-1(7-36)amide; Val$^8$Arg$^{26,34}$Lys$^{36}$-GLP-1(7-36)amide; Val$^8$Arg$^{26}$-GLP-1(7-37); Val$^8$Arg$^{34}$-GLP-1(7-37); Val$^8$Arg$^{26,34}$Lys$^{36}$-GLP-1(7-37); Val$^8$Arg$^{26}$-GLP-1(7-38); Val$^8$Arg$^{34}$-GLP-1(7-38); Val$^8$Arg$^{26,34}$Lys$^{38}$GLP-1(7-38); Val$^8$Arg$^{26}$-GLP-1(7-39); Val$^8$Arg$^{34}$-GLP-1(7-39); Val$^8$Arg$^{26,34}$Lys$^{39}$-GLP-1(7-39); Ser$^8$Arg$^{26}$-GLP-1(7-36); Ser$^8$Arg$^{34}$-GLP-1(7-36); Ser$^8$Arg$^{26,34}$Lys$^{36}$-GLP-1(7-36); Ser$^8$Arg$^{26}$-GLP-1(7-36)amide; Ser$^8$Arg$^{34}$-GLP-1(7-36)amide; Ser$^8$Arg$^{26,34}$Lys$^{36}$-GLP-1(7-36)amide; Ser$^8$Arg$^{26}$-GLP-1(7-37); Ser$^8$Arg$^{34}$-GLP-1(7-37); Ser$^8$Arg$^{26,34}$Lys$^{36}$-GLP-1(7-37); Ser$^8$Arg$^{26}$-GLP-1(7-38); Ser$^8$Arg$^{34}$-GLP-1(7-38); Ser$^8$Arg$^{26,34}$Lys$^{38}$GLP-1(7-38); Ser$^8$Arg$^{26}$-GLP-1(7-39); Ser$^8$Arg$^{34}$-GLP-1(7-39); Ser$^8$Arg$^{26,34}$Lys$^{39}$-GLP-1(7-39); Thr$^8$Arg$^{26}$-GLP-1(7-36); Thr$^8$Arg$^{34}$-GLP-1(7-36); Thr$^8$Arg$^{26,34}$Lys$^{36}$-GLP-1(7-36); Thr$^8$Arg$^{26}$-GLP-1(7-36)amide; Thr$^8$Arg$^{34}$-GLP-1(7-36)amide; Thr$^8$Arg$^{26,34}$Lys$^{36}$-GLP-1(7-36)amide; Thr$^8$Arg$^{26}$-GLP-1(7-37); Thr$^8$Arg$^{34}$-GLP-1(7-37); Thr$^8$Arg$^{26,34}$Lys$^{36}$-GLP-1(7-37); Thr$^8$Arg$^{26}$-GLP-1(7-38); Thr$^8$Arg$^{34}$-GLP-1(7-38); Thr$^8$Arg$^{26,34}$Lys$^{38}$GLP-1(7-38); Thr$^8$Arg$^{26}$-GLP-1(7-39); Thr$^8$Arg$^{34}$-GLP-1(7-39); Thr$^8$Arg$^{26,34}$Lys$^{39}$-GLP-1(7-39); Val$^8$Glu$^{35}$Arg$^{26,34}$Lys$^{36}$-GLP-1(7-36); Val$^8$Glu$^{35}$Arg$^{26,34}$Lys$^{36}$-GLP-1(7-36)amide; Val$^8$Glu$^{36}$Arg$^{26,34}$Lys$^{37}$GLP-1(7-37); Val$^8$Glu$^{37}$Arg$^{26,34}$Lys$^{38}$GLP-1(7-38); Val$^8$Glu$^{38}$Arg$^{26,34}$Lys$^{39}$-GLP-1(7-39); Val$^8$Glu$^{35}$Arg$^{26,34}$Lys$^{36}$-GLP-1(7-36); Val$^8$Glu$^{35}$Arg$^{26,34}$Lys$^{36}$-GLP-1(7-36)amide; Val$^8$Glu$^{36}$Arg$^{26,34}$Lys$^{37}$GLP-1(7-37); Val$^8$Glu$^{37}$Arg$^{26,34}$Lys$^3$GLP-1(7-38); Val$^8$Glu$^{38}$Arg$^{26,34}$Lys$^{39}$-GLP-1(7-39); Val$^8$Asp$^{35}$Arg$^{26,34}$Lys$^{36}$-GLP-1(7-36); Val$^8$Asp$^{35}$Arg$^{26,34}$Lys$^{36}$-GLP-1(7-36)amide; Val$^8$Asp$^{36}$Arg$^{26,34}$Lys$^{37}$GLP-1(7-37); Val$^8$Asp$^{37}$Arg$^{26,34}$Lys$^{38}$GLP-1(7-38); Val$^8$Asp$^{38}$Arg$^{26,34}$Lys$^{39}$-GLP-1(7-39); Val$^8$Asp$^{35}$Arg$^{26,34}$Lys$^{36}$-GLP-1(7-36); Val$^8$Asp$^{35}$Arg$^{26,34}$Lys$^{36}$-GLP-1(7-36)amide; Val$^8$Asp$^{36}$Arg$^{26,34}$Lys$^{37}$GLP-1(7-37); Val$^8$Asp$^{37}$Arg$^{26,34}$Lys$^{38}$GLP-1(7-38); Val$^8$Asp$^{38}$Arg$^{26,34}$Lys$^{39}$-GLP-1(7-39); Ser$^8$Glu$^{35}$Arg$^{26,34}$Lys$^{36}$-GLP-1(7-36); Ser$^8$Glu$^{35}$Arg$^{26,34}$Lys$^{36}$-GLP-1(7-36)amide; Ser$^8$Glu$^{36}$Arg$^{26,34}$Lys$^{37}$GLP-1(7-37); Ser$^8$Glu$^{37}$Arg$^{26,34}$Lys$^{38}$GLP-1(7-38); Ser$^8$Glu$^{38}$Arg$^{26,34}$Lys$^{39}$-GLP-1(7-39); Ser$^8$Glu$^{35}$Arg$^{26,34}$Lys$^{36}$-GLP-1(7-36); Ser$^8$Glu$^{35}$Arg$^{26,34}$Lys$^{36}$-GLP-1(7-36)amide; Ser$^8$Glu$^{36}$Arg$^{26,34}$Lys$^{37}$GLP-1(7-37); Ser$^8$Glu$^{37}$Arg$^{26,34}$Lys$^{38}$GLP-1(7-38); Ser$^8$Glu$^{38}$Arg$^{26,34}$Lys$^{39}$-GLP-1(7-39); Ser$^8$Asp$^{35}$Arg$^{26,34}$Lys$^{36}$-GLP-1(7-36); Ser$^8$Asp$^{35}$Arg$^{26,34}$Lys$^{36}$-GLP-1(7-36)amide; Ser$^8$Asp$^{36}$Arg$^{26,34}$Lys$^{37}$GLP-1(7-37); Ser$^8$Asp$^{37}$Arg$^{26,34}$Lys$^{38}$GLP-1(7-38); Ser$^8$Asp$^{38}$Arg$^{26,34}$Lys$^{39}$-GLP-1(7-39); Ser$^8$Asp$^{35}$Arg$^{26,34}$Lys$^{36}$-GLP-1(7-36); Ser$^8$Asp$^{35}$Arg$^{26,34}$Lys$^{36}$-GLP-1(7-36)amide; Ser$^8$Asp$^{36}$Arg$^{26,34}$Lys$^{37}$GLP-1(7-37); Ser$^8$Asp$^{37}$Arg$^{26,34}$Lys$^{38}$GLP-1(7-38); Ser$^8$Asp$^{38}$Arg$^{26,34}$Lys$^{39}$-GLP-1(7-39); Thr$^8$Glu$^{35}$Arg$^{26,34}$Lys$^{36}$-GLP-1(7-36); Thr$^8$Glu$^{35}$Arg$^{26,34}$Lys$^{36}$-GLP-1(7-36)amide; Thr$^8$Glu$^{36}$Arg$^{26,34}$Lys$^{37}$GLP-1(7-37); Thr$^8$Glu$^{37}$Arg$^{26,34}$Lys$^{38}$GLP-1(7-38); Thr$^8$Glu$^{38}$Arg$^{26,34}$Lys$^{39}$-GLP-1(7-39); Thr$^8$Glu$^{35}$Arg$^{26,34}$Lys$^{36}$-GLP-1(7-36); Thr$^8$Glu$^{35}$Arg$^{26,34}$Lys$^{36}$-GLP-1(7-36)amide; Thr$^8$Glu$^{36}$ Arg$^{26,34}$Lys$^{37}$GLP-1(7-37); Thr$^8$Glu$^{37}$Arg$^{26,34}$Lys$^{38}$GLP-1(7-38); Thr$^8$Glu$^{38}$Arg$^{26,34}$Lys$^{39}$-GLP-1(7-39); Thr$^8$Asp$^{35}$Arg$^{26,34}$Lys$^{36}$-GLP-1(7-36); Thr$^8$Asp$^{35}$Arg$^{26,34}$Lys$^{36}$-GLP-1(7-36)amide; Thr$^8$Asp$^{36}$Arg$^{26,34}$Lys$^{37}$GLP-1(7-37); Thr$^8$Asp$^{37}$Arg$^{26,34}$Lys$^{38}$GLP-1(7-38); Thr$^8$Asp$^{38}$Arg$^{26,34}$Lys$^{39}$-GLP-1(7-39); Thr$^8$Asp$^{35}$Arg$^{26,34}$Lys$^{36}$-GLP-1(7-36); Thr$^8$Asp$^{35}$Arg$^{26,34}$Lys$^{36}$-GLP-1(7-36)amide; Thr$^8$Asp$^{36}$Arg$^{26,34}$Lys$^{37}$GLP-1(7-37); Thr$^8$Asp$^{37}$Arg$^{26,34}$Lys$^{38}$GLP-1(7-38); Thr$^8$Asp$^{38}$Arg$^{26,34}$Lys$^{39}$-GLP-1(7-39); Gly$^8$Glu$^{35}$Arg$^{26,34}$Lys$^{36}$-GLP-1(7-36); Gly$^8$Glu$^{35}$Arg$^{26,34}$Lys$^{36}$-GLP-1(7-36)amide; Gly$^8$Glu$^{36}$Arg$^{26,34}$Lys$^{37}$GLP-1(7-37); Gly$^8$Glu$^{37}$Arg$^{26,34}$Lys$^{38}$GLP-1(7-38); Gly$^8$Glu$^{38}$Arg$^{26,34}$Lys$^{39}$-GLP-1(7-39); Gly$^8$Glu$^{35}$Arg$^{26,34}$Lys$^{36}$-GLP-1(7-36); Gly$^8$Glu$^{35}$Arg$^{26,34}$Lys$^{36}$-GLP-1(7-36)amide; Gly$^8$Glu$^{36}$Arg$^{26,34}$Lys$^{37}$GLP-1(7-37); Gly$^8$Glu$^{37}$Arg$^{26,34}$Lys$^{38}$GLP-1(7-38); Gly$^8$Glu$^{38}$Arg$^{26,34}$Lys$^{39}$-GLP-1(7-39); Gly$^8$Asp$^{35}$Arg$^{26,34}$Lys$^{36}$-GLP-1(7-36); Gly$^8$Asp$^{35}$Arg$^{26,34}$Lys$^{36}$-GLP-1(7-36)amide; Gly$^8$Asp$^{36}$Arg$^{26,34}$Lys$^{37}$GLP-1(7-37); Gly$^8$Asp$^{37}$Arg$^{26,34}$Lys$^{38}$GLP-1(7-38); Gly$^8$Asp$^{38}$Arg$^{26,34}$Lys$^{39}$-GLP-1(7-39); Gly$^8$Asp$^{35}$Arg$^{26,34}$Lys$^{36}$-GLP-1(7-36); Gly$^8$Asp$^{35}$Arg$^{26,34}$Lys$^{36}$-GLP-1(7-36)amide; Gly$^8$Asp$^{36}$Arg$^{26,34}$Lys$^{37}$GLP-1(7-37); Gly$^8$Asp$^{37}$Arg$^{26,34}$Lys$^{38}$GLP-1(7-38); Gly$^8$Asp$^{38}$Arg$^{26,34}$Lys$^{39}$-GLP-1(7-39); Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Gly$^8$Asp$^{19}$Arg$^{26,34}$Lys$^{18}$GLP-1(7-36); Gly$^8$Asp$^{17}$Arg$^{26,34}$Lys$^{18}$-GLP-1(7-36); Gly$^8$Asp$^{19}$Arg$^{26,34}$Lys$^{18}$-GLP-1(7-36)amide; Gly$^8$Asp$^{17}$Arg$^{26,34}$Lys$^{18}$-GLP-1(7-36)amide; Gly$^8$Asp$^{19}$Arg$^{26,34}$Lys$^{18}$GLP-1(7-37); Gly$^8$Asp$^{19}$Arg$^{26,34}$Lys$^{18}$GLP-1(7-38); Gly$^8$Asp$^{17}$Arg$^{26,34}$Lys$^{18}$GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Gly$^8$Asp$^{24}$Arg$^{26,34}$Lys$^{23}$-GLP-1(7-36); Gly$^8$Asp$^{22}$Arg$^{26,34}$Lys$^{23}$-GLP-1(7-36); Gly$^8$Asp$^{24}$Arg$^{26,34}$Lys$^{23}$-GLP-1(7-36)amide; Gly$^8$Asp$^{22}$Arg$^{26,34}$Lys$^{23}$-GLP-1(7-36)amide; Gly$^8$Asp$^{24}$Arg$^{26,34}$Lys$^{23}$GLP-1(7-37); Gly$^8$Asp$^{24}$Arg$^{26,34}$Lys$^{23}$GLP-1(7-38); Gly$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Gly$^8$Asp$^{28}$Arg$^{26,34}$Lys$^{27}$GLP-1(7-36); Gly$^8$Asp$^{26}$Arg$^{26,34}$Lys$^{27}$-GLP-1(7-36); Gly$^8$Asp$^{28}$Arg$^{26,34}$Lys$^{27}$-GLP-1(7-36)amide; Gly$^8$Asp$^{26}$Arg$^{26,34}$Lys$^{27}$-GLP-1(7-36)amide; Gly$^8$Asp$^{28}$Arg$^{26,34}$Lys$^{27}$GLP-1(7-37); Gly$^8$Asp$^{28}$Arg$^{26,34}$Lys$^{27}$GLP-1(7-38); Gly$^8$Asp$^{26}$Arg$^{26,34}$Lys$^{27}$GLP-1(7-38); Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Val$^8$Asp$^{19}$Arg$^{26,34}$Lys$^{18}$-GLP-1(7-36); Val$^8$Asp$^{17}$Arg$^{26,34}$Lys$^{18}$-GLP-1(7-36); Val$^8$Asp$^{19}$Arg$^{26,34}$Lys$^{18}$-GLP-1(7-36)amide; Val$^8$Asp$^{17}$Arg$^{26,34}$Lys$^{18}$-GLP-1(7-36)amide; Val$^8$Asp$^{19}$Arg$^{26,34}$Lys$^{18}$GLP-1(7-37); Val$^8$Asp$^{19}$Arg$^{26,34}$Lys$^{18}$GLP-1(7-38); Val$^8$Asp$^{17}$Arg$^{26,34}$Lys$^{18}$GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Val$^8$Asp$^{24}$Arg$^{26,34}$Lys$^{23}$-GLP-1(7-36); Val$^8$Asp$^{22}$Arg$^{26,34}$Lys$^{23}$-GLP-1(7-36); Val$^8$Asp$^{24}$Arg$^{26,34}$Lys$^{23}$-GLP-1(7-36)amide; Val$^8$Asp$^{22}$Arg$^{26,34}$Lys$^{23}$-GLP-1(7-36)amide; Val$^8$Asp$^{24}$Arg$^{26,34}$Lys$^{23}$GLP-1(7-37); Val$^8$Asp$^{24}$Arg$^{26,34}$Lys$^{23}$GLP-1(7-38); Val$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Val$^8$Asp$^{28}$Arg$^{26,34}$Lys$^{27}$-GLP-1(7-36); Val$^8$Asp$^{26}$Arg$^{26,34}$Lys$^{27}$-GLP-1(7-36); Val$^8$Asp$^{28}$Arg$^{26,34}$Lys$^{27}$-GLP-1(7-36)amide; Val$^8$Asp$^{26}$Arg$^{26,34}$Lys$^{27}$-GLP-1(7-36)amide; Val$^8$Asp$^{28}$Arg$^{26,34}$Lys$^{27}$GLP-1(7-37); Val$^8$Asp$^{28}$Arg$^{26,34}$Lys$^{27}$GLP-1(7-38); Val$^8$Asp$^{26}$Arg$^{26,34}$Lys$^{27}$GLP-1(7-38); Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Ser$^8$Asp$^{19}$Arg$^{26,34}$Lys$^{18}$-GLP-1(7-36); Ser$^8$Asp$^{17}$Arg$^{26,34}$Lys$^{18}$-GLP-1(7-36); Ser$^8$Asp$^{19}$Arg$^{26,34}$Lys$^{18}$-GLP-1(7-36)amide; Ser$^8$Asp$^{17}$Arg$^{26,34}$Lys$^2$-GLP-1(7-36)amide; Ser$^8$Asp$^{19}$Arg$^{26,34}$Lys$^{18}$GLP-1(7-37); Ser$^8$Asp$^{19}$Arg$^{26,34}$Lys$^1$GLP-1(7-38); Ser$^8$Asp$^{17}$Arg$^{26,34}$Lys$^{18}$GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Ser$^8$Asp$^{24}$Arg$^{26,34}$Lys$^{23}$-GLP-1(7-36); Ser$^8$Asp$^{22}$Arg$^{26,34}$Lys$^{23}$-GLP-1(7-36); Ser$^8$Asp$^{24}$Arg$^{26,34}$Lys$^{23}$-GLP-1(7-36)amide; Ser$^8$Asp$^{22}$Arg$^{26,34}$Lys$^{23}$-GLP-1(7-36)amide; Ser$^8$Asp$^{24}$Arg$^{26,34}$Lys$^{23}$GLP-1(7-37); Ser$^8$Asp$^{24}$Arg$^{26,34}$Lys$^{23}$GLP-1(7-38); Ser$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Ser$^8$Asp$^{28}$Arg$^{26,34}$Lys$^{27}$-GLP-1(7-36); Ser$^8$Asp$^{26}$Arg$^{26,34}$Lys$^{27}$-GLP-1(7-36); Ser$^8$Asp$^{28}$Arg$^{26,34}$Lys$^{27}$-GLP-1(7-36)amide; Ser$^8$Asp$^{26}$Arg$^{26,34}$Lys$^{27}$-GLP-1(7-36)amide; Ser$^8$Asp$^{28}$Arg$^{26,34}$Lys$^{27}$GLP-1(7-37); Ser$^8$Asp$^{28}$Arg$^{26,34}$Lys$^{27}$GLP-1(7-38); Ser$^8$Asp$^{26}$Arg$^{26,34}$Lys$^{27}$GLP-1(7-38); Arg$^{26,34}$Lys$^{18}$-GLP-1(7-36); Arg$^{26,34}$Lys$^{18}$-GLP-1(7-36)amide; Arg$^{26,34}$Lys$^{18}$GLP-1(7-37); Arg$^{26,34}$Lys$^{18}$GLP-1(7-38); Thr$^8$Asp$^{19}$Arg$^{26,34}$Lys$^{18}$-GLP-1(7-36); Thr$^8$Asp$^{17}$Arg$^{26,34}$Lys$^{18}$-GLP-1(7-36); Thr$^8$Asp$^{19}$Arg$^{26,34}$Lys$^{18}$-GLP-1(7-36)amide; Thr$^8$Asp$^{17}$Arg$^{26,34}$Lys$^{18}$-GLP-1(7-36)amide; Thr$^8$Asp$^{19}$Arg$^{26,34}$Lys$^{18}$GLP-1(7-37); Thr$^8$Asp$^{19}$Arg$^{26,34}$Lys$^{18}$GLP-1(7-38); Thr$^8$Asp$^{17}$Arg$^{26,34}$Lys$^{18}$GLP-1(7-38); Arg$^{26,34}$Lys$^{23}$-GLP-1(7-36); Arg$^{26,34}$Lys$^{23}$-GLP-1(7-36)amide; Arg$^{26,34}$Lys$^{23}$GLP-1(7-37); Arg$^{26,34}$Lys$^{23}$GLP-1(7-38); Thr$^8$Asp$^{24}$Arg$^{26,34}$Lys$^{23}$-GLP-1(7-36); Thr$^8$Asp$^{22}$Arg$^{26,34}$Lys$^{23}$-GLP-1(7-36); Thr$^8$Asp$^{24}$Arg$^{26,34}$Lys$^{23}$-GLP-1(7-36)amide; Thr$^8$Asp$^{22}$Arg$^{26,34}$Lys$^{23}$-GLP-1(7-36)amide; Thr$^8$Asp$^{24}$Arg$^{26,34}$Lys$^{23}$GLP-1(7-37); Thr$^8$Asp$^{24}$Arg$^{26,34}$Lys$^{23}$GLP-1(7-38); Thr$^8$Asp$^{22}$Arg$^{26,34}$Lys$^{23}$GLP-1(7-38); Arg$^{26,34}$Lys$^{27}$-GLP-1(7-36); Arg$^{26,34}$Lys$^{27}$-GLP-1(7-36)amide; Arg$^{26,34}$Lys$^{27}$GLP-1(7-37); Arg$^{26,34}$Lys$^{27}$GLP-1(7-38); Thr$^8$Asp$^{28}$Arg$^{26,34}$Lys$^{27}$-GLP-1(7-36); Thr$^8$Asp$^{26}$Arg$^{26,34}$Lys$^{27}$-GLP-1(7-36); Thr$^8$Asp$^{28}$Arg$^{26,34}$Lys$^{27}$-GLP-1(7-36)amide; Thr$^8$Asp$^{26}$Arg$^{26,34}$Lys$^{27}$-GLP-1(7-36)amide; Thr$^8$Asp$^{28}$Arg$^{26,34}$Lys$^{27}$GLP-1(7-37); Thr$^8$Asp$^{28}$Arg$^{26,34}$Lys$^{27}$GLP-1(7-38); or Thr$^8$Asp$^{26}$Arg$^{26,34}$Lys$^{27}$GLP-1(7-38).

In a further preferred embodiment, the present invention relates to a GLP-1 derivative wherein the parent peptide is:
Arg$^{26}$Lys$^{36}$-GLP-1(7-36); Arg$^{34}$Lys$^{36}$-GLP-1(7-36); Arg$^{26}$Lys$^{36}$-GLP-1(7-37); Arg$^{34}$Lys$^{36}$-GLP-1(7-37); Arg$^{26}$Lys$^{37}$-GLP-1(7-37); Arg$^{34}$Lys$^{37}$-GLP-1(7-37); Arg$^{26}$Lys$^{39}$-GLP-1(7-39); Arg$^{34}$Lys$^{39}$-GLP-1(7-39); Arg$^{26,34}$Lys$^{36,39}$GLP-1(7-39); Arg$^{26}$Lys$^{18}$-GLP-1(7-36); Arg$^{34}$Lys$^{18}$-GLP-1(7-36); Arg$^{26}$Lys$^{18}$-GLP-1(7-37); Arg$^{34}$Lys$^{18}$GLP-1(7-37); Arg$^{26}$Lys$^{18}$GLP-1(7-38); Arg$^{34}$Lys$^{18}$GLP-1(7-38); Arg$^{26}$Lys$^{18}$-GLP-1(7-39); Arg$^{34}$Lys$^{18}$GLP-1(7-39); Arg$^{26}$Lys$^{23}$-GLP-1(7-36);

Arg³⁴Lys²³-GLP-1(7-36); Arg³⁴Lys²³GLP-1(7-37); Arg³⁴Lys²³GLP-1(7-38); Arg³⁴Lys²³GLP-1(7-39); Arg³⁴Lys²⁷-GLP-1(7-36); Arg³⁴Lys²⁷GLP-1(7-37); Arg³⁴Lys²⁷GLP-1(7-38); Arg³⁴Lys²⁷GLP-1(7-39); Arg²⁶,³⁴Lys¹⁸GLP-1(7-37); Arg²⁶,³⁴Lys¹⁸GLP-1(7-38); Arg²⁶,³⁴Lys²³,³⁶-GLP-1(7-36); Arg²⁶,³⁴Lys²³,³⁷GLP-1(7-37); Arg²⁶,³⁴Lys²³,³⁸GLP-1(7-38); Arg²⁶,³⁴Lys²³,³⁹GLP-1(7-39); Arg²⁶,³⁴Lys²⁷,³⁶-GLP-1(7-36); Arg²⁶,³⁴Lys²⁷GLP-1(7-37); Arg²⁶,³⁴Lys²⁷,³⁷GLP-1(7-37); Arg²⁶,³⁴Lys²⁷,³⁸GLP-1(7-38); Arg²⁶,³⁴Lys²⁷,³⁹-GLP-1(7-39); Gly⁸GLP-1(7-36); Gly⁸GLP-1(7-37); Gly⁸GLP-1(7-38); Gly⁸GLP-1(7-39); Gly⁸Arg²⁶Lys³⁶-GLP-1(7-36); Gly⁸Arg³⁴Lys³⁶-GLP-1(7-36); Gly⁸Arg²⁶Lys³⁶-GLP-1(7-37); Gly⁸Arg³⁴Lys³⁶-GLP-1(7-37); Gly⁸Arg²⁶Lys³⁷-GLP-1(7-37); Gly⁸Arg³⁴Lys³⁷-GLP-1(7-37); Gly⁸Arg²⁶Lys³⁹-GLP-1(7-39); Gly⁸Arg³⁴Lys³⁹-GLP-1(7-39); Gly⁸Arg²⁶,³⁴Lys³⁶,³⁹-GLP-1(7-39); Gly⁸Arg³⁴Lys¹⁸⁻ᴳᴸᴾ-1(7-36); Gly⁸Arg³⁴Lys¹⁸⁻ᴳᴸᴾ-1(7-36); Gly⁸Arg²⁶Lys¹⁸GLP-1(7-37); Gly⁸Arg³⁴Lys¹⁸GLP-1(7-37); Gly⁸Arg²⁶Lys¹⁸GLP-1(7-38); Gly⁸Arg³⁴Lys¹⁸GLP-1(7-38); Gly⁸Arg²⁶Lys¹⁸GLP-1(7-39); Gly⁸Arg³⁴Lys¹⁸GLP-1(7-39); Gly⁸Arg²⁶Lys²³-GLP-1(7-36); Gly⁸Arg³⁴Lys²³-GLP-1(7-36); Gly⁸Arg²⁶Lys²³GLP-1(7-37); Gly⁸Arg³⁴Lys²³GLP-1(7-37); Gly⁸Arg²⁶Lys²³GLP-1(7-38); Gly⁸Arg³⁴Lys²³GLP-1(7-38); Gly⁸Arg²⁶Lys²³GLP-1(7-39); Gly⁸Arg³⁴Lys²³GLP-1(7-39); Gly⁸Arg²⁶Lys²⁷-GLP-1(7-36); Gly⁸Arg³⁴Lys²⁷-GLP-1(7-36); Gly⁸Arg²⁶Lys²⁷GLP-1(7-37); Gly⁸Arg³⁴Lys²⁷GLP-1(7-37); Gly⁸Arg²⁶Lys²⁷GLP-1(7-38); Gly⁸Arg³⁴Lys²⁷GLP-1(7-38); Gly⁸Arg²⁶Lys²⁷GLP-1(7-39); Gly⁸Arg³⁴Lys²⁷GLP-1(7-39); Gly⁸Arg²⁶,³⁴Lys⁸,³⁶-GLP-1(7-36); Gly⁸Arg²⁶,³⁴Lys¹⁸GLP-1(7-37); Gly⁸Arg²⁶,³⁴Lys¹⁸,³⁷GLP-1(7-37); Gly⁸Arg²⁶,³⁴Lys¹⁸,³⁸GLP-1(7-38); Gly⁸Arg²⁶,³⁴Lys¹⁸,³⁹GLP-1(7-39); Gly⁸Arg²⁶,³⁴Lys²³,³⁶-GLP-1(7-36); Gly⁸Arg²⁶,³⁴Lys²³GLP-1(7-37); Gly⁸Arg²⁶,³⁴Lys²³,³⁷GLP-1(7-37); Gly⁸Arg²⁶,³⁴Lys²³,³⁸GLP-1(7-38); Gly⁸Arg²⁶,³⁴Lys²³,³⁹GLP-1(7-39); Gly⁸Arg²⁶,³⁴Lys²⁷,³⁶-GLP-1(7-36); Gly⁸Arg²⁶,³⁴Lys²⁷GLP-1(7-37); Gly⁸Arg²⁶,³⁴Lys²⁷,³⁷GLP-1(7-37); Gly⁸Arg²⁶,³⁴Lys²⁷,³⁸GLP-1(7-38); Gly⁸Arg²⁶,³⁴Lys²⁷,³⁹GLP-1(7-39); Val⁸GLP-(7-36); Val⁸GLP-1(7-37); Val⁸GLP-1(7-38); Val⁸GLP-1(7-39); Val⁸Arg²⁶Lys³⁶-GLP-1(7-36); Val⁸Arg³⁴Lys³⁶-GLP-1(7-36); Val⁸Arg²⁶Lys³⁶-GLP-1(7-37); Val⁸Arg³⁴Lys³⁶-GLP-1(7-37); Val⁸Arg²⁶Lys³⁷-GLP-1(7-37); Val⁸Arg³⁴Lys³⁷-GLP-1(7-37); Val⁸Arg²⁶Lys³⁹-GLP-1(7-39); Val⁸Arg³⁴Lys³⁹-GLP-1(7-39); Val⁸Arg²⁶,³⁴Lys³⁶,³⁹-GLP-1(7-39); Val⁸Arg²⁶Lys¹⁸-GLP-1(7-36); Val⁸Arg³⁴Lys¹⁸-GLP-1(7-36); Val⁸Arg²⁶Lys¹⁸-GLP-1(7-37); Val⁸Arg³⁴Lys¹⁸GLP-1(7-37); Val⁸Arg²⁶Lys¹⁸-GLP-1(7-38); Val⁸Arg³⁴Lys¹⁸-GLP-1(7-38); Val⁸Arg²⁶Lys¹⁸-GLP-1(7-39); Val⁸Arg³⁴Lys¹⁸-GLP-1(7-39); Val⁸Arg²⁶Lys²³-GLP-1(7-36); Val⁸Arg³⁴Lys²³-GLP-1(7-36); Val⁸Arg²⁶Lys²³GLP-1(7-37); Val⁸Arg³⁴Lys²³GLP-1(7-37); Val⁸Arg²⁶Lys²³GLP-1(7-38); Val⁸Arg³⁴Lys²³GLP-1(7-38); Val⁸Arg²⁶Lys²³GLP-1(7-39); Val⁸Arg³⁴Lys²³GLP-1(7-39); Val⁸Arg²⁶Lys²⁷-GLP-1(7-36); Val⁸Arg³⁴Lys²⁷-GLP-1(7-36); Val⁸Arg²⁶Lys²⁷GLP-1(7-37); Val⁸Arg³⁴Lys²⁷GLP-1(7-37); Val⁸Arg²⁶Lys²⁷GLP-1(7-38); Val⁸Arg³⁴Lys²⁷GLP-1(7-38); Val⁸Arg²⁶Lys²⁷GLP-1(7-39); Val⁸Arg³⁴Lys²⁷GLP-1(7-39); Val⁸Arg²⁶,³⁴Lys¹⁸,³⁶-GLP-1(7-36); Val⁸Arg²⁶,³⁴Lys¹⁸GLP-1(7-37); Val⁸Arg²⁶,³⁴Lys⁸,³⁷GLP-1(7-37); Val⁸Arg²⁶,³⁴Lys⁸,³⁸GLP-1(7-38); Val⁸Arg²⁶,³⁴Lys¹⁸,³⁹GLP-1(7-39); Val⁸Arg²⁶,³⁴Lys²³,³⁶-GLP-1(7-36); Val⁸Arg²⁶,³⁴Lys²³GLP-1(7-37); Val⁸Arg²⁶,³⁴Lys²³,³⁷GLP-1(7-37); Val⁸Arg²⁶,³⁴Lys²³,³⁸GLP-1(7-38); Val⁸Arg²⁶,³⁴Lys²³,³⁹GLP-1(7-39); Val⁸Arg²⁶,³⁴Lys²⁷,³⁶-GLP-1(7-36); Val⁸Arg²⁶,³⁴Lys²⁷GLP-1(7-37); Val⁸Arg²⁶,³⁴Lys²⁷,³⁷GLP-1(7-37); Val⁸Arg²⁶,³⁴Lys²⁷,³⁸GLP-1(7-38); or Val⁸Arg²⁶,³⁴Lys²⁷,³⁹GLP-1(7-39).

In a further preferred embodiment, the present invention relates to a GLP-1 derivative wherein the parent peptide is: Arg²⁶-GLP-1(8-37); Arg³⁴-GLP-1(8-37); Lys³⁶-GLP-1(8-37); Arg²⁶,³⁴Lys³⁶-GLP-1(8-37); Arg²⁶,³⁴Lys³⁸GLP-1(8-38); Arg²⁶,³⁴Lys³⁹-GLP-1(8-39); Arg²⁶,³⁴Lys⁴⁰-GLP-1(8-40); Arg²⁶Lys³⁶-GLP-1(8-37); Arg³⁴Lys³⁶-GLP-1(8-37); Arg²⁶Lys³⁹-GLP-1(8-39); Arg³⁴Lys⁴⁰-GLP-1(8-40); Arg²⁶,³⁴Lys³⁶,³⁹-GLP-1(8-39); Arg²⁶,³⁴Lys³⁶,⁴⁰-GLP-1(8-40); Gly⁸Arg²⁶-GLP-1(8-37); Gly⁸Arg³⁴-GLP-1(8-37); Gly⁸Lys³⁶-GLP-1(8-37); Gly⁸Arg²⁶,³⁴Lys³⁶-GLP-1(8-37); Gly⁸Arg²⁶,³⁴Lys³⁹-GLP-1(8-39); Gly⁸Arg²⁶,³⁴Lys⁴⁰-GLP-1(8-40); Gly⁸Arg²⁶Lys³⁶-GLP-1(8-37); Gly⁸Arg³⁴Lys³⁶-GLP-1(8-37); Gly⁸Arg²⁶Lys³⁹-GLP-1(8-39); Gly⁸Arg³⁴Lys⁴⁰-GLP-1(8-40); Gly⁸Arg²⁶,³⁴Lys³⁶,³⁹-GLP-1(8-39); or Gly⁸Arg²⁶,³⁴Lys³⁶,⁴⁰-GLP-1(8-40).

In a further preferred embodiment, the parent peptide is: Arg²⁶,³⁴Lys³⁸GLP-1(8-38); Arg²⁶,³⁴Lys³⁹GLP-1(8-39); Arg²⁶,³⁴Lys⁴⁰GLP-1(8-40); Arg²⁶,³⁴Lys⁴¹GLP-1(8-41); Arg²⁶,³⁴Lys⁴²GLP-1(8-42); Arg²⁶,³⁴Lys⁴³GLP-1(8-43); Arg²⁶,³⁴Lys⁴⁴GLP-1(8-44); Arg²⁶,³⁴Lys⁴⁵GLP-1(8-45); Arg²⁶Lys³⁸GLP-1(8-38); Arg³⁴Lys³⁸GLP-1(8-38); Arg²⁶,³⁴Lys³⁶,³⁸GLP-1(8-38); Arg²⁶,³⁴Lys³⁸GLP-1(8-38); Arg²⁶Lys³⁹GLP-1(8-39); Arg³⁴Lys³⁹GLP-1(8-39); or Arg²⁶,³⁴Lys³⁶,³⁹GLP-1(8-39).

In a further preferred embodiment, the parent peptide is Arg²⁶-GLP-1(8-37), Arg³⁴-GLP-1(8-37), Lys³⁶-GLP-1(8-37), Arg²⁶,³⁴Lys³⁶-GLP-1(8-37), Arg²⁶Lys³⁶-GLP-1(8-37), Arg³⁴Lys³⁶-GLP-1(8-37), Gly⁸Arg²⁶-GLP-1(8-37), Gly⁸Arg³⁴-GLP-1(8-37), Gly⁸Lys³⁶-GLP-1(8-37), Gly⁸Arg²⁶,³⁴Lys³⁶-GLP-1(8-37), Gly⁸Arg²⁶Lys³⁶-GLP-1(8-37), or Gly⁸Arg³⁴Lys³⁶-GLP-1(8-37).

In a further preferred embodiment, the parent peptide is Arg²⁶Lys³⁸-GLP-1(8-38), Arg²⁶,³⁴Lys³⁸-GLP-1(8-38), Arg²⁶,³⁴Lys³⁶,³⁸-GLP-1(8-38), Gly⁸Arg²⁶Lys³⁸-GLP-1(8-38) or Gly⁸Arg²⁶,³⁴Lys³⁶,³⁸-GLP-1(8-38).

In a further preferred embodiment, the parent peptide is Arg²⁶Lys³⁹-GLP-1(8-39), Arg²⁶,³⁴Lys³⁶,³⁹-GLP-1(8-39), Gly⁸Arg²⁶Lys³⁹-GLP-1(8-39) or Gly⁸Arg²⁶,³⁴Lys³⁶,³⁹-GLP-1(8-39).

In a further preferred embodiment, the present invention relates to a GLP-1 derivative wherein the parent peptide is Arg³⁴Lys⁴⁰-GLP-1(8-40), Arg²⁶,³⁴Lys³⁶,⁴⁰-GLP-1(8-40), Gly⁸Arg³⁴Lys⁴⁰-GLP-1(8-40) or Gly⁸Arg²⁶,³⁴Lys³⁶,⁴⁰-GLP-1(8-40).

In a further preferred embodiment, the present invention relates to a GLP-1 derivative wherein the parent peptide is: Arg²⁶-GLP-1(8-36); Arg³⁴-GLP-1(8-36); Arg²⁶,³⁴Lys³⁶-GLP-1(8-36); Arg²⁶-GLP-1(8-36)amide; Arg³⁴-GLP-1(8-36)amide; Arg²⁶,³⁴Lys³⁶-GLP-1(8-36)amide; Arg²⁶-GLP-1(8-37); Arg³⁴-GLP-1(8-37); Arg²⁶,³⁴Lys³⁶-GLP-1(8-37); Arg²⁶-GLP-1(8-38); Arg³⁴-GLP-1(8-38); Arg²⁶,³⁴Lys³⁸GLP-1(8-38); Arg²⁶-GLP-1(8-39); Arg³⁴-GLP-1(8-39); Arg²⁶,³⁴Lys³⁹-GLP-1(8-39); Gly⁸Arg²⁶-GLP-1(8-36); Gly⁸Arg³⁴-GLP-1(8-36); Gly⁸Arg²⁶,³⁴Lys³⁶-GLP-1(8-36); Gly⁸Arg²⁶-GLP-1(8-36)amide; Gly⁸Arg³⁴-GLP-1(8-36)amide; Gly⁸Arg²⁶,³⁴Lys³⁶-GLP-1(8-36)amide; Gly⁸Arg²⁶-GLP-1(8-37); Gly⁸Arg³⁴-GLP-1(8-37); Gly⁸Arg²⁶,³⁴Lys³⁶-GLP-1(8-37); Gly⁸Arg²⁶-GLP-1(8-38); Gly⁸Arg³⁴-GLP-1(8-38); Gly⁸Arg²⁶,³⁴Lys³⁸GLP-1(8-38); Gly⁸Arg²⁶-GLP-1(8-39); Gly⁸Arg³⁴-GLP-1(8-39); Gly⁸Arg²⁶,³⁴Lys³⁹-GLP-1(8-39); Val⁸Arg²⁶-GLP-1(8-36); Val⁸Arg³⁴-GLP-1(8-36);

Val$^8$Arg$^{26,34}$Lys$^{36}$-GLP-1(8-36); Val$^8$Arg$^{26}$-GLP-1(8-36)amide; Val$^8$Arg$^{34}$-GLP-1(8-36)amide; Val$^8$Arg$^{26,34}$Lys$^{36}$-GLP-1(8-36)amide; Val$^8$Arg$^{26}$-GLP-1(8-37); Val$^8$Arg$^{34}$-GLP-1(8-37); Val$^8$Arg$^{26,34}$Lys$^{36}$-GLP-1(8-37); Val$^8$Arg$^{26}$-GLP-1(8-38); Val$^8$Arg$^{34}$-GLP-1(8-38); Val$^8$Arg$^{26,34}$Lys$^{38}$GLP-1(8-38); Val$^8$Arg$^{26}$-GLP-1(8-39); Val$^8$Arg$^{34}$-GLP-1(8-39); Val$^8$Arg$^{26,34}$Lys$^{39}$-GLP-1(8-39); Ser$^8$Arg$^{26}$-GLP-1(8-36); Ser$^8$Arg$^{34}$-GLP-1(8-36); Ser$^8$Arg$^{26,34}$Lys$^{36}$-GLP-1(8-36); Ser$^8$Arg$^{26}$-GLP-1(8-36)amide; Ser$^8$Arg$^{34}$-GLP-1(8-36)amide; Ser$^8$Arg$^{26,34}$Lys$^{36}$-GLP-1(8-36)amide; Ser$^8$Arg$^{26}$-GLP-1(8-37); Ser$^8$Arg$^{34}$-GLP-1(8-37); Ser$^8$Arg$^{26,34}$Lys$^{36}$ GLP-1(8-37); Ser$^8$Arg$^{26}$-GLP-1(8-38); Ser$^8$Arg$^{34}$-GLP-1(8-38); Ser$^8$Arg$^{26,34}$Lys$^{38}$GLP-1(8-38); Ser$^8$Arg$^{26}$-GLP-1(8-39); Ser$^8$Arg$^{34}$-GLP-1(8-39); Ser$^8$Arg$^{26,34}$Lys$^{39}$-GLP-1(8-39); Thr$^8$Arg$^{26}$-GLP-1(8-36); Thr$^8$Arg$^{34}$-GLP-1(8-36); Thr$^8$Arg$^{26,34}$Lys$^{36}$-GLP-1(8-36); Thr$^8$Arg$^{26}$-GLP-1(8-36)amide; Thr$^8$Arg$^{34}$-GLP-1(8-36)amide; Thr$^8$Arg$^{26,34}$Lys$^{36}$-GLP-1(8-36)amide; Thr$^8$Arg$^{26}$-GLP-1(8-37); Thr$^8$Arg$^{34}$-GLP-1(8-37); Thr$^8$Arg$^{26,34}$Lys$^{36}$-GLP-1(8-37); Thr$^8$Arg$^{26}$-GLP-1(8-38); Thr$^8$Arg$^{34}$-GLP-1(8-38); Thr$^8$Arg$^{26,34}$Lys$^{38}$GLP-1(8-38); Thr$^8$Arg$^{26}$-GLP-1(8-39); Thr$^8$Arg$^{34}$-GLP-1(8-39); Thr$^8$Arg$^{26,34}$Lys$^{39}$-GLP-1(8-39); Val$^8$Glu$^{35}$Arg$^{26,34}$Lys$^{36}$-GLP-1(8-36); Val$^8$Glu$^{35}$Arg$^{26,34}$Lys$^{36}$-GLP-1(8-36)amide; Val$^8$Glu$^{36}$Arg$^{26,34}$Lys$^{37}$GLP-1(8-37); Val$^8$Glu$^{37}$Arg$^{26,34}$Lys$^{38}$GLP-1(8-38); Val$^8$Glu$^{38}$Arg$^{26,34}$Lys$^{39}$-GLP-1(8-39); Val$^8$Glu$^{35}$Arg$^{26,34}$Lys$^{36}$-GLP-1(8-36); Val$^8$Glu$^{35}$Arg$^{26,34}$Lys$^{36}$-GLP-1(8-36)amide; Val$^8$Glu$^{36}$Arg$^{26,34}$Lys$^{37}$GLP-1(8-37); Val$^8$Glu$^{37}$Arg$^{26,34}$Lys$^{38}$GLP-1(8-38); Val$^8$Glu$^{38}$Arg$^{26,34}$Lys$^{39}$-GLP-1(8-39); Val$^8$Asp$^{35}$Arg$^{26,34}$Lys$^{36}$-GLP-1(8-36); Val$^8$Asp$^{35}$Arg$^{26,34}$Lys$^{36}$-GLP-1(8-36)amide; Val$^8$Asp$^{36}$Arg$^{26,34}$Lys$^{37}$GLP-1(8-37); Val$^8$Asp$^{37}$Arg$^{26,34}$Lys$^{38}$GLP-1(8-38); Val$^8$Asp$^{38}$Arg$^{26,34}$Lys$^{39}$-GLP-1(8-39); Val$^8$Asp$^{35}$Arg$^{26,34}$Lys$^{36}$-GLP-1(8-36); Val$^8$Asp$^{35}$Arg$^{26,34}$Lys$^{36}$-GLP-1(8-36)amide; Val$^8$Asp$^{36}$Arg$^{26,34}$Lys$^{37}$GLP-1(8-37); Val$^8$Asp$^{37}$Arg$^{26,34}$Lys$^{38}$GLP-1(8-38); Val$^8$Asp$^{38}$Arg$^{26,34}$Lys$^{39}$-GLP-1(8-39); Ser$^8$Glu$^{35}$Arg$^{26,34}$Lys$^{36}$-GLP-1(8-36); Ser$^8$Glu$^{35}$Arg$^{26,34}$Lys$^{36}$-GLP-1(8-36)amide; Ser$^8$Glu$^{36}$Arg$^{26,34}$Lys$^{37}$GLP-1(8-37); Ser$^8$Glu$^{37}$Arg$^{26,34}$Lys$^{38}$GLP-1(8-38); Ser$^8$Glu$^{38}$Arg$^{26,34}$Lys$^{39}$-GLP-1(8-39); Ser$^8$Glu$^{35}$Arg$^{26,34}$Lys$^{36}$-GLP-1(8-36); Ser$^8$Glu$^{35}$Arg$^{26,34}$Lys$^{36}$-GLP-1(8-36)amide; Ser$^8$Glu$^{36}$Arg$^{26,34}$Lys$^{37}$GLP-1(8-37); Ser$^8$Glu$^{37}$Arg$^{26,34}$Lys$^{38}$GLP-1(8-38); Ser$^8$Glu$^{38}$Arg$^{26,34}$Lys$^{39}$-GLP-1(8-39); Ser$^8$Asp$^{35}$Arg$^{26,34}$Lys$^{36}$ GLP-1(8-36); Ser$^8$Asp$^{35}$Arg$^{26,34}$Lys$^{36}$-GLP-1(8-36)amide; Ser$^8$Asp$^{36}$Arg$^{26,34}$Lys$^{37}$GLP-1(8-37); Ser$^8$Asp$^{37}$Arg$^{26,34}$Lys$^{38}$GLP-1(8-38); Ser$^8$Asp$^{38}$Arg$^{26,34}$Lys$^{39}$-GLP-1(8-39); Ser$^8$Asp$^{35}$Arg$^{26,34}$Lys$^{36}$-GLP-1(8-36); Ser$^8$Asp$^{35}$Arg$^{26,34}$Lys$^{36}$-GLP-1(8-36)amide; Ser$^8$Asp$^{36}$Arg$^{26,34}$Lys$^{37}$GLP-1(8-37); Ser$^8$Asp$^{37}$Arg$^{26,34}$Lys$^{38}$GLP-1(8-38); Ser$^8$Asp$^{38}$Arg$^{26,34}$Lys$^{39}$-GLP-1(8-39); Thr$^8$Glu$^{35}$Arg$^{26,34}$Lys$^{36}$-GLP-1(8-36); Thr$^8$Glu$^{35}$Arg$^{26,34}$Lys$^{36}$-GLP-1(8-36)amide; Thr$^8$Glu$^{36}$Arg$^{26,34}$Lys$^{37}$GLP-1(8-37); Thr$^8$Glu$^{37}$Arg$^{26,34}$Lys$^{38}$GLP-1(8-38); Thr$^8$Glu$^{38}$Arg$^{26,34}$Lys$^{39}$-GLP-1(8-39); Thr$^8$Glu$^{35}$Arg$^{26,34}$Lys$^{36}$-GLP-1(8-36); Thr$^8$Glu$^{35}$Arg$^{26,34}$Lys$^{36}$-GLP-1(8-36)amide; Thr$^8$Glu$^{36}$Arg$^{26,34}$Lys$^{37}$GLP-1(8-37); Thr$^8$Glu$^{37}$Arg$^{26,34}$Lys$^{38}$GLP-1(8-38); Thr$^8$Glu$^{38}$Arg$^{26,34}$Lys$^{39}$-GLP-1(8-39); Thr$^8$Asp$^{35}$Arg$^{26,34}$Lys$^{36}$-GLP-1(8-36); Thr$^8$Asp$^{35}$Arg$^{26,34}$Lys$^{36}$-GLP-1(8-36)amide; Thr$^8$Asp$^{36}$Arg$^{26,34}$Lys$^{37}$GLP-1(8-37); Thr$^8$Asp$^{37}$Arg$^{26,34}$Lys$^{38}$GLP-1(8-38); Thr$^8$Asp$^{38}$Arg$^{26,34}$Lys$^{39}$-GLP-1(8-39); Thr$^8$Asp$^{35}$Arg$^{26,34}$Lys$^{36}$-GLP-1(8-36); Thr$^8$Asp$^{35}$Arg$^{26,34}$Lys$^{36}$-GLP-1(8-36)amide; Thr$^8$Asp$^{36}$Arg$^{26,34}$Lys$^{37}$GLP-1(8-37); Thr$^8$Asp$^{37}$Arg$^{26,34}$Lys$^{3}$GLP-1(8-38); Thr$^8$Asp$^{38}$Arg$^{26,34}$Lys$^{39}$-GLP-1(8-39); Gly$^8$Glu$^{35}$Arg$^{26,34}$Lys$^{36}$-GLP-1(8-36); Gly$^8$Glu$^{35}$Arg$^{26,34}$Lys$^{36}$-GLP-1(8-36)amide; Gly$^8$Glu$^{36}$Arg$^{26,34}$Lys$^{37}$GLP-1(8-37); Gly$^8$Glu$^{37}$Arg$^{26,34}$Lys$^{3}$GLP-1(8-38); Gly$^8$Glu$^{38}$Arg$^{26,34}$Lys$^{39}$-GLP-1(8-39); Gly$^8$Glu$^{35}$Arg$^{26,34}$Lys$^{36}$-GLP-1(8-36); Gly$^8$Glu$^{35}$Arg$^{26,34}$Lys$^{36}$-GLP-1(8-36)amide; Gly$^8$Glu$^{36}$Arg$^{26,34}$Lys$^{37}$GLP-1(8-37); Gly$^8$Glu$^{37}$Arg$^{26,34}$Lys$^{38}$GLP-1(8-38); Gly$^8$Glu$^{38}$Arg$^{26,34}$Lys$^{39}$-GLP-1(8-39); Gly$^8$Asp$^{35}$Arg$^{26,34}$Lys$^{36}$-GLP-1(8-36); Gly$^8$Asp$^{35}$Arg$^{26,34}$Lys$^{36}$-GLP-1(8-36)amide; Gly$^8$Asp$^{36}$Arg$^{26,34}$Lys$^{37}$GLP-1(8-37); Gly$^8$Asp$^{37}$Arg$^{26,34}$Lys$^{3}$GLP-1(8-38); Gly$^8$Asp$^{38}$Arg$^{26,34}$Lys$^{39}$-GLP-1(8-39); Gly$^8$Asp$^{35}$Arg$^{26,34}$Lys$^{36}$-GLP-1(8-36); Gly$^8$Asp$^{35}$Arg$^{26,34}$Lys$^{36}$-GLP-1(8-36)amide; Gly$^8$Asp$^{36}$Arg$^{26,34}$Lys$^{37}$GLP-1(8-37); Gly$^8$Asp$^{37}$Arg$^{26,34}$Lys$^{38}$GLP-1(8-38); Gly$^8$Asp$^{38}$Arg$^{26,34}$Lys$^{39}$-GLP-1(8-39); Arg$^{26,34}$Lys$^{18}$-GLP-1(8-36); Arg$^{26,34}$Lys$^{18}$-GLP-1(8-36)amide; Arg$^{26,34}$Lys$^{18}$GLP-1(8-37); Arg$^{26,34}$Lys$^{18}$GLP-1(8-38); Gly$^8$Asp$^{19}$Arg$^{26,34}$Lys$^{18}$-GLP-1(8-36); Gly$^8$Asp$^{17}$Arg$^{26,34}$Lys$^{18}$-GLP-1(8-36); Gly$^8$Asp$^{19}$Arg$^{26,34}$Lys$^{18}$-GLP-1(8-36)amide; Gly$^8$Asp$^{17}$Arg$^{26,34}$Lys$^{18}$-GLP-1(8-36)amide; Gly$^8$Asp$^{19}$Arg$^{26,34}$Lys$^{18}$GLP-1(8-37); Gly$^8$Asp$^{19}$Arg$^{26,34}$Lys$^{18}$GLP-1(8-38); Gly$^8$Asp$^{17}$Arg$^{26,34}$Lys$^{18}$GLP-1(8-38); Arg$^{26,34}$Lys$^{23}$-GLP-1(8-36); Arg$^{26,34}$Lys$^{23}$-GLP-1(8-36)amide; Arg$^{26,34}$Lys$^{23}$GLP-1(8-37); Arg$^{26,34}$Lys$^{23}$GLP-1(8-38); Gly$^8$Asp$^{24}$Arg$^{26,34}$Lys$^{23}$-GLP-1(8-36); Gly$^8$Asp$^{22}$Arg$^{26,34}$Lys$^{23}$-GLP-1(8-36); Gly$^8$Asp$^{24}$Arg$^{26,34}$Lys$^{23}$-GLP-1(8-36)amide; Gly$^8$Asp$^{22}$Arg$^{26,34}$Lys$^{23}$-GLP-1(8-36)amide; Gly$^8$Asp$^{24}$Arg$^{26,34}$Lys$^{23}$GLP-1(8-37); Gly$^8$Asp$^{24}$Arg$^{26,34}$Lys$^{23}$GLP-1(8-38); Gly$^8$Asp$^{22}$Arg$^{26,34}$Lys$^{23}$GLP-1(8-38); Arg$^{26,34}$Lys$^{27}$-GLP-1(8-36); Arg$^{26,34}$Lys$^{27}$-GLP-1(8-36)amide; Arg$^{26,34}$Lys$^{27}$GLP-1(8-37); Arg$^{26,34}$Lys$^{27}$GLP-1(8-38); Gly$^8$Asp$^{28}$Arg$^{26,34}$Lys$^{27}$-GLP-1(8-36); Gly$^8$Asp$^{26}$Arg$^{26,34}$Lys$^{27}$-GLP-1(8-36); Gly$^8$Asp$^{28}$Arg$^{26,34}$Lys$^{27}$-GLP-1(8-36)amide; Gly$^8$Asp$^{26}$Arg$^{26,34}$Lys$^{27}$-GLP-1(8-36)amide; Gly$^8$Asp$^{28}$Arg$^{26,34}$Lys$^{27}$GLP-1(8-37); Gly$^8$Asp$^{28}$Arg$^{26,34}$Lys$^{27}$GLP-1(8-38); Gly$^8$Asp$^{26}$Arg$^{26,34}$Lys$^{27}$GLP-1(8-38); Arg$^{26,34}$Lys$^{18}$-GLP-1(8-36); Arg$^{26,34}$Lys$^{18}$-GLP-1(8-36)amide; Arg$^{26,34}$Lys$^{18}$GLP-1(8-37); Arg$^{26,34}$Lys$^{18}$GLP-1(8-38); Val$^8$Asp$^{19}$Arg$^{26,34}$Lys$^{18}$-GLP-1(8-36); Val$^8$Asp$^{17}$Arg$^{26,34}$Lys$^{18}$-GLP-1(8-36); Val$^8$Asp$^{19}$Arg$^{26,34}$Lys$^{18}$-GLP-1(8-36)amide; Val$^8$Asp$^{17}$Arg$^{26,34}$Lys$^{18}$-GLP-1(8-36)amide; Val$^8$Asp$^{19}$Arg$^{26,34}$Lys$^{18}$GLP-1(8-37); Val$^8$Asp$^{19}$Arg$^{26,34}$Lys$^{1}$GLP-1(8-38); Val$^8$Asp$^{17}$Arg$^{26,34}$Lys$^{1}$GLP-1(8-38); Arg$^{26,34}$Lys$^{23}$-GLP-1(8-36); Arg$^{26,34}$Lys$^{23}$-GLP-1(8-36)amide; Arg$^{26,34}$Lys$^{23}$GLP-1(8-37); Arg$^{26,34}$Lys$^{23}$GLP-1(8-38); Val$^8$Asp$^{24}$Arg$^{26,34}$Lys$^{23}$-GLP-1(8-36); Val$^8$Asp$^{22}$Arg$^{26,34}$Lys$^{23}$-GLP-1(8-36); Val$^8$Asp$^{24}$Arg$^{26,34}$Lys$^{23}$-GLP-1(8-36)amide; Val$^8$Asp$^{22}$Arg$^{26,34}$Lys$^{23}$-GLP-1(8-36)amide; Val$^8$Asp$^{24}$Arg$^{26,34}$Lys$^{23}$GLP-1(8-37); Val$^8$Asp$^{24}$Arg$^{26,34}$Lys$^{23}$GLP-1(8-38); Val$^8$Asp$^{22}$Arg$^{26,34}$Lys$^{23}$GLP-1(8-38); Arg$^{26,34}$Lys$^{27}$-GLP-1(8-36); Arg$^{26,34}$Lys$^{27}$-GLP-1(8-36)amide; Arg$^{26,34}$Lys$^{27}$GLP-1(8-37); Arg$^{26,34}$Lys$^{27}$GLP-1(8-38); Val$^8$Asp$^{28}$Arg$^{26,34}$Lys$^{27}$-GLP-1(8-36); Val$^8$Asp$^{26}$Arg$^{26,34}$Lys$^{27}$-GLP-1(8-36); Val$^8$Asp$^{28}$Arg$^{26,34}$Lys$^{27}$-GLP-1(8-36)amide; Val$^8$Asp$^{26}$Arg$^{26,34}$Lys$^{27}$-GLP-1(8-36)amide; Val$^8$Asp$^{28}$Arg$^{26,34}$Lys$^{27}$GLP-1(8-37); Val$^8$Asp$^{28}$Arg$^{26,34}$Lys$^{27}$GLP-1(8-38); Val$^8$Asp$^{26}$Arg$^{26,34}$Lys$^{27}$GLP-1

(8-38); Arg$^{26,34}$Lys$^{18}$-GLP-1(8-36); Arg$^{26,34}$Lys$^{18}$-GLP-1(8-36)amide; Arg$^{26,34}$Lys$^{18}$GLP-1(8-37); Arg$^{26,34}$Lys$^{18}$GLP-1(8-38); Ser$^8$Asp$^{19}$Arg$^{26,34}$Lys$^{18}$-GLP-1(8-36); Ser$^8$Asp$^{17}$Arg$^{26,34}$Lys$^{18}$-GLP-1(8-36); Ser$^8$Asp$^{19}$Arg$^{26,34}$Lys$^{18}$-GLP-1(8-36)amide; Ser$^8$Asp$^{17}$Arg$^{26,34}$Lys$^2$-GLP-1(8-36)amide; Ser$^8$Asp$^{19}$Arg$^{26,34}$Lys$^{18}$GLP-1(8-37); Ser$^8$Asp$^{19}$Arg$^{26,34}$Lys$^1$GLP-1(8-38); Ser$^8$Asp$^{17}$Arg$^{26,34}$Lys$^{17}$GLP-1(8-38); Arg$^{26,34}$Lys$^{23}$-GLP-1(8-36); Arg$^{26,34}$Lys$^{23}$-GLP-1(8-36)amide; Arg$^{26,34}$Lys$^{23}$GLP-1(8-37); Arg$^{26,34}$Lys$^{23}$GLP-1(8-38); Ser$^8$Asp$^{24}$Arg$^{26,34}$Lys$^{23}$-GLP-1(8-36); Ser$^8$Asp$^{22}$Arg$^{26,34}$Lys$^{23}$-GLP-1(8-36); Ser$^8$Asp$^{24}$Arg$^{26,34}$Lys$^{23}$-GLP-1(8-36)amide; Ser$^8$Asp$^{22}$Arg$^{26,34}$Lys$^{23}$-GLP-1(8-36)amide; Ser$^8$Asp$^{24}$Arg$^{26,34}$Lys$^{23}$GLP-1(8-37); Ser$^8$Asp$^{24}$Arg$^{26,34}$Lys$^{23}$GLP-1(8-38); Ser$^8$Asp$^{22}$Arg$^{26,34}$Lys$^{23}$GLP-1(8-38); Arg$^{26,34}$Lys$^{27}$-GLP-1(8-36); Arg$^{26,34}$Lys$^{27}$-GLP-1(8-36)amide; Arg$^{26,34}$Lys$^{27}$GLP-1(8-37); Arg$^{26,34}$Lys$^{27}$GLP-1(8-38); Ser$^8$Asp$^{28}$Arg$^{26,34}$Lys$^{27}$-GLP-1(8-36); Ser$^8$Asp$^{26}$Arg$^{26,34}$Lys$^{27}$-GLP-1(8-36); Ser$^8$Asp$^{28}$Arg$^{26,34}$Lys$^{27}$-GLP-1(8-36)amide; Ser$^8$Asp$^{26}$Arg$^{26,34}$Lys$^{27}$-GLP-1(8-36)amide; Ser$^8$Asp$^{28}$Arg$^{26,34}$Lys$^{27}$GLP-1(8-37); Ser$^8$Asp$^{28}$Arg$^{26,34}$Lys$^{27}$GLP-1(8-38); Ser$^8$Asp$^{26}$Arg$^{26,34}$Lys$^{27}$GLP-1(8-38); Arg$^{26,34}$Lys$^{18}$-GLP-1(8-36); Arg$^{26,34}$Lys$^{18}$-GLP-1(8-36)amide; Arg$^{26,34}$Lys$^{18}$-GLP-1(8-37); Arg$^{26,34}$Lys$^{18}$GLP-1(8-38); Thr$^8$Asp$^{19}$Arg$^{26,34}$Lys$^{18}$-GLP-1(8-36); Thr$^8$Asp$^{17}$Arg$^{26,34}$Lys$^{18}$-GLP-1(8-36); Thr$^8$Asp$^{19}$Arg$^{26,34}$Lys$^{18}$-GLP-1(8-36)amide; Thr$^8$Asp$^{17}$Arg$^{26,34}$Lys$^{18}$-GLP-1(8-36)amide; Thr$^8$Asp$^{19}$Arg$^{26,34}$Lys$^{18}$GLP-1(8-37); Thr$^8$Asp$^{19}$Arg$^{26,34}$Lys$^{18}$GLP-1(8-38); Thr$^8$Asp$^{17}$Arg$^{26,34}$Lys$^{18}$GLP-1(8-38); Arg$^{26,34}$Lys$^{23}$-GLP-1(8-36); Arg$^{26,34}$Lys$^{23}$-GLP-1(8-36)amide; Arg$^{26,34}$Lys$^{23}$GLP-1(8-37); Arg$^{26,34}$Lys$^{23}$GLP-1(8-38); Thr$^8$Asp$^{24}$Arg$^{26,34}$Lys$^{23}$-GLP-1(8-36); Thr$^8$Asp$^{22}$Arg$^{26,34}$Lys$^{23}$-GLP-1(8-36); Thr$^8$Asp$^{24}$Arg$^{26,34}$Lys$^{23}$-GLP-1(8-36)amide; Thr$^8$Asp$^{22}$Arg$^{26,34}$Lys$^{23}$-GLP-1(8-36)amide; Thr$^8$Asp$^{24}$Arg$^{26,34}$Lys$^{23}$GLP-1(8-37); Thr$^8$Asp$^{24}$Arg$^{26,34}$Lys$^{23}$GLP-1(8-38); Thr$^8$Asp$^{22}$Arg$^{26,34}$Lys$^{23}$GLP-1(8-38); Arg$^{26,34}$Lys$^{27}$-GLP-1(8-36); Arg$^{26,34}$Lys$^{27}$-GLP-1(8-36)amide; Arg$^{26,34}$Lys$^{27}$GLP-1(8-37); Arg$^{26,34}$Lys$^{27}$GLP-1(8-38); Thr$^8$Asp$^{28}$Arg$^{26,34}$Lys$^{27}$-GLP-1(8-36); Thr$^8$Asp$^{26}$Arg$^{26,34}$Lys$^{27}$-GLP-1(8-36); Thr$^8$Asp$^{28}$Arg$^{26,34}$Lys$^{27}$-GLP-1(8-36)amide; Thr$^8$Asp$^{26}$Arg$^{26,34}$Lys$^{27}$-GLP-1(8-36)amide; Thr$^8$Asp$^{28}$Arg$^{26,34}$Lys$^{27}$GLP-1(8-37); Thr$^8$Asp$^{28}$Arg$^{26,34}$Lys$^{27}$GLP-1(8-38); or Thr$^8$Asp$^{26}$Arg$^{26,34}$Lys$^{27}$GLP-1(8-38).

In a further preferred embodiment, the present invention relates to a GLP-1 derivative wherein the parent peptide is:
Arg$^{26}$Lys$^{36}$-GLP-1(8-36); Arg$^{34}$Lys$^{36}$-GLP-1(8-36); Arg$^{26}$Lys$^{36}$-GLP-1(8-37); Arg$^{34}$Lys$^{36}$-GLP-1(8-37); Arg$^{26}$Lys$^{37}$-GLP-1(8-37); Arg$^{34}$Lys$^{37}$-GLP-1(8-37); Arg$^{26}$Lys$^{39}$-GLP-1(8-39); Arg$^{34}$Lys$^{39}$-GLP-1(8-39); Arg$^{26,34}$Lys$^{36,39}$-GLP-1(8-39); Arg$^{26}$Lys$^{18}$GLP-1(8-36); Arg$^{34}$Lys$^{18}$-GLP-1(8-36); Arg$^{26}$Lys$^{18}$GLP-1(8-37); Arg$^{34}$Lys$^{18}$GLP-1(8-37); Arg$^{26}$Lys$^{18}$GLP-1(8-38); Arg$^{34}$Lys$^{18}$GLP-1(8-38); Arg$^{26}$Lys$^{18}$GLP-1(8-39); Arg$^{34}$Lys$^{18}$GLP-1(8-39); Arg$^{26}$Lys$^{23}$-GLP-1(8-36); Arg$^{34}$Lys$^{23}$-GLP-1(8-36); Arg$^{26}$Lys$^{23}$GLP-1(8-37); Arg$^{34}$Lys$^{23}$GLP-1(8-37); Arg$^{26}$Lys$^{23}$GLP-1(8-38); Arg$^{34}$Lys$^{23}$GLP-1(8-38); Arg$^{26}$Lys$^{23}$GLP-1(8-39); Arg$^{34}$Lys$^{23}$GLP-1(8-39); Arg$^{26}$Lys$^{27}$-GLP-1(8-36); Arg$^{26,34}$Lys$^{27}$-GLP-1(8-36); Arg$^{34}$Lys$^{27}$GLP-1(8-37); Arg$^{26}$Lys$^{27}$GLP-1(8-37); Arg$^{34}$Lys$^{27}$GLP-1(8-38); Arg$^{26}$Lys$^{27}$GLP-1(8-38); Arg$^{26}$Lys$^{27}$GLP-1(8-39); Arg$^{34}$Lys$^{27}$GLP-1(8-39); Arg$^{26,34}$Lys$^{18,36}$-GLP-1(8-36); Arg$^{26,34}$Lys$^{18}$GLP-1(8-37); Arg$^{26,34}$Lys$^{18,37}$GLP-1(8-37); Arg$^{26,34}$Lys$^{18,38}$GLP-1(8-38); Arg$^{26,34}$Lys$^{18,39}$GLP-1(8-39); Arg$^{26,34}$Lys$^{23,36}$-GLP-1(8-36); Arg$^{26,34}$Lys$^{23}$GLP-1(8-37); Arg$^{26,34}$Lys$^{23,37}$GLP-1(8-37); Arg$^{26,34}$Lys$^{23,38}$GLP-1(8-38); Arg$^{26,34}$Lys$^{23,39}$GLP-1(8-39); Arg$^{26,34}$Lys$^{27,36}$-GLP-1(8-36); Arg$^{26,34}$Lys$^{27}$GLP-1(8-37); Arg$^{26,34}$Lys$^{27,37}$GLP-1(8-37); Arg$^{26,34}$Lys$^{27,38}$GLP-1(8-38); Arg$^{26,34}$Lys$^{27,39}$GLP-1(8-39); Gly$^8$GLP-1(8-36); Gly$^8$GLP-1(8-37); Gly$^7$GLP-1(8-38); Gly$^8$GLP-1(8-39); Gly$^8$Arg$^{26}$Lys$^{36}$-GLP-1(8-36); Gly$^8$Arg$^{34}$Lys$^{36}$-GLP-1(8-36); Gly$^8$Arg$^{26}$Lys$^{36}$-GLP-1(8-3); Gly$^8$Arg$^{34}$Lys$^{36}$-GLP-1(8-37); Gly$^8$Arg$^{26}$Lys$^{37}$-GLP-1(8-37); Gly$^8$Arg$^{34}$Lys$^{37}$-GLP-1(8-37); Gly$^8$Arg$^{26}$Lys$^{39}$-GLP-1(8-39); Gly$^8$Arg$^{34}$Lys$^{39}$-GLP-1(8-39); Gly$^8$Arg$^{26,34}$Lys$^{36,39}$-GLP-1(8-39); Gly$^8$Arg$^{26}$Lys$^{18}$-GLP-1(8-36); Gly$^8$Arg$^{34}$Lys$^8$-GLP-1(8-36); Gly$^8$Arg$^{26}$Lys$^{18}$GLP-1(8-37); Gly$^8$Arg$^{34}$Lys$^{18}$GLP-1(8-37); Gly$^8$Arg$^{26}$Lys$^{18}$GLP-1(8-38); Gly$^8$Arg$^{34}$Lys$^{18}$GLP-1(8-38); Gly$^8$Arg$^{26}$Lys$^{18}$GLP-1(8-39); Gly$^8$Arg$^{34}$Lys$^{18}$GLP-1(8-39); Gly$^8$Arg$^{26}$Lys$^{23}$-GLP-1(8-36); Gly$^8$Arg$^{34}$Lys$^{23}$-GLP-1(8-36); Gly$^8$Arg$^{26}$Lys$^{23}$GLP-1(8-37); Gly$^8$Arg$^{34}$Lys$^{23}$GLP-1(8-37); Gly$^8$Arg$^{26}$Lys$^{23}$GLP-1(8-38); Gly$^8$Arg$^{34}$Lys$^{23}$GLP-1(8-38); Gly$^8$Arg$^{26}$Lys$^{23}$GLP-1(8-39); Gly$^8$Arg$^{34}$Lys$^{23}$GLP-1(8-39); Gly$^8$Arg$^{26}$Lys$^{27}$-GLP-1(8-36); Gly$^8$Arg$^{34}$Lys$^{27}$-GLP-1(8-36); Gly$^8$Arg$^{26}$Lys$^{27}$GLP-1(8-37); Gly$^8$Arg$^{34}$Lys$^{27}$GLP-1(8-37); Gly$^8$Arg$^{26}$Lys$^{27}$GLP-1(8-38); Gly$^8$Arg$^{34}$Lys$^{27}$GLP-1(8-38); Gly$^8$Arg$^{26}$Lys$^{27}$GLP-1(8-39); Gly$^8$Arg$^{34}$Lys$^{27}$GLP-1(8-39); Gly$^8$Arg$^{26,34}$Lys$^{18,36}$-GLP-1(8-36); Gly$^8$Arg$^{26,34}$Lys$^{18}$GLP-1(8-37); Gly$^8$Arg$^{26,34}$Lys$^{18,37}$GLP-1(8-37); Gly$^8$Arg$^{26,34}$Lys$^{18,38}$GLP-1(8-38); Gly$^8$Arg$^{26,34}$Lys$^{18,39}$GLP-1(8-39); Gly$^8$Arg$^{26,34}$Lys$^{23,36}$-GLP-1(8-36); Gly$^8$Arg$^{26,34}$Lys$^{23}$GLP-1(8-37); Gly$^8$Arg$^{26,34}$Lys$^{23,37}$GLP-1(8-37); Gly$^8$Arg$^{26,34}$Lys$^{23,38}$GLP-1(8-38); Gly$^8$Arg$^{26,34}$Lys$^{23,39}$GLP-1(8-39); Gly$^8$Arg$^{26,34}$Lys$^{27,36}$-GLP-1(8-36); Gly$^8$Arg$^{26,34}$Lys$^{27}$GLP-1(8-37); Gly$^8$Arg$^{26,34}$Lys$^{27,37}$GLP-1(8-37); Gly$^8$Arg$^{26,34}$Lys$^{27,38}$GLP-1(8-38); Gly$^8$Arg$^{26,34}$Lys$^{27,39}$GLP-1(8-39); Val$^8$GLP-1(8-36); Val$^8$GLP-1(8-37); Val$^8$GLP-1(8-38); Val$^8$GLP-1(8-39); Val$^8$Arg$^{26}$Lys$^{36}$-GLP-1(8-36); Val$^8$Arg$^{34}$Lys$^{36}$-GLP-1(7-36); Val$^8$Arg$^{26}$Lys$^{36}$-GLP-1(8-37); Val$^8$Arg$^{34}$Lys$^{36}$-GLP-1(8-37); Val$^8$Arg$^{26}$Lys$^{37}$-GLP-1(8-37); Val$^8$Arg$^{34}$Lys$^{37}$-GLP-1(8-37); Val$^8$Arg$^{26}$Lys$^{39}$-GLP-1(8-39); Val$^8$Arg$^{34}$Lys$^{39}$-GLP-1(8-39); Val$^8$Arg$^{26,34}$Lys$^{36,39}$-GLP-1(8-39); Val$^8$Arg$^{26}$Lys$^{18}$-GLP-1(8-36); Val$^8$Arg$^{34}$Lys$^{18}$-GLP-1(8-36); Val$^8$Arg$^{26}$Lys$^{18}$GLP-1(8-37); Val$^8$Arg$^{34}$Lys$^{18}$-GLP-1(8-37); Val$^8$Arg$^{26}$Lys$^{18}$GLP-1(8-38); Val$^8$Arg$^{34}$Lys$^{18}$GLP-1(8-38); Val$^8$Arg$^{26}$Lys$^{18}$GLP-1(8-39); Val$^8$Arg$^{34}$Lys$^{18}$GLP-1(8-39); Val$^8$Arg$^{26}$Lys$^{23}$-GLP-1(8-36); Val$^8$Arg$^{34}$Lys$^{23}$-GLP-1(8-36); Val$^8$Arg$^{26}$Lys$^{23}$GLP-1(8-37); Val$^8$Arg$^{34}$Lys$^{23}$GLP-1(8-37); Val$^8$Arg$^{26}$Lys$^{23}$GLP-1(8-38); Val$^8$Arg$^{34}$Lys$^{23}$GLP-1(8-38); Val$^8$Arg$^{26}$Lys$^{23}$GLP-1(8-39); Val$^8$Arg$^{34}$Lys$^{23}$GLP-1(8-39); Val$^8$Arg$^{26}$Lys$^{27}$-GLP-1(8-36); Val$^8$Arg$^{34}$Lys$^{27}$-GLP-1(8-36); Val$^8$Arg$^{26}$Lys$^{27}$GLP-1(8-37); Val$^8$Arg$^{34}$Lys$^{27}$GLP-1(8-37); Val$^8$Arg$^{26}$Lys$^{27}$GLP-1(8-38); Val$^8$Arg$^{34}$Lys$^{27}$GLP-1(8-38); Val$^8$Arg$^{26}$Lys$^{27}$GLP-1(8-39); Val$^8$Arg$^{34}$Lys$^{27}$GLP-1(8-39); Val$^8$Arg$^{26,34}$Lys$^{18,36}$-GLP-1(8-36); Val$^8$Arg$^{26,34}$Lys$^{18}$GLP-1(8-37); Val$^8$Arg$^{26,34}$Lys$^{8,37}$GLP-1(8-37); Val$^8$Arg$^{26,34}$Lys$^{18,38}$GLP-1(8-38); Val$^8$Arg$^{26,34}$Lys$^{18,39}$GLP-1(8-39); Val$^8$Arg$^{26,34}$Lys$^{23,36}$-GLP-1(8-36); Val$^8$Arg$^{26,34}$Lys$^{23}$GLP-1(8-37); Val$^8$Arg$^{26,34}$Lys$^{23,37}$GLP-1(8-37); Val$^8$Arg$^{26,34}$Lys$^{23,38}$GLP-1(8-38); Val$^8$Arg$^{26,34}$Lys$^{23,39}$GLP-1(8-39); Val$^8$Arg$^{26,34}$Lys$^{27,36}$-GLP-1(8-36); Val$^8$Arg$^{26,34}$Lys$^{27}$GLP-1(8-37); Val$^8$Arg$^{26,34}$Lys$^{27,37}$GLP-1(8-37); Val$^8$Arg$^{26,34}$Lys$^{27,38}$GLP-1(8-38); or Val$^8$Arg$^{26,34}$Lys$^{27,39}$GLP-1(8-39).

In a further preferred embodiment, the GLP-1 derivative is Lys$^{26}$(N$^\epsilon$-tetradecanoyl)-GLP-1(7-37).

In a further preferred embodiment, the GLP-1 derivative is Lys$^{3}$(N$^\epsilon$-tetradecanoyl)-GLP-1(7-37).

In a further preferred embodiment, the GLP-1 derivative is Lys$^{26,34}$-bis(N$^\epsilon$-tetradecanoyl)-GLP-1(7-37).

In a further preferred embodiment, the GLP-1 derivative is Gly$^{8}$Lys$^{26}$-(N$^\epsilon$-tetradecanoyl)-GLP-1(7-37).

In a further preferred embodiment, the GLP-1 derivative is Gly$^{8}$Lys$^{34}$(N$^\epsilon$-tetradecanoyl)-GLP-1(7-37).

In a further preferred embodiment, the GLP-1 derivative is Gly$^{8}$Lys$^{26,34}$-bis(N$^\epsilon$-tetradecanoyl)-GLP-1(7-37).

In a further preferred embodiment, the GLP-1 derivative is Arg$^{26}$Lys$^{34}$(N$^\epsilon$-tetradecanoyl)-GLP-1(7-37).

In a further preferred embodiment, the GLP-1 derivative is Lys$^{26}$(N$^\epsilon$-tetradecanoyl)-GLP-1(7-38).

In a further preferred embodiment, the GLP-1 derivative is Lys$^{34}$(N$^\epsilon$-tetradecanoyl)-GLP-1(7-38).

In a further preferred embodiment, the GLP-1 derivative is Lys$^{26,34}$-bis(N$^\epsilon$-tetradecanoyl)-GLP-1(7-38).

In a further preferred embodiment, the GLP-1 derivative is Gly$^{8}$Lys$^{26}$(N$^\epsilon$-tetradecanoyl)-GLP-1(7-38).

In a further preferred embodiment, the GLP-1 derivative is Gly$^{8}$Lys$^{34}$(N$^\epsilon$-tetradecanoyl)-GLP-1(7-38).

In a further preferred embodiment, the GLP-1 derivative is Gly$^{8}$Lys$^{26,34}$-bis(N$^\epsilon$-tetradecanoyl)-GLP-1(7-38).

In a further preferred embodiment, the GLP-1 derivative is Arg$^{26}$Lys$^{34}$(N$^\epsilon$-tetradecanoyl)-GLP-1(7-38).

In a further preferred embodiment, the GLP-1 derivative is Lys$^{26}$(N$^\epsilon$-tetradecanoyl)-GLP-1(7-39).

In a further preferred embodiment, the GLP-1 derivative is Lys$^{34}$(N$^\epsilon$-tetradecanoyl)-GLP-1(7-39).

In a further preferred embodiment, the GLP-1 derivative is Lys$^{26,34}$-bis(N$^\epsilon$-tetradecanoyl)-GLP-1(7-39).

In a further preferred embodiment, the GLP-1 derivative is Gly$^{8}$Lys$^{26}$(N$^\epsilon$-tetradecanoyl)-GLP-1(7-39).

In a further preferred embodiment, the GLP-1 derivative is Gly$^{8}$Lys$^{34}$(N$^\epsilon$-tetradecanoyl)-GLP-1(7-39).

In a further preferred embodiment, the GLP-1 derivative is Gly$^{8}$Lys$^{26,34}$-bis(N$^\epsilon$-tetradecanoyl)-GLP-1(7-39).

In a further preferred embodiment, the GLP-1 derivative is Arg$^{26}$Lys$^{34}$(N$^\epsilon$-tetradecanoyl)-GLP-1(7-39).

In a further preferred embodiment, the GLP-1 derivative is Lys$^{26}$(N$^\epsilon$-tetradecanoyl)-GLP-1(7-40).

In a further preferred embodiment, the GLP-1 derivative is Lys$^{26,34}$-bis(N$^\epsilon$-tetradecanoyl)-GLP-1(7-40).

In a further preferred embodiment, the GLP-1 derivative is Gly$^{8}$Lys$^{26}$(N$^\epsilon$-tetradecanoyl)-GLP-1(7-40).

In a further preferred embodiment, the GLP-1 derivative is Gly$^{8}$Lys$^{34}$(N$^\epsilon$-tetradecanoyl)-GLP-1(7-40).

In a further preferred embodiment, the GLP-1 derivative is Gly$^{8}$Lys$^{26,34}$-bis(N$^\epsilon$-tetradecanoyl)-GLP-1(7-40).

In a further preferred embodiment, the GLP-1 derivative is Arg$^{26}$Lys$^{34}$(N$^\epsilon$-tetradecanoyl)-GLP-1(7-40).

In a further preferred embodiment, the GLP-1 derivative is Lys$^{26}$(N$^\epsilon$-tetradecanoyl)-GLP-1(7-36).

In a further preferred embodiment, the GLP-1 derivative is Lys$^{34}$(N$^\epsilon$-tetradecanoyl)-GLP-1(7-36).

In a further preferred embodiment, the GLP-1 derivative is Lys$^{26,34}$-bis(N$^\epsilon$-tetradecanoyl)-GLP-1(7-36).

In a further preferred embodiment, the GLP-1 derivative is Gly$^{8}$Lys$^{26,34}$-bis(N$^\epsilon$-tetradecanoyl)-GLP-1(7-36).

In a further preferred embodiment, the GLP-1 derivative is Gly$^{8}$Lys$^{34}$(N$^\epsilon$-tetradecanoyl)-GLP-1(7-36).

In a further preferred embodiment, the GLP-1 derivative is Gly$^{8}$Lys$^{26,34}$-bis(N$^\epsilon$-tetradecanoyl)-GLP-1(7-36).

In a further preferred embodiment, the GLP-1 derivative is Arg$^{26}$Lys$^{34}$(N$^\epsilon$-tetradecanoyl)-GLP-1(7-36).

In a further preferred embodiment, the GLP-1 derivative is Lys$^{26}$(N$^\epsilon$-tetradecanoyl)-GLP-1(7-35).

In a further preferred embodiment, the GLP-1 derivative is Lys$^{34}$(N$^\epsilon$-tetradecanoyl)-GLP-1(7-35).

In a further preferred embodiment, the GLP-1 derivative is Lys$^{26,34}$-bis(N$^\epsilon$-tetradecanoyl)-GLP-1(7-35).

In a further preferred embodiment, the GLP-1 derivative is Gly$^{8}$Lys$^{26}$(N$^\epsilon$-tetradecanoyl)-GLP-1(7-35).

In a further preferred embodiment, the GLP-1 derivative is Gly$^{8}$Lys$^{34}$(N$^\epsilon$-tetradecanoyl)-GLP-1(7-35).

In a further preferred embodiment, the GLP-1 derivative is Gly$^{8}$Lys$^{26,34}$-bis(N$^\epsilon$-tetradecanoyl)-GLP-1(7-35).

In a further preferred embodiment, the GLP-1 derivative is Arg$^{26}$Lys$^{34}$(N$^\epsilon$-tetradecanoyl)-GLP-1(7-35).

In a further preferred embodiment, the GLP-1 derivative is Lys$^{26}$(N$^\epsilon$-tetradecanoyl)-GLP-1(7-36)amide.

In a further preferred embodiment, the GLP-1 derivative is Lys$^{34}$(N$^\epsilon$-tetradecanoyl)-GLP-1(7-36)amide.

In a further preferred embodiment, the GLP-1 derivative is Lys$^{26,34}$-bis(N$^\epsilon$-tetradecanoyl)-GLP-1(7-36)amide.

In a further preferred embodiment, the GLP-1 derivative is Gly$^{8}$Lys$^{26}$(N$^\epsilon$-tetradecanoyl)-GLP-1(7-36)amide.

In a further preferred embodiment, the GLP-1 derivative is Gly$^{8}$Lys$^{34}$(N$^\epsilon$-tetradecanoyl)-GLP-1(7-36)amide.

In a further preferred embodiment, the GLP-1 derivative is Gly$^{8}$Lys$^{26,34}$-bis(N$^\epsilon$-tetradecanoyl)-GLP-1(7-36)amide.

In a further preferred embodiment, the GLP-1 derivative is Arg$^{26}$Lys$^{34}$(N$^\epsilon$-tetradecanoyl)-GLP-1(7-36)amide.

In a further preferred embodiment, the GLP-1 derivative is Gly$^{8}$Arg$^{26}$Lys$^{34}$(N$^\epsilon$-tetradecanoyl)-GLP-1(7-37).

In a further preferred embodiment, the GLP-1 derivative is Lys$^{26}$(N$^\epsilon$-tetradecanoyl)Arg$^{34}$-GLP-1(7-37).

In a further preferred embodiment, the GLP-1 derivative is Gly$^{8}$Lys$^{26}$(N$^\epsilon$-tetradecanoyl)Arg$^{34}$-GLP-1(7-37).

In a further preferred embodiment, the GLP-1 derivative is Arg$^{26,34}$Lys$^{36}$(N$^\epsilon$-tetradecanoyl)-GLP-1(7-37).

In a further preferred embodiment, the GLP-1 derivative is Gly$^{8}$Arg$^{26,34}$Lys$^{36}$(N$^\epsilon$-tetradecanoyl)-GLP-1(7-37).

In a further preferred embodiment, the GLP-1 derivative is Gly$^{8}$Arg$^{26}$Lys$^{34}$(N$^\epsilon$-tetradecanoyl)-GLP-1(7-38).

In a further preferred embodiment, the GLP-1 derivative is Lys$^{26}$(N$^\epsilon$-tetradecanoyl)Arg$^{34}$-GLP-1(7-38).

In a further preferred embodiment, the GLP-1 derivative is Gly$^{8}$Lys$^{26}$(N$^\epsilon$-tetradecanoyl)Arg$^{34}$-GLP-1(7-38).

In a further preferred embodiment, the GLP-1 derivative is Arg$^{26,34}$Lys$^{36}$(N$^\epsilon$-tetradecanoyl)-GLP-1(7-38).

In a further preferred embodiment, the GLP-1 derivative is Arg$^{26,34}$Lys$^{38}$(N$^\epsilon$-tetradecanoyl)-GLP-1(7-38).

In a further preferred embodiment, the GLP-1 derivative is Gly$^{8}$Arg$^{26,34}$Lys$^{36}$(N$^\epsilon$-tetradecanoyl)-GLP-1(7-38).

In a further preferred embodiment, the GLP-1 derivative is Gly$^{8}$Arg$^{26}$Lys$^{34}$(N$^\epsilon$-tetradecanoyl)-GLP-1(7-39).

In a further preferred embodiment, the GLP-1 derivative is Lys$^{26}$(N$^\epsilon$-tetradecanoyl)Arg$^{34}$-GLP-1(7-39).

In a further preferred embodiment, the GLP-1 derivative is Gly$^{8}$Lys$^{26}$(N$^\epsilon$-tetradecanoyl)Arg$^{34}$-GLP-1(7-39).

In a further preferred embodiment, the GLP-1 derivative is Arg$^{26,34}$Lys$^{36}$(N$^\epsilon$-tetradecanoyl)-GLP-1(7-39).

In a further preferred embodiment, the GLP-1 derivative is Gly$^{8}$Arg$^{26,34}$Lys$^{36}$(N$^\epsilon$-tetradecanoyl)-GLP-1(7-39).

In a further preferred embodiment, the GLP-1 derivative is Gly$^{8}$Arg$^{26}$Lys$^{34}$(N$^\epsilon$-tetradecanoyl)-GLP-1(7-40).

In a further preferred embodiment, the GLP-1 derivative is Lys$^{26}$(N$^\epsilon$-tetradecanoyl)Arg$^{34}$-GLP-1(7-40).

In a further preferred embodiment, the GLP-1 derivative is Gly$^8$Lys$^{26}$(N$^\epsilon$-tetradecanoyl)Arg$^{34}$-GLP-1(7-40).

In a further preferred embodiment, the GLP-1 derivative is Arg$^{26,34}$Lys$^{36}$(N$^\epsilon$-tetradecanoyl)-GLP-1(7-40).

In a further preferred embodiment, the GLP-1 derivative is Gly$^8$Arg$^{26,34}$Lys$^{36}$(N$^\epsilon$-tetradecanoyl)-GLP-1(7-40).

In a further preferred embodiment, the GLP-1 derivative is Lys$^{26}$(N$^\epsilon$-(ω-carboxynonadecanoyl))-GLP-1(7-37).

In a further preferred embodiment, the GLP-1 derivative is Lys$^{34}$(N$^\epsilon$-(ω-carboxynonadecanoyl))-GLP-1(7-37).

In a further preferred embodiment, the GLP-1 derivative is Lys$^{26,34}$-bis(N$^\epsilon$-(ω-carboxynonadecanoyl))-GLP-1(7-37).

In a further preferred embodiment, the GLP-1 derivative is Gly$^8$Lys$^{26}$(N$^\epsilon$-(ω-carboxynonadecanoyl))-GLP-1(7-37).

In a further preferred embodiment, the GLP-1 derivative is Gly$^8$Lys$^{34}$(N$^\epsilon$-(ω-carboxynonadecanoyl))-GLP-1(7-37).

In a further preferred embodiment, the GLP-1 derivative is Gly$^8$Lys$^{26,34}$-bis(N$^\epsilon$-(ω-carboxynonadecanoyl))-GLP-1(7-37).

In a further preferred embodiment, the GLP-1 derivative is Lys$^{26}$(N$^\epsilon$-(ω-carboxynonadecanoyl))-GLP-1(7-38).

In a further preferred embodiment, the GLP-1 derivative is Lys$^{34}$(N$^\epsilon$-(ω-carboxynonadecanoyl))-GLP-1(7-38).

In a further preferred embodiment, the GLP-1 derivative is Lys$^{26,34}$-bis(N$^\epsilon$-(ω-carboxynonadecanoyl))-GLP-1(7-38).

In a further preferred embodiment, the GLP-1 derivative is Gly$^8$Lys$^{26}$(N$^\epsilon$-(ω-carboxynonadecanoyl))-GLP-1(7-38).

In a further preferred embodiment, the GLP-1 derivative is Gly$^8$Lys$^{34}$(N$^\epsilon$-(ω-carboxynonadecanoyl))-GLP-1(7-38).

In a further preferred embodiment, the GLP-1 derivative is Gly$^8$Lys$^{26,34}$-bis(N$^\epsilon$-(ω-carboxynonadecanoyl))-GLP-1(7-38).

In a further preferred embodiment, the GLP-1 derivative is Lys$^{26}$(N$^\epsilon$-(ω-carboxynonadecanoyl))-GLP-1(7-39).

In a further preferred embodiment, the GLP-1 derivative is Lys$^{34}$(N$^\epsilon$-(ω-carboxynonadecanoyl))-GLP-1(7-39).

In a further preferred embodiment, the GLP-1 derivative is Lys$^{26,34}$-bis(N$^\epsilon$-(ω-carboxynonadecanoyl))-GLP-1(7-39).

In a further preferred embodiment, the GLP-1 derivative is Gly$^8$Lys$^{26}$(N$^\epsilon$-(ω-carboxynonadecanoyl))-GLP-1(7-39).

In a further preferred embodiment, the GLP-1 derivative is Gly$^8$Lys$^{34}$(N$^\epsilon$-(ω-carboxynonadecanoyl))-GLP-1(7-39).

In a further preferred embodiment, the GLP-1 derivative is Gly$^8$Lys$^{26,34}$-bis(N$^\epsilon$-(ω-carboxynonadecanoyl))-GLP-1(7-39).

In a further preferred embodiment, the GLP-1 derivative is Lys$^{34}$(N$^\epsilon$-(ω-carboxynonadecanoyl))-GLP-1(7-40).

In a further preferred embodiment, the GLP-1 derivative is Lys$^{34}$(N$^\epsilon$-(ω-carboxynonadecanoyl))-GLP-1(7-40).

In a further preferred embodiment, the GLP-1 derivative is Lys$^{26,34}$-bis(N$^\epsilon$-(ω-carboxynonadecanoyl))-GLP-1(7-40).

In a further preferred embodiment, the GLP-1 derivative is Gly$^8$Lys$^{26}$(N$^\epsilon$-(ω-carboxynonadecanoyl))-GLP-1(7-40).

In a further preferred embodiment, the GLP-1 derivative is Gly$^8$Lys$^{34}$(N$^\epsilon$-(ω-carboxynonadecanoyl))-GLP-1(7-40).

In a further preferred embodiment, the GLP-1 derivative is Gly$^8$Lys$^{26,34}$-bis(N$^\epsilon$-(ω-carboxynonadecanoyl))-GLP-1(7-40).

In a further preferred embodiment, the GLP-1 derivative is Lys$^{26}$(N$^\epsilon$-(ω-carboxynonadecanoyl))-GLP-1(7-36).

In a further preferred embodiment, the GLP-1 derivative is Lys$^{34}$(N$^\epsilon$-(ω-carboxynonadecanoyl))-GLP-1(7-36).

In a further preferred embodiment, the GLP-1 derivative is Lys$^{26,34}$-bis(N$^\epsilon$-(ω-carboxynonadecanoyl))-GLP-1(7-36).

In a further preferred embodiment, the GLP-1 derivative is Gly$^8$Lys$^{26}$(N$^\epsilon$-(ω-carboxynonadecanoyl))-GLP-1(7-36).

In a further preferred embodiment, the GLP-1 derivative is Gly$^8$Lys$^{34}$(N$^\epsilon$-(ω-carboxynonadecanoyl))-GLP-1(7-36).

In a further preferred embodiment, the GLP-1 derivative is Gly$^8$Lys$^{26,34}$-bis(N$^\epsilon$-(ω-carboxynonadecanoyl))-GLP-1(7-36).

In a further preferred embodiment, the GLP-1 derivative is Lys$^{26}$(N$^\epsilon$-(ω-carboxynonadecanoyl))-GLP-1(7-36)amide.

In a further preferred embodiment, the GLP-1 derivative is Lys$^{34}$(N$^\epsilon$-(ω-carboxynonadecanoyl))-GLP-1(7-36)amide.

In a further preferred embodiment, the GLP-1 derivative is Lys$^{26,34}$-bis(N$^\epsilon$-(ω-carboxynonadecanoyl))-GLP-1(7-36)amide.

In a further preferred embodiment, the GLP-1 derivative is Gly$^8$Lys$^{26}$(N$^\epsilon$-(ω-carboxynonadecanoyl))-GLP-1(7-36)amide.

In a further preferred embodiment, the GLP-1 derivative is Gly$^8$Lys$^{34}$(N$^\epsilon$-(ω-carboxynonadecanoyl))-GLP-1(7-36)amide.

In a further preferred embodiment, the GLP-1 derivative is Gly$^8$Lys$^{26,34}$-bis(N$^\epsilon$-(ω-carboxynonadecanoyl))-GLP-1(7-36)amide.

In a further preferred embodiment, the GLP-1 derivative is Lys$^{26}$(N$^\epsilon$-(ω-carboxynonadecanoyl))-GLP-1(7-35).

In a further preferred embodiment, the GLP-1 derivative is Lys$^{34}$(N$^\epsilon$-(ω-carboxynonadecanoyl))-GLP-1(7-35).

In a further preferred embodiment, the GLP-1 derivative is Lys$^{26,34}$-bis(N$^\epsilon$-(ω-carboxynonadecanoyl))-GLP-1(7-35).

In a further preferred embodiment, the GLP-1 derivative is Gly$^8$Lys$^{26}$(N$^\epsilon$-(ω-carboxynonadecanoyl))-GLP-1(7-35).

In a further preferred embodiment, the GLP-1 derivative is Gly$^8$Lys$^{34}$(N$^\epsilon$-(ω-carboxynonadecanoyl))-GLP-1(7-35).

In a further preferred embodiment, the GLP-1 derivative is Gly$^8$Lys$^{26,34}$-bis(N$^\epsilon$-(ω-carboxynonadecanoyl))-GLP-1(7-35).

In a further preferred embodiment, the GLP-1 derivative is Arg$^{26}$Lys$^{34}$(N$^\epsilon$-(ω-carboxynonadecanoyl))-GLP-1(7-37).

In a further preferred embodiment, the GLP-1 derivative is Gly$^8$Arg$^{26}$Lys$^{34}$(N$^\epsilon$-(ω-carboxynonadecanoyl))-GLP-1(7-37).

In a further preferred embodiment, the GLP-1 derivative is Lys$^{26}$(N$^\epsilon$-(ω-carboxynonadecanoyl))Arg$^{34}$-GLP-1(7-37).

In a further preferred embodiment, the GLP-1 derivative is Gly$^8$Lys$^{26}$(N$^\epsilon$-(ω-carboxynonadecanoyl))Arg$^{34}$-GLP-1(7-37).

In a further preferred embodiment, the GLP-1 derivative is Arg$^{26,34}$Lys$^{36}$(N$^\epsilon$-(ω-carboxynonadecanoyl))-GLP-1(7-37).

In a further preferred embodiment, the GLP-1 derivative is Gly$^8$Arg$^{26,34}$Lys$^{36}$(N$^\epsilon$-(ω-carboxynonadecanoyl))-GLP-1(7-37).

In a further preferred embodiment, the GLP-1 derivative is Arg$^{26}$Lys$^{34}$(N$^\epsilon$-(ω-carboxynonadecanoyl))-GLP-1(7-38).

In a further preferred embodiment, the GLP-1 derivative is Gly$^8$Arg$^{26}$Lys$^{34}$(N$^\epsilon$-(ω-carboxynonadecanoyl))-GLP-1(7-38).

In a further preferred embodiment, the GLP-1 derivative is Lys$^{26}$(N$^\epsilon$-(ω-carboxynonadecanoyl))Arg$^{34}$-GLP-1(7-38).

In a further preferred embodiment, the GLP-1 derivative is Gly$^8$Lys$^{26}$(N$^\epsilon$-(ω-carboxynonadecanoyl))Arg$^{34}$-GLP-1(7-38).

In a further preferred embodiment, the GLP-1 derivative is Arg$^{26,34}$Lys$^{36}$(N$^\epsilon$-(ω-carboxynonadecanoyl))-GLP-1(7-38).

In a further preferred embodiment, the GLP-1 derivative is Arg$^{26,34}$Lys$^{38}$(N$^\epsilon$-(ω-carboxynonadecanoyl))-GLP-1(7-38).

In a further preferred embodiment, the GLP-1 derivative is Gly$^8$Arg$^{26,34}$Lys$^{36}$(N$^\epsilon$-(ω-carboxynonadecanoyl))-GLP-1(7-38).

In a further preferred embodiment, the GLP-1 derivative is Arg$^{26}$Lys$^{34}$(N$^\epsilon$-(ω-carboxynonadecanoyl))-GLP-1(7-39).

In a further preferred embodiment, the GLP-1 derivative is Gly$^8$Arg$^{26}$Lys$^{34}$(N$^\epsilon$-(ω-carboxynonadecanoyl))-GLP-1(7-39).

In a further preferred embodiment, the GLP-1 derivative is Lys$^{26}$(N$^\epsilon$-(ω-carboxynonadecanoyl))Arg$^{34}$-GLP-1(7-39).

In a further preferred embodiment, the GLP-1 derivative is Gly$^8$Lys$^{26}$(N$^\epsilon$-(ω-carboxynonadecanoyl))Arg$^{34}$-GLP-1(7-39).

In a further preferred embodiment, the GLP-1 derivative is Arg$^{26,34}$Lys$^{36}$-(N$^\epsilon$(ω-carboxynonadecanoyl))-GLP-1(7-39).

In a further preferred embodiment, the GLP-1 derivative is Gly$^8$Arg$^{26,34}$Lys$^{36}$(N$^\epsilon$-(ω-carboxynonadecanoyl))-GLP-1(7-39).

In a further preferred embodiment, the GLP-1 derivative is Arg$^{26}$Lys$^{34}$(N$^\epsilon$-(ω-carboxynonadecanoyl))-GLP-1(7-40).

In a further preferred embodiment, the GLP-1 derivative is Gly$^8$Arg$^{26}$Lys$^{34}$(N$^\epsilon$-(ω-carboxynonadecanoyl))-GLP-1(7-40).

In a further preferred embodiment, the GLP-1 derivative is Lys$^{26}$(N$^\epsilon$-(ω-carboxynonadecanoyl))Arg$^{34}$-GLP-1(7-40).

In a further preferred embodiment, the GLP-1 derivative is Gly$^8$Lys$^{26}$(N$^\epsilon$-(ω-carboxynonadecanoyl))Arg$^{34}$-GLP-1(7-40).

In a further preferred embodiment, the GLP-1 derivative is Arg$^{26,34}$Lys$^{36}$-(N$^\epsilon$-(ω-carboxynonadecanoyl))-GLP-1(7-40).

In a further preferred embodiment, the GLP-1 derivative is Gly$^8$Arg$^{26,34}$Lys$^{36}$(N$^\epsilon$-(ω-carboxynonadecanoyl))-GLP-1(7-40).

In a further preferred embodiment, the GLP-1 derivative is Lys$^{26}$(N$^\epsilon$-(7-deoxycholoyl))-GLP-1(7-37).

In a further preferred embodiment, the GLP-1 derivative is Lys$^{34}$(N$^\epsilon$-(7-deoxycholoyl))-GLP-1(7-37).

In a further preferred embodiment, the GLP-1 derivative is Lys$^{26,34}$-bis(N$^\epsilon$-(7-deoxycholoyl))-GLP-1(7-37).

In a further preferred embodiment, the GLP-1 derivative is Gly$^8$Lys$^{26}$(N$^\epsilon$-(7-deoxycholoyl))-GLP-1(7-37).

In a further preferred embodiment, the GLP-1 derivative is Gly$^8$Lys$^{34}$(N$^\epsilon$-(7-deoxycholoyl))-GLP-1(7-37).

In a further preferred embodiment, the GLP-1 derivative is Gly$^8$Lys$^{26,34}$-bis(N$^\epsilon$-(7-deoxycholoyl))-GLP-1(7-37).

In a further preferred embodiment, the GLP-1 derivative is Arg$^{26}$Lys$^{34}$(N$^\epsilon$-(7-deoxycholoyl))-GLP-1(7-37).

In a further preferred embodiment, the GLP-1 derivative is Lys$^{26}$(N$^\epsilon$-(7-deoxycholoyl))-GLP-1(7-38).

In a further preferred embodiment, the GLP-1 derivative is Lys$^{34}$(N$^\epsilon$-(7-deoxycholoyl))-GLP-1(7-38).

In a further preferred embodiment, the GLP-1 derivative is Lys$^{26,34}$-bis(N$^\epsilon$-(7-deoxycholoyl))-GLP-1(7-38).

In a further preferred embodiment, the GLP-1 derivative is Gly$^8$Lys$^{26}$(N$^\epsilon$-(7-deoxycholoyl))-GLP-1(7-38).

In a further preferred embodiment, the GLP-1 derivative is Gly$^8$Lys$^{34}$(N$^\epsilon$-(7-deoxycholoyl))-GLP-1(7-38).

In a further preferred embodiment, the GLP-1 derivative is Gly$^8$Lys$^{26,34}$-bis(N$^\epsilon$-(7-deoxycholoyl))-GLP-1(7-38).

In a further preferred embodiment, the GLP-1 derivative is Arg$^{26}$Lys$^{34}$(N$^\epsilon$-(7-deoxycholoyl))-GLP-1(7-38).

In a further preferred embodiment, the GLP-1 derivative is Lys$^{26}$(N$^\epsilon$-(7-deoxycholoyl))-GLP-1(7-39).

In a further preferred embodiment, the GLP-1 derivative is Lys$^{34}$(N$^\epsilon$-(7-deoxycholoyl))-GLP-1(7-39).

In a further preferred embodiment, the GLP-1 derivative is Lys$^{26,34}$-bis(N$^\epsilon$-(7-deoxycholoyl))-GLP-1(7-39).

In a further preferred embodiment, the GLP-1 derivative is Gly$^8$Lys$^{26}$(N$^\epsilon$-(7-deoxycholoyl))-GLP-1(7-39).

In a further preferred embodiment, the GLP-1 derivative is Gly$^8$Lys$^{34}$(N$^\epsilon$-(7-deoxycholoyl))-GLP-1(7-39).

In a further preferred embodiment, the GLP-1 derivative is Gly$^8$Lys$^{26,34}$-bis(N$^\epsilon$-(7-deoxycholoyl))-GLP-1(7-39).

In a further preferred embodiment, the GLP-1 derivative is Arg$^{26}$Lys$^{34}$(N$^\epsilon$-(7-deoxycholoyl))-GLP-1(7-39).

In a further preferred embodiment, the GLP-1 derivative is Lys$^{26}$(N$^\epsilon$-(7-deoxycholoyl))-GLP-1(7-40).

In a further preferred embodiment, the GLP-1 derivative is Lys$^{34}$(N$^\epsilon$-(7-deoxycholoyl))-GLP-1(7-40).

In a further preferred embodiment, the GLP-1 derivative is Lys$^{26,34}$-bis(N$^\epsilon$-(7-deoxycholoyl))-GLP-1(7-40).

In a further preferred embodiment, the GLP-1 derivative is Gly$^8$Lys$^{26}$(N$^\epsilon$-(7-deoxycholoyl))-GLP-1(7-40).

In a further preferred embodiment, the GLP-1 derivative is Gly$^8$Lys$^{34}$(N$^\epsilon$-(7-deoxycholoyl))-GLP-1(7-40).

In a further preferred embodiment, the GLP-1 derivative is Gly$^8$Lys$^{26,34}$-bis(N$^\epsilon$-(7-deoxycholoyl))-GLP-1(7-40).

In a further preferred embodiment, the GLP-1 derivative is Arg$^{26}$Lys$^{34}$(N$^\epsilon$-(7-deoxycholoyl))-GLP-1(7-40).

In a further preferred embodiment, the GLP-1 derivative is Lys$^{26}$(N$^\epsilon$-(7-deoxycholoyl))-GLP-1(7-36).

In a further preferred embodiment, the GLP-1 derivative is Lys$^{34}$(N$^\epsilon$-(7-deoxycholoyl))-GLP-1(7-36).

In a further preferred embodiment, the GLP-1 derivative is Lys$^{26,34}$-bis(N$^\epsilon$-(7-deoxycholoyl))-GLP-1(7-36).

In a further preferred embodiment, the GLP-1 derivative is Gly$^8$Lys$^{26}$(N$^\epsilon$-(7-deoxycholoyl))-GLP-1(7-36).

In a further preferred embodiment, the GLP-1 derivative is Gly$^8$Lys$^{34}$(N$^\epsilon$-(7-deoxycholoyl))-GLP-1(7-36).

In a further preferred embodiment, the GLP-1 derivative is Gly$^8$Lys$^{26,34}$-bis(N$^\epsilon$-(7-deoxycholoyl))-GLP-1(7-36).

In a further preferred embodiment, the GLP-1 derivative is Arg$^{26}$Lys$^{34}$(N$^\epsilon$-(7-deoxycholoyl))-GLP-1(7-36).

In a further preferred embodiment, the GLP-1 derivative is Lys$^{26}$(N$^\epsilon$-(7-deoxycholoyl))-GLP-1(7-35).

In a further preferred embodiment, the GLP-1 derivative is Lys$^{34}$(N$^\epsilon$-(7-deoxycholoyl))-GLP-1(7-35).

In a further preferred embodiment, the GLP-1 derivative is Lys$^{26,34}$-bis(N$^\epsilon$-(7-deoxycholoyl))-GLP-1(7-35).

In a further preferred embodiment, the GLP-1 derivative is Gly$^8$Lys$^{26}$(N$^\epsilon$-(7-deoxycholoyl))-GLP-1(7-35).

In a further preferred embodiment, the GLP-1 derivative is Gly$^8$Lys$^{34}$(N$^\epsilon$-(7-deoxycholoyl))-GLP-1(7-35).

In a further preferred embodiment, the GLP-1 derivative is Gly$^8$Lys$^{26,34}$-bis(N$^\epsilon$-(7-deoxycholoyl))-GLP-1(7-35).

In a further preferred embodiment, the GLP-1 derivative is Arg$^{26}$Lys$^{34}$(N$^\epsilon$-(7-deoxycholoyl))-GLP-1(7-35).

In a further preferred embodiment, the GLP-1 derivative is Lys$^{26}$(N$^\epsilon$-(7-deoxycholoyl))-GLP-1(7-36)amide.

In a further preferred embodiment, the GLP-1 derivative is Lys$^{34}$(N$^\epsilon$-(7-deoxycholoyl))-GLP-1(7-36)amide.

In a further preferred embodiment, the GLP-1 derivative is Lys$^{26,34}$-bis(N$^\epsilon$-(7-deoxycholoyl))-GLP-1(7-36)amide.

In a further preferred embodiment, the GLP-1 derivative is Gly$^8$Lys$^{26}$(N$^\epsilon$-(7-deoxycholoyl))-GLP-1(7-36)amide.

In a further preferred embodiment, the GLP-1 derivative is Gly$^8$Lys$^{34}$(N$^\epsilon$-(7-deoxycholoyl))-GLP-1(7-36)amide.

In a further preferred embodiment, the GLP-1 derivative is Gly$^8$Lys$^{26,34}$-bis(N$^\epsilon$-(7-deoxycholoyl))-GLP-1(7-36)amide.

In a further preferred embodiment, the GLP-1 derivative is Arg$^{26}$Lys$^{34}$(N$^\epsilon$-(7-deoxycholoyl))-GLP-1(7-36)amide.

In a further preferred embodiment, the GLP-1 derivative is Gly$^8$Arg$^{26}$Lys$^{34}$(N$^\epsilon$-(7-deoxycholoyl))-GLP-1(7-37).

In a further preferred embodiment, the GLP-1 derivative is Lys$^{26}$(N$^\epsilon$-(7-deoxycholoyl))Arg$^{34}$-GLP-1(7-37).

In a further preferred embodiment, the GLP-1 derivative is Gly$^8$Lys$^{26}$(N$^\epsilon$-(7-deoxycholoyl))Arg$^{34}$-GLP-1(7-37).

In a further preferred embodiment, the GLP-1 derivative is Arg$^{26,34}$Lys$^{36}$(N$^\epsilon$-(7-deoxycholoyl))-GLP-1(7-37).

In a further preferred embodiment, the GLP-1 derivative is Gly$^8$Arg$^{26,34}$Lys$^{36}$(N$^\epsilon$-(7-deoxycholoyl))-GLP-1(7-37).

In a further preferred embodiment, the GLP-1 derivative is Lys$^{26}$(N$^\epsilon$-(choloyl))-GLP-1(7-37).

In a further preferred embodiment, the GLP-1 derivative is Lys$^{34}$(N$^\epsilon$-(choloyl))-GLP-1(7-37).

In a further preferred embodiment, the GLP-1 derivative is Lys$^{26,34}$-bis(N$^\epsilon$-(choloyl))-GLP-1(7-37).

In a further preferred embodiment, the GLP-1 derivative is Gly$^8$Lys$^{26}$(N$^\epsilon$-(choloyl))-GLP-1(7-37).

In a further preferred embodiment, the GLP-1 derivative is Gly$^8$Lys$^{34}$(N$^\epsilon$-(choloyl))-GLP-1(7-37).

In a further preferred embodiment, the GLP-1 derivative is Gly$^8$Lys$^{26,34}$-bis(N$^\epsilon$-(choloyl))-GLP-1(7-37).

In a further preferred embodiment, the GLP-1 derivative is Arg$^{26}$Lys$^{34}$(N$^\epsilon$-(choloyl))-GLP-1(7-37).

In a further preferred embodiment, the GLP-1 derivative is Gly$^8$Arg$^{26}$Lys$^{34}$(N$^\epsilon$-(7-deoxycholoyl))-GLP-1(7-38).

In a further preferred embodiment, the GLP-1 derivative is Lys$^{26}$(N$^\epsilon$-(7-deoxycholoyl))Arg$^{34}$-GLP-1(7-38).

In a further preferred embodiment, the GLP-1 derivative is Gly$^8$Lys$^{26}$(N$^\epsilon$-(7-deoxycholoyl))Arg$^{34}$-GLP-1(7-38).

In a further preferred embodiment, the GLP-1 derivative is Arg$^{26,34}$Lys$^{36}$(N$^\epsilon$-(7-deoxycholoyl))-GLP-1(7-38).

In a further preferred embodiment, the GLP-1 derivative is Arg$^{26,34}$Lys$^{38}$(N$^\epsilon$-(7-deoxycholoyl))-GLP-1(7-38).

In a further preferred embodiment, the GLP-1 derivative is Gly$^8$Arg$^{26,34}$Lys$^{36}$(N$^\epsilon$-(7-deoxycholoyl))-GLP-1(7-38).

In a further preferred embodiment, the GLP-1 derivative is Lys$^{26}$(N$^\epsilon$-(choloyl))-GLP-1(7-38).

In a further preferred embodiment, the GLP-1 derivative is Lys$^{34}$(N$^\epsilon$-(choloyl))-GLP-1(7-38).

In a further preferred embodiment, the GLP-1 derivative is Lys$^{26,34}$-bis(N$^\epsilon$-(choloyl))-GLP-1(7-38).

In a further preferred embodiment, the GLP-1 derivative is Gly$^8$Lys$^{26}$(N$^\epsilon$-(choloyl))-GLP-1(7-38).

In a further preferred embodiment, the GLP-1 derivative is Gly$^8$Lys$^{34}$(N$^\epsilon$-(choloyl))-GLP-1(7-38).

In a further preferred embodiment, the GLP-1 derivative is Gly$^8$Lys$^{26,34}$-bis(N$^\epsilon$-(choloyl))-GLP-1(7-38).

In a further preferred embodiment, the GLP-1 derivative is Arg$^{26}$Lys$^{34}$(N$^\epsilon$-(choloyl))-GLP-1(7-38).

In a further preferred embodiment, the GLP-1 derivative is Gly$^8$Arg$^{26}$Lys$^{34}$(N$^\epsilon$-(7-deoxycholoyl))-GLP-1(7-39).

In a further preferred embodiment, the GLP-1 derivative is Lys$^{26}$(N$^\epsilon$-(7-deoxycholoyl))Arg$^{34}$-GLP-1(7-39).

In a further preferred embodiment, the GLP-1 derivative is Gly$^8$Lys$^{26}$(N$^\epsilon$-(7-deoxycholoyl))Arg$^{34}$-GLP-1(7-39).

In a further preferred embodiment, the GLP-1 derivative is Arg$^{26,34}$Lys$^{36}$(N$^\epsilon$-(7-deoxycholoyl))-GLP-1(7-39).

In a further preferred embodiment, the GLP-1 derivative is Gly$^8$Arg$^{26,34}$Lys$^{36}$(N$^\epsilon$-(7-deoxycholoyl))-GLP-1(7-39).

In a further preferred embodiment, the GLP-1 derivative is Lys$^{26}$(N$^\epsilon$-(choloyl))-GLP-1(7-39).

In a further preferred embodiment, the GLP-1 derivative is Lys$^{34}$(N$^\epsilon$-(choloyl))-GLP-1(7-39).

In a further preferred embodiment, the GLP-1 derivative is Lys$^{26,34}$-bis(N$^\epsilon$-(choloyl))-GLP-1(7-39).

In a further preferred embodiment, the GLP-1 derivative is Gly$^8$Lys$^{26}$(N$^\epsilon$-(choloyl))-GLP-1(7-39).

In a further preferred embodiment, the GLP-1 derivative is Gly$^8$Lys$^{34}$(N$^\epsilon$-(choloyl))-GLP-1(7-39).

In a further preferred embodiment, the GLP-1 derivative is Gly$^8$Lys$^{26,34}$-bis(N$^\epsilon$-(choloyl))-GLP-1(7-39).

In a further preferred embodiment, the GLP-1 derivative is Arg$^{26}$Lys$^{34}$(N$^\epsilon$-(choloyl))-GLP-1(7-39).

In a further preferred embodiment, the GLP-1 derivative is Gly$^8$Arg$^{26}$Lys$^{34}$(N$^\epsilon$-(7-deoxycholoyl))-GLP-1(7-40).

In a further preferred embodiment, the GLP-1 derivative is Lys$^{26}$(N$^\epsilon$-(7-deoxycholoyl))Arg$^{34}$-GLP-1(7-40).

In a further preferred embodiment, the GLP-1 derivative is Gly$^8$Lys$^{26}$(N$^\epsilon$-(7-deoxycholoyl))Arg$^{34}$-GLP-1(7-40).

In a further preferred embodiment, the GLP-1 derivative is Arg$^{26,34}$Lys$^{36}$(N$^\epsilon$-(7-deoxycholoyl))-GLP-1(7-40).

In a further preferred embodiment, the GLP-1 derivative is Gly$^8$Arg$^{26,34}$Lys$^{36}$(N$^\epsilon$-(7-deoxycholoyl))-GLP-1(7-40).

In a further preferred embodiment, the GLP-1 derivative is Lys$^{26}$(N$^\epsilon$-(choloyl))-GLP-1(7-40).

In a further preferred embodiment, the GLP-1 derivative is Lys$^{34}$(N$^\epsilon$-(choloyl))-GLP-1(7-40).

In a further preferred embodiment, the GLP-1 derivative is Lys$^{26,34}$-bis(N$^\epsilon$-(choloyl))-GLP-1(7-40).

In a further preferred embodiment, the GLP-1 derivative is Gly$^8$Lys$^{26}$(N$^\epsilon$-(choloyl))-GLP-1(7-40).

In a further preferred embodiment, the GLP-1 derivative is Gly$^8$Lys$^{34}$(N$^\epsilon$-(choloyl))-GLP-1(7-40).

In a further preferred embodiment, the GLP-1 derivative is Gly$^8$Lys$^{26,34}$-bis N$^\epsilon$-(choloyl))-GLP-1(7-40).

In a further preferred embodiment, the GLP-1 derivative is Arg$^{26}$Lys$^{34}$(N$^\epsilon$-(choloyl))-GLP-1(7-40).

In a further preferred embodiment, the GLP-1 derivative is Lys$^{26}$(N$^\epsilon$-(choloyl))-GLP-1(7-36).

In a further preferred embodiment, the GLP-1 derivative is Lys$^{34}$(N$^\epsilon$-(choloyl))-GLP-1(7-36).

In a further preferred embodiment, the GLP-1 derivative is Lys$^{26,34}$-bis(N$^\epsilon$-(choloyl))-GLP-1(7-36).

In a further preferred embodiment, the GLP-1 derivative is Gly$^8$Lys$^{26}$(N$^\epsilon$-(choloyl))-GLP-1(7-36).

In a further preferred embodiment, the GLP-1 derivative is Gly$^8$Lys$^{34}$(N$^\epsilon$-(choloyl))-GLP-1(7-36).

In a further preferred embodiment, the GLP-1 derivative is Gly$^8$Lys$^{26}$N$^{34}$-bis(N$^\epsilon$-(choloyl))-GLP-1(7-36).

In a further preferred embodiment, the GLP-1 derivative is Arg$^{26}$Lys$^{34}$(N$^\epsilon$-(choloyl))-GLP-1(7-36).

In a further preferred embodiment, the GLP-1 derivative is Lys$^{26}$(N$^\epsilon$-(choloyl))-GLP-1(7-35).

In a further preferred embodiment, the GLP-1 derivative is Gly$^8$Lys$^{34}$(N$^\epsilon$-(choloyl))-GLP-1(7-35).

In a further preferred embodiment, the GLP-1 derivative is Lys$^{26,34}$-bis(N$^\epsilon$-(choloyl))-GLP-1(7-35).

In a further preferred embodiment, the GLP-1 derivative is Gly$^8$Lys$^{26}$(N$^\epsilon$-(choloyl))-GLP-1(7-35).

In a further preferred embodiment, the GLP-1 derivative is Gly$^8$Lys$^{34}$(N$^\epsilon$-(choloyl))-GLP-1(7-35).

In a further preferred embodiment, the GLP-1 derivative is Gly$^8$Lys$^{26,34}$-bis(N$^\epsilon$-(choloyl))-GLP-1(7-35).

In a further preferred embodiment, the GLP-1 derivative is Arg$^{26}$Lys$^{34}$(N$^\epsilon$-6-(choloyl))-GLP-1(7-35).

In a further preferred embodiment, the GLP-1 derivative is Lys$^{26}$(N$^\epsilon$-(choloyl))-GLP-1(7-36)amide.

In a further preferred embodiment, the GLP-1 derivative is Lys$^{34}$(N$^\epsilon$-(choloyl))-GLP-1(7-36)amide.

In a further preferred embodiment, the GLP-1 derivative is Lys$^{26,34}$-bis(N$^\epsilon$-(choloyl))-GLP-1(7-36)amide.

In a further preferred embodiment, the GLP-1 derivative is Gly$^8$Lys$^{26}$(N$^\epsilon$-(choloyl))-GLP-1(7-36)amide.

In a further preferred embodiment, the GLP-1 derivative is Gly$^8$Lys$^{34}$(N$^\epsilon$-(choloyl))-GLP-1(7-36)amide.

In a further preferred embodiment, the GLP-1 derivative is Gly$^8$Lys$^{26,34}$-bis(N$^\epsilon$-(choloyl))-GLP-1(7-36)amide.

In a further preferred embodiment, the GLP-1 derivative is Arg$^{26}$Lys$^{34}$(N$^\epsilon$-(choloyl))-GLP-1(7-36)amide.

In a further preferred embodiment, the GLP-1 derivative is Gly$^8$Arg$^{26}$Lys$^{34}$(N$^\epsilon$-(choloyl))-GLP-1(7-37).

In a further preferred embodiment, the GLP-1 derivative is Lys$^{26}$(N$^\epsilon$-(choloyl))Arg$^{34}$-GLP-1(7-37).

In a further preferred embodiment, the GLP-1 derivative is Gly$^8$Lys$^{26}$(N$^\epsilon$-(choloyl))Arg$^{34}$-GLP-1(7-37).

In a further preferred embodiment, the GLP-1 derivative is Arg$^{26,34}$Lys$^{36}$(N$^\epsilon$-(choloyl))-GLP-1(7-37).

In a further preferred embodiment, the GLP-1 derivative is Gly$^8$Arg$^{26,34}$Lys$^{36}$(N$^\epsilon$-(choloyl))-GLP-1(7-37).

In a further preferred embodiment, the GLP-1 derivative is Lys$^{26}$(N$^\epsilon$-(lithocholoyl))-GLP-1(7-37).

In a further preferred embodiment, the GLP-1 derivative is Lys$^{34}$(N$^\epsilon$-(lithocholoyl))-GLP-1(7-37).

In a further preferred embodiment, the GLP-1 derivative is Lys$^{26,34}$-bis(N$^\epsilon$-(lithocholoyl))-GLP-1(7-37).

In a further preferred embodiment, the GLP-1 derivative is Gly$^8$Lys$^{26}$(N$^\epsilon$-(lithocholoyl))-GLP-1(7-37).

In a further preferred embodiment, the GLP-1 derivative is Gly$^8$Lys$^{34}$(N$^\epsilon$-(lithocholoyl))-GLP-1(7-37).

In a further preferred embodiment, the GLP-1 derivative is Gly$^8$Lys$^{26,34}$-bis(N$^\epsilon$-(lithocholoyl))-GLP-1(7-37).

In a further preferred embodiment, the GLP-1 derivative is Arg$^{26}$Lys$^{34}$(N$^\epsilon$-(lithocholoyl))-GLP-1(7-37).

In a further preferred embodiment, the GLP-1 derivative is Gly$^8$Arg$^{26}$Lys$^{34}$-(N$^\epsilon$-(choloyl))-GLP-1(7-38).

In a further preferred embodiment, the GLP-1 derivative is Lys$^{26}$(N$^\epsilon$-(choloyl))Arg$^{34}$-GLP-1(7-38).

In a further preferred embodiment, the GLP-1 derivative is Gly$^8$Lys$^{26}$(N$^\epsilon$-(choloyl))Arg$^{34}$-GLP-1(7-38).

In a further preferred embodiment, the GLP-1 derivative is Arg$^{26,34}$Lys$^{36}$(N$^\epsilon$-(choloyl))-GLP-1(7-38).

In a further preferred embodiment, the GLP-1 derivative is Arg$^{26,34}$Lys$^{38}$(N$^\epsilon$-(choloyl))-GLP-1(7-38).

In a further preferred embodiment, the GLP-1 derivative is Gly$^8$Arg$^{26,34}$Lys$^{36}$(N$^\epsilon$-(choloyl))-GLP-1(7-38).

In a further preferred embodiment, the GLP-1 derivative is Lys$^{26}$(N$^\epsilon$-(lithocholoyl))-GLP-1(7-38).

In a further preferred embodiment, the GLP-1 derivative is Lys$^{26}$(N$^\epsilon$-(choloyl))-GLP-1(7-38).

In a further preferred embodiment, the GLP-1 derivative is Gly$^8$Lys$^{26}$(N$^\epsilon$-(lithocholoyl))-GLP-1(7-38).

In a further preferred embodiment, the GLP-1 derivative is Gly$^8$Lys$^{34}$(N$^\epsilon$-(lithocholoyl))-GLP-1(7-38).

In a further preferred embodiment, the GLP-1 derivative is Gly$^8$Lys$^{26,34}$-bis(N$^\epsilon$-(lithocholoyl))-GLP-1(7-38).

In a further preferred embodiment, the GLP-1 derivative is Arg$^{26}$Lys$^{36}$(N$^\epsilon$-(lithocholoyl))-GLP-1(7-38).

In a further preferred embodiment, the GLP-1 derivative is Gly$^8$Arg$^{26}$Lys$^{34}$(N$^\epsilon$-(choloyl))-GLP-1(7-39).

In a further preferred embodiment, the GLP-1 derivative is Lys$^{26}$(N$^\epsilon$-(choloyl))Arg$^{34}$-GLP-1(7-39).

In a further preferred embodiment, the GLP-1 derivative is Gly$^8$Lys$^{26}$(N$^\epsilon$-(choloyl))Arg$^{34}$-GLP-1(7-39).

In a further preferred embodiment, the GLP-1 derivative is Arg$^{26,34}$Lys$^{36}$(N$^\epsilon$-(choloyl))-GLP-1(7-39).

In a further preferred embodiment, the GLP-1 derivative is Gly$^8$Arg$^{26,34}$Lys$^{36}$(N$^\epsilon$-(choloyl))-GLP-1(7-39).

In a further preferred embodiment, the GLP-1 derivative is Lys$^{26}$(N$^\epsilon$-(lithocholoyl))-GLP-1(7-39).

In a further preferred embodiment, the GLP-1 derivative is Lys$^{26}$(N$^\epsilon$-(lithocholoyl))-GLP-1(7-39).

In a further preferred embodiment, the GLP-1 derivative is Lys$^{26,34}$-bis(N$^\epsilon$-(lithocholoyl))-GLP-1(7-39).

In a further preferred embodiment, the GLP-1 derivative is Gly$^8$Lys$^{26}$(N$^\epsilon$-(lithocholoyl))-GLP-1(7-39).

In a further preferred embodiment, the GLP-1 derivative is Gly$^8$Lys$^{34}$(N$^\epsilon$-(lithocholoyl))-GLP-1(7-39).

In a further preferred embodiment, the GLP-1 derivative is Gly$^8$Lys$^{26,34}$-bis(N$^\epsilon$-(lithocholoyl))-GLP-1(7-39).

In a further preferred embodiment, the GLP-1 derivative is Arg$^{26}$Lys$^{34}$(N$^\epsilon$-(lithocholoyl))-GLP-1(7-39).

In a further preferred embodiment, the GLP-1 derivative is Gly$^8$Arg$^{26}$Lys$^{34}$(N$^\epsilon$-(choloyl))-GLP-1(7-40).

In a further preferred embodiment, the GLP-1 derivative is Lys$^{26}$(N$^\epsilon$-(choloyl))Arg$^{34}$-GLP-1(7-40).

In a further preferred embodiment, the GLP-1 derivative is Gly$^8$Lys$^{26}$ (N$^\epsilon$-(choloyl))Arg$^{34}$-GLP-1(7-40).

In a further preferred embodiment, the GLP-1 derivative is Arg$^{26,34}$Lys$^{36}$(N$^\epsilon$-(choloyl))-GLP-1(7-40).

In a further preferred embodiment, the GLP-1 derivative is Gly$^8$Arg$^{26,34}$Lys$^{36}$(N$^\epsilon$-(choloyl))-GLP-1(7-40).

In a further preferred embodiment, the GLP-1 derivative is Lys$^{26}$(N$^\epsilon$-(lithocholoyl))-GLP-1(7-40).

In a further preferred embodiment, the GLP-1 derivative is Lys$^{26,34}$-bis(N$^\epsilon$-(lithocholoyl))-GLP-1(7-40).

In a further preferred embodiment, the GLP-1 derivative is Gly$^8$Lys$^{26}$(N$^\epsilon$-(lithocholoyl))-GLP-1(7-40).

In a further preferred embodiment, the GLP-1 derivative is Gly$^8$Lys$^{34}$(N$^\epsilon$-(lithocholoyl))-GLP-1(7-40).

In a further preferred embodiment, the GLP-1 derivative is Gly$^8$Lys$^{26,34}$-bis(N$^\epsilon$-(lithocholoyl))-GLP-1(7-40).

In a further preferred embodiment, the GLP-1 derivative is Arg$^{26}$Lys$^{34}$(N$^\epsilon$-(lithocholoyl))-GLP-1(7-37).

In a further preferred embodiment, the GLP-1 derivative is Lys$^{26}$(N$^\epsilon$-(lithocholoyl))-GLP-1(7-36).

In a further preferred embodiment, the GLP-1 derivative is Lys$^{34}$(N$^\epsilon$-(lithocholoyl))-GLP-1(7-36).

In a further preferred embodiment, the GLP-1 derivative is Lys$^{26,34}$-bis(N$^\epsilon$-(lithocholoyl))-GLP-1(7-36).

In a further preferred embodiment, the GLP-1 derivative is Gly$^8$Lys$^{26}$(N$^\epsilon$-(lithocholoyl))-GLP-1(7-36).

In a further preferred embodiment, the GLP-1 derivative is Gly$^8$Lys$^{34}$(N$^\epsilon$-(lithocholoyl))-GLP-1(7-36).

In a further preferred embodiment, the GLP-1 derivative is Gly$^8$Lys$^{26,34}$-bis(N$^\epsilon$-(lithocholoyl))-GLP-1(7-36).

In a further preferred embodiment, the GLP-1 derivative is Arg$^{26}$Lys$^{34}$(N$^\epsilon$-(lithocholoyl))-GLP-1(7-36).

In a further preferred embodiment, the GLP-1 derivative is Lys$^{26}$(N$^\epsilon$-(lithocholoyl))-GLP-1(7-35).

In a further preferred embodiment, the GLP-1 derivative is Lys$^{34}$(N$^\epsilon$-(lithocholoyl))-GLP-1(7-35).

In a further preferred embodiment, the GLP-1 derivative is Lys$^{26,34}$-bis(N$^\epsilon$-(lithocholoyl))-GLP-1(7-35).

In a further preferred embodiment, the GLP-1 derivative is Gly$^8$Lys$^{26}$(N$^\epsilon$-(lithocholoyl))-GLP-1(7-35).

In a further preferred embodiment, the GLP-1 derivative is Gly$^8$Lys$^{34}$(N$^\epsilon$-(lithocholoyl))-GLP-1(7-35).

In a further preferred embodiment, the GLP-1 derivative is Gly$^8$Lys$^{26,34}$-bis(N$^\epsilon$-(lithocholoyl))-GLP-1(7-35).

In a further preferred embodiment, the GLP-1 derivative is Arg$^{26}$Lys$^{34}$(N$^\epsilon$-(lithocholoyl))-GLP-1(7-35).

In a further preferred embodiment, the GLP-1 derivative is Lys$^{26}$(N$^\epsilon$-(lithocholoyl))-GLP-1(7-36)amide.

In a further preferred embodiment, the GLP-1 derivative is Lys$^{34}$(N$^\epsilon$-(lithocholoyl))-GLP-1(7-36)amide.

In a further preferred embodiment, the GLP-1 derivative is Lys$^{26,34}$-bis(N$^\epsilon$-(lithocholoyl))-GLP-1(7-36)amide.

In a further preferred embodiment, the GLP-1 derivative is Gly$^8$Lys$^{26}$(N$^\epsilon$-(lithocholoyl))-GLP-1(7-36)amide.

In a further preferred embodiment, the GLP-1 derivative is Gly$^8$Lys$^{34}$(N$^\epsilon$-(lithocholoyl))-GLP-1(7-36)amide.

In a further preferred embodiment, the GLP-1 derivative is Gly$^8$Lys$^{26,34}$-bis(N$^\epsilon$-(lithocholoyl))-GLP-1(7-36)amide.

In a further preferred embodiment, the GLP-1 derivative is Arg$^{26}$Lys$^{34}$(N$^\epsilon$-(lithocholoyl))-GLP-1(7-36)amide.

In a further preferred embodiment, the GLP-1 derivative is Gly$^8$Arg$^{26}$Lys$^{34}$(N$^\epsilon$-(lithocholoyl))-GLP-1(7-37).

In a further preferred embodiment, the GLP-1 derivative is Lys$^{26}$-(N$^\epsilon$-(lithocholoyl))Arg$^{34}$-GLP-1(7-37).

In a further preferred embodiment, the GLP-1 derivative is Gly$^8$Lys$^{26}$(N$^\epsilon$-(lithocholoyl))Arg$^{34}$-GLP-1(7-37).

In a further preferred embodiment, the GLP-1 derivative is Arg$^{26,34}$Lys$^{36}$(N$^\epsilon$-(lithocholoyl))-GLP-1021(7-37).

In a further preferred embodiment, the GLP-1 derivative is Arg$^{26,34}$Lys$^{38}$(N$^\epsilon$-(lithocholoyl))-GLP-1(7-37).

In a further preferred embodiment, the GLP-1 derivative is Gly$^8$Arg$^{26,34}$Lys$^{36}$(N$^\epsilon$-(lithocholoyl))-GLP-1(7-37).

In a further preferred embodiment, the GLP-1 derivative is Gly$^8$Arg$^{26}$Lys$^{34}$(N$^\epsilon$-(lithocholoyl))-GLP-1(7-38).

In a further preferred embodiment, the GLP-1 derivative is Lys$^{26}$(N$^\epsilon$-(lithocholoyl))Arg$^{34}$-GLP-1(7-38).

In a further preferred embodiment, the GLP-1 derivative is Gly$^8$Lys$^{26}$(N$^\epsilon$-(lithocholoyl))Arg$^{34}$-GLP-1(7-38).

In a further preferred embodiment, the GLP-1 derivative is Arg$^{26,34}$Lys$^{36}$(N$^\epsilon$-(lithocholoyl))-GLP-1(7-38).

In a further preferred embodiment, the GLP-1 derivative is Arg$^{26,34}$Lys$^{38}$(N$^\epsilon$-(lithocholoyl))-GLP-1(7-38).

In a further preferred embodiment, the GLP-1 derivative is Gly$^8$Arg$^{26,34}$Lys$^{36}$(N$^\epsilon$-(lithocholoyl))-GLP-1(7-38).

In a further preferred embodiment, the GLP-1 derivative is Gly$^8$Arg$^{26}$Lys$^{34}$(N$^\epsilon$-(lithocholoyl))-GLP-1(7-39).

In a further preferred embodiment, the GLP-1 derivative is Lys$^{26}$(N$^\epsilon$-(lithocholoyl))Arg$^{34}$-GLP-1(7-39).

In a further preferred embodiment, the GLP-1 derivative is Gly$^8$Lys$^{26}$(N$^\epsilon$-(lithocholoyl))Arg$^{34}$-GLP-1(7-39).

In a further preferred embodiment, the GLP-1 derivative is Arg$^{26,34}$Lys$^{36}$(N$^\epsilon$-(lithocholoyl))-GLP-1(7-39).

In a further preferred embodiment, the GLP-1 derivative is Gly$^8$Arg$^{26,34}$Lys$^{36}$(N$^\epsilon$-(lithocholoyl))-GLP-1(7-39).

In a further preferred embodiment, the GLP-1 derivative is Gly$^8$Arg$^{26}$Lys$^{34}$(N$^\epsilon$-(lithocholoyl))-GLP-1(7-40).

In a further preferred embodiment, the GLP-1 derivative is Lys$^{26}$(N$^\epsilon$-(lithocholoyl))Arg$^{34}$-GLP-1(7-40).

In a further preferred embodiment, the GLP-1 derivative is Gly$^8$Lys$^{26}$(N$^\epsilon$-(lithocholoyl))Arg$^{34}$-GLP-1(7-40).

In a further preferred embodiment, the GLP-1 derivative is Arg$^{26,34}$Lys$^{36}$(N$^\epsilon$-(lithocholoyl))-GLP-1(7-40).

In a further preferred embodiment, the GLP-1 derivative is Gly$^8$Arg$^{26,34}$Lys$^{36}$(N$^\epsilon$-(lithocholoyl))-GLP-1(7-40).

Other preferred embodiments will be described using the following abbreviations:

Glut=N$^\epsilon$-(γ-L-glutamyl)
Aspa=N$^\epsilon$-(β-L-asparagyl)
Glyc=N$^\epsilon$-glycyl
GAB=N$^\alpha$-(α-(γ-aminobutanoyl)
ADod=N$^\alpha$-dodecanoyl
ATet=N$^\alpha$-tetradecanoyl
AHex=N$^\alpha$-hexadecanoyl
AOct=N$^\gamma$-octadecanoyl
ALit=N$^\alpha$-lithocholyl
GDod=N$^\gamma$-dodecanoyl
GTet=N$^\gamma$-tetradecanoyl
GHex=N$^\gamma$-hexadecanoyl
GOct=N$^\gamma$-octadecanoyl
GLit=N$^\gamma$-lithocholyl Other preferred GLP-1 derivatives of the present invention are:

Arg$^{26}$Lys$^{34}$-(Glut-ADod)-GLP-1(7-36); Arg$^{34}$Lys$^{26}$-(Glut-ADod)-GLP-1(7-36); Arg$^{26,34}$Lys$^{36}$-(Glut-ADod)-GLP-1(7-36); Arg$^{26}$Lys$^{34}$-(Glut-ADod)-GLP-1(7-36)amide; Arg$^{34}$Lys$^{26}$-(Glut-ADod)-GLP-1(7-36)amide; Arg$^{26,34}$Lys$^{36}$-(Glut-ADod)-GLP-1(7-36)amide; Arg$^{26}$Lys$^{34}$-(Glut-ADod)-GLP-1(7-37); Arg$^{34}$Lys$^{26}$-(Glut-ADod)-GLP-1(7-37); Arg$^{26,34}$Lys$^{36}$-(Glut-ADod)-GLP-1(7-37); Arg$^{26}$Lys$^{34}$-(Glut-ADod)-GLP-1(7-38); Arg$^{34}$Lys$^{26}$-(Glut-ADod)-GLP-1(7-38); Arg$^{26,34}$Lys$^{38}$-(Glut-ADod)-GLP-1(7-38); Arg$^{26}$Lys$^{34}$-(Glut-ADod)-GLP-1(7-39); Arg$^{34}$Lys$^{26}$-(Glut-ADod)-GLP-1(7-39); Arg$^{26,34}$Lys$^{39}$-(Glut-ADod)-GLP-1(7-39);

Gly$^8$Arg$^{26}$Lys$^{34}$-(Glut-ADod)-GLP-1(7-36); Gly$^8$Arg$^{34}$Lys$^{26}$-(Glut-ADod)-GLP-1(7-36); Gly$^8$Arg$^{26,34}$Lys$^{36}$-(Glut-ADod)-GLP-1(7-36); Gly$^8$Arg$^{26}$Lys$^{34}$-(Glut-ADod)-GLP-1(7-36)amide; Gly$^8$Arg$^{34}$Lys$^{26}$-(Glut-ADod)-GLP-1(7-36)amide; Gly$^8$Arg$^{26,34}$Lys$^{36}$-(Glut-ADod)-GLP-1(7-36)amide; Gly$^8$Arg$^{26}$Lys$^{34}$-(Glut-ADod)-GLP-1(7-37); Gly$^8$Arg$^{34}$Lys$^{26}$-(Glut-ADod)-GLP-1(7-37); Gly$^8$Arg$^{26,34}$Lys$^{36}$-(Glut-ADod)-GLP-1(7-37); Gly$^8$Arg$^{26}$Lys$^{34}$-(Glut-ADod)-GLP-1(7-38); Gly$^8$Arg$^{34}$Lys$^{26}$-(Glut-ADod)-GLP-1(7-38); Gly$^8$Arg$^{26,34}$Lys$^{38}$-(Glut-ADod)-GLP-1(7-38); Gly$^8$Arg$^{26}$Lys$^{34}$-(Glut-ADod)-GLP-1(7-39); Gly$^8$Arg$^{34}$Lys$^{26}$-(Glut-ADod)-GLP-1(7-39); Gly$^8$Arg$^{26,34}$Lys$^{39}$-(Glut-ADod)-GLP-1(7-39);

Val$^8$Arg$^{26}$Lys$^{34}$-(Glut-ADod)-GLP-1(7-36); Val$^8$Arg$^{34}$Lys$^{26}$-(Glut-ADod)-GLP-1(7-36); Val$^8$Arg$^{26,34}$Lys$^{36}$-(Glut-ADod)-GLP-1(7-36); Val$^8$Arg$^{26}$Lys$^{34}$-(Glut-ADod)-GLP-1(7-36)amide; Val$^8$Arg$^{34}$Lys$^{26}$-(Glut-ADod)-GLP-1(7-36)amide; Val$^8$Arg$^{26,34}$Lys$^{36}$-(Glut-ADod)-GLP-1(7-36)amide; Val$^8$Arg$^{26}$Lys$^{34}$-(Glut-ADod)-GLP-1(7-37); Val$^8$Arg$^{34}$Lys$^{26}$-(Glut-ADod)-GLP-1(7-37); Val$^8$Arg$^{26,34}$Lys$^{36}$-(Glut-ADod)-GLP-1(7-37); Val$^8$Arg$^{26}$Lys$^{34}$-(Glut-ADod)-GLP-1(7-38); Val$^8$Arg$^{34}$Lys$^{26}$-(Glut-ADod)-GLP-1(7-38); Val$^8$Arg$^{26,34}$Lys$^{38}$-(Glut-ADod)-GLP-1(7-38); Val$^8$Arg$^{26}$Lys$^{34}$-(Glut-ADod)-GLP-1(7-39); Val$^8$Arg$^{34}$Lys$^{26}$-(Glut-ADod)-GLP-1(7-39); Val$^8$Arg$^{26,34}$Lys$^{39}$-(Glut-ADod)-GLP-1(7-39);

Ser$^8$Arg$^{26}$Lys$^{34}$-(Glut-ADod)-GLP-1(7-36); Ser$^8$Arg$^{34}$Lys$^{26}$-(Glut-ADod)-GLP-1(7-36); Ser$^8$Arg$^{26,34}$Lys$^{36}$-(Glut-ADod)-GLP-1(7-36); Ser$^8$Arg$^{26}$Lys$^{34}$-(Glut-ADod)-GLP-1(7-36)amide; Ser$^8$Arg$^{34}$Lys$^{26}$-(Glut-ADod)-GLP-1(7-36)amide; Ser$^8$Arg$^{26,34}$Lys$^{36}$-(Glut-ADod)-GLP-1(7-36)amide; Ser$^8$Arg$^{26}$Lys$^{34}$-(Glut-ADod)-GLP-1(7-37); Ser$^8$Arg$^{34}$Lys$^{26}$-(Glut-ADod)-GLP-1(7-37); Ser$^8$Arg$^{26,34}$Lys$^{36}$-(Glut-ADod)-GLP-1(7-37); Ser$^8$Arg$^{26}$Lys$^{34}$-(Glut-ADod)-GLP-1(7-38); Ser$^8$Arg$^{34}$Lys$^{26}$-(Glut-ADod)-GLP-1(7-38); Ser$^8$Arg$^{26,34}$Lys$^{38}$-(Glut-ADod)-GLP-1(7-38); Ser$^8$Arg$^{26}$Lys$^{34}$-(Glut-ADod)-GLP-1(7-39); Ser$^8$Arg$^{34}$Lys$^{26}$-(Glut-ADod)-GLP-1(7-39); Ser$^8$Arg$^{26,34}$Lys$^{39}$-(Glut-ADod)-GLP-1(7-39);

Thr$^8$Arg$^{26}$Lys$^{34}$-(Glut-ADod)-GLP-1(7-36); Thr$^8$Arg$^{34}$Lys$^{26}$-(Glut-ADod)-GLP-1(7-36); Thr$^8$Arg$^{26,34}$Lys$^{36}$-(Glut-ADod)-GLP-1(7-36); Thr$^8$Arg$^{26}$Lys$^{34}$-(Glut-ADod)-GLP-1(7-36)amide; Thr$^8$Arg$^{34}$Lys$^{26}$-(Glut-ADod)-GLP-1(7-36)amide; Thr$^8$Arg$^{26,34}$Lys$^{36}$-(Glut-ADod)-GLP-1(7-36)amide; Thr$^8$Arg$^{26}$Lys$^{34}$-(Glut-ADod)-GLP-1(7-37); Thr$^8$Arg$^{34}$Lys$^{26}$-(Glut-ADod)-GLP-1(7-37); Thr$^8$Arg$^{26,34}$Lys$^{36}$-(Glut-ADod)-GLP-1(7-37); Thr$^8$Arg$^{26}$Lys$^{34}$-(Glut-ADod)-GLP-1(7-38); Thr$^8$Arg$^{34}$Lys$^{26}$-(Glut-ADod)-GLP-1(7-38); Thr$^8$ Arg$^{26,34}$Lys$^{38}$-(Glut-ADod)-GLP-1(7-38); Thr$^8$Arg$^{26}$Lys$^{34}$-(Glut-ADod)-GLP-1(7-39); Thr$^8$Arg$^{34}$Lys$^{26}$-(Glut-ADod)-GLP-1(7-39); Thr$^8$Arg$^{26,34}$Lys$^{39}$-(Glut-ADod)-GLP-1(7-39);
Gly$^8$Glu$^{35}$Arg$^{26,34}$Lys$^{36}$-(Glut-ADod)-GLP-1(7-36);
Gly$^8$Glu$^{35}$Arg$^{26,34}$Lys$^{36}$-(Glut-ADod)-GLP-1(7-36)amide;
Gly$^8$Glu$^{36}$Arg$^{26,34}$Lys$^{37}$-(Glut-ADod)-GLP-1(7-37);
Gly$^8$Glu$^{37}$Arg$^{26,34}$Lys$^{38}$-(Glut-ADod)-GLP-1(7-38);
Gly$^8$Glu$^{38}$Arg$^{26,34}$Lys$^{39}$-(Glut-ADod)-GLP-1(7-39);
Gly$^8$Glu$^{35}$Arg$^{26,34}$Lys$^{36}$-(Glut-ADod)-GLP-1(7-36);
Gly$^8$Glu$^{35}$Arg$^{26,34}$Lys$^{36}$-(Glut-ADod)-GLP-1(7-36)amide;
Gly$^8$Glu$^{36}$Arg$^{26,34}$Lys$^{37}$-(Glut-ADod)-GLP-1(7-37);
Gly$^8$Glu$^{37}$Arg$^{26,34}$Lys$^{38}$-(Glut-ADod)-GLP-1(7-38);
Gly$^8$Glu$^{38}$Arg$^{26,34}$Lys$^{39}$-(Glut-ADod)-GLP-1(7-39);
Gly$^8$Asp$^{35}$Arg$^{26,34}$Lys$^{36}$-(Glut-ADod)-GLP-1(7-36);
Gly$^8$Asp$^{35}$Arg$^{26,34}$Lys$^{36}$-(Glut-ADod)-GLP-1(7-36)amide;
Gly$^8$Asp$^{36}$Arg$^{26,34}$Lys$^{37}$-(Glut-ADod)-GLP-1(7-37);
Gly$^8$Asp$^{37}$Arg$^{26,34}$Lys$^{38}$-(Glut-ADod)-GLP-1(7-38);
Gly$^8$Asp$^{38}$Arg$^{26,34}$Lys$^{39}$-(Glut-ADod)-GLP-1(7-39);
Gly$^8$Asp$^{35}$Arg$^{26,34}$Lys$^{36}$-(Glut-ADod)-GLP-1(7-36);
Gly$^8$Asp$^{35}$Arg$^{26,34}$Lys$^{36}$-(Glut-ADod)-GLP-1(7-36)amide;
Gly$^8$Asp$^{36}$Arg$^{26,34}$Lys$^{37}$-(Glut-ADod)-GLP-1(7-37);
Gly$^8$Asp$^{37}$Arg$^{26,34}$Lys$^{38}$-(Glut-ADod)-GLP-1(7-38);
Gly$^8$Asp$^{38}$Arg$^{26,34}$Lys$^{39}$-(Glut-ADod)-GLP-1(7-39);
Val$^8$Glu$^{35}$Arg$^{26,34}$Lys$^{36}$-(Glut-ADod)-GLP-1(7-36);
Val$^8$Glu$^{35}$Arg$^{26,34}$Lys$^{36}$-(Glut-ADod)-GLP-1(7-36)amide;
Val$^8$Glu$^{36}$Arg$^{26,34}$Lys$^{37}$-(Glut-ADod)-GLP-1(7-37);
Val$^8$Glu$^{37}$Arg$^{26,34}$Lys$^{38}$-(Glut-ADod)-GLP-1(7-38);
Val$^8$Glu$^{38}$Arg$^{26,34}$Lys$^{39}$-(Glut-ADod)-GLP-1(7-39);
Val$^8$Glu$^{35}$Arg$^{26,34}$Lys$^{36}$-(Glut-ADod)-GLP-1(7-36);
Val$^8$Glu$^{35}$Arg$^{26,34}$Lys$^{36}$-(Glut-ADod)-GLP-1(7-36)amide;
Val$^8$Glu$^{36}$Arg$^{26,34}$Lys$^{37}$-(Glut-ADod)-GLP-1(7-37);
Val$^8$Glu$^{37}$Arg$^{26,34}$Lys$^{38}$-(Glut-ADod)-GLP-1(7-38);
Val$^8$Glu$^{38}$Arg$^{26,34}$Lys$^{39}$-(Glut-ADod)-GLP-1(7-39);
Val$^8$Asp$^{35}$Arg$^{26,34}$Lys$^{36}$-(Glut-ADod)-GLP-1(7-36);
Val$^8$Asp$^{35}$Arg$^{26,34}$Lys$^{36}$-(Glut-ADod)-GLP-1(7-36)amide;
Val$^8$Asp$^{36}$Arg$^{26,34}$Lys$^{37}$-(Glut-ADod)-GLP-1(7-37);
Val$^8$Asp$^{37}$Arg$^{26,34}$Lys$^{38}$-(Glut-ADod)-GLP-1(7-38);
Val$^8$Asp$^{38}$Arg$^{26,34}$Lys$^{39}$-(Glut-ADod)-GLP-1(7-39);
Val$^8$Asp$^{35}$Arg$^{26,34}$Lys$^{36}$-(Glut-ADod)-GLP-1(7-36);
Val$^8$Asp$^{35}$Arg$^{26,34}$Lys$^{36}$-(Glut-ADod)-GLP-1(7-36)amide;
Val$^8$Asp$^{36}$Arg$^{26,34}$Lys$^{37}$-(Glut-ADod)-GLP-1(7-37);
Val$^8$Asp$^{37}$Arg$^{26,34}$Lys$^{38}$-(Glut-ADod)-GLP-1(7-38);
Val$^8$Asp$^{38}$Arg$^{26,34}$Lys$^{39}$-(Glut-ADod)-GLP-1(7-39);
Ser$^8$Glu$^{35}$Arg$^{26,34}$Lys$^{36}$-(Glut-ADod)-GLP-1(7-36);
Ser$^8$Glu$^{35}$Arg$^{26,34}$Lys$^{36}$-(Glut-ADod)-GLP-1(7-36)amide;
Ser$^8$Glu$^{36}$Arg$^{26,34}$Lys$^{37}$-(Glut-ADod)-GLP-1(7-37);
Ser$^8$Glu$^{37}$Arg$^{26,34}$Lys$^{38}$-(Glut-ADod)-GLP-1(7-38);
Ser$^8$Glu$^{38}$Arg$^{26,34}$Lys$^{39}$-(Glut-ADod)-GLP-1(7-39);
Ser$^8$Glu$^{35}$Arg$^{26,34}$Lys$^{36}$-(Glut-ADod)-GLP-1(7-36);
Ser$^8$Glu$^{35}$Arg$^{26,34}$Lys$^{36}$-(Glut-ADod)-GLP-1(7-36)amide;
Ser$^8$Glu$^{36}$Arg$^{26,34}$Lys$^{37}$-(Glut-ADod)-GLP-1(7-37);
Ser$^8$Glu$^{37}$Arg$^{26,34}$Lys$^{38}$-(Glut-ADod)-GLP-1(7-38);
Ser$^8$Glu$^{38}$Arg$^{26,34}$Lys$^{39}$-(Glut-ADod)-GLP-1(7-39);
Ser$^8$Asp$^{35}$Arg$^{26,34}$Lys$^{36}$-(Glut-ADod)-GLP-1(7-36);
Ser$^8$Asp$^{35}$Arg$^{26,34}$Lys$^{36}$-(Glut-ADod)-GLP-1(7-36)amide;
Ser$^8$Asp$^{36}$Arg$^{26,34}$Lys$^{37}$-(Glut-ADod)-GLP-1(7-37);
Ser$^8$Asp$^{37}$Arg$^{26,34}$Lys$^{38}$-(Glut-ADod)-GLP-1(7-38);
Ser$^8$Asp$^{38}$Arg$^{26,34}$Lys$^{39}$-(Glut-ADod)-GLP-1(7-39);
Ser$^8$Asp$^{35}$Arg$^{26,34}$Lys$^{36}$-(Glut-ADod)-GLP-1(7-36);
Ser$^8$Asp$^{35}$Arg$^{26,34}$Lys$^{36}$-(Glut-ADod)-GLP-1(7-36)amide;
Ser$^8$Asp$^{36}$Arg$^{26,34}$Lys$^{37}$-(Glut-ADod)-GLP-1(7-37);
Ser$^8$Asp$^{37}$Arg$^{26,34}$Lys$^{38}$-(Glut-ADod)-GLP-1(7-38);
Ser$^8$Asp$^{38}$Arg$^{26,34}$Lys$^{39}$-(Glut-ADod)-GLP-1(7-39);
Thr$^8$Glu$^{35}$Arg$^{26,34}$Lys$^{36}$-(Glut-ADod)-GLP-1(7-36);
Thr$^8$Glu$^{35}$Arg$^{26,34}$Lys$^{36}$-(Glut-ADod)-GLP-1(7-36)amide;
Thr$^8$Glu$^{36}$Arg$^{26,34}$Lys$^{37}$-(Glut-ADod)-GLP-1(7-37);
Thr$^8$Glu$^{37}$Arg$^{26,34}$Lys$^{38}$-(Glut-ADod)-GLP-1(7-38);
Thr$^8$Glu$^{38}$Arg$^{26,34}$Lys$^{39}$-(Glut-ADod)-GLP-1(7-39);
Thr$^8$Glu$^{35}$Arg$^{26,34}$Lys$^{36}$-(Glut-ADod)-GLP-1(7-36);
Thr$^8$Glu$^{35}$Arg$^{26,34}$Lys$^{36}$-(Glut-ADod)-GLP-1(7-36)amide;
Thr$^8$Glu$^{36}$Arg$^{26,34}$Lys$^{37}$-(Glut-ADod)-GLP-1(7-37);
Thr$^8$Glu$^{37}$Arg$^{26,34}$Lys$^{38}$-(Glut-ADod)-GLP-1(7-38);
Thr$^8$Glu$^{38}$Arg$^{26,34}$Lys$^{39}$-(Glut-ADod)-GLP-1(7-39);
Thr$^8$Asp$^{35}$Arg$^{26,34}$Lys$^{36}$-(Glut-ADod)-GLP-1(7-36);
Thr$^8$Asp$^{35}$Arg$^{26,34}$Lys$^{36}$-(Glut-ADod)-GLP-1(7-36)amide;
Thr$^8$Asp$^{36}$Arg$^{26,34}$Lys$^{37}$-(Glut-ADod)-GLP-1(7-37);
Thr$^8$Asp$^{37}$Arg$^{26,34}$Lys$^{38}$-(Glut-ADod)-GLP-1(7-38);
Thr$^8$Asp$^{38}$Arg$^{26,34}$Lys$^{39}$-(Glut-ADod)-GLP-1(7-39);
Thr$^8$Asp$^{35}$Arg$^{26,34}$Lys$^{36}$-(Glut-ADod)-GLP-1(7-36);
Thr$^8$Asp$^{35}$Arg$^{26,34}$Lys$^{36}$-(Glut-ADod)-GLP-1(7-36)amide;
Thr$^8$Asp$^{36}$Arg$^{26,34}$Lys$^{37}$-(Glut-ADod)-GLP-1(7-37);
Thr$^8$Asp$^{37}$Arg$^{26,34}$Lys$^{38}$-(Glut-ADod)-GLP-1(7-38);
Thr$^8$Asp$^{38}$Arg$^{26,34}$Lys$^{39}$-(Glut-ADod)-GLP-1(7-39);
Arg$^{26,34}$Lys$^{18}$-(Glut-ADod)-GLP-1(7-36); Arg$^{26,34}$Lys$^{18}$-(Glut-ADod)-GLP-1(7-36)amide; Arg$^{26,34}$Lys$^{18}$-(Glut-ADod)-GLP-1(7-37);Arg$^{26,34}$Lys$^{18}$-(Glut-ADod)-GLP-1(7-38); Gly$^8$Asp$^{19}$Arg$^{26,34}$Lys$^{18}$-(Glut-ADod)-GLP-1(7-36);
Gly$^8$Asp$^{17}$Arg$^{26,34}$Lys$^{18}$-(Glut-ADod)-GLP-1(7-36);
Gly$^8$Asp$^{19}$Arg$^{26,34}$Lys$^{18}$-(Glut-ADod)-GLP-1(7-36)amide;
Gly$^8$Asp$^{17}$Arg$^{26,34}$Lys$^{18}$-(Glut-ADod)-GLP-1(7-36)amide;
Gly$^8$Asp$^{19}$Arg$^{26,34}$Lys$^{18}$-(Glut-ADod)-GLP-1(7-37);
Gly$^8$Asp$^{19}$Arg$^{26,34}$Lys$^{18}$-(Glut-ADod)-GLP-1(7-38);
Gly$^8$Asp$^{17}$Arg$^{26,34}$Lys$^{18}$-(Glut-ADod)-GLP-1(7-38);
Arg$^{26,34}$Lys$^{23}$-(Glut-ADod)-GLP-1(7-36); Arg$^{26,34}$Lys$^{23}$-(Glut-ADod)-GLP-1(7-36)amide; Arg$^{26,34}$Lys$^{23}$-(Glut-ADod)-GLP-1(7-37);Arg$^{26,34}$Lys$^{23}$-(Glut-ADod)-GLP-1(7-38); Gly$^8$Asp$^{19}$Arg$^{26,34}$Lys$^{23}$-(Glut-ADod)-GLP-1(7-36);
Gly$^8$Asp$^{17}$Arg$^{26,34}$Lys$^{23}$-(Glut-ADod)-GLP-1(7-36);
Gly$^8$Asp$^{19}$Arg$^{26,34}$Lys$^{23}$-(Glut-ADod)-GLP-1(7-36)amide;
Gly$^8$Asp$^{17}$Arg$^{26,34}$Lys$^{23}$-(Glut-ADod)-GLP-1(7-36)amide;
Gly$^8$Asp$^{19}$Arg$^{26,34}$Lys$^{23}$-(Glut-ADod)-GLP-1(7-37);
Gly$^8$Asp$^{19}$Arg$^{26,34}$Lys$^{23}$-(Glut-ADod)-GLP-1(7-38);
Gly$^8$Asp$^{17}$Arg$^{26,34}$Lys$^{23}$-(Glut-ADod)-GLP-1(7-38);
Arg$^{26,34}$Lys$^{27}$-(Glut-ADod)-GLP-1(7-36); Arg$^{26,34}$Lys$^{27}$-(Glut-ADod)-GLP-1(7-36)amide; Arg$^{26,34}$Lys$^{27}$-(Glut-ADod)-GLP-1(7-37);Arg$^{26,34}$Lys$^{27}$-(Glut-ADod)-GLP-1(7-38); Gly$^8$Asp$^{19}$Arg$^{26,34}$Lys$^{27}$-(Glut-ADod)-GLP-1(7-36);
Gly$^8$Asp$^{17}$Arg$^{26,34}$Lys$^{27}$-(Glut-ADod)-GLP-1(7-36);
Gly$^8$Asp$^{19}$Arg$^{26,34}$Lys$^{27}$-(Glut-ADod)-GLP-1(7-36)amide;
Gly$^8$Asp$^{17}$Arg$^{26,34}$Lys$^{27}$-(Glut-ADod)-GLP-1(7-36)amide;
Gly$^8$Asp$^{19}$Arg$^{26,34}$Lys$^{27}$-(Glut-ADod)-GLP-1(7-37);
Gly$^8$Asp$^{19}$Arg$^{26,34}$Lys$^{27}$-(Glut-ADod)-GLP-1(7-38);
Gly$^8$Asp$^{17}$Arg$^{26,34}$Lys$^{27}$-(Glut-ADod)-GLP-1(7-38);
Arg$^{26,34}$Lys$^{18}$-(Glut-ADod)-GLP-1(7-36); Arg$^{26,34}$Lys$^{18}$-(Glut-ADod)-GLP-1(7-36)amide; Arg$^{26,34}$Lys$^{18}$-(Glut-ADod)-GLP-1(7-37);Arg$^{26,34}$Lys$^{18}$-(Glut-ADod)-GLP-1(7-38); Val$^8$Asp$^{19}$Arg$^{26,34}$Lys$^{18}$-(Glut-ADod)-GLP-1(7-36);
Val$^8$Asp$^{17}$Arg$^{26,34}$Lys$^{18}$-(Glut-ADod)-GLP-1(7-36);
Val$^8$Asp$^{19}$Arg$^{26,34}$Lys$^{18}$-(Glut-ADod)-GLP-1(7-36)amide;
Val$^8$Asp$^{17}$Arg$^{26,34}$Lys$^{18}$-(Glut-ADod)-GLP-1(7-36)amide;
Val$^8$Asp$^{19}$Arg$^{26,34}$Lys$^{18}$-(Glut-ADod)-GLP-1(7-37);
Val$^8$Asp$^{19}$Arg$^{26,34}$Lys$^{18}$-(Glut-ADod)-GLP-1(7-38);
Val$^8$Asp$^{17}$Arg$^{26,34}$Lys$^{18}$-(Glut-ADod)-GLP-1(7-38);
Arg$^{26,34}$Lys$^{23}$-(Glut-ADod)-GLP-1(7-36); Arg$^{26,34}$Lys$^{23}$-(Glut-ADod)-GLP-1(7-36)amide; Arg$^{26,34}$Lys$^{23}$-(Glut-ADod)-GLP-1(7-37);Arg$^{26,34}$Lys$^{23}$-(Glut-ADod)-GLP-1(7-38); Val$^8$Asp$^{19}$Arg$^{26,34}$Lys$^{23}$-(Glut-ADod)-GLP-1(7-36);
Val$^8$Asp$^{17}$Arg$^{26,34}$Lys$^{23}$-(Glut-ADod)-GLP-1(7-36);
Val$^8$Asp$^{19}$Arg$^{26,34}$Lys$^{23}$-(Glut-ADod)-GLP-1(7-36)amide;
Val$^8$Asp$^{17}$Arg$^{26,34}$Lys$^{23}$-(Glut-ADod)-GLP-1(7-36)amide;
Val$^8$Asp$^{19}$Arg$^{26,34}$Lys$^{23}$-(Glut-ADod)-GLP-1(7-37);
Val$^8$Asp$^{19}$Arg$^{26,34}$Lys$^{23}$-(Glut-ADod)-GLP-1(7-38);
Val$^8$Asp$^{17}$Arg$^{26,34}$Lys$^{23}$-(Glut-ADod)-GLP-1(7-38);

Arg$^{26,34}$Lys$^{27}$-(Glut-ADod)-GLP-1(7-36); Arg$^{26,34}$Lys$^{27}$-(Glut-ADod)-GLP-1(7-36)amide; Arg$^{26,34}$Lys$^{27}$-(Glut-ADod)-GLP-1(7-37);Arg$^{26,34}$Lys$^{27}$-(Glut-ADod)-GLP-1(7-38); Val$^8$Asp$^{19}$Arg$^{26,34}$Lys$^{27}$-(Glut-ADod)-GLP-1(7-36); Val$^8$Asp$^{17}$Arg$^{26,34}$Lys$^{27}$-(Glut-ADod)-GLP-1(7-36); Val$^8$Asp$^{19}$Arg$^{26,34}$Lys$^{27}$-(Glut-ADod)-GLP-1(7-36)amide; Val$^8$Asp$^{17}$Arg$^{26,34}$Lys$^{27}$-(Glut-ADod)-GLP-1(7-36)amide; Val$^8$Asp$^{19}$Arg$^{26,34}$Lys$^{27}$-(Glut-ADod)-GLP-1(7-37); Val$^8$Asp$^{19}$Arg$^{26,34}$Lys$^{27}$-(Glut-ADod)-GLP-1(7-38); Val$^8$Asp$^{17}$Arg$^{26,34}$Lys$^{27}$-(Glut-ADod)-GLP-1(7-38); Arg$^{26,34}$Lys$^{18}$-(Glut-ADod)-GLP-1(7-36); Arg$^{26,34}$Lys$^{18}$-(Glut-ADod)-GLP-1(7-36)amide; Arg$^{26,34}$Lys$^{18}$-(Glut-ADod)-GLP-1(7-37);Arg$^{26,34}$Lys$^{18}$-(Glut-ADod)-GLP-1(7-38); Ser$^8$Asp$^{19}$Arg$^{26,34}$Lys$^{18}$-(Glut-ADod)-GLP-1(7-36); Ser$^8$Asp$^{17}$Arg$^{26,34}$Lys$^{18}$-(Glut-ADod)-GLP-1(7-36); Ser$^8$Asp$^{19}$Arg$^{26,34}$Lys$^{18}$-(Glut-ADod)-GLP-1(7-36)amide; Ser$^8$Asp$^{17}$Arg$^{26,34}$Lys$^{18}$-(Glut-ADod)-GLP-1(7-36)amide; Ser$^8$Asp$^{19}$Arg$^{26,34}$Lys$^{18}$-(Glut-ADod)-GLP-1(7-37); Ser$^8$Asp$^{19}$Arg$^{26,34}$Lys$^{18}$-(Glut-ADod)-GLP-1(7-38); Ser$^8$Asp$^{17}$Arg$^{26,34}$Lys$^{18}$-(Glut-ADod)-GLP-1(7-38); Arg$^{26,34}$Lys$^{23}$-(Glut-ADod)-GLP-1(7-36); Arg$^{26,34}$Lys$^{23}$-(Glut-ADod)-GLP-1(7-36)amide; Arg$^{26,34}$Lys$^{23}$-(Glut-ADod)-GLP-1(7-37);Arg$^{26,34}$Lys$^{23}$-(Glut-ADod)-GLP-1(7-38); Ser$^8$Asp$^{19}$Arg$^{26,34}$Lys$^{23}$-(Glut-ADod)-GLP-1(7-36); Ser$^8$Asp$^{17}$Arg$^{26,34}$Lys$^{23}$-(Glut-ADod)-GLP-1(7-36); Ser$^8$Asp$^{19}$Arg$^{26,34}$Lys$^{23}$-(Glut-ADod)-GLP-1(7-36)amide; Ser$^8$Asp$^{17}$Arg$^{26,34}$Lys$^{23}$-(Glut-ADod)-GLP-1(7-36)amide; Ser$^8$Asp$^{19}$Arg$^{26,34}$Lys$^{23}$-(Glut-ADod)-GLP-1(7-37); Ser$^8$Asp$^{19}$Arg$^{26,34}$Lys$^{23}$-(Glut-ADod)-GLP-1(7-38); Ser$^8$Asp$^{17}$Arg$^{26,34}$Lys$^{23}$-(Glut-ADod)-GLP-1(7-38); Arg$^{26,34}$Lys$^{27}$-(Glut-ADod)-GLP-1(7-36); Arg$^{26,34}$Lys$^{27}$-(Glut-ADod)-GLP-1(7-36)amide; Arg$^{26,34}$Lys$^{27}$-(Glut-ADod)-GLP-1(7-37);Arg$^{26,34}$Lys$^{27}$-(Glut-ADod)-GLP-1(7-38); Ser$^8$Asp$^{19}$Arg$^{26,34}$Lys$^{27}$-(Glut-ADod)-GLP-1(7-36); Ser$^8$Asp$^{17}$Arg$^{26,34}$Lys$^{27}$-(Glut-ADod)-GLP-1(7-36); Ser$^8$Asp$^{19}$Arg$^{26,34}$Lys$^{27}$-(Glut-ADod)-GLP-1(7-36)amide; Ser$^8$Asp$^{17}$Arg$^{26,34}$Lys$^{27}$-(Glut-ADod)-GLP-1(7-36)amide; Ser$^8$Asp$^{19}$Arg$^{26,34}$Lys$^{27}$-(Glut-ADod)-GLP-1(7-37); Ser$^8$Asp$^{19}$Arg$^{26,34}$Lys$^{27}$-(Glut-ADod)-GLP-1(7-38); Ser$^8$Asp$^{17}$Arg$^{26,34}$Lys$^{27}$-(Glut-ADod)-GLP-1(7-38); Arg$^{26,34}$Lys$^{18}$-(Glut-ADod)-GLP-1(7-36); Arg$^{26,34}$Lys$^{18}$-(Glut-ADod)-GLP-1(7-36)amide; Arg$^{26,34}$Lys$^{18}$-(Glut-ADod)-GLP-1(7-37);Arg$^{26,34}$Lys$^{18}$-(Glut-ADod)-GLP-1(7-38); Thr$^8$Asp$^{19}$Arg$^{26,34}$Lys$^{18}$-(Glut-ADod)-GLP-1(7-36); Thr$^8$Asp$^{17}$Arg$^{26,34}$Lys$^{18}$-(Glut-ADod)-GLP-1(7-36); Thr$^8$Asp$^{19}$Arg$^{26,34}$Lys$^{18}$-(Glut-ADod)-GLP-1(7-36)amide; Thr$^8$Asp$^{17}$Arg$^{26,34}$Lys$^{18}$-(Glut-ADod)-GLP-1(7-36)amide; Thr$^8$Asp$^{19}$Arg$^{26,34}$Lys$^{18}$-(Glut-ADod)-GLP-1(7-37); Thr$^8$Asp$^{19}$Arg$^{26,34}$Lys$^{18}$-(Glut-ADod)-GLP-1(7-38); Thr$^8$Asp$^{17}$Arg$^{26,34}$Lys$^{18}$-(Glut-ADod)-GLP-1(7-38); Arg$^{26,34}$Lys$^{23}$-(Glut-ADod)-GLP-1(7-36); Arg$^{26,34}$Lys$^{23}$-(Glut-ADod)-GLP-1(7-36)amide; Arg$^{26,34}$Lys$^{23}$-(Glut-ADod)-GLP-1(7-37);Arg$^{26,34}$Lys$^{23}$-(Glut-ADod)-GLP-1(7-38); Thr$^8$Asp$^{19}$Arg$^{26,34}$Lys$^{23}$-(Glut-ADod)-GLP-1(7-36); Thr$^8$Asp$^{17}$Arg$^{26,34}$Lys$^{23}$-(Glut-ADod)-GLP-1(7-36); Thr$^8$Asp$^{19}$Arg$^{26,34}$Lys$^{23}$-(Glut-ADod)-GLP-1(7-36)amide; Thr$^8$Asp$^{17}$Arg$^{26,34}$Lys$^{23}$-(Glut-ADod)-GLP-1(7-36)amide; Thr$^8$Asp$^{19}$Arg$^{26,34}$Lys$^{23}$-(Glut-ADod)-GLP-1(7-37); Thr$^8$Asp$^{19}$Arg$^{26,34}$Lys$^{23}$-(Glut-ADod)-GLP-1(7-38); Thr$^8$Asp$^{17}$Arg$^{26,34}$Lys$^{23}$-(Glut-ADod)-GLP-1(7-38); Arg$^{26,34}$Lys$^{27}$-(Glut-ADod)-GLP-1(7-36); Arg$^{26,34}$Lys$^{27}$-(Glut-ADod)-GLP-1(7-36)amide; Arg$^{26,34}$Lys$^{27}$-(Glut-ADod)-GLP-1(7-37);Arg$^{26,34}$Lys$^{27}$-(Glut-ADod)-GLP-1(7-38); Thr$^8$Asp$^{19}$Arg$^{26,34}$Lys$^{27}$-(Glut-ADod)-GLP-1(7-36); Thr$^8$Asp$^{17}$Arg$^{26,34}$Lys$^{27}$-(Glut-ADod)-GLP-1(7-36); Thr$^8$Asp$^{19}$Arg$^{26,34}$Lys$^{27}$-(Glut-ADod)-GLP-1(7-36)amide; Thr$^8$Asp$^{17}$Arg$^{26,34}$Lys$^{27}$-(Glut-ADod)-GLP-1(7-36)amide; Thr$^8$Asp$^{19}$Arg$^{26,34}$Lys$^{27}$-(Glut-ADod)-GLP-1(7-37); Thr$^8$Asp$^{19}$Arg$^{26,34}$Lys$^{27}$-(Glut-ADod)-GLP-1(7-38); Thr$^8$Asp$^{17}$Arg$^{26,34}$Lys$^{27}$-(Glut-ADod)-GLP-1(7-38); Arg$^{26}$Lys$^{34}$-(Glut-ATet)-GLP-1(7-36); Arg$^{34}$Lys$^{26}$-(Glut-ATet)-GLP-1(7-36); Arg$^{26,34}$Lys$^{36}$-(Glut-ATet)-GLP-1(7-36); Arg$^{26}$Lys$^{34}$-(Glut-ATet)-GLP-1(7-36)amide; Arg$^{34}$Lys$^{26}$-(Glut-ATet)-GLP-1(7-36)amide; Arg$^{26,34}$Lys$^{36}$-(Glut-ATet)-GLP-1(7-36)amide; Arg$^{26}$Lys$^{34}$-(Glut-ATet)-GLP-1(7-37); Arg$^{34}$Lys$^{26}$-(Glut-ATet)-GLP-1(7-37); Arg$^{26,34}$Lys$^{36}$-(Glut-ATet)-GLP-1(7-37); Arg$^{26}$Lys$^{34}$-(Glut-ATet)-GLP-1(7-38); Arg$^{34}$Lys$^{26}$-(Glut-ATet)-GLP-1(7-38); Arg$^{26,34}$Lys$^{38}$-(Glut-ATet)-GLP-1(7-38); Arg$^{26}$Lys$^{34}$-(Glut-ATet)-GLP-1(7-39); Arg$^{34}$Lys$^{26}$-(Glut-ATet)-GLP-1(7-39); Arg$^{26,34}$Lys$^{39}$-(Glut-ATet)-GLP-1(7-39); Gly$^8$Arg$^{26}$Lys$^{34}$-(Glut-ATet)-GLP-1(7-36); Gly$^8$Arg$^{34}$Lys$^{26}$-(Glut-ATet)-GLP-1(7-36); Gly$^8$Arg$^{26,34}$Lys$^{36}$-(Glut-ATet)-GLP-1(7-36); Gly$^8$Arg$^{26}$Lys$^{34}$-(Glut-ATet)-GLP-1(7-36)amide; Gly$^8$Arg$^{34}$Lys$^{26}$-(Glut-ATet)-GLP-1(7-36)amide; Gly$^8$Arg$^{26,34}$Lys$^{36}$-(Glut-ATet)-GLP-1(7-36)amide; Gly$^8$Arg$^{26}$Lys$^{34}$-(Glut-ATet)-GLP-1(7-37); Gly$^8$Arg$^{34}$Lys$^{26}$-(Glut-ATet)-GLP-1(7-37); Gly$^8$Arg$^{26,34}$Lys$^{36}$-(Glut-ATet)-GLP-1(7-37); Gly$^8$Arg$^{26}$Lys$^{34}$-(Glut-ATet)-GLP-1(7-38); Gly$^8$Arg$^{34}$Lys$^{26}$-(Glut-ATet)-GLP-1(7-38); Gly$^8$Arg$^{26,34}$Lys$^{38}$-(Glut-ATet)-GLP-1(7-38); Gly$^8$Arg$^{26}$Lys$^{34}$-(Glut-ATet)-GLP-1(7-39); Gly$^8$Arg$^{34}$Lys$^{26}$-(Glut-ATet)-GLP-1(7-39); Gly$^8$Arg$^{26,34}$Lys$^{39}$-(Glut-ATet)-GLP-1(7-39); Val$^8$Arg$^{26}$Lys$^{34}$-(Glut-ATet)-GLP-1(7-36); Val$^8$Arg$^{34}$Lys$^{26}$-(Glut-ATet)-GLP-1(7-36); Val$^8$Arg$^{26,34}$Lys$^{36}$-(Glut-ATet)-GLP-1(7-36); Val$^8$Arg$^{26}$Lys$^{34}$-(Glut-ATet)-GLP-1(7-36) amide; Val$^8$Arg$^{34}$Lys$^{26}$-(Glut-ATet)-GLP-1(7-36)amide; Val$^8$Arg$^{26,34}$Lys$^{36}$-(Glut-ATet)-GLP-1(7-36)amide; Val$^8$Arg$^{26}$Lys$^{34}$-(Glut-ATet)-GLP-1(7-37); Val$^8$Arg$^{34}$Lys$^{26}$-(Glut-ATet)-GLP-1(7-37); Val$^8$Arg$^{26,34}$Lys$^{36}$-(Glut-ATet)-GLP-1(7-37); Val$^8$Arg$^{26}$Lys$^{34}$-(Glut-ATet)-GLP-1(7-38); Val$^8$Arg$^{34}$Lys$^{26}$-(Glut-ATet)-GLP-1(7-38); Val$^8$Arg$^{26,34}$Lys$^{38}$-(Glut-ATet)-GLP-1(7-38); Val$^8$Arg$^{26}$Lys$^{34}$-(Glut-ATet)-GLP-1(7-39); Val$^8$Arg$^{34}$Lys$^{26}$-(Glut-ATet)-GLP-1(7-39); Val$^8$Arg$^{26,34}$Lys$^{39}$-(Glut-ATet)-GLP-1(7-39); Ser$^8$Arg$^{26}$Lys$^{34}$-(Glut-ATet)-GLP-1(7-36); Ser$^8$Arg$^{34}$Lys$^{26}$-(Glut-ATet)-GLP-1(7-36); Ser$^8$Arg$^{26,34}$Lys$^{36}$-(Glut-ATet)-GLP-1(7-36); Ser$^8$Arg$^{26}$Lys$^{34}$-(Glut-ATet)-GLP-1(7-36) amide; Ser$^8$Arg$^{34}$Lys$^{26}$-(Glut-ATet)-GLP-1(7-36)amide; Ser$^8$Arg$^{26,34}$Lys$^{36}$-(Glut-ATet)-GLP-1(7-36)amide; Ser$^8$Arg$^{26}$Lys$^{34}$-(Glut-ATet)-GLP-1(7-37); Ser$^8$Arg$^{34}$Lys$^{26}$-(Glut-ATet)-GLP-1(7-37); Ser$^8$Arg$^{26,34}$Lys$^{36}$-(Glut-ATet)-GLP-1(7-37); Ser$^8$Arg$^{26}$Lys$^{34}$-(Glut-ATet)-GLP-1(7-38); Ser$^8$Arg$^{34}$Lys$^{26}$-(Glut-ATet)-GLP-1(7-38); Ser$^8$Arg$^{26,34}$Lys$^{38}$-(Glut-ATet)-GLP-1(7-38); Ser$^8$Arg$^{26}$Lys$^{34}$-(Glut-ATet)-GLP-1(7-39); Ser$^8$Arg$^{34}$Lys$^{26}$-(Glut-ATet)-GLP-1(7-39); Ser$^8$Arg$^{26,34}$Lys$^{39}$-(Glut-ATet)-GLP-1(7-39); Thr$^8$Arg$^{26}$Lys$^{34}$-(Glut-ATet)-GLP-1(7-36); Thr$^8$Arg$^{34}$Lys$^{26}$-(Glut-ATet)-GLP-1(7-36); Thr$^8$Arg$^{26,34}$Lys$^{36}$-(Glut-ATet)-GLP-1(7-36); Thr$^8$Arg$^{26}$Lys$^{34}$-(Glut-ATet)-GLP-1(7-36)amide; Thr$^8$Arg$^{34}$Lys$^{26}$-(Glut-ATet)-GLP-1(7-36)amide; Thr$^8$Arg$^{26,34}$Lys$^{36}$-(Glut-ATet)-GLP-1(7-36)amide; Thr$^8$Arg$^{26}$Lys$^{34}$-(Glut-ATet)-GLP-1(7-37); Thr$^8$Arg$^{34}$Lys$^{26}$-(Glut-ATet)-GLP-1(7-37); Thr$^8$Arg$^{26,34}$Lys$^{36}$-(Glut-ATet)-GLP-1(7-37); Thr$^8$Arg$^{26}$Lys$^{34}$-(Glut-ATet)-GLP-1(7-38); Thr$^8$Arg$^{34}$Lys$^{26}$-(Glut-ATet)-GLP-1(7-38); Thr$^8$Arg$^{26,34}$Lys$^{38}$-(Glut-ATet)-GLP-1(7-38); Thr$^8$Arg$^{26}$Lys$^{34}$-(Glut-ATet)-GLP-1(7-39); Thr$^8$Arg$^{34}$Lys$^{26}$-(Glut-ATet)-GLP-1(7-39); Thr$^8$Arg$^{26,34}$Lys$^{39}$-(Glut-ATet)-GLP-1(7-39); Gly$^8$Glu$^{35}$Arg$^{26,34}$Lys$^{36}$-(Glut-ATet)-GLP-1(7-36); Gly$^8$Glu$^{35}$Arg$^{26,34}$Lys$^{36}$-(Glut-ATet)-GLP-1(7-36)amide; Gly$^8$Glu$^{36}$Arg$^{26,34}$Lys$^{37}$-(Glut-ATet)-GLP-1(7-37);

Gly⁸Glu³⁷Arg²⁶,³⁴Lys³⁸-(Glut-ATet)-GLP-1(7-38);
Gly⁸Glu³⁸Arg²⁶,³⁴Lys³⁹-(Glut-ATet)-GLP-1(7-39);
Gly⁸Glu³⁵Arg²⁶,³⁴Lys³⁶-(Glut-ATet)-GLP-1(7-36);
Gly⁸Glu³⁵Arg²⁶,³⁴Lys³⁶-(Glut-ATet)-GLP-1(7-36)amide;
Gly⁸Glu³⁶Arg²⁶,³⁴Lys³⁷-(Glut-ATet)-GLP-1(7-37);
Gly⁸Glu³⁷Arg²⁶,³⁴Lys³⁸-(Glut-ATet)-GLP-1(7-38);
Gly⁸Glu³⁸Arg²⁶,³⁴Lys³⁹-(Glut-ATet)-GLP-1(7-39);
Gly⁸Asp³⁵Arg²⁶,³⁴Lys³⁶-(Glut-ATet)-GLP-1(7-36);
Gly⁸Asp³⁵Arg²⁶,³⁴Lys³⁶-(Glut-ATet)-GLP-1(7-36)amide;
Gly⁸Asp³⁶Arg²⁶,³⁴Lys³⁷-(Glut-ATet)-GLP-1(7-37);
Gly⁸Asp³⁷Arg²⁶,³⁴Lys³⁸-(Glut-ATet)-GLP-1(7-38);
Gly⁸Asp³⁸Arg²⁶,³⁴Lys³⁹-(Glut-ATet)-GLP-1(7-39);
Gly⁸Asp³⁵Arg²⁶,³⁴Lys³⁶-(Glut-ATet)-GLP-1(7-36);
Gly⁸Asp³⁵Arg²⁶,³⁴Lys³⁶-(Glut-ATet)-GLP-1(7-36)amide;
Gly⁸Asp³⁶Arg²⁶,³⁴Lys³⁷-(Glut-ATet)-GLP-1(7-37);
Gly⁸Asp³⁷Arg²⁶,³⁴Lys³⁸-(Glut-ATet)-GLP-1(7-38);
Gly⁸Asp³⁸Arg²⁶,³⁴Lys³⁹-(Glut-ATet)-GLP-1(7-39);
Val⁸Glu³⁵Arg²⁶,³⁴Lys³⁶-(Glut-ATet)-GLP-1(7-36);
Val⁸Glu³⁵Arg²⁶,³⁴Lys³⁶-(Glut-ATet)-GLP-1(7-36)amide;
Val⁸Glu³⁶Arg²⁶,³⁴Lys³⁷-(Glut-ATet)-GLP-1(7-37);
Val⁸Glu³⁷Arg²⁶,³⁴Lys³⁸-(Glut-ATet)-GLP-1(7-38);
Val⁸Glu³⁸Arg²⁶,³⁴Lys³⁹-(Glut-ATet)-GLP-1(7-39);
Val⁸Glu³⁵Arg²⁶,³⁴Lys³⁶-(Glut-ATet)-GLP-1(7-36);
Val⁸Glu³⁵Arg²⁶,³⁴Lys³⁶-(Glut-ATet)-GLP-1(7-36)amide;
Val⁸Glu³⁶Arg²⁶,³⁴Lys³⁷-(Glut-ATet)-GLP-1(7-37);
Val⁸Glu³⁷Arg²⁶,³⁴Lys³⁹(Glut-ATet)-GLP-1(7-3   (7-39);
Val⁸Asp³⁵Arg²⁶,³⁴Lys³⁶-(Glut-ATet)-GLP-1(7-36);
Val⁸Asp³⁵Arg²⁶,³⁴Lys³⁶-(Glut-ATet)-GLP-1(7-36)amide;
Val⁸Asp³⁶Arg²⁶,³⁴Lys³⁷-(Glut-ATet)-GLP-1(7-37);
Val⁸Asp³⁷Arg²⁶,³⁴Lys³⁸-(Glut-ATet)-GLP-1(7-38);
Val⁸Asp³⁸Arg²⁶,³⁴Lys³⁹-(Glut-ATet)-GLP-1(7-39);
Val⁸Asp³⁵Arg²⁶,³⁴Lys³⁶-(Glut-ATet)-GLP-1(7-36);
Val⁸Asp³⁵Arg²⁶,³⁴Lys³⁶-(Glut-ATet)-GLP-1(7-36)amide;
Val⁸Asp³⁶Arg²⁶,³⁴Lys³⁷-(Glut-ATet)-GLP-1(7-37);
Val⁸Asp³⁷Arg²⁶,³⁴Lys³⁸-(Glut-ATet)-GLP-1(7-38);
Val⁸Asp³⁸Arg²⁶,³⁴Lys³⁹-(Glut-ATet)-GLP-1(7-39);
Ser⁸Glu³⁵Arg²⁶,³⁴Lys³⁶-(Glut-ATet)-GLP-1(7-36);
Ser⁸Glu³⁵Arg²⁶,³⁴Lys³⁶-(Glut-ATet)-GLP-1(7-36)amide;
Ser⁸Glu³⁶Arg²⁶,³⁴Lys³⁷-(Glut-ATet)-GLP-1(7-37);
Ser⁸Glu³⁷Arg²⁶,³⁴Lys³⁸-(Glut-ATet)-GLP-1(7-38);
Ser⁸Glu³⁸Arg²⁶,³⁴Lys³⁹-(Glut-ATet)-GLP-1(7-39);
Ser⁸Glu³⁵Arg²⁶,³⁴Lys³⁶-(Glut-ATet)-GLP-1(7-36);
Ser⁸Glu³⁵Arg²⁶,³⁴Lys³⁶-(Glut-ATet)-GLP-1(7-36)amide;
Ser⁸Glu³⁶Arg²⁶,³⁴Lys³⁷-(Glut-ATet)-GLP-1(7-37);
Ser⁸Glu³⁷Arg²⁶,³⁴Lys³⁶-(Glut-ATet)-GLP-1(7-38)    Se;
Ser⁸Glu³⁸Arg²⁶,³⁴Lys³Lys¹⁸-(Glut-ATet)-GLP-1(7-39);
Ser⁸Asp³⁵Arg²⁶,³⁴Lys³⁶-(Glut-ATet)-GLP-1(7-36);
Ser⁸Asp³⁵Arg²⁶,³⁴Lys³⁶-(Glut-ATet)-GLP-1(7-3)amide;
Ser⁸Asp³⁶Arg²⁶,³⁴Lys³⁷-(Glut-ATet)-GLP-1(7-37);
Ser⁸Asp⁷Arg²⁶,³⁴Lys³⁸-(Glut-ADod)-GLP-1(7-38);
Ser⁸Asp³⁸Arg²⁶,³⁴Lys³⁹-(Glut-ATet)-GLP-1(7-39);
Ser⁸Asp³⁵Arg²⁶,³⁴Lys³⁶-(Glut-ATet)-GLP-1(7-36);
Ser⁸Asp³⁵Arg²⁶,³⁴Lys³⁶-(Glut-ATet)-GLP-1(7-36)amide;
Ser⁸Asp³⁶Arg²⁶,³⁴Lys³⁷-(Glut-ATet)-GLP-1(7-37);
Ser⁸Asp³⁷Arg²⁶,³⁴Lys³⁸-(Glut-ATet)-GLP-1(7-38);
Ser⁸Asp³³Arg²⁶,³⁴Lys³⁹-(Glut-ATet)-GLP-1(7-39);
Thr⁸Glu³⁵Arg²⁶,³⁴Lys³⁶-(Glut-ATet)-GLP-1(7-36);
Thr⁸Glu³⁵Arg²⁶,³⁴Lys³⁶,³⁴(Glut-ATet)-GLP-1(7-3)amide;
Thr⁸Glu³⁶Arg²⁶,³⁴Lys³⁷-(Glut-ATet)-GLP-1(7-37);
Thr⁸Glu³⁷Arg²⁶,³⁴Lys¹⁸-(Glut-ATet)-GLP-1(7-38);
Thr⁸Glu³Arg²⁶,³⁴Lys³⁹-(Glut-ATet)-GLP-1(7-39);
Thr⁸Glu³⁵Arg²⁶,³⁴Lys³⁶-(Glut-ATet)-GLP-1(7-36);
Thr⁸Glu³⁵Arg²⁶,³⁴Lys³⁶-(Glut-ATet)-GLP-1(7-36)amide;
Thr⁸Glu³⁶Arg²⁶,³⁴Lys³⁷-(Glut-ATet)-GLP-1(7-37);
Thr⁸Glu³⁷Arg²⁶,³⁴Lys³⁸-(Glut-ATet)-GLP-1(7-38);
Thr⁸Glu³⁸Arg²⁶,³⁴Lys³⁹-(Glut-ATet)-GLP-1(7-39);
Thr⁸Asp³⁵Arg²⁶,³⁴Lys³⁶-(Glut-ATet)-GLP-1(7-36);
Thr⁸Asp³⁵Arg²⁶,³⁴Lys³⁶-(Glut-ATet)-GLP-1(7-36)amide;
Thr⁸Asp³⁶Arg²⁶,³⁴Lys³⁷-(Glut-ATet)-GLP-1(7-37);
Thr⁸Asp³⁷Arg²⁶,³⁴Lys³⁸-(Glut-ATet)-GLP-1(7-38);
Thr⁸Asp³⁸Arg²⁶,³⁴Lys³⁹-(Glut-ATet)-GLP-1(7-39);
Thr⁸Asp³⁵Arg²⁶,³⁴Lys³⁶-(Glut-ATet)-GLP-1(7-36);
Thr⁸Asp³⁵Arg²⁶,³⁴Lys³⁶-(Glut-ATet)-GLP-1(7-36)amide;
Thr⁸Asp³⁶Arg²⁶,³⁴Lys³⁷-(Glut-ATet)-GLP-1(7-37);
Thr⁸Asp³⁷Arg²⁶,³⁴Lys³⁸-(Glut-ATet)-GLP-1(7-38);
Thr⁸Asp³⁸Arg²⁶,³⁴Lys³⁹-(Glut-ATet)-GLP-1(7-39);
Arg²⁶,³⁴Lys⁵Arg²⁶,³⁴Lys³⁶-(Glut-ATet)-GLP-1(7-36);
Arg²⁶,³⁴Lys¹⁸-(Glut-ATet)-GLP-1(7-36)amide;
Arg²⁶,³⁴Lys¹⁸-(Glut-ATet)-GLP-1(7-37);   Arg²⁶,³⁴Lys¹⁸-(Glut-ATet)-GLP-1(7-3   (7-38);   Gly⁸Asp¹⁹Arg²⁶,³⁴Lys¹⁸-(Glut-ATet)-GLP-1(7-36);   Gly⁸Asp¹⁷Arg²⁶,³⁴Lys¹⁸-(Glut-ATet)-GLP-1(7-36);   Gly⁸Asp¹⁹Arg²⁶,³⁴Lys¹⁸-(Glut-ATet)-GLP-1(7-36)amide;   Gly⁸Asp¹⁷Arg²⁶,³⁴Lys¹⁸(Glut-ATet)-GLP-1(7-36)amide;   Gly⁸Asp¹⁹Arg²⁶,³⁴Lys¹⁸-(Glut-ATet)-GLP-1(7-37);   Gly⁸Asp¹⁹Arg²⁶,³⁴Lys¹⁸-(Glut-ATet)-GLP-1(7-38);   Gly⁸Asp¹⁷Arg²⁶,³⁴Lys¹⁸-(Glut-ATet)-GLP-1(7-38)
Arg²⁶,³⁴Lys²³-(Glut-ATet)-GLP-1(7-36);   Arg²⁶,³⁴Lys²³-(Glut-ATet)-GLP-1(7-36)amide; Arg²⁶,³⁴Lys²³-(Glut-ATet)-GLP-1(7-37);   Arg²⁶,³⁴Lys²³-(Glut-ATet)-GLP-1(7-38);
Gly⁸Asp¹⁹Arg²⁶,³⁴Lys²³-(Glut-ATet)-GLP-1(7-36);
Gly⁸Asp¹⁷Arg²⁶,³⁴Lys²³-(Glut-ATet)-GLP-1(7-36);
Gly⁸Asp¹⁹Arg²⁶,³⁴Lys²³-(Glut-ATet)-GLP-1(7-36)amide;
Gly⁸Asp¹⁷Arg²⁶,³⁴Lys²³-(Glut-ATet)-GLP-1(7-36)amide;
Gly⁸Asp¹⁹Arg²⁶,³⁴Lys²³-(Glut-ATet)-GLP-1(7-37);
Gly⁸Asp¹⁹Arg²⁶,³⁴Lys²³-(Glut-ATet)-GLP-1(7-38);
Gly⁸Asp¹⁷Arg²⁶,³⁴Lys²³-(Glut-ATet)-GLP-1(7-38);
Arg²⁶,³⁴Lys²⁷-(Glut-ATet)-GLP-1(7-36);   Arg²⁶,³⁴Lys²⁷-(Glut-ATet)-GLP-1(7-36)amide; Arg²⁶,³⁴Lys²⁷-(Glut-ATet)-GLP-1(7-37);   Arg²⁶,³⁴Lys²⁷-(Glut-ATet)-GLP-1(7-38);
Gly⁸Asp¹⁹Arg²⁶,³⁴Lys²⁷-(Glut-ATet)-GLP-1(7-36);
Gly⁸Asp¹⁷Arg²⁶,³⁴Lys²⁷-(Glut-ATet)-GLP-1(7-36);
Gly⁸Asp¹⁹Arg²⁶,³⁴Lys²⁷-(Glut-ATet)-GLP-1(7-36)amide;
Gly⁸Asp¹⁷Arg²⁶,³⁴Lys²⁷-(Glut-ATet)-GLP-1(7-36)amide;
Gly⁸Asp¹⁹Arg²⁶,³⁴Lys²⁷-(Glut-ATet)-GLP-1(7-37);
Gly⁸Asp¹⁹Arg²⁶,³⁴Lys²⁷-(Glut-ATet)-GLP-1(7-38);
Gly⁸Asp¹⁷Arg²⁶,³⁴Lys²⁷-(Glut-ATet)-GLP-1(7-38);
Arg²⁶,³⁴Lys¹⁸-(Glut-ATet)-GLP-1(7-36);   Arg²⁶,³⁴Lys¹⁸-(Glut-ATet)-GLP-1(7-36)amide; Arg²⁶,³⁴Lys¹⁸-(Glut-ATet)-GLP-1(7-37);   Arg²⁶,³⁴Lys¹⁸-(Glut-ATet)-GLP-1(7-38);
Val⁸Asp¹⁹Arg²⁶,³⁴Lys¹⁸-(Glut-ATet)-GLP-1(7-36);
Val⁸Asp¹⁷Arg²⁶,³⁴Lys¹⁸-(Glut-ATet)-GLP-1(7-36);
Val⁸Asp¹⁹Arg²⁶,³⁴Lys¹⁸-(Glut-ATet)-GLP-1(7-36)amide;
Val⁸Asp¹⁷Arg²⁶,³⁴Lys¹⁸-(Glut-ATet)-GLP-1(7-36)amide;
Val⁸Asp¹⁹Arg²⁶,³⁴Lys¹⁸-(Glut-ATet)-GLP-1(7-37);
Val⁸Asp¹⁹Arg²⁶,³⁴Lys¹⁸-(Glut-ATet)-GLP-1(7-38);
Val⁸Asp¹⁷Arg²⁶,³⁴Lys¹⁸-(Glut-ATet)-GLP-1(7-38);
Arg²⁶,³⁴Lys²³-(Glut-ATet)-GLP-1(7-36);   Arg²⁶,³⁴Lys²³-(Glut-ATet)-GLP-1(7-36)amide; Arg²⁶,³⁴Lys²³-(Glut-ATet)-GLP-1(7-37);   Arg²⁶,³⁴Lys²³-(Glut-ATet)-GLP-1(7-38);
Val⁸Asp¹⁹Arg²⁶,³⁴Lys²³-(Glut-ATet)-GLP-1(7-36);
Val⁸Asp¹⁷Arg²⁶,³⁴Lys²³-(Glut-ATet)-GLP-1(7-36);
Val⁸Asp¹⁹Arg²⁶,³⁴Lys²³-(Glut-ATet)-GLP-1(7-36)amide;
Val⁸Asp¹⁷Arg²⁶,³⁴Lys²³-(Glut-ATet)-GLP-1(7-36)amide;
Val⁸Asp¹⁹Arg²⁶,³⁴Lys²³-(Glut-ATet)-GLP-1(7-37);
Val⁸Asp¹⁹Arg²⁶,³⁴Lys²³-(Glut-ATet)-GLP-1(7-38);
Val⁸Asp¹⁷Arg²⁶,³⁴Lys²³-(Glut-ATet)-GLP-1(7-38);
Arg²⁶,³⁴Lys²⁷-(Glut-ATet)-GLP-1(7-36);   Arg²⁶,³⁴Lys²⁷-(Glut-ATet)-GLP-1(7-36)amide; Arg²⁶,³⁴Lys²⁷-(Glut-ATet)-GLP-1(7-37);   Arg²⁶,³⁴Lys²⁷-(Glut-ATet)-GLP-1(7-38);
Val⁸Asp¹⁹Arg²⁶,³⁴Lys²⁷-(Glut-ATet)-GLP-1(7-36);
Val⁸Asp¹⁷Arg²⁶,³⁴Lys²⁷-(Glut-ATet)-GLP-1(7-36);
Val⁸Asp¹⁹Arg²⁶,³⁴Lys²⁷-(Glut-ATet)-GLP-1(7-36)amide;
Val⁸Asp¹⁷Arg²⁶,³⁴Lys²⁷-(Glut-ATet)-GLP-1(7-36)amide;
Val⁸Asp¹⁹Arg²⁶,³⁴Lys²⁷-(Glut-ATet)-GLP-1(7-37);

Val$^8$Asp$^{19}$Arg$^{26,34}$Lys$^{27}$-(Glut-ATet)-GLP-1(7-38);
Val$^8$Asp$^{17}$Arg$^{26,34}$Lys$^{27}$-(Glut-ATet)-GLP-1(7-38);
Arg$^{26,34}$Lys$^{18}$-(Glut-ATet)-GLP-1(7-36)amide; Arg$^{26,34}$Lys$^{18}$-(Glut-ATet)-GLP-1(7-37); Arg$^{26,34}$Lys$^{18}$-(Glut-ATet)-GLP-1(7-38);
Ser$^8$Asp$^{19}$Arg$^{26,34}$Lys$^{18}$-(Glut-ATet)-GLP-1(7-36);
Ser$^8$Asp$^{17}$Arg$^{26,34}$Lys$^{18}$-(Glut-ATet)-GLP-1(7-36);
Ser$^8$Asp$^{19}$Arg$^{26,34}$Lys$^{18}$-(Glut-ATet)-GLP-1(7-36)amide;
Ser$^8$Asp$^{17}$Arg$^{26,34}$Lys$^{18}$-(Glut-ATet)-GLP-1(7-36)amide;
Ser$^8$Asp$^{19}$Arg$^{26,34}$Lys$^{18}$-(Glut-ATet)-GLP-1(7-37);
Ser$^8$Asp$^{19}$Arg$^{26,34}$Lys$^{18}$-(Glut-ATet)-GLP-1(7-38);
Ser$^8$Asp$^{17}$Arg$^{26,34}$Lys$^{18}$-(Glut-ATet)-GLP-11(7-38);
Arg$^{26,34}$Lys$^{23}$-(Glut-ATet)-GLP-1(7-36); Arg$^{26,34}$Lys$^{23}$-(Glut-ATet)-GLP-1(7-36)amide; Arg$^{26,34}$Lys$^{23}$-(Glut-ATet)-GLP-1(7-37); Arg$^{26,34}$Lys$^{23}$-(Glut-ATet)-GLP-1(7-38);
Ser$^8$Asp$^{19}$Arg$^{26,34}$Lys$^{23}$-(Glut-ATet)-GLP-1(7-36);
Ser$^8$Asp$^{17}$Arg$^{26,34}$Lys$^{23}$-(Glut-ATet)-GLP-1(7-36);
Ser$^8$Asp$^{19}$Arg$^{26,34}$Lys$^{23}$-(Glut-ATet)-GLP-1(7-36)amide;
Ser$^8$Asp$^{17}$Arg$^{26,34}$Lys$^{23}$-(Glut-ATet)-GLP-1(7-36)amide;
Ser$^8$Asp$^{19}$Arg$^{26,34}$Lys$^{23}$-(Glut-ATet)-GLP-1(7-37);
Ser$^8$Asp$^{19}$Arg$^{26,34}$Lys$^{23}$-(Glut-ATet)-GLP-1(7-38);
Ser$^8$Asp$^{17}$Arg$^{26,34}$Lys$^{23}$-(Glut-ATet)-GLP-1(7-38);
Arg$^{26,34}$Lys$^{27}$-(Glut-ATet)-GLP-1(7-36); Arg$^{26,34}$Lys$^{27}$-(Glut-ATet)-GLP-1(7-36)amide; Arg$^{26,34}$Lys$^{27}$-(Glut-ATet)-GLP-1(7-37); Arg$^{26,34}$Lys$^{27}$-(Glut-ATet)-GLP-1(7-38);
Ser$^8$Asp$^{19}$Arg$^{26,34}$Lys$^{27}$-(Glut-ATet)-GLP-1(7-36);
Ser$^8$Asp$^{17}$Arg$^{26,34}$Lys$^{27}$-(Glut-ATet)-GLP-1(7-36);
Ser$^8$Asp$^{19}$Arg$^{26,34}$Lys$^{27}$-(Glut-ATet)-GLP-1(7-36)amide;
Ser$^8$Asp$^{17}$Arg$^{26,34}$Lys$^{27}$-(Glut-ATet)-GLP-1(7-36)amide;
Ser$^8$Asp$^{19}$Arg$^{26,34}$Lys$^{27}$-(Glut-ATet)-GLP-1(7-37);
Ser$^8$Asp$^{19}$Arg$^{26,34}$Lys$^{27}$-(Glut-ATet)-GLP-1(7-38);
Ser$^8$Asp$^{17}$Arg$^{26,34}$Lys$^{27}$-(Glut-ATet)-GLP-1(7-38);
Arg$^{26,34}$Lys$^{18}$-(Glut-ATet)-GLP-1(7-36); Arg$^{26,34}$Lys$^{18}$-(Glut-ATet)-GLP-1(7-36)amide; Arg$^{26,34}$Lys$^{18}$-(Glut-ATet)-GLP-1(7-37); Arg$^{26,34}$Lys$^{18}$-(Glut-ATet)-GLP-1(7-38);
Thr$^8$Asp$^{19}$Arg$^{26,34}$Lys$^{18}$-(Glut-ATet)-GLP-1(7-36);
Thr$^8$Asp$^{17}$Arg$^{26,34}$Lys$^{18}$-(Glut-ATet)-GLP-1(7-36);
Thr$^8$Asp$^{19}$Arg$^{26,34}$Lys$^{18}$-(Glut-ATet)-GLP-1(7-36)amide;
Thr$^8$Asp$^{17}$Arg$^{26,34}$Lys$^{18}$-(Glut-ATet)-GLP-1(7-36)amide;
Thr$^8$Asp$^{19}$Arg$^{26,34}$Lys$^{18}$-(Glut-ATet)-GLP-1(7-37);
Thr$^8$Asp$^{19}$Arg$^{26,34}$Lys$^{18}$-(Glut-ATet)-GLP-1(7-38);
Thr$^8$Asp$^{17}$Arg$^{26,34}$Lys$^{18}$-(Glut-ATet)-GLP-1(7-38);
Arg$^{26,34}$Lys$^{23}$-(Glut-ATet)-GLP-1(7-36); Arg$^{26,34}$Lys$^{23}$-(Glut-ATet)-GLP-1(7-36)amide; Arg$^{26,34}$Lys$^{23}$-(Glut-ATet)-GLP-1(7-37); Arg$^{26,34}$Lys$^{23}$-(Glut-ATet)-GLP-1(7-38);
Thr$^8$Asp$^{19}$Arg$^{26,34}$Lys$^{23}$-(Glut-ATet)-GLP-1(7-36);
Thr$^8$Asp$^{17}$Arg$^{26,34}$Lys$^{23}$-(Glut-ATet)-GLP-1(7-36);
Thr$^8$Asp$^{19}$Arg$^{26,34}$Lys$^{23}$-(Glut-ATet)-GLP-1(7-36)amide;
Thr$^8$Asp$^{17}$Arg$^{26,34}$Lys$^{23}$-(Glut-ATet)-GLP-1(7-36)amide;
Thr$^8$Asp$^{19}$Arg$^{26,34}$Lys$^{23}$-(Glut-ATet)-GLP-1(7-37);
Thr$^8$Asp$^{19}$Arg$^{26,34}$Lys$^{23}$-(Glut-ATet)-GLP-1(7-38);
Thr$^8$Asp$^{17}$Arg$^{26,34}$Lys$^{23}$-(Glut-ATet)-GLP-1(7-38);
Arg$^{26,34}$Lys$^{27}$-(Glut-ATet)-GLP-1(7-36); Arg$^{26,34}$Lys$^{27}$-(Glut-ATet)-GLP-1(7-36)amide; Arg$^{26,34}$Lys$^{27}$-(Glut-ATet)-GLP-1(7-37); Arg$^{26,34}$Lys$^{27}$-(Glut-ATet)-GLP-1(7-38);
Thr$^8$Asp$^{19}$Arg$^{26,34}$Lys$^{27}$-(Glut-ATet)-GLP-1(7-36);
Thr$^8$Asp$^{17}$Arg$^{26,34}$Lys$^{27}$-(Glut-ATet)-GLP-1(7-36);
Thr$^8$Asp$^{19}$Arg$^{26,34}$Lys$^{27}$-(Glut-ATet)-GLP-1(7-36)amide;
Thr$^8$Asp$^{17}$Arg$^{26,34}$Lys$^{27}$-(Glut-ATet)-GLP-1(7-36)amide;
Thr$^8$Asp$^{19}$Arg$^{26,34}$Lys$^{27}$-(Glut-ATet)-GLP-1(7-37);
Thr$^8$Asp$^{19}$Arg$^{26,34}$Lys$^{27}$-(Glut-ATet)-GLP-1(7-38);
Thr$^8$Asp$^{17}$Arg$^{26,34}$Lys$^{27}$-(Glut-ATet)-GLP-1(7-38);
Arg$^{26}$Lys$^{34}$-(Glut-AHex)-GLP-1(7-36); Arg$^{34}$Lys$^{26}$-(Glut-AHex)-GLP-1(7-36); Arg$^{26,34}$Lys$^{36}$-(Glut-AHex)-GLP-1(7-36); Arg$^{26}$Lys$^{34}$-(Glut-AHex)-GLP-1(7-36)amide; Arg$^{34}$Lys$^{26}$-(Glut-AHex)-GLP-1(7-36)amide; Arg$^{26,34}$Lys$^{36}$-(Glut-AHex)-GLP-1(7-36)amide;
Arg$^{26}$Lys$^{34}$-(Glut-AHex)-GLP-1(7-37); Arg$^{34}$Lys$^{26}$-(Glut-AHex)-GLP-1(7-37); Arg$^{26,34}$Lys$^{36}$-(Glut-AHex)-GLP-1(7-37); Arg$^{26}$Lys$^{34}$-(Glut-AHex)-GLP-1(7-38); Arg$^{34}$Lys$^{26}$-(Glut-AHex)-GLP-1(7-38); Arg$^{26,34}$Lys$^{38}$-(Glut-AHex)-GLP-1(7-38); Arg$^{26}$Lys$^{34}$-(Glut-AHex)-GLP-1(7-39); Arg$^{34}$Lys$^{26}$-(Glut-AHex)-GLP-1(7-39); Arg$^{26,34}$Lys$^{39}$-(Glut-AHex)-GLP-1(7-39);
Gly$^8$Arg$^{26}$Lys$^{34}$-(Glut-AHex)-GLP-1(7-36); Gly$^8$Arg$^{34}$Lys$^{26}$-(Glut-AHex)-GLP-1(7-36); Gly$^8$Arg$^{26,34}$Lys$^{36}$-(Glut-AHex)-GLP-1(7-36); Gly$^8$Arg$^{26}$Lys$^{34}$-(Glut-AHex)-GLP-1(7-36)amide; Gly$^8$Arg$^{34}$Lys$^{26}$-(Glut-AHex)-GLP-1(7-36)amide; Gly$^8$Arg$^{26,34}$Lys$^{36}$-(Glut-AHex)-GLP-1(7-36)amide; Gly$^8$Arg$^{26}$Lys$^{34}$-(Glut-AHex)-GLP-1(7-37); Gly$^8$Arg$^{34}$Lys$^{26}$-(Glut-AHex)-GLP-1(7-37); Gly$^8$Arg$^{26,34}$Lys$^{36}$-(Glut-AHex)-GLP-1(7-37);
Gly$^8$Arg$^{26}$Lys$^{34}$-(Glut-AHex)-GLP-1(7-38);
Gly$^8$Arg$^{34}$Lys$^{26}$-(Glut-AHex)-GLP-1(7-38); Gly$^8$Arg$^{26,34}$Lys$^{38}$-(Glut-AHex)-GLP-1(7-38); Gly$^8$Arg$^{26}$Lys$^{34}$-(Glut-AHex)-GLP-1(7-39); Gly$^8$Arg$^{34}$Lys$^{26}$-(Glut-AHex)-GLP-1(7-39); Gly$^8$Arg$^{26,34}$Lys$^{39}$-(Glut-AHex)-GLP-1(7-39);
Val$^8$Arg$^{26}$Lys$^{34}$-(Glut-AHex)-GLP-1(7-36); Val$^8$Arg$^{34}$Lys$^{26}$-(Glut-AHex)-GLP-1(7-36); Val$^8$Arg$^{26,34}$Lys$^{36}$-(Glut-AHex)-GLP-1(7-36); Val$^8$Arg$^{26}$Lys$^{34}$-(Glut-AHex)-GLP-1(7-36)amide; Val$^8$Arg$^{34}$Lys$^{26}$-(Glut-AHex)-GLP-1(7-36)amide; Val$^8$Arg$^{26,34}$Lys$^{36}$-(Glut-AHex)-GLP-1(7-36)amide; Val$^8$Arg$^{26}$Lys$^{34}$-(Glut-AHex)-GLP-1(7-37); Val$^8$Arg$^{34}$Lys$^{26}$-(Glut-AHex)-GLP-1(7-37); Val$^8$Arg$^{26,34}$Lys$^{36}$-(Glut-AHex)-GLP-1(7-37);
Val$^8$Arg$^{26}$Lys$^{34}$-(Glut-AHex)-GLP-1(7-38); Val$^8$Arg$^{34}$Lys$^{26}$-(Glut-AHex)-GLP-1(7-38); Val$^8$Arg$^{26,34}$Lys$^{38}$-(Glut-AHex)-GLP-1(7-38); Val$^8$Arg$^{26}$Lys$^{34}$-(Glut-AHex)-GLP-1(7-39); Val$^8$Arg$^{34}$Lys$^{26}$-(Glut-AHex)-GLP-1(7-39); Val$^8$Arg$^{26,34}$Lys$^{39}$-(Glut-AHex)-GLP-1(7-39);
Ser$^8$Arg$^{26}$Lys$^{34}$-(Glut-AHex)-GLP-1(7-36); Ser$^8$Arg$^{34}$Lys$^{26}$-(Glut-AHex)-GLP-1(7-36); Ser$^8$Arg$^{26,34}$Lys$^{36}$-(Glut-AHex)-GLP-1(7-36); Ser$^8$Arg$^{26}$Lys$^{34}$-(Glut-AHex)-GLP-1(7-36)amide; Ser$^8$Arg$^{34}$Lys$^{26}$-(Glut-AHex)-GLP-1(7-36)amide; Ser$^8$Arg$^{26,34}$Lys$^{36}$-(Glut-AHex)-GLP-1(7-36)amide; Ser$^8$Arg$^{26}$Lys$^{34}$-(Glut-AHex)-GLP-1(7-37); Ser$^8$Arg$^{34}$Lys$^{26}$-(Glut-AHex)-GLP-1(7-37); Ser$^8$Arg$^{26,34}$Lys$^{36}$-(Glut-AHex)-GLP-1(7-37);
Ser$^8$Arg$^{26}$Lys$^{34}$-(Glut-AHex)-GLP-1(7-38); Ser$^8$Arg$^{34}$Lys$^{26}$-(Glut-AHex)-GLP-1(7-38); Ser$^8$Arg$^{26,34}$Lys$^{38}$-(Glut-AHex)-GLP-1(7-38); Ser$^8$Arg$^{26}$Lys$^{34}$-(Glut-AHex)-GLP-1(7-39); Ser$^8$Arg$^{34}$Lys$^{26}$-(Glut-AHex)-GLP-1(7-39); Ser$^8$Arg$^{26,34}$Lys$^{39}$-(Glut-AHex)-GLP-1(7-39);
Thr$^8$Arg$^{26}$Lys$^{34}$-(Glut-AHex)-GLP-1(7-36); Thr$^8$Arg$^{34}$Lys$^{26}$-(Glut-AHex)-GLP-1(7-36); Thr$^8$Arg$^{26,34}$Lys$^{36}$-(Glut-AHex)-GLP-1(7-36); Thr$^8$Arg$^{26}$Lys$^{34}$-(Glut-AHex)-GLP-1(7-36)amide; Thr$^8$Arg$^{34}$Lys$^{26}$-(Glut-AHex)-GLP-1(7-36)amide; Thr$^8$Arg$^{26,34}$Lys$^{36}$-(Glut-AHex)-GLP-1(7-36)amide; Thr$^8$Arg$^{26}$Lys$^{34}$-(Glut-AHex)-GLP-1(7-37); Thr$^8$Arg$^{34}$Lys$^{26}$-(Glut-AHex)-GLP-1(7-37); Thr$^8$Arg$^{26,34}$Lys$^{36}$-(Glut-AHex)-GLP-1(7-37);
Thr$^8$Arg$^{26}$Lys$^{34}$-(Glut-AHex)-GLP-1(7-38); Thr$^8$Arg$^{34}$Lys$^{26}$-(Glut-AHex)-GLP-1(7-38); Thr$^8$Arg$^{26,34}$Lys$^{38}$-(Glut-AHex)-GLP-1(7-38); Thr$^8$Arg$^{26}$Lys$^{34}$-(Glut-AHex)-GLP-1(7-39); Thr$^8$Arg$^{34}$Lys$^{26}$-(Glut-AHex)-GLP-1(7-39); Thr$^8$Arg$^{26,34}$Lys$^{39}$-(Glut-AHex)-GLP-1(7-39);
Gly$^8$Glu$^{35}$Arg$^{26,34}$Lys$^{36}$-(Glut-AHex)-GLP-1(7-36);
Gly$^8$Glu$^{35}$Arg$^{26,34}$Lys$^{36}$-(Glut-AHex)-GLP-1(7-36)amide;
Gly$^8$Glu$^{36}$Arg$^{26,34}$Lys$^{37}$-(Glut-AHex)-GLP-1(7-37);
Gly$^8$Glu$^{37}$Arg$^{26,34}$Lys$^{38}$-(Glut-AHex)-GLP-1(7-38);

Gly$^8$Glu$^{38}$Arg$^{26,34}$Lys$^{39}$-(Glut-AHex)-GLP-1(7-39);
Gly$^8$Glu$^{35}$Arg$^{26,34}$Lys$^{36}$-(Glut-AHex)-GLP-1(7-36);
Gly$^8$Glu$^{35}$Arg$^{26,34}$Lys$^{36}$-(Glut-AHex)-GLP-1(7-36)amide;
Gly$^8$Glu$^{36}$Arg$^{26,34}$Lys$^{37}$-(Glut-AHex)-GLP-1(7-37);
Gly$^8$Glu$^{37}$Arg$^{26,34}$Lys$^{38}$-(Glut-AHex)-GLP-1(7-38);
Gly$^8$Glu$^{38}$Arg$^{26,34}$Lys$^{39}$-(Glut-AHex)-GLP-1(7-39);
Gly$^8$Asp$^{35}$Arg$^{26,34}$Lys$^{36}$-(Glut-AHex)-GLP-1(7-36);
Gly$^8$Asp$^{35}$Arg$^{26,34}$Lys$^{36}$-(Glut-AHex)-GLP-1(7-36)amide;
Gly$^8$Asp$^{36}$Arg$^{26,34}$Lys$^{37}$-(Glut-AHex)-GLP-1(7-37);
Gly$^8$Asp$^{37}$Arg$^{26,34}$Lys$^{38}$-(Glut-AHex)-GLP-1(7-38);
Gly$^8$Asp$^{38}$Arg$^{26,34}$Lys$^{39}$-(Glut-AHex)-GLP-1(7-39);
Gly$^8$Asp$^{35}$Arg$^{26,34}$Lys$^{36}$-(Glut-AHex)-GLP-1(7-36);
Gly$^8$Asp$^{35}$Arg$^{26,34}$Lys$^{36}$-(Glut-AHex)-GLP-1(7-36)amide;
Gly$^8$Asp$^{36}$Arg$^{26,34}$Lys$^{37}$-(Glut-AHex)-GLP-1(7-37);
Gly$^8$Asp$^{37}$Arg$^{26,34}$Lys$^{38}$-(Glut-AHex)-GLP-1(7-38);
Gly$^8$Asp$^{38}$Arg$^{26,34}$Lys$^{39}$-(Glut-AHex)-GLP-1(7-39);
Val$^8$Glu$^{35}$Arg$^{26,34}$Lys$^{36}$-(Glut-AHex)-GLP-1(7-36);
Val$^8$Glu$^{35}$Arg$^{26,34}$Lys$^{36}$-(Glut-AHex)-GLP-1(7-36)amide;
Val$^8$Glu$^{36}$Arg$^{26,34}$Lys$^{37}$-(Glut-AHex)-GLP-1(7-37);
Val$^8$Glu$^{37}$Arg$^{26,34}$Lys$^{38}$-(Glut-AHex)-GLP-1(7-38);
Val$^8$Glu$^{38}$Arg$^{26,34}$Lys$^{39}$-(Glut-AHex)-GLP-1(7-39);
Val$^8$Glu$^{35}$Arg$^{26,34}$Lys$^{36}$-(Glut-AHex)-GLP-1(7-36);
Val$^8$Glu$^{35}$Arg$^{26,34}$Lys$^{36}$-(Glut-AHex)-GLP-1(7-36)amide;
Val$^8$Glu$^{36}$Arg$^{26,34}$Lys$^{37}$-(Glut-AHex)-GLP-1(7-37);
Val$^8$Glu$^{37}$Arg$^{26,34}$Lys$^{38}$-(Glut-AHex)-GLP-1(7-38);
Val$^8$Glu$^{38}$Arg$^{26,34}$Lys$^{39}$-(Glut-AHex)-GLP-1(7-39);
Val$^8$Asp$^{35}$Arg$^{26,34}$Lys$^{36}$-(Glut-AHex)-GLP-1(7-36);
Val$^8$Asp$^{35}$Arg$^{26,34}$Lys$^{36}$-(Glut-AHex)-GLP-1(7-36)amide;
Val$^8$Asp$^{36}$Arg$^{26,34}$Lys$^{37}$-(Glut-AHex)-GLP-1(7-37);
Val$^8$Asp$^{37}$Arg$^{26,34}$Lys$^{38}$-(Glut-AHex)-GLP-1(7-38);
Val$^8$Asp$^{38}$Arg$^{26,34}$Lys$^{39}$-(Glut-AHex)-GLP-1(7-39);
Val$^8$Asp$^{35}$Arg$^{26,34}$Lys$^{36}$-(Glut-AHex)-GLP-1(7-36);
Val$^8$Asp$^{35}$Arg$^{26,34}$Lys$^{36}$-(Glut-AHex)-GLP-1(7-36)amide;
Val$^8$Asp$^{36}$Arg$^{26,34}$Lys$^{37}$-(Glut-AHex)-GLP-1(7-37);
Val$^8$Asp$^{37}$Arg$^{26,34}$Lys$^{38}$-(Glut-AHex)-GLP-1(7-38);
Val$^8$Asp$^{38}$Arg$^{26,34}$Lys$^{39}$-(Glut-AHex)-GLP-1(7-39);
Ser$^8$Glu$^{35}$Arg$^{26,34}$Lys$^{36}$ (Glut-AHex)-GLP-1(7-36);
Ser$^8$Glu$^{35}$Arg$^{26,34}$Lys$^{36}$-(Glut-AHex)-GLP-1(7-36)amide;
Ser$^8$Glu$^{36}$Arg$^{26,34}$Lys$^{37}$-(Glut-AHex)-GLP-1(7-37);
Ser$^8$Glu$^{37}$Arg$^{26,34}$Lys$^{36}$-(Glut-AHex)-GLP-1(7-38);
Ser$^8$Glu$^3$Arg$^{26,34}$Lys$^{39}$-(Glut-AHex)-GLP-1(7-39);
Ser$^8$Glu$^{35}$Arg$^{26,34}$Lys$^{36}$-(Glut-AHex)-GLP-1(7-36);
Ser$^8$Glu$^{35}$Arg$^{26,34}$Lys$^{36}$-(Glut-AHex)-GLP-1(7-36)amide;
Ser$^8$Glu$^{36}$Arg$^{26,34}$Lys$^{37}$-(Glut-AHex)-GLP-1(7-37);
Ser$^8$Glu$^{37}$Arg$^{26,34}$Lys$^{23}$-(Glut-AHex)-GLP-1(7-38);
Ser$^8$Glu$^{38,35}$Arg$^2$Arg$^{26,34}$Lys$^{39}$-(Glut-AHex)-GLP-1(7-39)
Ser$^8$Asp$^{35}$Arg$^{26,34}$Lys$^{36}$-(Glut-AHex)-GLP-1(7-36);
Ser$^8$Asp$^3$Arg$^{26,34}$Lys$^{36}$-(Glut-AHex)-GLP-1(7-36)amide;
Ser$^8$Asp$^{36}$Arg$^{26,34}$Lys$^{37}$-(Glut-AHex)-GLP-1(7-37);
Ser$^8$Asp$^{37}$Arg$^{26,34}$Lys$^{38}$-(Glut-AHex)-GLP-1(7-38);
Ser$^8$Asp$^{38}$Arg$^{26,34}$Lys$^{39}$-(Glut-AHex)-GLP-1(7-39);
Ser$^8$Asp$^{35}$Arg$^{26,34}$Lys$^{36}$-(Glut-AHex)-GLP-1(7-36);
Ser$^8$Asp$^{35}$Arg$^{26,34}$Lys$^{36}$-(Glut-AHex)-GLP-1(7-36)amide;
Ser$^8$Asp$^{36}$Arg$^{26,34}$Lys$^{37}$-(Glut-AHex)-GLP-1(7-37);
Ser$^8$Asp$^{37}$Arg$^{26,34}$Lys$^{23}$-(Glut-AHex)-GLP-1(7-38);
Ser$^8$Asp$^{38}$Arg$^{26,34}$Lys$^{39}$-(Glut-AHex)-GLP-1(7-39)
Thr$^8$Glu$^{35}$Arg$^{26,34}$Lys$^{36}$-(Glut-AHex)-GLP-1(7-36);
Thr$^8$Glu$^{35}$Arg$^{26,34}$Lys$^{36}$-(Glut-AHex)-GLP-1(7-36)amide;
Thr$^8$Glu$^{36}$Arg$^{26,34}$Lys$^{37}$-(Glut-AHex)-GLP-1(7-37);
Thr$^8$Glu$^{37}$Arg$^{26,34}$Lys$^{38}$-(Glut-AHex)-GLP-1(7-38);
Thr$^8$Glu$^3$Arg$^{26,34}$Lys$^{39}$-(Glut-AHex)-GLP-1(7-39);
Thr$^8$Glu$^{35}$Arg$^{26,34}$Lys$^{36}$-(Glut-AHex)-GLP-1(7-36);
Thr$^8$Glu$^{35}$Arg$^{26,34}$Lys$^{36}$-(Glut-AHex)-GLP-1(7-36)amide;
Thr$^8$Glu$^{36}$Arg$^{26,34}$Lys$^{37}$-(Glut-AHex)-GLP-1(7-37);
Thr$^8$Glu$^{37}$Arg$^{26,34}$Lys$^{38}$-(Glut-AHex)-GLP-1(7-38);
Thr$^8$Glu$^{38}$Arg$^{26,34}$Lys$^{39}$-(Glut-AHex)-GLP-1(7-39);
Thr$^8$Asp$^{35}$Arg$^{26,34}$Lys$^{36}$-(Glut-AHex)-GLP-1(7-36);
Thr$^8$Asp$^{35}$Arg$^{26,34}$Lys$^{36}$-(Glut-AHex)-GLP-1(7-36)amide;
Thr$^8$Asp$^{36}$Arg$^{26,34}$Lys$^{37}$-(Glut-AHex)-GLP-1(7-37);
Thr$^8$Asp$^{37}$Arg$^{26,34}$Lys$^{38}$-(Glut-AHex)-GLP-1(7-38);
Thr$^8$Asp$^{38}$Arg$^{26,34}$Lys$^{39}$-(Glut-AHex)-GLP-1(7-39);
Thr$^8$Asp$^{35}$Arg$^{26,34}$Lys$^{36}$-(Glut-AHex)-GLP-1(7-36);
Thr$^8$Asp$^{35}$Arg$^{26,34}$Lys$^{36}$-(Glut-AHex)-GLP-1(7-36)amide;
Thr$^8$Asp$^{36}$Arg$^{26,34}$Lys$^{37}$-(Glut-AHex)-GLP-1(7-37);
Thr$^8$Asp$^{37}$Arg$^{26,34}$Lys$^{38}$-(Glut-AHex)-GLP-1(7-38);
Thr$^8$Asp$^{38}$Arg$^{26,34}$Lys$^{39}$-(Glut-AHex)-GLP-1(7-39);
Arg$^{26,34}$Lys$^{18}$-(Glut-AHex)-GLP-1(7-36); Arg$^{26,34}$Lys$^{18}$-(Glut-AHex)-GLP-1(7-36)amide; Arg$^{26,34}$Lys$^{18}$-(Glut-AHex)-GLP-1(7-37); Arg$^{26,34}$Lys$^{18}$-(Glut-AHex)-GLP-1(7-38); Gly$^8$Asp$^{19}$Arg$^{26,34}$Lys$^{18}$-(Glut-AHex)-GLP-1(7-36); Gly$^8$Asp$^{17}$Arg$^{26,34}$Lys$^{18}$-(Glut-AHex)-GLP-1(7-36);
Gly$^8$Asp$^{19}$Arg$^{26,34}$Lys$^{18}$-(Glut-AHex)-GLP-1(7-36)amide;
Gly$^8$Asp$^{17}$Arg$^{26,34}$Lys$^{18}$-(Glut-AHex)-GLP-1(7-36)amide;
Gly$^8$Asp$^{19}$Arg$^{26,34}$Lys$^{18}$-(Glut-AHex)-GLP-1(7-37);
Gly$^8$Asp$^{19}$Arg$^{26,34}$Lys$^{18}$-(Glut-AHex)-GLP-1(7-38);
Gly$^8$Asp$^{17}$Arg$^{26,34}$Lys$^{18}$-(Glut-AHex)-GLP-1(7-38);
Arg$^{26,34}$Lys$^{23}$-(Glut-AHex)-GLP-1(7-36); Arg$^{26,34}$Lys$^{23}$-(Glut-AHex)-GLP-1(7-36)amide; Arg$^{26,34}$Lys$^{23}$-(Glut-AHex)-GLP-1(7-37); Arg$^{26,34}$Lys$^{23}$-(Glut-AHex)-GLP-1(7-38); Gly$^8$Asp$^{19}$Arg$^{26,34}$Lys$^{23}$-(Glut-AHex)-GLP-1(7-36); Gly$^8$Asp$^{17}$Arg$^{26,34}$Lys$^{23}$-(Glut-AHex)-GLP-1(7-36);
Gly$^8$Asp$^{19}$Arg$^{26,34}$Lys$^{23}$-(Glut-AHex)-GLP-1(7-36)amide;
Gly$^8$Asp$^{17}$Arg$^{26,34}$Lys$^{23}$-(Glut-AHex)-GLP-1(7-36)amide;
Gly$^8$Asp$^{19}$Arg$^{26,34}$Lys$^{23}$-(Glut-AHex)-GLP-1(7-37);
Gly$^8$Asp$^{19}$Arg$^{26,34}$Lys$^{23}$-(Glut-AHex)-GLP-1(7-38);
Gly$^8$Asp$^{17}$Arg$^{26,34}$Lys$^{23}$-(Glut-AHex)-GLP-1(7-38);
Arg$^{26,34}$Lys$^{27}$-(Glut-AHex)-GLP-1(7-36); Arg$^{26,34}$Lys$^{27}$-(Glut-AHex)-GLP-1(7-36)amide; Arg$^{26,34}$Lys$^{27}$-(Glut-AHex)-GLP-1(7-37); Arg$^{26,34}$Lys$^{27}$-(Glut-AHex)-GLP-1(7-38); Gly$^8$Asp$^{19}$Arg$^{26,34}$Lys$^{27}$-(Glut-AHex)-GLP-1(7-36); Gly$^8$Asp$^{17}$Arg$^{26,34}$Lys$^{27}$-(Glut-AHex)-GLP-1(7-36);
Gly$^8$Asp$^{19}$Arg$^{26,34}$Lys$^{27}$-(Glut-AHex)-GLP-1(7-36)amide;
Gly$^8$Asp$^{17}$Arg$^{26,34}$Lys$^{27}$-(Glut-AHex)-GLP-1(7-36)amide;
Gly$^8$Asp$^{19}$Arg$^{26,34}$Lys$^{27}$-(Glut-AHex)-GLP-1(7-37);
Gly$^8$Asp$^{19}$Arg$^{26,34}$Lys$^{27}$-(Glut-AHex)-GLP-1(7-38);
Gly$^8$Asp$^{17}$Arg$^{26,34}$Lys$^{27}$-(Glut-AHex)-GLP-1(7-38);
Arg$^{26,34}$Lys$^{18}$-(Glut-AHex)-GLP-1(7-36); Arg$^{26,34}$Lys$^{18}$-(Glut-AHex)-GLP-1(7-36)amide; Arg$^{26,34}$Lys$^{18}$-(Glut-AHex)-GLP-1(7-37); Arg$^{26,34}$Lys$^{18}$-(Glut-AHex)-GLP-1(7-38); Val$^8$Asp$^{19}$Arg$^{26,34}$Lys$^{18}$-(Glut-AHex)-GLP-1(7-36); Val$^8$Asp$^{17}$Arg$^{26,34}$Lys$^{18}$-(Glut-AHex)-GLP-1(7-36);
Val$^8$Asp$^{19}$Arg$^{26,34}$Lys$^{18}$-(Glut-AHex)-GLP-1(7-36)amide;
Val$^8$Asp$^{17}$Arg$^{26,34}$Lys$^{18}$-(Glut-AHex)-GLP-1(7-36)amide;
Val$^8$Asp$^{19}$Arg$^{26,34}$Lys$^{18}$-(Glut-AHex)-GLP-1(7-37);
Val$^8$Asp$^{19}$Arg$^{26,34}$Lys$^{18}$-(Glut-AHex)-GLP-1(7-38);
Val$^8$Asp$^{17}$Arg$^{26,34}$Lys$^{18}$-(Glut-AHex)-GLP-1(7-38);
Arg$^{26,34}$Lys$^{23}$-(Glut-AHex)-GLP-1(7-36); Arg$^{26,34}$Lys$^{23}$-(Glut-AHex)-GLP-1(7-36)amide; Arg$^{26,34}$Lys$^{23}$-(Glut-AHex)-GLP-1(7-37); Arg$^{26,34}$Lys$^{23}$-(Glut-AHex)-GLP-1(7-38); Val$^8$Asp$^{19}$Arg$^{26,34}$Lys$^{23}$-(Glut-AHex)-GLP-1(7-36); Val$^8$Asp$^{17}$Arg$^{26,34}$Lys$^{23}$-(Glut-AHex)-GLP-1(7-36);
Val$^8$Asp$^{19}$Arg$^{26,34}$Lys$^{23}$-(Glut-AHex)-GLP-1(7-36)amide;
Val$^8$Asp$^{17}$Arg$^{26,34}$Lys$^{23}$-(Glut-AHex)-GLP-1(7-36)amide;
Val$^8$Asp$^{19}$Arg$^{26,34}$Lys$^{23}$-(Glut-AHex)-GLP-1(7-37);
Val$^8$Asp$^{19}$Arg$^{26,34}$Lys$^{23}$-(Glut-AHex)-GLP-1(7-38);
Val$^8$Asp$^{17}$Arg$^{26,34}$Lys$^{23}$-(Glut-AHex)-GLP-1(7-38);
Arg$^{26,34}$Lys$^{27}$-(Glut-AHex)-GLP-1(7-36); Arg$^{26,34}$Lys$^{27}$-(Glut-AHex)-GLP-1(7-36)amide; Arg$^{26,34}$Lys$^{27}$-(Glut-AHex)-GLP-1(7-37); Arg$^{26,34}$Lys$^{27}$-(Glut-AHex)-GLP-1(7-38); Val$^8$Asp$^{19}$Arg$^{26,34}$Lys$^{27}$-(Glut-AHex)-GLP-1(7-36); Val$^8$Asp$^{17}$Arg$^{26,34}$Lys$^{27}$-(Glut-AHex)-GLP-1(7-36);
Val$^8$Asp$^{19}$Arg$^{26,34}$Lys$^{27}$-(Glut-AHex)-GLP-1(7-36)amide;
Val$^8$Asp$^{17}$Arg$^{26,34}$Lys$^{27}$-(Glut-AHex)-GLP-1(7-36)amide;
Val$^8$Asp$^{19}$Arg$^{26,34}$Lys$^{27}$-(Glut-AHex)-GLP-1(7-37);

Val⁸Asp¹⁹Arg²⁶,³⁴Lys²⁷-(Glut-AHex)-GLP-1(7-38);
Val⁸Asp¹⁷Arg²⁶,³⁴Lys²⁷-(Glut-AHex)-GLP-1(7-38);
Arg²⁶,³⁴Lys¹⁸-(Glut-AHex)-GLP-1(7-36); Arg²⁶,³⁴Lys¹⁸-(Glut-AHex)-GLP-1(7-36)amide; Arg²⁶,³⁴Lys¹⁸-(Glut-AHex)-GLP-1(7-37); Arg²⁶,³⁴Lys¹⁸-(Glut-AHex)-GLP-1(7-38); Ser⁸Asp¹⁹Arg²⁶,³⁴Lys¹⁸-(Glut-AHex)-GLP-1(7-36); Ser⁸Asp¹⁷Arg²⁶,³⁴Lys¹⁸-(Glut-AHex)-GLP-1(7-36); Ser⁸Asp¹⁹Arg²⁶,³⁴Lys¹⁸-(Glut-AHex)-GLP-1(7-36)amide; Ser⁸Asp¹⁷Arg²⁶,³⁴Lys¹⁸-(Glut-AHex)-GLP-1(7-36)amide; Ser⁸Asp¹⁹Arg²⁶,³⁴Lys¹⁸-(Glut-AHex)-GLP-1(7-37); Ser⁸Asp¹⁹Arg²⁶,³⁴Lys¹⁸-(Glut-AHex)-GLP-1(7-38); Ser⁸Asp¹⁷Arg²⁶,³⁴Lys¹⁸-(Glut-AHex)-GLP-1(7-38);
Arg²⁶,³⁴Lys²³-(Glut-AHex)-GLP-1(7-36); Arg²⁶,³⁴Lys²³-(Glut-AHex)-GLP-1(7-36)amide; Arg²⁶,³⁴Lys²³-(Glut-AHex)-GLP-1(7-37); Arg²⁶,³⁴Lys²³-(Glut-AHex)-GLP-1(7-38); Ser⁸Asp¹⁹Arg²⁶,³⁴Lys²³-(Glut-AHex)-GLP-1(7-36); Ser⁸Asp¹⁷Arg²⁶,³⁴Lys²³-(Glut-AHex)-GLP-1(7-36); Ser⁸Asp¹⁹Arg²⁶,³⁴Lys²³-(Glut-AHex)-GLP-1(7-36)amide; Ser⁸Asp¹⁷Arg²⁶,³⁴Lys²³-(Glut-AHex)-GLP-1(7-36)amide; Ser⁸Asp¹⁹Arg²⁶,³⁴Lys²³-(Glut-AHex)-GLP-1(7-37); Ser⁸Asp¹⁹Arg²⁶,³⁴Lys²³-(Glut-AHex)-GLP-1(7-38); Ser⁸Asp¹⁷Arg²⁶,³⁴Lys²³-(Glut-AHex)-GLP-1(7-38);
Arg²⁶,³⁴Lys²⁷-(Glut-AHex)-GLP-1(7-36); Arg²⁶,³⁴Lys²⁷-(Glut-AHex)-GLP-1(7-36)amide; Arg²⁶,³⁴Lys²⁷-(Glut-AHex)-GLP-1(7-37); Arg²⁶,³⁴Lys²⁷-(Glut-AHex)-GLP-1(7-38); Ser⁸Asp¹⁹Arg²⁶,³⁴Lys²⁷-(Glut-AHex)-GLP-1(7-36); Ser⁸Asp¹⁷Arg²⁶,³⁴Lys²⁷-(Glut-AHex)-GLP-1(7-36); Ser⁸Asp¹⁹Arg²⁶,³⁴Lys²⁷-(Glut-AHex)-GLP-1(7-36)amide; Ser⁸Asp¹⁷Arg²⁶,³⁴Lys²⁷-(Glut-AHex)-GLP-1(7-36)amide; Ser⁸Asp¹⁹Arg²⁶,³⁴Lys²⁷-(Glut-AHex)-GLP-1(7-37); Ser⁸Asp¹⁹Arg²⁶,³⁴Lys²⁷-(Glut-AHex)-GLP-1(7-38); Ser⁸Asp¹⁷Arg²⁶,³⁴Lys²⁷-(Glut-AHex)-GLP-1(7-38);
Arg²⁶,³⁴Lys¹⁸-(Glut-AHex)-GLP-1(7-36); Arg²⁶,³⁴Lys¹⁸-(Glut-AHex)-GLP-1(7-36)amide; Arg²⁶,³⁴Lys¹⁸-(Glut-AHex)-GLP-1(7-37); Arg²⁶,³⁴Lys¹⁸-(Glut-AHex)-GLP-1(7-38); Thr⁸Asp¹⁹Arg²⁶,³⁴Lys¹⁸-(Glut-AHex)-GLP-1(7-36); Thr⁸Asp¹⁷Arg²⁶,³⁴Lys¹⁸-(Glut-AHex)-GLP-1(7-36); Thr⁸Asp¹⁹Arg²⁶,³⁴Lys¹⁸-(Glut-AHex)-GLP-1(7-36)amide; Thr⁸Asp¹⁷Arg²⁶,³⁴Lys¹⁸-(Glut-AHex)-GLP-1(7-36)amide; Thr⁸Asp¹⁹Arg²⁶,³⁴Lys¹⁸-(Glut-AHex)-GLP-1(7-37); Thr⁸Asp¹⁹Arg²⁶,³⁴Lys¹⁸-(Glut-AHex)-GLP-1(7-38); Thr⁸Asp¹⁷Arg²⁶,³⁴Lys¹⁸-(Glut-AHex)-GLP-1(7-38);
Arg²⁶,³⁴Lys²³-(Glut-AHex)-GLP-1(7-36); Arg²⁶,³⁴Lys²³-(Glut-AHex)-GLP-1(7-36)amide; Arg²⁶,³⁴Lys²³-(Glut-AHex)-GLP-1(7-37); Arg²⁶,³⁴Lys²³-(Glut-AHex)-GLP-1(7-38); Thr⁸Asp¹⁹Arg²⁶,³⁴Lys²³-(Glut-AHex)-GLP-1(7-36); Thr⁸Asp¹⁷Arg²⁶,³⁴Lys²³-(Glut-AHex)-GLP-1(7-36); Thr⁸Asp¹⁹Arg²⁶,³⁴Lys²³-(Glut-AHex)-GLP-1(7-36)amide; Thr⁸Asp¹⁷Arg²⁶,³⁴Lys²³-(Glut-AHex)-GLP-1(7-36)amide; Thr⁸Asp¹⁹Arg²⁶,³⁴Lys²³-(Glut-AHex)-GLP-1(7-37); Thr⁸Asp¹⁹Arg²⁶,³⁴Lys²³-(Glut-AHex)-GLP-1(7-38); Thr⁸Asp¹⁷Arg²⁶,³⁴Lys²³-(Glut-AHex)-GLP-1(7-38);
Arg²⁶,³⁴Lys²⁷-(Glut-AHex)-GLP-1(7-36); Arg²⁶,³⁴Lys²⁷-(Glut-AHex)-GLP-1(7-36)amide; Arg²⁶,³⁴Lys²⁷-(Glut-AHex)-GLP-1(7-37); Arg²⁶,³⁴Lys²⁷-(Glut-AHex)-GLP-1(7-38); Thr⁸Asp¹⁹Arg²⁶,³⁴Lys²⁷-(Glut-AHex)-GLP-1(7-36); Thr⁸Asp¹⁷Arg²⁶,³⁴Lys²⁷-(Glut-AHex)-GLP-1(7-36); Thr⁸Asp¹⁹Arg²⁶,³⁴Lys²⁷-(Glut-AHex)-GLP-1(7-36)amide; Thr⁸Asp¹⁷Arg²⁶,³⁴Lys²⁷-(Glut-AHex)-GLP-1(7-36)amide; Thr⁸Asp¹⁹Arg²⁶,³⁴Lys²⁷-(Glut-AHex)-GLP-1(7-37); Thr⁸Asp¹⁹Arg²⁶,³⁴Lys²⁷-(Glut-AHex)-GLP-1(7-38); Thr⁸Asp¹⁷Arg²⁶,³⁴Lys²⁷-(Glut-AHex)-GLP-1(7-38);
Arg²⁶Lys³⁴-(Glut-AOct)-GLP-1(7-36); Arg³⁴Lys²⁶-(Glut-AOct)-GLP-1(7-36); Arg²⁶,³⁴Lys³⁶-(Glut-AOct)-GLP-1(7-36); Arg²⁶Lys³⁴-(Glut-AOct)-GLP-1(7-36)amide; Arg³⁴Lys²⁶-(Glut-AOct)-GLP-1(7-36)amide; Arg²⁶,³⁴Lys³⁶-(Glut-AOct)-GLP-1(7-36)amide; Arg²⁶Lys³⁴-(Glut-AOct)-GLP-1(7-37); Arg³⁴Lys²⁶-(Glut-AOct)-GLP-1(7-37); Arg²⁶,³⁴Lys³⁶-(Glut-AOct)-GLP-1(7-37); Arg²⁶Lys³⁴-(Glut-AOct)-GLP-1(7-38); Arg³⁴Lys²⁶-(Glut-AOct)-GLP-1(7-38); Arg²⁶,³⁴Lys³⁸-(Glut-AOct)-GLP-1(7-38); Arg²⁶Lys³⁴-(Glut-AOct)-GLP-1(7-39); Arg³⁴Lys²⁶-(Glut-AOct)-GLP-1(7-39); Arg²⁶,³⁴Lys³⁹-(Glut-AOct)-GLP-1(7-39);
Gly⁸Arg²⁶Lys³⁴-(Glut-AOct)-GLP-1(7-36); Gly⁸Arg³⁴Lys²⁶-(Glut-AOct)-GLP-1(7-36); Gly⁸Arg²⁶,³⁴Lys³⁶-(Glut-AOct)-GLP-1(7-36); Gly⁸Arg²⁶Lys³⁴-(Glut-AOct)-GLP-1(7-36)amide; Gly⁸Arg³⁴Lys²⁶-(Glut-AOct)-GLP-1(7-36)amide; Gly⁸Arg²⁶,³⁴Lys³⁶-(Glut-AOct)-GLP-1(7-36)amide; Gly⁸Arg²⁶Lys³⁴-(Glut-AOct)-GLP-1(7-37); Gly⁸Arg³⁴Lys²⁶-(Glut-AOct)-GLP-1(7-37); Gly⁸Arg²⁶,³⁴Lys³⁶-(Glut-AOct)-GLP-1(7-37); Gly⁸Arg²⁶Lys³⁴-(Glut-AOct)-GLP-1(7-38); Gly⁸Arg³⁴Lys²⁶-(Glut-AOct)-GLP-1(7-38); Gly⁸Arg²⁶,³⁴Lys³⁸-(Glut-AOct)-GLP-1(7-38); Gly⁸Arg²⁶Lys³⁴-(Glut-AOct)-GLP-1(7-39); Gly⁸Arg³⁴Lys²⁶-(Glut-AOct)-GLP-1(7-39); Gly⁸Arg²⁶,³⁴Lys³⁹-(Glut-AOct)-GLP-1(7-39);
Val⁸Arg²⁶Lys³⁴-(Glut-AOct)-GLP-1(7-36); Val⁸Arg³⁴Lys²⁶-(Glut-AOct)-GLP-1(7-36); Val⁸Arg²⁶,³⁴Lys³⁶-(Glut-AOct)-GLP-1(7-36); Val⁸Arg²⁶Lys³⁴-(Glut-AOct)-GLP-1(7-36)amide; Val⁸Arg³⁴Lys²⁶-(Glut-AOct)-GLP-1(7-36)amide; Val⁸Arg²⁶,³⁴Lys³⁶-(Glut-AOct)-GLP-1(7-36)amide; Val⁸Arg²⁶Lys³⁴-(Glut-AOct)-GLP-1(7-37); Val⁸Arg³⁴Lys²⁶-(Glut-AOct)-GLP-1(7-37); Val⁸Arg²⁶,³⁴Lys³⁶-(Glut-AOct)-GLP-1(7-37); Val⁸Arg²⁶Lys³⁴-(Glut-AOct)-GLP-1(7-38); Val⁸Arg³⁴Lys²⁶-(Glut-AOct)-GLP-1(7-38); Val⁸Arg²⁶,³⁴Lys³⁸-(Glut-AOct)-GLP-1(7-38); Val⁸Arg²⁶Lys³⁴-(Glut-AOct)-GLP-1(7-39); Val⁸Arg³⁴Lys²⁶-(Glut-AOct)-GLP-1(7-39); Val⁸Arg²⁶,³⁴Lys³⁹-(Glut-AOct)-GLP-1(7-39);
Ser⁸Arg²⁶Lys³⁴-(Glut-AOct)-GLP-1(7-36); Ser⁸Arg³⁴Lys²⁶-(Glut-AOct)-GLP-1(7-36); Ser⁸Arg²⁶,³⁴Lys³⁶-(Glut-AOct)-GLP-1(7-36); Ser⁸Arg²⁶Lys³⁴-(Glut-AOct)-GLP-1(7-36)amide; Ser⁸Arg³⁴Lys²⁶-(Glut-AOct)-GLP-1(7-36)amide; Ser⁸Arg²⁶,³⁴Lys³⁶-(Glut-AOct)-GLP-1(7-36)amide; Ser⁸Arg²⁶Lys³⁴-(Glut-AOct)-GLP-1(7-37); Ser⁸Arg³⁴Lys²⁶-(Glut-AOct)-GLP-1(7-37); Ser⁸Arg²⁶,³⁴Lys³⁶-(Glut-AOct)-GLP-1(7-37); Ser⁸Arg²⁶Lys³⁴-(Glut-AOct)-GLP-1(7-38); Ser⁸Arg³⁴Lys²⁶-(Glut-AOct)-GLP-1(7-38); Ser⁸Arg²⁶,³⁴Lys³⁸-(Glut-AOct)-GLP-1(7-38); Ser⁸Arg²⁶Lys³⁴-(Glut-AOct)-GLP-1(7-39); Ser⁸Arg³⁴Lys²⁶-(Glut-AOct)-GLP-1(7-39); Ser⁸Arg²⁶,³⁴Lys³⁹-(Glut-AOct)-GLP-1(7-39);
Thr⁸Arg²⁶Lys³⁴-(Glut-AOct)-GLP-1(7-36); Thr⁸Arg³⁴Lys²⁶-(Glut-AOct)-GLP-1(7-36); Thr⁸Arg²⁶,³⁴Lys³⁶-(Glut-AOct)-GLP-1(7-36); Thr⁸Arg²⁶Lys³⁴-(Glut-AOct)-GLP-1(7-36)amide; Thr⁸Arg³⁴Lys²⁶-(Glut-AOct)-GLP-1(7-36)amide; Thr⁸Arg²⁶,³⁴Lys³⁶-(Glut-AOct)-GLP-1(7-36)amide; Thr⁸Arg²⁶Lys³⁴-(Glut-AOct)-GLP-1(7-37); Thr⁸Arg³⁴Lys²⁶-(Glut-AOct)-GLP-1(7-37); Thr⁸Arg²⁶,³⁴Lys³⁶-(Glut-AOct)-GLP-1(7-37); Thr⁸Arg²⁶Lys³⁴-(Glut-AOct)-GLP-1(7-38); Thr⁸Arg³⁴Lys²⁶-(Glut-AOct)-GLP-1(7-38); Thr⁸Arg²⁶,³⁴Lys³⁸-(Glut-AOct)-GLP-1(7-38); Thr⁸Arg²⁶Lys³⁴-(Glut-AOct)-GLP-1(7-39); Thr⁸Arg³⁴Lys²⁶-(Glut-AOct)-GLP-1(7-39); Thr⁸Arg²⁶,³⁴Lys³⁹-(Glut-AOct)-GLP-1(7-39);
Gly⁸Glu³⁵Arg²⁶,³⁴Lys³⁶-(Glut-AOct)-GLP-1(7-36); Gly⁸Glu³⁵Arg²⁶,³⁴Lys³⁶-(Glut-AOct)-GLP-1(7-36)amide; Gly⁸Glu³⁶Arg²⁶,³⁴Lys³⁷-(Glut-AOct)-GLP-1(7-37); Gly⁸Glu³⁷Arg²⁶,³⁴Lys³⁸-(Glut-AOct)-GLP-1(7-38); Gly⁸Glu³⁸Arg²⁶,³⁴Lys³⁹-(Glut-AOct)-GLP-1(7-39); Gly⁸Glu³⁵Arg²⁶,³⁴Lys³⁶-(Glut-AOct)-GLP-1(7-36); Gly⁸Glu³⁵Arg²⁶,³⁴Lys³⁶-(Glut-AOct)-GLP-1(7-36)amide; Gly⁸Glu³⁶Arg²⁶,³⁴Lys³⁷-(Glut-AOct)-GLP-1(7-37); Gly⁸Glu³⁷Arg²⁶,³⁴Lys³⁸-(Glut-AOct)-GLP-1(7-38); Gly⁸Glu³⁸Arg²⁶,³⁴Lys³⁹-(Glut-AOct)-GLP-1(7-39);

Gly$^8$Asp$^{35}$Arg$^{26,34}$Lys$^{36}$-(Glut-AOct)-GLP-1(7-36);
Gly$^8$Asp$^{35}$Arg$^{26,34}$Lys$^{36}$-(Glut-AOct)-GLP-1(7-36)amide;
Gly$^8$Asp$^{36}$Arg$^{26,34}$Lys$^{37}$-(Glut-AOct)-GLP-1(7-37);
Gly$^8$Asp$^{37}$Arg$^{26,34}$Lys$^{38}$-(Glut-AOct)-GLP-1(7-38);
Gly$^8$Asp$^{38}$Arg$^{26,34}$Lys$^{39}$-(Glut-AOct)-GLP-1(7-39);
Gly$^8$Asp$^{35}$Arg$^{26,34}$Lys$^{36}$-(Glut-AOct)-GLP-1(7-36);
Gly$^8$Asp$^{35}$Arg$^{26,34}$Lys$^{36}$-(Glut-AOct)-GLP-1(7-36)amide;
Gly$^8$Asp$^{36}$Arg$^{26,34}$Lys$^{37}$-(Glut-AOct)-GLP-1(7-37);
Gly$^8$Asp$^{37}$Arg$^{26,34}$Lys$^{38}$-(Glut-AOct)-GLP-1(7-38);
Gly$^8$Asp$^{38}$Arg$^{26,34}$Lys$^{39}$-(Glut-AOct)-GLP-1(7-39);
Val$^8$Glu$^{35}$Arg$^{26,34}$Lys$^{36}$-(Glut-AOct)-GLP-1(7-36);
Val$^8$Glu$^{35}$Arg$^{26,34}$Lys$^{36}$-(Glut-AOct)-GLP-1(7-36)amide;
Val$^8$Glu$^{36}$Arg$^{26,34}$Lys$^{37}$-(Glut-AOct)-GLP-1(7-37);
Val$^8$Glu$^{37}$Arg$^{26,34}$Lys$^{38}$-(Glut-AOct)-GLP-1(7-38);
Val$^8$Glu$^{38}$Arg$^{26,34}$Lys$^{39}$-(Glut-AOct)-GLP-1(7-39);
Val$^8$Glu$^{35}$Arg$^{26,34}$Lys$^{36}$-(Glut-AOct)-GLP-1(7-36);
Val$^8$Glu$^{35}$Arg$^{26,34}$Lys$^{36}$-(Glut-AOct)-GLP-1(7-36)amide;
Val$^8$Glu$^{36}$Arg$^{26,34}$Lys$^{37}$-(Glut-AOct)-GLP-1(7-37);
Val$^8$Glu$^{37}$Arg$^{26,34}$Lys$^{37}$-(Glut-AOct)-GLP-1(7-38);
Val$^8$Glu$^{38}$Arg$^{26,34}$Lys$^{39}$-(Glut-AOct)-GLP-1(7-39);
Val$^8$Asp$^{35}$Arg$^{26,34}$Lys$^{36}$-(Glut-AOct)-GLP-1(7-36);
Val$^8$Asp$^{35}$Arg$^{26,34}$Lys$^{36}$-(Glut-AOct)-GLP-1(7-36)amide;
Val$^8$Asp$^{36}$Arg$^{26,34}$Lys$^{37}$-(Glut-AOct)-GLP-1(7-37);
Val$^8$Asp$^{37}$Arg$^{26,34}$Lys$^{38}$-(Glut-AOct)-GLP-1(7-38);
Val$^8$Asp$^{38}$Arg$^{26,34}$Lys$^{39}$-(Glut-AOct)-GLP-1(7-39);
Val$^8$Asp$^{35}$Arg$^{26,34}$Lys$^{36}$-(Glut-AOct)-GLP-1(7-36);
Val$^8$Asp$^{35}$Arg$^{26,34}$Lys$^{36}$-(Glut-AOct)-GLP-1(7-36)amide;
Val$^8$Asp$^{36}$Arg$^{26,34}$Lys$^{37}$-(Glut-AOct)-GLP-1(7-37);
Val$^8$Asp$^{37}$Arg$^{26,34}$Lys$^{38}$-(Glut-AOct)-GLP-1(7-38);
Val$^8$Asp$^{38}$Arg$^{26,34}$Lys$^{39}$-(Glut-AOct)-GLP-1(7-39);
Ser$^8$Glu$^{35}$Arg$^{26,34}$Lys$^{36}$-(Glut-AOct)-GLP-1(7-36);
Ser$^8$Glu$^{35}$Arg$^{26,34}$Lys$^{36}$-(Glut-AOct)-GLP-1(7-36)amide;
Ser$^8$Glu$^{36}$Arg$^{26,34}$Lys$^{37}$-(Glut-AOct)-GLP-1(7-37);
Ser$^8$Glu$^{37}$Arg$^{26,34}$Lys$^{38}$-(Glut-AOct)-GLP-1(7-38);
Ser$^8$Glu$^{38}$Arg$^{26,34}$Lys$^{39}$-(Glut-AOct)-GLP-1(7-39);
Ser$^8$Glu$^{35}$Arg$^{26,34}$Lys$^{36}$-(Glut-AOct)-GLP-1(7-36);
Ser$^8$Glu$^{35}$Arg$^{26,34}$Lys$^{36}$-(Glut-AOct)-GLP-1(7-36)amide;
Ser$^8$Glu$^{36}$Arg$^{26,34}$Lys$^{37}$-(Glut-AOct)-GLP-1(7-37);
Ser$^8$Glu$^{37}$Arg$^{26,34}$Lys$^{38}$-(Glut-AOct)-GLP-1(7-38);
Ser$^8$Glu$^{38}$Arg$^{26,34}$Lys$^{39}$-(Glut-AOct)-GLP-1(7-39);
Ser$^8$Asp$^{35}$Arg$^{26,34}$Lys$^{36}$-(Glut-AOct)-GLP-1(7-36);
Ser$^8$Asp$^{35}$Arg$^{26,34}$Lys$^{36}$-(Glut-AOct)-GLP-1(7-36)amide;
Ser$^8$Asp$^{36}$Arg$^{26,34}$Lys$^{37}$-(Glut-AOct)-GLP-1(7-37);
Ser$^8$Asp$^{37}$Arg$^{26,34}$Lys$^{38}$-(Glut-AOct)-GLP-1(7-38);
Ser$^8$Asp$^{38}$Arg$^{26,34}$Lys$^{39}$-(Glut-AOct)-GLP-1(7-39);
Ser$^8$Asp$^{35}$Arg$^{26,34}$Lys$^{36}$-(Glut-AOct)-GLP-1(7-36);
Ser$^8$Asp$^{35}$Arg$^{26,34}$Lys$^{36}$-(Glut-AOct)-GLP-1(7-36)amide;
Ser$^8$Asp$^{36}$Arg$^{26,34}$Lys$^{37}$-(Glut-AOct)-GLP-1(7-37);
Ser$^8$Asp$^{37}$Arg$^{26,34}$Lys$^{38}$-(Glut-AOct)-GLP-1(7-38);
Ser$^8$Asp$^{38}$Arg$^{26,34}$Lys$^{39}$-(Glut-AOct)-GLP-1(7-39);
Thr$^8$Glu$^{35}$Arg$^{26,34}$Lys$^{36}$-(Glut-AOct)-GLP-1(7-36);
Thr$^8$Glu$^{35}$Arg$^{26,34}$Lys$^{36}$-(Glut-AOct)-GLP-1(7-36)amide;
Thr$^8$Glu$^{36}$Arg$^{26,34}$Lys$^{37}$-(Glut-AOct)-GLP-1(7-37);
Thr$^8$Glu$^{37}$Arg$^{26,34}$Lys$^{38}$-(Glut-AOct)-GLP-1(7-38);
Thr$^8$Glu$^{38}$Arg$^{26,34}$Lys$^{39}$-(Glut-AOct)-GLP-1(7-39);
Thr$^8$Glu$^{35}$Arg$^{26,34}$Lys$^{36}$-(Glut-AOct)-GLP-1(7-36);
Thr$^8$Glu$^{35}$Arg$^{26,34}$Lys$^{36}$-(Glut-AOct)-GLP-1(7-36)amide;
Thr$^8$Glu$^{36}$Arg$^{26,34}$Lys$^{37}$-(Glut-AOct)-GLP-1(7-37);
Thr$^8$Glu$^{37}$Arg$^{26,34}$Lys$^{38}$-(Glut-AOct)-GLP-1(7-38);
Thr$^8$Glu$^{38}$Arg$^{26,34}$Lys$^{39}$-(Glut-AOct)-GLP-1(7-39);
Thr$^8$Asp$^{35}$Arg$^{26,34}$Lys$^{36}$-(Glut-AOct)-GLP-1(7-36);
Thr$^8$Asp$^{35}$Arg$^{26,34}$Lys$^{36}$-(Glut-AOct)-GLP-1(7-36)amide;
Thr$^8$Asp$^{36}$Arg$^{26,34}$Lys$^{37}$-(Glut-AOct)-GLP-1(7-37);
Thr$^8$Asp$^{37}$Arg$^{26,34}$Lys$^{38}$-(Glut-AOct)-GLP-1(7-38);
Thr$^8$Asp$^{38}$Arg$^{26,34}$Lys$^{39}$-(Glut-AOct)-GLP-1(7-39);
Thr$^8$Asp$^{35}$Arg$^{26,34}$Lys$^{36}$-(Glut-AOct)-GLP-1(7-36);
Thr$^8$Asp$^{35}$Arg$^{26,34}$Lys$^{36}$-(Glut-AOct)-GLP-1(7-36)amide;
Thr$^8$Asp$^{36}$Arg$^{26,34}$Lys$^{37}$-(Glut-AOct)-GLP-1(7-37);
Thr$^8$Asp$^{37}$Arg$^{26,34}$Lys$^{38}$-(Glut-AOct)-GLP-1(7-38);
Thr$^8$Asp$^{38}$Arg$^{26,34}$Lys$^{39}$-(Glut-AOct)-GLP-1(7-39);
Arg$^{26,34}$Lys$^{18}$-(Glut-AOct)-GLP-1(7-36); Arg$^{26,34}$Lys$^{18}$-(Glut-AOct)-GLP-1(7-36)amide; Arg$^{26,34}$Lys$^{18}$-(Glut-AOct)-GLP-1(7-37); Arg$^{26,34}$Lys$^{18}$-(Glut-AOct)-GLP-1(7-38); Gly$^8$Asp$^{19}$Arg$^{26,34}$Lys$^{18}$-(Glut-AOct)-GLP-1(7-36);
Gly$^8$Asp$^{17}$Arg$^{26,34}$Lys$^{18}$-(Glut-AOct)-GLP-1(7-36);
Gly$^8$Asp$^{19}$Arg$^{26,34}$Lys$^{18}$-(Glut-AOct)-GLP-1(7-36)amide;
Gly$^8$Asp$^{17}$Arg$^{26,34}$Lys$^{18}$-(Glut-AOct)-GLP-1(7-36)amide;
Gly$^8$Asp$^{19}$Arg$^{26,34}$Lys$^{18}$-(Glut-AOct)-GLP-1(7-37);
Gly$^8$Asp$^{19}$Arg$^{26,34}$Lys$^{18}$-(Glut-AOct)-GLP-1(7-38);
Gly$^8$Asp$^{17}$Arg$^{26,34}$Lys$^{18}$-(Glut-AOct)-GLP-1(7-38);
Arg$^{26,34}$Lys$^{23}$-(Glut-AOct)-GLP-1(7-36); Arg$^{26,34}$Lys$^{23}$-(Glut-AOct)-GLP-1(7-36)amide; Arg$^{26,34}$Lys$^{23}$-(Glut-AOct)-GLP-1(7-37); Arg$^{26,34}$Lys$^{23}$-(Glut-AOct)-GLP-1(7-38); Gly$^8$Asp$^{19}$Arg$^{26,34}$Lys$^{23}$-(Glut-AOct)-GLP-1(7-36);
Gly$^8$Asp$^{17}$Arg$^{26,34}$Lys$^{23}$-(Glut-AOct)-GLP-1(7-36);
Gly$^8$Asp$^{19}$Arg$^{26,34}$Lys$^{23}$-(Glut-AOct)-GLP-1(7-36)amide;
Gly$^8$Asp$^{17}$Arg$^{26,34}$Lys$^{23}$-(Glut-AOct)-GLP-1(7-36)amide;
Gly$^8$Asp$^{19}$Arg$^{26,34}$Lys$^{23}$-(Glut-AOct)-GLP-1(7-37);
Gly$^8$Asp$^{19}$Arg$^{26,34}$Lys$^{23}$-(Glut-AOct)-GLP-1(7-38);
Gly$^8$Asp$^{17}$Arg$^{26,34}$Lys$^{23}$-(Glut-AOct)-GLP-1(7-38);
Arg$^{26,34}$Lys$^{27}$-(Glut-AOct)-GLP-1(7-36); Arg$^{26,34}$Lys$^{27}$-(Glut-AOct)-GLP-1(7-36)amide; Arg$^{26,34}$Lys$^{27}$-(Glut-AOct)-GLP-1(7-37); Arg$^{26,34}$Lys$^{27}$-(Glut-AOct)-GLP-1(7-38); Gly$^8$Asp$^{19}$Arg$^{26,34}$Lys$^{27}$-(Glut-AOct)-GLP-1(7-36);
Gly$^8$Asp$^{17}$Arg$^{26,34}$Lys$^{27}$-(Glut-AOct)-GLP-1(7-36);
Gly$^8$Asp$^{19}$Arg$^{26,34}$Lys$^{27}$-(Glut-AOct)-GLP-1(7-36)amide;
Gly$^8$Asp$^{17}$Arg$^{26,34}$Lys$^{27}$-(Glut-AOct)-GLP-1(7-36)amide;
Gly$^8$Asp$^{19}$Arg$^{26,34}$Lys$^{27}$-(Glut-AOct)-GLP-1(7-37);
Gly$^8$Asp$^{19}$Arg$^{26,34}$Lys$^{27}$-(Glut-AOct)-GLP-1(7-38);
Gly$^8$Asp$^{17}$Arg$^{26,34}$Lys$^{27}$-(Glut-AOct)-GLP-1(7-38);
Arg$^{26,34}$Lys$^{18}$-(Glut-AOct)-GLP-1(7-36); Arg$^{26,34}$Lys$^{18}$-(Glut-AOct)-GLP-1(7-36)amide; Arg$^{26,34}$Lys$^{18}$-(Glut-AOct)-GLP-1(7-37); Arg$^{26,34}$Lys$^{18}$-(Glut-AOct)-GLP-1(7-38); Val$^8$Asp$^{19}$Arg$^{26,34}$Lys$^{18}$-(Glut-AOct)-GLP-1(7-36);
Val$^8$Asp$^{17}$Arg$^{26,34}$Lys$^{18}$-(Glut-AOct)-GLP-1(7-36);
Val$^8$Asp$^{19}$Arg$^{26,34}$Lys$^{18}$-(Glut-AOct)-GLP-1(7-36)amide;
Val$^8$Asp$^{17}$Arg$^{26,34}$Lys$^{18}$-(Glut-AOct)-GLP-1(7-36)amide;
Val$^8$Asp$^{19}$Arg$^{26,34}$Lys$^{18}$-(Glut-AOct)-GLP-1(7-37);
Val$^8$Asp$^{19}$Arg$^{26,34}$Lys$^{18}$-(Glut-AOct)-GLP-1(7-38);
Val$^8$Asp$^{17}$Arg$^{26,34}$Lys$^{18}$-(Glut-AOct)-GLP-1(7-38);
Arg$^{26,34}$Lys$^{23}$-(Glut-AOct)-GLP-1(7-36); Arg$^{26,34}$Lys$^{23}$-(Glut-AOct)-GLP-1(7-36)amide; Arg$^{26,34}$Lys$^{23}$-(Glut-AOct)-GLP-1(7-37); Arg$^{26,34}$Lys$^{23}$-(Glut-AOct)-GLP-1(7-38); Val$^8$Asp$^{19}$Arg$^{26,34}$Lys$^{23}$-(Glut-AOct)-GLP-1(7-36);
Val$^8$Asp$^{17}$Arg$^{26,34}$Lys$^{23}$-(Glut-AOct)-GLP-1(7-36);
Val$^8$Asp$^{19}$Arg$^{26,34}$Lys$^{23}$-(Glut-AOct)-GLP-1(7-36)amide;
Val$^8$Asp$^{17}$Arg$^{26,34}$Lys$^{23}$-(Glut-AOct)-GLP-1(7-36)amide;
Val$^8$Asp$^{19}$Arg$^{26,34}$Lys$^{23}$-(Glut-AOct)-GLP-1(7-37);
Val$^8$Asp$^{19}$Arg$^{26,34}$Lys$^{23}$-(Glut-AOct)-GLP-1(7-38);
Val$^8$Asp$^{17}$Arg$^{26,34}$Lys$^{23}$-(Glut-AOct)-GLP-1(7-38);
Arg$^{26,34}$Lys$^{27}$-(Glut-AOct)-GLP-1(7-36); Arg$^{26,34}$Lys$^{27}$-(Glut-AOct)-GLP-1(7-36)amide; Arg$^{26,34}$Lys$^{27}$-(Glut-AOct)-GLP-1(7-37); Arg$^{26,34}$Lys$^{27}$-(Glut-AOct)-GLP-1(7-38); Val$^8$Asp$^{19}$Arg$^{26,34}$Lys$^{27}$ (Glut-AOct)-GLP-1(7-36);
Val$^8$Asp$^{17}$Arg$^{26,34}$Lys$^{27}$-(Glut-AOct)-GLP-1(7-36);
Val$^8$Asp$^{19}$Arg$^{26,34}$Lys$^{27}$-(Glut-AOct)-GLP-1(7-36)amide;
Val$^8$Asp$^{17}$Arg$^{26,34}$Lys$^{27}$-(Glut-AOct)-GLP-1(7-36)amide;
Val$^8$Asp$^{19}$Arg$^{26,34}$Lys$^{27}$-(Glut-AOct)-GLP-1(7-37);
Val$^8$Asp$^{19}$Arg$^{26,34}$Lys$^{27}$-(Glut-AOct)-GLP-1(7-38);
Val$^8$Asp$^{17}$Arg$^{26,34}$Lys$^{27}$-(Glut-AOct)-GLP-1(7-38);
Arg$^{26,34}$Lys$^{18}$-(Glut-AOct)-GLP-1(7-36); Arg$^{26,34}$Lys$^{18}$-(Glut-AOct)-GLP-1(7-36)amide; Arg$^{26,34}$Lys$^{18}$-(Glut-AOct)-GLP-1(7-37); Arg$^{26,34}$Lys$^{18}$-(Glut-AOct)-GLP-1(7-38); Ser$^8$Asp$^{19}$Arg$^{26,34}$Lys$^{18}$-(Glut-AOct)-GLP-1(7-36);

Ser⁸Asp¹⁷Arg²⁶,³⁴Lys¹⁸-(Glut-AOct)-GLP-1(7-36);
Ser⁸Asp¹⁹Arg²⁶,³⁴Lys¹⁸-(Glut-AOct)-GLP-1(7-36)amide;
Ser⁸Asp¹⁷Arg²⁶,³⁴Lys¹⁸-(Glut-AOct)-GLP-1(7-36)amide;
Ser⁸Asp¹⁹Arg²⁶,³⁴Lys¹⁸-(Glut-AOct)-GLP-1(7-37);
Ser⁸Asp¹⁹Arg²⁶,³⁴Lys¹⁸-(Glut-AOct)-GLP-1(7-38);
Ser⁸Asp¹⁷Arg²⁶,³⁴Lys¹⁸-(Glut-AOct)-GLP-1(7-38);
Arg²⁶,³⁴Lys²³-(Glut-AOct)-GLP-1(7-36);  Arg²⁶,³⁴Lys²³-(Glut-AOct)-GLP-1(7-36)amide;  Arg²⁶,³⁴Lys²³-(Glut-AOct)-GLP-1(7-37); Arg²⁶,³⁴Lys²³-(Glut-AOct)-GLP-1(7-38); Ser⁸Asp¹⁹Arg²⁶,³⁴Lys²³-(Glut-AOct)-GLP-1(7-36);
Ser⁸Asp¹⁷Arg²⁶,³⁴Lys²³-(Glut-AOct)-GLP-1(7-36);
Ser⁸Asp¹⁹Arg²⁶,³⁴Lys²³-(Glut-AOct)-GLP-1(7-36)amide;
Ser⁸Asp¹⁷Arg²⁶,³⁴Lys²³-(Glut-AOct)-GLP-1(7-36)amide;
Ser⁸Asp¹⁹Arg²⁶,³⁴Lys²³-(Glut-AOct)-GLP-1(7-37);
Ser⁸Asp¹⁹Arg²⁶,³⁴Lys²³-(Glut-AOct)-GLP-1(7-38);
Ser⁸Asp¹⁷Arg²⁶,³⁴Lys²³-(Glut-AOct)-GLP-1(7-38);
Arg²⁶,³⁴Lys²⁷-(Glut-AOct)-GLP-1(7-36); Arg²⁶,³⁴Lys²⁷-(Glut-AOct)-GLP-1(7-36)amide; Arg²⁶,³⁴Lys²⁷-(Glut-AOct)-GLP-1(7-37); Arg²⁶,³⁴Lys²⁷-(Glut-AOct)-GLP-1(7-38); Ser⁸Asp¹⁹Arg²⁶,³⁴Lys²⁷-(Glut-AOct)-GLP-1(7-36);
Ser⁸Asp¹⁷Arg²⁶,³⁴Lys²⁷-(Glut-AOct)-GLP-1(7-36);
Ser⁸Asp¹⁹Arg²⁶,³⁴Lys²⁷-(Glut-AOct)-GLP-1(7-36)amide;
Ser⁸Asp¹⁷Arg²⁶,³⁴Lys²⁷-(Glut-AOct)-GLP-1(7-36)amide;
Ser⁸Asp¹⁹Arg²⁶,³⁴Lys²⁷-(Glut-AOct)-GLP-1(7-37);
Ser⁸Asp¹⁹Arg²⁶,³⁴Lys²⁷-(Glut-AOct)-GLP-1(7-38);
Ser⁸Asp¹⁷Arg²⁶,³⁴Lys²⁷-(Glut-AOct)-GLP-1(7-38);
Arg²⁶,³⁴Lys¹⁸-(Glut-AOct)-GLP-1(7-36); Arg²⁶,³⁴Lys¹⁸-(Glut-AOct)-GLP-1(7-36)amide; Arg²⁶,³⁴Lys¹⁸-(Glut-AOct)-GLP-1(7-37); Arg²⁶,³⁴Lys¹⁸-(Glut-AOct)-GLP-1(7-38); Thr⁸Asp¹⁹Arg²⁶,³⁴Lys¹⁸-(Glut-AOct)-GLP-1(7-36);
Thr⁸Asp¹⁷Arg²⁶,³⁴Lys¹⁸-(Glut-AOct)-GLP-1(7-36);
Thr⁸Asp¹⁹Arg²⁶,³⁴Lys¹⁸-(Glut-AOct)-GLP-1(7-36)amide;
Thr⁸Asp¹⁷Arg²⁶,³⁴Lys¹⁸-(Glut-AOct)-GLP-1(7-36)amide;
Thr⁸Asp¹⁹Arg²⁶,³⁴Lys¹⁸-(Glut-AOct)-GLP-1(7-37);
Thr⁸Asp¹⁹Arg²⁶,³⁴Lys¹⁸-(Glut-AOct)-GLP-1(7-38);
Thr⁸Asp¹⁷Arg²⁶,³⁴Lys¹⁸-(Glut-AOct)-GLP-1(7-38);
Arg²⁶,³⁴Lys²³-(Glut-AOct)-GLP-1(7-36); Arg²⁶,³⁴Lys²³-(Glut-AOct)-GLP-1(7-36)amide; Arg²⁶,³⁴Lys²³-(Glut-AOct)-GLP-1(7-37); Arg²⁶,³⁴Lys²³-(Glut-AOct)-GLP-1(7-38); Thr⁸Asp¹⁹Arg²⁶,³⁴Lys²³-(Glut-AOct)-GLP-1(7-36);
Thr⁸Asp¹⁷Arg²⁶,³⁴Lys²³-(Glut-AOct)-GLP-1(7-36);
Thr⁸Asp¹⁹Arg²⁶,³⁴Lys²³-(Glut-AOct)-GLP-1(7-36)amide;
Thr⁸Asp¹⁷Arg²⁶,³⁴Lys²³-(Glut-AOct)-GLP-1(7-36)amide;
Thr⁸Asp¹⁹Arg²⁶,³⁴Lys²³-(Glut-AOct)-GLP-1(7-37);
Thr⁸Asp¹⁹Arg²⁶,³⁴Lys²³-(Glut-AOct)-GLP-1(7-38);
Thr⁸Asp¹⁷Arg²⁶,³⁴Lys²³-(Glut-AOct)-GLP-1(7-38);
Arg²⁶,³⁴Lys²⁷-(Glut-AOct)-GLP-1(7-36); Arg²⁶,³⁴Lys²⁷-(Glut-AOct)-GLP-1(7-36)amide; Arg²⁶,³⁴Lys²⁷-(Glut-AOct)-GLP-1(7-37); Arg²⁶,³⁴Lys²⁷-(Glut-AOct)-GLP-1(7-38); Thr⁸Asp¹⁹Arg²⁶,³⁴Lys²⁷ (Glut-AOct) GLP-1(7-36);
Thr⁸Asp¹⁷Arg²⁶,³⁴Lys²⁷-(Glut-AOct)-GLP-1(7-36);
Thr⁸Asp¹⁹Arg²⁶,³⁴Lys²⁷-(Glut-AOct)-GLP-1(7-36)amide;
Thr⁸Asp¹⁷Arg²⁶,³⁴Lys²⁷-(Glut-AOct)-GLP-1(7-36)amide;
Thr⁸Asp¹⁹Arg²⁶,³⁴Lys²⁷-(Glut-AOct)-GLP-1(7-37);
Thr⁸Asp¹⁹Arg²⁶,³⁴Lys²⁷-(Glut-AOct)-GLP-1(7-38);
Thr⁸Asp¹⁷Arg²⁶,³⁴Lys²⁷-(Glut-AOct)-GLP-1(7-38);
Arg²⁶Lys³⁴-(Glut-ALit)-GLP-1(7-36); Arg³⁴Lys²⁶-(Glut-ALit)-GLP-1(7-36); Arg²⁶,³⁴Lys³⁶-(Glut-ALit)-GLP-1(7-36); Arg²⁶Lys³⁴-(Glut-ALit)-GLP-1(7-36)amide; Arg³⁴Lys²⁶-(Glut-ALit)-GLP-1(7-36)amide; Arg²⁶,³⁴Lys³⁶-(Glut-ALit)-GLP-1(7-36)amide; Arg²⁶Lys³⁴-(Glut-ALit)-GLP-1(7-37); Arg³⁴Lys²⁶-(Glut-ALit)-GLP-1(7-37); Arg²⁶,³⁴Lys³⁶-(Glut-ALit)-GLP-1(7-37); Arg²⁶Lys³⁴-(Glut-ALit)-GLP-1(7-38); Arg³⁴Lys²⁶-(Glut-ALit)-GLP-1(7-38); Arg²⁶,³⁴Lys³⁸-(Glut-ALit)-GLP-1(7-38); Arg²⁶Lys³⁴-(Glut-ALit)-GLP-1(7-39); Arg³⁴Lys²⁶-(Glut-ALit)-GLP-1(7-39); Arg²⁶,³⁴Lys³⁹-(Glut-ALit)-GLP-1(7-39);
Gly⁸Arg²⁶Lys³⁴-(Glut-ALit)-GLP-1(7-36); Gly⁸Arg³⁴Lys²⁶-(Glut-ALit)-GLP-1(7-36); Gly⁸Arg²⁶,³⁴Lys³⁶-(Glut-ALit)-GLP-1(7-36); Gly⁸Arg²⁶Lys³⁴-(Glut-ALit)-GLP-1(7-36)amide; Gly⁸Arg³⁴Lys²⁶-(Glut-ALit)-GLP-1(7-36)amide; Gly⁸Arg²⁶,³⁴Lys³⁶-(Glut-ALit)-GLP-1(7-36)amide; Gly⁸Arg²⁶Lys³⁴-(Glut-ALit)-GLP-1(7-37); Gly⁸Arg³⁴Lys²⁶-(Glut-ALit)-GLP-1(7-37); Gly⁸Arg²⁶,³⁴Lys³⁶-(Glut-ALit)-GLP-1(7-37); Gly⁸Arg²⁶Lys³⁴-(Glut-ALit)-GLP-1(7-38); Gly⁸Arg³⁴Lys²⁶-(Glut-ALit)-GLP-1(7-38); Gly⁸Arg²⁶,³⁴Lys³⁸-(Glut-ALit)-GLP-1(7-38); Gly⁸Arg²⁶Lys³⁴-(Glut-ALit)-GLP-1(7-39); Gly⁸Arg³⁴Lys²⁶-(Glut-ALit)-GLP-1(7-39); Gly⁸Arg²⁶,³⁴Lys³⁹-(Glut-ALit)-GLP-1(7-39);
Val⁸Arg²⁶Lys³⁴-(Glut-ALit)-GLP-1(7-36); Val⁸Arg³⁴Lys²⁶-(Glut-ALit)-GLP-1(7-36); Val⁸Arg²⁶,³⁴Lys³⁶-(Glut-ALit)-GLP-1(7-36); Val⁸Arg²⁶Lys³⁴-(Glut-ALit)-GLP-1(7-36)amide; Val⁸Arg³⁴Lys²⁶-(Glut-ALit)-GLP-1(7-36)amide; Val⁸Arg²⁶,³⁴Lys³⁶-(Glut-ALit)-GLP-1(7-36)amide; Val⁸Arg²⁶Lys³⁴-(Glut-ALit)-GLP-1(7-37); Val⁸Arg³⁴Lys²⁶-(Glut-ALit)-GLP-1(7-37); Val⁸Arg²⁶,³⁴Lys³⁶-(Glut-ALit)-GLP-1(7-37); Val⁸Arg²⁶Lys³⁴-(Glut-ALit)-GLP-1(7-38); Val⁸Arg³⁴Lys²⁶-(Glut-ALit)-GLP-1(7-38); Val⁸Arg²⁶,³⁴Lys³⁸-(Glut-ALit)-GLP-1(7-38); Val⁸Arg²⁶Lys³⁴-(Glut-ALit)-GLP-1(7-39); Val⁸Arg³⁴Lys²⁶-(Glut-ALit)-GLP-1(7-39); Val⁸Arg²⁶,³⁴Lys³⁹-(Glut-ALit)-GLP-1(7-39);
Ser⁸Arg²⁶Lys³⁴-(Glut-ALit)-GLP-1(7-36); Ser⁸Arg³⁴Lys²⁶-(Glut-ALit)-GLP-1(7-36); Ser⁸Arg²⁶,³⁴Lys³⁶-(Glut-ALit)-GLP-1(7-36); Ser⁸Arg²⁶Lys³⁴-(Glut-ALit)-GLP-1(7-36)amide; Ser⁸Arg³⁴Lys²⁶-(Glut-ALit)-GLP-1(7-36)amide; Ser⁸Arg²⁶,³⁴Lys³⁶-(Glut-ALit)-GLP-1(7-36)amide; Ser⁸Arg²⁶Lys³⁴-(Glut-ALit)-GLP-1(7-37); Ser⁸Arg³⁴Lys²⁶-(Glut-ALit)-GLP-1(7-37); Ser⁸Arg²⁶,³⁴Lys³⁶-(Glut-ALit)-GLP-1(7-37); Ser⁸Arg²⁶Lys³⁴-(Glut-ALit)-GLP-1(7-38); Ser⁸Arg³⁴Lys²⁶-(Glut-ALit)-GLP-1(7-38); Ser⁸Arg²⁶,³⁴Lys³⁸-(Glut-ALit)-GLP-1(7-38); Ser⁸Arg²⁶Lys³⁴-(Glut-ALit)-GLP-1(7-39); Ser⁸Arg³⁴Lys²⁶-(Glut-ALit)-GLP-1(7-39); Ser⁸Arg²⁶,³⁴Lys³⁹-(Glut-ALit)-GLP-1(7-39);
Thr⁸Arg²⁶Lys³⁴-(Glut-ALit)-GLP-1(7-36); Thr⁸Arg³⁴Lys²⁶-(Glut-ALit)-GLP-1(7-36); Thr⁸Arg²⁶,³⁴Lys³⁶-(Glut-ALit)-GLP-1(7-36); Thr⁸Arg²⁶Lys³⁴-(Glut-ALit)-GLP-1(7-36)amide; Thr⁸Arg³⁴Lys²⁶-(Glut-ALit)-GLP-1(7-36)amide; Thr⁸Arg²⁶,³⁴Lys³⁶-(Glut-ALit)-GLP-1(7-36)amide; Thr⁸Arg²⁶Lys³⁴-(Glut-ALit)-GLP-1(7-37); Thr⁸Arg³⁴Lys²⁶-(Glut-ALit)-GLP-1(7-37); Thr⁸Arg²⁶,³⁴Lys³⁶-(Glut-ALit)-GLP-1(7-37); Thr⁸Arg²⁶Lys³⁴-(Glut-ALit)-GLP-1(7-38); Thr⁸Arg³⁴Lys²⁶-(Glut-ALit)-GLP-1(7-38); Thr⁸Arg²⁶,³⁴Lys³⁸-(Glut-ALit)-GLP-1(7-38); Thr⁸Arg²⁶Lys³⁴-(Glut-ALit)-GLP-1(7-39); Thr⁸Arg³⁴Lys²⁶-(Glut-ALit)-GLP-1(7-39); Thr⁸Arg²⁶,³⁴Lys³⁹-(Glut-ALit)-GLP-1(7-39);
Gly⁸Glu³⁵Arg²⁶,³⁴Lys³⁶-(Glut-ALit)-GLP-1(7-36);
Gly⁸Glu³⁵Arg²⁶,³⁴Lys³⁶-(Glut-ALit)-GLP-1(7-36)amide;
Gly⁸Glu³⁶Arg²⁶,³⁴Lys³⁷-(Glut-ALit)-GLP-1(7-37);
Gly⁸Glu³⁷Arg²⁶,³⁴Lys³⁸-(Glut-ALit)-GLP-1(7-38);
Gly⁸Glu³⁸Arg²⁶,³⁴Lys³⁹-(Glut-ALit)-GLP-1(7-39);
Gly⁸Glu³⁵Arg²⁶,³⁴Lys³⁶-(Glut-ALit)-GLP-1(7-36);
Gly⁸Glu³⁵Arg²⁶,³⁴Lys³⁶-(Glut-ALit)-GLP-1(7-36)amide;
Gly⁸Glu³⁶Arg²⁶,³⁴Lys³⁷-(Glut-ALit)-GLP-1(7-37);
Gly⁸Glu³⁷Arg²⁶,³⁴Lys³⁸-(Glut-ALit)-GLP-1(7-38);
Gly⁸Glu³⁸Arg²⁶,³⁴Lys³⁹-(Glut-ALit)-GLP-1(7-39);
Gly⁸Asp³⁵Arg²⁶,³⁴Lys³⁶-(Glut-ALit)-GLP-1(7-36);
Gly⁸Asp³⁵Arg²⁶,³⁴Lys³⁶-(Glut-ALit)-GLP-1(7-36)amide;
Gly⁸Asp³⁶Arg²⁶,³⁴Lys³⁷-(Glut-ALit)-GLP-1(7-37);
Gly⁸Asp³⁷Arg²⁶,³⁴Lys³⁸-(Glut-ALit)-GLP-1(7-38);
Gly⁸Asp³⁸Arg²⁶,³⁴Lys³⁹-(Glut-ALit)-GLP-1(7-39);
Gly⁸Asp³⁵Arg²⁶,³⁴Lys³⁶-(Glut-ALit)-GLP-1(7-36);
Gly⁸Asp³⁵Arg²⁶,³⁴Lys³⁶-(Glut-ALit)-GLP-1(7-36)amide;

Gly⁸Asp³⁶Arg²⁶,³⁴Lys³⁷-(Glut-ALit)-GLP-1(7-37);
Gly⁸Asp³⁷Arg²⁶,³⁴Lys³⁸-(Glut-ALit)-GLP-1(7-38);
Gly⁸Asp³⁸Arg²⁶,³⁴Lys³⁹-(Glut-ALit)-GLP-1(7-39);
Val⁸Glu³⁵Arg²⁶,³⁴Lys³⁶-(Glut-ALit)-GLP-1(7-36);
Val⁸Glu³⁵Arg²⁶,³⁴Lys³⁶-(Glut-ALit)-GLP-1(7-36)amide;
Val⁸Glu³⁶Arg²⁶,³⁴Lys³⁷-(Glut-ALit)-GLP-1(7-37);
Val⁸Glu³⁷Arg²⁶,³⁴Lys³⁸-(Glut-ALit)-GLP-1(7-38);
Val⁸Glu³⁸Arg²⁶,³⁴Lys³⁹-(Glut-ALit)-GLP-1(7-39);
Val⁸Glu³⁵Arg²⁶,³⁴Lys³⁶-(Glut-ALit)-GLP-1(7-36);
Val⁸Glu³⁵Arg²⁶,³⁴Lys³⁶-(Glut-ALit)-GLP-1(7-36)amide;
Val⁸Glu³⁶Arg²⁶,³⁴Lys³⁷-(Glut-ALit)-GLP-1(7-37);
Val⁸Glu³⁷Arg²⁶,³⁴Lys³⁸-(Glut-ALit)-GLP-1(7-38);
Val⁸Glu³⁸Arg²⁶,³⁴Lys³⁹-(Glut-ALit)-GLP-1(7-39);
Val⁸Asp³⁵Arg²⁶,³⁴Lys³⁶-(Glut-ALit)-GLP-1(7-36);
Val⁸Asp³⁵Arg²⁶,³⁴Lys³⁶-(Glut-ALit)-GLP-1(7-36)amide;
Val⁸Asp³⁶Arg²⁶,³⁴Lys³⁷-(Glut-ALit)-GLP-1(7-37);
Val⁸Asp³⁷Arg²⁶,³⁴Lys³⁸-(Glut-ALit)-GLP-1(7-38);
Val⁸Asp³⁸Arg²⁶,³⁴Lys³⁹-(Glut-ALit)-GLP-1(7-39);
Val⁸Asp³⁵Arg²⁶,³⁴Lys³⁶-(Glut-ALit)-GLP-1(7-36);
Val⁸Asp³⁵Arg²⁶,³⁴Lys³⁶-(Glut-ALit)-GLP-1(7-36)amide;
Val⁸Asp³⁶Arg²⁶,³⁴Lys³⁷-(Glut-ALit)-GLP-1(7-37);
Val⁸Asp³⁷Arg²⁶,³⁴Lys³⁸-(Glut-ALit)-GLP-1(7-38);
Val⁸Asp³⁸Arg²⁶,³⁴Lys³⁹-(Glut-ALit)-GLP-1(7-39);
Ser⁸Glu³⁵Arg²⁶,³⁴Lys³⁶-(Glut-ALit)-GLP-1(7-36);
Ser⁸Glu³⁵Arg²⁶,³⁴Lys³⁶-(Glut-ALit)-GLP-1(7-36)amide;
Ser⁸Glu³⁶Arg²⁶,³⁴Lys³⁷-(Glut-ALit)-GLP-1(7-37);
Ser⁸Glu³⁷Arg²⁶,³⁴Lys³⁸-(Glut-ALit)-GLP-1(7-38);
Ser⁸Glu³⁸Arg²⁶,³⁴Lys³⁹-(Glut-ALit)-GLP-1(7-39);
Ser⁸Glu³⁵Arg²⁶,³⁴Lys³⁶-(Glut-ALit)-GLP-1(7-36);
Ser⁸Glu³⁵Arg²⁶,³⁴Lys³⁶-(Glut-ALit)-GLP-1(7-36)amide;
Ser⁸Glu³⁶Arg²⁶,³⁴Lys³⁷-(Glut-ALit)-GLP-1(7-37);
Ser⁸Glu³⁷Arg²⁶,³⁴Lys³⁸-(Glut-ALit)-GLP-1(7-38);
Ser⁸Glu³⁸Arg²⁶,³⁴Lys³⁹-(Glut-ALit)-GLP-1(7-39);
Ser⁸Asp³⁵Arg²⁶,³⁴Lys³⁶-(Glut-ALit)-GLP-1(7-36);
Ser⁸Asp³⁵Arg²⁶,³⁴Lys³⁶-(Glut-ALit)-GLP-1(7-36)amide;
Ser⁸Asp³⁶Arg²⁶,³⁴Lys³⁷-(Glut-ALit)-GLP-1(7-37);
Ser⁸Asp³⁷Arg²⁶,³⁴Lys³⁸-(Glut-ALit)-GLP-1(7-38);
Ser⁸Asp³⁸Arg²⁶,³⁴Lys³⁹-(Glut-ALit)-GLP-1(7-39);
Ser⁸Asp³⁵Arg²⁶,³⁴Lys³⁶-(Glut-ALit)-GLP-1(7-36);
Ser⁸Asp³⁵Arg²⁶,³⁴Lys³⁶-(Glut-ALit)-GLP-1(7-36)amide;
Ser⁸Asp³⁶Arg²⁶,³⁴Lys³⁷(Glut-ALit)-GLP-1(7-37);
Ser⁸Asp³⁷Arg²⁶,³⁴Lys³⁸-(Glut-ALit)-GLP-1(7-38);
Ser⁸Asp³⁸Arg²⁶,³⁴Lys³⁹-(Glut-ALit)-GLP-1(7-39);
Thr⁸Glu³⁵Arg²⁶,³⁴Lys³⁶-(Glut-ALit)-GLP-1(7-36);
Thr⁸Glu³⁵Arg²⁶,³⁴Lys³⁶-(Glut-ALit)-GLP-1(7-36)amide;
Thr⁸Glu³⁶Arg²⁶,³⁴Lys³⁷-(Glut-ALit)-GLP-1(7-37);
Thr⁸Glu³⁷Arg²⁶,³⁴Lys³⁸-(Glut-ALit)-GLP-1(7-38);
Thr⁸Glu³⁸Arg²⁶,³⁴Lys³⁹-(Glut-ALit)-GLP-1(7-39);
Thr⁸Glu³⁵Arg²⁶,³⁴Lys³⁶-(Glut-ALit)-GLP-1(7-36);
Thr⁸Glu³⁵Arg²⁶,³⁴Lys³⁶-(Glut-ALit)-GLP-1(7-36)amide;
Thr⁸Glu³⁶Arg²⁶,³⁴Lys³⁷-(Glut-ALit)-GLP-1(7-37);
Thr⁸Glu³⁷Arg²⁶,³⁴Lys³⁸-(Glut-ALit)-GLP-1(7-38);
Thr⁸Glu³⁸Arg²⁶,³⁴Lys³⁹-(Glut-ALit)-GLP-1(7-39);
Thr⁸Asp³⁵Arg²⁶,³⁴Lys³⁶-(Glut-ALit)-GLP-1(7-36);
Thr⁸Asp³⁵Arg²⁶,³⁴Lys³⁶-(Glut-ALit)-GLP-1(7-36)amide;
Thr⁸Asp³⁶Arg²⁶,³⁴Lys³⁷-(Glut-ALit)-GLP-1(7-37);
Thr⁸Asp³⁷Arg²⁶,³⁴Lys³⁸-(Glut-ALit)-GLP-1(7-38);
Thr⁸Asp³⁸Arg²⁶,³⁴Lys³⁹-(Glut-ALit)-GLP-1(7-39);
Thr⁸Asp³⁵Arg²⁶,³⁴Lys³⁶-(Glut-ALit)-GLP-1(7-36);
Thr⁸Asp³⁵Arg²⁶,³⁴Lys³⁶-(Glut-ALit)-GLP-1(7-36)amide;
Thr⁸Asp³⁶Arg²⁶,³⁴Lys³⁷-(Glut-ALit)-GLP-1(7-37);
Thr⁸Asp³⁷Arg²⁶,³⁴Lys³⁸-(Glut-ALit)-GLP-1(7-38);
Thr⁸Asp³Arg²⁶,³⁴Lys³⁹-(Glut-ALit)-GLP-1(7-39);
Arg²⁶,³⁴Lys¹⁸-(Glut-ALit)-GLP-1(7-36); Arg²⁶,³⁴Lys¹⁸-(Glut-ALit)-GLP-1(7-36)amide; Arg²⁶,³⁴Lys¹⁸-(Glut-ALit)-GLP-1(7-37); Arg²⁶,³⁴Lys¹⁸-(Glut-ALit)-GLP-1(7-38);
Gly⁸Asp¹⁹Arg²⁶,³⁴Lys¹⁸-(Glut-ALit)-GLP-1(7-36);
Gly⁸Asp¹⁷Arg²⁶,³⁴Lys¹⁸-(Glut-ALit)-GLP-1(7-36);
Gly⁸Asp¹⁹Arg²⁶,³⁴Lys¹⁸-(Glut-ALit)-GLP-1(7-36)amide;
Gly⁸Asp¹⁷Arg²⁶,³⁴Lys¹⁸-(Glut-ALit)-GLP-1(7-36)amide;
Gly⁸Asp¹⁹Arg²⁶,³⁴Lys¹⁸-(Glut-ALit)-GLP-1(7-37);
Gly⁸Asp¹⁷Arg²⁶,³⁴Lys¹⁸-(Glut-ALit)-GLP-1(7-37);
Gly⁸Asp¹⁹Arg²⁶,³⁴Lys¹⁸-(Glut-ALit)-GLP-1(7-38);
Gly⁸Asp¹⁷Arg²⁶,³⁴Lys¹⁸-(Glut-ALit)-GLP-1(7-38);
Arg²⁶,³⁴Lys²³-(Glut-ALit)-GLP-1(7-36); Arg²⁶,³⁴Lys²³-(Glut-ALit)-GLP-1(7-36)amide; Arg²⁶,³⁴Lys²³-(Glut-ALit)-GLP-1(7-37); Arg²⁶,³⁴Lys²³-(Glut-ALit)-GLP-1(7-38);
Gly⁸Asp¹⁹Arg²⁶,³⁴Lys²³-(Glut-ALit)-GLP-1(7-36);
Gly⁸Asp¹⁷Arg²⁶,³⁴Lys²³-(Glut-ALit)-GLP-1(7-36);
Gly⁸Asp¹⁹Arg²⁶,³⁴Lys²³-(Glut-ALit)-GLP-1(7-36)amide;
Gly⁸Asp¹⁷Arg²⁶,³⁴Lys²³-(Glut-ALit)-GLP-1(7-36)amide;
Gly⁸Asp¹⁹Arg²⁶,³⁴Lys²³-(Glut-ALit)-GLP-1(7-37);
Gly⁸Asp¹⁹Arg²⁶,³⁴Lys²³-(Glut-ALit)-GLP-1(7-38);
Gly⁸Asp¹⁷Arg²⁶,³⁴Lys²³-(Glut-ALit)-GLP-1(7-38);
Arg²⁶,³⁴Lys²⁷-(Glut-ALit)-GLP-1(7-36); Arg²⁶,³⁴Lys²⁷-(Glut-ALit)-GLP-1(7-36)amide; Arg²⁶,³⁴Lys²⁷-(Glut-ALit)-GLP-1(7-37); Arg²⁶,³⁴Lys²⁷-(Glut-ALit)-GLP-1(7-38);
Gly⁸Asp¹⁹Arg²⁶,³⁴Lys²⁷-(Glut-ALit)-GLP-1(7-36);
Gly⁸Asp¹⁷Arg²⁶,³⁴Lys²⁷-(Glut-ALit)-GLP-1(7-36);
Gly⁸Asp¹⁹Arg²⁶,³⁴Lys²⁷-(Glut-ALit)-GLP-1(7-36)amide;
Gly⁸Asp¹⁷Arg²⁶,³⁴Lys²⁷-(Glut-ALit)-GLP-1(7-36)amide;
Gly⁸Asp¹⁹Arg²⁶,³⁴Lys²⁷-(Glut-ALit)-GLP-1(7-37);
Gly⁸Asp¹⁹Arg²⁶,³⁴Lys²⁷-(Glut-ALit)-GLP-1(7-38);
Gly⁸Asp¹⁷Arg²⁶,³⁴Lys²⁷-(Glut-ALit)-GLP-1(7-38);
Arg²⁶,³⁴Lys¹⁸-(Glut-ALit)-GLP-1(7-36); Arg²⁶,³⁴Lys¹⁸-(Glut-ALit)-GLP-1(7-36)amide; Arg²⁶,³⁴Lys¹⁸-(Glut-ALit)-GLP-1(7-37); Arg²⁶,³⁴Lys¹⁸-(Glut-ALit)-GLP-1(7-38);
Val⁸Asp¹⁹Arg²⁶,³⁴Lys¹⁸-(Glut-ALit)-GLP-1(7-36);
Val⁸Asp¹⁷Arg²⁶,³⁴Lys¹⁸-(Glut-ALit)-GLP-1(7-36);
Val⁸Asp¹⁹Arg²⁶,³⁴Lys¹⁸-(Glut-ALit)-GLP-1(7-36)amide;
Val⁸Asp¹⁷Arg²⁶,³⁴Lys¹⁸-(Glut-ALit)-GLP-1(7-36)amide;
Val⁸Asp¹⁹Arg²⁶,³⁴Lys¹⁸-(Glut-ALit)-GLP-1(7-37);
Val⁸Asp¹⁹Arg²⁶,³⁴Lys¹⁸-(Glut-ALit)-GLP-1(7-38);
Val⁸Asp¹⁷Arg²⁶,³⁴Lys¹⁸-(Glut-ALit)-GLP-1(7-38);
Arg²⁶,³⁴Lys²³-(Glut-ALit)-GLP-1(7-36); Arg²⁶,³⁴Lys²³-(Glut-ALit)-GLP-1(7-36)amide; Arg²⁶,³⁴Lys²³-(Glut-ALit)-GLP-1(7-37); Arg²⁶,³⁴Lys²³-(Glut-ALit)-GLP-1(7-38);
Val⁸Asp¹⁹Arg²⁶,³⁴Lys²³-(Glut-ALit)-GLP-1(7-36);
Val⁸Asp¹⁷Arg²⁶,³⁴Lys²³-(Glut-ALit)-GLP-1(7-36);
Val⁸Asp¹⁹Arg²⁶,³⁴Lys²³-(Glut-ALit)-GLP-1(7-36)amide;
Val⁸Asp¹⁷Arg²⁶,³⁴Lys²³-(Glut-ALit)-GLP-1(7-36)amide;
Val⁸Asp¹⁹Arg²⁶,³⁴Lys²³-(Glut-ALit)-GLP-1(7-37);
Val⁸Asp¹⁹Arg²⁶,³⁴Lys²³-(Glut-ALit)-GLP-1(7-38);
Val⁸Asp¹⁷Arg²⁶,³⁴Lys²³-(Glut-ALit)-GLP-1(7-38);
Arg²⁶,³⁴Lys²⁷-(Glut-ALit)-GLP-1(7-36); Arg²⁶,³⁴Lys²⁷-(Glut-ALit)-GLP-1(7-36)amide; Arg²⁶,³⁴Lys²⁷-(Glut-ALit)-GLP-1(7-37); Arg²⁶,³⁴Lys²⁷-(Glut-ALit)-GLP-1(7-38);
Val⁸Asp¹⁹Arg²⁶,³⁴Lys²⁷-(Glut-ALit)-GLP-1(7-36);
Val⁸Asp¹⁷Arg²⁶,³⁴Lys²⁷-(Glut-ALit)-GLP-1(7-36);
Val⁸Asp¹⁹Arg²⁶,³⁴Lys²⁷-(Glut-ALit)-GLP-1(7-36)amide;
Val⁸Asp¹⁷Arg²⁶,³⁴Lys²⁷-(Glut-ALit)-GLP-1(7-36)amide;
Val⁸Asp¹⁹Arg²⁶,³⁴Lys²⁷-(Glut-ALit)-GLP-1(7-37);
Val⁸Asp¹⁹Arg²⁶,³⁴Lys²⁷-(Glut-ALit)-GLP-1(7-38);
Val⁸Asp¹⁷Arg²⁶,³⁴Lys²⁷-(Glut-ALit)-GLP-1(7-38);
Arg²⁶,³⁴Lys¹⁸-(Glut-ALit)-GLP-1(7-36); Arg²⁶,³⁴Lys¹⁸-(Glut-ALit)-GLP-1(7-36)amide; Arg²⁶,³⁴Lys¹⁸-(Glut-ALit)-GLP-1(7-37); Arg²⁶,³⁴Lys¹⁸-(Glut-ALit)-GLP-1(7-38);
Ser⁸Asp¹⁹Arg²⁶,³⁴Lys¹⁸-(Glut-ALit)-GLP-1(7-36);
Ser⁸Asp¹⁷Arg²⁶,³⁴Lys¹⁸-(Glut-ALit)-GLP-1(7-36);
Ser⁸Asp¹⁹Arg²⁶,³⁴Lys¹⁸-(Glut-ALit)-GLP-1(7-36)amide;
Ser⁸Asp¹⁷Arg²⁶,³⁴Lys¹⁸-(Glut-ALit)-GLP-1(7-36)amide;
Ser⁸Asp¹⁹Arg²⁶,³⁴Lys¹⁸-(Glut-ALit)-GLP-1(7-37);
Ser⁸Asp¹⁹Arg²⁶,³⁴Lys¹⁸-(Glut-ALit)-GLP-1(7-38);
Ser⁸Asp⁷Arg²⁶,³⁴Lys¹⁸-(Glut-ALit)-GLP-1(7-38);
Arg²⁶,³⁴Lys²³-(Glut-ALit)-GLP-1(7-36); Arg²⁶,³⁴Lys²³-

(Glut-ALit)-GLP-1(7-36)amide; Arg²⁶,³⁴Lys²³-(Glut-ALit)-GLP-1(7-37); Arg²⁶,³⁴Lys²³-(Glut-ALit)-GLP-1(7-38);
Ser⁸Asp¹⁹Arg²⁶,³⁴Lys²³-(Glut-ALit)-GLP-1(7-36);
Ser⁸Asp¹⁷Arg²⁶,³⁴Lys²³-(Glut-ALit)-GLP-1(7-36);
Ser⁸Asp¹⁹Arg²⁶,³⁴Lys²³-(Glut-ALit)-GLP-1(7-36)amide;
Ser⁸Asp¹⁷Arg²⁶,³⁴Lys²³-(Glut-ALit)-GLP-1(7-36)amide;
Ser⁸Asp¹⁹Arg²⁶,³⁴Lys²³-(Glut-ALit)-GLP-1(7-37);
Ser⁸Asp¹⁹Arg²⁶,³⁴Lys²³-(Glut-ALit)-GLP-1(7-38);
Ser⁸Asp¹⁷Arg²⁶,³⁴Lys²³-(Glut-ALit)-GLP-1(7-38);
Arg²⁶,³⁴Lys²⁷-(Glut-ALit)-GLP-1(7-36); Arg²⁶,³⁴Lys²⁷-(Glut-ALit)-GLP-1(7-36)amide; Arg²⁶,³⁴Lys²⁷-(Glut-ALit)-GLP-1(7-37); Arg²⁶,³⁴Lys²⁷-(Glut-ALit)-GLP-1(7-38);
Ser⁸Asp¹⁹Arg²⁶,³⁴Lys²⁷-(Glut-ALit)-GLP-1(7-36);
Ser⁸Asp¹⁷Arg²⁶,³⁴Lys²⁷-(Glut-ALit)-GLP-1(7-36);
Ser⁸Asp¹⁹Arg²⁶,³⁴Lys²⁷-(Glut-ALit)-GLP-1(7-36)amide;
Ser⁸Asp¹⁷Arg²⁶,³⁴Lys²⁷-(Glut-ALit)-GLP-1(7-36)amide;
Ser⁸Asp¹⁹Arg²⁶,³⁴Lys²⁷-(Glut-ALit)-GLP-1(7-37);
Ser⁸Asp¹⁹Arg²⁶,³⁴Lys²⁷-(Glut-ALit)-GLP-1(7-38);
Ser⁸Asp¹⁷Arg²⁶,³⁴Lys²⁷-(Glut-ALit)-GLP-1(7-38);
Arg²⁶,³⁴Lys¹⁸-(Glut-ALit)-GLP-1(7-36); Arg²⁶,³⁴Lys¹⁸-(Glut-ALit)-GLP-1(7-36)amide; Arg²⁶,³⁴Lys¹⁸-(Glut-ALit)-GLP-1(7-37); Arg²⁶,³⁴Lys¹⁸-(Glut-ALit)-GLP-1(7-38);
Thr⁸Asp¹⁹Arg²⁶,³⁴Lys¹⁸-(Glut-ALit)-GLP-1(7-36);
Thr⁸Asp¹⁷Arg²⁶,³⁴Lys¹⁸-(Glut-ALit)-GLP-1(7-36);
Thr⁸Asp¹⁹Arg²⁶,³⁴Lys¹⁸-(Glut-ALit)-GLP-1(7-36)amide;
Thr⁸Asp¹⁷Arg²⁶,³⁴Lys¹⁸-(Glut-ALit)-GLP-1(7-36)amide;
Thr⁸Asp¹⁹Arg²⁶,³⁴Lys¹⁸-(Glut-ALit)-GLP-1(7-37);
Thr⁸Asp¹⁹Arg²⁶,³⁴Lys¹⁸-(Glut-ALit)-GLP-1(7-38);
Thr⁸Asp¹⁷Arg²⁶,³⁴Lys¹⁸-(Glut-ALit)-GLP-1(7-38);
Arg²⁶,³⁴Lys²³-(Glut-ALit)-GLP-1(7-36); Arg²⁶,³⁴Lys²³-(Glut-ALit)-GLP-1(7-36)amide; Arg²⁶,³⁴Lys²³-(Glut-ALit)-GLP-1(7-37); Arg²⁶,³⁴Lys²³-(Glut-ALit)-GLP-1(7-38);
Thr⁸Asp¹⁹Arg²⁶,³⁴Lys²³ (Glut-ALit)-GLP-1(7-36);
Thr⁸Asp¹⁷Arg²⁶,³⁴Lys²³-(Glut-ALit)-GLP-1(7-36);
Thr⁸Asp¹⁹Arg²⁶,³⁴Lys²³-(Glut-ALit)-GLP-1(7-36)amide;
Thr⁸Asp¹⁷Arg²⁶,³⁴Lys²³-(Glut-ALit)-GLP-1(7-36)amide;
Thr⁸Asp¹⁹Arg²⁶,³⁴Lys²³-(Glut-ALit)-GLP-1(7-37);
Thr⁸Asp¹⁹Arg²⁶,³⁴Lys²³-(Glut-ALit)-GLP-1(7-38);
Thr⁸Asp¹⁷Arg²⁶,³⁴Lys²³-(Glut-ALit)-GLP-1(7-38);
Arg²⁶,³⁴Lys²⁷-(Glut-ALit)-GLP-1(7-36); Arg²⁶,³⁴Lys²⁷-(Glut-ALit)-GLP-1(7-36)amide; Arg²⁶,³⁴Lys²⁷-(Glut-ALit)-GLP-1(7-37); Arg²⁶,³⁴Lys²⁷-(Glut-ALit)-GLP-1(7-38);
Thr⁸Asp¹⁹Arg²⁶,³⁴Lys²⁷-(Glut-ALit)-GLP-1(7-36);
Thr⁸Asp¹⁷Arg²⁶,³⁴Lys²⁷-(Glut-ALit)-GLP-1(7-36);
Thr⁸Asp¹⁹Arg²⁶,³⁴Lys²⁷-(Glut-ALit)-GLP-1(7-36)amide;
Thr⁸Asp¹⁷Arg²⁶,³⁴Lys²⁷-(Glut-ALit)-GLP-1(7-36)amide;
Thr⁸Asp¹⁹Arg²⁶,³⁴Lys²⁷-(Glut-ALit)-GLP-1(7-37);
Thr⁸Asp¹⁹Arg²⁶,³⁴Lys²⁷-(Glut-ALit)-GLP-1(7-38);
Thr⁸Asp¹⁷Arg²⁶,³⁴Lys²⁷-(Glut-ALit)-GLP-1(7-38);
Arg²⁶Lys³⁴-(Aspa-ADod)-GLP-1(7-36); Arg³⁴Lys²⁶-(Aspa-ADod)-GLP-1(7-36); Arg²⁶,³⁴Lys³⁶-(Aspa-ADod)-GLP-1(7-36); Arg²⁶Lys³⁴-(Aspa-ADod)-GLP-1(7-36)amide; Arg³⁴Lys²⁶-(Aspa-ADod)-GLP-1(7-36)amide;
Arg²⁶,³⁴Lys³⁶-(Aspa-ADod)-GLP-1(7-36)amide;
Arg²⁶Lys³⁴-(Aspa-ADod)-GLP-1(7-37); Arg³⁴Lys²⁶-(Aspa-ADod)-GLP-1(7-37); Arg²⁶,³⁴Lys³⁶-(Aspa-ADod)-GLP-1(7-37); Arg²⁶Lys³⁴-(Aspa-ADod)-GLP-1(7-38); Arg³⁴Lys²⁶-(Aspa-ADod)-GLP-1(7-38); Arg²⁶Lys³⁸-(Aspa-ADod)-GLP-1(7-38); Arg²⁶Lys³⁴-(Aspa-ADod)-GLP-1(7-39); Arg³⁴Lys²⁶-(Aspa-ADod)-GLP-1(7-39); Arg²⁶,³⁴Lys³⁹-(Aspa-ADod)-GLP-1(7-39);
Gly⁸Arg²⁶Lys³⁴-(Aspa-ADod)-GLP-1(7-36);
Gly⁸Arg³⁴Lys²⁶-(Aspa-ADod)-GLP-1(7-36); Gly⁸Arg²⁶,³⁴Lys³⁶-(Aspa-ADod)-GLP-1(7-36);
Gly⁸Arg²⁶Lys³⁴-(Aspa-ADod)-GLP-1(7-36)amide;
Gly⁸Arg³⁴Lys²⁶-(Aspa-ADod)-GLP-1(7-36)amide;
Gly⁸Arg²⁶,³⁴Lys³⁶-(Aspa-ADod)-GLP-1(7-36)amide;
Gly⁸Arg²⁶Lys³⁴-(Aspa-ADod)-GLP-1(7-37);
Gly⁸Arg³⁴Lys²⁶-(Aspa-ADod)-GLP-1(7-37); Gly⁸Arg²⁶,³⁴Lys³⁶-(Aspa-ADod)-GLP-1(7-37);
Gly⁸Arg²⁶Lys³⁴-(Aspa-ADod)-GLP-1(7-38);
Gly⁸Arg³⁴Lys²⁶-(Aspa-ADod)-GLP-1(7-38); Gly⁸Arg²⁶,³⁴Lys³⁸-(Aspa-ADod)-GLP-1(7-38);
Gly⁸Arg²⁶Lys³⁴-(Aspa-ADod)-GLP-1(7-39);
Gly⁸Arg³⁴Lys²⁶-(Aspa-ADod)-GLP-1(7-39); Gly⁸Arg²⁶,³⁴Lys³⁹-(Aspa-ADod)-GLP-1(7-39);
Val⁸Arg²⁶Lys³⁴-(Aspa-ADod)-GLP-1(7-36);
Val⁸Arg³⁴Lys²⁶-(Aspa-ADod)-GLP-1(7-36); Val⁸Arg²⁶,³⁴Lys³⁶-(Aspa-ADod)-GLP-1(7-36); Val⁸Arg²⁶Lys³⁴-(Aspa-ADod)-GLP-1(7-36)amide; Val⁸Arg³⁴Lys²⁶-(Aspa-ADod)-GLP-1(7-36)amide; Val⁸Arg²⁶,³⁴Lys³⁶-(Aspa-ADod)-GLP-1(7-36)amide; Val⁸Arg²⁶Lys³⁴-(Aspa-ADod)-GLP-1(7-37); Val⁸Arg³⁴Lys²⁶-(Aspa-ADod)-GLP-1(7-37); Val⁸Arg²⁶,³⁴Lys³⁶-(Aspa-ADod)-GLP-1(7-37);
Val⁸Arg²⁶Lys³⁴-(Aspa-ADod)-GLP-1(7-38);
Val⁸Arg³⁴Lys²⁶-(Aspa-ADod)-GLP-1(7-38); Val⁸Arg²⁶,³⁴Lys³⁸-(Aspa-ADod)-GLP-1(7-38); Val⁸Arg²⁶Lys³⁴-(Aspa-ADod)-GLP-1(7-39); Val⁸Arg³⁴Lys²⁶-(Aspa-ADod)-GLP-1(7-39); Val⁸Arg²⁶,³⁴Lys³⁹-(Aspa-ADod)-GLP-1(7-39);
Ser⁸Arg²⁶Lys³⁴-(Aspa-ADod)-GLP-1(7-36);
Ser⁸Arg³⁴Lys²⁶-(Aspa-ADod)-GLP-1(7-36); Ser⁸Arg²⁶,³⁴Lys³⁶-(Aspa-ADod)-GLP-1(7-36); Ser⁸Arg²⁶Lys³⁴-(Aspa-ADod)-GLP-1(7-36)amide; Ser⁸Arg³⁴Lys²⁶-(Aspa-ADod)-GLP-1(7-36)amide; Ser⁸Arg²⁶,³⁴Lys³⁶-(Aspa-ADod)-GLP-1(7-36)amide; Ser⁸Arg²⁶Lys³⁴-(Aspa-ADod)-GLP-1(7-37); Ser⁸Arg³⁴Lys²⁶-(Aspa-ADod)-GLP-1(7-37); Ser⁸Arg²⁶,³⁴Lys³⁶-(Aspa-ADod)-GLP-1(7-37);
Ser⁸Arg²⁶Lys³⁴-(Aspa-ADod)-GLP-1(7-38);
Ser⁸Arg³⁴Lys²⁶-(Aspa-ADod)-GLP-1(7-38); Ser⁸Arg²⁶,³⁴Lys¹⁸-(Aspa-ADod)-GLP-1(7-38); Ser⁸Arg²⁶Lys³⁴-(Aspa-ADod)-GLP-1(7-39); Ser⁸Arg³⁴Lys²⁶-(Aspa-ADod)-GLP-1(7-39); Ser⁸Arg²⁶,³⁴Lys³⁹-(Aspa-ADod)-GLP-1(7-39);
Thr⁸Arg²⁶Lys³⁴-(Aspa-ADod)-GLP-1(7-36);
Thr⁸Arg³⁴Lys²⁶-(Aspa-ADod)-GLP-1(7-36); Thr⁸Arg²⁶,³⁴Lys³⁶-(Aspa-ADod)-GLP-1(7-36);
Thr⁸Arg²⁶Lys³⁴-(Aspa-ADod)-GLP-1(7-36)amide;
Thr⁸Arg³⁴Lys²⁶-(Aspa-ADod)-GLP-1(7-36)amide;
Thr⁸Arg²⁶,³⁴Lys³⁶-(Aspa-ADod)-GLP-1(7-36)amide;
Thr⁸Arg²⁶Lys³⁴-(Aspa-ADod)-GLP-1(7-37);
Thr⁸Arg³⁴Lys²⁶-(Aspa-ADod)-GLP-1(7-37); Thr⁸Arg²⁶,³⁴Lys³⁶-(Aspa-ADod)-GLP-1(7-37);
Thr⁸Arg²⁶Lys³⁴-(Aspa-ADod)-GLP-1(7-38);
Thr⁸Arg³⁴Lys²⁶-(Aspa-ADod)-GLP-1(7-38); Thr⁸Arg²⁶,³⁴Lys³⁸-(Aspa-ADod)-GLP-1(7-38);
Thr⁸Arg²⁶Lys³⁴-(Aspa-ADod)-GLP-1(7-39);
Thr⁸Arg³⁴Lys²⁶-(Aspa-ADod)-GLP-1(7-39); Thr⁸Arg²⁶,³⁴Lys³⁹-(Aspa-ADod)-GLP-1(7-39); Gly⁸Glu³⁵Arg²⁶,³⁴Lys³⁶-(Aspa-ADod)-GLP-1(7-36); Gly⁸Glu³⁵Arg²⁶,³⁴Lys³⁶-(Aspa-ADod)-GLP-1(7-36)amide; Gly⁸Glu³⁶Arg²⁶,³⁴Lys³⁷-(Aspa-ADod)-GLP-1(7-37); Gly⁸Glu³⁷Arg²⁶,³⁴Lys³⁸-(Aspa-ADod)-GLP-1(7-38); Gly⁸Glu³⁸Arg²⁶,³⁴Lys³⁹-(Aspa-ADod)-GLP-1(7-39); Gly⁸Glu³⁵Arg²⁶,³⁴Lys³⁶-(Aspa-ADod)-GLP-1(7-36); Gly⁸Glu³⁵Arg²⁶,³⁴Lys³⁶-(Aspa-ADod)-GLP-1(7-36)amide;
Gly⁸Glu³⁶Arg²⁶,³⁴Lys³⁷-(Aspa-ADod)-GLP-1(7-37);
Gly⁸Glu³⁷Arg²⁶,³⁴Lys³⁸-(Aspa-ADod)-GLP-1(7-38);
Gly⁸Glu³⁸Arg²⁶,³⁴Lys³⁹-(Aspa-ADod)-GLP-1(7-39);
Gly⁸Asp³⁵Arg²⁶,³⁴Lys³⁶-(Aspa-ADod)-GLP-1(7-36);
Gly⁸Asp³⁵Arg²⁶,³⁴Lys³⁶-(Aspa-ADod)-GLP-1(7-36)amide;
Gly⁸Asp³⁶Arg²⁶,³⁴Lys³⁷-(Aspa-ADod)-GLP-1(7-37);
Gly⁸Asp³⁷Arg²⁶,³⁴Lys³⁸-(Aspa-ADod)-GLP-1(7-38);
Gly⁸Asp³⁸Arg²⁶,³⁴Lys³⁹-(Aspa-ADod)-GLP-1(7-39);

Gly$^8$Asp$^{35}$Arg$^{26,34}$Lys$^{36}$-(Aspa-ADod)-GLP-1(7-36);
Gly$^8$Asp$^{35}$Arg$^{26,34}$Lys$^{36}$-(Aspa-ADod)-GLP-1(7-36)amide;
Gly$^8$Asp$^{36}$Arg$^{26,34}$Lys$^{37}$-(Aspa-ADod)-GLP-1(7-37);
Gly$^8$Asp$^{37}$Arg$^{26,34}$Lys$^{38}$-(Aspa-ADod)-GLP-1(7-38);
Gly$^8$Asp$^{38}$Arg$^{26,34}$Lys$^{39}$-(Aspa-ADod)-GLP-1(7-39);
Val$^8$Glu$^{35}$Arg$^{26,34}$Lys$^{36}$-(Aspa-ADod)-GLP-1(7-36);
Val$^8$Glu$^{35}$Arg$^{26,34}$Lys$^{36}$-(Aspa-ADod)-GLP-1(7-36)amide;
Val$^8$Glu$^{36}$Arg$^{26,34}$Lys$^{37}$-(Aspa-ADod)-GLP-1(7-37);
Val$^8$Glu$^{37}$Arg$^{26,34}$Lys$^{38}$-(Aspa-ADod)-GLP-1(7-38);
Val$^8$Glu$^{38}$Arg$^{26,34}$Lys$^{39}$-(Aspa-ADod)-GLP-1(7-39);
Val$^8$Glu$^{35}$Arg$^{26,34}$Lys$^{36}$-(Aspa-ADod)-GLP-1(7-36);
Val$^8$Glu$^{35}$Arg$^{26,34}$Lys$^{36}$-(Aspa-ADod)-GLP-1(7-36)amide;
Val$^8$Glu$^{36}$Arg$^{26,34}$Lys$^{37}$-(Aspa-ADod)-GLP-1(7-37);
Val$^8$Glu$^{37}$Arg$^{26,34}$Lys$^{38}$-(Aspa-ADod)-GLP-1(7-38);
Val$^8$Glu$^{38}$Arg$^{26,34}$Lys$^{39}$-(Aspa-ADod)-GLP-1(7-39);
Val$^8$Asp$^{35}$Arg$^{26,34}$Lys$^{36}$-(Aspa-ADod)-GLP-1(7-36);
Val$^8$Asp$^{35}$Arg$^{26,34}$Lys$^{36}$-(Aspa-ADod)-GLP-1(7-36)amide;
Val$^8$Asp$^{36}$Arg$^{26,34}$Lys$^{37}$-(Aspa-ADod)-GLP-1(7-37);
Val$^8$Asp$^{37}$Arg$^{26,34}$Lys$^{38}$-(Aspa-ADod)-GLP-1(7-38);
Val$^8$Asp$^{38}$Arg$^{26,34}$Lys$^{39}$-(Aspa-ADod)-GLP-1(7-39);
Val$^8$Asp$^{35}$Arg$^{26,34}$Lys$^{36}$-(Aspa-ADod)-GLP-1(7-36);
Val$^8$Asp$^{35}$Arg$^{26,34}$Lys$^{36}$-(Aspa-ADod)-GLP-1(7-36)amide;
Val$^8$Asp$^{36}$Arg$^{26,34}$Lys$^{37}$-(Aspa-ADod)-GLP-1(7-37);
Val$^8$Asp$^{37}$Arg$^{26,34}$Lys$^{38}$-(Aspa-ADod)-GLP-1(7-38);
Val$^8$Asp$^{38}$Arg$^{26,34}$Lys$^{39}$-(Aspa-ADod)-GLP-1(7-39);
Ser$^8$Glu$^{35}$Arg$^{26,34}$Lys$^{36}$-(Aspa-ADod)-GLP-1(7-36);
Ser$^8$Glu$^{35}$Arg$^{26,34}$Lys$^{36}$-(Aspa-ADod)-GLP-1(7-36)amide;
Ser$^8$Glu$^{36}$Arg$^{26,34}$Lys$^{37}$-(Aspa-ADod)-GLP-1(7-37);
Ser$^8$Glu$^{37}$Arg$^{26,34}$Lys$^{38}$-(Aspa-ADod)-GLP-1(7-38);
Ser$^8$Glu$^{38}$Arg$^{26,34}$Lys$^{39}$-(Aspa-ADod)GLP-1(7-39);
Ser$^8$Glu$^{35}$Arg$^{26,34}$Lys$^{36}$-(Aspa-ADod)-GLP-1(7-36);
Ser$^8$Glu$^{35}$Arg$^{26,34}$Lys$^{36}$-(Aspa-ADod)-GLP-1(7-36)amide;
Ser$^8$Glu$^{36}$Arg$^{26,34}$Lys$^{37}$-(Aspa-ADod)-GLP-1(7-37);
Ser$^8$Glu$^{37}$Arg$^{26,34}$Lys$^{38}$-(Aspa-ADod)-GLP-1(7-38);
Ser$^8$Glu$^{38}$Arg$^{26,34}$Lys$^{39}$-(Aspa-ADod)-GLP-1(7-39);
Ser$^8$Asp$^{35}$Arg$^{26,34}$Lys$^{36}$-(Aspa-ADod)-GLP-1(7-36);
Ser$^8$Asp$^{35}$Arg$^{26,34}$Lys$^{36}$-(Aspa-ADod)-GLP-1(7-36)amide;
Ser$^8$Asp$^{36}$Arg$^{26,34}$Lys$^{37}$-(Aspa-ADod)-GLP-1(7-37);
Ser$^8$Asp$^{37}$Arg$^{26,34}$Lys$^{38}$-(Aspa-ADod)-GLP-1(7-38);
Ser$^8$Asp$^{38}$Arg$^{26,34}$Lys$^{39}$-(Aspa-ADod)-GLP-1(7-39);
Ser$^8$Asp$^{35}$Arg$^{26,34}$Lys$^{36}$-(Aspa-ADod)-GLP-1(7-36);
Ser$^8$Asp$^{35}$Arg$^{26,34}$Lys$^{36}$-(Aspa-ADod)-GLP-1(7-36)amide;
Ser$^8$Asp$^{36}$Arg$^{26,34}$Lys$^{37}$-(Aspa-ADod)-GLP-1(7-37);
Ser$^8$Asp$^{37}$Arg$^{26,34}$Lys$^{38}$-(Aspa-ADod)-GLP-1(7-38);
Ser$^8$Asp$^{38}$Arg$^{26,34}$Lys$^{39}$-(Aspa-ADod)-GLP-1(7-39);
Thr$^8$Glu$^{35}$Arg$^{26,34}$Lys$^{36}$-(Aspa-ADod)-GLP-1(7-36);
Thr$^8$Glu$^{35}$Arg$^{26,34}$Lys$^{36}$-(Aspa-ADod)-GLP-1(7-36)amide;
Thr$^8$Glu$^{36}$Arg$^{26,34}$Lys$^{37}$-(Aspa-ADod)-GLP-1(7-37);
Thr$^8$Glu$^{37}$Arg$^{26,34}$Lys$^{38}$-(Aspa-ADod)-GLP-1(7-38);
Thr$^8$Glu$^{38}$Arg$^{26,34}$Lys$^{39}$-(Aspa-ADod)-GLP-1(7-39);
Thr$^8$Glu$^{35}$Arg$^{26,34}$Lys$^{36}$-(Aspa-ADod)-GLP-1(7-36);
Thr$^8$Glu$^{35}$Arg$^{26,34}$Lys$^{36}$-(Aspa-ADod)-GLP-1(7-36)amide;
Thr$^8$Glu$^{36}$Arg$^{26,34}$Lys$^{37}$-(Aspa-ADod)-GLP-1(7-37);
Thr$^8$Glu$^{37}$Arg$^{26,34}$Lys$^{38}$-(Aspa-ADod)-GLP-1(7-38);
Thr$^8$Glu$^{38}$Arg$^{26,34}$Lys$^{39}$-(Aspa-ADod)-GLP-1(7-39);
Thr$^8$Asp$^{35}$Arg$^{26,34}$Lys$^{36}$-(Aspa-ADod)-GLP-1(7-36);
Thr$^8$Asp$^{35}$Arg$^{26,34}$Lys$^{36}$-(Aspa-ADod)-GLP-1(7-36)amide;
Thr$^8$Asp$^{36}$Arg$^{26,34}$Lys$^{37}$-(Aspa-ADod)-GLP-1(7-37);
Thr$^8$Asp$^{37}$Arg$^{26,34}$Lys$^{38}$-(Aspa-ADod)-GLP-1(7-38);
Thr$^8$Asp$^{38}$Arg$^{26,34}$Lys$^{39}$-(Aspa-ADod)-GLP-1(7-39);
Thr$^8$Asp$^{35}$Arg$^{26,34}$Lys$^{36}$-(Aspa-ADod)-GLP-1(7-36);
Thr$^8$Asp$^{35}$Arg$^{26,34}$Lys$^{36}$-(Aspa-ADod)-GLP-1(7-36)amide;
Thr$^8$Asp$^{36}$Arg$^{26,34}$Lys$^{37}$-(Aspa-ADod)-GLP-1(7-37);
Thr$^8$Asp$^{37}$Arg$^{26,34}$Lys$^{38}$-(Aspa-ADod)-GLP-1(7-38);
Thr$^8$Asp$^{38}$Arg$^{26,34}$Lys$^{39}$-(Aspa-ADod)-GLP-1(7-39);
Arg$^{26,34}$Lys$^{18}$-(Aspa-ADod)-GLP-1(7-36); Arg$^{26,34}$Lys$^{18}$-(Aspa-ADod)-GLP-1(7-36)amide; Arg$^{26,34}$Lys$^{18}$-(Aspa-ADod)-GLP-1(7-37); Arg$^{26,34}$Lys$^{18}$-(Aspa-ADod)-GLP-1(7-38); Gly$^8$Asp$^{19}$Arg$^{26,34}$Lys$^{18}$-(Aspa-ADod)-GLP-1(7-36); Gly$^8$Asp$^{17}$Arg$^{26,34}$Lys$^{18}$-(Aspa-ADod)-GLP-1(7-36); Gly$^8$Asp$^{19}$Arg$^{26,34}$Lys$^{18}$-(Aspa-ADod)-GLP-1(7-36)amide; Gly$^8$Asp$^{17}$Arg$^{26,34}$Lys$^{18}$-(Aspa-ADod)-GLP-1(7-36)amide; Gly$^8$Asp$^{19}$Arg$^{26,34}$Lys$^{18}$-(Aspa-ADod)-GLP-1(7-37); Gly$^8$Asp$^{19}$Arg$^{26,34}$Lys$^{18}$-(Aspa-ADod)-GLP-1(7-38); Gly$^8$Asp$^{17}$Arg$^{26,34}$Lys$^{18}$-(Aspa-ADod)-GLP-1(7-38); Arg$^{26,34}$Lys$^{23}$-(Aspa-ADod)-GLP-1(7-36); Arg$^{26,34}$Lys$^{23}$-(Aspa-ADod)-GLP-1(7-36)amide; Arg$^{26,34}$Lys$^{23}$-(Aspa-ADod)-GLP-1(7-37); Arg$^{26,34}$Lys$^{23}$-(Aspa-ADod)-GLP-1(7-38); Gly$^8$Asp$^{19}$Arg$^{26,34}$Lys$^{23}$-(Aspa-ADod)-GLP-1(7-36); Gly$^8$Asp$^{17}$Arg$^{26,34}$Lys$^{23}$-(Aspa-ADod)-GLP-1(7-36); Gly$^8$Asp$^{19}$Arg$^{26,34}$Lys$^{23}$-(Aspa-ADod)-GLP-1(7-36)amide; Gly$^8$Asp$^{17}$Arg$^{26,34}$Lys$^{23}$-(Aspa-ADod)-GLP-1(7-36)amide; Gly$^8$Asp$^{19}$Arg$^{26,34}$Lys$^{23}$-(Aspa-ADod)-GLP-1(7-37); Gly$^8$Asp$^{19}$Arg$^{26,34}$Lys$^{23}$-(Aspa-ADod)-GLP-1(7-38); Gly$^8$Asp$^{17}$Arg$^{26,34}$Lys$^{23}$-(Aspa-ADod)-GLP-1(7-38); Arg$^{26,34}$Lys$^{27}$-(Aspa-ADod)-GLP-1(7-36); Arg$^{26,34}$Lys$^{27}$-(Aspa-ADod)-GLP-1(7-36)amide; Arg$^{26,34}$Lys$^{27}$-(Aspa-ADod)-GLP-1(7-37); Arg$^{26,34}$Lys$^{27}$-(Aspa-ADod)-GLP-1(7-38); Gly$^8$Asp$^{19}$Arg$^{26,34}$Lys$^{27}$-(Aspa-ADod)-GLP-1(7-36); Gly$^8$Asp$^{17}$Arg$^{26,34}$Lys$^{27}$-(Aspa-ADod)-GLP-1(7-36); Gly$^8$Asp$^{19}$Arg$^{26,34}$Lys$^{27}$-(Aspa-ADod)-GLP-1(7-36)amide; Gly$^8$Asp$^{17}$Arg$^{26,34}$Lys$^{27}$-(Aspa-ADod)-GLP-1(7-36)amide; Gly$^8$Asp$^{19}$Arg$^{26,34}$Lys$^{27}$-(Aspa-ADod)-GLP-1(7-37); Gly$^8$Asp$^{19}$Arg$^{26,34}$Lys$^{27}$-(Aspa-ADod)-GLP-1(7-38); Gly$^8$Asp$^{17}$Arg$^{26,34}$Lys$^{27}$-(Aspa-ADod)-GLP-1(7-38); Arg$^{26,34}$Lys$^{18}$-(Aspa-ADod)-GLP-1(7-36); Arg$^{26,34}$Lys$^{18}$-(Aspa-ADod)-GLP-1(7-36)amide; Arg$^{26,34}$Lys$^{18}$-(Aspa-ADod)-GLP-1(7-37); Arg$^{26,34}$Lys$^{18}$-(Aspa-ADod)-GLP-1(7-38); Val$^8$Asp$^{19}$Arg$^{26,34}$Lys$^{18}$-(Aspa-ADod)-GLP-1(7-36); Val$^8$Asp$^{17}$Arg$^{26,34}$Lys$^{18}$-(Aspa-ADod)-GLP-1(7-36); Val$^8$Asp$^{19}$Arg$^{26,34}$Lys$^{18}$-(Aspa-ADod)-GLP-1(7-36)amide; Val$^8$Asp$^{17}$Arg$^{26,34}$Lys$^{18}$-(Aspa-ADod)-GLP-1(7-36)amide; Val$^8$Asp$^{19}$Arg$^{26,34}$Lys$^{18}$-(Aspa-ADod)-GLP-1(7-37); Val$^8$Asp$^{19}$Arg$^{26,34}$Lys$^{18}$-(Aspa-ADod)-GLP-1(7-38); Val$^8$Asp$^{17}$Arg$^{26,34}$Lys$^{18}$-(Aspa-ADod)-GLP-1(7-38); Arg$^{26,34}$Lys$^{23}$-(Aspa-ADod)-GLP-1(7-36); Arg$^{26,34}$Lys$^{23}$-(Aspa-ADod)-GLP-1(7-36)amide; Arg$^{26,34}$Lys$^{23}$-(Aspa-ADod)-GLP-1(7-37); Arg$^{26,34}$Lys$^{23}$-(Aspa-ADod)-GLP-1(7-38); Val$^8$Asp$^{19}$Arg$^{26,34}$Lys$^{23}$-(Aspa-ADod)-GLP-1(7-36); Val$^8$Asp$^{17}$Arg$^{26,34}$Lys$^{23}$-(Aspa-ADod)-GLP-1(7-36); Val$^8$Asp$^{19}$Arg$^{26,34}$Lys$^{23}$-(Aspa-ADod)-GLP-1(7-36)amide; Val$^8$Asp$^{17}$Arg$^{26,34}$Lys$^{23}$-(Aspa-ADod)-GLP-1(7-36)amide; Val$^8$Asp$^{19}$Arg$^{26,34}$Lys$^{23}$-(Aspa-ADod)-GLP-1(7-37); Val$^8$Asp$^{19}$Arg$^{26,34}$Lys$^{23}$-(Aspa-ADod)-GLP-1(7-38); Val$^8$Asp$^{17}$Arg$^{26,34}$Lys$^{23}$-(Aspa-ADod)-GLP-1(7-38); Arg$^{26,34}$Lys$^{27}$-(Aspa-ADod)-GLP-1(7-36); Arg$^{26,34}$Lys$^{27}$-(Aspa-ADod)-GLP-1(7-36)amide; Arg$^{26,34}$Lys$^{27}$-(Aspa-ADod)-GLP-1(7-37); Arg$^{26,34}$Lys$^{27}$-(Aspa-ADod)-GLP-1(7-38); Val$^8$Asp$^{19}$Arg$^{26,34}$Lys$^{27}$-(Aspa-ADod)-GLP-1(7-36); Val$^8$Asp$^{17}$Arg$^{26,34}$Lys$^{27}$-(Aspa-ADod)-GLP-1(7-36); Val$^8$Asp$^{19}$Arg$^{26,34}$Lys$^{27}$-(Aspa-ADod)-GLP-1(7-36)amide; Val$^8$Asp$^{17}$Arg$^{26,34}$Lys$^{27}$-(Aspa-ADod)-GLP-1(7-36)amide; Val$^8$Asp$^{19}$Arg$^{26,34}$Lys$^{27}$-(Aspa-ADod)-GLP-1(7-37); Val$^8$Asp$^{19}$Arg$^{26,34}$Lys$^{27}$-(Aspa-ADod)-GLP-1(7-38); Val$^8$Asp$^{17}$Arg$^{26,34}$Lys$^{27}$-(Aspa-ADod)-GLP-1(7-38); Arg$^{26,34}$Lys$^{18}$-(Aspa-ADod)-GLP-1(7-36); Arg$^{26,34}$Lys$^{18}$-(Aspa-ADod)-GLP-1(7-36)amide; Arg$^{26,34}$Lys$^{18}$-(Aspa-ADod)-GLP-1(7-37); Arg$^{26,34}$Lys$^{18}$-(Aspa-ADod)-GLP-1(7-38); Ser$^8$Asp$^{19}$Arg$^{26,34}$Lys$^{18}$-(Aspa-ADod)-GLP-1(7-36); Ser$^8$Asp$^{17}$Arg$^{26,34}$Lys$^{18}$-(Aspa-ADod)-GLP-1(7-36); Ser$^8$Asp$^{19}$Arg$^{26,34}$Lys$^{18}$-(Aspa-ADod)-GLP-1(7-36)amide; Ser$^8$Asp$^{19}$Arg$^{26,34}$Lys$^{18}$-(Aspa-ADod)-GLP-1(7-37);

Ser⁸Asp¹⁹Arg²⁶,³⁴Lys¹⁸-(Aspa-ADod)-GLP-1(7-38);
Ser⁸Asp¹⁷Arg²⁶,³⁴Lys¹⁸-(Aspa-ADod)-GLP-1(7-38);
Arg²⁶,³⁴Lys²³-(Aspa-ADod)-GLP-1(7-36); Arg²⁶,³⁴Lys²³-(Aspa-ADod)-GLP-1(7-36)amide; Arg²⁶,³⁴Lys²³-(Aspa-ADod)-GLP-1(7-37); Arg²⁶,³⁴Lys²³-(Aspa-ADod)-GLP-1(7-38); Ser⁸Asp¹⁹Arg²⁶,³⁴Lys²³-(Aspa-ADod)-GLP-1(7-36); Ser⁸Asp¹⁷Arg²⁶,³⁴Lys²³-(Aspa-ADod)-GLP-1(7-36); Ser⁸Asp¹⁹Arg²⁶,³⁴Lys²³-(Aspa-ADod)-GLP-1(7-36)amide; Ser⁸Asp¹⁷Arg²⁶,³⁴Lys²³-(Aspa-ADod)-GLP-1(7-36)amide; Ser⁸Asp¹⁹Arg²⁶,³⁴Lys²³-(Aspa-ADod)-GLP-1(7-37); Ser⁸Asp¹⁹Arg²⁶,³⁴Lys²³-(Aspa-ADod)-GLP-1(7-38); Ser⁸Asp¹⁷Arg²⁶,³⁴Lys²³-(Aspa-ADod)-GLP-1(7-38); Arg²⁶,³⁴Lys²⁷-(Aspa-ADod)-GLP-1(7-36); Arg²⁶,³⁴Lys²⁷-(Aspa-ADod)-GLP-1(7-36)amide; Arg²⁶,³⁴Lys²⁷-(Aspa-ADod)-GLP-1(7-37); Arg²⁶,³⁴Lys²⁷-(Aspa-ADod)-GLP-1(7-38); Ser⁸Asp¹⁹Arg²⁶,³⁴Lys²⁷-(Aspa-ADod)-GLP-1(7-36); Ser⁸Asp¹⁷Arg²⁶,³⁴Lys²⁷-(Aspa-ADod)-GLP-1(7-36); Ser⁸Asp¹⁹Arg²⁶,³⁴Lys²⁷-(Aspa-ADod)-GLP-1(7-36)amide; Ser⁸Asp¹⁷Arg²⁶,³⁴Lys²⁷-(Aspa-ADod)-GLP-1(7-36)amide; Ser⁸Asp¹⁹Arg²⁶,³⁴Lys²⁷-(Aspa-ADod)-GLP-1(7-37); Ser⁸Asp¹⁹Arg²⁶,³⁴Lys²⁷-(Aspa-ADod)-GLP-1(7-38); Ser⁸Asp¹⁷Arg²⁶,³⁴Lys²⁷-(Aspa-ADod)-GLP-1(7-38); Arg²⁶,³⁴Lys¹⁸-(Aspa-ADod)-GLP-1(7-36); Arg²⁶,³⁴Lys¹⁸-(Aspa-ADod)-GLP-1(7-36)amide; Arg²⁶,³⁴Lys¹⁸-(Aspa-ADod)-GLP-1(7-37); Arg²⁶,³⁴Lys¹⁸-(Aspa-ADod)-GLP-1(7-38); Thr⁸Asp¹⁹Arg²⁶,³⁴Lys¹⁸-(Aspa-ADod)-GLP-1(7-36); Thr⁸Asp¹⁷Arg²⁶,³⁴Lys¹⁸-(Aspa-ADod)-GLP-1(7-36); Thr⁸Asp¹⁹Arg²⁶,³⁴Lys¹⁸-(Aspa-ADod)-GLP-1(7-36)amide; Thr⁸Asp¹⁷Arg²⁶,³⁴Lys¹⁸-(Aspa-ADod)-GLP-1(7-36)amide; Thr⁸Asp¹⁹Arg²⁶,³⁴Lys¹⁸-(Aspa-ADod)-GLP-1(7-37); Thr⁸Asp¹⁹Arg²⁶,³⁴Lys¹⁸-(Aspa-ADod)-GLP-1(7-38); Thr⁸Asp¹⁷Arg²⁶,³⁴Lys¹⁸-(Aspa-ADod)-GLP-1(7-38); Arg²⁶,³⁴Lys²³-(Aspa-ADod)-GLP-1(7-36); Arg²⁶,³⁴Lys²³-(Aspa-ADod)-GLP-1(7-36)amide; Arg²⁶,³⁴Lys²³-(Aspa-ADod)-GLP-1(7-37); Arg²⁶,³⁴Lys²³-(Aspa-ADod)-GLP-1(7-38); Thr⁸Asp¹⁹Arg²⁶,³⁴Lys²³-(Aspa-ADod)-GLP-1(7-36); Thr⁸Asp¹⁷Arg²⁶,³⁴Lys²³-(Aspa-ADod)-GLP-1(7-36); Thr⁸Asp¹⁹Arg²⁶,³⁴Lys²³-(Aspa-ADod)-GLP-1(7-36)amide; Thr⁸Asp¹⁷Arg²⁶,³⁴Lys²³-(Aspa-ADod)-GLP-1(7-36)amide; Thr⁸Asp¹⁹Arg²⁶,³⁴Lys²³-(Aspa-ADod)-GLP-1(7-37); Thr⁸Asp¹⁹Arg²⁶,³⁴Lys²³-(Aspa-ADod)-GLP-1(7-38); Thr⁸Asp¹⁷Arg²⁶,³⁴Lys²³-(Aspa-ADod)-GLP-1(7-38); Arg²⁶,³⁴Lys²⁷-(Aspa-ADod)-GLP-1(7-36); Arg²⁶,³⁴Lys²⁷-(Aspa-ADod)-GLP-1(7-36)amide; Arg²⁶,³⁴Lys²⁷-(Aspa-ADod)-GLP-1(7-37); Arg²⁶,³⁴Lys²⁷-(Aspa-ADod)-GLP-1(7-38); Thr⁸Asp¹⁹Arg²⁶,³⁴Lys²⁷-(Aspa-ADod)-GLP-1(7-36); Thr⁸Asp¹⁷Arg²⁶,³⁴Lys²⁷-(Aspa-ADod)-GLP-1(7-36); Thr⁸Asp¹⁹Arg²⁶,³⁴Lys²⁷-(Aspa-ADod)-GLP-1(7-36)amide; Thr⁸Asp¹⁷Arg²⁶,³⁴Lys²⁷-(Aspa-ADod)-GLP-1(7-36)amide; Thr⁸Asp¹⁹Arg²⁶,³⁴Lys²⁷-(Aspa-ADod)-GLP-1(7-37); Thr⁸Asp¹⁹Arg²⁶,³⁴Lys²⁷-(Aspa-ADod)-GLP-1(7-38); Thr⁸Asp¹⁷Arg²⁶,³⁴Lys²⁷-(Aspa-ADod)-GLP-1(7-38); Arg²⁶Lys³⁴-(Aspa-ATet)-GLP-1(7-36); Arg³⁴Lys²⁶-(Aspa-ATet)-GLP-1(7-36); Arg²⁶,³⁴Lys³⁶-(Aspa-ATet)-GLP-1(7-36); Arg²⁶Lys³⁴-(Aspa-ATet)-GLP-1(7-36)amide; Arg³⁴Lys²⁶-(Aspa-ATet)-GLP-1(7-36)amide; Arg²⁶,³⁴Lys³⁶-(Aspa-ATet)-GLP-1(7-36)amide; Arg²⁶Lys³⁴-(Aspa-ATet)-GLP-1(7-37); Arg³⁴Lys²⁶-(Aspa-ATet)-GLP-1(7-37); Arg²⁶,³⁴Lys³⁶-(Aspa-ATet)-GLP-1(7-37); Arg²⁶Lys³⁴-(Aspa-ATet)-GLP-1(7-38); Arg³⁴Lys²⁶-(Aspa-ATet)-GLP-1(7-38); Arg²⁶,³⁴Lys³⁸-(Aspa-ATet)-GLP-1(7-38); Arg²⁶Lys³⁴-(Aspa-ATet)-GLP-1(7-39); Arg³⁴Lys²⁶-(Aspa-ATet)-GLP-1(7-39); Arg²⁶,³⁴Lys³⁹-(Aspa-ATet)-GLP-1(7-39); Gly⁸Arg²⁶Lys³⁴-(Aspa-ATet)-GLP-1(7-36); Gly⁸Arg³⁴Lys²⁶-(Aspa-ATet)-GLP-1(7-36); Gly⁸Arg²⁶,³⁴Lys³⁶-(Aspa-ATet)-GLP-1(7-36); Gly⁸Arg²⁶Lys³⁴-(Aspa-ATet)-GLP-1(7-36)amide; Gly⁸Arg³⁴Lys²⁶-(Aspa-ATet)-GLP-1(7-36)amide; Gly⁸Arg²⁶,³⁴Lys³⁶-(Aspa-ATet)-GLP-1(7-36)amide; Gly⁸Arg²⁶Lys³⁴-(Aspa-ATet)-GLP-1(7-37); Gly⁸Arg³⁴Lys²⁶-(Aspa-ATet)-GLP-1(7-37); Gly⁸Arg²⁶,³⁴Lys³⁶-(Aspa-ATet)-GLP-1(7-37); Gly⁸Arg²⁶Lys³⁴-(Aspa-ATet)-GLP-1(7-38); Gly⁸Arg³⁴Lys²⁶-(Aspa-ATet)-GLP-1(7-38); Gly⁸Arg²⁶,³⁴Lys³⁸-(Aspa-ATet)-GLP-1(7-38); Gly⁸Arg²⁶Lys³⁴-(Aspa-ATet)-GLP-1(7-39); Gly⁸Arg³⁴Lys²⁶-(Aspa-ATet)-GLP-1(7-39); Gly⁸Arg²⁶,³⁴Lys³⁹-(Aspa-ATet)-GLP-1(7-39);
Val⁸Arg²⁶Lys³⁴-(Aspa-ATet)-GLP-1(7-36); Val⁸Arg³⁴Lys²⁶-(Aspa-ATet)-GLP-1(7-36); Val⁸Arg²⁶,³⁴Lys³⁶-(Aspa-ATet)-GLP-1(7-36); Val⁸Arg²⁶Lys³⁴-(Aspa-ATet)-GLP-1(7-36)amide; Val⁸Arg³⁴Lys²⁶-(Aspa-ATet)-GLP-1(7-36)amide; Val⁸Arg²⁶,³⁴Lys³⁶-(Aspa-ATet)-GLP-1(7-36)amide; Val⁸Arg²⁶Lys³⁴-(Aspa-ATet)-GLP-1(7-37); Val⁸Arg³⁴Lys²⁶-(Aspa-ATet)-GLP-1(7-37); Val⁸Arg²⁶,³⁴Lys³⁶-(Aspa-ATet)-GLP-1(7-37); Val⁸Arg²⁶Lys³⁴-(Aspa-ATet)-GLP-1(7-38); Val⁸Arg³⁴Lys²⁶-(Aspa-ATet)-GLP-1(7-38); Val⁸Arg²⁶,³⁴Lys³⁸-(Aspa-ATet)-GLP-1(7-38); Val⁸Arg²⁶Lys³⁴-(Aspa-ATet)-GLP-1(7-39); Val⁸Arg³⁴Lys²⁶-(Aspa-ATet)-GLP-1(7-39); Val⁸Arg²⁶,³⁴Lys³⁹-(Aspa-ATet)-GLP-1(7-39);
Ser⁸Arg²⁶Lys³⁴-(Aspa-ATet)-GLP-1(7-36); Ser⁸Arg³⁴Lys²⁶-(Aspa-ATet)-GLP-1(7-36); Ser⁸Arg²⁶,³⁴Lys³⁶-(Aspa-ATet)-GLP-1(7-36); Ser⁸Arg²⁶Lys³⁴-(Aspa-ATet)-GLP-1(7-36)amide; Ser⁸Arg³⁴Lys²⁶-(Aspa-ATet)-GLP-1(7-36)amide; Ser⁸Arg²⁶,³⁴Lys³⁶-(Aspa-ATet)-GLP-1(7-36)amide; Ser⁸Arg²⁶Lys³⁴-(Aspa-ATet)-GLP-1(7-37); Ser⁸Arg³⁴Lys²⁶-(Aspa-ATet)-GLP-1(7-37); Ser⁸Arg²⁶,³⁴Lys³⁶-(Aspa-ATet)-GLP-1(7-37); Ser⁸Arg²⁶Lys³⁴-(Aspa-ATet)-GLP-1(7-38); Ser⁸Arg³⁴Lys²⁶-(Aspa-ATet)-GLP-1(7-38); Ser⁸Arg²⁶,³⁴Lys³⁸-(Aspa-ATet)-GLP-1(7-38); Ser⁸Arg²⁶Lys³⁴-(Aspa-ATet)-GLP-1(7-39); Ser⁸Arg³⁴Lys²⁶-(Aspa-ATet)-GLP-1(7-39); Ser⁸Arg²⁶,³⁴Lys³⁹-(Aspa-ATet)-GLP-1(7-39);
Thr⁸Arg²⁶Lys³⁴-(Aspa-ATet)-GLP-1(7-36); Thr⁸Arg³⁴Lys²⁶-(Aspa-ATet)-GLP-1(7-36); Thr⁸Arg²⁶,³⁴Lys³⁶-(Aspa-ATet)-GLP-1(7-36); Thr⁸Arg²⁶Lys³⁴-(Aspa-ATet)-GLP-1(7-36)amide; Thr⁸Arg³⁴Lys²⁶-(Aspa-ATet)-GLP-1(7-36)amide; Thr⁸Arg²⁶,³⁴Lys³⁶-(Aspa-ATet)-GLP-1(7-36)amide; Thr⁸Arg²⁶Lys³⁴-(Aspa-ATet)-GLP-1(7-37); Thr⁸Arg³⁴Lys²⁶-(Aspa-ATet)-GLP-1(7-37); Thr⁸Arg²⁶,³⁴Lys³⁶-(Aspa-ATet)-GLP-1(7-37); Thr⁸Arg²⁶Lys³⁴-(Aspa-ATet)-GLP-1(7-38); Thr⁸Arg³⁴Lys²⁶-(Aspa-ATet)-GLP-1(7-38); Thr⁸Arg²⁶,³⁴Lys³⁸-(Aspa-ATet)-GLP-1(7-38); Thr⁸Arg²⁶Lys³⁴-(Aspa-ATet)-GLP-1(7-39); Thr⁸Arg³⁴Lys²⁶-(Aspa-ATet)-GLP-1(7-39); Thr⁸Arg²⁶,³⁴Lys³⁹-(Aspa-ATet)-GLP-1(7-39);
Gly⁸Glu³⁵Arg²⁶,³⁴Lys³⁶-(Aspa-ATet)-GLP-1(7-36); Gly⁸Glu³⁵Arg²⁶,³⁴Lys³⁶-(Aspa-ATet)-GLP-1(7-36)amide; Gly⁸Glu³⁶Arg²⁶,³⁴Lys³⁷-(Aspa-ATet)-GLP-1(7-37); Gly⁸Glu³⁷Arg²⁶,³⁴Lys³⁸-(Aspa-ATet)-GLP-1(7-38); Gly⁸Glu³⁸Arg²⁶,³⁴Lys³⁹-(Aspa-ATet)-GLP-1(7-39); Gly⁸Glu³⁵Arg²⁶,³⁴Lys³⁶-(Aspa-ATet)-GLP-1(7-36); Gly⁸Glu³⁵Arg²⁶,³⁴Lys³⁶-(Aspa-ATet)-GLP-1(7-36)amide; Gly⁸Glu³⁶Arg²⁶,³⁴Lys³⁷-(Aspa-ATet)-GLP-1(7-37); Gly⁸Glu³⁷Arg²⁶,³⁴Lys³⁸-(Aspa-ATet)-GLP-1(7-38); Gly⁸Glu³⁸Arg²⁶,³⁴Lys³⁹-(Aspa-ATet)-GLP-1(7-39); Gly⁸Asp³⁵Arg²⁶,³⁴Lys³⁶-(Aspa-ATet)-GLP-1(7-36); Gly⁸Asp³⁵Arg²⁶,³⁴Lys³⁶-(Aspa-ATet)-GLP-1(7-36)amide; Gly⁸Asp³⁶Arg²⁶,³⁴Lys³⁷-(Aspa-ATet)-GLP-1(7-37); Gly⁸Asp³⁷Arg²⁶,³⁴Lys¹⁸-(Aspa-ATet)-GLP-1(7-38); Gly⁸Asp³⁸Arg²⁶,³⁴Lys³⁹-(Aspa-ATet)-GLP-1(7-39); Gly⁸Asp³⁵Arg²⁶,³⁴Lys³⁶(Aspa-ATet)-GLP-1(7-36); Gly⁸Asp³⁵Arg²⁶,³⁴Lys³⁶-(Aspa-ATet)-GLP-1(7-36)amide; Gly⁸Asp³⁶Arg²⁶,³⁴Lys³⁷-(Aspa-ATet)-GLP-1(7-37);

Gly⁸Asp³⁷Arg²⁶,³⁴Lys³⁸-(Aspa-ATet)-GLP-1(7-38);
Gly⁸Asp³⁸Arg²⁶,³⁴Lys³⁹-(Aspa-ATet)-GLP-1(7-39);
Val⁸Glu³⁵Arg²⁶,³⁴Lys³⁶-(Aspa-ATet)-GLP-1(7-3);
Val⁸Glu³⁵Arg²⁶,³⁴Lys³⁶-(Aspa-ATet)-GLP-1(7-36)amide;
Val⁸Glu³⁶Arg²⁶,³⁴Lys³⁷-(Aspa-ATet)-GLP-1(7-37);
Val⁸Glu³⁷Arg²⁶,³⁴Lys³⁸-(Aspa-ATet)-GLP-1(7-38);
Val⁸Glu³⁸Arg²⁶,³⁴Lys³⁹-(Aspa-ATet)-GLP-1(7-39);
Val⁸Glu³⁵Arg²⁶,³⁴Lys³⁶-(Aspa-ATet)-GLP-1(7-36);
Val⁸Glu³⁵Arg²⁶,³⁴Lys³⁶-(Aspa-ATet)-GLP-1(7-36)amide;
Val⁸Glu³⁶Arg²⁶,³⁴Lys³⁷-(Aspa-ATet)-GLP-1(7-37);
Val⁸Glu³⁷Arg²⁶,³⁴Lys³⁸-(Aspa-ATet)-GLP-1(7-38);
Val⁸Glu³⁸Arg²⁶,³⁴Lys³⁹-(Aspa-ATet)-GLP-1(7-39);
Val⁸Asp³⁵Arg²⁶,³⁴Lys³⁶-(Aspa-ATet)-GLP-1(7-36);
Val⁸Asp³⁵Arg²⁶,³⁴Lys³⁶-(Aspa-ATet)-GLP-1(7-36)amide;
Val⁸Asp³⁶Arg²⁶,³⁴Lys³⁷-(Aspa-ATet)-GLP-1(7-37);
Val⁸Asp³⁷Arg²⁶,³⁴Lys³⁸-(Aspa-ATet)-GLP-1(7-38);
Val⁸Asp³⁸Arg²⁶,³⁴Lys³⁹-(Aspa-ATet)-GLP-1(7-39);
Val⁸Asp³⁵Arg²⁶,³⁴Lys³⁶-(Aspa-ATet)-GLP-1(7-36);
Val⁸Asp³⁵Arg²⁶,³⁴Lys³⁶-(Aspa-ATet)-GLP-1(7-36)amide;
Val⁸Asp³⁶Arg²⁶,³⁴Lys³⁷-(Aspa-ATet)-GLP-1(7-37);
Val⁸Asp³⁷Arg²⁶,³⁴Lys³⁸-(Aspa-ATet)-GLP-1(7-38);
Val⁸Asp³⁸Arg²⁶,³⁴Lys³⁹-(Aspa-ATet)-GLP-1(7-39);
Ser⁸Glu³⁵Arg²⁶,³⁴Lys³⁶-(Aspa-ATet)-GLP-1(7-36);
Ser⁸Glu³⁵Arg²⁶,³⁴Lys³⁶-(Aspa-ATet)-GLP-1(7-36)amide;
Ser⁸Glu³⁶Arg²⁶,³⁴Lys³⁷-(Aspa-ATet)-GLP-1(7-37);
Ser⁸Glu³⁷Arg²⁶,³⁴Lys³⁸-(Aspa-ATet)-GLP-1(7-38);
Ser⁸Glu³⁸Arg²⁶,³⁴Lys³⁹-(Aspa-ATet)-GLP-1(7-39);
Ser⁸Glu³⁵Arg²⁶,³⁴Lys³⁶-(Aspa-ATet)-GLP-1(7-36);
Ser⁸Glu³⁵Arg²⁶,³⁴Lys³⁶(Aspa-ATet)-GLP-1(7-36)amide;
Ser⁸Glu³⁶Arg²⁶,³⁴Lys³⁷-(Aspa-ATet)-GLP-1(7-37);
Ser⁸Glu³⁷Arg²⁶,³⁴Lys³⁸-(Aspa-ATet)-GLP-1(7-38);
Ser⁸Glu³⁸Arg²⁶,³⁴Lys³⁹-(Aspa-ATet)-GLP-1(7-39);
Ser⁸Asp³⁵Arg²⁶,³⁴Lys³⁶-(Aspa-ATet)-GLP-1(7-36);
Ser⁸Asp³⁵Arg²⁶,³⁴Lys³⁶-(Aspa-ATet)-GLP-1(7-36)amide;
Ser⁸Asp³⁶Arg²⁶,³⁴Lys³⁷-(Aspa-ATet)-GLP-1(7-37);
Ser⁸Asp³⁷Arg²⁶,³⁴Lys³⁸-(Aspa-ATet)-GLP-1(7-38);
Ser⁸Asp³⁸Arg²⁶,³⁴Lys³⁹-(Aspa-ATet)-GLP-1(7-39);
Ser⁸Asp³⁵Arg²⁶,³⁴Lys³⁶-(Aspa-ATet)-GLP-1(7-36);
Ser⁸Asp³⁵Arg²⁶,³⁴Lys³⁶-(Aspa-ATet)-GLP-1(7-36)amide;
Ser⁸Asp³⁶Arg²⁶,³⁴Lys³⁷-(Aspa-ATet)-GLP-1(7-37);
Ser⁸Asp³⁷Arg²⁶,³⁴Lys³⁸-(Aspa-ATet)-GLP-1(7-38);
Ser⁸Asp³⁸Arg²⁶,³⁴Lys³⁹-(Aspa-ATet)-GLP-1(7-39);
Thr⁸Glu³⁵Arg²⁶,³⁴Lys³⁶-(Aspa-ATet)-GLP-1(7-36);
Thr⁸Glu³⁵Arg²⁶,³⁴Lys³⁶-(Aspa-ATet)-GLP-1(7-36)amide;
Thr⁸Glu³⁶Arg²⁶,³⁴Lys³⁷-(Aspa-ATet)-GLP-1(7-37);
Thr⁸Glu³⁷Arg²⁶,³⁴Lys³⁸-(Aspa-ATet)-GLP-1(7-38);
Thr⁸Glu³⁸Arg²⁶,³⁴Lys³⁹-(Aspa-ATet)-GLP-1(7-39);
Thr⁸Glu³⁵Arg²⁶,³⁴Lys³⁶-(Aspa-ATet)-GLP-1(7-36);
Thr⁸Glu³⁵Arg²⁶,³⁴Lys³⁶-(Aspa-ATet)-GLP-1(7-36)amide;
Thr⁸Glu³⁶Arg²⁶,³⁴Lys³⁷-(Aspa-ATet)-GLP-1(7-37);
Thr⁸Glu³⁷Arg²⁶,³⁴Lys³⁸-(Aspa-ATet)-GLP-1(7-38);
Thr⁸Glu³⁸Arg²⁶,³⁴Lys³⁹-(Aspa-ATet)-GLP-1(7-39);
Thr⁸Asp³⁵Arg²⁶,³⁴Lys³⁶-(Aspa-ATet)-GLP-1(7-36);
Thr⁸Asp³⁵Arg²⁶,³⁴Lys³⁶-(Aspa-ATet)-GLP-1(7-36)amide;
Thr⁸Asp³⁶Arg²⁶,³⁴Lys³⁷-(Aspa-ATet)-GLP-1(7-37);
Thr⁸Asp³⁷Arg²⁶,³⁴Lys³⁸-(Aspa-ATet)-GLP-1(7-38);
Thr⁸Asp³⁸Arg²⁶,³⁴Lys³⁹-(Aspa-ATet)-GLP-1(7-39);
Thr⁸Asp³⁵Arg²⁶,³⁴Lys³⁶-(Aspa-ATet)-GLP-1(7-36);
Thr⁸Asp³⁵Arg²⁶,³⁴Lys³⁶-(Aspa-ATet)-GLP-1(7-36)amide;
Thr⁸Asp³⁶Arg²⁶,³⁴Lys³⁷-(Aspa-ATet)-GLP-1(7-37);
Thr⁸Asp³⁷Arg²⁶,³⁴Lys³⁸-(Aspa-ATet)-GLP-1(7-38);
Thr⁸Asp³Arg²⁶,³⁴Lys³⁹-(Aspa-ATet)-GLP-1(7-39);
Arg²⁶,³⁴Lys¹⁸-(Aspa-ATet)-GLP-1(7-36); Arg²⁶,³⁴Lys¹⁸-(Aspa-ATet)-GLP-1(7-36)amide; Arg²⁶,³⁴Lys¹⁸-(Aspa-ATet)-GLP-1(7-37); Arg²⁶,³⁴Lys¹⁸-(Aspa-ATet)-GLP-1(7-38); Gly⁸Asp¹⁹Arg²⁶,³⁴Lys¹⁸-(Aspa-ATet)-GLP-1(7-36);
Gly⁸Asp¹⁷Arg²⁶,³⁴Lys¹⁸-(Aspa-ATet)-GLP-1(7-36);
Gly⁸Asp¹⁹Arg²⁶,³⁴Lys¹⁸-(Aspa-ATet)-GLP-1(7-36)amide;
Gly⁸Asp¹⁷Arg²⁶,³⁴Lys¹⁸-(Aspa-ATet)-GLP-1(7-36)amide;
Gly⁸Asp¹⁹Arg²⁶,³⁴Lys¹⁸-(Aspa-ATet)-GLP-1(7-37);
Gly⁸Asp¹⁹Arg²⁶,³⁴Lys¹⁸-(Aspa-ATet)-GLP-1(7-38);
Gly⁸Asp¹⁷Arg²⁶,³⁴Lys¹⁸-(Aspa-ATet)-GLP-1(7-38);
Arg²⁶,³⁴Lys²³-(Aspa-ATet)-GLP-1(7-36); Arg²⁶,³⁴Lys²³-(Aspa-ATet)-GLP-1(7-36)amide; Arg²⁶,³⁴Lys²³-(Aspa-ATet)-GLP-1(7-37); Arg²⁶,³⁴Lys²³-(Aspa-ATet)-GLP-1(7-38); Gly⁸Asp¹⁹Arg²⁶,³⁴Lys²³-(Aspa-ATet)-GLP-1(7-36);
Gly⁸Asp¹⁷Arg²⁶,³⁴Lys²³-(Aspa-ATet)-GLP-1(7-36);
Gly⁸Asp¹⁹Arg²⁶,³⁴Lys²³-(Aspa-ATet)-GLP-1(7-36)amide;
Gly⁸Asp¹⁷Arg²⁶,³⁴Lys²³-(Aspa-ATet)-GLP-1(7-36)amide;
Gly⁸Asp¹⁹Arg²⁶,³⁴Lys²³-(Aspa-ATet)-GLP-1(7-37);
Gly⁸Asp¹⁹Arg²⁶,³⁴Lys²³-(Aspa-ATet)-GLP-1(7-38);
Gly⁸Asp¹⁷Arg²⁶,³⁴Lys²³-(Aspa-ATet)-GLP-1(7-38);
Arg²⁶,³⁴Lys²⁷-(Aspa-ATet)-GLP-1(7-36); Arg²⁶,³⁴Lys²⁷-(Aspa-ATet)-GLP-1(7-36)amide; Arg²⁶,³⁴Lys²⁷-(Aspa-ATet)-GLP-1(7-37); Arg²⁶,³⁴Lys²⁷-(Aspa-ATet)-GLP-1(7-38); Gly⁸Asp¹⁹Arg²⁶,³⁴Lys²⁷-(Aspa-ATet)-GLP-1(7-36);
Gly⁸Asp¹⁷Arg²⁶,³⁴Lys²⁷-(Aspa-ATet)-GLP-1(7-36);
Gly⁸Asp¹⁹Arg²⁶,³⁴Lys²⁷-(Aspa-ATet)-GLP-1(7-36)amide;
Gly⁸Asp¹⁷Arg²⁶,³⁴Lys²⁷-(Aspa-ATet)-GLP-1(7-36)amide;
Gly⁸Asp¹⁹Arg²⁶,³⁴Lys²⁷-(Aspa-ATet)-GLP-1(7-37);
Gly⁸Asp¹⁹Arg²⁶,³⁴Lys²⁷-(Aspa-ATet)-GLP-1(7-38);
Gly⁸Asp¹⁷Arg²⁶,³⁴Lys²⁷-(Aspa-ATet)-GLP-1(7-38);
Arg²⁶,³⁴Lys¹⁸-(Aspa-ATet)-GLP-1(7-36); Arg²⁶,³⁴Lys¹⁸-(Aspa-ATet)-GLP-1(7-36)amide; Arg²⁶,³⁴Lys¹⁸-(Aspa-ATet)-GLP-1(7-37); Arg²⁶,³⁴Lys¹⁸-(Aspa-ATet)-GLP-1(7-38); Val⁸Asp¹⁹Arg²⁶,³⁴Lys¹⁸-(Aspa-ATet)-GLP-1(7-36);
Val⁸Asp¹⁷Arg²⁶,³⁴Lys¹⁸-(Aspa-ATet)-GLP-1(7-36);
Val⁸Asp¹⁹Arg²⁶,³⁴Lys¹⁸-(Aspa-ATet)-GLP-1(7-36)amide;
Val⁸Asp¹⁷Arg²⁶,³⁴Lys¹⁸-(Aspa-ATet)-GLP-1(7-36)amide;
Val⁸Asp¹⁹Arg²⁶,³⁴Lys¹⁸-(Aspa-ATet)-GLP-1(7-37);
Val⁸Asp¹⁹Arg²⁶,³⁴Lys¹⁸-(Aspa-ATet)-GLP-1(7-38);
Val⁸Asp¹⁷Arg²⁶,³⁴Lys¹⁸-(Aspa-ATet)-GLP-1(7-38);
Arg²⁶,³⁴Lys²³-(Aspa-ATet)-GLP-1(7-36); Arg²⁶,³⁴Lys²³-(Aspa-ATet)-GLP-1(7-36)amide; Arg²⁶,³⁴Lys²³-(Aspa-ATet)-GLP-1(7-37); Arg²⁶,³⁴Lys²³-(Aspa-ATet)-GLP-1(7-38); Val⁸Asp¹⁹Arg²⁶,³⁴Lys²³-(Aspa-ATet)-GLP-1(7-36);
Val⁸Asp¹⁷Arg²⁶,³⁴Lys²³-(Aspa-ATet)-GLP-1(7-36);
Val⁸Asp¹⁹Arg²⁶,³⁴Lys²³-(Aspa-ATet)-GLP-1(7-36)amide;
Val⁸Asp¹⁷Arg²⁶,³⁴Lys²³-(Aspa-ATet)-GLP-1(7-36)amide;
Val⁸Asp¹⁹Arg²⁶,³⁴Lys²³-(Aspa-ATet)-GLP-1(7-37);
Val⁸Asp¹⁹Arg²⁶,³⁴Lys²³-(Aspa-ATet)-GLP-1(7-38);
Val⁸Asp¹⁷Arg²⁶,³⁴Lys²³-(Aspa-ATet)-GLP-1(7-38);
Arg²⁶,³⁴Lys²⁷-(Aspa-ATet)-GLP-1(7-36); Arg²⁶,³⁴Lys²⁷-(Aspa-ATet)-GLP-1(7-36)amide; Arg²⁶,³⁴Lys²⁷-(Aspa-ATet)-GLP-1(7-37); Arg²⁶,³⁴Lys²⁷-(Aspa-ATet)-GLP-1(7-38); Val⁸Asp¹⁹Arg²⁶,³⁴Lys²⁷-(Aspa-ATet)-GLP-1(7-36);
Val⁸Asp¹⁷Arg²⁶,³⁴Lys²⁷-(Aspa-ATet)-GLP-1(7-36);
Val⁸Asp¹⁹Arg²⁶,³⁴Lys²⁷-(Aspa-ATet)-GLP-1(7-36)amide;
Val⁸Asp¹⁷Arg²⁶,³⁴Lys²⁷-(Aspa-ATet)-GLP-1(7-36)amide;
Val⁸Asp¹⁹Arg²⁶,³⁴Lys²⁷-(Aspa-ATet)-GLP-1(7-37);
Val⁸Asp¹⁹Arg²⁶,³⁴Lys²⁷-(Aspa-ATet)-GLP-1(7-38);
Val⁸Asp¹⁷Arg²⁶,³⁴Lys²⁷-(Aspa-ATet)-GLP-1(7-38);
Arg²⁶,³⁴Lys¹⁸-(Aspa-ATet)-GLP-1(7-36); Arg²⁶,³⁴Lys¹⁸-(Aspa-ATet)-GLP-1(7-36)amide; Arg²⁶,³⁴Lys¹⁸-(Aspa-ATet)-GLP-1(7-37); Arg²⁶,³⁴Lys¹⁸-(Aspa-ATet)-GLP-1(7-38); Ser⁸Asp¹⁹Arg²⁶,³⁴Lys¹⁸-(Aspa-ATet)-GLP-1(7-36);
Ser⁸Asp¹⁷Arg²⁶,³⁴Lys¹⁸-(Aspa-ATet)-GLP-1(7-36);
Ser⁸Asp¹⁹Arg²⁶,³⁴Lys¹⁸-(Aspa-ATet)-GLP-1(7-36)amide;
Ser⁸Asp¹⁷Arg²⁶,³⁴Lys¹⁸-(Aspa-ATet)-GLP-1(7-36)amide;
Ser⁸Asp¹⁹Arg²⁶,³⁴Lys¹⁸-(Aspa-ATet)-GLP-1(7-37);
Ser⁸Asp¹⁹Arg²⁶,³⁴Lys¹⁸-(Aspa-ATet)-GLP-1(7-38);
Ser⁸Asp¹⁷Arg²⁶,³⁴Lys¹⁸-(Aspa-ATet)-GLP-1(7-38);
Arg²⁶,³⁴Lys²³-(Aspa-ATet)-GLP-1(7-36); Arg²⁶,³⁴Lys²³-(Aspa-ATet)-GLP-1(7-36)amide; Arg²⁶,³⁴Lys²³-(Aspa- ATet)-GLP-1(7-37); Arg$^{26,34}$Lys$^{23}$-(Aspa-ATet)-GLP-1(7-38); Ser$^8$Asp$^{19}$Arg$^{26,34}$Lys$^{23}$-(Aspa-ATet)-GLP-1(7-36); Ser$^8$Asp$^{17}$Arg$^{26,34}$Lys$^{23}$-(Aspa-ATet)-GLP-1(7-36); Ser$^8$Asp$^{19}$Arg$^{26,34}$Lys$^{23}$-(Aspa-ATet)-GLP-1(7-36)amide; Ser$^8$Asp$^{17}$Arg$^{26,34}$Lys$^{23}$-(Aspa-ATet)-GLP-1(7-36)amide; Ser$^8$Asp$^{19}$Arg$^{26,34}$Lys$^{23}$-(Aspa-ATet)-GLP-1(7-37); Ser$^8$Asp$^{19}$Arg$^{26,34}$Lys$^{23}$-(Aspa-ATet)-GLP-1(7-38); Ser$^8$Asp$^{17}$Arg$^{26,34}$Lys$^{23}$-(Aspa-ATet)-GLP-1(7-38); Arg$^{26,34}$Lys$^{27}$-(Aspa-ATet)-GLP-1(7-36); Arg$^{26,34}$Lys$^{27}$-(Aspa-ATet)-GLP-1(7-36)amide; Arg$^{26,34}$Lys$^{27}$-(Aspa-ATet)-GLP-1(7-37); Arg$^{26,34}$Lys$^{27}$-(Aspa-ATet)-GLP-1(7-38); Ser$^8$Asp$^{19}$Arg$^{26,34}$Lys$^{27}$-(Aspa-ATet)-GLP-1(7-36); Ser$^8$Asp$^{17}$Arg$^{26,34}$Lys$^{27}$-(Aspa-ATet)-GLP-1(7-36); Ser$^8$Asp$^{19}$Arg$^{26,34}$Lys$^{27}$-(Aspa-ATet)-GLP-1(7-36)amide; Ser$^8$Asp$^{17}$Arg$^{26,34}$Lys$^{27}$-(Aspa-ATet)-GLP-1(7-36)amide; Ser$^8$Asp$^{19}$Arg$^{26,34}$Lys$^{27}$-(Aspa-ATet)-GLP-1(7-37); Ser$^8$Asp$^{19}$Arg$^{26,34}$Lys$^{27}$-(Aspa-ATet)-GLP-1(7-38); Ser$^8$Asp$^{17}$Arg$^{26,34}$Lys$^{27}$-(Aspa-ATet)-GLP-1(7-38); Arg$^{26,34}$Lys$^{18}$-(Aspa-ATet)-GLP-1(7-36); Arg$^{26,34}$Lys$^{18}$-(Aspa-ATet)-GLP-1(7-36)amide; Arg$^{26,34}$Lys$^{18}$-(Aspa-ATet)-GLP-1(7-37); Arg$^{26,34}$Lys$^{18}$-(Aspa-ATet)-GLP-1(7-38); Thr$^8$Asp$^{19}$Arg$^{26,34}$Lys$^{18}$-(Aspa-ATet)-GLP-1(7-36); Thr$^8$Asp$^{17}$Arg$^{26,34}$Lys$^{18}$-(Aspa-ATet)-GLP-1(7-36); Thr$^8$Asp$^{19}$Arg$^{26,34}$Lys$^{18}$-(Aspa-ATet)-GLP-1(7-36)amide; Thr$^8$Asp$^{17}$Arg$^{26,34}$Lys$^{18}$-(Aspa-ATet)-GLP-1(7-36)amide; Thr$^8$Asp$^{19}$Arg$^{26,34}$Lys$^{18}$-(Aspa-ATet)-GLP-1(7-37); Thr$^8$Asp$^{19}$Arg$^{26,34}$Lys$^{18}$-(Aspa-ATet)-GLP-1(7-38); Thr$^8$Asp$^{17}$Arg$^{26,34}$Lys$^{18}$-(Aspa-ATet)-GLP-1(7-38); Arg$^{26,34}$Lys$^{23}$-(Aspa-ATet)-GLP-1(7-36); Arg$^{26,34}$Lys$^{23}$-(Aspa-ATet)-GLP-1(7-36)amide; Arg$^{26,34}$Lys$^{23}$-(Aspa-ATet)-GLP-1(7-37); Arg$^{26,34}$Lys$^{23}$-(Aspa-ATet)-GLP-1(7-38); Thr$^8$Asp$^{19}$Arg$^{26,34}$Lys$^{23}$-(Aspa-ATet)-GLP-1(7-36); Thr$^8$Asp$^{17}$Arg$^{26,34}$Lys$^{23}$-(Aspa-ATet)-GLP-1(7-36); Thr$^8$Asp$^{19}$Arg$^{26,34}$Lys$^{23}$-(Aspa-ATet)-GLP-1(7-36)amide; Thr$^8$Asp$^{17}$Arg$^{26,34}$Lys$^{23}$-(Aspa-ATet)-GLP-1(7-36)amide; Thr$^8$Asp$^{19}$Arg$^{26,34}$Lys$^{23}$-(Aspa-ATet)-GLP-1(7-37); Thr$^8$Asp$^{19}$Arg$^{26,34}$Lys$^{23}$-(Aspa-ATet)-GLP-1(7-38); Thr$^8$Asp$^{17}$Arg$^{26,34}$Lys$^{23}$-(Aspa-ATet)-GLP-1(7-38); Arg$^{26,34}$Lys$^{27}$-(Aspa-ATet)-GLP-1(7-36); Arg$^{26,34}$Lys$^{27}$-(Aspa-ATet)-GLP-1(7-36)amide; Arg$^{26,34}$Lys$^{27}$-(Aspa-ATet)-GLP-1(7-37); Arg$^{26,34}$Lys$^{27}$-(Aspa-ATet)-GLP-1(7-38); Thr$^8$Asp$^{19}$Arg$^{26,34}$Lys$^{27}$-(Aspa-ATet)-GLP-1(7-36); Thr$^8$Asp$^{17}$Arg$^{26,34}$Lys$^{27}$-(Aspa-ATet)-GLP-1(7-36); Thr$^8$Asp$^{19}$Arg$^{26,34}$Lys$^{27}$-(Aspa-ATet)-GLP-1(7-36)amide; Thr$^8$Asp$^{17}$Arg$^{26,34}$Lys$^{27}$-(Aspa-ATet)-GLP-1(7-36)amide; Thr$^8$Asp$^{19}$Arg$^{26,34}$Lys$^{27}$-(Aspa-ATet)-GLP-1(7-37); Thr$^8$Asp$^{19}$Arg$^{26,34}$Lys$^{27}$-(Aspa-ATet)-GLP-1(7-38); Thr$^8$Asp$^{17}$Arg$^{26,34}$Lys$^{27}$-(Aspa-ATet)-GLP-1(7-38); Arg$^{26}$Lys$^{34}$-(Aspa-AHex)-GLP-1(7-36); Arg$^{34}$Lys$^{26}$-(Aspa-AHex)-GLP-1(7-36); Arg$^{26,34}$Lys$^{36}$-(Aspa-AHex)-GLP-1(7-36); Arg$^{26}$Lys$^{34}$-(Aspa-AHex)-GLP-1(7-36)amide; Arg$^{34}$Lys$^{26}$-(Aspa-AHex)-GLP-1(7-36)amide; Arg$^{26,34}$Lys$^{36}$-(Aspa-AHex)-GLP-1(7-36)amide; Arg$^{26}$Lys$^{34}$-(Aspa-AHex)-GLP-1(7-37); Arg$^{34}$Lys$^{26}$-(Aspa-AHex)-GLP-1(7-37); Arg$^{26,34}$Lys$^{36}$-(Aspa-AHex)-GLP-1(7-37); Arg$^{26}$Lys$^{34}$-(Aspa-AHex)-GLP-1(7-38); Arg$^{34}$Lys$^{26}$-(Aspa-AHex)-GLP-1(7-38); Arg$^{26,34}$Lys$^{38}$-(Aspa-AHex)-GLP-1(7-38); Arg$^{26}$Lys$^{34}$-(Aspa-AHex)-GLP-1(7-39); Arg$^{34}$Lys$^{26}$-(Aspa-AHex)-GLP-1(7-39); Arg$^{26,34}$Lys$^{39}$-(Aspa-AHex)-GLP-1(7-39); Gly$^8$Arg$^{26}$Lys$^{34}$-(Aspa-AHex)-GLP-1(7-36); Gly$^8$Arg$^{34}$Lys$^{26}$-(Aspa-AHex)-GLP-1(7-36); Gly$^8$Arg$^{26,34}$Lys$^{36}$-(Aspa-AHex)-GLP-1(7-36); Gly$^8$Arg$^{26}$Lys$^{34}$-(Aspa-AHex)-GLP-1(7-36)amide; Gly$^8$Arg$^{34}$Lys$^{26}$-(Aspa-AHex)-GLP-1(7-36)amide; Gly$^8$Arg$^{26,34}$Lys$^{36}$-(Aspa-AHex)-GLP-1(7-36)amide; Gly$^8$Arg$^{26}$Lys$^{34}$-(Aspa-AHex)-GLP-1(7-37); Gly$^8$Arg$^{34}$Lys$^{26}$-(Aspa-AHex)-GLP-1(7-37); Gly$^8$Arg$^{26,34}$Lys$^{36}$-(Aspa-AHex)-GLP-1(7-37); Gly$^8$Arg$^{26}$Lys$^{34}$-(Aspa-AHex)-GLP-1(7-38); Gly$^8$Arg$^{34}$Lys$^{26}$-(Aspa-AHex)-GLP-1(7-38); Gly$^8$Arg$^{26,34}$Lys$^{38}$-(Aspa-AHex)-GLP-1(7-38); Gly$^8$Arg$^{26}$Lys$^{34}$-(Aspa-AHex)-GLP-1(7-39); Gly$^8$Arg$^{34}$Lys$^{26}$-(Aspa-AHex)-GLP-1(7-39); Gly$^8$Arg$^{26,34}$Lys$^{39}$-(Aspa-AHex)-GLP-1(7-39); Val$^8$Arg$^{26}$Lys$^{34}$-(Aspa-AHex)-GLP-1(7-36); Val$^8$Arg$^{34}$Lys$^{26}$-(Aspa-AHex)-GLP-1(7-36); Val$^8$Arg$^{26,34}$Lys$^{36}$-(Aspa-AHex)-GLP-1(7-36); Val$^8$Arg$^{26}$Lys$^{34}$-(Aspa-AHex)-GLP-1(7-36)amide; Val$^8$Arg$^{34}$Lys$^{26}$-(Aspa-AHex)-GLP-1(7-36)amide; Val$^8$Arg$^{26,34}$Lys$^{36}$-(Aspa-AHex)-GLP-1(7-36)amide; Val$^8$Arg$^{26}$Lys$^{34}$-(Aspa-AHex)-GLP-1(7-37); Val$^8$Arg$^{34}$Lys$^{26}$-(Aspa-AHex)-GLP-1(7-37); Val$^8$Arg$^{26,34}$Lys$^{36}$-(Aspa-AHex)-GLP-1(7-37); Val$^8$Arg$^{26}$Lys$^{34}$-(Aspa-AHex)-GLP-1(7-38); Val$^8$Arg$^{34}$Lys$^{26}$-(Aspa-AHex)-GLP-1(7-38); Val$^8$Arg$^{26,34}$Lys$^{38}$-(Aspa-AHex)-GLP-1(7-38); Val$^8$Arg$^{26}$Lys$^{34}$-(Aspa-AHex)-GLP-1(7-39); Val$^8$Arg$^{34}$Lys$^{26}$-(Aspa-AHex)-GLP-1(7-39); Val$^8$Arg$^{26,34}$Lys$^{39}$-(Aspa-AHex)-GLP-1(7-39); Ser$^8$Arg$^{26}$Lys$^{34}$-(Aspa-AHex)-GLP-1(7-36); Ser$^8$Arg$^{34}$Lys$^{26}$-(Aspa-AHex)-GLP-1(7-36); Ser$^8$Arg$^{26,34}$Lys$^{36}$-(Aspa-AHex)-GLP-1(7-36); Ser$^8$Arg$^{26}$Lys$^{34}$-(Aspa-AHex)-GLP-1(7-36)amide; Ser$^8$Arg$^{34}$Lys$^{26}$-(Aspa-AHex)-GLP-1(7-36)amide; Ser$^8$Arg$^{26,34}$Lys$^{36}$-(Aspa-AHex)-GLP-1(7-36)amide; Ser$^8$Arg$^{26}$Lys$^{34}$-(Aspa-AHex)-GLP-1(7-37); Ser$^8$Arg$^{34}$Lys$^{26}$-(Aspa-AHex)-GLP-1(7-37); Ser$^8$Arg$^{26,34}$Lys$^{36}$-(Aspa-AHex)-GLP-1(7-37); Ser$^8$Arg$^{26}$Lys$^{34}$-(Aspa-AHex)-GLP-1(7-38); Ser$^8$Arg$^{34}$Lys$^{26}$-(Aspa-AHex)-GLP-1(7-38); Ser$^8$Arg$^{26,34}$Lys$^{38}$-(Aspa-AHex)-GLP-1(7-38); Ser$^8$Arg$^{34}$Lys$^{26}$-(Aspa-AHex)-GLP-1(7-39); Ser$^8$Arg$^{34}$Lys$^{26}$-(Aspa-AHex)-GLP-1(7-39); Ser$^8$Arg$^{26,34}$Lys$^{39}$-(Aspa-AHex)-GLP-1(7-39); Thr$^8$Arg$^{26}$Lys$^{34}$-(Aspa-AHex)-GLP-1(7-36); Thr$^8$Arg$^{34}$Lys$^{26}$-(Aspa-AHex)-GLP-1(7-36); Thr$^8$Arg$^{26,34}$Lys$^{36}$-(Aspa-AHex)-GLP-1(7-36); Thr$^8$Arg$^{26}$Lys$^{34}$-(Aspa-AHex)-GLP-1(7-36)amide; Thr$^8$Arg$^{34}$Lys$^{26}$-(Aspa-AHex)-GLP-1(7-36)amide; Thr$^8$Arg$^{26,34}$Lys$^{36}$-(Aspa-AHex)-GLP-1(7-36)amide; Thr$^8$Arg$^{26}$Lys$^{34}$-(Aspa-AHex)-GLP-1(7-37); Thr$^8$Arg$^{34}$Lys$^{26}$-(Aspa-AHex)-GLP-1(7-37); Thr$^8$Arg$^{26,34}$Lys$^{36}$-(Aspa-AHex)-GLP-1(7-37); Thr$^8$Arg$^{26}$Lys$^{34}$-(Aspa-AHex)-GLP-1(7-38); Thr$^8$Arg$^{34}$Lys$^{26}$-(Aspa-AHex)-GLP-1(7-38); Thr$^8$Arg$^{26,34}$Lys$^{38}$-(Aspa-AHex)-GLP-1(7-38); Thr$^8$Arg$^{26}$Lys$^{34}$-(Aspa-AHex)-GLP-1(7-39); Thr$^8$Arg$^{34}$Lys$^{26}$-(Aspa-AHex)-GLP-1(7-39); Thr$^8$Arg$^{26,34}$Lys$^{39}$-(Aspa-AHex)-GLP-1(7-39); Gly$^8$Glu$^{35}$Arg$^{26,34}$Lys$^{36}$-(Aspa-AHex)-GLP-1(7-36); Gly$^8$Glu$^{35}$Arg$^{26,34}$Lys$^{36}$-(Aspa-AHex)-GLP-1(7-36)amide; Gly$^8$Glu$^{36}$Arg$^{26,34}$Lys$^{37}$-(Aspa-AHex)-GLP-1(7-37); Gly$^8$Glu$^{37}$Arg$^{26,34}$Lys$^{38}$-(Aspa-AHex)-GLP-1(7-38); Gly$^8$Glu$^{38}$Arg$^{26,34}$Lys$^{39}$-(Aspa-AHex)-GLP-1(7-39); Gly$^8$Glu$^{35}$Arg$^{26,34}$Lys$^{36}$-(Aspa-AHex)-GLP-1(7-36); Gly$^8$Glu$^{35}$Arg$^{26,34}$Lys$^{36}$-(Aspa-AHex)-GLP-1(7-36)amide; Gly$^8$Glu$^{36}$Arg$^{26,34}$Lys$^{37}$-(Aspa-AHex)-GLP-1(7-37); Gly$^8$Glu$^{37}$Arg$^{26,34}$Lys$^{38}$-(Aspa-AHex)-GLP-1(7-38); Gly$^8$Glu$^{38}$Arg$^{26,34}$Lys$^{39}$-(Aspa-AHex)-GLP-1(7-39); Gly$^8$Asp$^{35}$Arg$^{26,34}$Lys$^{36}$-(Aspa-AHex)-GLP-1(7-36); Gly$^8$Asp$^{35}$Arg$^{26,34}$Lys$^{36}$-(Aspa-AHex)-GLP-1(7-36)amide; Gly$^8$Asp$^{36}$Arg$^{26,34}$Lys$^{37}$-(Aspa-AHex)-GLP-1(7-37); Gly$^8$Asp$^{37}$Arg$^{26,34}$Lys$^{38}$-(Aspa-AHex)-GLP-1(7-38); Gly$^8$Asp$^{38}$Arg$^{26,34}$Lys$^{39}$-(Aspa-AHex)-GLP-1(7-39); Gly$^8$Asp$^{35}$Arg$^{26,34}$Lys$^{36}$-(Aspa-AHex)-GLP-1(7-36); Gly$^8$Asp$^{35}$Arg$^{26,34}$Lys$^{36}$-(Aspa-AHex)-GLP-1(7-36)amide;

Gly$^8$Asp$^{36}$Arg$^{26,34}$Lys$^{37}$-(Aspa-AHex)-GLP-1(7-37);
Gly$^8$Asp$^{37}$Arg$^{26,34}$Lys$^{38}$-(Aspa-AHex)-GLP-1(7-38);
Gly$^8$Asp$^{38}$Arg$^{26,34}$Lys$^{39}$-(Aspa-AHex)-GLP-1(7-39);
Val$^8$Glu$^{35}$Arg$^{26,34}$Lys$^{36}$-(Aspa-AHex)-GLP-1(7-36);
Val$^8$Glu$^{35}$Arg$^{26,34}$Lys$^{36}$ (Aspa-AHex)-GLP-1(7-36)amide;
Val$^8$Glu$^{36}$Arg$^{26,34}$Lys$^{37}$-(Aspa-AHex)-GLP-1(7-37);
Val$^8$Glu$^{37}$Arg$^{26,34}$Lys$^{38}$-(Aspa-AHex)-GLP-1(7-38);
Val$^8$Glu$^{38}$Arg$^{26,34}$Lys$^{39}$-(Aspa-AHex)-GLP-1(7-39);
Val$^8$Glu$^{35}$Arg$^{26,34}$Lys$^{36}$-(Aspa-AHex)-GLP-1(7-36);
Val$^8$Glu$^{35}$Arg$^{26,34}$Lys$^{36}$-(Aspa-AHex)-GLP-1(7-36)amide;
Val$^8$Glu$^{36}$Arg$^{26,34}$Lys$^{37}$-(Aspa-AHex)-GLP-1(7-37);
Val$^8$Glu$^{37}$Arg$^{26,34}$Lys$^{38}$-(Aspa-AHex)-GLP-1(7-38);
Val$^8$Glu$^{38}$Arg$^{26,34}$Lys$^{39}$-(Aspa-AHex)-GLP-1(7-39);
Val$^8$Asp$^{35}$Arg$^{26,34}$Lys$^{36}$-(Aspa-AHex)-GLP-1(7-36);
Val$^8$Asp$^{35}$Arg$^{26,34}$Lys$^{36}$-(Aspa-AHex)-GLP-1(7-36)amide;
Val$^8$Asp$^{36}$Arg$^{26,34}$Lys$^{37}$-(Aspa-AHex)-GLP-1(7-37);
Val$^8$Asp$^{37}$Arg$^{26,34}$Lys$^{38}$-(Aspa-AHex)-GLP-1(7-38);
Val$^8$Asp$^{38}$Arg$^{26,34}$Lys$^{39}$-(Aspa-AHex)-GLP-1(7-39);
Val$^8$Asp$^{35}$Arg$^{26,34}$Lys$^{36}$-(Aspa-AHex)-GLP-1(7-36);
Val$^8$Asp$^{35}$Arg$^{26,34}$Lys$^{36}$-(Aspa-AHex)-GLP-1(7-36)amide;
Val$^8$Asp$^{36}$Arg$^{26,34}$Lys$^{37}$-(Aspa-AHex)-GLP-1(7-37);
Val$^8$Asp$^{37}$Arg$^{26,34}$Lys$^{38}$-(Aspa-AHex)-GLP-1(7-38);
Val$^8$Asp$^{38}$Arg$^{26,34}$Lys$^{39}$-(Aspa-AHex)-GLP-1(7-39);
Ser$^8$Glu$^{35}$Arg$^{26,34}$Lys$^{36}$-(Aspa-AHex)-GLP-1(7-36);
Ser$^8$Glu$^{35}$Arg$^{26,34}$Lys$^{36}$ (Aspa-AHex)-GLP-1(7-36)amide;
Ser$^8$Glu$^{36}$Arg$^{26,34}$Lys$^{37}$-(Aspa-AHex)-GLP-1(7-37);
Ser$^8$Glu$^{37}$Arg$^{26,34}$Lys$^{38}$-(Aspa-AHex)-GLP-1(7-38);
Ser$^8$Glu$^{38}$Arg$^{26,34}$Lys$^{39}$-(Aspa-AHex)-GLP-1(7-39);
Ser$^8$Glu$^{35}$Arg$^{26,34}$Lys$^{36}$-(Aspa-AHex)-GLP-1(7-36);
Ser$^8$Glu$^{35}$Arg$^{26,34}$Lys$^{36}$-(Aspa-AHex)-GLP-1(7-36)amide;
Ser$^8$Glu$^{36}$Arg$^{26,34}$Lys$^{37}$-(Aspa-AHex)-GLP-1(7-37);
Ser$^8$Glu$^{37}$Arg$^{26,34}$Lys$^{38}$-(Aspa-AHex)-GLP-1(7-38);
Ser$^8$Glu$^{38}$Arg$^{26,34}$Lys$^{39}$-(Aspa-AHex)-GLP-1(7-39);
Ser$^8$Asp$^{35}$Arg$^{26,34}$Lys$^{36}$-(Aspa-AHex)-GLP-1(7-36);
Ser$^8$Asp$^3$Arg$^{26,34}$Lys$^{36}$-(Aspa-AHex)-GLP-1(7-36); GLP-1 (7-36)amide; Ser$^8$Asp$^{36}$Arg$^{26,34}$Lys$^{37}$ (Aspa-AHex)-GLP-1 (7-37); Se Asp$^{37}$Arg$^{26,34}$Lys$^{38}$(Aspa-AHex)-GLP-1(7-38);
Ser$^8$Asp$^3$Arg$^{26,34}$Lys$^{39}$-(Aspa-AHex)-GLP-1(7-39);
Ser$^8$Asp$^{35}$Arg$^{26,34}$Lys$^{36}$-(Aspa-AHex)-GLP-1(7-36);
Ser$^8$Asp$^{35}$Arg$^{26,34}$Lys$^{36}$-(Aspa-AHex)-GLP-1(7-36)amide;
Ser$^8$Asp$^{36}$Arg$^{26,34}$Lys$^{37}$-(Aspa-AHex)-GLP-1(7-37);
Ser$^8$Asp$^{37}$Arg$^{26,34}$Lys$^{38}$-(Aspa-AHex)-GLP-1(7-38);
Ser$^8$Asp$^{35}$Arg$^{26,34}$Lys$^{39}$-(Aspa-AHex)-GLP-1(7-39);
Thr$^8$Glu$^{35}$Arg$^{26,34}$Lys$^{36}$-(Aspa-AHex)-GLP-1(7-36);
Thr$^8$Glu$^{35}$Arg$^{26,34}$Lys$^{36}$Arg$^2$Lys$^{36}$(Aspa-AHex)-GLP-1(7-36)amide; Thr$^8$Glu$^{36}$Arg$^{26,34}$Lys$^{37}$-(Aspa-AHex)-GLP-1(7-37); Thr$^8$Glu$^{37}$Arg$^{26,34}$Lys$^{39}$-(Aspa-AHex)-GLP-1(7-38);
Thr$^8$Glu$^{35}$Arg$^{26,34}$Lys$^{39}$-(Aspa-AHex)-GLP-1(7-39);
Thr$^8$Glu$^{35}$Arg$^{26,34}$Lys$^{36}$-(Aspa-AHex)-GLP-1(7-36);
Thr$^8$Glu$^{35}$Arg$^{26,34}$Lys$^{36}$-(Aspa-AHex)-GLP-1(7-36)amide;
Thr$^8$Glu$^{36}$Arg$^{26,34}$Lys$^{37}$-(Aspa-AHex)-GLP-1(7-37);
Thr$^8$Glu$^{37}$Arg$^{26,34}$Lys$^{38}$-(Aspa-AHex)-GLP-1(7-38);
Thr$^8$Glu$^{38}$Arg$^{26,34}$Lys$^{39}$-(Aspa-AHex)-GLP-1(7-39);
Thr$^8$Asp$^{35}$Arg$^{26,34}$Lys$^{36}$-(Aspa-AHex)-GLP-1(7-36);
Thr$^8$Asp$^{35}$Arg$^{26,34}$Lys$^{36}$-(Aspa-AHex)-GLP-1(7-36)amide;
Thr$^8$Asp$^{26,34}$Lys$^{37}$-(Aspa-AHex)-GLP-1(7-3); (7-37);
Thr$^8$Asp$^{37}$Arg$^{26,34}$Lys$^{38}$-(Aspa-AHex)-GLP-1(7-38);
Thr$^8$Asp$^8$Arg$^{26,34}$Lys$^{39}$-(Aspa-AHex)-GLP-1(7-39);
Thr$^8$Asp$^{35}$Arg$^{26,34}$Lys$^{36}$-(Aspa-AHex)-GLP-1(7-36);
Thr$^8$Asp$^{35}$Arg$^{26,34}$Lys$^{36}$-(Aspa-AHex)-GLP-1(7-36)amide;
Thr$^8$Asp$^{36}$Arg$^{26,34}$Lys$^{37}$-(Aspa-AHex)-GLP-1(7-37);
Thr$^8$Asp$^{37}$Arg$^{26,34}$Lys$^{38}$-(Aspa-AHex)-GLP-1(7-38);
Thr$^8$Asp$^{38}$Arg$^{26,34}$Lys$^{39}$-(Aspa-AHex)-GLP-1(7-39);
Arg$^{26,34}$Lys$^{18}$-(Aspa-AHex)-GLP-1(7-36); Arg$^{26,34}$Lys$^{18}$-(Aspa-AHex)-GLP-1(7-36)amide; Arg$^{26,34}$Lys$^{18}$-(Aspa-AHex)-GLP-1(7-37); Arg$^{26,34}$Lys$^{18}$-(Aspa-AHex)-GLP-1 (7-38); Gly$^8$Asp$^{19}$ Arg$^{26,34}$Lys$^{18}$(Aspa-AHex)-GLP-1(7-36); Gly$^8$Asp$^{17}$Arg$^{26,34}$Lys$^{18}$-(Aspa-AHex)-GLP-1(7-36);
Gly$^8$Asp$^{19}$Arg$^{26,34}$Lys$^{18}$-(Aspa-AHex)-GLP-1(7-36)amide;
Gly$^8$Asp$^{17}$Arg$^{26,34}$Lys$^{18}$-(Aspa-AHex)-GLP-1(7-36)amide;
Gly$^8$Asp$^{19}$Arg$^{26,34}$Lys$^{18}$-(Aspa-AHex)-GLP-1(7-37);
Gly$^8$Asp$^{19}$Arg$^{26,34}$Lys$^{18}$-(Aspa-AHex)-GLP-1(7-38);
Gly$^8$Asp$^{17}$Arg$^{26,34}$Lys$^{18}$-(Aspa-AHex)-GLP-1(7-38);
Arg$^{26,34}$Lys$^{23}$-(Aspa-AHex)-GLP-1(7-36); Arg$^{26,34}$Lys$^{23}$-(Aspa-AHex)-GLP-1(7-36)amide; Arg$^{26,34}$Lys$^{23}$-(Aspa-AHex)-GLP-1(7-37); Arg$^{26,34}$Lys$^{23}$-(Aspa-AHex)-GLP-1 (7-38); Gly$^8$Asp$^{19}$Arg$^{26,34}$Lys$^{23}$-(Aspa-AHex)-GLP-1(7-36); Gly$^8$Asp$^{17}$Arg$^{26,34}$Lys$^{23}$-(Aspa-AHex)GLP-1(7-36);
Gly$^8$Asp$^{19}$Arg$^{26,34}$Lys$^{23}$ (Aspa-AHex)-GLP-1(7-36)amide;
Gly$^8$Asp$^{17}$Arg$^{26,34}$Lys$^{23}$-(Aspa-AHex)-GLP-1(7-36)amide;
Gly$^8$Asp$^{19}$Arg$^{26,34}$Lys$^{23}$-(Aspa-AHex)-GLP-1(7-37);
Gly$^8$Asp$^{19}$Arg$^{26,34}$Lys$^{23}$-(Aspa-AHex)-GLP-1(7-38);
Gly$^8$Asp$^{17}$Arg$^{26,34}$Lys$^{23}$-(Aspa-AHex)-GLP-1(7-38);
Arg$^{26,34}$Lys$^{27}$-(Aspa-AHex)-GLP-1(7-36); Arg$^{26,34}$Lys$^{27}$-(Aspa-AHex)-GLP-1(7-36)amide; Arg$^{26,34}$Lys$^{27}$-(Aspa-AHex)-GLP-1(7-37); Arg$^{26,34}$Lys$^{27}$-(Aspa-AHex)-GLP-1 (7-38); Gly$^8$Asp$^{19}$Arg$^{26,34}$Lys$^{27}$-(Aspa-AHex)-GLP-1(7-36); Gly$^8$Asp$^{17}$Arg$^{26,34}$Lys$^{27}$-(Aspa-AHex)-GLP-1(7-36);
Gly$^8$Asp$^{19}$Arg$^{26,34}$Lys$^{27}$-(Aspa-AHex)-GLP-1(7-36)amide;
Gly$^8$Asp$^{17}$Arg$^{26,34}$Lys$^{27}$-(Aspa-AHex)-GLP-1(7-36)amide;
Gly$^8$Asp$^{19}$Arg$^{26,34}$Lys$^{27}$-(Aspa-AHex)-GLP-1(7-37);
Gly$^8$Asp$^{19}$Arg$^{26,34}$Lys$^{27}$-(Aspa-AHex)-GLP-1(7-38);
Gly$^8$Asp$^{17}$Arg$^{26,34}$Lys$^{27}$-(Aspa-AHex)-GLP-1(7-38);
Arg$^{26,34}$Lys$^{18}$-(Aspa-AHex)-GLP-1(7-36); Arg$^{26,34}$Lys$^{18}$-(Aspa-AHex)-GLP-1(7-36)amide; Arg$^{26,34}$Lys$^{18}$-(Aspa-AHex)-GLP-1(7-37); Arg$^{26,34}$Lys$^{18}$-(Aspa-AHex)-GLP-1 (7-38); Val$^8$Asp$^{19}$Arg$^{26,34}$Lys$^{18}$-(Aspa-AHex)-GLP-1(7-36); Val$^8$Asp$^{17}$Arg$^{26,34}$Lys$^{18}$-(Aspa-AHex)-GLP-1(7-36);
Val$^8$Asp$^{19}$Arg$^{26,34}$Lys$^{18}$-(Aspa-AHex)-GLP-1(7-36)amide;
Val$^8$Asp$^{17}$Arg$^{26,34}$Lys$^{18}$-(Aspa-AHex)-GLP-1(7-36)amide;
Val$^8$Asp$^{19}$Arg$^{26,34}$Lys$^{18}$-(Aspa-AHex)-GLP-1(7-37);
Val$^8$Asp$^{19}$Arg$^{26,34}$Lys$^{18}$-(Aspa-AHex)-GLP-1(7-38);
Val$^8$Asp$^{17}$Arg$^{26,34}$Lys$^{18}$-(Aspa-AHex)-GLP-1(7-38);
Arg$^{26,34}$Lys$^{23}$-(Aspa-AHex)-GLP-1(7-36); Arg$^{26,34}$Lys$^{23}$-(Aspa-AHex)-GLP-1(7-36)amide; Arg$^{26,34}$Lys$^{23}$-(Aspa-AHex)-GLP-1(7-37); Arg$^{26,34}$Lys$^{23}$-(Aspa-AHex)-GLP-1 (7-38); Val$^8$Asp$^{19}$Arg$^{26,34}$Lys$^{23}$-(Aspa-AHex)-GLP-1(7-36); Val$^8$Asp$^{17}$Arg$^{26,34}$Lys$^{23}$(Aspa-AHex)-GLP-1(7-36);
Val$^8$Asp$^{19}$Arg$^{26,34}$Lys$^{23}$-(Aspa-AHex)-GLP-1(7-36)amide;
Val$^8$Asp$^{17}$Arg$^{26,34}$Lys$^{23}$-(Aspa-AHex)-GLP-1(7-36)amide;
Val$^8$Asp$^{19}$Arg$^{26,34}$Lys$^{23}$-(Aspa-AHex)-GLP-1(7-37);
Val$^8$Asp$^{19}$Arg$^{26,34}$Lys$^{23}$-(Aspa-AHex)-GLP-1(7-38);
Val$^8$Asp$^{17}$Arg$^{26,34}$Lys$^{23}$-(Aspa-AHex)-GLP-1(7-38);
Arg$^{26,34}$Lys$^{27}$-(Aspa-AHex)-GLP-1(7-36); Arg$^{26,34}$Lys$^{27}$-(Aspa-AHex)-GLP-1(7-36)amide; Arg$^{26,34}$Lys$^{27}$-(Aspa-AHex)-GLP-1(7-37); Arg$^{26,34}$Lys$^{27}$-(Aspa-AHex)-GLP-1 (7-38); Val$^8$Asp$^{19}$Arg$^{26,34}$Lys$^{27}$-(Aspa-AHex)-GLP-1(7-36); Val$^8$Asp$^{17}$Arg$^{26,34}$Lys$^{27}$(Aspa-AHex)-GLP-1(7-36);
Val$^8$Asp$^{19}$Arg$^{26,34}$Lys$^{27}$-(Aspa-AHex)-GLP-1(7-36)amide;
Val$^8$Asp$^{17}$Arg$^{26,34}$Lys$^{27}$-(Aspa-AHex)-GLP-1(7-36)amide;
Val$^8$Asp$^{19}$Arg$^{26,34}$Lys$^{27}$-(Aspa-AHex)-GLP-1(7-37);
Val$^8$Asp$^{19}$Arg$^{26,34}$Lys$^{27}$-(Aspa-AHex)-GLP-1(7-38);
Val$^8$Asp$^{17}$Arg$^{26,34}$Lys$^{27}$-(Aspa-AHex)-GLP-1(7-38);
Arg$^{26,34}$Lys$^{18}$-(Aspa-AHex)-GLP-1(7-36); Arg$^{26,34}$Lys$^{18}$-(Aspa-AHex)-GLP-1(7-36)amide; Arg$^{26,34}$Lys$^{18}$-(Aspa-AHex)-GLP-1(7-37); Arg$^{26,34}$Lys$^{18}$-(Aspa-AHex)-GLP-1 (7-38); Ser$^8$Asp$^{19}$Arg$^{26,34}$Lys$^{18}$-(Aspa-AHex)-GLP-1(7-36); Ser$^8$Asp$^{17}$Arg$^{26,34}$Lys$^{18}$-(Aspa-AHex)-GLP-1(7-36);
Ser$^8$Asp$^{19}$Arg$^{26,34}$Lys$^{18}$-(Aspa-AHex)-GLP-1(7-36)amide;
Ser$^8$Asp$^{17}$Arg$^{26,34}$Lys$^{18}$-(Aspa-AHex)-GLP-1(7-36)amide;
Ser$^8$Asp$^{19}$Arg$^{26,34}$Lys$^{18}$-(Aspa-AHex)-GLP-1(7-37);
Ser$^8$Asp$^{19}$Arg$^{26,34}$Lys$^{18}$-(Aspa-AHex)-GLP-1(7-38);
Ser$^8$Asp$^{17}$Arg$^{26,34}$Lys$^{18}$-(Aspa-AHex)-GLP-1(7-38);

Arg$^{26,34}$Lys$^{23}$-(Aspa-AHex)-GLP-1(7-36); Arg$^{26,34}$Lys$^{23}$-(Aspa-AHex)-GLP-1(7-36)amide; Arg$^{26,34}$Lys$^{23}$-(Aspa-AHex)-GLP-1(7-37); Arg$^{26,34}$Lys$^{23}$-(Aspa-AHex)-GLP-1(7-38); Ser$^8$Asp$^{19}$Arg$^{26,34}$Lys$^{23}$-(Aspa-AHex)-GLP-1(7-36); Ser$^8$Asp$^{17}$Arg$^{26,34}$Lys$^{23}$-(Aspa-AHex)-GLP-1(7-36); Ser$^8$Asp$^{19}$Arg$^{26,34}$Lys$^{23}$-(Aspa-AHex)-GLP-1(7-36)amide; Ser$^8$Asp$^{17}$Arg$^{26,34}$Lys$^{23}$-(Aspa-AHex)-GLP-1(7-36)amide; Ser$^8$Asp$^{19}$Arg$^{26,34}$Lys$^{23}$-(Aspa-AHex)-GLP-1(7-37); Ser$^8$Asp$^{19}$Arg$^{26,34}$Lys$^{23}$-(Aspa-AHex)-GLP-1(7-38); Ser$^8$Asp$^{17}$Arg$^{26,34}$Lys$^{23}$-(Aspa-AHex)-GLP-1(7-38); Arg$^{26,34}$Lys$^{27}$-(Aspa-AHex)-GLP-1(7-36); Arg$^{26,34}$Lys$^{27}$-(Aspa-AHex)-GLP-1(7-36)amide; Arg$^{26,34}$Lys$^{27}$-(Aspa-AHex)-GLP-1(7-37); Arg$^{26,34}$Lys$^{27}$-(Aspa-AHex)-GLP-1(7-38); Ser$^B$Asp$^{19}$Arg$^{26,34}$Lys$^{27}$-(Aspa-AHex)-GLP-1(7-36); Ser$^8$Asp$^{17}$Arg$^{26,34}$Lys$^{27}$-(Aspa-AHex)-GLP-1(7-36); Ser$^8$Asp$^{19}$Arg$^{26,34}$Lys$^{27}$-(Aspa-AHex)-GLP-1(7-36)amide; Ser$^8$Asp$^{17}$Arg$^{26,34}$Lys$^{27}$-(Aspa-AHex)-GLP-1(7-36)amide; Ser$^8$Asp$^{19}$Arg$^{26,34}$Lys$^{27}$-(Aspa-AHex)-GLP-1(7-37); Ser$^8$Asp$^{19}$Arg$^{26,34}$Lys$^{27}$-(Aspa-AHex)-GLP-1(7-38); Ser$^8$Asp$^{17}$Arg$^{26,34}$Lys$^{27}$-(Aspa-AHex)-GLP-1(7-38); Arg$^{26,34}$Lys$^{18}$-(Aspa-AHex)-GLP-1(7-36); Arg$^{26,34}$Lys$^{18}$-(Aspa-AHex)-GLP-1(7-36)amide; Arg$^{26,34}$Lys$^{18}$-(Aspa-AHex)-GLP-1(7-37); Arg$^{26,34}$Lys$^{18}$-(Aspa-AHex)-GLP-1(7-38); Thr$^8$Asp$^{19}$Arg$^{26,34}$Lys$^{18}$-(Aspa-AHex)-GLP-1(7-36); Thr$^8$Asp$^{17}$Arg$^{26,34}$Lys$^{18}$-(Aspa-AHex)-GLP-1(7-36); Thr$^8$Asp$^{19}$Arg$^{26,34}$Lys$^{18}$-(Aspa-AHex)-GLP-1(7-36)amide; Thr$^8$Asp$^{17}$Arg$^{26,34}$Lys$^{18}$-(Aspa-AHex)-GLP-1(7-36)amide; Thr$^8$Asp$^{19}$Arg$^{26,34}$Lys$^{18}$-(Aspa-AHex)-GLP-1(7-37); Thr$^8$Asp$^{19}$Arg$^{26,34}$Lys$^{18}$-(Aspa-AHex)-GLP-1(7-38); Thr$^8$Asp$^{17}$Arg$^{26,34}$Lys$^{18}$-(Aspa-AHex)-GLP-1(7-38); Arg$^{26,34}$Lys$^{23}$-(Aspa-AHex)-GLP-1(7-36); Arg$^{26,34}$Lys$^{23}$-(Aspa-AHex)-GLP-1(7-36)amide; Arg$^{26,34}$Lys$^{23}$-(Aspa-AHex)-GLP-1(7-37); Arg$^{26,34}$Lys$^{23}$-(Aspa-AHex)-GLP-1(7-38); Thr$^8$Asp$^{19}$Arg$^{26,34}$Lys$^{23}$-(Aspa-AHex)-GLP-1(7-36); Thr$^8$Asp$^{17}$Arg$^{26,34}$Lys$^{23}$(Aspa-AHex)-GLP-1(7-36); Thr$^8$Asp$^{19}$Arg$^{26,34}$Lys$^{23}$-(Aspa-AHex)-GLP-1(7-36)amide; Thr$^8$Asp$^{17}$Arg$^{26,34}$Lys$^{23}$-(Aspa-AHex)-GLP-1(7-36)amide; Thr$^8$Asp$^{19}$Arg$^{26,34}$Lys$^{23}$-(Aspa-AHex)-GLP-1(7-37); Thr$^8$Asp$^{19}$Arg$^{26,34}$Lys$^{23}$-(Aspa-AHex)-GLP-1(7-38); Thr$^8$Asp$^{17}$Arg$^{26,34}$Lys$^{23}$-(Aspa-AHex)-GLP-1(7-38); Arg$^{26,34}$Lys$^{27}$-(Aspa-AHex)-GLP-1(7-36); Arg$^{26,34}$Lys$^{27}$-(Aspa-AHex)-GLP-1(7-36)amide; Arg$^{26,34}$Lys$^{27}$-(Aspa-AHex)-GLP-1(7-37); Arg$^{26,34}$Lys$^{27}$-(Aspa-AHex)-GLP-1(7-38); Thr$^8$Asp$^{19}$Arg$^{26,34}$Lys$^{27}$-(Aspa-AHex)-GLP-1(7-36); Thr$^8$Asp$^{17}$Arg$^{26,34}$Lys$^{27}$(Aspa-AHex)-GLP-1(7-36); Thr$^8$Asp$^{19}$Arg$^{26,34}$Lys$^{27}$-(Aspa-AHex)-GLP-1(7-36)amide; Thr$^8$Asp$^{17}$Arg$^{26,34}$Lys$^{27}$-(Aspa-AHex)-GLP-1(7-36)amide; Thr$^8$Asp$^{19}$Arg$^{26,34}$Lys$^{27}$-(Aspa-AHex)-GLP-1(7-37); Thr$^8$Asp$^{19}$Arg$^{26,34}$Lys$^{27}$-(Aspa-AHex)-GLP-1(7-38); Thr$^8$Asp$^{17}$Arg$^{26,34}$Lys$^{27}$-(Aspa-AHex)-GLP-1(7-38); Arg$^{26}$Lys$^{34}$-(Aspa-AOct)-GLP-1(7-36); Arg$^{34}$Lys$^{26}$-(Aspa-AOct)-GLP-1(7-36); Arg$^{26,34}$Lys$^{36}$-(Aspa-AOct)-GLP-1(7-36); Arg$^{26}$Lys$^{34}$-(Aspa-AOct)-GLP-1(7-36)amide; Arg$^{34}$Lys$^{26}$-(Aspa-AOct)-GLP-1(7-36)amide; Arg$^{26,34}$Lys$^{36}$-(Aspa-AOct)-GLP-1(7-36)amide; Arg$^{26}$Lys$^{34}$-(Aspa-AOct)-GLP-1(7-37); Arg$^{34}$Lys$^{26}$-(Aspa-AOct)-GLP-1(7-37); Arg$^{26,34}$Lys$^{36}$-(Aspa-AOct)-GLP-1(7-37); Arg$^{26}$Lys$^{34}$-(Aspa-AOct)-GLP-1(7-38); Arg$^{34}$Lys$^{26}$-(Aspa-AOct)-GLP-1(7-38); Arg$^{26,34}$Lys$^{38}$-(Aspa-AOct)-GLP-1(7-38); Arg$^{26}$Lys$^{34}$-(Aspa-AOct)-GLP-1(7-39); Arg$^{34}$Lys$^{26}$-(Aspa-AOct)-GLP-1(7-39); Arg$^{26,34}$Lys$^{39}$-(Aspa-AOct)-GLP-1(7-39); Gly$^8$Arg$^{26}$Lys$^{34}$-(Aspa-AOct)-GLP-1(7-36); Gly$^8$Arg$^{34}$Lys$^{26}$-(Aspa-AOct)-GLP-1(7-36); Gly$^8$Arg$^{26,34}$Lys$^{36}$-(Aspa-AOct)-GLP-1(7-36); Gly$^8$Arg$^{26}$Lys$^{34}$-(Aspa-AOct)-GLP-1(7-36)amide; Gly$^8$Arg$^{34}$Lys$^{26}$-(Aspa-AOct)-GLP-1(7-36)amide; Gly$^8$Arg$^{26,34}$Lys$^{36}$-(Aspa-AOct)-GLP-1(7-36)amide; Gly$^8$Arg$^{26}$Lys$^{34}$-(Aspa-AOct)-GLP-1(7-37); Gly$^8$Arg$^{34}$Lys$^{26}$-(Aspa-AOct)-GLP-1(7-37); Gly$^8$Arg$^{26,34}$Lys$^{36}$-(Aspa-AOct)-GLP-1(7-37); Gly$^8$Arg$^{26}$Lys$^{34}$-(Aspa-AOct)-GLP-1(7-38); Gly$^8$Arg$^{34}$Lys$^{26}$-(Aspa-AOct)-GLP-1(7-38); Gly$^8$Arg$^{26,34}$Lys$^{38}$-(Aspa-AOct)-GLP-1(7-38); Gly$^8$Arg$^{26}$Lys$^{34}$-(Aspa-AOct)-GLP-1(7-39); Gly$^8$Arg$^{34}$Lys$^{26}$-(Aspa-AOct)-GLP-1(7-39); Gly$^8$Arg$^{26,34}$Lys$^{39}$-(Aspa-AOct)-GLP-1(7-39);
Val$^8$Arg$^{26}$Lys$^{34}$-(Aspa-AOct)-GLP-1(7-36); Val$^8$Arg$^{34}$Lys$^{26}$-(Aspa-AOct)-GLP-1(7-36); Val$^8$Arg$^{26,34}$Lys$^{36}$-(Aspa-AOct)-GLP-1(7-36); Val$^8$Arg$^{26}$Lys$^{34}$-(Aspa-AOct)-GLP-1(7-36)amide; Val$^8$Arg$^{34}$Lys$^{26}$-(Aspa-AOct)-GLP-1(7-36)amide; Val$^8$Arg$^{26,34}$Lys$^{36}$-(Aspa-AOct)-GLP-1(7-36)amide; Val$^8$Arg$^{26}$Lys$^{34}$-(Aspa-AOct)-GLP-1(7-37); Val$^8$Arg$^{34}$Lys$^{26}$-(Aspa-AOct)-GLP-1(7-37); Val$^8$Arg$^{26,34}$Lys$^{36}$-(Aspa-AOct)-GLP-1(7-37); Val$^8$Arg$^{26}$Lys$^{34}$-(Aspa-AOct)-GLP-1(7-38); Val$^8$Arg$^{34}$Lys$^{26}$-(Aspa-AOct)-GLP-1(7-38); Val$^8$Arg$^{26,34}$Lys$^{38}$-(Aspa-AOct)-GLP-1(7-38); Val$^8$Arg$^{26}$Lys$^{34}$-(Aspa-AOct)-GLP-1(7-39); Val$^8$Arg$^{34}$Lys$^{26}$-(Aspa-AOct)-GLP-1(7-39); Val$^8$Arg$^{26,34}$Lys$^{39}$-(Aspa-AOct)-GLP-1(7-39);
Ser$^8$Arg$^{26}$Lys$^{34}$-(Aspa-AOct)-GLP-1(7-36); Ser$^8$Arg$^{34}$Lys$^{26}$-(Aspa-AOct)-GLP-1(7-36); Ser$^8$Arg$^{26,34}$Lys$^{36}$-(Aspa-AOct)-GLP-1(7-36); Ser$^8$Arg$^{26}$Lys$^{34}$-(Aspa-AOct)-GLP-1(7-36)amide; Ser$^8$Arg$^{34}$Lys$^{26}$-(Aspa-AOct)-GLP-1(7-36)amide; Ser$^8$Arg$^{26,34}$Lys$^{36}$-(Aspa-AOct)-GLP-1(7-36)amide; Ser$^8$Arg$^{26}$Lys$^{34}$-(Aspa-AOct)-GLP-1(7-37); Ser$^8$Arg$^{34}$Lys$^{26}$-(Aspa-AOct)-GLP-1(7-37); Ser$^8$Arg$^{26,34}$Lys$^{36}$-(Aspa-AOct)-GLP-1(7-37); Ser$^8$Arg$^{26}$Lys$^{34}$-(Aspa-AOct)-GLP-1(7-38); Ser$^8$Arg$^{34}$Lys$^{26}$-(Aspa-AOct)-GLP-1(7-38); Ser$^8$Arg$^{26,34}$Lys$^{38}$-(Aspa-AOct)-GLP-1(7-38); Ser$^8$Arg$^{26}$Lys$^{34}$-(Aspa-AOct)-GLP-1(7-39); Ser$^8$Arg$^{34}$Lys$^{26}$-(Aspa-AOct)-GLP-1(7-39); Ser$^8$Arg$^{26,34}$Lys$^{39}$-(Aspa-AOct)-GLP-1(7-39);
Thr$^8$Arg$^{26}$Lys$^{34}$-(Aspa-AOct)-GLP-1(7-36); Thr$^8$Arg$^{34}$Lys$^{26}$-(Aspa-AOct)-GLP-1(7-36); Thr$^8$Arg$^{26,34}$Lys$^{36}$-(Aspa-AOct)-GLP-1(7-36); Thr$^8$Arg$^{26}$Lys$^{34}$-(Aspa-AOct)-GLP-1(7-36)amide; Thr$^8$Arg$^{34}$Lys$^{26}$-(Aspa-AOct)-GLP-1(7-36)amide; Thr$^8$Arg$^{26,34}$Lys$^{36}$-(Aspa-AOct)-GLP-1(7-36)amide; Thr$^8$Arg$^{26}$Lys$^{34}$-(Aspa-AOct)-GLP-1(7-37); Thr$^8$Arg$^{34}$Lys$^{26}$-(Aspa-AOct)-GLP-1(7-37); Thr$^8$Arg$^{26,34}$Lys$^{36}$-(Aspa-AOct)-GLP-1(7-37); Thr$^8$Arg$^{26}$Lys$^{34}$-(Aspa-AOct)-GLP-1(7-38); Thr$^8$Arg$^{34}$Lys$^{26}$-(Aspa-AOct)-GLP-1(7-38); Thr$^8$Arg$^{26,34}$Lys$^{38}$-(Aspa-AOct)-GLP-1(7-38); Thr$^8$Arg$^{26}$Lys$^{34}$-(Aspa-AOct)-GLP-1(7-39); Thr$^8$Arg$^{34}$Lys$^{26}$-(Aspa-AOct)-GLP-1(7-39); Thr$^8$Arg$^{26,34}$Lys$^{39}$-(Aspa-AOct)-GLP-1(7-39);
Gly$^8$Glu$^{35}$Arg$^{26,34}$Lys$^{36}$-(Aspa-AOct)-GLP-1(7-36); Gly$^8$Glu$^{35}$Arg$^{26,34}$Lys$^{36}$-(Aspa-AOct)-GLP-1(7-36)amide; Gly$^8$Glu$^{36}$Arg$^{26,34}$Lys$^{37}$-(Aspa-AOct)-GLP-1(7-37); Gly$^8$Glu$^{37}$Arg$^{26,34}$Lys$^{38}$-(Aspa-AOct)-GLP-1(7-38); Gly$^8$Glu$^{38}$Arg$^{26,34}$Lys$^{39}$-(Aspa-AOct)-GLP-1(7-39); Gly$^8$Glu$^{35}$Arg$^{26,34}$Lys$^{36}$-(Aspa-AOct)-GLP-1(7-36); Gly$^8$Glu$^{35}$Arg$^{26,34}$Lys$^{36}$-(Aspa-AOct)-GLP-1(7-36)amide; Gly$^8$Glu$^{36}$Arg$^{26,34}$Lys$^{37}$-(Aspa-AOct)-GLP-1(7-37); Gly$^8$Glu$^{37}$Arg$^{26,34}$Lys$^{18,38}$-(Aspa-AOct)-GLP-1(7-38); Gly$^8$Glu$^{38}$Arg$^{26,34}$Lys$^{39}$-(Aspa-AOct)-GLP-1(7-39); Gly$^8$Asp$^{35}$Arg$^{26,34}$Lys$^{36}$-(Aspa-AOct)-GLP-1(7-36); Gly$^8$Asp$^{35}$Arg$^{26,34}$Lys$^{36}$-(Aspa-AOct)-GLP-1(7-36)amide; Gly$^8$Asp$^{36}$Arg$^{26,34}$Lys$^{37}$-(Aspa-AOct)-GLP-1(7-37); Gly$^8$Asp$^{37}$Arg$^{26,34}$Lys$^{38}$-(Aspa-AOct)-GLP-1(7-38); Gly$^8$Asp$^{38}$Arg$^{26,34}$Lys$^{39}$-(Aspa-AOct)-GLP-1(7-39); Gly$^8$Asp$^{35}$Arg$^{26,34}$Lys$^{36}$-(Aspa-AOct)-GLP-1(7-36);

Gly$^8$Asp$^{35}$Arg$^{26,34}$Lys$^{36}$-(Aspa-AOct)-GLP-1(7-36)amide;
Gly$^8$Asp$^{36}$Arg$^{26,34}$Lys$^{37}$-(Aspa-AOct)-GLP-1(7-37);
Gly$^8$Asp$^{37}$Arg$^{26,34}$Lys$^{38}$-(Aspa-AOct)-GLP-1(7-38);
Gly$^8$Asp$^{38}$Arg$^{26,34}$Lys$^{39}$-(Aspa-AOct)-GLP-1(7-39);
Val$^8$Glu$^{35}$Arg$^{26,34}$Lys$^{36}$-(Aspa-AOct)-GLP-1(7-36);
Val$^8$Glu$^3$Arg$^{26,34}$Lys$^{36}$-(Aspa-AOct)-GLP-1(7-36)amide;
Val$^8$Glu$^{36}$Arg$^{26,34}$Lys$^{37}$-(Aspa-AOct)-GLP-1(7-37);
Val$^8$Glu$^{37}$Arg$^{26,34}$Lys$^{38}$-(Aspa-AOct)-GLP-1(7-38);
Val$^8$Glu$^{38}$Arg$^{26,34}$Lys$^{39}$-(Aspa-AOct)-GLP-1(7-39);
Val$^8$Glu$^{35}$Arg$^{26,34}$Lys$^{36}$-(Aspa-AOct)-GLP-1(7-36);
Val$^8$Glu$^{35}$Arg$^{26,34}$Lys$^{36}$-(Aspa-AOct)-GLP-1(7-36)amide;
Val$^8$Glu$^{36}$Arg$^{26,34}$Lys$^{37}$-(Aspa-AOct)-GLP-1(7-37);
Val$^8$Glu$^{37}$Arg$^{26,34}$Lys$^{38}$-(Aspa-AOct)-GLP-1(7-38);
Val$^8$Glu$^{38}$Arg$^{26,34}$Lys$^{39}$-(Aspa-AOct)-GLP-1(7-39);
Val$^8$Asp$^{35}$Arg$^{26,34}$Lys$^{36}$-(Aspa-AOct)-GLP-1(7-36);
Val$^8$Asp$^{35}$Arg$^{26,34}$Lys$^{36}$-(Aspa-AOct)-GLP-1(7-36)amide;
Val$^8$Asp$^{36}$Arg$^{26,34}$Lys$^{37}$-(Aspa-AOct)-GLP-1(7-37);
Val$^8$Asp$^{37}$Arg$^{26,34}$Lys$^{38}$-(Aspa-AOct)-GLP-1(7-38);
Val$^8$Asp$^{38}$Arg$^{26,34}$Lys$^{39}$-(Aspa-AOct)-GLP-1(7-39);
Val$^8$Asp$^{35}$Arg$^{26,34}$Lys$^{36}$-(Aspa-AOct)-GLP-1(7-36);
Val$^8$Asp$^{35}$Arg$^{26,34}$Lys$^{36}$-(Aspa-AOct)-GLP-1(7-36)amide;
Val$^8$Asp$^{36}$Arg$^{26,34}$Lys$^{37}$-(Aspa-AOct)-GLP-1(7-37);
Val$^8$Asp$^{37}$Arg$^{26,34}$Lys$^{38}$-(Aspa-AOct)-GLP-1(7-38);
Val$^8$Asp$^{38}$Arg$^{26,34}$Lys$^{39}$-(Aspa-AOct)-GLP-1(7-39);
Ser$^8$Glu$^{35}$Arg$^{26,34}$Lys$^{36}$-(Aspa-AOct)-GLP-1(7-36);
Ser$^8$Glu$^{35}$Arg$^{26,34}$Lys$^{36}$-(Aspa-AOct)-GLP-1(7-36)amide;
Ser$^8$Glu$^{36}$Arg$^{26,34}$Lys$^{37}$-(Aspa-AOct)-GLP-1(7-37);
Ser$^8$Glu$^{37}$Arg$^{26,34}$Lys$^{38}$-(Aspa-AOct)-GLP-1(7-38);
Ser$^8$Glu$^{38}$Arg$^{26,34}$Lys$^{39}$-(Aspa-AOct)-GLP-1(7-39);
Ser$^8$Glu$^{35}$Arg$^{26,34}$Lys$^{36}$-(Aspa-AOct)-GLP-1(7-36);
Ser$^8$Glu$^{35}$Arg$^{26,34}$Lys$^{36}$-(Aspa-AOct)-GLP-1(7-36)amide;
Ser$^8$Glu$^{36}$Arg$^{26,34}$Lys$^{37}$-(Aspa-AOct)-GLP-1(7-37);
Ser$^8$Glu$^{37}$Arg$^{26,34}$Lys$^{38}$-(Aspa-AOct)-GLP-1(7-38);
Ser$^8$Glu$^{38}$Arg$^{26,34}$Lys$^{39}$-(Aspa-AOct)-GLP-1(7-39);
Ser$^8$Asp$^{35}$Arg$^{26,34}$Lys$^{36}$-(Aspa-AOct)-GLP-1(7-36);
Ser$^8$Asp$^{35}$Arg$^{26,34}$Lys$^{36}$-(Aspa-AOct)-GLP-1(7-36)amide;
Ser$^8$Asp$^{36}$Arg$^{26,34}$Lys$^{37}$-(Aspa-AOct)-GLP-1(7-37);
Ser$^8$Asp$^{37}$Arg$^{26,34}$Lys$^{38}$-(Aspa-AOct)-GLP-1(7-38);
Ser$^8$Asp$^{38}$Arg$^{26,34}$Lys$^{39}$-(Aspa-AOct)-GLP-1(7-39);
Ser$^8$Asp$^{35}$Arg$^{26,34}$Lys$^{36}$-(Aspa-AOct)-GLP-1(7-36);
Ser$^8$Asp$^{35}$Arg$^{26,34}$Lys$^{36}$-(Aspa-AOct)-GLP-1(7-36)amide;
Ser$^8$Asp$^{36}$Arg$^{26,34}$Lys$^{37}$-(Aspa-AOct)-GLP-1(7-37);
Ser$^8$Asp$^{37}$Arg$^{26,34}$Lys$^{38}$-(Aspa-AOct)-GLP-1(7-38);
Ser$^8$Asp$^{38}$Arg$^{26,34}$Lys$^{39}$-(Aspa-AOct)-GLP-1(7-39);
Thr$^8$Glu$^{35}$Arg$^{26,34}$Lys$^{36}$-(Aspa-AOct)-GLP-1(7-36);
Thr$^8$Glu$^{35}$Arg$^{26,34}$Lys$^{36}$-(Aspa-AOct)-GLP-1(7-36)amide;
Thr$^8$Glu$^{36}$Arg$^{26,34}$Lys$^{37}$-(Aspa-AOct)-GLP-1(7-37);
Thr$^8$Glu$^{37}$Arg$^{26,34}$Lys$^{38}$-(Aspa-AOct)-GLP-1(7-38);
Thr$^8$Glu$^{38}$Arg$^{26,34}$Lys$^{39}$-(Aspa-AOct)-GLP-1(7-39);
Thr$^8$Glu$^{35}$Arg$^{26,34}$Lys$^{36}$-(Aspa-AOct)-GLP-1(7-36);
Thr$^8$Glu$^{35}$Arg$^{26,34}$Lys$^{36}$-(Aspa-AOct)-GLP-1(7-36)amide;
Thr$^8$Glu$^{36}$Arg$^{26,34}$Lys$^{37}$-(Aspa-AOct)-GLP-1(7-37);
Thr$^8$Glu$^{37}$Arg$^{26,34}$Lys$^{38}$-(Aspa-AOct)-GLP-1(7-38);
Thr$^8$Glu$^{38}$Arg$^{26,34}$Lys$^{39}$-(Aspa-AOct)-GLP-1(7-39);
Thr$^8$Asp$^{35}$Arg$^{26,34}$Lys$^{36}$-(Aspa-AOct)-GLP-1(7-36);
Thr$^8$Asp$^{35}$Arg$^{26,34}$Lys$^{36}$-(Aspa-AOct)-GLP-1(7-36)amide;
Thr$^8$Asp$^{36}$Arg$^{26,34}$Lys$^{37}$-(Aspa-AOct)-GLP-1(7-37);
Thr$^8$Asp$^{37}$Arg$^{26,34}$Lys$^{38}$-(Aspa-AOct)-GLP-1(7-38);
Thr$^8$Asp$^{38}$Arg$^{26,34}$Lys$^{39}$-(Aspa-AOct)-GLP-1(7-39);
Thr$^8$Asp$^{35}$Arg$^{26,34}$Lys$^{36}$-(Aspa-AOct)-GLP-1(7-36);
Thr$^8$Asp$^{35}$Arg$^{26,34}$Lys$^{36}$-(Aspa-AOct)-GLP-1(7-36)amide;
Thr$^8$Asp$^{36}$Arg$^{26,34}$Lys$^{37}$-(Aspa-AOct)-GLP-1(7-37);
Thr$^8$Asp$^{37}$Arg$^{26,34}$Lys$^{38}$-(Aspa-AOct)-GLP-1(7-38);
Thr$^8$Asp$^3$Arg$^{26,34}$Lys$^{39}$-(Aspa-AOct)-GLP-1(7-39);
Arg$^{26,34}$Lys$^{18}$-(Aspa-AOct)-GLP-1(7-36); Arg$^{26,34}$Lys$^{18}$-(Aspa-AOct)-GLP-1(7-36)amide; Arg$^{26,34}$Lys$^{18}$-(Aspa-AOct)-GLP-1(7-37); Arg$^{26,34}$Lys$^{18}$-(Aspa-AOct)-GLP-1(7-38); Gly$^8$Asp$^{19}$Arg$^{26,34}$Lys$^{18}$-(Aspa-AOct)-GLP-1(7-36); Gly$^8$Asp$^{17}$Arg$^{26,34}$Lys$^{18}$-(Aspa-AOct)-GLP-1(7-36); Gly$^8$Asp$^{19}$Arg$^{26,34}$Lys$^{18}$-(Aspa-AOct)-GLP-1(7-36)amide; Gly$^8$Asp$^{17}$Arg$^{26,34}$Lys$^{18}$-(Aspa-AOct)-GLP-1(7-36)amide; Gly$^8$Asp$^{19}$Arg$^{26,34}$Lys$^{18}$-(Aspa-AOct)-GLP-1(7-37); Gly$^8$Asp$^{19}$Arg$^{26,34}$Lys$^{18}$-(Aspa-AOct)-GLP-1(7-38); Gly$^8$Asp$^{17}$Arg$^{26,34}$Lys$^{18}$-(Aspa-AOct)-GLP-1(7-38); Arg$^{26,34}$Lys$^{23}$-(Aspa-AOct)-GLP-1(7-36); Arg$^{26,34}$Lys$^{23}$-(Aspa-AOct)-GLP-1(7-36)amide; Arg$^{26,34}$Lys$^{23}$-(Aspa-AOct)-GLP-1(7-37); Arg$^{26,34}$Lys$^{23}$-(Aspa-AOct)-GLP-1(7-38); Gly$^8$Asp$^{19}$Arg$^{26,34}$Lys$^{23}$-(Aspa-AOct)-GLP-1(7-36); Gly$^8$Asp$^{17}$Arg$^{26,34}$Lys$^{23}$-(Aspa-AOct)-GLP-1(7-36); Gly$^8$Asp$^{19}$Arg$^{26,34}$Lys$^{23}$-(Aspa-AOct)-GLP-1(7-36)amide; Gly$^8$Asp$^{17}$Arg$^{26,34}$Lys$^{23}$-(Aspa-AOct)-GLP-1(7-36)amide; Gly$^8$Asp$^{19}$Arg$^{26,34}$Lys$^{23}$-(Aspa-AOct)-GLP-1(7-37); Gly$^8$Asp$^{19}$Arg$^{26,34}$Lys$^{23}$-(Aspa-AOct)-GLP-1(7-38); Gly$^8$Asp$^{17}$Arg$^{26,34}$Lys$^{23}$-(Aspa-AOct)-GLP-1(7-38); Arg$^{26,34}$Lys$^{27}$-(Aspa-AOct)-GLP-1(7-36); Arg$^{26,34}$Lys$^{27}$-(Aspa-AOct)-GLP-1(7-36)amide; Arg$^{26,34}$Lys$^{27}$-(Aspa-AOct)-GLP-1(7-37); Arg$^{26,34}$Lys$^{27}$-(Aspa-AOct)-GLP-1(7-38); Gly$^8$Asp$^{19}$Arg$^{26,34}$Lys$^{27}$-(Aspa-AOct)-GLP-1(7-36); Gly$^8$Asp$^{17}$Arg$^{26,34}$Lys$^{27}$-(Aspa-AOct)-GLP-1(7-36); Gly$^8$Asp$^{19}$Arg$^{26,34}$Lys$^{27}$-(Aspa-AOct)-GLP-1(7-36)amide; Gly$^8$Asp$^{17}$Arg$^{26,34}$Lys$^{27}$-(Aspa-AOct)-GLP-1(7-36)amide; Gly$^8$Asp$^{19}$Arg$^{26,34}$Lys$^{27}$-(Aspa-AOct)-GLP-1(7-37); Gly$^8$Asp$^{19}$Arg$^{26,34}$Lys$^{27}$-(Aspa-AOct)-GLP-1(7-38); Gly$^8$Asp$^{17}$Arg$^{26,34}$Lys$^{27}$-(Aspa-AOct)-GLP-1(7-38); Arg$^{26,34}$Lys$^{18}$-(Aspa-AOct)-GLP-1(7-36); Arg$^{26,34}$Lys$^{18}$-(Aspa-AOct)-GLP-1(7-36)amide; Arg$^{26,34}$Lys$^{18}$-(Aspa-AOct)-GLP-1(7-37); Arg$^{26,34}$Lys$^{18}$-(Aspa-AOct)-GLP-1(7-38); Val$^8$Asp$^{19}$Arg$^{26,34}$Lys$^{18}$-(Aspa-AOct)-GLP-1(7-36); Val$^8$Asp$^{17}$Arg$^{26,34}$Lys$^{18}$-(Aspa-AOct)-GLP-1(7-36); Val$^8$Asp$^{19}$Arg$^{26,34}$Lys$^{18}$-(Aspa-AOct)-GLP-1(7-36)amide; Val$^8$Asp$^{17}$Arg$^{26,34}$Lys$^{18}$-(Aspa-AOct)-GLP-1(7-36)amide; Val$^8$Asp$^{19}$Arg$^{26,34}$Lys$^{18}$-(Aspa-AOct)-GLP-1(7-37); Val$^8$Asp$^{19}$Arg$^{26,34}$Lys$^{18}$-(Aspa-AOct)-GLP-1(7-38); Val$^8$Asp$^{17}$Arg$^{26,34}$Lys$^{18}$-(Aspa-AOct)-GLP-1(7-38); Arg$^{26,34}$Lys$^{23}$-(Aspa-AOct)-GLP-1(7-36); Arg$^{26,34}$Lys$^{23}$-(Aspa-AOct)-GLP-1(7-36)amide; Arg$^{26,34}$Lys$^{23}$-(Aspa-AOct)-GLP-1(7-37); Arg$^{26,34}$Lys$^{23}$-(Aspa-AOct)-GLP-1(7-38); Val$^8$Asp$^{19}$Arg$^{26,34}$Lys$^{23}$-(Aspa-AOct)-GLP-1(7-36); Val$^8$Asp$^{17}$Arg$^{26,34}$Lys$^{23}$-(Aspa-AOct)-GLP-1(7-36); Val$^8$Asp$^{19}$Arg$^{26,34}$Lys$^{23}$-(Aspa-AOct)-GLP-1(7-36)amide; Val$^8$Asp$^{17}$Arg$^{26,34}$Lys$^{23}$-(Aspa-AOct)-GLP-1(7-36)amide; Val$^8$Asp$^{19}$Arg$^{26,34}$Lys$^{23}$-(Aspa-AOct)-GLP-1(7-37); Val$^8$Asp$^{19}$Arg$^{26,34}$Lys$^{23}$-(Aspa-AOct)-GLP-1(7-38); Val$^8$Asp$^{17}$Arg$^{26,34}$Lys$^{23}$-(Aspa-AOct)-GLP-1(7-38); Arg$^{26,34}$Lys$^{27}$-(Aspa-AOct)-GLP-1(7-36); Arg$^{26,34}$Lys$^{27}$-(Aspa-AOct)-GLP-1(7-36)amide; Arg$^{26,34}$Lys$^{27}$-(Aspa-AOct)-GLP-1(7-37); Arg$^{26,34}$Lys$^{27}$-(Aspa-AOct)-GLP-1(7-38); Val$^8$Asp$^{19}$Arg$^{26,34}$Lys$^{27}$-(Aspa-AOct)-GLP-1(7-36); Val$^8$Asp$^{17}$Arg$^{26,34}$Lys$^{27}$-(Aspa-AOct)-GLP-1(7-36); Val$^8$Asp$^{19}$Arg$^{26,34}$Lys$^{27}$-(Aspa-AOct)-GLP-1(7-36)amide; Val$^8$Asp$^{17}$Arg$^{26,34}$Lys$^{27}$-(Aspa-AOct)-GLP-1(7-36)amide; Val$^8$Asp$^{19}$Arg$^{26,34}$Lys$^{27}$-(Aspa-AOct)-GLP-1(7-37); Val$^8$Asp$^{19}$Arg$^{26,34}$Lys$^{27}$-(Aspa-AOct)-GLP-1(7-38); Val$^8$Asp$^{17}$Arg$^{26,34}$Lys$^{27}$-(Aspa-AOct)-GLP-1(7-38); Arg$^{26,34}$Lys$^{18}$-(Aspa-AOct)-GLP-1(7-36); Arg$^{26,34}$Lys$^{18}$-(Aspa-AOct)-GLP-1(7-36)amide; Arg$^{26,34}$Lys$^{18}$-(Aspa-AOct)-GLP-1(7-37); Arg$^{26,34}$Lys$^{18}$-(Aspa-AOct)-GLP-1(7-38); Ser$^8$Asp$^{19}$Arg$^{26,34}$Lys$^{18}$-(Aspa-AOct)-GLP-1(7-36); Ser$^8$Asp$^{17}$Arg$^{26,34}$Lys$^{18}$-(Aspa-AOct)-GLP-1(7-36); Ser$^8$Asp$^{19}$Arg$^{26,34}$Lys$^{18}$-(Aspa-AOct)-GLP-1(7-36)amide; Ser$^8$Asp$^{17}$Arg$^{26,34}$Lys$^{18}$-(Aspa-AOct)-GLP-1(7-36)amide; Ser$^8$Asp$^{19}$Arg$^{26,34}$Lys$^{18}$-(Aspa-AOct)-GLP-1(7-37); Ser$^8$Asp$^{19}$Arg$^{26,34}$Lys$^{18}$-(Aspa-AOct)-GLP-1(7-38); Ser$^8$Asp$^{17}$Arg$^{26,34}$Lys$^{18}$-(Aspa-AOct)-GLP-1(7-38);

Arg$^{26,34}$Lys$^{23}$-(Aspa-AOct)-GLP-1(7-36); Arg$^{26,34}$Lys$^{23}$-(Aspa-AOct)-GLP-1(7-36)amide; Arg$^{26,34}$Lys$^{23}$-(Aspa-AOct)-GLP-1(7-37); Arg$^{26,34}$Lys$^{23}$-(Aspa-AOct)-GLP-1(7-38); Ser$^8$Asp$^{19}$Arg$^{26,34}$Lys$^{23}$-(Aspa-AOct)-GLP-1(7-36); Ser$^8$Asp$^{17}$Arg$^{26,34}$Lys$^{23}$-(Aspa-AOct)-GLP-1(7-36); Ser$^8$Asp$^{19}$Arg$^{26,34}$Lys$^{23}$-(Aspa-AOct)-GLP-1(7-36)amide; Ser$^8$Asp$^{17}$Arg$^{26,34}$Lys$^{23}$-(Aspa-AOct)-GLP-1(7-36)amide; Ser$^8$Asp$^{19}$Arg$^{26,34}$Lys$^{23}$-(Aspa-AOct)-GLP-1(7-37); Ser$^8$Asp$^{19}$Arg$^{26,34}$Lys$^{23}$-(Aspa-AOct)-GLP-1(7-38); Ser$^8$Asp$^{17}$Arg$^{26,34}$Lys$^{23}$-(Aspa-AOct)-GLP-1(7-38); Arg$^{26,34}$Lys$^{27}$-(Aspa-AOct)-GLP-1(7-36); Arg$^{26,34}$Lys$^{27}$-(Aspa-AOct)-GLP-1(7-36)amide; Arg$^{26,34}$Lys$^{27}$-(Aspa-AOct)-GLP-1(7-37); Arg$^{26,34}$Lys$^{27}$-(Aspa-AOct)-GLP-1(7-38); Ser$^8$Asp$^{19}$Arg$^{26,34}$Lys$^{27}$-(Aspa-AOct)-GLP-1(7-36); Ser$^8$Asp$^{17}$Arg$^{26,34}$Lys$^{27}$-(Aspa-AOct)-GLP-1(7-36); Ser$^8$Asp$^{19}$Arg$^{26,34}$Lys$^{27}$-(Aspa-AOct)-GLP-1(7-36)amide; Ser$^8$Asp$^{17}$Arg$^{26,34}$Lys$^{27}$-(Aspa-AOct)-GLP-1(7-36)amide; Ser$^8$Asp$^{19}$Arg$^{26,34}$Lys$^{27}$-(Aspa-AOct)-GLP-1(7-37); Ser$^8$Asp$^{19}$Arg$^{26,34}$Lys$^{27}$-(Aspa-AOct)-GLP-1(7-38); Ser$^8$Asp$^{17}$Arg$^{26,34}$Lys$^{27}$-(Aspa-AOct)-GLP-1(7-38); Arg$^{26,34}$Lys$^{18}$-(Aspa-AOct)-GLP-1(7-36); Arg$^{26,34}$Lys$^{18}$-(Aspa-AOct)-GLP-1(7-36)amide; Arg$^{26,34}$Lys$^{18}$-(Aspa-AOct)-GLP-1(7-37); Arg$^{26,34}$Lys$^{18}$-(Aspa-AOct)-GLP-1(7-38); Thr$^8$Asp$^{19}$Arg$^{26,34}$Lys$^{18}$-(Aspa-AOct)-GLP-1(7-36); Thr$^8$Asp$^{17}$Arg$^{26,34}$Lys$^{18}$-(Aspa-AOct)-GLP-1(7-36); Thr$^8$Asp$^{19}$Arg$^{26,34}$Lys$^{18}$-(Aspa-AOct)-GLP-1(7-36)amide; Thr$^8$Asp$^{17}$Arg$^{26,34}$Lys$^{18}$-(Aspa-AOct)-GLP-1(7-36)amide; Thr$^8$Asp$^{19}$Arg$^{26,34}$Lys$^{18}$-(Aspa-AOct)-GLP-1(7-37); Thr$^8$Asp$^{19}$Arg$^{26,34}$Lys$^{18}$-(Aspa-AOct)-GLP-1(7-38); Thr$^8$Asp$^{17}$Arg$^{26,34}$Lys$^{18}$-(Aspa-AOct)-GLP-1(7-38); Arg$^{26,34}$Lys$^{23}$-(Aspa-AOct)-GLP-1(7-36); Arg$^{26,34}$Lys$^{23}$-(Aspa-AOct)-GLP-1(7-36)amide; Arg$^{26,34}$Lys$^{23}$-(Aspa-AOct)-GLP-1(7-37); Arg$^{26,34}$Lys$^{23}$-(Aspa-AOct)-GLP-1(7-38); Thr$^8$Asp$^{19}$Arg$^{26,34}$Lys$^{23}$-(Aspa-AOct)-GLP-1(7-36); Thr$^8$Asp$^{17}$Arg$^{26,34}$Lys$^{23}$-(Aspa-AOct)-GLP-1(7-36); Thr$^8$Asp$^{19}$Arg$^{26,34}$Lys$^{23}$-(Aspa-AOct)-GLP-1(7-36)amide; Thr$^8$Asp$^{17}$Arg$^{26,34}$Lys$^{23}$-(Aspa-AOct)-GLP-1(7-36)amide; Thr$^8$Asp$^{19}$Arg$^{26,34}$Lys$^{23}$-(Aspa-AOct)-GLP-1(7-37); Thr$^8$Asp$^{19}$Arg$^{26,34}$Lys$^{23}$-(Aspa-AOct)-GLP-1(7-38); Thr$^8$Asp$^{17}$Arg$^{26,34}$Lys$^{23}$-(Aspa-AOct)-GLP-1(7-38); Arg$^{26,34}$Lys$^{27}$-(Aspa-AOct)-GLP-1(7-36); Arg$^{26,34}$Lys$^{27}$-(Aspa-AOct)-GLP-1(7-36)amide; Arg$^{26,34}$Lys$^{27}$-(Aspa-AOct)-GLP-1(7-37); Arg$^{26,34}$Lys$^{27}$-(Aspa-AOct)-GLP-1(7-38); Thr$^8$Asp$^{19}$Arg$^{26,34}$Lys$^{27}$-(Aspa-AOct)-GLP-1(7-36); Thr$^8$Asp$^{17}$Arg$^{26,34}$Lys$^{27}$-(Aspa-AOct)-GLP-1(7-36); Thr$^8$Asp$^{19}$Arg$^{26,34}$Lys$^{27}$-(Aspa-AOct)-GLP-1(7-36)amide; Thr$^8$Asp$^{17}$Arg$^{26,34}$Lys$^{27}$-(Aspa-AOct)-GLP-1(7-36)amide; Thr$^8$Asp$^{19}$Arg$^{26,34}$Lys$^{27}$-(Aspa-AOct)-GLP-1(7-37); Thr$^8$Asp$^{19}$Arg$^{26,34}$Lys$^{27}$-(Aspa-AOct)-GLP-1(7-38); Thr$^8$Asp$^{17}$Arg$^{26,34}$Lys$^{27}$-(Aspa-AOct)-GLP-1(7-38); Arg$^{26}$Lys$^{34}$-(Aspa-ALit)-GLP-1(7-36); Arg$^{34}$Lys$^{26}$-(Aspa-ALit)-GLP-1(7-36); Arg$^{26,34}$Lys$^{36}$-(Aspa-ALit)-GLP-1(7-36); Arg$^{26}$Lys$^{34}$-(Aspa-ALit)-GLP-1(7-36)amide; Arg$^{34}$Lys$^{26}$-(Aspa-ALit)-GLP-1(7-36)amide; Arg$^{26,34}$Lys$^{36}$-(Aspa-ALit)-GLP-1(7-36)amide; Arg$^{26}$Lys$^{34}$-(Aspa-ALit)-GLP-1(7-37); Arg$^{34}$Lys$^{26}$-(Aspa-ALit)-GLP-1(7-37); Arg$^{26,34}$Lys$^{36}$-(Aspa-ALit)-GLP-1(7-37); Arg$^{26}$Lys$^{34}$-(Aspa-ALit)-GLP-1(7-38); Arg$^{34}$Lys$^{26}$-(Aspa-ALit)-GLP-1(7-38); Arg$^{26,34}$Lys$^{38}$-(Aspa-ALit)-GLP-1(7-38); Arg$^{26}$Lys$^{34}$-(Aspa-ALit)-GLP-1(7-39); Arg$^{34}$Lys$^{26}$-(Aspa-ALit)-GLP-1(7-39); Arg$^{26,34}$Lys$^{39}$-(Aspa-ALit)-GLP-1(7-39); Gly$^8$Arg$^{26}$Lys$^{34}$-(Aspa-ALit)-GLP-1(7-36); Gly$^8$Arg$^{34}$Lys$^{26}$-(Aspa-ALit)-GLP-1(7-36); Gly$^8$Arg$^{26,34}$Lys$^{36}$-(Aspa-ALit)-GLP-1(7-36); Gly$^8$Arg$^{26}$Lys$^{34}$-(Aspa-ALit)-GLP-1(7-36)amide; Gly$^8$Arg$^{34}$Lys$^{26}$-(Aspa-ALit)-GLP-1(7-36)amide; Gly$^8$Arg$^{26,34}$Lys$^{36}$-(Aspa-ALit)-GLP-1(7-36)amide; Gly$^8$Arg$^{26}$Lys$^{34}$-(Aspa-ALit)-GLP-1(7-37); Gly$^8$Arg$^{34}$Lys$^{26}$-(Aspa-ALit)-GLP-1(7-37); Gly$^8$Arg$^{26,34}$Lys$^{36}$-(Aspa-ALit)-GLP-1(7-37); Gly$^8$Arg$^{26}$Lys$^{34}$-(Aspa-ALit)-GLP-1(7-38); Gly$^8$Arg$^{34}$Lys$^{26}$-(Aspa-ALit)-GLP-1(7-38); Gly$^8$Arg$^{26,34}$Lys$^{38}$-(Aspa-ALit)-GLP-1(7-38); Gly$^8$Arg$^{26}$Lys$^{34}$-(Aspa-ALit)-GLP-1(7-39); Gly$^8$Arg$^{34}$Lys$^{26}$-(Aspa-ALit)-GLP-1(7-39); Gly$^8$Arg$^{26,34}$Lys$^{39}$-(Aspa-ALit)-GLP-1(7-39); Val$^8$Arg$^{26}$Lys$^{34}$-(Aspa-ALit)-GLP-1(7-36); Val$^8$Arg$^{34}$Lys$^{26}$-(Aspa-ALit)-GLP-1(7-36); Val$^8$Arg$^{26,34}$Lys$^{36}$-(Aspa-ALit)-GLP-1(7-36); Val$^8$Arg$^{26}$Lys$^{34}$-(Aspa-ALit)-GLP-1(7-36)amide; Val$^8$Arg$^{34}$Lys$^{26}$-(Aspa-ALit)-GLP-1(7-36)amide; Val$^8$Arg$^{26,34}$Lys$^{36}$-(Aspa-ALit)-GLP-1(7-36)amide; Val$^8$Arg$^{26}$Lys$^{34}$-(Aspa-ALit)-GLP-1(7-37); Val$^8$Arg$^{34}$Lys$^{26}$-(Aspa-ALit)-GLP-1(7-37); Val$^8$Arg$^{26,34}$Lys$^{36}$-(Aspa-ALit)-GLP-1(7-37); Val$^8$Arg$^{26}$Lys$^{34}$-(Aspa-ALit)-GLP-1(7-38); Val$^8$Arg$^{34}$Lys$^{26}$-(Aspa-ALit)-GLP-1(7-38); Val$^8$Arg$^{26,34}$Lys$^{38}$-(Aspa-ALit)-GLP-1(7-38); Val$^8$Arg$^{26}$Lys$^{34}$-(Aspa-ALit)-GLP-1(7-39); Val$^8$Arg$^{34}$Lys$^{26}$-(Aspa-ALit)-GLP-1(7-39); Val$^8$Arg$^{26,34}$Lys$^{39}$-(Aspa-ALit)-GLP-1(7-39); Ser$^8$Arg$^{26}$Lys$^{34}$-(Aspa-ALit)-GLP-1(7-36); Ser$^8$Arg$^{34}$Lys$^{26}$-(Aspa-ALit)-GLP-1(7-36); Ser$^8$Arg$^{26,34}$Lys$^{36}$-(Aspa-ALit)-GLP-1(7-36); Ser$^8$Arg$^{26}$Lys$^{34}$-(Aspa-ALit)-GLP-1(7-36)amide; Ser$^8$Arg$^{34}$Lys$^{26}$-(Aspa-ALit)-GLP-1(7-36)amide; Ser$^8$Arg$^{26,34}$Lys$^{36}$-(Aspa-ALit)-GLP-1(7-36)amide; Ser$^8$Arg$^{26}$Lys$^{34}$-(Aspa-ALit)-GLP-1(7-37); Ser$^8$Arg$^{34}$Lys$^{26}$-(Aspa-ALit)-GLP-1(7-37); Ser$^8$Arg$^{26,34}$Lys$^{36}$-(Aspa-ALit)-GLP-1(7-37); Ser$^8$Arg$^{26}$Lys$^{34}$-(Aspa-ALit)-GLP-1(7-38); Ser$^8$Arg$^{34}$Lys$^{26}$-(Aspa-ALit)-GLP-1(7-38); Ser$^8$Arg$^{26,34}$Lys$^{38}$-(Aspa-ALit)-GLP-1(7-38); Ser$^8$Arg$^{26}$Lys$^{34}$-(Aspa-ALit)-GLP-1(7-39); Ser$^8$Arg$^{34}$Lys$^{26}$-(Aspa-ALit)-GLP-1(7-39); Ser$^8$Arg$^{26,34}$Lys$^{39}$-(Aspa-ALit)-GLP-1(7-39); Thr$^8$Arg$^{26}$Lys$^{34}$-(Aspa-ALit)-GLP-1(7-36); Thr$^8$Arg$^{34}$Lys$^{26}$-(Aspa-ALit)-GLP-1(7-36); Thr$^8$Arg$^{26,34}$Lys$^{36}$-(Aspa-ALit)-GLP-1(7-36); Thr$^8$Arg$^{26}$Lys$^{34}$-(Aspa-ALit)-GLP-1(7-36)amide; Thr$^8$Arg$^{34}$Lys$^{26}$-(Aspa-ALit)-GLP-1(7-36)amide; Thr$^8$Arg$^{26,34}$Lys$^{36}$-(Aspa-ALit)-GLP-1(7-36)amide; Thr$^8$Arg$^{26}$Lys$^{34}$-(Aspa-ALit)-GLP-1(7-37); Thr$^8$Arg$^{34}$Lys$^{26}$-(Aspa-ALit)-GLP-1(7-37); Thr$^8$Arg$^{26,34}$Lys$^{36}$-(Aspa-ALit)-GLP-1(7-37); Thr$^8$Arg$^{26}$Lys$^{34}$-(Aspa-ALit)-GLP-1(7-38); Thr$^8$Arg$^{34}$Lys$^{26}$-(Aspa-ALit)-GLP-1(7-38); Thr$^8$Arg$^{26,34}$Lys$^{38}$-(Aspa-ALit)-GLP-1(7-38); Thr$^8$Arg$^{26}$Lys$^{34}$-(Aspa-ALit)-GLP-1(7-39); Thr$^8$Arg$^{34}$Lys$^{26}$-(Aspa-ALit)-GLP-1(7-39); Thr$^8$Arg$^{26,34}$Lys$^{39}$-(Aspa-ALit)-GLP-1(7-39); Gly$^8$Glu$^{35}$Arg$^{26,34}$Lys$^{36}$-(Aspa-ALit)-GLP-1(7-36); Gly$^8$Glu$^{35}$Arg$^{26,34}$Lys$^{36}$-(Aspa-ALit)-GLP-1(7-36)amide; Gly$^8$Glu$^{36}$Arg$^{26,34}$Lys$^{37}$-(Aspa-ALit)-GLP-1(7-37); Gly$^8$Glu$^{37}$Arg$^{26,34}$Lys$^{38}$-(Aspa-ALit)-GLP-1(7-38); Gly$^8$Glu$^{38}$Arg$^{26,34}$Lys$^{39}$-(Aspa-ALit)-GLP-1(7-39); Gly$^8$Glu$^{35}$Arg$^{26,34}$Lys$^{36}$-(Aspa-ALit)-GLP-1(7-36); Gly$^8$Glu$^{35}$Arg$^{26,34}$Lys$^{36}$-(Aspa-ALit)-GLP-1(7-36)amide; Gly$^8$Glu$^{36}$Arg$^{26,34}$Lys$^{37}$-(Aspa-ALit)-GLP-1(7-37); Gly$^8$Glu$^{37}$Arg$^{26,34}$Lys$^{38}$-(Aspa-ALit)-GLP-1(7-38); Gly$^8$Glu$^{38}$Arg$^{26,34}$Lys$^{39}$-(Aspa-ALit)-GLP-1(7-39); Gly$^8$Asp$^{35}$Arg$^{26,34}$Lys$^{36}$-(Aspa-ALit)-GLP-1(7-36); Gly$^8$Asp$^{35}$Arg$^{26,34}$Lys$^{36}$-(Aspa-ALit)-GLP-1(7-36)amide; Gly$^8$Asp$^{36}$Arg$^{26,34}$Lys$^{37}$-(Aspa-ALit)-GLP-1(7-37); Gly$^8$Asp$^{37}$Arg$^{26,34}$Lys$^{38}$-(Aspa-ALit)-GLP-1(7-38); Gly$^8$Asp$^{38}$Arg$^{26,34}$Lys$^{39}$-(Aspa-ALit)-GLP-1(7-39); Gly$^8$Asp$^{35}$Arg$^{26,34}$Lys$^{36}$-(Aspa-ALit)-GLP-1(7-36); Gly$^8$Asp$^{35}$Arg$^{26,34}$Lys$^{36}$-(Aspa-ALit)-GLP-1(7-36)amide; Gly$^8$Asp$^{36}$Arg$^{26,34}$Lys$^{37}$-(Aspa-ALit)-GLP-1(7-37); Gly$^8$Asp$^{37}$Arg$^{26,34}$Lys$^{38}$-(Aspa-ALit)-GLP-1(7-38); Gly$^8$Asp$^{38}$Arg$^{26,34}$Lys$^{39}$-(Aspa-ALit)-GLP-1(7-39);

Val⁸Glu³⁵Arg²⁶,³⁴Lys³⁶-(Aspa-ALit)-GLP-1(7-36);
Val⁸Glu³⁵Arg²⁶,³⁴Lys³⁶-(Aspa-ALit)-GLP-1(7-36)amide;
Val⁸Glu³⁶Arg²⁶,³⁴Lys³⁷-(Aspa-ALit)-GLP-1(7-37);
Val⁸Glu³⁷Arg²⁶,³⁴Lys³⁸-(Aspa-ALit)-GLP-1(7-38);
Val⁸Glu³⁸Arg²⁶,³⁴Lys³⁹-(Aspa-ALit)-GLP-1(7-39);
Val⁸Glu³⁵Arg²⁶,³⁴Lys³⁶-(Aspa-ALit)-GLP-1(7-36);
Val⁸Glu³⁵Arg²⁶,³⁴Lys³⁶-(Aspa-ALit)-GLP-1(7-36)amide;
Val⁸Glu³⁶Arg²⁶,³⁴Lys³⁷-(Aspa-ALit)-GLP-1(7-37);
Val⁸Glu³⁷Arg²⁶,³⁴Lys³⁸-(Aspa-ALit)-GLP-1(7-38);
Val⁸Glu³⁸Arg²⁶,³⁴Lys³⁹-(Aspa-ALit)-GLP-1(7-39);
Val⁸Asp³⁵Arg²⁶,³⁴Lys³⁶-(Aspa-ALit)-GLP-1(7-36);
Val⁸Asp³⁵Arg²⁶,³⁴Lys³⁶-(Aspa-ALit)-GLP-1(7-36)amide;
Val⁸Asp³⁶Arg²⁶,³⁴Lys³⁷-(Aspa-ALit)-GLP-1(7-37);
Val⁸Asp³⁷Arg²⁶,³⁴Lys³⁸-(Aspa-ALit)-GLP-1(7-38);
Val⁸Asp³⁸Arg²⁶,³⁴Lys³⁹-(Aspa-ALit)-GLP-1(7-39);
Val⁸Asp³⁵Arg²⁶,³⁴Lys³⁶-(Aspa-ALit)-GLP-1(7-36);
Val⁸Asp³⁵Arg²⁶,³⁴Lys³⁶-(Aspa-ALit)-GLP-1(7-36)amide;
Val⁸Asp³⁶Arg²⁶,³⁴Lys³⁷-(Aspa-ALit)-GLP-1(7-37);
Val⁸Asp³⁷Arg²⁶,³⁴Lys³⁸-(Aspa-ALit)-GLP-1(7-38);
Val⁸Asp³⁸Arg²⁶,³⁴Lys³⁹-(Aspa-ALit)-GLP-1(7-39);
Ser⁸Glu³⁵Arg²⁶,³⁴Lys³⁶-(Aspa-ALit)GLP-1(7-36);
Ser⁸Glu³⁵Arg²⁶,³⁴Lys³⁶ (Aspa-ALit)-GLP-1(7-36)amide;
Ser⁸Glu³⁶Arg²⁶,³⁴Lys³⁷-(Aspa-ALit)-GLP-1(7-37);
Ser⁸Glu³⁷Arg²⁶,³⁴Lys³⁸-(Aspa-ALit)-GLP-1(7-38);
Ser⁸Glu³⁸Arg²⁶,³⁴Lys³⁹-(Aspa-ALit)-GLP-1(7-39);
Ser⁸Glu³⁵Arg²⁶,³⁴Lys³⁶-(Aspa-ALit)-GLP-1(7-36);
Ser⁸Glu³⁵Arg²⁶,³⁴Lys³⁶-(Aspa-ALit)-GLP-1(7-36)amide;
Ser⁸Glu³⁶Arg²⁶,³⁴Lys³⁷-(Aspa-ALit)-GLP-1(7-37);
Ser⁸Glu³⁷Arg²⁶,³⁴Lys³⁸-(Aspa-ALit)-GLP-1(7-38);
Ser⁸Glu³⁸Arg²⁶,³⁴Lys³⁹-(Aspa-ALit)GLP-1(7-39);
Ser⁸Asp³⁵Arg²⁶,³⁴Lys³⁶-(Aspa-ALit)-GLP-1(7-36);
Ser⁸Asp³⁵Arg²⁶,³⁴Lys³⁶-(Aspa-ALit)-GLP-1(7-36)amide;
Ser⁸Asp³⁶Arg²⁶,³⁴Lys³⁷-(Aspa-ALit)-GLP-1(7-37);
Ser⁸Asp³⁷Arg²⁶,³⁴Lys³⁸-(Aspa-ALit)-GLP-1(7-38);
Ser⁸Asp³⁸Arg²⁶,³⁴Lys³⁹-(Aspa-ALit)-GLP-1(7-39);
Ser⁸Asp³⁵Arg²⁶,³⁴Lys³⁶-(Aspa-ALit)-GLP-1(7-36);
Ser⁸Asp³⁵Arg²⁶,³⁴Lys³⁶-(Aspa-ALit)-GLP-1(7-36)amide;
Ser⁸Asp³⁶Arg²⁶,³⁴Lys³⁷-(Aspa-ALit)-GLP-1(7-37);
Ser⁸Asp³⁷Arg²⁶,³⁴Lys³⁸-(Aspa-ALit)-GLP-1(7-38);
Ser⁸Asp³⁸Arg²⁶,³⁴Lys³⁹-(Aspa-ALit)-GLP-1(7-39);
Thr⁸Glu³⁵Arg²⁶,³⁴Lys³⁶-(Aspa-ALit)-GLP-1(7-36);
Thr⁸Glu³⁵Arg²⁶,³⁴Lys³⁶-(Aspa-ALit)-GLP-1(7-36)amide;
Thr⁸Glu³⁶Arg²⁶,³⁴Lys³⁷-(Aspa-ALit)-GLP-1(7-37);
Thr⁸Glu³⁷Arg²⁶,³⁴Lys³⁸-(Aspa-ALit)-GLP-1(7-38);
Thr⁸Glu³⁸Arg²⁶,³⁴Lys³⁹-(Aspa-ALit)-GLP-1(7-39);
Thr⁸Glu³⁵Arg²⁶,³⁴Lys³⁶-(Aspa-ALit)-GLP-1(7-36);
Thr⁸Glu³⁵Arg²⁶,³⁴Lys³⁶-(Aspa-ALit)-GLP-1(7-36)amide;
Thr⁸Glu³⁶Arg²⁶,³⁴Lys³⁷-(Aspa-ALit)-GLP-1(7-37);
Thr⁸Glu³⁷Arg²⁶,³⁴Lys³⁸-(Aspa-ALit)-GLP-1(7-38);
Thr⁸Glu³⁸Arg²⁶,³⁴Lys³⁹-(Aspa-ALit)-GLP-1(7-39);
Thr⁸Asp³⁵Arg²⁶,³⁴Lys³⁶-(Aspa-ALit)-GLP-1(7-36);
Thr⁸Asp³⁵Arg²⁶,³⁴Lys³⁶-(Aspa-ALit)-GLP-1(7-36)amide;
Thr⁸Asp³⁶Arg²⁶,³⁴Lys³⁷-(Aspa-ALit)-GLP-1(7-37);
Thr⁸Asp³⁷Arg²⁶,³⁴Lys³⁸-(Aspa-ALit)-GLP-1(7-38);
Thr⁸Asp³⁸Arg²⁶,³⁴Lys³⁹-(Aspa-ALit)-GLP-1(7-39);
Thr⁸Asp³⁵Arg²⁶,³⁴Lys³⁶-(Aspa-ALit)-GLP-1(7-36);
Thr⁸Asp³⁵Arg²⁶,³⁴Lys³⁶-(Aspa-ALit)-GLP-1(7-36)amide;
Thr⁸Asp³⁶Arg²⁶,³⁴Lys³⁷-(Aspa-ALit)-GLP-1(7-37);
Thr⁸Asp³⁷Arg²⁶,³⁴Lys³⁸-(Aspa-ALit)-GLP-1(7-38);
Thr⁸Asp³⁸Arg²⁶,³⁴Lys³⁹-(Aspa-ALit)-GLP-1(7-39);
Arg²⁶,³⁴Lys¹⁸-(Aspa-ALit)-GLP-1(7-36); Arg²⁶,³⁴Lys¹⁸-(Aspa-ALit)-GLP-1(7-36)amide; Arg²⁶,³⁴Lys¹⁸-(Aspa-ALit)-GLP-1(7-37); Arg²⁶,³⁴Lys¹⁸-(Aspa-ALit)-GLP-1(7-38); Gly⁸Asp¹⁹Arg²⁶,³⁴Lys¹⁸-(Aspa-ALit)-GLP-1(7-36); Gly⁸Asp¹⁷Arg²⁶,³⁴Lys¹⁸-(Aspa-ALit)-GLP-1(7-36); Gly⁸Asp¹⁹Arg²⁶,³⁴Lys¹⁸-(Aspa-ALit)-GLP-1(7-36)amide; Gly⁸Asp¹⁷Arg²⁶,³⁴Lys¹⁸-(Aspa-ALit)-GLP-1(7-36)amide;
Gly⁸Asp¹⁹Arg²⁶,³⁴Lys¹⁸-(Aspa-ALit)-GLP-1(7-37);
Gly⁸Asp¹⁹Arg²⁶,³⁴Lys¹⁸-(Aspa-ALit)-GLP-1(7-38);
Gly⁸Asp¹⁷Arg²⁶,³⁴Lys¹⁸-(Aspa-ALit)-GLP-1(7-38);
Arg²⁶,³⁴Lys²³-(Aspa-ALit)-GLP-1(7-36); Arg²⁶,³⁴Lys²³-(Aspa-ALit)-GLP-1(7-36)amide; Arg²⁶,³⁴Lys²³-(Aspa-ALit)-GLP-1(7-37); Arg²⁶,³⁴Lys²³-(Aspa-ALit)-GLP-1(7-38); Gly⁸Asp¹⁹Arg²⁶,³⁴Lys²³-(Aspa-ALit)-GLP-1(7-36); Gly⁸Asp¹⁷Arg²⁶,³⁴Lys²³-(Aspa-ALit)-GLP-1(7-36); Gly⁸Asp¹⁹Arg²⁶,³⁴Lys²³-(Aspa-ALit)-GLP-1(7-36)amide; Gly⁸Asp¹⁷Arg²⁶,³⁴Lys²³-(Aspa-ALit)-GLP-1(7-36)amide;
Gly⁸Asp¹⁹Arg²⁶,³⁴Lys²³-(Aspa-ALit)-GLP-1(7-37);
Gly⁸Asp¹⁹Arg²⁶,³⁴Lys²³-(Aspa-ALit)-GLP-1(7-38);
Gly⁸Asp¹⁷Arg²⁶,³⁴Lys²³-(Aspa-ALit)-GLP-1(7-38);
Arg²⁶,³⁴Lys²⁷-(Aspa-ALit)-GLP-1(7-36); Arg²⁶,³⁴Lys²⁷-(Aspa-ALit)-GLP-1(7-36)amide; Arg²⁶,³⁴Lys²⁷-(Aspa-ALit)-GLP-1(7-37); Arg²⁶,³⁴Lys²⁷-(Aspa-ALit)-GLP-1(7-38); Gly⁸Asp¹⁹Arg²⁶,³⁴Lys²⁷-(Aspa-ALit)-GLP-1(7-36); Gly⁸Asp¹⁷Arg²⁶,³⁴Lys²⁷-(Aspa-ALit)-GLP-1(7-36); Gly⁸Asp¹⁹Arg²⁶,³⁴Lys²⁷-(Aspa-ALit)-GLP-1(7-36)amide; Gly⁸Asp¹⁷Arg²⁶,³⁴Lys²⁷-(Aspa-ALit)-GLP-1(7-36)amide;
Gly⁸Asp¹⁹Arg²⁶,³⁴Lys²⁷-(Aspa-ALit)-GLP-1(7-37);
Gly⁸Asp¹⁹Arg²⁶,³⁴Lys²⁷-(Aspa-ALit)-GLP-1(7-38);
Gly⁸Asp¹⁷Arg²⁶,³⁴Lys²⁷-(Aspa-ALit)-GLP-1(7-38);
Arg²⁶,³⁴Lys¹⁸-(Aspa-ALit)-GLP-1(7-36); Arg²⁶,³⁴Lys¹⁸-(Aspa-ALit)-GLP-1(7-36)amide; Arg²⁶,³⁴Lys¹⁸-(Aspa-ALit)-GLP-1(7-37); Arg²⁶,³⁴Lys¹⁸-(Aspa-ALit)-GLP-1(7-38); Val⁸Asp¹⁹Arg²⁶,³⁴Lys¹⁸-(Aspa-ALit)-GLP-1(7-36); Val⁸Asp¹⁷Arg²⁶,³⁴Lys¹⁸-(Aspa-ALit)-GLP-1(7-36); Val⁸Asp¹⁹Arg²⁶,³⁴Lys¹⁸-(Aspa-ALit)-GLP-1(7-36)amide; Val⁸Asp¹⁷Arg²⁶,³⁴Lys¹⁸-(Aspa-ALit)-GLP-1(7-36)amide;
Val⁸Asp¹⁹Arg²⁶,³⁴Lys¹⁸-(Aspa-ALit)-GLP-1(7-37);
Val⁸Asp¹⁹Arg²⁶,³⁴Lys¹⁸-(Aspa-ALit)-GLP-1(7-38);
Val⁸Asp¹⁷Arg²⁶,³⁴Lys¹⁸-(Aspa-ALit)-GLP-1(7-38);
Arg²⁶,³⁴Lys²³-(Aspa-ALit)-GLP-1(7-36); Arg²⁶,³⁴Lys²³-(Aspa-ALit)-GLP-1(7-36)amide; Arg²⁶,³⁴Lys²³-(Aspa-ALit)-GLP-1(7-37); Arg²⁶,³⁴Lys²³-(Aspa-ALit)-GLP-1(7-38); Val⁸Asp¹⁹Arg²⁶,³⁴Lys²³-(Aspa-ALit)-GLP-1(7-36); Val⁸Asp¹⁷Arg²⁶,³⁴Lys²³-(Aspa-ALit)-GLP-1(7-36); Val⁸Asp¹⁹Arg²⁶,³⁴Lys²³-(Aspa-ALit)-GLP-1(7-36)amide; Val⁸Asp¹⁷Arg²⁶,³⁴Lys²³-(Aspa-ALit)-GLP-1(7-36)amide;
Val⁸Asp¹⁹Arg²⁶,³⁴Lys²³-(Aspa-ALit)-GLP-1(7-37);
Val⁸Asp¹⁹Arg²⁶,³⁴Lys²³-(Aspa-ALit)-GLP-1(7-38);
Val⁸Asp¹⁷Arg²⁶,³⁴Lys²³-(Aspa-ALit)-GLP-1(7-38);
Arg²⁶,³⁴Lys²⁷-(Aspa-ALit)-GLP-1(7-36); Arg²⁶,³⁴Lys²⁷-(Aspa-ALit)-GLP-1(7-36)amide; Arg²⁶,³⁴Lys²⁷-(Aspa-ALit)-GLP-1(7-37); Arg²⁶,³⁴Lys²⁷-(Aspa-ALit)-GLP-1(7-38); Val⁸Asp¹⁹Arg²⁶,³⁴Lys²⁷-(Aspa-ALit)-GLP-1(7-36); Val⁸Asp¹⁷Arg²⁶,³⁴Lys²⁷-(Aspa-ALit)-GLP-1(7-36); Val⁸Asp¹⁹Arg²⁶,³⁴Lys²⁷-(Aspa-ALit)-GLP-1(7-36)amide; Val⁸Asp¹⁷Arg²⁶,³⁴Lys²⁷-(Aspa-ALit)-GLP-1(7-36)amide;
Val⁸Asp¹⁹Arg²⁶,³⁴Lys²⁷-(Aspa-ALit)-GLP-1(7-37);
Val⁸Asp¹⁹Arg²⁶,³⁴Lys²⁷-(Aspa-ALit)-GLP-1(7-38);
Val⁸Asp¹⁷Arg²⁶,³⁴Lys²⁷-(Aspa-ALit)-GLP-1(7-38);
Arg²⁶,³⁴Lys¹⁸-(Aspa-ALit)-GLP-1(7-36); Arg²⁶,³⁴Lys¹⁸-(Aspa-ALit)-GLP-1(7-36)amide; Arg²⁶,³⁴Lys¹⁸-(Aspa-ALit)-GLP-1(7-37); Arg²⁶,³⁴Lys¹⁸-(Aspa-ALit)-GLP-1(7-38); Ser⁸Asp¹⁹Arg²⁶,³⁴Lys¹⁸-(Aspa-ALit)-GLP-1(7-36); Ser⁸Asp¹⁷Arg²⁶,³⁴Lys¹⁸-(Aspa-ALit)-GLP-1(7-36); Ser⁸Asp¹⁹Arg²⁶,³⁴Lys¹⁸-(Aspa-ALit)-GLP-1(7-36)amide; Ser⁸Asp¹⁷Arg²⁶,³⁴Lys¹⁸-(Aspa-ALit)-GLP-1(7-36)amide;
Ser⁸Asp¹⁹Arg²⁶,³⁴Lys¹⁸-(Aspa-ALit)-GLP-1(7-37);
Ser⁸Asp¹⁹Arg²⁶,³⁴Lys¹⁸-(Aspa-ALit)-GLP-1(7-38);
Ser⁸Asp¹⁷Arg²⁶,³⁴Lys¹⁸-(Aspa-ALit)-GLP-1(7-38);
Arg²⁶,³⁴Lys²³-(Aspa-ALit)-GLP-1(7-36); Arg²⁶,³⁴Lys²³-(Aspa-ALit)-GLP-1(7-36)amide; Arg²⁶,³⁴Lys²³-(Aspa-ALit)-GLP-1(7-37); Arg²⁶,³⁴Lys²³-(Aspa-ALit)-GLP-1(7-38); Ser⁸Asp¹⁹Arg²⁶,³⁴Lys²³-(Aspa-ALit)-GLP-1(7-36);

Ser$^8$Asp$^{17}$Arg$^{26,34}$Lys$^{23}$-(Aspa-ALit)-GLP-1(7-36);
Ser$^8$Asp$^{19}$Arg$^{26,34}$Lys$^{23}$-(Aspa-ALit)-GLP-1(7-36)amide;
Ser$^8$Asp$^{17}$Arg$^{26,34}$Lys$^{23}$-(Aspa-ALit)-GLP-1(7-36)amide;
Ser$^8$Asp$^{19}$Arg$^{26,34}$Lys$^{23}$-(Aspa-ALit)-GLP-1(7-37);
Ser$^8$Asp$^{19}$Arg$^{26,34}$Lys$^{23}$-(Aspa-ALit)-GLP-1(7-38);
Ser$^8$Asp$^{17}$Arg$^{26,34}$Lys$^{23}$-(Aspa-ALit)-GLP-1(7-38);
Arg$^{26,34}$Lys$^{27}$-(Aspa-ALit)-GLP-1(7-36); Arg$^{26,34}$Lys$^{27}$-(Aspa-ALit)-GLP-1(7-36)amide; Arg$^{26,34}$Lys$^{27}$-(Aspa-ALit)-GLP-1(7-37); Arg$^{26,34}$Lys$^{27}$-(Aspa-ALit)-GLP-1(7-38); Ser$^8$Asp$^{19}$Arg$^{26,34}$Lys$^{27}$-(Aspa-ALit)-GLP-1(7-36);
Ser$^8$Asp$^{17}$Arg$^{26,34}$Lys$^{27}$-(Aspa-ALit)-GLP-1(7-36);
Ser$^8$Asp$^{19}$Arg$^{26,34}$Lys$^{27}$-(Aspa-ALit)-GLP-1(7-36)amide;
Ser$^8$Asp$^{17}$Arg$^{26,34}$Lys$^{27}$-(Aspa-ALit)-GLP-1(7-36)amide;
Ser$^8$Asp$^{19}$Arg$^{26,34}$Lys$^{27}$-(Aspa-ALit)-GLP-1(7-37);
Ser$^8$Asp$^{19}$Arg$^{26,34}$Lys$^{27}$-(Aspa-ALit)-GLP-1(7-38);
Ser$^8$Asp$^{17}$Arg$^{26,34}$Lys$^{27}$-(Aspa-ALit)-GLP-1(7-38);
Arg$^{26,34}$Lys$^{18}$-(Aspa-ALit)-GLP-1(7-36); Arg$^{26,34}$Lys$^{18}$-(Aspa-ALit)-GLP-1(7-36)amide; Arg$^{26,34}$Lys$^{18}$-(Aspa-ALit)-GLP-1(7-37); Arg$^{26,34}$Lys$^{18}$-(Aspa-ALit)-GLP-1(7-38); Thr$^8$Asp$^{19}$Arg$^{26,34}$Lys$^{18}$-(Aspa-ALit)-GLP-1(7-36);
Thr$^8$Asp$^{17}$Arg$^{26,34}$Lys$^{18}$-(Aspa-ALit)-GLP-1(7-36);
Thr$^8$Asp$^{19}$Arg$^{26,34}$Lys$^{18}$-(Aspa-ALit)-GLP-1(7-36)amide;
Thr$^8$Asp$^{17}$Arg$^{26,34}$Lys$^{18}$-(Aspa-ALit)-GLP-1(7-36)amide;
Thr$^8$Asp$^{19}$Arg$^{26,34}$Lys$^{18}$-(Aspa-ALit)-GLP-1(7-37);
Thr$^8$Asp$^{19}$Arg$^{26,34}$Lys$^{18}$-(Aspa-ALit)-GLP-1(7-38);
Thr$^8$Asp$^{17}$Arg$^{26,34}$Lys$^{18}$-(Aspa-ALit)-GLP-1(7-38);
Arg$^{26,34}$Lys$^{23}$-(Aspa-ALit)-GLP-1(7-36); Arg$^{26,34}$Lys$^{23}$-(Aspa-ALit)-GLP-1(7-36)amide; Arg$^{26,34}$Lys$^{23}$-(Aspa-ALit)-GLP-1(7-37); Arg$^{26,34}$Lys$^{23}$-(Aspa-ALit)-GLP-1(7-38); Thr$^8$Asp$^{19}$Arg$^{26,34}$Lys$^{23}$-(Aspa-ALit)-GLP-1(7-36);
Thr$^8$Asp$^{17}$Arg$^{26,34}$Lys$^{23}$-(Aspa-ALit)-GLP-1(7-36);
Thr$^8$Asp$^{19}$Arg$^{26,34}$Lys$^{23}$-(Aspa-ALit)-GLP-1(7-36)amide;
Thr$^8$Asp$^{17}$Arg$^{26,34}$Lys$^{23}$-(Aspa-ALit)-GLP-1(7-36)amide;
Thr$^8$Asp$^{19}$Arg$^{26,34}$Lys$^{23}$-(Aspa-ALit)-GLP-1(7-37);
Thr$^8$Asp$^{19}$Arg$^{26,34}$Lys$^{23}$-(Aspa-ALit)-GLP-1(7-38);
Thr$^8$Asp$^{17}$Arg$^{26,34}$Lys$^{23}$-(Aspa-ALit)-GLP-1(7-38);
Arg$^{26,34}$Lys$^{27}$-(Aspa-ALit)-GLP-1(7-36); Arg$^{26,34}$Lys$^{27}$-(Aspa-ALit)-GLP-1(7-36)amide; Arg$^{26,34}$Lys$^{27}$-(Aspa-ALit)-GLP-1(7-37); Arg$^{26,34}$Lys$^{27}$-(Aspa-ALit)-GLP-1(7-38); Thr$^8$Asp$^{19}$Arg$^{26,34}$Lys$^{27}$ (Aspa-ALit)-GLP-1(7-36);
Thr$^8$Asp$^{17}$Arg$^{26,34}$Lys$^{27}$-(Aspa-ALit)-GLP-1(7-36);
Thr$^8$Asp$^{19}$Arg$^{26,34}$Lys$^{27}$-(Aspa-ALit)-GLP-1(7-36)amide;
Thr$^8$Asp$^{17}$Arg$^{26,34}$Lys$^{27}$-(Aspa-ALit)-GLP-1(7-36)amide;
Thr$^8$Asp$^{19}$Arg$^{26,34}$Lys$^{27}$-(Aspa-ALit)-GLP-1(7-37);
Thr$^8$Asp$^{19}$Arg$^{26,34}$Lys$^{27}$-(Aspa-ALit)-GLP-1(7-38);
Thr$^8$Asp$^{17}$Arg$^{26,34}$Lys$^{27}$-(Aspa-ALit)-GLP-1(7-38);
Arg$^{26}$Lys$^{34}$-(Glyc-ADod)-GLP-1(7-36); Arg$^{34}$Lys$^{26}$-(Glyc-ADod)-GLP-1(7-36); Arg$^{26,34}$Lys$^{36}$-(Glyc-ADod)-GLP-1(7-36); Arg$^{26}$Lys$^{34}$-(Glyc-ADod)-GLP-1(7-36)amide; Arg$^{34}$Lys$^{26}$-(Glyc-ADod)-GLP-1(7-36)amide; Arg$^{26,34}$Lys$^{36}$-(Glyc-ADod)-GLP-1(7-36)amide; Arg$^{26}$Lys$^{34}$-(Glyc-ADod)-GLP-1(7-37); Arg$^{34}$Lys$^{26}$-(Glyc-ADod)-GLP-1(7-37); Arg$^{26,34}$Lys$^{36}$-(Glyc-ADod)-GLP-1(7-37); Arg$^{26}$Lys$^{34}$-(Glyc-ADod)-GLP-1(7-38); Arg$^{34}$Lys$^{26}$-(Glyc-ADod)-GLP-1(7-38); Arg$^{26,34}$Lys$^{38}$-(Glyc-ADod)-GLP-1(7-38); Arg$^{26}$Lys$^{34}$-(Glyc-ADod)-GLP-1(7-39); Arg$^{34}$Lys$^{26}$-(Glyc-ADod)-GLP-1(7-39); Arg$^{26,34}$Lys$^{39}$-(Glyc-ADod)-GLP-1(7-39); Gly$^8$Arg$^{26}$Lys$^{34}$-(Glyc-ADod)-GLP-1(7-36); Gly$^8$Arg$^{34}$Lys$^{26}$-(Glyc-ADod)-GLP-1(7-36);
Gly$^8$Arg$^{26,34}$Lys$^{36}$-(Glyc-ADod)-GLP-1(7-36);
Gly$^8$Arg$^{26}$Lys$^{34}$-(Glyc-ADod)-GLP-1(7-36)amide;
Gly$^8$Arg$^{34}$Lys$^{26}$-(Glyc-ADod)-GLP-1(7-36)amide;
Gly$^8$Arg$^{26,34}$Lys$^{36}$-(Glyc-ADod)-GLP-1(7-36)amide;
Gly$^8$Arg$^{26}$Lys$^{34}$-(Glyc-ADod)-GLP-1(7-37);
Gly$^8$Arg$^{34}$Lys$^{26}$-(Glyc-ADod)-GLP-1(7-37); Gly$^8$Arg$^{26,34}$Lys$^{36}$-(Glyc-ADod)-GLP-1(7-37); Gly$^8$Arg$^{26}$Lys$^{34}$-(Glyc-ADod)-GLP-1(7-38); Gly$^8$Arg$^{34}$Lys$^{26}$-(Glyc-ADod)-GLP-1(7-38); Gly$^8$Arg$^{26,34}$Lys$^{38}$-(Glyc-ADod)-GLP-1(7-38); Gly$^8$Arg$^{26}$Lys$^{34}$-(Glyc-ADod)-GLP-1(7-39);
Gly$^8$Arg$^{34}$Lys$^{26}$-(Glyc-ADod)-GLP-1(7-39); Gly$^8$Arg$^{26,34}$Lys$^{39}$-(Glyc-ADod)-GLP-1(7-39);
Val$^8$Arg$^{26}$Lys$^{34}$-(Glyc-ADod)-GLP-1(7-36);
Val$^8$Arg$^{34}$Lys$^{26}$-(Glyc-ADod)-GLP-1(7-36); Val$^8$Arg$^{26,34}$Lys$^{36}$-(Glyc-ADod)-GLP-1(7-36); Val$^8$Arg$^{26}$Lys$^{34}$-(Glyc-ADod)-GLP-1(7-36)amide; Val$^8$Arg$^{34}$Lys$^{26}$-(Glyc-ADod)-GLP-1(7-36)amide; Val$^8$Arg$^{26,34}$Lys$^{36}$-(Glyc-ADod)-GLP-1(7-36)amide; Val$^8$Arg$^{26}$Lys$^{34}$-(Glyc-ADod)-GLP-1(7-37); Val$^8$Arg$^{34}$Lys$^{26}$-(Glyc-ADod)-GLP-1(7-37); Val$^8$Arg$^{26,34}$Lys$^{36}$-(Glyc-ADod)-GLP-1(7-37);
Val$^8$Arg$^{26}$Lys$^{34}$-(Glyc-ADod)-GLP-1(7-38);
Val$^8$Arg$^{34}$Lys$^{26}$-(Glyc-ADod)-GLP-1(7-38); Val$^8$Arg$^{26,34}$Lys$^{38}$-(Glyc-ADod)-GLP-1(7-38); Val$^8$Arg$^{34}$Lys$^{26}$-(Glyc-ADod)-GLP-1(7-39); Val$^8$Arg$^{34}$Lys$^{26}$-(Glyc-ADod)-GLP-1(7-39); Val$^8$Arg$^{26,34}$Lys$^{39}$-(Glyc-ADod)-GLP-1(7-39);
Ser$^8$Arg$^{26}$Lys$^{34}$-(Glyc-ADod)-GLP-1(7-36);
Ser$^8$Arg$^{34}$Lys$^{26}$-(Glyc-ADod)-GLP-1(7-36); Ser$^8$Arg$^{26,34}$Lys$^{36}$-(Glyc-ADod)-GLP-1(7-36); Ser$^8$Arg$^{26}$Lys$^{34}$-(Glyc-ADod)-GLP-1(7-36)amide; Ser$^8$Arg$^{34}$Lys$^{26}$-(Glyc-ADod)-GLP-1(7-36)amide; Ser$^8$Arg$^{26,34}$Lys$^{36}$-(Glyc-ADod)-GLP-1(7-36)amide; Ser$^8$Arg$^{26}$Lys$^{34}$-(Glyc-ADod)-GLP-1(7-37); Ser$^8$Arg$^{34}$Lys$^{26}$-(Glyc-ADod)-GLP-1(7-37); Ser$^8$Arg$^{26,34}$Lys$^{36}$-(Glyc-ADod)-GLP-1(7-37);
Ser$^8$Arg$^{26}$Lys$^{34}$-(Glyc-ADod)-GLP-1(7-38);
Ser$^8$Arg$^{34}$Lys$^{26}$-(Glyc-ADod)-GLP-1(7-38); Ser$^8$Arg$^{26,34}$Lys$^{38}$-(Glyc-ADod)-GLP-1(7-38); Ser$^8$Arg$^{26}$Lys$^{34}$-(Glyc-ADod)-GLP-1(7-39); Ser$^8$Arg$^{34}$Lys$^{26}$-(Glyc-ADod)-GLP-1(7-39); Ser$^8$Arg$^{26,34}$Lys$^{39}$-(Glyc-ADod)-GLP-1(7-39);
Thr$^8$Arg$^{26}$Lys$^{34}$-(Glyc-ADod)-GLP-1(7-36);
Thr$^8$Arg$^{34}$Lys$^{26}$-(Glyc-ADod)-GLP-1(7-36); Thr$^8$Arg$^{26,34}$Lys$^{36}$-(Glyc-ADod)-GLP-1(7-36); Thr$^8$Arg$^{26}$Lys$^{34}$-(Glyc-ADod)-GLP-1(7-36)amide; Thr$^8$Arg$^{34}$Lys$^{26}$-(Glyc-ADod)-GLP-1(7-36)amide; Thr$^8$Arg$^{26,34}$Lys$^{36}$-(Glyc-ADod)-GLP-1(7-36)amide; Thr$^8$Arg$^{26}$Lys$^{34}$-(Glyc-ADod)-GLP-1(7-37); Thr$^8$Arg$^{34}$Lys$^{26}$-(Glyc-ADod)-GLP-1(7-37); Thr$^8$Arg$^{26,34}$Lys$^{36}$-(Glyc-ADod)-GLP-1(7-37);
Thr$^8$Arg$^{26}$Lys$^{34}$-(Glyc-ADod)-GLP-1(7-38);
Thr$^8$Arg$^{34}$Lys$^{26}$-(Glyc-ADod)-GLP-1(7-38); Thr$^8$Arg$^{26,34}$Lys$^{38}$-(Glyc-ADod)-GLP-1(7-38); Thr$^8$Arg$^{26}$Lys$^{34}$-(Glyc-ADod)-GLP-1(7-39); Thr$^8$Arg$^{34}$Lys$^{26}$-(Glyc-ADod)-GLP-1(7-39); Thr$^8$Arg$^{26,34}$Lys$^{39}$-(Glyc-ADod)-GLP-1(7-39);
Gly$^8$Glu$^{35}$Arg$^{26,34}$Lys$^{36}$-(Glyc-ADod)-GLP-1(7-36);
Gly$^8$Glu$^{35}$Arg$^{26,34}$Lys$^{36}$-(Glyc-ADod)-GLP-1(7-36)amide;
Gly$^8$Glu$^{36}$Arg$^{26,34}$Lys$^{37}$-(Glyc-ADod)-GLP-1(7-37);
Gly$^8$Glu$^{37}$Arg$^{26,34}$Lys$^{38}$-(Glyc-ADod)-GLP-1(7-38);
Gly$^8$Glu$^{38}$Arg$^{26,34}$Lys$^{39}$-(Glyc-ADod)-GLP-1(7-39);
Gly$^8$Glu$^{35}$Arg$^{26,34}$Lys$^{36}$-(Glyc-ADod)-GLP-1(7-36);
Gly$^8$Glu$^{35}$Arg$^{26,34}$Lys$^{36}$-(Glyc-ADod)-GLP-1(7-36)amide;
Gly$^8$Glu$^{36}$Arg$^{26,34}$Lys$^{37}$-(Glyc-ADod)-GLP-1(7-37);
Gly$^8$Glu$^{37}$Arg$^{26,34}$Lys$^{38}$-(Glyc-ADod)-GLP-1(7-38);
Gly$^8$Glu$^{38}$Arg$^{26,34}$Lys$^{39}$-(Glyc-ADod)-GLP-1(7-39);
Gly$^8$Asp$^{35}$Arg$^{26,34}$Lys$^{36}$-(Glyc-ADod)-GLP-1(7-36);
Gly$^8$Asp$^{35}$Arg$^{26,34}$Lys$^{36}$-(Glyc-ADod)-GLP-1(7-36)amide;
Gly$^8$Asp$^{36}$Arg$^{26,34}$Lys$^{37}$-(Glyc-ADod)-GLP-1(7-37);
Gly$^8$Asp$^{37}$Arg$^{26,34}$Lys$^{38}$-(Glyc-ADod)-GLP-1(7-38);
Gly$^8$Asp$^{38}$Arg$^{26,34}$Lys$^{39}$-(Glyc-ADod)-GLP-1(7-39);
Gly$^8$Asp$^{35}$Arg$^{26,34}$Lys$^{36}$-(Glyc-ADod)-GLP-1(7-36);
Gly$^8$Asp$^{35}$Arg$^{26,34}$Lys$^{36}$-(Glyc-ADod)-GLP-1(7-36)amide;
Gly$^8$Asp$^{36}$Arg$^{26,34}$Lys$^{37}$-(Glyc-ADod)-GLP-1(7-37);
Gly$^8$Asp$^{37}$Arg$^{26,34}$Lys$^{38}$-(Glyc-ADod)-GLP-1(7-38);
Gly$^8$Asp$^{38}$Arg$^{26,34}$Lys$^{39}$-(Glyc-ADod)-GLP-1(7-39);

Val$^8$Glu$^{35}$Arg$^{26,34}$Lys$^{36}$-(Glyc-ADod)-GLP-1(7-36);
Val$^8$Glu$^{35}$Arg$^{26,34}$Lys$^{36}$-(Glyc-ADod)-GLP-1(7-36)amide;
Val$^8$Glu$^{36}$Arg$^{26,34}$Lys$^{37}$-(Glyc-ADod)-GLP-1(7-37);
Val$^8$Glu$^{37}$Arg$^{26,34}$Lys$^{38}$-(Glyc-ADod)-GLP-1(7-38);
Val$^8$Glu$^{38}$Arg$^{26,34}$Lys$^{39}$-(Glyc-ADod)-GLP-1(7-39);
Val$^8$Glu$^{35}$Arg$^{26,34}$Lys$^{36}$-(Glyc-ADod)-GLP-1(7-36);
Val$^8$Glu$^{35}$Arg$^{26,34}$Lys$^{36}$-(Glyc-ADod)-GLP-1(7-36)amide;
Val$^8$Glu$^{36}$Arg$^{26,34}$Lys$^{37}$-(Glyc-ADod)-GLP-1(7-37);
Val$^8$Glu$^{37}$Arg$^{26,34}$Lys$^{38}$-(Glyc-ADod)-GLP-1(7-38);
Val$^8$Glu$^{38}$Arg$^{26,34}$Lys$^{39}$-(Glyc-ADod)-GLP-1(7-39);
Val$^8$Asp$^{35}$Arg$^{26,34}$Lys$^{36}$-(Glyc-ADod)-GLP-1(7-36);
Val$^8$Asp$^{35}$Arg$^{26,34}$Lys$^{36}$-(Glyc-ADod)-GLP-1(7-36)amide;
Val$^8$Asp$^{36}$Arg$^{26,34}$Lys$^{37}$-(Glyc-ADod)-GLP-1(7-37);
Val$^8$Asp$^{37}$Arg$^{26,34}$Lys$^{38}$-(Glyc-ADod)-GLP-1(7-38);
Val$^8$Asp$^{38}$Arg$^{26,34}$Lys$^{39}$-(Glyc-ADod)-GLP-1(7-39);
Val$^8$Asp$^{35}$Arg$^{26,34}$Lys$^{36}$-(Glyc-ADod)-GLP-1(7-36);
Val$^8$Asp$^{35}$Arg$^{26,34}$Lys$^{36}$-(Glyc-ADod)-GLP-1(7-36)amide;
Val$^8$Asp$^{36}$Arg$^{26,34}$Lys$^{37}$-(Glyc-ADod)-GLP-1(7-37);
Val$^8$Asp$^{37}$Arg$^{26,34}$Lys$^{38}$-(Glyc-ADod)-GLP-1(7-38);
Val$^8$Asp$^{38}$Arg$^{26,34}$Lys$^{39}$-(Glyc-ADod)-GLP-1(7-39);
Ser$^8$Glu$^{35}$Arg$^{26,34}$Lys$^{36}$-(Glyc-ADod)-GLP-1(7-36);
Ser$^8$Glu$^{35}$Arg$^{26,34}$Lys$^{36}$-(Glyc-ADod)-GLP-1(7-36)amide;
Ser$^8$Glu$^{36}$Arg$^{26,34}$Lys$^{37}$-(Glyc-ADod)-GLP-1(7-37);
Ser$^8$Glu$^{37}$Arg$^{26,34}$Lys$^{38}$-(Glyc-ADod)-GLP-1(7-38);
Ser$^8$Glu$^{38}$Arg$^{26,34}$Lys$^{39}$-(Glyc-ADod)-GLP-1(7-39);
Ser$^8$Glu$^{35}$Arg$^{26,34}$Lys$^{36}$-(Glyc-ADod)-GLP-1(7-36);
Ser$^8$Glu$^{35}$Arg$^{26,34}$Lys$^{36}$-(Glyc-ADod)-GLP-1(7-36)amide;
Ser$^8$Glu$^{36}$Arg$^{26,34}$Lys$^{37}$-(Glyc-ADod)-GLP-1(7-37);
Ser$^8$Glu$^{37}$Arg$^{26,34}$Lys$^{38}$-(Glyc-ADod)-GLP-1(7-38);
Ser$^8$Glu$^{38}$Arg$^{26,34}$Lys$^{39}$-(Glyc-ADod)-GLP-1(7-39);
Ser$^8$Asp$^{35}$Arg$^{26,34}$Lys$^{36}$-(Glyc-ADod)-GLP-1(7-36);
Ser$^8$Asp$^{35}$Arg$^{26,34}$Lys$^{36}$-(Glyc-ADod)-GLP-1(7-36)amide;
Ser$^8$Asp$^{36}$Arg$^{26,34}$Lys$^{37}$-(Glyc-ADod)-GLP-1(7-37);
Ser$^8$Asp$^{37}$Arg$^{26,34}$Lys$^{38}$-(Glyc-ADod)-GLP-1(7-38);
Ser$^8$Asp$^{38}$Arg$^{26,34}$Lys$^{39}$-(Glyc-ADod)-GLP-1(7-39);
Ser$^8$Asp$^{35}$Arg$^{26,34}$Lys$^{36}$-(Glyc-ADod)-GLP-1(7-36);
Ser$^8$Asp$^{35}$Arg$^{26,34}$Lys$^{36}$-(Glyc-ADod)-GLP-1(7-36)amide;
Ser$^8$Asp$^{36}$Arg$^{26,34}$Lys$^{37}$-(Glyc-ADod)-GLP-1(7-37);
Ser$^8$Asp$^{37}$Arg$^{26,34}$Lys$^{38}$-(Glyc-ADod)-GLP-1(7-38);
Ser$^8$Asp$^{38}$Arg$^{26,34}$Lys$^{39}$-(Glyc-ADod)-GLP-1(7-39);
Thr$^8$Glu$^{35}$Arg$^{26,34}$Lys$^{36}$-(Glyc-ADod)-GLP-1(7-36);
Thr$^8$Glu$^{35}$Arg$^{26,34}$Lys$^{36}$-(Glyc-ADod)-GLP-1(7-36)amide;
Thr$^8$Glu$^{36}$Arg$^{26,34}$Lys$^{37}$-(Glyc-ADod)-GLP-1(7-37);
Thr$^8$Glu$^{37}$Arg$^{26,34}$Lys$^{38}$-(Glyc-ADod)-GLP-1(7-38);
Thr$^8$Glu$^{38}$Arg$^{26,34}$Lys$^{39}$-(Glyc-ADod)-GLP-1(7-39);
Thr$^8$Glu$^{35}$Arg$^{26,34}$Lys$^{36}$-(Glyc-ADod)-GLP-1(7-36);
Thr$^8$Glu$^{35}$Arg$^{26,34}$Lys$^{36}$-(Glyc-ADod)-GLP-1(7-36)amide;
Thr$^8$Glu$^{36}$Arg$^{26,34}$Lys$^{37}$-(Glyc-ADod)-GLP-1(7-37);
Thr$^8$Glu$^{37}$Arg$^{26,34}$Lys$^{38}$-(Glyc-ADod)-GLP-1(7-38);
Thr$^8$Glu$^{38}$Arg$^{26,34}$Lys$^{39}$-(Glyc-ADod)-GLP-1(7-39);
Thr$^8$Asp$^{35}$Arg$^{26,34}$Lys$^{36}$-(Glyc-ADod)-GLP-1(7-36);
Thr$^8$Asp$^{35}$Arg$^{26,34}$Lys$^{36}$-(Glyc-ADod)-GLP-1(7-36)amide;
Thr$^8$Asp$^{36}$Arg$^{26,34}$Lys$^{37}$-(Glyc-ADod)-GLP-1(7-37);
Thr$^8$Asp$^{37}$Arg$^{26,34}$Lys$^{38}$-(Glyc-ADod)-GLP-1(7-38);
Thr$^8$Asp$^{38}$Arg$^{26,34}$Lys$^{39}$-(Glyc-ADod)-GLP-1(7-39);
Thr$^8$Asp$^{35}$Arg$^{26,34}$Lys$^{36}$-(Glyc-ADod)-GLP-1(7-36);
Thr$^8$Asp$^{35}$Arg$^{26,34}$Lys$^{36}$-(Glyc-ADod)-GLP-1(7-36)amide;
Thr$^8$Asp$^{36}$Arg$^{26,34}$Lys$^{37}$-(Glyc-ADod)-GLP-1(7-37);
Thr$^8$Asp$^{37}$Arg$^{26,34}$Lys$^{38}$-(Glyc-ADod)-GLP-1(7-38);
Thr$^8$Asp$^{38}$Arg$^{26,34}$Lys$^{39}$-(Glyc-ADod)-GLP-1(7-39);
Arg$^{26,34}$Lys$^{18}$-(Glyc-ADod)-GLP-1(7-36); Arg$^{26,34}$Lys$^{18}$-(Glyc-ADod)-GLP-1(7-36)amide; Arg$^{26,34}$Lys$^{18}$-(Glyc-ADod)-GLP-1(7-37); Arg$^{26,34}$Lys$^{18}$-(Glyc-ADod)-GLP-1(7-38); Gly$^8$Asp$^{19}$Arg$^{26,34}$Lys$^{18}$-(Glyc-ADod)-GLP-1(7-36); Gly$^8$Asp$^{17}$Arg$^{26,34}$Lys$^{18}$-(Glyc-ADod)-GLP-1(7-36); Gly$^8$Asp$^{19}$Arg$^{26,34}$Lys$^{18}$-(Glyc-ADod)-GLP-1(7-36)amide; Gly$^8$Asp$^{17}$Arg$^{26,34}$Lys$^{18}$-(Glyc-ADod)-GLP-1(7-36)amide; Gly$^8$Asp$^{19}$Arg$^{26,34}$Lys$^{18}$-(Glyc-ADod)-GLP-1(7-37); Gly$^8$Asp$^{19}$Arg$^{26,34}$Lys$^{18}$-(Glyc-ADod)-GLP-1(7-38); Gly$^8$Asp$^{17}$Arg$^{26,34}$Lys$^{18}$-(Glyc-ADod)-GLP-1(7-38); Arg$^{26,34}$Lys$^{23}$-(Glyc-ADod)-GLP-1(7-36); Arg$^{26,34}$Lys$^{23}$-(Glyc-ADod)-GLP-1(7-36)amide; Arg$^{26,34}$Lys$^{23}$-(Glyc-ADod)-GLP-1(7-37); Arg$^{26,34}$Lys$^{23}$-(Glyc-ADod)-GLP-1(7-38); Gly$^8$Asp$^{19}$Arg$^{26,34}$Lys$^{23}$-(Glyc-ADod)-GLP-1(7-36); Gly$^8$Asp$^{17}$Arg$^{26,34}$Lys$^{23}$-(Glyc-ADod)-GLP-1(7-36); Gly$^8$Asp$^9$Arg$^{26,34}$Lys$^{23}$-(Glyc-ADod)-GLP-1(7-36)amide; Gly$^8$Asp$^{17}$Arg$^{26,34}$Lys$^{23}$-(Glyc-ADod)-GLP-1(7-36)amide; Gly$^8$Asp$^9$Arg$^{26,34}$Lys$^{23}$-(Glyc-ADod)-GLP-1(7-37); Gly$^8$Asp$^{19}$Arg$^{26,34}$Lys$^{23}$-(Glyc-ADod)-GLP-1(7-38); Gly$^8$Asp$^{17}$Arg$^{26,34}$Lys$^{23}$-(Glyc-ADod)-GLP-1(7-38); Arg$^{26,34}$Lys$^{27}$-(Glyc-ADod)-GLP-1(7-36); Arg$^{26,34}$Lys$^{27}$-(Glyc-ADod)-GLP-1(7-36)amide; Arg$^{26,34}$Lys$^{27}$-(Glyc-ADod)-GLP-1(7-37); Arg$^{26,34}$Lys$^{27}$-(Glyc-ADod)-GLP-1(7-38); Gly$^8$Asp$^{19}$Arg$^{26,34}$Lys$^{27}$-(Glyc-ADod)-GLP-1(7-36); Gly$^8$Asp$^{17}$Arg$^{26,34}$Lys$^{27}$-(Glyc-ADod)-GLP-1(7-36); Gly$^8$Asp$^{19}$Arg$^{26,34}$Lys$^{27}$-(Glyc-ADod)-GLP-1(7-36)amide; Gly$^8$Asp$^{17}$Arg$^{26,34}$Lys$^{27}$-(Glyc-ADod)-GLP-1(7-36)amide; Gly$^8$Asp$^{19}$Arg$^{26,34}$Lys$^{27}$-(Glyc-ADod)-GLP-1(7-37); Gly$^8$Asp$^{19}$Arg$^{26,34}$Lys$^{27}$-(Glyc-ADod)-GLP-1(7-38); Gly$^8$Asp$^{17}$Arg$^{26,34}$Lys$^{27}$-(Glyc-ADod)-GLP-1(7-38); Arg$^{26,34}$Lys$^{18}$-(Glyc-ADod)-GLP-1(7-36); Arg$^{26,34}$Lys$^{18}$-(Glyc-ADod)-GLP-1(7-36)amide; Arg$^{26,34}$Lys$^{18}$-(Glyc-ADod)-GLP-1(7-37); Arg$^{26,34}$Lys$^{18}$-(Glyc-ADod)-GLP-1(7-38); Val$^8$Asp$^{19}$Arg$^{26,34}$Lys$^{18}$-(Glyc-ADod)-GLP-1(7-36); Val$^8$Asp$^{17}$Arg$^{26,34}$Lys$^{18}$-(Glyc-ADod)-GLP-1(7-36); Val$^8$Asp$^{19}$Arg$^{26,34}$Lys$^{18}$-(Glyc-ADod)-GLP-1(7-36)amide; Val$^8$Asp$^{17}$Arg$^{26,34}$Lys$^{18}$-(Glyc-ADod)-GLP-1(7-36)amide; Val$^8$Asp$^{19}$Arg$^{26,34}$Lys$^{18}$-(Glyc-ADod)-GLP-1(7-37); Val$^8$Asp$^{19}$Arg$^{26,34}$Lys$^{18}$-(Glyc-ADod)-GLP-1(7-38); Val$^8$Asp$^{17}$Arg$^{26,34}$Lys$^{18}$-(Glyc-ADod)-GLP-1(7-38); Arg$^{26,34}$Lys$^{23}$-(Glyc-ADod)-GLP-1(7-36); Arg$^{26,34}$Lys$^{23}$-(Glyc-ADod)-GLP-1(7-36)amide; Arg$^{26,34}$Lys$^{23}$-(Glyc-ADod)-GLP-1(7-37); Arg$^{26,34}$Lys$^{23}$-(Glyc-ADod)-GLP-1(7-38); Val$^8$Asp$^{19}$Arg$^{26,34}$Lys$^{23}$-(Glyc-ADod)-GLP-1(7-36); Val$^8$Asp$^{17}$Arg$^{26,34}$Lys$^{23}$-(Glyc-ADod)-GLP-1(7-36); Val$^8$Asp$^{19}$Arg$^{26,34}$Lys$^{23}$-(Glyc-ADod)-GLP-1(7-36)amide; Val$^8$Asp$^{17}$Arg$^{26,34}$Lys$^{23}$-(Glyc-ADod)-GLP-1(7-36)amide; Val$^8$Asp$^{19}$Arg$^{26,34}$Lys$^{23}$-(Glyc-ADod)-GLP-1(7-37); Val$^8$Asp$^{19}$Arg$^{26,34}$Lys$^{23}$-(Glyc-ADod)-GLP-1(7-38); Val$^8$Asp$^{17}$Arg$^{26,34}$Lys$^{23}$-(Glyc-ADod)-GLP-1(7-38); Arg$^{26,34}$Lys$^{27}$-(Glyc-ADod)-GLP-1(7-36); Arg$^{26,34}$Lys$^{27}$-(Glyc-ADod)-GLP-1(7-36)amide; Arg$^{26,34}$Lys$^{27}$-(Glyc-ADod)-GLP-1(7-37); Arg$^{26,34}$Lys$^{27}$-(Glyc-ADod)-GLP-1(7-38); Val$^8$Asp$^{19}$Arg$^{26,34}$Lys$^{27}$-(Glyc-ADod)-GLP-1(7-36); Val$^8$Asp$^{17}$Arg$^{26,34}$Lys$^{27}$-(Glyc-ADod)-GLP-1(7-36); Val$^8$Asp$^{19}$Arg$^{26,34}$Lys$^{27}$-(Glyc-ADod)-GLP-1(7-36)amide; Val$^8$Asp$^{17}$Arg$^{26,34}$Lys$^{27}$-(Glyc-ADod)-GLP-1(7-36)amide; Val$^8$Asp$^{19}$Arg$^{26,34}$Lys$^{27}$-(Glyc-ADod)-GLP-1(7-37); Val$^8$Asp$^{19}$Arg$^{26,34}$Lys$^{27}$-(Glyc-ADod)-GLP-1(7-38); Val$^8$Asp$^{17}$Arg$^{26,34}$Lys$^{27}$-(Glyc-ADod)-GLP-1(7-38); Arg$^{26,34}$Lys$^{18}$-(Glyc-ADod)-GLP-1(7-36); Arg$^{26,34}$Lys$^{18}$-(Glyc-ADod)-GLP-1(7-36)amide; Arg$^{26,34}$Lys$^{18}$-(Glyc-ADod)-GLP-1(7-37); Arg$^{26,34}$Lys$^{18}$-(Glyc-ADod)-GLP-1(7-38); Ser$^8$Asp$^{19}$Arg$^{26,34}$Lys$^{18}$-(Glyc-ADod)-GLP-1(7-36); Ser$^8$Asp$^{17}$Arg$^{26,34}$Lys$^{18}$-(Glyc-ADod)-GLP-1(7-36); Ser$^8$Asp$^{19}$Arg$^{26,34}$Lys$^{18}$-(Glyc-ADod)-GLP-1(7-36)amide; Ser$^8$Asp$^{17}$Arg$^{26,34}$Lys$^{18}$-(Glyc-ADod)-GLP-1(7-36)amide; Ser$^8$Asp$^{19}$Arg$^{26,34}$Lys$^{18}$-(Glyc-ADod)-GLP-1(7-37); Ser$^8$Asp$^{19}$Arg$^{26,34}$Lys$^{18}$-(Glyc-ADod)-GLP-1(7-38); Ser$^8$Asp$^{17}$Arg$^{26,34}$Lys$^{18}$-(Glyc-ADod)-GLP-1(7-38); Arg$^{26,34}$Lys$^{23}$-(Glyc-ADod)-GLP-1(7-36); Arg$^{26,34}$Lys$^{23}$-(Glyc-ADod)-GLP-1(7-36)amide; Arg$^{26,34}$Lys$^{23}$-(Glyc-ADod)-GLP-1(7-37); Arg$^{26,34}$Lys$^{23}$-(Glyc-ADod)-GLP-1(7-38); Ser$^8$Asp$^{19}$Arg$^{26,34}$Lys$^{23}$-(Glyc-ADod)-GLP-1(7-

36); Ser⁸Asp¹⁷Arg²⁶,³⁴Lys²³-(Glyc-ADod)-GLP-1(7-36); Ser⁸Asp¹⁹Arg²⁶,³⁴Lys²³-(Glyc-ADod)-GLP-1(7-36)amide; Ser⁸Asp¹⁷Arg²⁶,³⁴Lys²³-(Glyc-ADod)-GLP-1(7-36)amide; Ser⁸Asp¹⁹Arg²⁶,³⁴Lys²³-(Glyc-ADod)-GLP-1(7-37); Ser⁸Asp¹⁹Arg²⁶,³⁴Lys²³-(Glyc-ADod)-GLP-1(7-38); Ser⁸Asp¹⁷Arg²⁶,³⁴Lys²³-(Glyc-ADod)-GLP-1(7-38); Arg²⁶,³⁴Lys²⁷-(Glyc-ADod)-GLP-1(7-36); Arg²⁶,³⁴Lys²⁷-(Glyc-ADod)-GLP-1(7-36)amide; Arg²⁶,³⁴Lys²⁷-(Glyc-ADod)-GLP-1(7-37); Arg²⁶,³⁴Lys²⁷-(Glyc-ADod)-GLP-1(7-38); Ser⁸Asp¹⁹Arg²⁶,³⁴Lys²⁷-(Glyc-ADod)-GLP-1(7-36); Ser⁸Asp¹⁷Arg²⁶,³⁴Lys²⁷-(Glyc-ADod)-GLP-1(7-36); Ser⁸Asp¹⁹Arg²⁶,³⁴Lys²⁷-(Glyc-ADod)-GLP-1(7-36)amide; Ser⁸Asp¹⁷Arg²⁶,³⁴Lys²⁷-(Glyc-ADod)-GLP-1(7-36)amide; Ser⁸Asp¹⁹Arg²⁶,³⁴Lys²⁷-(Glyc-ADod)-GLP-1(7-37); Ser⁸Asp¹⁹Arg²⁶,³⁴Lys²⁷-(Glyc-ADod)-GLP-1(7-38); Ser⁸Asp¹⁷Arg²⁶,³⁴Lys²⁷-(Glyc-ADod)-GLP-1(7-38); Arg²⁶,³⁴Lys¹⁸-(Glyc-ADod)-GLP-1(7-36); Arg²⁶,³⁴Lys¹⁸-(Glyc-ADod)-GLP-1(7-36)amide; Arg²⁶,³⁴Lys¹⁸-(Glyc-ADod)-GLP-1(7-37); Arg²⁶,³⁴Lys¹⁸-(Glyc-ADod)-GLP-1(7-38); Thr⁸Asp¹⁹Arg²⁶,³⁴Lys¹⁸(Glyc-ADod)-GLP-1(7-36); Thr⁸Asp¹⁷Arg²⁶,³⁴Lys¹⁸-(Glyc-ADod)-GLP-1(7-36); Thr⁸Asp¹⁹Arg²⁶,³⁴Lys¹⁸-(Glyc-ADod)-GLP-1(7-36)amide; Thr⁸Asp¹⁷Arg²⁶,³⁴Lys¹⁸-(Glyc-ADod)-GLP-1(7-36)amide; Thr⁸Asp¹⁹Arg²⁶,³⁴Lys¹⁸-(Glyc-ADod)-GLP-1(7-37); Thr⁸Asp¹⁹Arg²⁶,³⁴Lys¹⁸-(Glyc-ADod)-GLP-1(7-38); Thr⁸Asp¹⁷Arg²⁶,³⁴Lys¹⁸-(Glyc-ADod)-GLP-1(7-38); Arg²⁶,³⁴Lys²³-(Glyc-ADod)-GLP-1(7-36); Arg²⁶,³⁴Lys²³-(Glyc-ADod)-GLP-1(7-36)amide; Arg²⁶,³⁴Lys²³-(Glyc-ADod)-GLP-1(7-37); Arg²⁶,³⁴Lys²³-(Glyc-ADod)-GLP-1(7-38); Thr⁸Asp¹⁹Arg²⁶,³⁴Lys²³-(Glyc-ADod)-GLP-1(7-36); Thr⁸Asp¹⁷Arg²⁶,³⁴Lys²³-(Glyc-ADod)-GLP-1(7-36); Thr⁸Asp¹⁹Arg²⁶,³⁴Lys²³-(Glyc-ADod)-GLP-1(7-36)amide; Thr⁸Asp¹⁷Arg²⁶,³⁴Lys²³-(Glyc-ADod)-GLP-1(7-36)amide; Thr⁸Asp¹⁹Arg²⁶,³⁴Lys²³-(Glyc-ADod)-GLP-1(7-37); Thr⁸Asp¹⁹Arg²⁶,³⁴Lys²³-(Glyc-ADod)-GLP-1(7-38); Thr⁸Asp¹⁷Arg²⁶,³⁴Lys²³-(Glyc-ADod)-GLP-1(7-38); Arg²⁶,³⁴Lys²⁷-(Glyc-ADod)-GLP-1(7-36); Arg²⁶,³⁴Lys²⁷-(Glyc-ADod)-GLP-1(7-36)amide; Arg²⁶,³⁴Lys²⁷-(Glyc-ADod)-GLP-1(7-37); Arg²⁶,³⁴Lys²⁷-(Glyc-ADod)-GLP-1(7-38); Thr⁸Asp¹⁹Arg²⁶,³⁴Lys²⁷-(Glyc-ADod)-GLP-1(7-36); Thr⁸Asp¹⁷Arg²⁶,³⁴Lys²⁷-(Glyc-ADod)-GLP-1(7-36); Thr⁸Asp¹⁹Arg²⁶,³⁴Lys²⁷-(Glyc-ADod)-GLP-1(7-36)amide; Thr⁸Asp¹⁷Arg²⁶,³⁴Lys²⁷-(Glyc-ADod)-GLP-1(7-36)amide; Thr⁸Asp¹⁹Arg²⁶,³⁴Lys²⁷-(Glyc-ADod)-GLP-1(7-37); Thr⁸Asp¹⁹Arg²⁶,³⁴Lys²⁷-(Glyc-ADod)-GLP-1(7-38); Thr⁸Asp¹⁷Arg²⁶,³⁴Lys²⁷-(Glyc-ADod)-GLP-1(7-38); Arg²⁶Lys³⁴-(Glyc-ATet)-GLP-1(7-36); Arg³⁴Lys²⁶-(Glyc-ATet)-GLP-1(7-36); Arg²⁶,³⁴Lys³⁶-(Glyc-ATet)-GLP-1(7-36); Arg²⁶Lys³⁴-(Glyc-ATet)-GLP-1(7-36)amide; Arg³⁴Lys²⁶-(Glyc-ATet)-GLP-1(7-36)amide; Arg²⁶,³⁴Lys³⁶-(Glyc-ATet)-GLP-1(7-36)amide; Arg²⁶Lys³⁴-(Glyc-ATet)-GLP-1(7-37); Arg³⁴Lys²⁶-(Glyc-ATet)-GLP-1(7-37); Arg²⁶,³⁴Lys³⁶-(Glyc-ATet)-GLP-1(7-37); Arg²⁶Lys³⁴-(Glyc-ATet)-GLP-1(7-38); Arg³⁴Lys²⁶-(Glyc-ATet)-GLP-1(7-38); Arg²⁶,³⁴Lys³⁸-(Glyc-ATet)-GLP-1(7-38); Arg²⁶Lys³⁴-(Glyc-ATet)-GLP-1(7-39); Arg³⁴Lys²⁶-(Glyc-ATet)-GLP-1(7-39); Arg²⁶,³⁴Lys³⁹-(Glyc-ATet)-GLP-1(7-39); Gly⁸Arg²⁶Lys³⁴-(Glyc-ATet)-GLP-1(7-36); Gly⁸Arg³⁴Lys²⁶-(Glyc-ATet)-GLP-1(7-36); Gly⁸Arg²⁶,³⁴Lys³⁶-(Glyc-ATet)-GLP-1(7-36); Gly⁸Arg²⁶Lys³⁴-(Glyc-ATet)-GLP-1(7-36)amide; Gly⁸Arg³⁴Lys²⁶-(Glyc-ATet)-GLP-1(7-36)amide; Gly⁸Arg²⁶,³⁴Lys³⁶-(Glyc-ATet)-GLP-1(7-36)amide; Gly⁸Arg²⁶Lys³⁴-(Glyc-ATet)-GLP-1(7-37); Gly⁸Arg³⁴Lys²⁶-(Glyc-ATet)-GLP-1(7-37); Gly⁸Arg²⁶,³⁴Lys³⁶-(Glyc-ATet)-GLP-1(7-37); Gly⁸Arg²⁶Lys³⁴-(Glyc-ATet)-GLP-1(7-38); Gly⁸Arg³⁴Lys²⁶-(Glyc-ATet)-GLP-1(7-38); Gly⁸Arg²⁶,³⁴Lys³⁸-(Glyc-ATet)-GLP-1(7-38); Gly⁸Arg²⁶Lys³⁴-(Glyc-ATet)-GLP-1(7-39); Gly⁸Arg³⁴Lys²⁶-(Glyc-ATet)-GLP-1(7-39); Gly⁸Arg²⁶,³⁴Lys³⁹-(Glyc-ATet)-GLP-1(7-39); Val⁸Arg²⁶Lys³⁴-(Glyc-ATet)-GLP-1(7-36); Val⁸Arg³⁴Lys²⁶-(Glyc-ATet)-GLP-1(7-36); Val⁸Arg²⁶,³⁴Lys³⁶-(Glyc-ATet)-GLP-1(7-36); Val⁸Arg²⁶Lys³⁴-(Glyc-ATet)-GLP-1(7-36)amide; Val⁸Arg³⁴Lys²⁶-(Glyc-ATet)-GLP-1(7-36)amide; Val⁸Arg²⁶,³⁴Lys³⁶-(Glyc-ATet)-GLP-1(7-36)amide; Val⁸Arg²⁶Lys³⁴-(Glyc-ATet)-GLP-1(7-37); Val⁸Arg³⁴Lys²⁶-(Glyc-ATet)-GLP-1(7-37); Val⁸Arg²⁶,³⁴Lys³⁶-(Glyc-ATet)-GLP-1(7-37); Val⁸Arg²⁶Lys³⁴-(Glyc-ATet)-GLP-1(7-38); Val⁸Arg³⁴Lys²⁶-(Glyc-ATet)-GLP-1(7-38); Val⁸Arg²⁶,³⁴Lys³⁸-(Glyc-ATet)-GLP-1(7-38); Val⁸Arg²⁶Lys³⁴-(Glyc-ATet)-GLP-1(7-39); Val⁸Arg³⁴Lys²⁶-(Glyc-ATet)-GLP-1(7-39); Val⁸Arg²⁶,³⁴Lys³⁹-(Glyc-ATet)-GLP-1(7-39); Ser⁸Arg²⁶Lys³⁴-(Glyc-ATet)-GLP-1(7-36); Ser⁸Arg³⁴Lys²⁶-(Glyc-ATet)-GLP-1(7-36); Ser⁸Arg²⁶,³⁴Lys³⁶-(Glyc-ATet)-GLP-1(7-36); Ser⁸Arg²⁶Lys³⁴-(Glyc-ATet)-GLP-1(7-36)amide; Ser⁸Arg³⁴Lys²⁶-(Glyc-ATet)-GLP-1(7-36)amide; Ser⁸Arg²⁶,³⁴Lys³⁶-(Glyc-ATet)-GLP-1(7-36)amide; Ser⁸Arg²⁶Lys³⁴-(Glyc-ATet)-GLP-1(7-37); Ser⁸Arg³⁴Lys²⁶-(Glyc-ATet)-GLP-1(7-37); Ser⁸Arg²⁶,³⁴Lys³⁶-(Glyc-ATet)-GLP-1(7-37); Ser⁸Arg²⁶Lys³⁴-(Glyc-ATet)-GLP-1(7-38); Ser⁸Arg³⁴Lys²⁶-(Glyc-ATet)-GLP-1(7-38); Ser⁸Arg²⁶,³⁴Lys³⁸-(Glyc-ATet)-GLP-1(7-38); Ser⁸Arg²⁶Lys³⁴-(Glyc-ATet)-GLP-1(7-39); Ser⁸Arg³⁴Lys²⁶-(Glyc-ATet)-GLP-1(7-39); Ser⁸Arg²⁶,³⁴Lys³⁹-(Glyc-ATet)-GLP-1(7-39); Thr⁸Arg²⁶Lys³⁴-(Glyc-ATet)-GLP-1(7-36); Thr⁸Arg³⁴Lys²⁶-(Glyc-ATet)-GLP-1(7-36); Thr⁸Arg²⁶,³⁴Lys³⁶-(Glyc-ATet)-GLP-1(7-36); Thr⁸Arg²⁶Lys³⁴-(Glyc-ATet)-GLP-1(7-36)amide; Thr⁸Arg³⁴Lys²⁶-(Glyc-ATet)-GLP-1(7-36)amide; Thr⁸Arg²⁶,³⁴Lys³⁶-(Glyc-ATet)-GLP-1(7-36)amide; Thr⁸Arg²⁶Lys³⁴-(Glyc-ATet)-GLP-1(7-37); Thr⁸Arg³⁴Lys²⁶-(Glyc-ATet)-GLP-1(7-37); Thr⁸Arg²⁶,³⁴Lys³⁶-(Glyc-ATet)-GLP-1(7-37); Thr⁸Arg²⁶Lys³⁴-(Glyc-ATet)-GLP-1(7-38); Thr⁸Arg³⁴Lys²⁶-(Glyc-ATet)-GLP-1(7-38); Thr⁸Arg²⁶,³⁴Lys³⁸-(Glyc-ATet)-GLP-1(7-38); Thr⁸Arg²⁶Lys³⁴-(Glyc-ATet)-GLP-1(7-39); Thr⁸Arg³⁴Lys²⁶-(Glyc-ATet)-GLP-1(7-39); Thr⁸Arg²⁶,³⁴Lys³⁹-(Glyc-ATet)-GLP-1(7-39); Gly⁸Glu³⁵Arg²⁶,³⁴Lys³⁶-(Glyc-ATet)-GLP-1(7-36); Gly⁸Glu³⁵Arg²⁶,³⁴Lys³⁶-(Glyc-ATet)-GLP-1(7-36)amide; Gly⁸Glu³⁶Arg²⁶,³⁴Lys³⁷-(Glyc-ATet)-GLP-1(7-37); Gly⁸Glu³⁷Arg²⁶,³⁴Lys³⁸-(Glyc-ATet)-GLP-1(7-38); Gly⁸Glu³⁸Arg²⁶,³⁴Lys³⁹-(Glyc-ATet)-GLP-1(7-39); Gly⁸Glu³⁵Arg²⁶,³⁴Lys³⁶-(Glyc-ATet)-GLP-1(7-36); Gly⁸Glu³⁵Arg²⁶,³⁴Lys³⁶-(Glyc-ATet)-GLP-1(7-36)amide; Gly⁸Glu³⁶Arg²⁶,³⁴Lys³⁷-(Glyc-ATet)-GLP-1(7-37); Gly⁸Glu³⁷Arg²⁶,³⁴Lys³⁸-(Glyc-ATet)-GLP-1(7-38); Gly⁸Glu³⁸Arg²⁶,³⁴Lys³⁹-(Glyc-ATet)-GLP-1(7-39); Gly⁸Asp³⁵Arg²⁶,³⁴Lys³⁶-(Glyc-ATet)-GLP-1(7-36); Gly⁸Asp³⁵Arg²⁶,³⁴Lys³⁶-(Glyc-ATet)-GLP-1(7-36)amide; Gly⁸Asp³⁶Arg²⁶,³⁴Lys³⁷-(Glyc-ATet)-GLP-1(7-37); Gly⁸Asp³⁷Arg²⁶,³⁴Lys³⁸-(Glyc-ATet)-GLP-1(7-38); Gly⁸Asp³⁸Arg²⁶,³⁴Lys³⁹-(Glyc-ATet)-GLP-1(7-39); Gly⁸Asp³⁵Arg²⁶,³⁴Lys³⁶-(Glyc-ATet)-GLP-1(7-36); Gly⁸Asp³⁵Arg²⁶,³⁴Lys³⁶-(Glyc-ATet)-GLP-1(7-36)amide; Gly⁸Asp³⁶Arg²⁶,³⁴Lys³⁷-(Glyc-ATet)-GLP-1(7-37); Gly⁸Asp³⁷Arg²⁶,³⁴Lys³⁸-(Glyc-ATet)-GLP-1(7-38); Gly⁸Asp³⁸Arg²⁶,³⁴Lys³⁹-(Glyc-ATet)-GLP-1(7-39); Val⁸Glu³⁵Arg²⁶,³⁴Lys³⁶-(Glyc-ATet)-GLP-1(7-36); Val⁸Glu³⁵Arg²⁶,³⁴Lys³⁶-(Glyc-ATet)-GLP-1(7-36)amide; Val⁸Glu³⁶Arg²⁶,³⁴Lys³⁷-(Glyc-ATet)-GLP-1(7-37); Val⁸Glu³⁷Arg²⁶,³⁴Lys³⁸-(Glyc-ATet)-GLP-1(7-38); Val⁸Glu³⁸Arg²⁶,³⁴Lys³⁹-(Glyc-ATet)-GLP-1(7-39); Val⁸Glu³⁵Arg²⁶,³⁴Lys³⁶-(Glyc-ATet)-GLP-1(7-36);

Val$^8$Glu$^{35}$Arg$^{26,34}$Lys$^{36}$-(Glyc-ATet)-GLP-1(7-36);
Val$^8$Glu$^{36}$Arg$^{26,34}$Lys$^{37}$-(Glyc-ATet)-GLP-1(7-37);
Val$^8$Glu$^{37}$Arg$^{26,34}$Lys$^{38}$-(Glyc-ATet)-GLP-1(7-38);
Val$^8$Glu$^{38}$Arg$^{26,34}$Lys$^{39}$-(Glyc-ATet)-GLP-1(7-39);
Val$^8$Asp$^{35}$Arg$^{26,34}$Lys$^{36}$-(Glyc-ATet)-GLP-1(7-36);
Val$^8$Asp$^{35}$Arg$^{26,34}$Lys$^{36}$-(Glyc-ATet)-GLP-1(7-36)amide;
Val$^8$Asp$^{36}$Arg$^{26,34}$Lys$^{37}$-(Glyc-ATet)-GLP-1(7-37);
Val$^8$Asp$^{37}$Arg$^{26,34}$Lys$^{38}$-(Glyc-ATet)-GLP-1(7-38);
Val$^8$Asp$^{38}$Arg$^{26,34}$Lys$^{39}$-(Glyc-ATet)-GLP-1(7-39);
Val$^8$Asp$^{35}$Arg$^{26,34}$Lys$^{36}$-(Glyc-ATet)-GLP-1(7-36);
Val$^8$Asp$^{35}$Arg$^{26,34}$Lys$^{36}$-(Glyc-ATet)-GLP-1(7-36)amide;
Val$^8$Asp$^{36}$Arg$^{26,34}$Lys$^{37}$-(Glyc-ATet)-GLP-1(7-37);
Val$^8$Asp$^{37}$Arg$^{26,34}$Lys$^{38}$-(Glyc-ATet)-GLP-1(7-38);
Val$^8$Asp$^{38}$Arg$^{26,34}$Lys$^{39}$-(Glyc-ATet)-GLP-1(7-39);
Ser$^8$Glu$^{35}$Arg$^{26,34}$Lys$^{36}$-(Glyc-ATet)-GLP-1(7-36);
Ser$^8$Glu$^{35}$Arg$^{26,34}$Lys$^{36}$-(Glyc-ATet)-GLP-1(7-36)amide;
Ser$^8$Glu$^{36}$Arg$^{26,34}$Lys$^{37}$-(Glyc-ATet)-GLP-1(7-37);
Ser$^8$Glu$^{37}$Arg$^{26,34}$Lys$^{38}$-(Glyc-ATet)-GLP-1(7-38);
Ser$^8$Glu$^{38}$Arg$^{26,34}$Lys$^{39}$-(Glyc-ATet)-GLP-1(7-39);
Ser$^8$Glu$^{35}$Arg$^{26,34}$Lys$^{36}$-(Glyc-ATet)-GLP-1(7-36);
Ser$^8$Glu$^{35}$Arg$^{26,34}$Lys$^{36}$-(Glyc-ATet)-GLP-1(7-36)amide;
Ser$^8$Glu$^{36}$Arg$^{26,34}$Lys$^{37}$-(Glyc-ATet)-GLP-1(7-37);
Ser$^8$Glu$^{37}$Arg$^{26,34}$Lys$^{38}$-(Glyc-ATet)-GLP-1(7-38);
Ser$^8$Glu$^{38}$Arg$^{26,34}$Lys$^{39}$-(Glyc-ATet)-GLP-1(7-39);
Ser$^8$Asp$^{35}$Arg$^{26,34}$Lys$^{36}$-(Glyc-ATet)-GLP-1(7-36);
Ser$^8$Asp$^{35}$Arg$^{26,34}$Lys$^{36}$-(Glyc-ATet)-GLP-1(7-36)amide;
Ser$^8$Asp$^{36}$Arg$^{26,34}$Lys$^{37}$-(Glyc-ATet)-GLP-1(7-37);
Ser$^8$Asp$^{37}$Arg$^{26,34}$Lys$^{38}$-(Glyc-ATet)-GLP-1(7-38);
Ser$^8$Asp$^{38}$Arg$^{26,34}$Lys$^{39}$-(Glyc-ATet)-GLP-1(7-39);
Ser$^8$Asp$^{35}$Arg$^{26,34}$Lys$^{36}$-(Glyc-ATet)-GLP-1(7-36);
Ser$^8$Asp$^{35}$Arg$^{26,34}$Lys$^{36}$-(Glyc-ATet)-GLP-1(7-36)amide;
Ser$^8$Asp$^{36}$Arg$^{26,34}$Lys$^{37}$-(Glyc-ATet)-GLP-1(7-37);
Ser$^8$Asp$^{37}$Arg$^{26,34}$Lys$^{38}$-(Glyc-ATet)-GLP-1(7-38);
Ser$^8$Asp$^{38}$Arg$^{26,34}$Lys$^{39}$-(Glyc-ATet)-GLP-1(7-39);
Thr$^8$Glu$^{35}$Arg$^{26,34}$Lys$^{36}$-(Glyc-ATet)-GLP-1(7-36);
Thr$^8$Glu$^{35}$Arg$^{26,34}$Lys$^{36}$-(Glyc-ATet)-GLP-1(7-36)amide;
Thr$^8$Glu$^{36}$Arg$^{26,34}$Lys$^{37}$-(Glyc-ATet)-GLP-1(7-37);
Thr$^8$Glu$^{37}$Arg$^{26,34}$Lys$^{38}$-(Glyc-ATet)-GLP-1(7-38);
Thr$^8$Glu$^{38}$Arg$^{26,34}$Lys$^{39}$-(Glyc-ATet)-GLP-1(7-39);
Thr$^8$Glu$^{35}$Arg$^{26,34}$Lys$^{36}$-(Glyc-ATet)-GLP-1(7-36);
Thr$^8$Glu$^{35}$Arg$^{26,34}$Lys$^{36}$-(Glyc-ATet)-GLP-1(7-36)amide;
Thr$^8$Glu$^{36}$Arg$^{26,34}$Lys$^{37}$-(Glyc-ATet)-GLP-1(7-37);
Thr$^8$Glu$^{37}$Arg$^{26,34}$Lys$^{38}$-(Glyc-ATet)-GLP-1(7-38);
Thr$^8$Glu$^{38}$Arg$^{26,34}$Lys$^{39}$-(Glyc-ATet)-GLP-1(7-39);
Thr$^8$Asp$^{35}$Arg$^{26,34}$Lys$^{36}$-(Glyc-ATet)-GLP-1(7-36);
Thr$^8$Asp$^{35}$Arg$^{26,34}$Lys$^{36}$-(Glyc-ATet)-GLP-1(7-36)amide;
Thr$^8$Asp$^{36}$Arg$^{26,34}$Lys$^{37}$-(Glyc-ATet)-GLP-1(7-37);
Thr$^8$Asp$^{37}$Arg$^{26,34}$Lys$^{38}$-(Glyc-ATet)-GLP-1(7-38);
Thr$^8$Asp$^{38}$Arg$^{26,34}$Lys$^{39}$-(Glyc-ATet)-GLP-1(7-39);
Thr$^8$Asp$^{35}$Arg$^{26,34}$Lys$^{36}$-(Glyc-ATet)-GLP-1(7-36);
Thr$^8$Asp$^{35}$Arg$^{26,34}$Lys$^{36}$-(Glyc-ATet)-GLP-1(7-36)amide;
Thr$^8$Asp$^{36}$Arg$^{26,34}$Lys$^{37}$-(Glyc-ATet)-GLP-1(7-37);
Thr$^8$Asp$^{37}$Arg$^{26,34}$Lys$^{38}$-(Glyc-ATet)-GLP-1(7-38);
Thr$^8$Asp$^{38}$Arg$^{26,34}$Lys$^{39}$-(Glyc-ATet)-GLP-1(7-39);
Arg$^{26,34}$Lys$^{18}$-(Glyc-ATet)-GLP-1(7-36); Arg$^{26,34}$Lys$^{18}$-(Glyc-ATet)-GLP-1(7-36)amide; Arg$^{26,34}$Lys$^{18}$-(Glyc-ATet)-GLP-1(7-37); Arg$^{26,34}$Lys$^{18}$-(Glyc-ATet)-GLP-1(7-38); Gly$^8$Asp$^{19}$Arg$^{26,34}$Lys$^{18}$-(Glyc-ATet)-GLP-1(7-36);
Gly$^8$Asp$^{17}$Arg$^{26,34}$Lys$^{18}$-(Glyc-ATet)-GLP-1(7-36);
Gly$^8$Asp$^{19}$Arg$^{26,34}$Lys$^{18}$-(Glyc-ATet)-GLP-1(7-36)amide;
Gly$^8$Asp$^{17}$Arg$^{26,34}$Lys$^{18}$-(Glyc-ATet)-GLP-1(7-36)amide;
Gly$^8$Asp$^{19}$Arg$^{26,34}$Lys$^{18}$-(Glyc-ATet)-GLP-1(7-37);
Gly$^8$Asp$^{19}$Arg$^{26,34}$Lys$^{18}$-(Glyc-ATet)-GLP-1(7-38);
Gly$^8$Asp$^{17}$Arg$^{26,34}$Lys$^{18}$-(Glyc-ATet)-GLP-1(7-38);
Arg$^{26,34}$Lys$^{23}$-(Glyc-ATet)-GLP-1(7-36); Arg$^{26,34}$Lys$^{23}$-(Glyc-ATet)-GLP-1(7-36)amide; Arg$^{26,34}$Lys$^{23}$-(Glyc-ATet)-GLP-1(7-37); Arg$^{26,34}$Lys$^{23}$-(Glyc-ATet)-GLP-1(7-38); Gly$^8$Asp$^{19}$Arg$^{26,34}$Lys$^{23}$-(Glyc-ATet)-GLP-1(7-36);
Gly$^8$Asp$^{17}$Arg$^{26,34}$Lys$^{23}$-(Glyc-ATet)-GLP-1(7-36);
Gly$^8$Asp$^{19}$Arg$^{26,34}$Lys$^{23}$-(Glyc-ATet)-GLP-1(7-36)amide;
Gly$^8$Asp$^{17}$Arg$^{26,34}$Lys$^{23}$-(Glyc-ATet)-GLP-1(7-36)amide;
Gly$^8$Asp$^{19}$Arg$^{26,34}$Lys$^{23}$-(Glyc-ATet)-GLP-1(7-37);
Gly$^8$Asp$^{19}$Arg$^{26,34}$Lys$^{23}$-(Glyc-ATet)-GLP-1(7-38);
Gly$^8$Asp$^{17}$Arg$^{26,34}$Lys$^{23}$-(Glyc-ATet)-GLP-1(7-38);
Arg$^{26,34}$Lys$^{27}$-(Glyc-ATet)-GLP-1(7-36); Arg$^{26,34}$Lys$^{27}$-(Glyc-ATet)-GLP-1(7-36)amide; Arg$^{26,34}$Lys$^{27}$-(Glyc-ATet)-GLP-1(7-37); Arg$^{26,34}$Lys$^{27}$-(Glyc-ATet)-GLP-1(7-38); Gly$^8$Asp$^{19}$Arg$^{26,34}$Lys$^{27}$-(Glyc-ATet)-GLP-1(7-36);
Gly$^8$Asp$^{17}$Arg$^{26,34}$Lys$^{27}$-(Glyc-ATet)-GLP-1(7-36);
Gly$^8$Asp$^{19}$Arg$^{26,34}$Lys$^{27}$-(Glyc-ATet)-GLP-1(7-36)amide;
Gly$^8$Asp$^{17}$Arg$^{26,34}$Lys$^{27}$-(Glyc-ATet)-GLP-1(7-36)amide;
Gly$^8$Asp$^{19}$Arg$^{26,34}$Lys$^{27}$-(Glyc-ATet)-GLP-1(7-37);
Gly$^8$Asp$^{19}$Arg$^{26,34}$Lys$^{27}$-(Glyc-ATet)-GLP-1(7-38);
Gly$^8$Asp$^{17}$Arg$^{26,34}$Lys$^{27}$-(Glyc-ATet)-GLP-1(7-38);
Arg$^{26,34}$Lys$^{18}$-(Glyc-ATet)-GLP-1(7-36); Arg$^{26,34}$Lys$^{18}$-(Glyc-ATet)-GLP-1(7-36)amide; Arg$^{26,34}$Lys$^{18}$-(Glyc-ATet)-GLP-1(7-37); Arg$^{26,34}$Lys$^{18}$-(Glyc-ATet)-GLP-1(7-38); Val$^8$Asp$^{19}$Arg$^{26,34}$Lys$^{18}$-(Glyc-ATet)-GLP-1(7-36);
Val$^8$Asp$^{17}$Arg$^{26,34}$Lys$^{18}$-(Glyc-ATet)-GLP-1(7-36);
Val$^8$Asp$^{19}$Arg$^{26,34}$Lys$^{18}$-(Glyc-ATet)-GLP-1(7-36)amide;
Val$^8$Asp$^{17}$Arg$^{26,34}$Lys$^{18}$-(Glyc-ATet)-GLP-1(7-36)amide;
Val$^8$Asp$^{19}$Arg$^{26,34}$Lys$^{18}$-(Glyc-ATet)-GLP-1(7-37);
Val$^8$Asp$^{19}$Arg$^{26,34}$Lys$^{18}$-(Glyc-ATet)-GLP-1(7-38);
Val$^8$Asp$^{17}$Arg$^{26,34}$Lys$^{18}$-(Glyc-ATet)-GLP-1(7-38);
Arg$^{26,34}$Lys$^{23}$-(Glyc-ATet)-GLP-1(7-36); Arg$^{26,34}$Lys$^{23}$-(Glyc-ATet)-GLP-1(7-36)amide; Arg$^{26,34}$Lys$^{23}$-(Glyc-ATet)-GLP-1(7-37); Arg$^{26,34}$Lys$^{23}$-(Glyc-ATet)-GLP-1(7-38); Val$^8$Asp$^{19}$Arg$^{26,34}$Lys$^{23}$-(Glyc-ATet)-GLP-1(7-36);
Val$^8$Asp$^{17}$Arg$^{26,34}$Lys$^{23}$-(Glyc-ATet)-GLP-1(7-36);
Val$^8$Asp$^{19}$Arg$^{26,34}$Lys$^{23}$-(Glyc-ATet)-GLP-1(7-36)amide;
Val$^8$Asp$^{17}$Arg$^{26,34}$Lys$^{23}$-(Glyc-ATet)-GLP-1(7-36)amide;
Val$^8$Asp$^{19}$Arg$^{26,34}$Lys$^{23}$-(Glyc-ATet)-GLP-1(7-37);
Val$^8$Asp$^{19}$Arg$^{26,34}$Lys$^{23}$-(Glyc-ATet)-GLP-1(7-38);
Val$^8$Asp$^{17}$Arg$^{26,34}$Lys$^{23}$-(Glyc-ATet)-GLP-1(7-38);
Arg$^{26,34}$Lys$^{27}$-(Glyc-ATet)-GLP-1(7-36); Arg$^{26,34}$Lys$^{27}$-(Glyc-ATet)-GLP-1(7-36)amide; Arg$^{26,34}$Lys$^{27}$-(Glyc-ATet)-GLP-1(7-37); Arg$^{26,34}$Lys$^{27}$-(Glyc-ATet)-GLP-1(7-38); Val$^8$Asp$^{19}$Arg$^{26,34}$Lys$^{27}$-(Glyc-ATet)-GLP-1(7-36);
Val$^8$Asp$^{17}$Arg$^{26,34}$Lys$^{27}$-(Glyc-ATet)-GLP-1(7-36);
Val$^8$Asp$^{19}$Arg$^{26,34}$Lys$^{27}$-(Glyc-ATet)-GLP-1(7-36)amide;
Val$^8$Asp$^{17}$Arg$^{26,34}$Lys$^{27}$-(Glyc-ATet)-GLP-1(7-36)amide;
Val$^8$Asp$^{19}$Arg$^{26,34}$Lys$^{27}$-(Glyc-ATet)-GLP-1(7-37);
Val$^8$Asp$^{19}$Arg$^{26,34}$Lys$^{27}$-(Glyc-ATet)-GLP-1(7-38);
Val$^8$Asp$^{17}$Arg$^{26,34}$Lys$^{27}$-(Glyc-ATet)-GLP-1(7-38);
Arg$^{26,34}$Lys$^{18}$-(Glyc-ATet)-GLP-1(7-36); Arg$^{26,34}$Lys$^{18}$-(Glyc-ATet)-GLP-1(7-36)amide; Arg$^{26,34}$Lys$^{18}$-(Glyc-ATet)-GLP-1(7-37); Arg$^{26,34}$Lys$^{18}$-(Glyc-ATet)-GLP-1(7-38); Ser$^8$Asp$^{19}$Arg$^{26,34}$Lys$^{18}$-(Glyc-ATet)-GLP-1(7-36);
Ser$^8$Asp$^{17}$Arg$^{26,34}$Lys$^{18}$-(Glyc-ATet)-GLP-1(7-36);
Ser$^8$Asp$^{19}$Arg$^{26,34}$Lys$^{18}$-(Glyc-ATet)-GLP-1(7-36)amide;
Ser$^8$Asp$^{17}$Arg$^{26,34}$Lys$^{18}$-(Glyc-ATet)-GLP-1(7-36)amide;
Ser$^8$Asp$^{19}$Arg$^{26,34}$Lys$^{18}$-(Glyc-ATet)-GLP-1(7-37);
Ser$^8$Asp$^{19}$Arg$^{26,34}$Lys$^{18}$-(Glyc-ATet)-GLP-1(7-38);
Ser$^8$Asp$^{17}$Arg$^{26,34}$Lys$^{18}$-(Glyc-ATet)-GLP-1(7-38);
Arg$^{26,34}$Lys$^{23}$-(Glyc-ATet)-GLP-1(7-36); Arg$^{26,34}$Lys$^{23}$-(Glyc-ATet)-GLP-1(7-36)amide; Arg$^{26,34}$Lys$^{23}$-(Glyc-ATet)-GLP-1(7-37); Arg$^{26,34}$Lys$^{23}$-(Glyc-ATet)-GLP-1(7-38); Ser$^8$Asp$^{19}$Arg$^{26,34}$Lys$^{23}$-(Glyc-ATet)-GLP-1(7-36);
Ser$^8$Asp$^{17}$Arg$^{26,34}$Lys$^{23}$-(Glyc-ATet)-GLP-1(7-36);
Ser$^8$Asp$^{19}$Arg$^{26,34}$Lys$^{23}$-(Glyc-ATet)-GLP-1(7-36)amide;
Ser$^8$Asp$^{17}$Arg$^{26,34}$Lys$^{23}$-(Glyc-ATet)-GLP-1(7-36)amide;
Ser$^8$Asp$^{19}$Arg$^{26,34}$Lys$^{23}$-(Glyc-ATet)-GLP-1(7-37);
Ser$^8$Asp$^{19}$Arg$^{26,34}$Lys$^{23}$-(Glyc-ATet)-GLP-1(7-38);
Ser$^8$Asp$^{17}$Arg$^{26,34}$Lys$^{23}$-(Glyc-ATet)-GLP-1(7-38);

Arg$^{26,34}$Lys$^{27}$-(Glyc-ATet)-GLP-1(7-36); Arg$^{26,34}$Lys$^{27}$-(Glyc-ATet)-GLP-1(7-36)amide; Arg$^{26,34}$Lys$^{27}$-(Glyc-ATet)-GLP-1(7-37); Arg$^{26,34}$Lys$^{27}$-(Glyc-ATet)-GLP-1(7-38); Ser$^8$Asp$^{19}$Arg$^{26,34}$Lys$^{27}$-(Glyc-ATet)-GLP-1(7-36); Ser$^8$Asp$^{17}$Arg$^{26,34}$Lys$^{27}$-(Glyc-ATet)-GLP-1(7-36); Ser$^8$Asp$^{19}$Arg$^{26,34}$Lys$^{27}$-(Glyc-ATet)-GLP-1(7-36)amide; Ser$^8$Asp$^{17}$Arg$^{26,34}$Lys$^{27}$-(Glyc-ATet)-GLP-1(7-36)amide; Ser$^8$Asp$^{19}$Arg$^{26,34}$Lys$^{27}$-(Glyc-ATet)-GLP-1(7-37); Ser$^8$Asp$^{19}$Arg$^{26,34}$Lys$^{27}$-(Glyc-ATet)-GLP-1(7-38); Ser$^8$Asp$^{17}$Arg$^{26,34}$Lys$^{27}$-(Glyc-ATet)-GLP-1(7-38); Arg$^{26,34}$Lys$^{18}$-(Glyc-ATet)-GLP-1(7-36); Arg$^{26,34}$Lys$^{18}$-(Glyc-ATet)-GLP-1(7-36)amide; Arg$^{26,34}$Lys$^{18}$-(Glyc-ATet)-GLP-1(7-37); Arg$^{26,34}$Lys$^{18}$-(Glyc-ATet)-GLP-1(7-38); Thr$^8$Asp$^{19}$Arg$^{26,34}$Lys$^{18}$-(Glyc-ATet)-GLP-1(7-36); Thr$^8$Asp$^{17}$Arg$^{26,34}$Lys$^{18}$-(Glyc-ATet)-GLP-1(7-36); Thr$^8$Asp$^{19}$Arg$^{26,34}$Lys$^{18}$-(Glyc-ATet)-GLP-1(7-36)amide; Thr$^8$Asp$^{17}$Arg$^{26,34}$Lys$^{18}$-(Glyc-ATet)-GLP-1(7-36)amide; Thr$^8$Asp$^{19}$Arg$^{26,34}$Lys$^{18}$-(Glyc-ATet)-GLP-1(7-37); Thr$^8$Asp$^{19}$Arg$^{26,34}$Lys$^{18}$-(Glyc-ATet)-GLP-1(7-38); Thr$^8$Asp$^{17}$Arg$^{26,34}$Lys$^{18}$-(Glyc-ATet)-GLP-1(7-38); Arg$^{26,34}$Lys$^{23}$-(Glyc-ATet)-GLP-1(7-36); Arg$^{26,34}$Lys$^{23}$-(Glyc-ATet)-GLP-1(7-36)amide; Arg$^{26,34}$Lys$^{23}$-(Glyc-ATet)-GLP-1(7-37); Arg$^{26,34}$Lys$^{23}$-(Glyc-ATet)-GLP-1(7-38); Thr$^8$Asp$^{19}$Arg$^{26,34}$Lys$^{23}$-(Glyc-ATet)-GLP-1(7-36); Thr$^8$Asp$^{17}$Arg$^{26,34}$Lys$^{23}$-(Glyc-ATet)-GLP-1(7-36); Thr$^8$Asp$^{19}$Arg$^{26,34}$Lys$^{23}$-(Glyc-ATet)-GLP-1(7-36)amide; Thr$^8$Asp$^{17}$Arg$^{26,34}$Lys$^{23}$-(Glyc-ATet)-GLP-1(7-36)amide; Thr$^8$Asp$^{19}$Arg$^{26,34}$Lys$^{23}$-(Glyc-ATet)-GLP-1(7-37); Thr$^8$Asp$^{19}$Arg$^{26,34}$Lys$^{23}$-(Glyc-ATet)-GLP-1(7-38); Thr$^8$Asp$^{17}$Arg$^{26,34}$Lys$^{23}$-(Glyc-ATet)-GLP-1(7-38); Arg$^{26,34}$Lys$^{27}$-(Glyc-ATet)-GLP-1(7-36); Arg$^{26,34}$Lys$^{27}$-(Glyc-ATet)-GLP-1(7-36)amide; Arg$^{26,34}$Lys$^{27}$-(Glyc-ATet)-GLP-1(7-37); Arg$^{26,34}$Lys$^{27}$-(Glyc-ATet)-GLP-1(7-38); Thr$^8$Asp$^{19}$Arg$^{26,34}$Lys$^{27}$-(Glyc-ATet)-GLP-1(7-36); Thr$^8$Asp$^{17}$Arg$^{26,34}$Lys$^{27}$-(Glyc-ATet)-GLP-1(7-36); Thr$^8$Asp$^{19}$Arg$^{26,34}$Lys$^{27}$-(Glyc-ATet)-GLP-1(7-36)amide; Thr$^8$Asp$^{17}$Arg$^{26,34}$Lys$^{27}$-(Glyc-ATet)-GLP-1(7-36)amide; Thr$^8$Asp$^{19}$Arg$^{26,34}$Lys$^{27}$-(Glyc-ATet)-GLP-1(7-37); Thr$^8$Asp$^{19}$Arg$^{26,34}$Lys$^{27}$-(Glyc-ATet)-GLP-1(7-38); Thr$^8$Asp$^{17}$Arg$^{26,34}$Lys$^{27}$-(Glyc-ATet)-GLP-1(7-38); Arg$^{26}$Lys$^{34}$-(Glyc-AHex)-GLP-1(7-36); Arg$^{34}$Lys$^{26}$-(Glyc-AHex)-GLP-1(7-36); Arg$^{26,34}$Lys$^{36}$-(Glyc-AHex)-GLP-1(7-36); Arg$^{26}$Lys$^{34}$-(Glyc-AHex)-GLP-1(7-36)amide; Arg$^{34}$Lys$^{26}$-(Glyc-AHex)-GLP-1(7-36)amide; Arg$^{26,34}$Lys$^{36}$-(Glyc-AHex)-GLP-1(7-36)amide; Arg$^{26}$Lys$^{34}$-(Glyc-AHex)-GLP-1(7-37); Arg$^{34}$Lys$^{26}$-(Glyc-AHex)-GLP-1(7-37); Arg$^{26,34}$Lys$^{36}$-(Glyc-AHex)-GLP-1(7-37); Arg$^{26}$Lys$^{34}$-(Glyc-AHex)-GLP-1(7-38); Arg$^{34}$Lys$^{26}$-(Glyc-AHex)-GLP-1(7-38); Arg$^{26,34}$Lys$^{38}$-(Glyc-AHex)-GLP-1(7-38); Arg$^{26}$Lys$^{34}$-(Glyc-AHex)-GLP-1(7-39); Arg$^{34}$Lys$^{26}$-(Glyc-AHex)-GLP-1(7-39); Arg$^{26,34}$Lys$^{39}$-(Glyc-AHex)-GLP-1(7-39); Gly$^8$Arg$^{26}$Lys$^{34}$-(Glyc-AHex)-GLP-1(7-36); Gly$^8$Arg$^{34}$Lys$^{26}$-(Glyc-AHex)-GLP-1(7-36); Gly$^8$Arg$^{26,34}$Lys$^{36}$-(Glyc-AHex)-GLP-1(7-36); Gly$^8$Arg$^{26}$Lys$^{34}$-(Glyc-AHex)-GLP-1(7-36)amide; Gly$^8$Arg$^{34}$Lys$^{26}$-(Glyc-AHex)-GLP-1(7-36)amide; Gly$^8$Arg$^{26,34}$Lys$^{36}$-(Glyc-AHex)-GLP-1(7-36)amide; Gly$^8$Arg$^{26}$Lys$^{34}$-(Glyc-AHex)-GLP-1(7-37); Gly$^8$Arg$^{34}$Lys$^{26}$-(Glyc-AHex)-GLP-1(7-37); Gly$^8$Arg$^{26,34}$Lys$^{36}$-(Glyc-AHex)-GLP-1(7-37); Gly$^8$Arg$^{26}$Lys$^{34}$-(Glyc-AHex)-GLP-1(7-38); Gly$^8$Arg$^{34}$Lys$^{26}$-(Glyc-AHex)-GLP-1(7-38); Gly$^8$Arg$^{26,34}$Lys$^{38}$-(Glyc-AHex)-GLP-1(7-38); Gly$^8$Arg$^{26}$Lys$^{34}$-(Glyc-AHex)-GLP-1(7-39); Gly$^8$Arg$^{34}$Lys$^{26}$-(Glyc-AHex)-GLP-1(7-39); Gly$^8$Arg$^{26,34}$Lys$^{39}$-(Glyc-AHex)-GLP-1(7-39);
Val$^8$Arg$^{26}$Lys$^{34}$-(Glyc-AHex)-GLP-1(7-36); Val$^8$Arg$^{34}$Lys$^{26}$-(Glyc-AHex)-GLP-1(7-36); Val$^8$Arg$^{26,34}$Lys$^{36}$-(Glyc-AHex)-GLP-1(7-36); Val$^8$Arg$^{26}$Lys$^{34}$-(Glyc-AHex)-GLP-1(7-36)amide; Val$^8$Arg$^{34}$Lys$^{26}$-(Glyc-AHex)-GLP-1(7-36)amide; Val$^8$Arg$^{26,34}$Lys$^{36}$-(Glyc-AHex)-GLP-1(7-36)amide; Val$^8$Arg$^{26}$Lys$^{34}$-(Glyc-AHex)-GLP-1(7-37); Val$^8$Arg$^{34}$Lys$^{26}$-(Glyc-AHex)-GLP-1(7-37); Val$^8$Arg$^{26,34}$Lys$^{36}$-(Glyc-AHex)-GLP-1(7-37); Val$^8$Arg$^{26}$Lys$^{34}$-(Glyc-AHex)-GLP-1(7-38); Val$^8$Arg$^{34}$Lys$^{26}$-(Glyc-AHex)-GLP-1(7-38); Val$^8$Arg$^{26,34}$Lys$^{38}$-(Glyc-AHex)-GLP-1(7-38); Val$^8$Arg$^{26}$Lys$^{34}$-(Glyc-AHex)-GLP-1(7-39); Val$^8$Arg$^{34}$Lys$^{26}$-(Glyc-AHex)-GLP-1(7-39); Val$^8$Arg$^{26,34}$Lys$^{39}$-(Glyc-AHex)-GLP-1(7-39);
Ser$^8$Arg$^{26}$Lys$^{34}$-(Glyc-AHex)-GLP-1(7-36); Ser$^8$Arg$^{34}$Lys$^{26}$-(Glyc-AHex)-GLP-1(7-36); Ser$^8$Arg$^{26,34}$Lys$^{36}$-(Glyc-AHex)-GLP-1(7-36); Ser$^8$Arg$^{26}$Lys$^{34}$-(Glyc-AHex)-GLP-1(7-36)amide; Ser$^8$Arg$^{34}$Lys$^{26}$-(Glyc-AHex)-GLP-1(7-36)amide; Ser$^8$Arg$^{26,34}$Lys$^{36}$-(Glyc-AHex)-GLP-1(7-36)amide; Ser$^8$Arg$^{26}$Lys$^{34}$-(Glyc-AHex)-GLP-1(7-37); Ser$^8$Arg$^{34}$Lys$^{26}$-(Glyc-AHex)-GLP-1(7-37); Ser$^8$Arg$^{26,34}$Lys$^{36}$-(Glyc-AHex)-GLP-1(7-37); Ser$^8$Arg$^{26}$Lys$^{34}$-(Glyc-AHex)-GLP-1(7-38); Ser$^8$Arg$^{34}$Lys$^{26}$-(Glyc-AHex)-GLP-1(7-38); Ser$^8$Arg$^{26,34}$Lys$^{18}$-(Glyc-AHex)-GLP-1(7-38); Ser$^8$Arg$^{26}$Lys$^{34}$-(Glyc-AHex)-GLP-1(7-39); Ser$^8$Arg$^{34}$Lys$^{26}$-(Glyc-AHex)-GLP-1(7-39); Ser$^8$Arg$^{26,34}$Lys$^{39}$-(Glyc-AHex)-GLP-1(7-39);
Thr$^8$Arg$^{26}$Lys$^{34}$-(Glyc-AHex)-GLP-1(7-36); Thr$^8$Arg$^{34}$Lys$^{26}$-(Glyc-AHex)-GLP-1(7-36); Thr$^8$Arg$^{26,34}$Lys$^{36}$-(Glyc-AHex)-GLP-1(7-36); Thr$^8$Arg$^{26}$Lys$^{34}$-(Glyc-AHex)-GLP-1(7-36)amide; Thr$^8$Arg$^{34}$Lys$^{26}$-(Glyc-AHex)-GLP-1(7-36)amide; Thr$^8$Arg$^{26,34}$Lys$^{36}$-(Glyc-AHex)-GLP-1(7-36)amide; Thr$^8$Arg$^{26}$Lys$^{34}$-(Glyc-AHex)-GLP-1(7-37); Thr$^8$Arg$^{34}$Lys$^{26}$-(Glyc-AHex)-GLP-1(7-37); Thr$^8$Arg$^{26,34}$Lys$^{36}$-(Glyc-AHex)-GLP-1(7-37); Thr$^8$Arg$^{26}$Lys$^{34}$-(Glyc-AHex)-GLP-1(7-38); Thr$^8$Arg$^{34}$Lys$^{26}$-(Glyc-AHex)-GLP-1(7-38); Thr$^8$Arg$^{26,34}$Lys$^{38}$-(Glyc-AHex)-GLP-1(7-38); Thr$^8$Arg$^{26}$Lys$^{34}$-(Glyc-AHex)-GLP-1(7-39); Thr$^8$Arg$^{34}$Lys$^{26}$-(Glyc-AHex)-GLP-1(7-39); Thr$^8$Arg$^{26,34}$Lys$^{39}$-(Glyc-AHex)-GLP-1(7-39);
Gly$^8$Glu$^{35}$Arg$^{26,34}$Lys$^{36}$-(Glyc-AHex)-GLP-1(7-36); Gly$^8$Glu$^{35}$Arg$^{26,34}$Lys$^{36}$-(Glyc-AHex)-GLP-1(7-36)amide; Gly$^8$Glu$^{36}$Arg$^{26,34}$Lys$^{37}$-(Glyc-AHex)-GLP-1(7-37); Gly$^8$Glu$^{37}$Arg$^{26,34}$Lys$^{38}$-(Glyc-AHex)-GLP-1(7-38); Gly$^8$Glu$^{38}$Arg$^{26,34}$Lys$^{39}$-(Glyc-AHex)-GLP-1(7-39); Gly$^8$Glu$^{35}$Arg$^{26,34}$Lys$^{36}$-(Glyc-AHex)-GLP-1(7-36); Gly$^8$Glu$^{35}$Arg$^{26,34}$Lys$^{36}$-(Glyc-AHex)-GLP-1(7-36)amide; Gly$^8$Glu$^{36}$Arg$^{26,34}$Lys$^{37}$-(Glyc-AHex)-GLP-1(7-37); Gly$^8$Glu$^{37}$Arg$^{26,34}$Lys$^{38}$-(Glyc-AHex)-GLP-1(7-38); Gly$^8$Glu$^{38}$Arg$^{26,34}$Lys$^{39}$-(Glyc-AHex)-GLP-1(7-39); Gly$^8$Asp$^{35}$Arg$^{26,34}$Lys$^{36}$-(Glyc-AHex)-GLP-1(7-36); Gly$^8$Asp$^{35}$Arg$^{26,34}$Lys$^{36}$-(Glyc-AHex)-GLP-1(7-36)amide; Gly$^8$Asp$^{36}$Arg$^{26,34}$Lys$^{37}$-(Glyc-AHex)-GLP-1(7-37); Gly$^8$Asp$^{37}$Arg$^{26,34}$Lys$^{38}$-(Glyc-AHex)-GLP-1(7-38); Gly$^8$Asp$^{38}$Arg$^{26,34}$Lys$^{39}$-(Glyc-AHex)-GLP-1(7-39); Gly$^8$Asp$^{35}$Arg$^{26,34}$Lys$^{36}$-(Glyc-AHex)-GLP-1(7-36); Gly$^8$Asp$^{35}$Arg$^{26,34}$Lys$^{36}$-(Glyc-AHex)-GLP-1(7-36)amide; Gly$^8$Asp$^{36}$Arg$^{26,34}$Lys$^{37}$-(Glyc-AHex)-GLP-1(7-37); Gly$^8$Asp$^{37}$Arg$^{26,34}$Lys$^{38}$-(Glyc-AHex)-GLP-1(7-38); Gly$^8$Asp$^{38}$Arg$^{26,34}$Lys$^{39}$-(Glyc-AHex)-GLP-1(7-39); Val$^8$Glu$^{35}$Arg$^{26,34}$Lys$^{36}$-(Glyc-AHex)-GLP-1(7-36); Val$^8$Glu$^{35}$Arg$^{26,34}$Lys$^{36}$-(Glyc-AHex)-GLP-1(7-36)amide; Val$^8$Glu$^{36}$Arg$^{26,34}$Lys$^{37}$-(Glyc-AHex)-GLP-1(7-37); Val$^8$Glu$^{37}$Arg$^{26,34}$Lys$^{38}$-(Glyc-AHex)-GLP-1(7-38); Val$^8$Glu$^{38}$Arg$^{26,34}$Lys$^{39}$-(Glyc-AHex)-GLP-1(7-39);

Val⁸Glu³⁵Arg²⁶,³⁴Lys³⁶-(Glyc-AHex)-GLP-1(7-36);
Val⁸Glu³⁵Arg²⁶,³⁴Lys³⁶-(Glyc-AHex)-GLP-1(7-36)amide;
Val⁸Glu³⁶Arg²⁶,³⁴Lys³⁷-(Glyc-AHex)-GLP-1(7-37);
Val⁸Glu³⁷Arg²⁶,³⁴Lys³⁸-(Glyc-AHex)-GLP-1(7-38);
Val⁸Glu³⁸Arg²⁶,³⁴Lys³⁹-(Glyc-AHex)-GLP-1(7-39);
Val⁸Asp³⁵Arg²⁶,³⁴Lys³⁶-(Glyc-AHex)-GLP-1(7-36);
Val⁸Asp³⁵Arg²⁶,³⁴Lys³⁶-(Glyc-AHex)-GLP-1(7-36)amide;
Val⁸Asp³⁶Arg²⁶,³⁴Lys³⁷-(Glyc-AHex)-GLP-1(7-37);
Val⁸Asp³⁷Arg²⁶,³⁴Lys³⁸-(Glyc-AHex)-GLP-1(7-38);
Val⁸Asp³⁸Arg²⁶,³⁴Lys³⁹-(Glyc-AHex)-GLP-1(7-39);
Val⁸Asp³⁵Arg²⁶,³⁴Lys³⁶-(Glyc-AHex)-GLP-1(7-36);
Val⁸Asp³⁵Arg²⁶,³⁴Lys³⁶-(Glyc-AHex)-GLP-1(7-36)amide;
Val⁸Asp³⁶Arg²⁶,³⁴Lys³⁷-(Glyc-AHex)-GLP-1(7-37);
Val⁸Asp³⁷Arg²⁶,³⁴Lys³⁸-(Glyc-AHex)-GLP-1(7-38);
Val⁸Asp³⁸Arg²⁶,³⁴Lys³⁹-(Glyc-AHex)-GLP-1(7-39);
Ser⁸Glu³⁵Arg²⁶,³⁴Lys³⁶-(Glyc-AHex)GLP-1(7-36);
Ser⁸Glu³⁵Arg²⁶,³⁴Lys³⁶-(Glyc-AHex)-GLP-1(7-36)amide;
Ser⁸Glu³⁶Arg²⁶,³⁴Lys³⁷-(Glyc-AHex)-GLP-1(7-37);
Ser⁸Glu³⁷Arg²⁶,³⁴Lys³⁸-(Glyc-AHex)-GLP-1(7-38);
Ser⁸Glu³⁸Arg²⁶,³⁴Lys³⁹-(Glyc-AHex)-GLP-1(7-39);
Ser⁸Glu³⁵Arg²⁶,³⁴Lys³⁶-(Glyc-AHex)-GLP-1(7-36);
Ser⁸Glu³⁵Arg²⁶,³⁴Lys³⁶-(Glyc-AHex)-GLP-1(7-36)amide;
Ser⁸Glu³⁶Arg²⁶,³⁴Lys³⁷-(Glyc-AHex)-GLP-1(7-37);
Ser⁸Glu³⁷Arg²⁶,³⁴Lys³⁸-(Glyc-AHex)-GLP-1(7-38);
Ser⁸Glu³⁸Arg²⁶,³⁴Lys³⁹-(Glyc-AHex)-GLP-1(7-39);
Ser⁸Asp³⁵Arg²⁶,³⁴Lys³⁶-(Glyc-AHex)-GLP-1(7-36);
Ser⁸Asp³⁵Arg²⁶,³⁴Lys³⁶-(Glyc-AHex)-GLP-1(7-36)amide;
Ser⁸Asp³⁶Arg²⁶,³⁴Lys³⁷ (Glyc-AHex)-GLP-1(7-37);
Ser⁸Asp³⁷Arg²⁶,³⁴Lys³⁸(Glyc-AHex)-GLP-1(7-38);
Ser⁸Asp³⁸Arg²⁶,³⁴Lys³⁹-(Glyc-AHex)-GLP-1(7-39);
Ser⁸Asp³⁵Arg²⁶,³⁴Lys³⁶-(Glyc-AHex)-GLP-1(7-36);
Ser⁸Asp³⁵Arg²⁶,³⁴Lys³⁶-(Glyc-AHex)-GLP-1(7-36)amide;
Ser⁸Asp³⁶Arg²⁶,³⁴Lys³⁷-(Glyc-AHex)-GLP-1(7-37);
Ser⁸Asp³⁷Arg²⁶,³⁴Lys³⁹-(Glyc-AHex)-GLP-1(7-3);
Ser⁸Asp³⁸Asp³⁵Arg²⁶,³⁴Lys³⁹-(Glyc-AHex)-GLP-1(7-39);
Thr⁸Glu³⁵Arg²⁶,³⁴Lys³⁶-(Glyc-AHex)-GLP-1(7-36);
Thr⁸Glu³Arg²⁶,³⁴Lys³⁶-(Glyc-AHex)-GLP-1(7-36)amide;
Thr⁸Glu³⁶Arg²⁶,³⁴Lys³⁷-(Glyc-AHex)-GLP-1(7-37);
Thr⁸Glu³⁷Arg²⁶,³⁴Lys³⁸-(Glyc-AHex)-GLP-1(7-38);
Thr⁸Glu³⁸Arg²⁶,³⁴Lys³⁹-(Glyc-AHex)-GLP-1(7-39);
Thr⁸Glu³Arg²⁶,³⁴Lys³⁶-(Glyc-AHex)-GLP-1(7-36);
Thr⁸Glu³⁵Arg²⁶,³⁴Lys³⁶-(Glyc-AHex)-GLP-1(7-36)amide;
Thr⁸Glu³⁶Arg²⁶,³⁴Lys³⁶-(Glyc-AHex)-GLP-1(7-37);
Thr⁸Glu³⁷Arg²⁶,³⁴Lys³⁸-(Glyc-AHex)-GLP-1(7-38);
Thr⁸Glu³⁸Arg²⁶,³⁴Lys³⁹-(Glyc-AHex)-GLP-1(7-39);
Thr⁸Asp³⁵Arg²⁶,³⁴Lys³⁶-(Glyc-AHex)-GLP-1(7-3);
Thr⁸Asp³⁵Arg²⁶,³⁴Lys³⁶-(Glyc-AHex)-GLP-1(7-36)amide;
Thr⁸Asp³⁶Arg²⁶,³⁴Lys³⁷-(Glyc-AHex)-GLP-1(7-367);
Thr⁸Asp³⁷Arg²⁶,³⁴Lys³⁸-(Glyc-AHex)-GLP-1(7-38);
Thr⁸Asp³⁸Arg²⁶,³⁴Lys³⁹-(Glyc-AHex)-GLP-1(7-39);
Thr⁸Asp³Arg²⁶,³⁴Lys³⁶-(Glyc-AHex)-GLP-1(7-36);
Thr⁸Asp³⁵Arg²⁶,³⁴Lys³⁶-(Glyc-AHex)-GLP-1(7-36)amide;
Thr⁸Asp³⁶Arg²⁶,³⁴Lys³⁷-(Glyc-AHex)-GLP-1(7-37);
Thr⁸Asp³⁷Arg²⁶,³⁴Lys³⁸-(Glyc-AHex)-GLP-1(7-38);
Thr⁸Asp³⁷Arg²⁶,³⁴Lys³⁹-(Glyc-AHex)-GLP-1(7-39);
Arg²⁶,³⁴Lys¹⁸-(Glyc-AHex)-GLP-1(7-36); Arg²⁶,³⁴Lys¹⁸-(Glyc-AHex)-GLP-1(7-36)amide; Arg²⁶,³⁴Lys¹⁸-(Glyc-AHex)-GLP-1(7-37); Arg²⁶,³⁴Lys¹⁸-(Glyc-AHex)-GLP-1(7-38); Gly⁸Asp¹⁹Arg²⁶,³⁴Lys¹⁸-(Glyc-AHex)-GLP-1(7-36); Gly⁸Asp¹⁷Arg²⁶,³⁴Lys¹⁸-(Glyc-AHex)-GLP-1(7-36);
Gly⁸Asp¹⁹Arg²⁶,³⁴Lys¹⁸-(Glyc-AHex)-GLP-1(7-36);
Gly⁸Asp¹⁷Arg²⁶,³⁴Lys¹⁸-(Glyc-AHex)-GLP-1(7-36)amide;
Gly⁸Asp¹⁹Arg²⁶,³⁴Lys¹⁸-(Glyc-AHex)-GLP-1(7-37);
Gly⁸Asp¹⁹Arg²⁶,³⁴Lys¹⁸-(Glyc-AHex)-GLP-1(7-38);
Gly⁸Asp¹⁷Arg²⁶,³⁴Lys¹⁸(Glyc-AHex)-GLP-1(7-38);
Arg²⁶,³⁴Lys²³-(Glyc-AHex)-GLP-1(7-36); Arg²⁶,³⁴Lys²³-(Glyc-AHex)-GLP-1(7-36)amide; Arg²⁶,³⁴Lys²³-(Glyc-AHex)-GLP-1(7-37); Arg²⁶,³⁴Lys²³-(Glyc-AHex)-GLP-1(7-38); Gly⁸Asp¹⁹Arg²⁶,³⁴Lys²³-(Glyc-AHex)-GLP-1(7-36); Gly⁸Asp¹⁷Arg²⁶,³⁴Lys²³-(Glyc-AHex)-GLP-1(7-36);
Gly⁸Asp¹⁹Arg²⁶,³⁴Lys²³-(Glyc-AHex)-GLP-1(7-36)amide;
Gly⁸Asp¹⁷Arg²⁶,³⁴Lys²³-(Glyc-AHex)-GLP-1(7-36)amide;
Gly⁸Asp¹⁹Arg²⁶,³⁴Lys²³-(Glyc-AHex)-GLP-1(7-37);
Gly⁸Asp¹⁹Arg²⁶,³⁴Lys²³-(Glyc-AHex)-GLP-1(7-38);
Gly⁸Asp¹⁷Arg²⁶,³⁴Lys³⁸-(Glyc-AHex)-GLP-1(7-38);
Arg²⁶,³⁴Lys²⁷-(Glyc-AHex)-GLP-1(7-36); Arg²⁶,³⁴Lys²⁷-(Glyc-AHex)-GLP-1(7-36)amide; Arg²⁶,³⁴Lys²⁷-(Glyc-AHex)-GLP-1(7-37); Arg²⁶,³⁴Lys²⁷-(Glyc-AHex)-GLP-1(7-38); Gly⁸Asp¹⁹Arg²⁶,³⁴Lys²⁷-(Glyc-AHex)-GLP-1(7-36); Gly⁸Asp¹⁷Arg²⁶,³⁴Lys²⁷-(Glyc-AHex)-GLP-1(7-36);
Gly⁸Asp¹⁹Arg²⁶,³⁴Lys²⁷-(Glyc-AHex)-GLP-1(7-36)amide;
Gly⁸Asp¹⁷Arg²⁶,³⁴Lys²⁷-(Glyc-AHex)-GLP-1(7-36)amide;
Gly⁸Asp¹⁹Arg²⁶,³⁴Lys²⁷-(Glyc-AHex)-GLP-1(7-37);
Gly⁸Asp¹⁹Arg²⁶,³⁴Lys²⁷-(Glyc-AHex)-GLP-1(7-38);
Gly⁸Asp¹⁷Arg²⁶,³⁴Lys²⁷-(Glyc-AHex)-GLP-1(7-38);
Arg²⁶,³⁴Lys¹⁸-(Glyc-AHex)-GLP-1(7-36); Arg²⁶,³⁴Lys¹⁸-(Glyc-AHex)-GLP-1(7-36)amide; Arg²⁶,³⁴Lys¹⁸-(Glyc-AHex)-GLP-1(7-37); Arg²⁶,³⁴Lys¹⁸-(Glyc-AHex)-GLP-1(7-38); Val⁸Asp¹⁹Arg²⁶,³⁴Lys¹⁸-(Glyc-AHex)-GLP-1(7-36); Val⁸Asp¹⁷Arg²⁶,³⁴Lys¹⁸-(Glyc-AHex)-GLP-1(7-36);
Val⁸Asp¹⁹Arg²⁶,³⁴Lys¹⁸-(Glyc-AHex)-GLP-1(7-36)amide;
Val⁸Asp¹⁷Arg²⁶,³⁴Lys¹⁸-(Glyc-AHex)-GLP-1(7-36)amide;
Val⁸Asp¹⁹Arg²⁶,³⁴Lys¹⁸-(Glyc-AHex)-GLP-1(7-37);
Val⁸Asp¹⁹Arg²⁶,³⁴Lys¹⁸-(Glyc-AHex)-GLP-1(7-38);
Val⁸Asp¹⁷Arg²⁶,³⁴Lys¹⁸-(Glyc-AHex)-GLP-1(7-38);
Arg²⁶,³⁴Lys²³-(Glyc-AHex)-GLP-1(7-36); Arg²⁶,³⁴Lys²³-(Glyc-AHex)-GLP-1(7-36)amide; Arg²⁶,³⁴Lys²³-(Glyc-AHex)-GLP-1(7-37); Arg²⁶,³⁴Lys²³-(Glyc-AHex)-GLP-1(7-38); Val⁸Asp¹⁹Arg²⁶,³⁴Lys²³-(Glyc-AHex)-GLP-1(7-36); Val⁸Asp¹⁷Arg²⁶,³⁴Lys²³-(Glyc-AHex)-GLP-1(7-36);
Val⁸Asp¹⁹Arg²⁶,³⁴Lys²³-(Glyc-AHex)-GLP-1(7-36)amide;
Val⁸Asp¹⁷Arg²⁶,³⁴Lys²³-(Glyc-AHex)-GLP-1(7-36)amide;
Val⁸Asp¹⁹Arg²⁶,³⁴Lys²³-(Glyc-AHex)-GLP-1(7-37);
Val⁸Asp¹⁹Arg²⁶,³⁴Lys²³-(Glyc-AHex)-GLP-1(7-38);
Val⁸Asp¹⁷Arg²⁶,³⁴Lys²³-(Glyc-AHex)-GLP-1(7-38);
Arg²⁶,³⁴Lys²⁷-(Glyc-AHex)-GLP-1(7-36); Arg²⁶,³⁴Lys²⁷-(Glyc-AHex)-GLP-1(7-37); Arg²⁶,³⁴Lys²⁷-(Glyc-AHex)-GLP-1(7-38); Val⁸Asp¹⁹Arg²⁶,³⁴Lys²⁷-(Glyc-AHex)-GLP-1(7-36); Val⁸Asp¹⁷Arg²⁶,³⁴Lys²⁷-(Glyc-AHex)-GLP-1(7-36);
Val⁸Asp¹⁹Arg²⁶,³⁴Lys²⁷-(Glyc-AHex)-GLP-1(7-36)amide;
Val⁸Asp¹⁷Arg²⁶,³⁴Lys²⁷-(Glyc-AHex)-GLP-1(7-36)amide;
Val⁸Asp¹⁹Arg²⁶,³⁴Lys²⁷-(Glyc-AHex)-GLP-1(7-37);
Val⁸Asp¹⁹Arg²⁶,³⁴Lys²⁷-(Glyc-AHex)-GLP-1(7-38);
Val⁸Asp¹⁷Arg²⁶,³⁴Lys²⁷-(Glyc-AHex)-GLP-1(7-38);
Arg²⁶,³⁴Lys¹⁸-(Glyc-AHex)-GLP-1(7-36); Arg²⁶,³⁴Lys¹⁸-(Glyc-AHex)-GLP-1(7-36)amide; Arg²⁶,³⁴Lys¹⁸-(Glyc-AHex)-GLP-1(7-37); Arg²⁶,³⁴Lys¹⁸-(Glyc-AHex)-GLP-1(7-38); Ser⁸Asp¹⁹Arg²⁶,³⁴Lys¹⁸-(Glyc-AHex)-GLP-1(7-36); Ser⁸Asp¹⁷Arg²⁶,³⁴Lys¹⁸-(Glyc-AHex)-GLP-1(7-36);
Ser⁸Asp¹⁹Arg²⁶,³⁴Lys¹⁸-(Glyc-AHex)-GLP-1(7-36)amide;
Ser⁸Asp¹⁷Arg²⁶,³⁴Lys¹⁸-(Glyc-AHex)-GLP-1(7-36)amide;
Ser⁸Asp¹⁹Arg²⁶,³⁴Lys¹⁸-(Glyc-AHex)-GLP-1(7-37);
Ser⁸Asp¹⁹Arg²⁶,³⁴Lys¹⁸-(Glyc-AHex)-GLP-1(7-38);
Ser⁸Asp¹⁷Arg²⁶,³⁴Lys¹⁸-(Glyc-AHex)-GLP-1(7-38);
Arg²⁶,³⁴Lys²³-(Glyc-AHex)-GLP-1(7-36); Arg²⁶,³⁴Lys²³-(Glyc-AHex)-GLP-1(7-36)amide; Arg²⁶,³⁴Lys²³-(Glyc-AHex)-GLP-1(7-37); Arg²⁶,³⁴Lys²³-(Glyc-AHex)-GLP-1(7-38); Ser⁸Asp¹⁹Arg²⁶,³⁴Lys²³-(Glyc-AHex)-GLP-1(7-36); Ser⁸Asp¹⁷Arg²⁶,³⁴Lys²³-(Glyc-AHex)-GLP-1(7-36);
Ser⁸Asp¹⁹Arg²⁶,³⁴Lys²³-(Glyc-AHex)-GLP-1(7-36)amide;
Ser⁸Asp¹⁷Arg²⁶,³⁴Lys²³-(Glyc-AHex)-GLP-1(7-36)amide;
Ser⁸Asp¹⁹Arg²⁶,³⁴Lys²³-(Glyc-AHex)-GLP-1(7-37);

Ser$^8$Asp$^{19}$Arg$^{26,34}$Lys$^{23}$-(Glyc-AHex)-GLP-1(7-38);
Ser$^8$Asp$^{17}$Arg$^{26,34}$Lys$^{23}$-(Glyc-AHex)-GLP-1(7-38);
Arg$^{26,34}$Lys$^{27}$-(Glyc-AHex)-GLP-1(7-36); Arg$^{26,34}$Lys$^{27}$-(Glyc-AHex)-GLP-1(7-36)amide; Arg$^{26,34}$Lys$^{27}$-(Glyc-AHex)-GLP-1(7-37); Arg$^{26,34}$Lys$^{27}$-(Glyc-AHex)-GLP-1(7-38); Ser$^8$Asp$^{19}$Arg$^{26,34}$Lys$^{27}$-(Glyc-AHex)-GLP-1(7-36); Ser$^8$Asp$^{17}$Arg$^{26,34}$Lys$^{27}$-(Glyc-AHex)-GLP-1(7-36); Ser$^8$Asp$^{19}$Arg$^{26,34}$Lys$^{27}$-(Glyc-AHex)-GLP-1(7-36)amide; Ser$^8$Asp$^{17}$Arg$^{26,34}$Lys$^{27}$-(Glyc-AHex)-GLP-1(7-36)amide; Ser$^8$Asp$^{19}$Arg$^{26,34}$Lys$^{27}$-(Glyc-AHex)-GLP-1(7-37); Ser$^8$Asp$^{19}$Arg$^{26,34}$Lys$^{27}$-(Glyc-AHex)-GLP-1(7-38); Ser$^8$Asp$^{17}$Arg$^{26,34}$Lys$^{27}$-(Glyc-AHex)-GLP-1(7-38);
Arg$^{26,34}$Lys$^{18}$-(Glyc-AHex)-GLP-1(7-36); Arg$^{26,34}$Lys$^{18}$-(Glyc-AHex)-GLP-1(7-36)amide; Arg$^{26,34}$Lys$^{18}$-(Glyc-AHex)-GLP-1(7-37); Arg$^{26,34}$Lys$^{18}$-(Glyc-AHex)-GLP-1(7-38); Thr$^8$Asp$^{19}$Arg$^{26,34}$Lys$^{18}$(Glyc-AHex)-GLP-1(7-36); Thr$^8$Asp$^{17}$Arg$^{26,34}$Lys$^{18}$-(Glyc-AHex)-GLP-1(7-36); Thr$^8$Asp$^{19}$Arg$^{26,34}$Lys$^{18}$-(Glyc-AHex)-GLP-1(7-36)amide; Thr$^8$Asp$^{17}$Arg$^{26,34}$Lys$^{18}$-(Glyc-AHex)-GLP-1(7-36)amide; Thr$^8$Asp$^{19}$Arg$^{26,34}$Lys$^{18}$-(Glyc-AHex)-GLP-1(7-37); Thr$^8$Asp$^{19}$Arg$^{26,34}$Lys$^{18}$-(Glyc-AHex)-GLP-1(7-38); Thr$^8$Asp$^{17}$Arg$^{26,34}$Lys$^{18}$-(Glyc-AHex)-GLP-1(7-38);
Arg$^{26,34}$Lys$^{23}$-(Glyc-AHex)-GLP-1(7-36); Arg$^{26,34}$Lys$^{23}$-(Glyc-AHex)-GLP-1(7-36)amide; Arg$^{26,34}$Lys$^{23}$-(Glyc-AHex)-GLP-1(7-37); Arg$^{26,34}$Lys$^{23}$-(Glyc-AHex)-GLP-1(7-38); Thr$^8$Asp$^{19}$Arg$^{26,34}$Lys$^{23}$-(Glyc-AHex)-GLP-1(7-36); Thr$^8$Asp$^{17}$Arg$^{26,34}$Lys$^{23}$-(Glyc-AHex)-GLP-1(7-36); Thr$^8$Asp$^{19}$Arg$^{26,34}$Lys$^{23}$-(Glyc-AHex)-GLP-1(7-36)amide; Thr$^8$Asp$^{17}$Arg$^{26,34}$Lys$^{23}$-(Glyc-AHex)-GLP-1(7-36)amide; Thr$^8$Asp$^{19}$Arg$^{26,34}$Lys$^{23}$-(Glyc-AHex)-GLP-1(7-37); Thr$^8$Asp$^{19}$Arg$^{26,34}$Lys$^{23}$-(Glyc-AHex)-GLP-1(7-38); Thr$^8$Asp$^{17}$Arg$^{26,34}$Lys$^{23}$-(Glyc-AHex)-GLP-1(7-38);
Arg$^{26,34}$Lys$^{27}$-(Glyc-AHex)-GLP-1(7-36); Arg$^{26,34}$Lys$^{27}$-(Glyc-AHex)-GLP-1(7-36)amide; Arg$^{26,34}$Lys$^{27}$-(Glyc-AHex)-GLP-1(7-37); Arg$^{26,34}$Lys$^{27}$-(Glyc-AHex)-GLP-1(7-38); Thr$^8$Asp$^{19}$Arg$^{26,34}$Lys$^{27}$-(Glyc-AHex)-GLP-1(7-36); Thr$^8$Asp$^{17}$Arg$^{26,34}$Lys$^{27}$-(Glyc-AHex)-GLP-1(7-36); Thr$^8$Asp$^{19}$Arg$^{26,34}$Lys$^{27}$-(Glyc-AHex)-GLP-1(7-36)amide; Thr$^8$Asp$^{17}$Arg$^{26,34}$Lys$^{27}$-(Glyc-AHex)-GLP-1(7-36)amide; Thr$^8$Asp$^{19}$Arg$^{26,34}$Lys$^{27}$-(Glyc-AHex)-GLP-1(7-37); Thr$^8$Asp$^{19}$Arg$^{26,34}$Lys$^{27}$-(Glyc-AHex)-GLP-1(7-38); Thr$^8$Asp$^{17}$Arg$^{26,34}$Lys$^{27}$-(Glyc-AHex)-GLP-1(7-38);
Arg$^{26}$Lys$^{34}$-(Glyc-AOct)-GLP-1(7-36); Arg$^{34}$Lys$^{26}$-(Glyc-AOct)-GLP-1(7-36); Arg$^{26,34}$Lys$^{36}$-(Glyc-AOct)-GLP-1(7-36); Arg$^{26}$Lys$^{34}$-(Glyc-AOct)-GLP-1(7-36)amide; Arg$^{34}$Lys$^{26}$-(Glyc-AOct)-GLP-1(7-36)amide; Arg$^{26,34}$Lys$^{36}$-(Glyc-AOct)-GLP-1(7-36)amide; Arg$^{26}$Lys$^{34}$-(Glyc-AOct)-GLP-1(7-37); Arg$^{34}$Lys$^{26}$-(Glyc-AOct)-GLP-1(7-37); Arg$^{26,34}$Lys$^{36}$-(Glyc-AOct)-GLP-1(7-37); Arg$^{26}$Lys$^{34}$-(Glyc-AOct)-GLP-1(7-38); Arg$^{34}$Lys$^{26}$-(Glyc-AOct)-GLP-1(7-38); Arg$^{26,34}$Lys$^{38}$-(Glyc-AOct)-GLP-1(7-38); Arg$^{26}$Lys$^{34}$-(Glyc-AOct)-GLP-1(7-39); Arg$^{34}$Lys$^{26}$-(Glyc-AOct)-GLP-1(7-39); Arg$^{26,34}$Lys$^{39}$-(Glyc-AOct)-GLP-1(7-39);
Gly$^8$Arg$^{26}$Lys$^{34}$-(Glyc-AOct)-GLP-1(7-36); Gly$^8$Arg$^{34}$Lys$^{26}$-(Glyc-AOct)-GLP-1(7-36); Gly$^8$Arg$^{26,34}$Lys$^{36}$-(Glyc-AOct)-GLP-1(7-36); Gly$^8$Arg$^{26}$Lys$^{34}$-(Glyc-AOct)-GLP-1(7-36)amide; Gly$^8$Arg$^{34}$Lys$^{26}$-(Glyc-AOct)-GLP-1(7-36)amide; Gly$^8$Arg$^{26,34}$Lys$^{36}$-(Glyc-AOct)-GLP-1(7-36)amide; Gly$^8$Arg$^{26}$Lys$^{34}$-(Glyc-AOct)-GLP-1(7-37); Gly$^8$Arg$^{34}$Lys$^{26}$-(Glyc-AOct)-GLP-1(7-37); Gly$^8$Arg$^{26,34}$Lys$^{36}$-(Glyc-AOct)-GLP-1(7-37); Gly$^8$Arg$^{26}$Lys$^{34}$-(Glyc-AOct)-GLP-1(7-38); Gly$^8$Arg$^{34}$Lys$^{26}$-(Glyc-AOct)-GLP-1(7-38); Gly$^8$Arg$^{26,34}$Lys$^{38}$-(Glyc-AOct)-GLP-1(7-38); Gly$^8$Arg$^{26}$Lys$^{34}$-(Glyc-AOct)-GLP-1(7-39); Gly$^8$Arg$^{34}$Lys$^{26}$-(Glyc-AOct)-GLP-1(7-39); Gly$^8$Arg$^{26,34}$Lys$^{39}$-(Glyc-AOct)-GLP-1(7-39);
Val$^8$Arg$^{26}$Lys$^{34}$-(Glyc-AOct)-GLP-1(7-36); Val$^8$Arg$^{34}$Lys$^{26}$-(Glyc-AOct)-GLP-1(7-36); Val$^8$Arg$^{26,34}$Lys$^{36}$-(Glyc-AOct)-GLP-1(7-36); Val$^8$Arg$^{26}$Lys$^{34}$-(Glyc-AOct)-GLP-1(7-36)amide; Val$^8$Arg$^{34}$Lys$^{26}$-(Glyc-AOct)-GLP-1(7-36)amide; Val$^8$Arg$^{26,34}$Lys$^{36}$-(Glyc-AOct)-GLP-1(7-36)amide; Val$^8$Arg$^{26}$Lys$^{34}$-(Glyc-AOct)-GLP-1(7-37); Val$^8$Arg$^{34}$Lys$^{26}$-(Glyc-AOct)-GLP-1(7-37); Val$^8$Arg$^{26,34}$Lys$^{36}$-(Glyc-AOct)-GLP-1(7-37); Val$^8$Arg$^{26}$Lys$^{34}$-(Glyc-AOct)-GLP-1(7-38); Val$^8$Arg$^{34}$Lys$^{26}$-(Glyc-AOct)-GLP-1(7-38); Val$^8$Arg$^{26,34}$Lys$^{38}$-(Glyc-AOct)-GLP-1(7-38); Val$^8$Arg$^{26}$Lys$^{34}$-(Glyc-AOct)-GLP-1(7-39); Val$^8$Arg$^{34}$Lys$^{26}$-(Glyc-AOct)-GLP-1(7-39); Val$^8$Arg$^{26,34}$Lys$^{39}$-(Glyc-AOct)-GLP-1(7-39);
Ser$^8$Arg$^{26}$Lys$^{34}$-(Glyc-AOct)-GLP-1(7-36); Ser$^8$Arg$^{34}$Lys$^{26}$-(Glyc-AOct)-GLP-1(7-36); Ser$^8$Arg$^{26,34}$Lys$^{36}$-(Glyc-AOct)-GLP-1(7-36); Ser$^8$Arg$^{26}$Lys$^{34}$-(Glyc-AOct)-GLP-1(7-36)amide; Ser$^8$Arg$^{34}$Lys$^{26}$-(Glyc-AOct)-GLP-1(7-36)amide; Ser$^8$Arg$^{26,34}$Lys$^{36}$-(Glyc-AOct)-GLP-1(7-36)amide; Ser$^8$Arg$^{26}$Lys$^{34}$-(Glyc-AOct)-GLP-1(7-37); Ser$^8$Arg$^{34}$Lys$^{26}$-(Glyc-AOct)-GLP-1(7-37); Ser$^8$Arg$^{26,34}$Lys$^{36}$-(Glyc-AOct)-GLP-1(7-37); Ser$^8$Arg$^{26}$Lys$^{34}$-(Glyc-AOct)-GLP-1(7-38); Ser$^8$Arg$^{34}$Lys$^{26}$-(Glyc-AOct)-GLP-1(7-38); Ser$^8$Arg$^{26,34}$Lys$^{38}$-(Glyc-AOct)-GLP-1(7-38); Ser$^8$Arg$^{26}$Lys$^{34}$-(Glyc-AOct)-GLP-1(7-39); Ser$^8$Arg$^{34}$Lys$^{26}$-(Glyc-AOct)-GLP-1(7-39); Ser$^8$Arg$^{26,34}$Lys$^{39}$-(Glyc-AOct)-GLP-1(7-39);
Thr$^8$Arg$^{26}$Lys$^{34}$-(Glyc-AOct)-GLP-1(7-36); Thr$^8$Arg$^{34}$Lys$^{26}$-(Glyc-AOct)-GLP-1(7-36); Thr$^8$Arg$^{26,34}$Lys$^{36}$-(Glyc-AOct)-GLP-1(7-36); Thr$^8$Arg$^{26}$Lys$^{34}$-(Glyc-AOct)-GLP-1(7-36)amide; Thr$^8$Arg$^{34}$Lys$^{26}$-(Glyc-AOct)-GLP-1(7-36)amide; Thr$^8$Arg$^{26,34}$Lys$^{36}$-(Glyc-AOct)-GLP-1(7-36)amide; Thr$^8$Arg$^{26}$Lys$^{34}$-(Glyc-AOct)-GLP-1(7-37); Thr$^8$Arg$^{34}$Lys$^{26}$-(Glyc-AOct)-GLP-1(7-37); Thr$^8$Arg$^{26,34}$Lys$^{36}$-(Glyc-AOct)-GLP-1(7-37); Thr$^8$Arg$^{26}$Lys$^{34}$-(Glyc-AOct)-GLP-1(7-38); Thr$^8$Arg$^{34}$Lys$^{26}$-(Glyc-AOct)-GLP-1(7-38); Thr$^8$Arg$^{26,34}$Lys$^{38}$-(Glyc-AOct)-GLP-1(7-38); Thr$^8$Arg$^{26}$Lys$^{34}$-(Glyc-AOct)-GLP-1(7-39); Thr$^8$Arg$^{34}$Lys$^{26}$-(Glyc-AOct)-GLP-1(7-39); Thr$^8$Arg$^{26,34}$Lys$^{39}$-(Glyc-AOct)-GLP-1(7-39);
Gly$^8$Glu$^{35}$Arg$^{26,34}$Lys$^{36}$-(Glyc-AOct)-GLP-1(7-36); Gly$^8$Glu$^{35}$Arg$^{26,34}$Lys$^{36}$-(Glyc-AOct)-GLP-1(7-36)amide; Gly$^8$Glu$^{36}$Arg$^{26,34}$Lys$^{37}$-(Glyc-AOct)-GLP-1(7-37); Gly$^8$Glu$^{37}$Arg$^{26,34}$Lys$^{38}$-(Glyc-AOct)-GLP-1(7-38); Gly$^8$Glu$^{38}$Arg$^{26,34}$Lys$^{39}$-(Glyc-AOct)-GLP-1(7-39); Gly$^8$Glu$^{35}$Arg$^{26,34}$Lys$^{36}$-(Glyc-AOct)-GLP-1(7-36); Gly$^8$Glu$^{35}$Arg$^{26,34}$Lys$^{36}$-(Glyc-AOct)-GLP-1(7-36)amide; Gly$^8$Glu$^{36}$Arg$^{26,34}$Lys$^{37}$-(Glyc-AOct)-GLP-1(7-37); Gly$^8$Glu$^{37}$Arg$^{26,34}$Lys$^{38}$-(Glyc-AOct)-GLP-1(7-38); Gly$^8$Glu$^{38}$Arg$^{26,34}$Lys$^{39}$-(Glyc-AOct)-GLP-1(7-39); Gly$^8$Asp$^{35}$Arg$^{26,34}$Lys$^{36}$-(Glyc-AOct)-GLP-1(7-36); Gly$^8$Asp$^{35}$Arg$^{26,34}$Lys$^{36}$-(Glyc-AOct)-GLP-1(7-36)amide; Gly$^8$Asp$^{36}$Arg$^{26,34}$Lys$^{37}$-(Glyc-AOct)-GLP-1(7-37); Gly$^8$Asp$^{37}$Arg$^{26,34}$Lys$^{38}$-(Glyc-AOct)-GLP-1(7-38); Gly$^8$Asp$^{38}$Arg$^{26,34}$Lys$^{39}$-(Glyc-AOct)-GLP-1(7-39); Gly$^8$Asp$^{35}$Arg$^{26,34}$Lys$^{36}$-(Glyc-AOct)-GLP-1(7-36); Gly$^8$Asp$^{35}$Arg$^{26,34}$Lys$^{36}$-(Glyc-AOct)-GLP-1(7-36)amide; Gly$^8$Asp$^{36}$Arg$^{26,34}$Lys$^{37}$-(Glyc-AOct)-GLP-1(7-37); Gly$^8$Asp$^{37}$Arg$^{26,34}$Lys$^{38}$-(Glyc-AOct)-GLP-1(7-38); Gly$^8$Asp$^{38}$Arg$^{26,34}$Lys$^{39}$-(Glyc-AOct)-GLP-1(7-39); Val$^8$Glu$^{35}$Arg$^{26,34}$Lys$^{36}$-(Glyc-AOct)-GLP-1(7-36); Val$^8$Glu$^{35}$Arg$^{26,34}$Lys$^{36}$-(Glyc-AOct)-GLP-1(7-36)amide; Val$^8$Glu$^{36}$Arg$^{26,34}$Lys$^{37}$-(Glyc-AOct)-GLP-1(7-37); Val$^8$Glu$^{37}$Arg$^{26,34}$Lys$^{38}$-(Glyc-AOct)-GLP-1(7-38);

Val⁸Glu³⁸Arg²⁶,³⁴Lys³⁹-(Glyc-AOct)-GLP-1(7-39);
Val⁸Glu³⁵Arg²⁶,³⁴Lys³⁶-(Glyc-AOct)-GLP-1(7-36);
Val⁸Glu³⁵Arg²⁶,³⁴Lys³⁶-(Glyc-AOct)-GLP-1(7-36)amide;
Val⁸Glu³⁶Arg²⁶,³⁴Lys³⁷-(Glyc-AOct)-GLP-1(7-37);
Val⁸Glu³⁷Arg²⁶,³⁴Lys³⁸-(Glyc-AOct)-GLP-1(7-38);
Val⁸Glu³⁸Arg²⁶,³⁴Lys³⁹-(Glyc-AOct)-GLP-1(7-39);
Val⁸Asp³⁵Arg²⁶,³⁴Lys³⁶-(Glyc-AOct)-GLP-1(7-36);
Val⁸Asp³⁵Arg²⁶,³⁴Lys³⁶-(Glyc-AOct)-GLP-1(7-36)amide;
Val⁸Asp³⁶Arg²⁶,³⁴Lys³⁷-(Glyc-AOct)-GLP-1(7-37);
Val⁸Asp³⁷Arg²⁶,³⁴Lys³⁸-(Glyc-AOct)-GLP-1(7-38);
Val⁸Asp³⁸Arg²⁶,³⁴Lys³⁹-(Glyc-AOct)-GLP-1(7-39);
Val⁸Asp³⁵Arg²⁶,³⁴Lys³⁶-(Glyc-AOct)-GLP-1(7-36);
Val⁸Asp³⁵Arg²⁶,³⁴Lys³⁶-(Glyc-AOct)-GLP-1(7-36)amide;
Val⁸Asp³⁶Arg²⁶,³⁴Lys³⁷-(Glyc-AOct)-GLP-1(7-37);
Val⁸Asp³⁷Arg²⁶,³⁴Lys³⁸-(Glyc-AOct)-GLP-1(7-38);
Val⁸Asp³⁸Arg²⁶,³⁴Lys³⁹-(Glyc-AOct)-GLP-1(7-39);
Ser⁸Glu³⁵Arg²⁶,³⁴Lys³⁶-(Glyc-AOct)-GLP-1(7-36);
Ser⁸Glu³⁵Arg²⁶,³⁴Lys³⁶-(Glyc-AOct)-GLP-1(7-36)amide;
Ser⁸Glu³⁶Arg²⁶,³⁴Lys³⁷-(Glyc-AOct)-GLP-1(7-37);
Ser⁸Glu³⁷Arg²⁶,³⁴Lys³⁸-(Glyc-AOct)-GLP-1(7-38);
Ser⁸Glu³⁸Arg²⁶,³⁴Lys³⁹-(Glyc-AOct)-GLP-1(7-39);
Ser⁸Glu³⁵Arg²⁶,³⁴Lys³⁶-(Glyc-AOct)-GLP-1(7-36);
Ser⁸Glu³⁵Arg²⁶,³⁴Lys³⁶-(Glyc-AOct)-GLP-1(7-36)amide;
Ser⁸Glu³⁶Arg²⁶,³⁴Lys³⁷-(Glyc-AOct)-GLP-1(7-37);
Ser⁸Glu³⁷Arg²⁶,³⁴Lys³⁸-(Glyc-AOct)-GLP-1(7-38);
Ser⁸Glu³⁸Arg²⁶,³⁴Lys³⁹-(Glyc-AOct)-GLP-1(7-39);
Ser⁸Asp³⁵Arg²⁶,³⁴Lys³⁶-(Glyc-AOct)-GLP-1(7-36);
Ser⁸Asp³⁵Arg²⁶,³⁴Lys³⁶-(Glyc-AOct)-GLP-1(7-36)amide;
Ser⁸Asp³⁶Arg²⁶,³⁴Lys³⁷-(Glyc-AOct)-GLP-1(7-37);
Ser⁸Asp³⁷Arg²⁶,³⁴Lys³⁸-(Glyc-AOct)-GLP-1(7-38);
Ser⁸Asp³⁸Arg²⁶,³⁴Lys³⁹-(Glyc-AOct)-GLP-1(7-39);
Ser⁸Asp³⁵Arg²⁶,³⁴Lys³⁶-(Glyc-AOct)-GLP-1(7-36);
Ser⁸Asp³⁵Arg²⁶,³⁴Lys³⁶-(Glyc-AOct)-GLP-1(7-36)amide;
Ser⁸Asp³⁶Arg²⁶,³⁴Lys³⁷-(Glyc-AOct)-GLP-1(7-37);
Ser⁸Asp³⁷Arg²⁶,³⁴Lys³⁸-(Glyc-AOct)-GLP-1(7-38);
Ser⁸Asp³⁸Arg²⁶,³⁴Lys³⁹-(Glyc-AOct)-GLP-1(7-39);
Thr⁸Glu³⁵Arg²⁶,³⁴Lys³⁶-(Glyc-AOct)-GLP-1(7-36);
Thr⁸Glu³⁵Arg²⁶,³⁴Lys³⁶-(Glyc-AOct)-GLP-1(7-36)amide;
Thr⁸Glu³⁶Arg²⁶,³⁴Lys³⁷-(Glyc-AOct)-GLP-1(7-37);
Thr⁸Glu³⁷Arg²⁶,³⁴Lys³⁸-(Glyc-AOct)-GLP-1(7-38);
Thr⁸Glu³⁸Arg²⁶,³⁴Lys³⁹-(Glyc-AOct)-GLP-1(7-39);
Thr⁸Glu³⁵Arg²⁶,³⁴Lys³⁶-(Glyc-AOct)-GLP-1(7-36);
Thr⁸Glu³⁵Arg²⁶,³⁴Lys³⁶-(Glyc-AOct)-GLP-1(7-36)amide;
Thr⁸Glu³⁶Arg²⁶,³⁴Lys³⁷-(Glyc-AOct)-GLP-1(7-37);
Thr⁸Glu³⁷Arg²⁶,³⁴Lys³⁸-(Glyc-AOct)-GLP-1(7-38);
Thr⁸Glu³⁸Arg²⁶,³⁴Lys³⁹-(Glyc-AOct)-GLP-1(7-39);
Thr⁸Asp³⁵Arg²⁶,³⁴Lys³⁶-(Glyc-AOct)-GLP-1(7-36);
Thr⁸Asp³⁵Arg²⁶,³⁴Lys³⁶-(Glyc-AOct)-GLP-1(7-36)amide;
Thr⁸Asp³⁶Arg²⁶,³⁴Lys³⁷-(Glyc-AOct)-GLP-1(7-37);
Thr⁸Asp³⁷Arg²⁶,³⁴Lys³⁸-(Glyc-AOct)-GLP-1(7-38);
Thr⁸Asp³⁸Arg²⁶,³⁴Lys³⁹-(Glyc-AOct)-GLP-1(7-39);
Thr⁸Asp³⁵Arg²⁶,³⁴Lys³⁶-(Glyc-AOct)-GLP-1(7-36);
Thr⁸Asp³⁵Arg²⁶,³⁴Lys³⁶-(Glyc-AOct)-GLP-1(7-36)amide;
Thr⁸Asp³⁶Arg²⁶,³⁴Lys³⁷-(Glyc-AOct)-GLP-1(7-37);
Thr⁸Asp³⁷Arg²⁶,³⁴Lys³⁸-(Glyc-AOct)-GLP-1(7-38);
Thr⁸Asp³⁸Arg²⁶,³⁴Lys³⁹-(Glyc-AOct)-GLP-1(7-39);
Arg²⁶,³⁴Lys¹⁸-(Glyc-AOct)-GLP-1(7-36); Arg²⁶,³⁴Lys¹⁸-(Glyc-AOct)GLP-1(7-36)amide; Arg²⁶,³⁴Lys¹⁸-(Glyc-AOct)-GLP-1(7-37); Arg²⁶,³⁴Lys¹⁸-(Glyc-AOct)-GLP-1(7-38); Gly⁸Asp¹⁹Arg²⁶,³⁴Lys¹⁸-(Glyc-AOct)-GLP-1(7-36);
Gly⁸Asp¹⁷Arg²⁶,³⁴Lys¹⁸-(Glyc-AOct)-GLP-1(7-36);
Gly⁸Asp¹⁹Arg²⁶,³⁴Lys¹⁸-(Glyc-AOct)-GLP-1(7-36)amide;
Gly⁸Asp¹⁷Arg²⁶,³⁴Lys¹⁸-(Glyc-AOct)-GLP-1(7-36)amide;
Gly⁸Asp¹⁹Arg²⁶,³⁴Lys¹⁸-(Glyc-AOct)-GLP-1(7-37);
Gly⁸Asp¹⁹Arg²⁶,³⁴Lys¹⁸-(Glyc-AOct)-GLP-1(7-38);
Gly⁸Asp¹⁷Arg²⁶,³⁴Lys¹⁸-(Glyc-AOct)-GLP-1(7-38);
Arg²⁶,³⁴Lys²³-(Glyc-AOct)-GLP-1(7-36); Arg²⁶,³⁴Lys²³-(Glyc-AOct)-GLP-1(7-36)amide; Arg²⁶,³⁴Lys²³-(Glyc-AOct)-GLP-1(7-37); Arg²⁶,³⁴Lys²³-(Glyc-AOct)-GLP-1(7-38); Gly⁸Asp¹⁹Arg²⁶,³⁴Lys²³-(Glyc-AOct)-GLP-1(7-36);
Gly⁸Asp¹⁷Arg²⁶,³⁴Lys²³-(Glyc-AOct)-GLP-1(7-36);
Gly⁸Asp¹⁹Arg²⁶,³⁴Lys²³-(Glyc-AOct)-GLP-1(7-36)amide;
Gly⁸Asp¹⁷Arg²⁶,³⁴Lys²³-(Glyc-AOct)-GLP-1(7-36)amide;
Gly⁸Asp¹⁹Arg²⁶,³⁴Lys²³-(Glyc-AOct)-GLP-1(7-37);
Gly⁸Asp¹⁹Arg²⁶,³⁴Lys²³-(Glyc-AOct)-GLP-1(7-38);
Gly⁸Asp¹⁷Arg²⁶,³⁴Lys²³-(Glyc-AOct)-GLP-1(7-38);
Arg²⁶,³⁴Lys²⁷-(Glyc-AOct)-GLP-1(7-36); Arg²⁶,³⁴Lys²⁷-(Glyc-AOct)-GLP-1(7-36)amide; Arg²⁶,³⁴Lys²⁷-(Glyc-AOct)-GLP-1(7-37); Arg²⁶,³⁴Lys²⁷-(Glyc-AOct)-GLP-1(7-38); Gly⁸Asp¹⁹Arg²⁶,³⁴Lys²⁷-(Glyc-AOct)-GLP-1(7-36);
Gly⁸Asp¹⁷Arg²⁶,³⁴Lys²⁷-(Glyc-AOct)-GLP-1(7-36);
Gly⁸Asp¹⁹Arg²⁶,³⁴Lys²⁷-(Glyc-AOct)-GLP-1(7-36)amide;
Gly⁸Asp¹⁷Arg²⁶,³⁴Lys²⁷-(Glyc-AOct)-GLP-1(7-36)amide;
Gly⁸Asp¹⁹Arg²⁶,³⁴Lys²⁷-(Glyc-AOct)-GLP-1(7-37);
Gly⁸Asp¹⁹Arg²⁶,³⁴Lys²⁷-(Glyc-AOct)-GLP-1(7-38);
Gly⁸Asp¹⁷Arg²⁶,³⁴Lys²⁷-(Glyc-AOct)-GLP-1(7-38);
Arg²⁶,³⁴Lys¹⁸-(Glyc-AOct)-GLP-1(7-36); Arg²⁶,³⁴Lys¹⁸-(Glyc-AOct)-GLP-1(7-36)amide; Arg²⁶,³⁴Lys¹⁸-(Glyc-AOct)-GLP-1(7-37); Arg²⁶,³⁴Lys¹⁸-(Glyc-AOct)-GLP-1(7-38); Val⁸Asp¹⁹Arg²⁶,³⁴Lys¹⁸-(Glyc-AOct)-GLP-1(7-36);
Val⁸Asp¹⁷Arg²⁶,³⁴Lys¹⁸-(Glyc-AOct)-GLP-1(7-36);
Val⁸Asp¹⁹Arg²⁶,³⁴Lys¹⁸-(Glyc-AOct)-GLP-1(7-36)amide;
Val⁸Asp¹⁷Arg²⁶,³⁴Lys¹⁸-(Glyc-AOct)-GLP-1(7-36)amide;
Val⁸Asp¹⁹Arg²⁶,³⁴Lys¹⁸-(Glyc-AOct)-GLP-1(7-37);
Val⁸Asp¹⁹Arg²⁶,³⁴Lys¹⁸-(Glyc-AOct)-GLP-1(7-38);
Val⁸Asp¹⁷Arg²⁶,³⁴Lys¹⁸-(Glyc-AOct)-GLP-1(7-38);
Arg²⁶,³⁴Lys²³-(Glyc-AOct)-GLP-1(7-36); Arg²⁶,³⁴Lys²³-(Glyc-AOct)-GLP-1(7-36)amide; Arg²⁶,³⁴Lys²³-(Glyc-AOct)-GLP-1(7-37); Arg²⁶,³⁴Lys²³-(Glyc-AOct)-GLP-1(7-38); Val⁸Asp¹⁹Arg²⁶,³⁴Lys²³-(Glyc-AOct)-GLP-1(7-36);
Val⁸Asp¹⁷Arg²⁶,³⁴Lys²³-(Glyc-AOct)-GLP-1(7-36);
Val⁸Asp¹⁹Arg²⁶,³⁴Lys²³-(Glyc-AOct)-GLP-1(7-36)amide;
Val⁸Asp¹⁷Arg²⁶,³⁴Lys²³-(Glyc-AOct)-GLP-1(7-36)amide;
Val⁸Asp¹⁹Arg²⁶,³⁴Lys²³-(Glyc-AOct)-GLP-1(7-37);
Val⁸Asp¹⁹Arg²⁶,³⁴Lys²³-(Glyc-AOct)-GLP-1(7-38);
Val⁸Asp¹⁷Arg²⁶,³⁴Lys²³-(Glyc-AOct)-GLP-1(7-38);
Arg²⁶,³⁴Lys²⁷-(Glyc-AOct)-GLP-1(7-36); Arg²⁶,³⁴Lys²⁷-(Glyc-AOct)-GLP-1(7-36)amide; Arg²⁶,³⁴Lys²⁷-(Glyc-AOct)-GLP-1(7-37); Arg²⁶,³⁴Lys²⁷-(Glyc-AOct)-GLP-1(7-38); Val⁸Asp¹⁹Arg²⁶,³⁴Lys²⁷-(Glyc-AOct)-GLP-1(7-36);
Val⁸Asp¹⁷Arg²⁶,³⁴Lys²⁷-(Glyc-AOct)-GLP-1(7-36);
Val⁸Asp¹⁹Arg²⁶,³⁴Lys²⁷-(Glyc-AOct)-GLP-1(7-36)amide;
Val⁸Asp¹⁷Arg²⁶,³⁴Lys²⁷-(Glyc-AOct)-GLP-1(7-36)amide;
Val⁸Asp¹⁹Arg²⁶,³⁴Lys²⁷-(Glyc-AOct)-GLP-1(7-37);
Val⁸Asp¹⁹Arg²⁶,³⁴Lys²⁷-(Glyc-AOct)-GLP-1(7-38);
Val⁸Asp¹⁷Arg²⁶,³⁴Lys²⁷-(Glyc-AOct)-GLP-1(7-38);
Arg²⁶,³⁴Lys¹⁸-(Glyc-AOct)-GLP-1(7-36); Arg²⁶,³⁴Lys¹⁸-(Glyc-AOct)-GLP-1(7-36)amide; Arg²⁶,³⁴Lys¹⁸-(Glyc-AOct)-GLP-1(7-37); Arg²⁶,³⁴Lys¹⁸-(Glyc-AOct)-GLP-1(7-38); Ser⁸Asp¹⁹Arg²⁶,³⁴Lys¹⁸-(Glyc-AOct)-GLP-1(7-36);
Ser⁸Asp¹⁷Arg²⁶,³⁴Lys¹⁸-(Glyc-AOct)-GLP-1(7-36);
Ser⁸Asp¹⁹Arg²⁶,³⁴Lys¹⁸-(Glyc-AOct)-GLP-1(7-36)amide;
Ser⁸Asp¹⁷Arg²⁶,³⁴Lys¹⁸-(Glyc-AOct)-GLP-1(7-36)amide;
Ser⁸Asp¹⁹Arg²⁶,³⁴Lys¹⁸-(Glyc-AOct)-GLP-1(7-37);
Ser⁸Asp¹⁹Arg²⁶,³⁴Lys¹⁸-(Glyc-AOct)-GLP-1(7-38);
Ser⁸Asp¹⁷Arg²⁶,³⁴Lys¹⁸-(Glyc-AOct)-GLP-1(7-38);
Arg²⁶,³⁴Lys²³-(Glyc-AOct)-GLP-1(7-36); Arg²⁶,³⁴Lys²³-(Glyc-AOct)-GLP-1(7-36)amide; Arg²⁶,³⁴Lys²³-(Glyc-AOct)-GLP-1(7-37); Arg²⁶,³⁴Lys²³-(Glyc-AOct)-GLP-1(7-38); Ser⁸Asp¹⁹Arg²⁶,³⁴Lys²³-(Glyc-AOct)-GLP-1(7-36);
Ser⁸Asp¹⁷Arg²⁶,³⁴Lys²³-(Glyc-AOct)-GLP-1(7-36);
Ser⁸Asp¹⁹Arg²⁶,³⁴Lys²³-(Glyc-AOct)-GLP-1(7-36)amide;
Ser⁸Asp¹⁷Arg²⁶,³⁴Lys²³-(Glyc-AOct)-GLP-1(7-36)amide;

Ser⁸Asp¹⁹Arg²⁶,³⁴Lys²³-(Glyc-AOct)-GLP-1(7-37);
Ser⁸Asp¹⁹Arg²⁶,³⁴Lys²³-(Glyc-AOct)-GLP-1(7-38);
Ser⁸Asp¹⁷Arg²⁶,³⁴Lys²³-(Glyc-AOct)-GLP-1(7-38);
Arg²⁶,³⁴Lys²⁷-(Glyc-AOct)-GLP-1(7-36); Arg²⁶,³⁴Lys²⁷-(Glyc-AOct)-GLP-1(7-36)amide; Arg²⁶,³⁴Lys²⁷-(Glyc-AOct)-GLP-1(7-37); Arg²⁶,³⁴Lys²⁷-(Glyc-AOct)-GLP-1(7-38); Ser⁸Asp¹⁹Arg²⁶,³⁴Lys²⁷-(Glyc-AOct)-GLP-1(7-36);
Ser⁸Asp¹⁷Arg²⁶,³⁴Lys²⁷-(Glyc-AOct)-GLP-1(7-36);
Ser⁸Asp¹⁹Arg²⁶,³⁴Lys²⁷-(Glyc-AOct)-GLP-1(7-36)amide;
Ser⁸Asp¹⁷Arg²⁶,³⁴Lys²⁷-(Glyc-AOct)-GLP-1(7-36)amide;
Ser⁸Asp¹⁹Arg²⁶,³⁴Lys²⁷-(Glyc-AOct)-GLP-1(7-37);
Ser⁸Asp¹⁹Arg²⁶,³⁴Lys²⁷-(Glyc-AOct)-GLP-1(7-38);
Ser⁸Asp¹⁷Arg²⁶,³⁴Lys²⁷-(Glyc-AOct)-GLP-1(7-38);
Arg²⁶,³⁴Lys¹⁸-(Glyc-AOct)-GLP-1(7-36); Arg²⁶,³⁴Lys¹⁸-(Glyc-AOct)-GLP-1(7-36)amide; Arg²⁶,³⁴Lys¹⁸-(Glyc-AOct)-GLP-1(7-37); Arg²⁶,³⁴Lys¹⁸-(Glyc-AOct)-GLP-1(7-38); Thr⁸Asp¹⁹Arg²⁶,³⁴Lys¹⁸-(Glyc-AOct)-GLP-1(7-36);
Thr⁸Asp¹⁷Arg²⁶,³⁴Lys¹⁸-(Glyc-AOct)-GLP-1(7-36);
Thr⁸Asp¹⁹Arg²⁶,³⁴Lys¹⁸-(Glyc-AOct)-GLP-1(7-36)amide;
Thr⁸Asp¹⁷Arg²⁶,³⁴Lys¹⁸-(Glyc-AOct)-GLP-1(7-36)amide;
Thr⁸Asp¹⁹Arg²⁶,³⁴Lys¹⁸-(Glyc-AOct)-GLP-1(7-37);
Thr⁸Asp¹⁹Arg²⁶,³⁴Lys¹⁸-(Glyc-AOct)-GLP-1(7-38);
Thr⁸Asp¹⁷Arg²⁶,³⁴Lys¹⁸-(Glyc-AOct)-GLP-1(7-38);
Arg²⁶,³⁴Lys²³-(Glyc-AOct)-GLP-1(7-36); Arg²⁶,³⁴Lys²³-(Glyc-AOct)-GLP-1(7-36)amide; Arg²⁶,³⁴Lys²³-(Glyc-AOct)-GLP-1(7-37); Arg²⁶,³⁴Lys²³-(Glyc-AOct)-GLP-1(7-38); Thr⁸Asp¹⁹Arg²⁶,³⁴Lys²³-(Glyc-AOct)-GLP-1(7-36);
Thr⁸Asp¹⁷Arg²⁶,³⁴Lys²³-(Glyc-AOct)-GLP-1(7-36);
Thr⁸Asp¹⁹Arg²⁶,³⁴Lys²³-(Glyc-AOct)-GLP-1(7-36)amide;
Thr⁸Asp¹⁷Arg²⁶,³⁴Lys²³-(Glyc-AOct)-GLP-1(7-36)amide;
Thr⁸Asp¹⁹Arg²⁶,³⁴Lys²³-(Glyc-AOct)-GLP-1(7-37);
Thr⁸Asp¹⁹Arg²⁶,³⁴Lys²³-(Glyc-AOct)-GLP-1(7-38);
Thr⁸Asp¹⁷Arg²⁶,³⁴Lys²³-(Glyc-AOct)-GLP-1(7-38);
Arg²⁶,³⁴Lys²⁷-(Glyc-AOct)-GLP-1(7-36); Arg²⁶,³⁴Lys²⁷-(Glyc-AOct)-GLP-1(7-36)amide; Arg²⁶,³⁴Lys²⁷-(Glyc-AOct)-GLP-1(7-37); Arg²⁶,³⁴Lys²⁷-(Glyc-AOct)-GLP-1(7-38); Thr⁸Asp¹⁹Arg²⁶,³⁴Lys²⁷-(Glyc-AOct)-GLP-1(7-36);
Thr⁸Asp¹⁷Arg²⁶,³⁴Lys²⁷-(Glyc-AOct)-GLP-1(7-36);
Thr⁸Asp¹⁹Arg²⁶,³⁴Lys²⁷-(Glyc-AOct)-GLP-1(7-36)amide;
Thr⁸Asp¹⁷Arg²⁶,³⁴Lys²⁷-(Glyc-AOct)-GLP-1(7-36)amide;
Thr⁸Asp¹⁹Arg²⁶,³⁴Lys²⁷-(Glyc-AOct)-GLP-1(7-37);
Thr⁸Asp¹⁹Arg²⁶,³⁴Lys²⁷-(Glyc-AOct)-GLP-1(7-38);
Thr⁸Asp¹⁷Arg²⁶,³⁴Lys²⁷-(Glyc-AOct)-GLP-1(7-38);
Arg²⁶Lys³⁴-(Glyc-ALit)-GLP-1(7-36); Arg³⁴Lys²⁶-(Glyc-ALit)-GLP-1(7-36); Arg²⁶,³⁴Lys³⁶-(Glyc-ALit)-GLP-1(7-36); Arg²⁶Lys³⁴-(Glyc-ALit)-GLP-1(7-36)amide; Arg³⁴Lys²⁶-(Glyc-ALit)-GLP-1(7-36)amide; Arg²⁶,³⁴Lys³⁶-(Glyc-ALit)-GLP-1(7-36)amide; Arg²⁶Lys³⁴-(Glyc-ALit)-GLP-1(7-37); Arg³⁴Lys²⁶-(Glyc-ALit)-GLP-1(7-37); Arg²⁶,³⁴Lys³⁶-(Glyc-ALit)-GLP-1(7-37); Arg²⁶Lys³⁴-(Glyc-ALit)-GLP-1(7-38); Arg³⁴Lys²⁶-(Glyc-ALit)-GLP-1(7-38); Arg²⁶,³⁴Lys³⁸-(Glyc-ALit)-GLP-1(7-38); Arg²⁶Lys³⁴-(Glyc-ALit)-GLP-1(7-39); Arg³⁴Lys²⁶-(Glyc-ALit)-GLP-1(7-39); Arg²⁶,³⁴Lys³⁹-(Glyc-ALit)-GLP-1(7-39);
Gly⁸Arg²⁶Lys³⁴-(Glyc-ALit)-GLP-1(7-36);
Gly⁸Arg³⁴Lys²⁶-(Glyc-ALit)-GLP-1(7-36); Gly⁸Arg²⁶,³⁴Lys³⁶-(Glyc-ALit)-GLP-1(7-36); Gly⁸Arg²⁶Lys³⁴-(Glyc-ALit)-GLP-1(7-36)amide; Gly⁸Arg³⁴Lys²⁶-(Glyc-ALit)-GLP-1(7-36)amide; Gly⁸Arg²⁶,³⁴Lys³⁶-(Glyc-ALit)-GLP-1(7-36)amide; Gly⁸Arg²⁶Lys³⁴-(Glyc-ALit)-GLP-1(7-37); Gly⁸Arg³⁴Lys²⁶-(Glyc-ALit)-GLP-1(7-37); Gly⁸Arg²⁶,³⁴Lys³⁶-(Glyc-ALit)-GLP-1(7-37); Gly⁸Arg²⁶Lys³⁴-(Glyc-ALit)-GLP-1(7-38); Gly⁸Arg³⁴Lys²⁶-(Glyc-ALit)-GLP-1(7-38); Gly⁸Arg²⁶,³⁴Lys³⁸-(Glyc-ALit)-GLP-1(7-38); Gly⁸Arg²⁶Lys³⁴-(Glyc-ALit)-GLP-1(7-39);
Gly⁸Arg³⁴Lys²⁶-(Glyc-ALit)-GLP-1(7-39); Gly⁸Arg²⁶,³⁴Lys³⁹-(Glyc-ALit)-GLP-1(7-39);
Val⁸Arg²⁶Lys³⁴-(Glyc-ALit)-GLP-1(7-36); Val⁸Arg³⁴Lys²⁶-(Glyc-ALit)-GLP-1(7-36); Val⁸Arg²⁶,³⁴Lys³⁶-(Glyc-ALit)-GLP-1(7-36); Val⁸Arg²⁶Lys³⁴-(Glyc-ALit)-GLP-1(7-36)amide; Val⁸Arg³⁴Lys²⁶-(Glyc-ALit)-GLP-1(7-36)amide; Val⁸Arg²⁶,³⁴Lys³⁶-(Glyc-ALit)-GLP-1(7-36)amide; Val⁸Arg²⁶Lys³⁴-(Glyc-ALit)-GLP-1(7-37); Val⁸Arg³⁴Lys²⁶-(Glyc-ALit)-GLP-1(7-37); Val⁸Arg²⁶,³⁴Lys³⁶-(Glyc-ALit)-GLP-1(7-37); Val⁸Arg²⁶Lys³⁴-(Glyc-ALit)-GLP-1(7-38); Val⁸Arg³⁴Lys²⁶-(Glyc-ALit)-GLP-1(7-38); Val⁸Arg²⁶,³⁴Lys³⁸-(Glyc-ALit)-GLP-1(7-38); Val⁸Arg²⁶Lys³⁴-(Glyc-ALit)-GLP-1(7-39); Val⁸Arg³⁴Lys²⁶-(Glyc-ALit)-GLP-1(7-39); Val⁸Arg²⁶,³⁴Lys³⁹-(Glyc-ALit)-GLP-1(7-39);
Ser⁸Arg²⁶Lys³⁴-(Glyc-ALit)-GLP-1(7-36); Ser⁸Arg³⁴Lys²⁶-(Glyc-ALit)-GLP-1(7-36); Ser⁸Arg²⁶,³⁴Lys³⁶-(Glyc-ALit)-GLP-1(7-36); Ser⁸Arg²⁶Lys³⁴-(Glyc-ALit)-GLP-1(7-36)amide; Ser⁸Arg³⁴Lys²⁶-(Glyc-ALit)-GLP-1(7-36)amide; Ser⁸Arg²⁶,³⁴Lys³⁶-(Glyc-ALit)-GLP-1(7-36)amide;
Ser⁸Arg²⁶Lys³⁴-(Glyc-ALit)-GLP-1(7-37); Ser⁸Arg³⁴Lys²⁶-(Glyc-ALit)-GLP-1(7-37); Ser⁸Arg²⁶,³⁴Lys³⁶-(Glyc-ALit)-GLP-1(7-37); Ser⁸Arg²⁶Lys³⁴-(Glyc-ALit)-GLP-1(7-38); Ser⁸Arg³⁴Lys²⁶-(Glyc-ALit)-GLP-1(7-38); Ser⁸Arg²⁶,³⁴Lys³⁸-(Glyc-ALit)-GLP-1(7-38); Ser⁸Arg²⁶Lys³⁴-(Glyc-ALit)-GLP-1(7-39); Ser⁸Arg³⁴Lys²⁶-(Glyc-ALit)-GLP-1(7-39); Ser⁸Arg²⁶,³⁴Lys³⁹-(Glyc-ALit)-GLP-1(7-39);
Thr⁸Arg²⁶Lys³⁴-(Glyc-ALit)-GLP-1(7-36);
Thr⁸Arg³⁴Lys²⁶-(Glyc-ALit)-GLP-1(7-36); Thr⁸Arg²⁶,³⁴Lys³⁶-(Glyc-ALit)-GLP-1(7-36); Thr⁸Arg²⁶Lys³⁴-(Glyc-ALit)-GLP-1(7-36)amide; Thr⁸Arg³⁴Lys²⁶-(Glyc-ALit)-GLP-1(7-36)amide; Thr⁸Arg²⁶,³⁴Lys³⁶-(Glyc-ALit)-GLP-1(7-36)amide; Thr⁸Arg²⁶Lys³⁴-(Glyc-ALit)-GLP-1(7-37); Thr⁸Arg³⁴Lys²⁶-(Glyc-ALit)-GLP-1(7-37); Thr⁸Arg²⁶,³⁴Lys³⁶-(Glyc-ALit)-GLP-1(7-37); Thr⁸Arg²⁶Lys³⁴-(Glyc-ALit)-GLP-1(7-38); Thr⁸Arg³⁴Lys²⁶-(Glyc-ALit)-GLP-1(7-38); Thr⁸Arg²⁶,³⁴Lys³⁸-(Glyc-ALit)-GLP-1(7-38);
Thr⁸Arg²⁶Lys³⁴-(Glyc-ALit)-GLP-1(7-39);
Thr⁸Arg³⁴Lys²⁶-(Glyc-ALit)-GLP-1(7-39); Thr⁸Arg²⁶,³⁴Lys³⁹-(Glyc-ALit)-GLP-1(7-39);
Gly⁸Glu³⁵Arg²⁶,³⁴Lys³⁶-(Glyc-ALit)-GLP-1(7-36);
Gly⁸Glu³⁵Arg²⁶,³⁴Lys³⁶-(Glyc-ALit)-GLP-1(7-36)amide;
Gly⁸Glu³⁶Arg²⁶,³⁴Lys³⁷-(Glyc-ALit)-GLP-1(7-37);
Gly⁸Glu³⁷Arg²⁶,³⁴Lys³⁸-(Glyc-ALit)-GLP-1(7-38);
Gly⁸Glu³⁸Arg²⁶,³⁴Lys³⁹-(Glyc-ALit)-GLP-1(7-39);
Gly⁸Glu³⁵Arg²⁶,³⁴Lys³⁶-(Glyc-ALit)-GLP-1(7-36);
Gly⁸Glu³⁵Arg²⁶,³⁴Lys³⁶-(Glyc-ALit)-GLP-1(7-36)amide;
Gly⁸Glu³⁶Arg²⁶,³⁴Lys³⁷-(Glyc-ALit)-GLP-1(7-37);
Gly⁸Glu³⁷Arg²⁶,³⁴Lys³⁸-(Glyc-ALit)-GLP-1(7-38);
Gly⁸Glu³⁸Arg²⁶,³⁴Lys³⁹-(Glyc-ALit)-GLP-1(7-39);
Gly⁸Asp³⁵Arg²⁶,³⁴Lys³⁶-(Glyc-ALit)-GLP-1(7-36);
Gly⁸Asp³⁵Arg²⁶,³⁴Lys³⁶-(Glyc-ALit)-GLP-1(7-36)amide;
Gly⁸Asp³⁶Arg²⁶,³⁴Lys³⁷-(Glyc-ALit)-GLP-1(7-37);
Gly⁸Asp³⁷Arg²⁶,³⁴Lys³⁸-(Glyc-ALit)-GLP-1(7-38);
Gly⁸Asp³⁸Arg²⁶,³⁴Lys³⁹-(Glyc-ALit)-GLP-1(7-39);
Gly⁸Asp³⁵Arg²⁶,³⁴Lys³⁶-(Glyc-ALit)-GLP-1(7-36);
Gly⁸Asp³⁵Arg²⁶,³⁴Lys³⁶-(Glyc-ALit)-GLP-1(7-36)amide;
Gly⁸Asp³⁶Arg²⁶,³⁴Lys³⁷-(Glyc-ALit)-GLP-1(7-37);
Gly⁸Asp³⁷Arg²⁶,³⁴Lys³⁸-(Glyc-ALit)-GLP-1(7-38);
Gly⁸Asp³⁸Arg²⁶,³⁴Lys³⁹-(Glyc-ALit)-GLP-1(7-39);
Val⁸Glu³⁵Arg²⁶,³⁴Lys³⁶-(Glyc-ALit)-GLP-1(7-36);
Val⁸Glu³⁵Arg²⁶,³⁴Lys³⁶-(Glyc-ALit)-GLP-1(7-36)amide;
Val⁸Glu³⁶Arg²⁶,³⁴Lys³⁷-(Glyc-ALit)-GLP-1(7-37);
Val⁸Glu³⁷Arg²⁶,³⁴Lys³⁸-(Glyc-ALit)-GLP-1(7-38);
Val⁸Glu³⁸Arg²⁶,³⁴Lys³⁹-(Glyc-ALit)-GLP-1(7-39);
Val⁸Glu³⁵Arg²⁶,³⁴Lys³⁶-(Glyc-ALit)-GLP-1(7-36);
Val⁸Glu³⁵Arg²⁶,³⁴Lys³⁶-(Glyc-ALit)-GLP-1(7-36)amide;
Val⁸Glu³⁶Arg²⁶,³⁴Lys³⁷-(Glyc-ALit)-GLP-1(7-37);

Val⁸Glu³⁷Arg²⁶,³⁴Lys³⁸-(Glyc-ALit)-GLP-1(7-38);
Val⁸Glu³⁸Arg²⁶,³⁴Lys³⁹-(Glyc-ALit)-GLP-1(7-39);
Val⁸Asp³⁵Arg²⁶,³⁴Lys³⁶-(Glyc-ALit)-GLP-1(7-36);
Val⁸Asp³⁵Arg²⁶,³⁴Lys³⁶-(Glyc-ALit)-GLP-1(7-36)amide;
Val⁸Asp³⁶Arg²⁶,³⁴Lys³⁷-(Glyc-ALit)-GLP-1(7-37);
Val⁸Asp³⁷Arg²⁶,³⁴Lys³⁸-(Glyc-ALit)-GLP-1(7-38);
Val⁸Asp³⁸Arg²⁶,³⁴Lys³⁹-(Glyc-ALit)-GLP-1(7-39);
Val⁸Asp³⁵Arg²⁶,³⁴Lys³⁶-(Glyc-ALit)-GLP-1(7-36);
Val⁸Asp³⁵Arg²⁶,³⁴Lys³⁶-(Glyc-ALit)-GLP-1(7-36)amide;
Val⁸Asp³⁶Arg²⁶,³⁴Lys³⁷-(Glyc-ALit)-GLP-1(7-37);
Val⁸Asp³⁷Arg²⁶,³⁴Lys³⁸-(Glyc-ALit)-GLP-1(7-38);
Val⁸Asp³⁸Arg²⁶,³⁴Lys³⁹-(Glyc-ALit)-GLP-1(7-39);
Ser⁸Glu³⁵Arg²⁶,³⁴Lys³⁶-(Glyc-ALit)-GLP-1(7-36);
Ser⁸Glu³⁵Arg²⁶,³⁴Lys³⁶-(Glyc-ALit)-GLP-1(7-36)amide;
Ser⁸Glu³⁶Arg²⁶,³⁴Lys³⁷-(Glyc-ALit)-GLP-1(7-37);
Ser⁸Glu³⁷Arg²⁶,³⁴Lys³⁸-(Glyc-ALit)-GLP-1(7-38);
Ser⁸Glu³⁸Arg²⁶,³⁴Lys³⁹-(Glyc-ALit)-GLP-1(7-39);
Ser⁸Glu³⁵Arg²⁶,³⁴Lys³⁶-(Glyc-ALit)-GLP-1(7-36);
Ser⁸Glu³⁵Arg²⁶,³⁴Lys³⁶-(Glyc-ALit)-GLP-1(7-36)amide;
Ser⁸Glu³⁶Arg²⁶,³⁴Lys³⁷-(Glyc-ALit)-GLP-1(7-37);
Ser⁸Glu³⁷Arg²⁶,³⁴Lys³⁸-(Glyc-ALit)-GLP-1(7-38);
Ser⁸Glu³⁸Arg²⁶,³⁴Lys³⁹-(Glyc-ALit)-GLP-1(7-39);
Ser⁸Asp³⁵Arg²⁶,³⁴Lys³⁶-(Glyc-ALit)-GLP-1(7-36);
Ser⁸Asp³⁵Arg²⁶,³⁴Lys³⁶-(Glyc-ALit)-GLP-1(7-36)amide;
Ser⁸Asp³⁶Arg²⁶,³⁴Lys³⁷-(Glyc-ALit)-GLP-1(7-37);
Ser⁸Asp³⁷Arg²⁶,³⁴Lys³⁷-(Glyc-ALit)-GLP-1(7-38);
Ser⁸Asp³⁸Arg²⁶,³⁴Lys³⁹-(Glyc-ALit)-GLP-1(7-39);
Ser⁸Asp³⁵Arg²⁶,³⁴Lys³⁶-(Glyc-ALit)-GLP-1(7-36);
Ser⁸Asp³⁵Arg²⁶,³⁴Lys³⁶-(Glyc-ALit)-GLP-1(7-36)amide;
Ser⁸Asp³⁶Arg²⁶,³⁴Lys³⁷-(Glyc-ALit)-GLP-1(7-37);
Ser⁸Asp³⁷Arg²⁶,³⁴Lys³⁸-(Glyc-ALit)-GLP-1(7-38);
Ser⁸Asp³⁸Arg²⁶,³⁴Lys³⁹-(Glyc-ALit)-GLP-1(7-39);
Thr⁸Glu³⁵Arg²⁶,³⁴Lys³⁶-(Glyc-ALit)-GLP-1(7-36);
Thr⁸Glu³⁵Arg²⁶,³⁴Lys³⁶-(Glyc-ALit)-GLP-1(7-36)amide;
Thr⁸Glu³⁶Arg²⁶,³⁴Lys³⁷-(Glyc-ALit)-GLP-1(7-37);
Thr⁸Glu³⁷Arg²⁶,³⁴Lys³⁸-(Glyc-ALit)-GLP-1(7-38);
Thr⁸Glu³⁸Arg²⁶,³⁴Lys³⁹-(Glyc-ALit)-GLP-1(7-39);
Thr⁸Glu³⁵Arg²⁶,³⁴Lys³⁶-(Glyc-ALit)-GLP-1(7-36);
Thr⁸Glu³⁵Arg²⁶,³⁴Lys³⁶-(Glyc-ALit)-GLP-1(7-36)amide;
Thr⁸Glu³⁶Arg²⁶,³⁴Lys³⁷-(Glyc-ALit)-GLP-1(7-37);
Thr⁸Glu³⁷Arg²⁶,³⁴Lys³⁸-(Glyc-ALit)-GLP-1(7-38);
Thr⁸Glu³⁸Arg²⁶,³⁴Lys³⁹-(Glyc-ALit)-GLP-1(7-39);
Thr⁸Asp³⁵Arg²⁶,³⁴Lys³⁶-(Glyc-ALit)-GLP-1(7-36);
Thr⁸Asp³⁵Arg²⁶,³⁴Lys³⁶-(Glyc-ALit)-GLP-1(7-36)amide;
Thr⁸Asp³⁶Arg²⁶,³⁴Lys³⁷-(Glyc-ALit)-GLP-1(7-37);
Thr⁸Asp³⁷Arg²⁶,³⁴Lys³⁸-(Glyc-ALit)-GLP-1(7-38);
Thr⁸Asp³⁸Arg²⁶,³⁴Lys³⁹-(Glyc-ALit)-GLP-1(7-39);
Thr⁸Asp³⁵Arg²⁶,³⁴Lys³⁶-(Glyc-ALit)-GLP-1(7-36);
Thr⁸Asp³⁵Arg²⁶,³⁴Lys³⁶-(Glyc-ALit)-GLP-1(7-36)amide;
Thr⁸Asp³⁶Arg²⁶,³⁴Lys³⁷-(Glyc-ALit)-GLP-1(7-37);
Thr⁸Asp³⁷Arg²⁶,³⁴Lys³⁸-(Glyc-ALit)-GLP-1(7-38);
Thr⁸Asp³⁸Arg²⁶,³⁴Lys³⁹-(Glyc-ALit)-GLP-1(7-39);
Arg²⁶,³⁴Lys¹⁸-(Glyc-ALit)-GLP-1(7-36); Arg²⁶,³⁴Lys¹⁸-(Glyc-ALit)-GLP-1(7-36)amide; Arg²⁶,³⁴Lys¹⁸-(Glyc-ALit)-GLP-1(7-37); Arg²⁶,³⁴Lys¹⁸-(Glyc-ALit)-GLP-1(7-38); Gly⁸Asp¹⁹Arg²⁶,³⁴Lys¹⁸-(Glyc-ALit)-GLP-1(7-36);
Gly⁸Asp¹⁷Arg²⁶,³⁴Lys¹⁸-(Glyc-ALit)-GLP-1(7-36);
Gly⁸Asp¹⁹Arg²⁶,³⁴Lys¹⁸-(Glyc-ALit)-GLP-1(7-36)amide;
Gly⁸Asp¹⁷Arg²⁶,³⁴Lys¹⁸-(Glyc-ALit)-GLP-1(7-36)amide;
Gly⁸Asp¹⁹Arg²⁶,³⁴Lys¹⁸-(Glyc-ALit)-GLP-1(7-37);
Gly⁸Asp¹⁹Arg²⁶,³⁴Lys¹⁸-(Glyc-ALit)-GLP-1(7-38);
Gly⁸Asp¹⁷Arg²⁶,³⁴Lys¹⁸ (Glyc-ALit)-GLP-1(7-38);
Arg²⁶,³⁴Lys²³-(Glyc-ALit)-GLP-1(7-36); Arg²⁶,³⁴Lys²³-(Glyc-ALit)-GLP-1(7-36)amide; Arg²⁶,³⁴Lys²³-(Glyc-ALit)-GLP-1(7-37); Arg²⁶,³⁴Lys²³-(Glyc-ALit)-GLP-1(7-38); Gly⁸Asp¹⁹Arg²⁶,³⁴Lys²³-(Glyc-ALit)-GLP-1(7-36);
Gly⁸Asp¹⁷Arg²⁶,³⁴Lys²³-(Glyc-ALit)-GLP-1(7-36);
Gly⁸Asp¹⁹Arg²⁶,³⁴Lys²³-(Glyc-ALit)-GLP-1(7-36)amide;
Gly⁸Asp¹⁷Arg²⁶,³⁴Lys²³-(Glyc-ALit)-GLP-1(7-36)amide;
Gly⁸Asp¹⁹Arg²⁶,³⁴Lys²³-(Glyc-ALit)-GLP-1(7-37);
Gly⁸Asp¹⁹Arg²⁶,³⁴Lys²³-(Glyc-ALit)-GLP-1(7-38);
Gly⁸Asp¹⁷Arg²⁶,³⁴Lys²³-(Glyc-ALit)-GLP-1(7-38);
Arg²⁶,³⁴Lys²⁷-(Glyc-ALit)-GLP-1(7-36); Arg²⁶,³⁴Lys²⁷-(Glyc-ALit)-GLP-1(7-36)amide; Arg²⁶,³⁴Lys²⁷-(Glyc-ALit)-GLP-1(7-37); Arg²⁶,³⁴Lys²⁷-(Glyc-ALit)-GLP-1(7-38); Gly⁸Asp¹⁹Arg²⁶,³⁴Lys²⁷-(Glyc-ALit)-GLP-1(7-36);
Gly⁸Asp¹⁷Arg²⁶,³⁴Lys²⁷-(Glyc-ALit)-GLP-1(7-36);
Gly⁸Asp¹⁹Arg²⁶,³⁴Lys²⁷-(Glyc-ALit)-GLP-1(7-36)amide;
Gly⁸Asp¹⁷Arg²⁶,³⁴Lys²⁷-(Glyc-ALit)-GLP-1(7-36)amide;
Gly⁸Asp¹⁹Arg²⁶,³⁴Lys²⁷-(Glyc-ALit)-GLP-1(7-37);
Gly⁸Asp¹⁹Arg²⁶,³⁴Lys²⁷-(Glyc-ALit)-GLP-1(7-38);
Gly⁸Asp¹⁷Arg²⁶,³⁴Lys²⁷-(Glyc-ALit)-GLP-1(7-38);
Arg²⁶,³⁴Lys¹⁸-(Glyc-ALit)-GLP-1(7-36); Arg²⁶,³⁴Lys¹⁸-(Glyc-ALit)-GLP-1(7-36)amide; Arg²⁶,³⁴Lys¹⁸-(Glyc-ALit)-GLP-1(7-37); Arg²⁶,³⁴Lys¹⁸-(Glyc-ALit)-GLP-1(7-38); Val⁸Asp¹⁹Arg²⁶,³⁴Lys¹⁸-(Glyc-ALit)-GLP-1(7-36);
Val⁸Asp¹⁷Arg²⁶,³⁴Lys¹⁸-(Glyc-ALit)-GLP-1(7-36);
Val⁸Asp¹⁹Arg²⁶,³⁴Lys¹⁸-(Glyc-ALit)-GLP-1(7-36)amide;
Val⁸Asp¹⁷Arg²⁶,³⁴Lys¹⁸-(Glyc-ALit)-GLP-1(7-36)amide;
Val⁸Asp¹⁹Arg²⁶,³⁴Lys¹⁸-(Glyc-ALit)-GLP-1(7-37);
Val⁸Asp¹⁹Arg²⁶,³⁴Lys¹⁸-(Glyc-ALit)-GLP-1(7-38);
Val⁸Asp¹⁷Arg²⁶,³⁴Lys¹⁸ (Glyc-ALit)-GLP-1(7-38);
Arg²⁶,³⁴Lys²³-(Glyc-ALit)-GLP-1(7-36); Arg²⁶,³⁴Lys²³-(Glyc-ALit)-GLP-1(7-36)amide; Arg²⁶,³⁴Lys²³-(Glyc-ALit)-GLP-1(7-37); Arg²⁶,³⁴Lys²³-(Glyc-ALit)-GLP-1(7-38); Val⁸Asp¹⁹Arg²⁶,³⁴Lys²³-(Glyc-ALit)-GLP-1(7-36);
Val⁸Asp¹⁷Arg²⁶,³⁴Lys²³-(Glyc-ALit)-GLP-1(7-36);
Val⁸Asp¹⁹Arg²⁶,³⁴Lys²³-(Glyc-ALit)-GLP-1(7-36)amide;
Val⁸Asp¹⁷Arg²⁶,³⁴Lys²³-(Glyc-ALit)-GLP-1(7-36)amide;
Val⁸Asp¹⁹Arg²⁶,³⁴Lys²³-(Glyc-ALit)-GLP-1(7-37);
Val⁸Asp¹⁹Arg²⁶,³⁴Lys²³-(Glyc-ALit)-GLP-1(7-38);
Val⁸Asp¹⁷Arg²⁶,³⁴Lys²³-(Glyc-ALit)-GLP-1(7-38);
Arg²⁶,³⁴Lys²⁷-(Glyc-ALit)-GLP-1(7-36); Arg²⁶,³⁴Lys²⁷-(Glyc-ALit)-GLP-1(7-36)amide; Arg²⁶,³⁴Lys²⁷-(Glyc-ALit)-GLP-1(7-37); Arg²⁶,³⁴Lys²⁷-(Glyc-ALit)-GLP-1(7-38); Val⁸Asp¹⁹Arg²⁶,³⁴Lys²⁷-(Glyc-ALit)-GLP-1(7-36);
Val⁸Asp¹⁷Arg²⁶,³⁴Lys²⁷-(Glyc-ALit)-GLP-1(7-36);
Val⁸Asp¹⁹Arg²⁶,³⁴Lys²⁷-(Glyc-ALit)-GLP-1(7-36)amide;
Val⁸Asp¹⁷Arg²⁶,³⁴Lys²⁷-(Glyc-ALit)-GLP-1(7-36)amide;
Val⁸Asp¹⁹Arg²⁶,³⁴Lys²⁷-(Glyc-ALit)-GLP-1(7-37);
Val⁸Asp¹⁹Arg²⁶,³⁴Lys²⁷-(Glyc-ALit)-GLP-1(7-38);
Val⁸Asp¹⁷Arg²⁶,³⁴Lys²⁷-(Glyc-ALit)-GLP-1(7-38);
Arg²⁶,³⁴Lys¹⁸-(Glyc-ALit)-GLP-1(7-36); Arg²⁶,³⁴Lys¹⁸-(Glyc-ALit)-GLP-1(7-36)amide; Arg²⁶,³⁴Lys¹⁸-(Glyc-ALit)-GLP-1(7-37); Arg²⁶,³⁴Lys¹⁸-(Glyc-ALit)-GLP-1(7-38); Ser⁸Asp¹⁹Arg²⁶,³⁴Lys¹⁸-(Glyc-ALit)-GLP-1(7-36);
Ser⁸Asp¹⁷Arg²⁶,³⁴Lys¹⁸-(Glyc-ALit)-GLP-1(7-36);
Ser⁸Asp¹⁹Arg²⁶,³⁴Lys¹⁸-(Glyc-ALit)-GLP-1(7-36)amide;
Ser⁸Asp¹⁷Arg²⁶,³⁴Lys¹⁸-(Glyc-ALit)-GLP-1(7-36)amide;
Ser⁸Asp¹⁹Arg²⁶,³⁴Lys¹⁸-(Glyc-ALit)-GLP-1(7-37);
Ser⁸Asp¹⁹Arg²⁶,³⁴Lys¹⁸-(Glyc-ALit)-GLP-1(7-38);
Ser⁸Asp¹⁷Arg²⁶,³⁴Lys¹⁸-(Glyc-ALit)-GLP-1(7-38);
Arg²⁶,³⁴Lys²³-(Glyc-ALit)-GLP-1(7-36); Arg²⁶,³⁴Lys²³-(Glyc-ALit)-GLP-1(7-36)amide; Arg²⁶,³⁴Lys²³-(Glyc-ALit)-GLP-1(7-37); Arg²⁶,³⁴Lys²³-(Glyc-ALit)-GLP-1(7-38); Ser⁸Asp¹⁹Arg²⁶,³⁴Lys²³-(Glyc-ALit)-GLP-1(7-36);
Ser⁸Asp¹⁷Arg²⁶,³⁴Lys²³-(Glyc-ALit)-GLP-1(7-36);
Ser⁸Asp¹⁹Arg²⁶,³⁴Lys²³-(Glyc-ALit)-GLP-1(7-36)amide;
Ser⁸Asp¹⁷Arg²⁶,³⁴Lys²³-(Glyc-ALit)-GLP-1(7-36)amide;
Ser⁸Asp¹⁹Arg²⁶,³⁴Lys²³-(Glyc-ALit)-GLP-1(7-37);
Ser⁸Asp¹⁹Arg²⁶,³⁴Lys²³-(Glyc-ALit)-GLP-1(7-38);
Ser⁸Asp¹⁷Arg²⁶,³⁴Lys²³-(Glyc-ALit)-GLP-1(7-38);
Arg²⁶,³⁴Lys²⁷-(Glyc-ALit)-GLP-1(7-36); Arg²⁶,³⁴Lys²⁷-(Glyc-ALit)-GLP-1(7-36)amide; Arg²⁶,³⁴Lys²⁷-(Glyc- ALit)-GLP-1(7-37); Arg$^{26,34}$Lys$^{27}$-(Glyc-ALit)-GLP-1(7-38); Ser$^8$Asp$^{19}$Arg$^{26,34}$Lys$^{27}$-(Glyc-ALit)-GLP-1(7-36); Ser$^8$Asp$^{17}$Arg$^{26,34}$Lys$^{27}$-(Glyc-ALit)-GLP-1(7-36); Ser$^8$Asp$^{19}$Arg$^{26,34}$Lys$^{27}$-(Glyc-ALit)-GLP-1(7-36)amide; Ser$^8$Asp$^{17}$Arg$^{26,34}$Lys$^{27}$-(Glyc-ALit)-GLP-1(7-36)amide; Ser$^8$Asp$^{19}$Arg$^{26,34}$Lys$^{27}$-(Glyc-ALit)-GLP-1(7-37); Ser$^8$Asp$^{19}$Arg$^{26,34}$Lys$^{27}$-(Glyc-ALit)-GLP-1(7-38); Ser$^8$Asp$^{17}$Arg$^{26,34}$Lys$^{27}$-(Glyc-ALit)-GLP-1(7-38); Arg$^{26,34}$Lys$^{18}$-(Glyc-ALit)-GLP-1(7-36); Arg$^{26,34}$Lys$^{18}$-(Glyc-ALit)-GLP-1(7-36)amide; Arg$^{26,34}$Lys$^{18}$-(Glyc-ALit)-GLP-1(7-37); Arg$^{26,34}$Lys$^{18}$-(Glyc-ALit)-GLP-1(7-38); Thr$^8$Asp$^{19}$Arg$^{26,34}$Lys$^{18}$-(Glyc-ALit)-GLP-1(7-36); Thr$^8$Asp$^{17}$Arg$^{26,34}$Lys$^{18}$-(Glyc-ALit)-GLP-1(7-36); Thr$^8$Asp$^{19}$Arg$^{26,34}$Lys$^{18}$-(Glyc-ALit)-GLP-1(7-36)amide; Thr$^8$Asp$^{17}$Arg$^{26,34}$Lys$^{18}$-(Glyc-ALit)-GLP-1(7-36)amide; Thr$^8$Asp$^{19}$Arg$^{26,34}$Lys$^{18}$-(Glyc-ALit)-GLP-1(7-37); Thr$^8$Asp$^{19}$Arg$^{26,34}$Lys$^{18}$-(Glyc-ALit)-GLP-1(7-38); Thr$^8$Asp$^{17}$Arg$^{26,34}$Lys$^{18}$-(Glyc-ALit)-GLP-1(7-38); Arg$^{26,34}$Lys$^{23}$-(Glyc-ALit)-GLP-1(7-36); Arg$^{26,34}$Lys$^{23}$-(Glyc-ALit)-GLP-1(7-36)amide; Arg$^{26,34}$Lys$^{23}$-(Glyc-ALit)-GLP-1(7-37); Arg$^{26,34}$Lys$^{23}$-(Glyc-ALit)-GLP-1(7-38); Thr$^8$Asp$^{19}$Arg$^{26,34}$Lys$^{23}$-(Glyc-ALit)-GLP-1(7-36); Thr$^8$Asp$^{17}$Arg$^{26,34}$Lys$^{23}$-(Glyc-ALit)-GLP-1(7-36); Thr$^8$Asp$^{19}$Arg$^{26,34}$Lys$^{23}$-(Glyc-ALit)-GLP-1(7-36)amide; Thr$^8$Asp$^{17}$Arg$^{26,34}$Lys$^{23}$-(Glyc-ALit)-GLP-1(7-36)amide; Thr$^8$Asp$^{19}$Arg$^{26,34}$Lys$^{23}$-(Glyc-ALit)-GLP-1(7-37); Thr$^8$Asp$^{19}$Arg$^{26,34}$Lys$^{23}$-(Glyc-ALit)-GLP-1(7-38); Thr$^8$Asp$^{17}$Arg$^{26,34}$Lys$^{23}$-(Glyc-ALit)-GLP-1(7-38); Arg$^{26,34}$Lys$^{27}$-(Glyc-ALit)-GLP-1(7-36); Arg$^{26,34}$Lys$^{27}$-(Glyc-ALit)-GLP-1(7-36)amide; Arg$^{26,34}$Lys$^{27}$-(Glyc-ALit)-GLP-1(7-37); Arg$^{26,34}$Lys$^{27}$-(Glyc-ALit)-GLP-1(7-38); Thr$^8$Asp$^{19}$Arg$^{26,34}$Lys$^{27}$-(Glyc-ALit)-GLP-1(7-36); Thr$^8$Asp$^{17}$Arg$^{26,34}$Lys$^{27}$-(Glyc-ALit)-GLP-1(7-36); Thr$^8$Asp$^{19}$Arg$^{26,34}$Lys$^{27}$-(Glyc-ALit)-GLP-1(7-36)amide; Thr$^8$Asp$^{17}$Arg$^{26,34}$Lys$^{27}$-(Glyc-ALit)-GLP-1(7-36)amide; Thr$^8$Asp$^{19}$Arg$^{26,34}$Lys$^{27}$-(Glyc-ALit)-GLP-1(7-37); Thr$^8$Asp$^{19}$Arg$^{26,34}$Lys$^{27}$-(Glyc-ALit)-GLP-1(7-38); Thr$^8$Asp$^{17}$Arg$^{26,34}$Lys$^{27}$-(Glyc-ALit)-GLP-1(7-38); Arg$^{26}$Lys$^{34}$-(GAB-GDod)-GLP-1(7-36); Arg$^{34}$Lys$^{26}$-(GAB-GDod)-GLP-1(7-36); Arg$^{26,34}$Lys$^{36}$-(GAB-GDod)-GLP-1(7-36); Arg$^{26}$Lys$^{34}$-(GAB-GDod)-GLP-1(7-36)amide; Arg$^{34}$Lys$^{26}$-(GAB-GDod)-GLP-1(7-36)amide; Arg$^{26,34}$Lys$^{36}$-(GAB-GDod)-GLP-1(7-36)amide; Arg$^{26}$Lys$^{34}$-(GAB-GDod)-GLP-1(7-37); Arg$^{34}$Lys$^{26}$-(GAB-GDod)-GLP-1(7-37); Arg$^{26,34}$Lys$^{36}$-(GAB-GDod)-GLP-1(7-37); Arg$^{26}$Lys$^{34}$-(GAB-GDod)-GLP-1(7-38); Arg$^{34}$Lys$^{26}$-(GAB-GDod)-GLP-1(7-38); Arg$^{26,34}$Lys$^{38}$-(GAB-GDod)-GLP-1(7-38); Arg$^{26}$Lys$^{34}$-(GAB-GDod)-GLP-1(7-39); Arg$^{34}$Lys$^{26}$-(GAB-GDod)-GLP-1(7-39); Arg$^{26,34}$Lys$^{39}$-(GAB-GDod)-GLP-1(7-39); Gly$^8$Arg$^{26}$Lys$^{34}$-(GAB-GDod)-GLP-1(7-36); Gly$^8$Arg$^{34}$Lys$^{26}$-(GAB-GDod)-GLP-1(7-36); Gly$^8$Arg$^{26,34}$Lys$^{36}$-(GAB-GDod)-GLP-1(7-36); Gly$^8$Arg$^{26}$Lys$^{34}$-(GAB-GDod)-GLP-1(7-36)amide; Gly$^8$Arg$^{34}$Lys$^{26}$-(GAB-GDod)-GLP-1(7-36)amide; Gly$^8$Arg$^{26,34}$Lys$^{36}$-(GAB-GDod)-GLP-1(7-36)amide; Gly$^8$Arg$^{26}$Lys$^{34}$-(GAB-GDod)-GLP-1(7-37); Gly$^8$Arg$^{34}$Lys$^{26}$-(GAB-GDod)-GLP-1(7-37); Gly$^8$Arg$^{26,34}$Lys$^{36}$-(GAB-GDod)-GLP-1(7-37); Gly$^8$Arg$^{26}$Lys$^{34}$-(GAB-GDod)-GLP-1(7-38); Gly$^8$Arg$^{34}$Lys$^{26}$-(GAB-GDod)-GLP-1(7-38); Gly$^8$Arg$^{26,34}$Lys$^{38}$-(GAB-GDod)-GLP-1(7-38); Gly$^8$Arg$^{26}$Lys$^{34}$-(GAB-GDod)-GLP-1(7-39); Gly$^8$Arg$^{34}$Lys$^{26}$-(GAB-GDod)-GLP-1(7-39); Gly$^8$Arg$^{26,34}$Lys$^{39}$-(GAB-GDod)-GLP-1(7-39); Val$^8$Arg$^{26}$Lys$^{34}$-(GAB-GDod)-GLP-1(7-36); Val$^8$Arg$^{34}$Lys$^{26}$-(GAB-GDod)-GLP-1(7-36); Val$^8$Arg$^{26,34}$Lys$^{36}$-(GAB-GDod)-GLP-1(7-36); Val$^8$Arg$^{26}$Lys$^{34}$-(GAB-GDod)-GLP-1(7-36)amide; Val$^8$Arg$^{34}$Lys$^{26}$-(GAB-GDod)-GLP-1(7-36)amide; Val$^8$Arg$^{26,34}$Lys$^{36}$-(GAB-GDod)-GLP-1(7-36)amide; Val$^8$Arg$^{26}$Lys$^{34}$-(GAB-GDod)-GLP-1(7-37); Val$^8$Arg$^{34}$Lys$^{26}$-(GAB-GDod)-GLP-1(7-37); Val$^8$Arg$^{26,34}$Lys$^{36}$-(GAB-GDod)-GLP-1(7-37); Val$^8$Arg$^{26}$Lys$^{34}$-(GAB-GDod)-GLP-1(7-38); Val$^8$Arg$^{34}$Lys$^{26}$-(GAB-GDod)-GLP-1(7-38); Val$^8$Arg$^{26,34}$Lys$^{38}$-(GAB-GDod)-GLP-1(7-38); Val$^8$Arg$^{26}$Lys$^{34}$-(GAB-GDod)-GLP-1(7-39); Val$^8$Arg$^{34}$Lys$^{26}$-(GAB-GDod)-GLP-1(7-39); Val$^8$Arg$^{26,34}$Lys$^{39}$-(GAB-GDod)-GLP-1(7-39); Ser$^8$Arg$^{26}$Lys$^{34}$-(GAB-GDod)-GLP-1(7-36); Ser$^8$Arg$^{34}$Lys$^{26}$-(GAB-GDod)-GLP-1(7-36); Ser$^8$Arg$^{26,34}$Lys$^{36}$-(GAB-GDod)-GLP-1(7-36); Ser$^8$Arg$^{26}$Lys$^{34}$-(GAB-GDod)-GLP-1(7-36)amide; Ser$^8$Arg$^{34}$Lys$^{26}$-(GAB-GDod)-GLP-1(7-36)amide; Ser$^8$Arg$^{26,34}$Lys$^{36}$-(GAB-GDod)-GLP-1(7-36)amide; Ser$^8$Arg$^{26}$Lys$^{34}$-(GAB-GDod)-GLP-1(7-37); Ser$^8$Arg$^{34}$Lys$^{26}$-(GAB-GDod)-GLP-1(7-37); Ser$^8$Arg$^{26,34}$Lys$^{36}$-(GAB-GDod)-GLP-1(7-37); Ser$^8$Arg$^{26}$Lys$^{34}$-(GAB-GDod)-GLP-1(7-38); Ser$^8$Arg$^{34}$Lys$^{26}$-(GAB-GDod)-GLP-1(7-38); Ser$^8$Arg$^{26,34}$Lys$^{38}$-(GAB-GDod)-GLP-1(7-38); Ser$^8$Arg$^{26}$Lys$^{34}$-(GAB-GDod)-GLP-1(7-39); Ser$^8$Arg$^{34}$Lys$^{26}$-(GAB-GDod)-GLP-1(7-39); Ser$^8$Arg$^{26,34}$Lys$^{39}$-(GAB-GDod)-GLP-1(7-39); Thr$^8$Arg$^{26}$Lys$^{34}$-(GAB-GDod)-GLP-1(7-36); Thr$^8$Arg$^{34}$Lys$^{26}$-(GAB-GDod)-GLP-1(7-36); Thr$^8$Arg$^{26,34}$Lys$^{36}$-(GAB-GDod)-GLP-1(7-36); Thr$^8$Arg$^{26}$Lys$^{34}$-(GAB-GDod)-GLP-1(7-36)amide; Thr$^8$Arg$^{34}$Lys$^{26}$-(GAB-GDod)-GLP-1(7-36)amide; Thr$^8$Arg$^{26,34}$Lys$^{36}$-(GAB-GDod)-GLP-1(7-36)amide; Thr$^8$Arg$^{26}$Lys$^{34}$-(GAB-GDod)-GLP-1(7-37); Thr$^8$Arg$^{34}$Lys$^{26}$-(GAB-GDod)-GLP-1(7-37); Thr$^8$Arg$^{26,34}$Lys$^{36}$-(GAB-GDod)-GLP-1(7-37); Thr$^8$Arg$^{26}$Lys$^{34}$-(GAB-GDod)-GLP-1(7-38); Thr$^8$Arg$^{34}$Lys$^{26}$-(GAB-GDod)-GLP-1(7-38); Thr$^8$Arg$^{26,34}$Lys$^{38}$-(GAB-GDod)-GLP-1(7-38); Thr$^8$Arg$^{26}$Lys$^{34}$-(GAB-GDod)-GLP-1(7-39); Thr$^8$Arg$^{34}$Lys$^{26}$-(GAB-GDod)-GLP-1(7-39); Thr$^8$Arg$^{26,34}$Lys$^{39}$-(GAB-GDod)-GLP-1(7-39); Gly$^8$Glu$^{35}$Arg$^{26,34}$Lys$^{36}$-(GAB-GDod)-GLP-1(7-36); Gly$^8$Glu$^{35}$Arg$^{26,34}$Lys$^{36}$-(GAB-GDod)-GLP-1(7-36)amide; Gly$^8$Glu$^{36}$Arg$^{26,34}$Lys$^{37}$-(GAB-GDod)-GLP-1(7-37); Gly$^8$Glu$^{37}$Arg$^{26,34}$Lys$^{38}$-(GAB-GDod)-GLP-1(7-38); Gly$^8$Glu$^{38}$Arg$^{26,34}$Lys$^{39}$-(GAB-GDod)-GLP-1(7-39); Gly$^8$Glu$^{35}$Arg$^{26,34}$Lys$^{36}$-(GAB-GDod)-GLP-1(7-36); Gly$^8$Glu$^{35}$Arg$^{26,34}$Lys$^{36}$-(GAB-GDod)-GLP-1(7-36)amide; Gly$^8$Glu$^{36}$Arg$^{26,34}$Lys$^{37}$-(GAB-GDod)-GLP-1(7-37); Gly$^8$Glu$^{37}$Arg$^{26,34}$Lys$^{38}$-(GAB-GDod)-GLP-1(7-38); Gly$^8$Glu$^{38}$Arg$^{26,34}$Lys$^{39}$-(GAB-GDod)-GLP-1(7-39); Gly$^8$Asp$^{35}$Arg$^{26,34}$Lys$^{36}$-(GAB-GDod)-GLP-1(7-36); Gly$^8$Asp$^{35}$Arg$^{26,34}$Lys$^{36}$-(GAB-GDod)-GLP-1(7-36)amide; Gly$^8$Asp$^{36}$Arg$^{26,34}$Lys$^{37}$-(GAB-GDod)-GLP-1(7-37); Gly$^8$Asp$^{37}$Arg$^{26,34}$Lys$^{38}$-(GAB-GDod)-GLP-1(7-38); Gly$^8$Asp$^{38}$Arg$^{26,34}$Lys$^{39}$-(GAB-GDod)-GLP-1(7-39); Gly$^8$Asp$^{35}$Arg$^{26,34}$Lys$^{36}$-(GAB-GDod)-GLP-1(7-36); Gly$^8$Asp$^{35}$Arg$^{26,34}$Lys$^{36}$-(GAB-GDod)-GLP-1(7-36)amide; Gly$^8$Asp$^{36}$Arg$^{26,34}$Lys$^{37}$-(GAB-GDod)-GLP-1(7-37); Gly$^8$Asp$^{37}$Arg$^{26,34}$Lys$^{38}$-(GAB-GDod)-GLP-1(7-38); Gly$^8$Asp$^{38}$Arg$^{26,34}$Lys$^{39}$-(GAB-GDod)-GLP-1(7-39); Val$^8$Glu$^{35}$Arg$^{26,34}$Lys$^{36}$-(GAB-GDod)-GLP-1(7-36); Val$^8$Glu$^{35}$Arg$^{26,34}$Lys$^{36}$-(GAB-GDod)-GLP-1(7-36)amide; Val$^8$Glu$^{36}$Arg$^{26,34}$Lys$^{37}$-(GAB-GDod)-GLP-1(7-37); Val$^8$Glu$^{37}$Arg$^{26,34}$Lys$^{38}$-(GAB-GDod)-GLP-1(7-38); Val$^8$Glu$^{38}$Arg$^{26,34}$Lys$^{39}$-(GAB-GDod)-GLP-1(7-39); Val$^8$Glu$^{35}$Arg$^{26,34}$Lys$^{36}$-(GAB-GDod)-GLP-1(7-36);

Val⁸Glu³⁵Arg²⁶,³⁴Lys³⁶-(GAB-GDod)-GLP-1(7-36)amide;
Val⁸Glu³⁶Arg²⁶,³⁴Lys³⁷-(GAB-GDod)-GLP-1(7-37);
Val⁸Glu³⁷Arg²⁶,³⁴Lys³⁸-(GAB-GDod)-GLP-1(7-38);
Val⁸Glu³⁸Arg²⁶,³⁴Lys³⁹-(GAB-GDod)-GLP-1(7-39);
Val⁸Asp³⁵Arg²⁶,³⁴Lys³⁶-(GAB-GDod)-GLP-1(7-36);
Val⁸Asp³⁵Arg²⁶,³⁴Lys³⁶-(GAB-GDod)-GLP-1(7-36)amide;
Val⁸Asp³⁶Arg²⁶,³⁴Lys³⁷-(GAB-GDod)-GLP-1(7-37);
Val⁸Asp³⁷Arg²⁶,³⁴Lys³⁸-(GAB-GDod)-GLP-1(7-38);
Val⁸Asp³⁸Arg²⁶,³⁴Lys³⁹-(GAB-GDod)-GLP-1(7-39);
Val⁸Asp³⁵Arg²⁶,³⁴Lys³⁶-(GAB-GDod)-GLP-1(7-36);
Val⁸Asp³⁵Arg²⁶,³⁴Lys³⁶-(GAB-GDod)-GLP-1(7-36)amide;
Val⁸Asp³⁶Arg²⁶,³⁴Lys³⁷-(GAB-GDod)-GLP-1(7-37);
Val⁸Asp³⁷Arg²⁶,³⁴Lys³⁸-(GAB-GDod)-GLP-1(7-38);
Val⁸Asp³⁸Arg²⁶,³⁴Lys³⁹-(GAB-GDod)-GLP-1(7-39);
Ser⁸Glu³⁵Arg²⁶,³⁴Lys³⁶-(GAB-GDod)-GLP-1(7-36);
Ser⁸Glu³⁵Arg²⁶,³⁴Lys³⁶-(GAB-GDod)-GLP-1(7-36)amide;
Ser⁸Glu³⁶Arg²⁶,³⁴Lys³⁷-(GAB-GDod)-GLP-1(7-37);
Ser⁸Glu³⁷Arg²⁶,³⁴Lys³⁸-(GAB-GDod)-GLP-1(7-38);
Ser⁸Glu³⁸Arg²⁶,³⁴Lys³⁹-(GAB-GDod)-GLP-1(7-39);
Ser⁸Glu³⁵Arg²⁶,³⁴Lys³⁶ (GAB-GDod)-GLP-1(7-36);
Ser⁸Glu³⁵Arg²⁶,³⁴Lys³⁶-(GAB-GDod)-GLP-1(7-36)amide;
Ser⁸Glu³⁶Arg²⁶,³⁴Lys³⁷-(GAB-GDod)-GLP-1(7-37);
Ser⁸Glu³⁷Arg²⁶,³⁴Lys³⁸-(GAB-GDod)-GLP-1(7-38);
Ser⁸Glu³⁸Arg²⁶,³⁴Lys³⁹-(GAB-GDod)-GLP-1(7-39);
Ser⁸Asp³⁵Arg²⁶,³⁴Lys³⁶-(GAB-GDod)-GLP-1(7-36);
Ser⁸Asp³⁵Arg²⁶,³⁴Lys³⁶-(GAB-GDod)-GLP-1(7-36)amide;
Ser⁸Asp³⁶Arg²⁶,³⁴Lys³⁷-(GAB-GDod)-GLP-1(7-37);
Ser⁸Asp³⁷Arg²⁶,³⁴Lys³⁸-(GAB-GDod)-GLP-1(7-38);
Ser⁸Asp³⁸Arg²⁶,³⁴Lys³⁹-(GAB-GDod)-GLP-1(7-39);
Ser⁸Asp³⁵Arg²⁶,³⁴Lys³⁶-(GAB-GDod)-GLP-1(7-36);
Ser⁸Asp³⁵Arg²⁶,³⁴Lys³⁶-(GAB-GDod)-GLP-1(7-36)amide;
Ser⁸Asp³⁶Arg²⁶,³⁴Lys³⁷-(GAB-GDod)-GLP-1(7-37);
Ser⁸Asp³⁷Arg²⁶,³⁴Lys³⁸-(GAB-GDod)-GLP-1(7-38);
Ser⁸Asp³⁸Arg²⁶,³⁴Lys³⁹-(GAB-GDod)-GLP-1(7-39);
Thr⁸Glu³⁵Arg²⁶,³⁴Lys³⁶-(GAB-GDod)-GLP-1(7-36);
Thr⁸Glu³⁵Arg²⁶,³⁴Lys³⁶-(GAB-GDod)-GLP-1(7-36)amide;
Thr⁸Glu³⁶Arg²⁶,³⁴Lys³⁷-(GAB-GDod)-GLP-1(7-37);
Thr⁸Glu³⁷Arg²⁶,³⁴Lys³⁸-(GAB-GDod)-GLP-1(7-38);
Thr⁸Glu³⁸Arg²⁶,³⁴Lys³⁹-(GAB-GDod)-GLP-1(7-39);
Thr⁸Glu³⁵Arg²⁶,³⁴Lys³⁶-(GAB-GDod)-GLP-1(7-36);
Thr⁸Glu³⁵Arg²⁶,³⁴Lys³⁶-(GAB-GDod)-GLP-1(7-36)amide;
Thr⁸Glu³⁶Arg²⁶,³⁴Lys³⁷-(GAB-GDod)-GLP-1(7-37);
Thr⁸Glu³⁷Arg²⁶,³⁴Lys³⁸-(GAB-GDod)-GLP-1(7-38);
Thr⁸Glu³⁸Arg²⁶,³⁴Lys³⁹-(GAB-GDod)-GLP-1(7-39);
Thr⁸Asp³⁵Arg²⁶,³⁴Lys³⁶-(GAB-GDod)-GLP-1(7-36);
Thr⁸Asp³⁵Arg²⁶,³⁴Lys³⁶-(GAB-GDod)-GLP-1(7-36)amide;
Thr⁸Asp³⁶Arg²⁶,³⁴Lys³⁷-(GAB-GDod)-GLP-1(7-37);
Thr⁸Asp³⁷Arg²⁶,³⁴Lys³⁸-(GAB-GDod)-GLP-1(7-38);
Thr⁸Asp³⁸Arg²⁶,³⁴Lys³⁹-(GAB-GDod)-GLP-1(7-39);
Thr⁸Asp³⁵Arg²⁶,³⁴Lys³⁶-(GAB-GDod)-GLP-1(7-36);
Thr⁸Asp³⁵Arg²⁶,³⁴Lys³⁶-(GAB-GDod)-GLP-1(7-36)amide;
Thr⁸Asp³⁶Arg²⁶,³⁴Lys³⁷-(GAB-GDod)-GLP-1(7-37);
Thr⁸Asp³⁷Arg²⁶,³⁴Lys³⁸-(GAB-GDod)-GLP-1(7-38);
Thr⁸Asp³⁸Arg²⁶,³⁴Lys³⁹-(GAB-GDod)-GLP-1(7-39);
Arg²⁶,³⁴Lys¹⁸-(GAB-GDod)-GLP-1(7-36); Arg²⁶,³⁴Lys¹⁸-(GAB-GDod)-GLP-1(7-36)amide; Arg²⁶,³⁴Lys¹⁸-(GAB-GDod)-GLP-1(7-37); Arg²⁶,³⁴Lys¹⁸-(GAB-GDod)-GLP-1(7-38); Gly⁸Asp¹⁹Arg²⁶,³⁴Lys¹⁸-(GAB-GDod)-GLP-1(7-36); Gly⁸Asp¹⁷Arg²⁶,³⁴Lys¹⁸-(GAB-GDod)-GLP-1(7-36); Gly⁸Asp¹⁹Arg²⁶,³⁴Lys¹⁸-(GAB-GDod)-GLP-1(7-36)amide; Gly⁸Asp¹⁷Arg²⁶,³⁴Lys¹⁸-(GAB-GDod)-GLP-1(7-36)amide; Gly⁸Asp¹⁹Arg²⁶,³⁴Lys¹⁸-(GAB-GDod)-GLP-1(7-37); Gly⁸Asp¹⁹Arg²⁶,³⁴Lys¹⁸-(GAB-GDod)-GLP-1(7-38); Gly⁸Asp¹⁷Arg²⁶,³⁴Lys¹⁸-(GAB-GDod)-GLP-1(7-38); Arg²⁶,³⁴Lys²³-(GAB-GDod)-GLP-1(7-36); Arg²⁶,³⁴Lys²³-(GAB-GDod)-GLP-1(7-36)amide; Arg²⁶,³⁴Lys²³-(GAB-GDod)-GLP-1(7-37); Arg²⁶,³⁴Lys²³-(GAB-GDod)-GLP-1(7-38); Gly⁸Asp¹⁹Arg²⁶,³⁴Lys²³-(GAB-GDod)-GLP-1(7-36); Gly⁸Asp¹⁷Arg²⁶,³⁴Lys²³-(GAB-GDod)-GLP-1(7-36); Gly⁸Asp¹⁹Arg²⁶,³⁴Lys²³ (GAB-GDod)-GLP-1(7-36)amide; Gly⁸Asp¹⁷Arg²⁶,³⁴Lys²³-(GAB-GDod)-GLP-1(7-36)amide; Gly⁸Asp¹⁹Arg²⁶,³⁴Lys²³-(GAB-GDod)-GLP-1(7-37); Gly⁸Asp¹⁹Arg²⁶,³⁴Lys²³-(GAB-GDod)-GLP-1(7-38); Gly⁸Asp¹⁷Arg²⁶,³⁴Lys²³-(GAB-GDod)-GLP-1(7-38); Arg²⁶,³⁴Lys²⁷-(GAB-GDod)-GLP-1(7-36); Arg²⁶,³⁴Lys²⁷-(GAB-GDod)-GLP-1(7-36)amide; Arg²⁶,³⁴Lys²⁷-(GAB-GDod)-GLP-1(7-37); Arg²⁶,³⁴Lys²⁷-(GAB-GDod)-GLP-1(7-38); Gly⁸Asp¹⁹Arg²⁶,³⁴Lys²⁷-(GAB-GDod)-GLP-1(7-36); Gly⁸Asp¹⁷Arg²⁶,³⁴Lys²⁷-(GAB-GDod)-GLP-1(7-36); Gly⁸Asp¹⁹Arg²⁶,³⁴Lys²⁷-(GAB-GDod)-GLP-1(7-36)amide; Gly⁸Asp¹⁷Arg²⁶,³⁴Lys²⁷-(GAB-GDod)-GLP-1(7-36)amide; Gly⁸Asp¹⁹Arg²⁶,³⁴Lys²⁷-(GAB-GDod)-GLP-1(7-37); Gly⁸Asp¹⁹Arg²⁶,³⁴Lys²⁷-(GAB-GDod)-GLP-1(7-38); Gly⁸Asp¹⁷Arg²⁶,³⁴Lys²⁷-(GAB-GDod)-GLP-1(7-38); Arg²⁶,³⁴Lys¹⁸-(GAB-GDod)-GLP-1(7-36); Arg²⁶,³⁴Lys¹⁸-(GAB-GDod)-GLP-1(7-36)amide; Arg²⁶,³⁴Lys¹⁸-(GAB-GDod)-GLP-1(7-37); Arg²⁶,³⁴Lys¹⁸-(GAB-GDod)-GLP-1(7-38); Val⁸Asp¹⁹Arg²⁶,³⁴Lys¹⁸-(GAB-GDod)-GLP-1(7-36); Val⁸Asp¹⁷Arg²⁶,³⁴Lys¹⁸-(GAB-GDod)-GLP-1(7-36); Val⁸Asp¹⁹Arg²⁶,³⁴Lys¹⁸-(GAB-GDod)-GLP-1(7-36)amide; Val⁸Asp¹⁷Arg²⁶,³⁴Lys¹⁸-(GAB-GDod)-GLP-1(7-36)amide; Val⁸Asp¹⁹Arg²⁶,³⁴Lys¹⁸-(GAB-GDod)-GLP-1(7-37); Val⁸Asp¹⁹Arg²⁶,³⁴Lys¹⁸-(GAB-GDod)-GLP-1(7-38); Val⁸Asp¹⁷Arg²⁶,³⁴Lys¹⁸-(GAB-GDod)-GLP-1(7-38); Arg²⁶,³⁴Lys²³-(GAB-GDod)-GLP-1(7-36); Arg²⁶,³⁴Lys²³-(GAB-GDod)-GLP-1(7-36)amide; Arg²⁶,³⁴Lys²³-(GAB-GDod)-GLP-1(7-37); Arg²⁶,³⁴Lys²³-(GAB-GDod)-GLP-1(7-38); Val⁸Asp¹⁹Arg²⁶,³⁴Lys²³ (GAB-GDod)-GLP-1(7-36); Val⁸Asp¹⁷Arg²⁶,³⁴Lys²³-(GAB-GDod)-GLP-1(7-36); Val⁸Asp¹⁹Arg²⁶,³⁴Lys²³-(GAB-GDod)-GLP-1(7-36)amide; Val⁸Asp¹⁷Arg²⁶,³⁴Lys²³-(GAB-GDod)-GLP-1(7-36)amide; Val⁸Asp¹⁹Arg²⁶,³⁴Lys²³-(GAB-GDod)-GLP-1(7-37); Val⁸Asp¹⁹Arg²⁶,³⁴Lys²³-(GAB-GDod)-GLP-1(7-38); Val⁸Asp¹⁷Arg²⁶,³⁴Lys²³-(GAB-GDod)-GLP-1(7-38); Arg²⁶,³⁴Lys²⁷-(GAB-GDod)-GLP-1(7-36); Arg²⁶,³⁴Lys²⁷-(GAB-GDod)-GLP-1(7-36)amide; Arg²⁶,³⁴Lys²⁷-(GAB-GDod)-GLP-1(7-37); Arg²⁶,³⁴Lys²⁷-(GAB-GDod)-GLP-1(7-38); Val⁸Asp¹⁹Arg²⁶,³⁴Lys²⁷-(GAB-GDod)-GLP-1(7-36); Val⁸Asp¹⁷Arg²⁶,³⁴Lys²⁷-(GAB-GDod)-GLP-1(7-36); Val⁸Asp¹⁹Arg²⁶,³⁴Lys²⁷-(GAB-GDod)-GLP-1(7-36)amide; Val⁸Asp¹⁷Arg²⁶,³⁴Lys²⁷-(GAB-GDod)-GLP-1(7-36)amide; Val⁸Asp¹⁹Arg²⁶,³⁴Lys²⁷-(GAB-GDod)-GLP-1(7-37); Val⁸Asp¹⁹Arg²⁶,³⁴Lys²⁷-(GAB-GDod)-GLP-1(7-38); Val⁸Asp¹⁷Arg²⁶,³⁴Lys²⁷-(GAB-GDod)-GLP-1(7-38); Arg²⁶,³⁴Lys¹⁸-(GAB-GDod)-GLP-1(7-36); Arg²⁶,³⁴Lys¹⁸-(GAB-GDod)-GLP-1(7-36)amide; Arg²⁶,³⁴Lys¹⁸-(GAB-GDod)-GLP-1(7-37); Arg²⁶,³⁴Lys¹⁸-(GAB-GDod)-GLP-1(7-38); Ser⁸Asp¹⁹Arg²⁶,³⁴Lys¹⁸-(GAB-GDod)-GLP-1(7-36); Ser⁸Asp¹⁷Arg²⁶,³⁴Lys¹⁸-(GAB-GDod)-GLP-1(7-36); Ser⁸Asp¹⁹Arg²⁶,³⁴Lys¹⁸-(GAB-GDod)-GLP-1(7-36)amide; Ser⁸Asp¹⁷Arg²⁶,³⁴Lys¹⁸-(GAB-GDod)-GLP-1(7-36)amide; Ser⁸Asp¹⁹Arg²⁶,³⁴Lys¹⁸-(GAB-GDod)-GLP-1(7-37); Ser⁸Asp¹⁹Arg²⁶,³⁴Lys¹⁸-(GAB-GDod)-GLP-1(7-38); Ser⁸Asp¹⁷Arg²⁶,³⁴Lys¹⁸-(GAB-GDod)-GLP-1(7-38); Arg²⁶,³⁴Lys²³-(GAB-GDod)-GLP-1(7-36); Arg²⁶,³⁴Lys²³-(GAB GDod) GLP-1(7-36)amide; Arg²⁶,³⁴Lys²³-(GAB-GDod)-GLP-1(7-37); Arg²⁶,³⁴Lys²³-(GAB-GDod)-GLP-1(7-38); Ser⁸Asp¹⁹Arg²⁶,³⁴Lys²³-(GAB-GDod)-GLP-1(7-36); Ser⁸Asp¹⁷Arg²⁶,³⁴Lys²³-(GAB-GDod)-GLP-1(7-36); Ser⁸Asp¹⁹Arg²⁶,³⁴Lys²³-(GAB-GDod)-GLP-1(7-36)amide; Ser⁸Asp¹⁷Arg²⁶,³⁴Lys²³-(GAB-GDod)-GLP-1(7-36)amide; Ser⁸Asp¹⁹Arg²⁶,³⁴Lys²³-(GAB-GDod)-GLP-1(7-37); Ser⁸Asp¹⁹Arg²⁶,³⁴Lys²³-(GAB-GDod)-GLP-1(7-38); Ser⁸Asp¹⁷Arg²⁶,³⁴Lys²³-(GAB-GDod)-GLP-1(7-38);

Arg²⁶,³⁴Lys²⁷-(GAB-GDod)-GLP-1(7-36); Arg²⁶,³⁴Lys²⁷-(GAB-GDod)-GLP-1(7-36)amide; Arg²⁶,³⁴Lys²⁷-(GAB-GDod)-GLP-1(7-37); Arg²⁶,³⁴Lys²⁷-(GAB-GDod)-GLP-1(7-38); Ser⁸Asp¹⁹Arg²⁶,³⁴Lys²⁷-(GAB-GDod)-GLP-1(7-36); Ser⁸Asp¹⁷Arg²⁶,³⁴Lys²⁷-(GAB-GDod)-GLP-1(7-36); Ser⁸Asp¹⁹Arg²⁶,³⁴Lys²⁷-(GAB-GDod)-GLP-1(7-36)amide; Ser⁸Asp¹⁷Arg²⁶,³⁴Lys²⁷-(GAB-GDod)-GLP-1(7-36)amide; Ser⁸Asp¹⁹Arg²⁶,³⁴Lys²⁷-(GAB-GDod)-GLP-1(7-37); Ser⁸Asp¹⁹Arg²⁶,³⁴Lys²⁷-(GAB-GDod)-GLP-1(7-38); Ser⁸Asp¹⁷Arg²⁶,³⁴Lys²⁷-(GAB-GDod)-GLP-1(7-38); Arg²⁶,³⁴Lys¹⁸-(GAB-GDod)-GLP-1(7-36); Arg²⁶,³⁴Lys¹⁸-(GAB-GDod)-GLP-1(7-36)amide; Arg²⁶,³⁴Lys¹⁸-(GAB-GDod)-GLP-1(7-37); Arg²⁶,³⁴Lys¹⁸-(GAB-GDod)-GLP-1(7-38); Thr⁸Asp¹⁹Arg²⁶,³⁴Lys¹⁸-(GAB-GDod)-GLP-1(7-36); Thr⁸Asp¹⁷Arg²⁶,³⁴Lys¹⁸-(GAB-GDod)-GLP-1(7-36); Thr⁸Asp¹⁹Arg²⁶,³⁴Lys¹⁸-(GAB-GDod)-GLP-1(7-36)amide; Thr⁸Asp¹⁷Arg²⁶,³⁴Lys¹⁸-(GAB-GDod)-GLP-1(7-36)amide; Thr⁸Asp¹⁹Arg²⁶,³⁴Lys¹⁸-(GAB-GDod)-GLP-1(7-37); Thr⁸Asp¹⁹Arg²⁶,³⁴Lys¹⁸-(GAB-GDod)-GLP-1(7-38); Thr⁸Asp¹⁷Arg²⁶,³⁴Lys¹⁸-(GAB-GDod)-GLP-1(7-38); Arg²⁶,³⁴Lys²³-(GAB-GDod)-GLP-1(7-36); Arg²⁶,³⁴Lys²³-(GAB-GDod)-GLP-1(7-36)amide; Arg²⁶,³⁴Lys²³-(GAB-GDod)-GLP-1(7-37); Arg²⁶,³⁴Lys²³-(GAB-GDod)-GLP-1(7-38); Thr⁸Asp¹⁹Arg²⁶,³⁴Lys²³-(GAB-GDod)-GLP-1(7-36); Thr⁸Asp¹⁷Arg²⁶,³⁴Lys²³-(GAB-GDod)-GLP-1(7-36); Thr⁸Asp¹⁹Arg²⁶,³⁴Lys²³ (GAB-GDod)-GLP-1(7-36)amide; Thr⁸Asp¹⁷Arg²⁶,³⁴Lys²³-(GAB-GDod)-GLP-1(7-36)amide; Thr⁸Asp¹⁹Arg²⁶,³⁴Lys²³-(GAB-GDod)-GLP-1(7-37); Thr⁸Asp¹⁹Arg²⁶,³⁴Lys²³-(GAB-GDod)-GLP-1(7-38); Thr⁸Asp¹⁷Arg²⁶,³⁴Lys²³-(GAB-GDod)-GLP-1(7-38); Arg²⁶,³⁴Lys²⁷-(GAB-GDod)-GLP-1(7-36); Arg²⁶,³⁴Lys²⁷-(GAB-GDod)-GLP-1(7-36)amide; Arg²⁶,³⁴Lys²⁷-(GAB-GDod)-GLP-1(7-37); Arg²⁶,³⁴Lys²⁷-(GAB-GDod)-GLP-1(7-38); Thr⁸Asp¹⁹Arg²⁶,³⁴Lys²⁷-(GAB-GDod)-GLP-1(7-36); Thr⁸Asp¹⁷Arg²⁶,³⁴Lys²⁷-(GAB-GDod)-GLP-1(7-36); Thr⁸Asp¹⁹Arg²⁶,³⁴Lys²⁷-(GAB-GDod)-GLP-1(7-36)amide; Thr⁸Asp¹⁷Arg²⁶,³⁴Lys²⁷-(GAB-GDod)-GLP-1(7-36)amide; Thr⁸Asp¹⁹Arg²⁶,³⁴Lys²⁷-(GAB-GDod)-GLP-1(7-37); Thr⁸Asp¹⁹Arg²⁶,³⁴Lys²⁷-(GAB-GDod)GLP-1(7-38); Thr⁸Asp¹⁷Arg²⁶,³⁴Lys²⁷-(GAB-GDod)-GLP-1(7-38); Arg²⁶Lys³⁴-(GAB-GTet)-GLP-1(7-36); Arg³⁴Lys²⁶-(GAB-GTet)-GLP-1(7-36); Arg²⁶Lys³⁶-(GAB-GTet)-GLP-1(7-36); Arg²⁶Lys³⁴-(GAB-GTet)-GLP-1(7-36)amide; Arg³⁴Lys²⁶-(GAB-GTet)-GLP-1(7-36)amide; Arg²⁶,³⁴Lys³⁶-(GAB-GTet)-GLP-1(7-36)amide; Arg²⁶Lys³⁴-(GAB-GTet)-GLP-1(7-37); Arg³⁴Lys²⁶-(GAB-GTet)-GLP-1(7-37); Arg²⁶,³⁴Lys³⁶-(GAB-GTet)-GLP-1(7-37); Arg²⁶Lys³⁴-(GAB-GTet)-GLP-1(7-38); Arg³⁴Lys²⁶-(GAB-GTet)-GLP-1(7-38); Arg²⁶,³⁴Lys³⁸-(GAB-GTet)-GLP-1(7-38); Arg²⁶Lys³⁴-(GAB-GTet)-GLP-1(7-39); Arg³⁴Lys²⁶-(GAB-GTet)-GLP-1(7-39); Arg²⁶,³⁴Lys³⁹-(GAB-GTet)-GLP-1(7-39); Gly⁸Arg²⁶Lys³⁴-(GAB-GTet)-GLP-1(7-36); Gly⁸Arg³⁴Lys²⁶-(GAB-GTet)-GLP-1(7-36); Gly⁸Arg²⁶,³⁴Lys³⁶-(GAB-GTet)-GLP-1(7-36); Gly⁸Arg²⁶Lys³⁴-(GAB-GTet)-GLP-1(7-36)amide; Gly⁸Arg²⁶Lys²⁶-(GAB-GTet)-GLP-1(7-36)amide; Gly⁸Arg²⁶,³⁴Lys³⁶-(GAB-GTet)-GLP-1(7-36)amide; Gly⁸Arg²⁶Lys³⁴-(GAB-GTet)-GLP-1(7-37); Gly⁸Arg³⁴Lys²⁶-(GAB-GTet)-GLP-1(7-37); Gly⁸Arg²⁶,³⁴Lys³⁶-(GAB-GTet)-GLP-1(7-37); Gly⁸Arg²⁶Lys³⁴-(GAB-GTet)-GLP-1(7-38); Gly⁸Arg³⁴Lys²⁶-(GAB-GTet)-GLP-1(7-38); Gly⁸Arg²⁶,³⁴Lys³⁸-(GAB-GTet)-GLP-1(7-38); Gly⁸Arg²⁶Lys³⁴-(GAB-GTet)-GLP-1(7-39); Gly⁸Arg³⁴Lys²⁶-(GAB-GTet)-GLP-1(7-39); Gly⁸Arg²⁶,³⁴Lys³⁹-(GAB-GTet)-GLP-1(7-39);
Val⁸Arg²⁶Lys³⁴-(GAB-GTet)-GLP-1(7-36); Val⁸Arg³⁴Lys²⁶-(GAB-GTet)-GLP-1(7-36); Val⁸Arg²⁶,³⁴Lys³⁶-(GAB-GTet)-GLP-1(7-36); Val⁸Arg²⁶Lys³⁴-(GAB-GTet)-GLP-1(7-36)amide; Val⁸Arg³⁴Lys²⁶-(GAB-GTet)-GLP-1(7-36)amide; Val⁸Arg²⁶,³⁴Lys³⁶-(GAB-GTet)-GLP-1(7-36)amide;Val⁸Arg²⁶Lys³⁴-(GAB-GTet)-GLP-1(7-37); Val⁸Arg³⁴Lys²⁶-(GAB-GTet)-GLP-1(7-37); Val⁸Arg²⁶,³⁴Lys³⁶-(GAB-GTet)-GLP-1(7-37); Val⁸Arg²⁶Lys³⁴-(GAB-GTet)-GLP-1(7-38); Val⁸Arg³⁴Lys²⁶-(GAB-GTet)-GLP-1(7-38); Val⁸Arg²⁶,³⁴Lys³⁸-(GAB-GTet)-GLP-1(7-38); Val⁸Arg²⁶Lys³⁴-(GAB-GTet)-GLP-1(7-39); Val⁸Arg³⁴Lys²⁶-(GAB-GTet)-GLP-1(7-39); Val⁸Arg²⁶,³⁴Lys³⁹-(GAB-GTet)-GLP-1(7-39); Ser⁸Arg²⁶Lys³⁴-(GAB-GTet)-GLP-1(7-36); Ser⁸Arg³⁴Lys²⁶-(GAB-GTet)-GLP-1(7-36); Ser⁸Arg²⁶,³⁴Lys³⁶-(GAB-GTet)-GLP-1(7-36); Ser⁸Arg²⁶Lys³⁴-(GAB-GTet)-GLP-1(7-36)amide; Ser⁸Arg³⁴Lys²⁶-(GAB-GTet)-GLP-1(7-36)amide; Ser⁸Arg²⁶,³⁴Lys³⁶-(GAB-GTet)-GLP-1(7-36)amide;Ser⁸Arg²⁶Lys³⁴-(GAB-GTet)-GLP-1(7-37); Ser⁸Arg³⁴Lys²⁶-(GAB-GTet)-GLP-1(7-37); Ser⁸Arg²⁶,³⁴Lys³⁶-(GAB-GTet)-GLP-1(7-37); Ser⁸Arg²⁶Lys³⁴-(GAB-GTet)-GLP-1(7-38); Ser⁸Arg³⁴Lys²⁶-(GAB-GTet)-GLP-1(7-38; Ser⁸Arg²⁶,³⁴Lys³⁸-(GAB-GTet)-GLP-1(7-38); Ser⁸Arg²⁶Lys³⁴-(GAB-GTet)-GLP-1(7-39); Ser⁸Arg³⁴Lys²⁶-(GAB-GTet)-GLP-1(7-39); Ser⁸Arg²⁶,³⁴Lys³⁹-(GAB-GTet)-GLP-1(7-39); Thr⁸Arg²⁶Lys³⁴-(GAB-GTet)-GLP-1(7-36); Thr⁸Arg³⁴Lys²⁶-(GAB-GTet)-GLP-1(7-36); Thr⁸Arg²⁶,³⁴Lys³⁶-(GAB-GTet)-GLP-1(7-36); Thr⁸Arg²⁶Lys³⁴-(GAB-GTet)-GLP-1(7-36)amide; Thr⁸Arg³⁴Lys²⁶-(GAB-GTet)-GLP-1(7-36)amide; Thr⁸Arg²⁶,³⁴Lys³⁶-(GAB-GTet)-GLP-1(7-36)amide; Thr⁸Arg²⁶Lys³⁴-(GAB-GTet)-GLP-1(7-37); Thr⁸Arg³⁴Lys²⁶-(GAB-GTet)-GLP-1(7-37); Thr⁸Arg²⁶,³⁴Lys³⁶-(GAB-GTet)-GLP-1(7-37); Thr⁸Arg²⁶Lys³⁴-(GAB-GTet)-GLP-1(7-38); Thr⁸Arg³⁴Lys²⁶-(GAB-GTet)-GLP-1(7-38); Thr⁸Arg²⁶,³⁴Lys³⁸-(GAB-GTet)-GLP-1(7-38); Thr⁸Arg²⁶Lys³⁴-(GAB-GTet)-GLP-1(7-39); Thr⁸Arg³⁴Lys²⁶-(GAB-GTet)-GLP-1(7-39); Thr⁸Arg²⁶,³⁴Lys³⁹-(GAB-GTet)-GLP-1(7-39);
Gly⁸Glu³⁵Arg²⁶,³⁴Lys³⁶-(GAB-GTet)GLP-1(7-36); Gly⁸Glu³⁵Arg²⁶,³⁴Lys³⁶ (GAB-GTet)-GLP-1(7-3)amide; Gly⁸Glu³⁶Arg²⁶,³⁴Lys³⁷(GAB-GTet)-GLP-1(7-37); Gly⁸Glu³⁷Arg²⁶,³⁴Lys³⁸-(GAB-GTet)-GLP-1(7-38); Gly⁸Glu³⁸Arg²⁶,³⁴Lys³⁹-(GAB-GTet)GLP-1(7-39); Gly⁸Glu³⁵Arg²⁶,³⁴Lys³⁶-(GAB-GTet)-GLP-1(7-36); Gly⁸Glu³⁵Arg²⁶,³⁴Lys³⁶-(GAB-GTet)-GLP-1(7-36)amide; Gly⁸Glu³⁶Arg²⁶,³⁴Lys³⁷-(GAB-GTet)-GLP-1(7-37); Gly⁸Glu³⁷Arg²⁶,³⁴Lys³⁸-(GAB-GTet)-GLP-1(7-38); Gly⁸Glu³⁸Arg²⁶,³⁴Lys³⁹-(GAB-GTet)-GLP-1(7-39); Gly⁸Asp³⁵Arg²⁶,³⁴Lys³⁶-(GAB-GTet)-GLP-1(7-36); Gly⁸Asp³⁵Arg²⁶,³⁴Lys³⁶ (GAB-GTet)-GLP-1(7-3)amide; Gly⁸Asp³⁶Arg²⁶,³⁴Lys³⁷-(GAB-GTet)-GLP-1(7-37); Gly⁸Asp³⁷Arg²⁶,³⁴Lys³⁸-(GAB-GTet)-GLP-1(7-38); Gly⁸Asp³⁸Arg²⁶,³⁴Lys³⁹-(GAB-GTet)-GLP-1(7-39); Gly⁸Asp³⁵Arg²⁶,³⁴Lys³⁶-(GAB-GTet)-GLP-1(7-36); Gly⁸Asp³⁵Arg²⁶,³⁴Lys³⁶-(GAB-GTet)-GLP-1(7-36)amide; Gly⁸Asp³⁶Arg²⁶,³⁴Lys³⁷-(GAB-GTet)-GLP-1(7-37); Gly⁸Asp³⁷Arg²⁶,³⁴Lys³⁸-(GAB-GTet)-GLP-1(7-38); Gly⁸Asp³⁸Arg²⁶,³⁴Lys³⁹-(GAB-GTet)-GLP-1(7-39); Val⁸Glu³⁵Arg²⁶,³⁴Lys³⁶-(GAB-GTet)-GLP-1(7-36); Val⁸Glu³⁵Arg²⁶,³⁴Lys³⁶-(GAB-GTet)-GLP-1(7-36)amide; Val⁸Glu³⁶Arg²⁶,³⁴Lys³⁷-(GAB-GTet)-GLP-1(7-37); Val⁸Glu³⁷Arg²⁶,³⁴Lys³⁸-(GAB-GTet)-GLP-1(7-38); Val⁸Glu³⁸Arg²⁶,³⁴Lys³⁹-(GAB-GTet)-GLP-1(7-39); Val⁸Glu³⁵Arg²⁶,³⁴Lys³⁶-(GAB-GTet)-GLP-1(7-36); Val⁸Glu³⁵Arg²⁶,³⁴Lys³⁶-(GAB-GTet)-GLP-1(7-36)amide;

Val⁸Glu³⁶Arg²⁶,³⁴Lys³⁷-(GAB-GTet)-GLP-1(7-37);
Val⁸Glu³⁷Arg²⁶,³⁴Lys³⁸-(GAB-GTet)-GLP-1(7-38);
Val⁸Glu³⁸Arg²⁶,³⁴Lys³⁹-(GAB-GTet)-GLP-1(7-39);
Val⁸Asp³⁵Arg²⁶,³⁴Lys³⁶-(GAB-GTet)-GLP-1(7-36);
Val⁸Asp³⁵Arg²⁶,³⁴Lys³⁶-(GAB-GTet)-GLP-1(7-36)amide;
Val⁸Asp³⁶Arg²⁶,³⁴Lys³⁷-(GAB-GTet)-GLP-1(7-37);
Val⁸Asp³⁷Arg²⁶,³⁴Lys³⁸-(GAB-GTet)-GLP-1(7-38);
Val⁸Asp³⁸Arg²⁶,³⁴Lys³⁹-(GAB-GTet)-GLP-1(7-39);
Val⁸Asp³⁵Arg²⁶,³⁴Lys³⁶-(GAB-GTet)-GLP-1(7-36);
Val⁸Asp³⁵Arg²⁶,³⁴Lys³⁸(GAB-GTet)-GLP-1(7-36)amide;
Val⁸Asp³⁶Arg²⁶,³⁴Lys³⁷-(GAB-GTet)-GLP-1(7-37);
Val⁸Asp³⁷Arg²⁶,³⁴Lys³⁸-(GAB-GTet)-GLP-1(7-38);
Val⁸Asp³⁸Arg²⁶,³⁴Lys³⁹-(GAB-GTet)-GLP-1(7-39);
Ser⁸Glu³⁵Arg²⁶,³⁴Lys³⁶-(GAB-GTet)-GLP-1(7-36);
Ser⁸Glu³⁵Arg²⁶,³⁴Lys³⁶-(GAB-GTet)-GLP-1(7-36)amide;
Ser⁸Glu³⁶Arg²⁶,³⁴Lys³⁷-(GAB-GTet)-GLP-1(7-37);
Ser⁸Glu³⁷Arg²⁶,³⁴Lys³⁸-(GAB-GTet)-GLP-1(7-38);
Ser⁸Glu³⁸Arg²⁶,³⁴Lys³⁹-(GAB-GTet)-GLP-1(7-39);
Ser⁸Glu³⁵Arg²⁶,³⁴Lys³⁶-(GAB-GTet)-GLP-1(7-36); Ser$^b$Glu³⁵Arg²⁶,³⁴Lys³⁶-(GAB-GTet)-GLP-1(7-36)amide;
Ser⁸Glu³⁶Arg²⁶,³⁴Lys³⁷-(GAB-GTet)-GLP-1(7-37);
Ser⁸Glu³⁷Arg²⁶,³⁴Lys³⁸-(GAB-GTet)-GLP-1(7-38);
Ser⁸Glu³⁸Arg²⁶,³⁴Lys³⁹-(GAB-GTet)-GLP-1(7-39);
Ser⁸Asp³⁵Arg²⁶,³⁴Lys³⁶-(GAB-GTet)-GLP-1(7-36);
Ser⁸Asp³⁵Arg²⁶,³⁴Lys³⁶-(GAB-GTet)-GLP-1(7-36)amide;
Ser⁸Asp³⁶Arg²⁶,³⁴Lys³⁷-(GAB-GTet)-GLP-1(7-37);
Ser⁸Asp³⁷Arg²⁶,³⁴Lys³⁸-(GAB-GTet)-GLP-1(7-38);
Ser⁸Asp³⁸Arg²⁶,³⁴Lys³⁹-(GAB-GTet)-GLP-1(7-39);
Ser⁸Asp³⁵Arg²⁶,³⁴Lys³⁶-(GAB-GTet)-GLP-1(7-36);
Ser⁸Asp³⁵Arg²⁶,³⁴Lys³⁶-(GAB-GTet)-GLP-1(7-36)amide;
Ser⁸Asp³⁶Arg²⁶,³⁴Lys³⁷-(GAB-GTet)-GLP-1(7-37);
Ser⁸Asp³⁷Arg²⁶,³⁴Lys³⁸-(GAB-GTet)-GLP-1(7-38);
Ser⁸Asp³⁸Arg²⁶,³⁴Lys³⁹-(GAB-GTet)-GLP-1(7-39);
Thr⁸Glu³⁵Arg²⁶,³⁴Lys³⁶-(GAB-GTet)-GLP-1(7-36);
Thr⁸Glu³⁵Arg²⁶,³⁴Lys³⁶-(GAB-GTet)-GLP-1(7-36)amide;
Thr⁸Glu³⁶Arg²⁶,³⁴Lys³⁷-(GAB-GTet)-GLP-1(7-37);
Thr⁸Glu³⁷Arg²⁶,³⁴Lys³⁸-(GAB-GTet)-GLP-1(7-38);
Thr⁸Glu³⁸Arg²⁶,³⁴Lys³⁹-(GAB-GTet)-GLP-1(7-39);
Thr⁸Glu³⁵Arg²⁶,³⁴Lys³⁶-(GAB-GTet)-GLP-1(7-36);
Thr⁸Glu³⁵Arg²⁶,³⁴Lys³⁶-(GAB-GTet)-GLP-1(7-36)amide;
Thr⁸Glu³⁶Arg²⁶,³⁴Lys³⁷-(GAB-GTet)-GLP-1(7-37);
Thr⁸Glu³⁷Arg²⁶,³⁴Lys³⁸-(GAB-GTet)-GLP-1(7-38);
Thr⁸Glu³⁸Arg²⁶,³⁴Lys³⁹-(GAB-GTet)-GLP-1(7-39);
Thr⁸Asp³⁵Arg²⁶,³⁴Lys³⁶-(GAB-GTet)-GLP-1(7-36);
Thr⁸Asp³⁵Arg²⁶,³⁴Lys³⁶-(GAB-GTet)-GLP-1(7-36)amide;
Thr⁸Asp³⁶Arg²⁶,³⁴Lys³⁷-(GAB-GTet)-GLP-1(7-37);
Thr⁸Asp³⁷Arg²⁶,³⁴Lys³⁸-(GAB-GTet)-GLP-1(7-38);
Thr⁸Asp³⁸Arg²⁶,³⁴Lys³⁹-(GAB-GTet)-GLP-1(7-39);
Thr⁸Asp³⁵Arg²⁶,³⁴Lys³⁶-(GAB-GTet)-GLP-1(7-36);
Thr⁸Asp³⁵Arg²⁶,³⁴Lys³⁶-(GAB-GTet)-GLP-1(7-36)amide;
Thr⁸Asp³⁶Arg²⁶,³⁴Lys³⁷-(GAB-GTet)-GLP-1(7-37);
Thr⁸Asp³⁷Arg²⁶,³⁴Lys³⁸-(GAB-GTet)-GLP-1(7-38);
Thr⁸Asp³⁸Arg²⁶,³⁴Lys³⁹-(GAB-GTet)-GLP-1(7-39);
Arg²⁶,³⁴Lys¹⁸-(GAB-GTet)-GLP-1(7-36); Arg²⁶,³⁴Lys¹⁸-(GAB GTet)GLP-1(7-36amide; Arg²⁶,³⁴Lys¹⁸-(GAB-GTet)-GLP-1(7-37); Arg²⁶,³⁴Lys¹⁸-(GAB-GTet)-GLP-1(7-38);
Gly⁸Asp¹⁹Arg²⁶,³⁴Lys¹⁸-(GAB-GTet)-GLP-1(7-36);
Gly⁸Asp¹⁷Arg²⁶,³⁴Lys¹⁸-(GAB-GTet)-GLP-1(7-36);
Gly⁸Asp¹⁹Arg²⁶,³⁴Lys¹⁸-(GAB-GTet)-GLP-1(7-36)amide;
Gly⁸Asp¹⁷Arg²⁶,³⁴Lys¹⁸-(GAB-GTet)-GLP-1(7-36)amide;
Gly⁸Asp¹⁹Arg²⁶,³⁴Lys¹⁸-(GAB-GTet)-GLP-1(7-37);
Gly⁸Asp¹⁹Arg²⁶,³⁴Lys¹⁸-(GAB-GTet)-GLP-1(7-38);
Gly⁸Asp¹⁷Arg²⁶,³⁴Lys¹⁸-(GAB-GTet)-GLP-1(7-38);
Arg²⁶,³⁴Lys²³-(GAB-GTet)-GLP-1(7-36); Arg²⁶,³⁴Lys²³-(GAB-GTet)-GLP-1(7-36)amide; Arg²⁶,³⁴Lys²³-(GAB-GTet)-GLP-1(7-37); Arg²⁶,³⁴Lys²³-(GAB-GTet)-GLP-1(7-38); Gly⁸Asp¹⁹Arg²⁶,³⁴Lys²³-(GAB-GTet)-GLP-1(7-36);
Gly⁸Asp¹⁷Arg²⁶,³⁴Lys²³-(GAB-GTet)-GLP-1(7-36);
Gly⁸Asp¹⁹Arg²⁶,³⁴Lys²³-(GAB-GTet)-GLP-1(7-36)amide;
Gly⁸Asp¹⁷Arg²⁶,³⁴Lys²³-(GAB-GTet)-GLP-1(7-36)amide;
Gly⁸Asp¹⁹Arg²⁶,³⁴Lys²³-(GAB-GTet)-GLP-1(7-37);
Gly⁸Asp¹⁹Arg²⁶,³⁴Lys²³-(GAB-GTet)-GLP-1(7-38);
Gly⁸Asp¹⁷Arg²⁶,³⁴Lys²³-(GAB-GTet)-GLP-1(7-38);
Arg²⁶,³⁴Lys²⁷-(GAB-GTet)-GLP-1(7-36); Arg²⁶,³⁴Lys²⁷-(GAB-GTet)-GLP-1(7-36)amide; Arg²⁶,³⁴Lys²⁷-(GAB-GTet)-GLP-1(7-37); Arg²⁶,³⁴Lys²⁷-(GAB-GTet)-GLP-1(7-38); Gly⁸Asp¹⁹Arg²⁶,³⁴Lys²⁷-(GAB-GTet)-GLP-1(7-36);
Gly⁸Asp¹⁷Arg²⁶,³⁴Lys²⁷-(GAB-GTet)-GLP-1(7-36);
Gly⁸Asp¹⁹Arg²⁶,³⁴Lys²⁷-(GAB-GTet)-GLP-1(7-36)amide;
Gly⁸Asp¹⁷Arg²⁶,³⁴Lys²⁷-(GAB-GTet)-GLP-1(7-36)amide;
Gly⁸Asp¹⁹Arg²⁶,³⁴Lys²⁷-(GAB-GTet)-GLP-1(7-37);
Gly⁸Asp¹⁹Arg²⁶,³⁴Lys²⁷-(GAB-GTet)-GLP-1(7-38);
Gly⁸Asp¹⁷Arg²⁶,³⁴Lys²⁷-(GAB-GTet)-GLP-1(7-38);
Arg²⁶,³⁴Lys¹⁸-(GAB-GTet)-GLP-1(7-36); Arg²⁶,³⁴Lys¹⁸-(GAB-GTet)-GLP-1(7-36)amide; Arg²⁶,³⁴Lys¹⁸-(GAB-GTet)-GLP-1(7-37); Arg²⁶,³⁴Lys¹⁸-(GAB-GTet)-GLP-1(7-38); Val⁸Asp¹⁹Arg²⁶,³⁴Lys¹⁸-(GAB-GTet)-GLP-1(7-36);
Val⁸Asp¹⁷Arg²⁶,³⁴Lys¹⁸-(GAB-GTet)-GLP-1(7-36);
Val⁸Asp¹⁹Arg²⁶,³⁴Lys¹⁸-(GAB-GTet)-GLP-1(7-36)amide;
Val⁸Asp¹⁷Arg²⁶,³⁴Lys¹⁸-(GAB-GTet)-GLP-1(7-36)amide;
Val⁸Asp¹⁹Arg²⁶,³⁴Lys¹⁸-(GAB-GTet)-GLP-1(7-37);
Val⁸Asp¹⁹Arg²⁶,³⁴Lys¹⁸-(GAB-GTet)-GLP-1(7-38);
Val⁸Asp¹⁷Arg²⁶,³⁴Lys¹⁸-(GAB-GTet)-GLP-1(7-38);
Arg²⁶,³⁴Lys²³-(GAB-GTet)-GLP-1(7-36); Arg²⁶,³⁴Lys²³-(GAB-GTet)-GLP-1(7-36)amide; Arg²⁶,³⁴Lys²³-(GAB-GTet)-GLP-1(7-37); Arg²⁶,³⁴Lys²³-(GAB-GTet)-GLP-1(7-38); Val⁸Asp¹⁹Arg²⁶,³⁴Lys²³-(GAB-GTet)-GLP-1(7-36);
Val⁸Asp¹⁷Arg²⁶,³⁴Lys²³-(GAB-GTet)-GLP-1(7-36);
Val⁸Asp¹⁹Arg²⁶,³⁴Lys²³-(GAB-GTet)-GLP-1(7-36)amide;
Val⁸Asp¹⁷Arg²⁶,³⁴Lys²³-(GAB-GTet)-GLP-1(7-36)amide;
Val⁸Asp¹⁹Arg²⁶,³⁴Lys²³-(GAB-GTet)-GLP-1(7-37);
Val⁸Asp¹⁹Arg²⁶,³⁴Lys²³-(GAB-GTet)-GLP-1(7-38);
Val⁸Asp¹⁷Arg²⁶,³⁴Lys²³-(GAB-GTet)-GLP-1(7-38);
Arg²⁶,³⁴Lys²⁷-(GAB-GTet)-GLP-1(7-36); Arg²⁶,³⁴Lys²⁷-(GAB-GTet)-GLP-1(7-36)amide; Arg²⁶,³⁴Lys²⁷-(GAB-GTet)-GLP-1(7-37); Arg²⁶,³⁴Lys²⁷-(GAB-GTet)-GLP-1(7-38); Val⁸Asp¹⁹Arg²⁶,³⁴Lys²⁷-(GAB-GTet)-GLP-1(7-36);
Val⁸Asp¹⁷Arg²⁶,³⁴Lys²⁷-(GAB-GTet)-GLP-1(7-36);
Val⁸Asp¹⁹Arg²⁶,³⁴Lys²⁷-(GAB-GTet)-GLP-1(7-36)amide;
Val⁸Asp¹⁷Arg²⁶,³⁴Lys²⁷-(GAB-GTet)-GLP-1(7-36)amide;
Val⁸Asp¹⁹Arg²⁶,³⁴Lys²⁷-(GAB-GTet)-GLP-1(7-37);
Val⁸Asp¹⁹Arg²⁶,³⁴Lys²⁷-(GAB-GTet)-GLP-1(7-38);
Val⁸Asp¹⁷Arg²⁶,³⁴Lys²⁷-(GAB-GTet)-GLP-1(7-38);
Arg²⁶,³⁴Lys¹⁸-(GAB-GTet)-GLP-1(7-36); Arg²⁶,³⁴Lys¹⁸-(GAB-GTet)-GLP-1(7-36)amide; Arg²⁶,³⁴Lys¹⁸-(GAB-GTet)-GLP-1(7-37); Arg²⁶,³⁴Lys¹⁸-(GAB-GTet)-GLP-1(7-38); Ser⁸Asp¹⁹Arg²⁶,³⁴Lys¹⁸-(GAB-GTet)-GLP-1(7-36);
Ser⁸Asp¹⁷Arg²⁶,³⁴Lys¹⁸-(GAB-GTet)-GLP-1(7-36);
Ser⁸Asp¹⁹Arg²⁶,³⁴Lys¹⁸-(GAB-GTet)-GLP-1(7-36)amide;
Ser⁸Asp¹⁷Arg²⁶,³⁴Lys¹⁸-(GAB-GTet)-GLP-1(7-36)amide;
Ser⁸Asp¹⁹Arg²⁶,³⁴Lys¹⁸-(GAB-GTet)-GLP-1(7-37);
Ser⁸Asp¹⁹Arg²⁶,³⁴Lys¹⁸-(GAB-GTet)-GLP-1(7-38);
Ser⁸Asp¹⁷Arg²⁶,³⁴Lys¹⁸-(GAB-GTet)-GLP-1(7-38);
Arg²⁶,³⁴Lys²³-(GAB-GTet)-GLP-1(7-36); Arg²⁶,³⁴Lys²³-(GAB-GTet)-GLP-1(7-36)amide; Arg²⁶,³⁴Lys²³-(GAB-GTet)-GLP-1(7-37); Arg²⁶,³⁴Lys²³-(GAB-GTet)-GLP-1(7-38); Ser⁸Asp¹⁹Arg²⁶,³⁴Lys²³-(GAB-GTet)-GLP-1(7-36);
Ser⁸Asp¹⁷Arg²⁶,³⁴Lys²³-(GAB-GTet)-GLP-1(7-36);
Ser⁸Asp¹⁹Arg²⁶,³⁴Lys²³-(GAB-GTet)-GLP-1(7-36)amide;
Ser⁸Asp¹⁷Arg²⁶,³⁴Lys²³-(GAB-GTet)-GLP-1(7-36)amide;
Ser⁸Asp¹⁹Arg²⁶,³⁴Lys²³-(GAB-GTet)-GLP-1(7-37);
Ser⁸Asp¹⁹Arg²⁶,³⁴Lys²³-(GAB-GTet)-GLP-1(7-38);
Ser⁸Asp¹⁷Arg²⁶,³⁴Lys²³-(GAB-GTet)-GLP-1(7-38);

Arg$^{26,34}$Lys$^{27}$-(GAB-GTet)-GLP-1(7-36); Arg$^{26,34}$Lys$^{27}$-(GAB-GTet)-GLP-1(7-36)amide; Arg$^{26,34}$Lys$^{27}$-(GAB-GTet)-GLP-1(7-37); Arg$^{26,34}$Lys$^{27}$-(GAB-GTet)-GLP-1(7-38); Ser$^8$Asp$^{19}$Arg$^{26,34}$Lys$^{27}$-(GAB-GTet)-GLP-1(7-36); Ser$^8$Asp$^{17}$Arg$^{26,34}$Lys$^{27}$-(GAB-GTet)-GLP-1(7-36); Ser$^8$Asp$^{19}$Arg$^{26,34}$Lys$^{27}$-(GAB-GTet)-GLP-1(7-36)amide; Ser$^8$Asp$^{17}$Arg$^{26,34}$Lys$^{27}$-(GAB-GTet)-GLP-1(7-36)amide; Ser$^8$Asp$^{19}$Arg$^{26,34}$Lys$^{27}$-(GAB-GTet)-GLP-1(7-37); Ser$^8$Asp$^{19}$Arg$^{26,34}$Lys$^{27}$-(GAB-GTet)-GLP-1(7-38); Ser$^8$Asp$^{17}$Arg$^{26,34}$Lys$^{27}$-(GAB-GTet)-GLP-1(7-38); Arg$^{26,34}$Lys$^{18}$-(GAB-GTet)-GLP-1(7-36); Arg$^{26,34}$Lys$^{18}$-(GAB-GTet)-GLP-1(7-36)amide; Arg$^{26,34}$Lys$^{18}$-(GAB-GTet)-GLP-1(7-37); Arg$^{26,34}$Lys$^{18}$-(GAB-GTet)-GLP-1(7-38); Thr$^8$Asp$^{19}$Arg$^{26,34}$Lys$^{18}$-(GAB-GTet)-GLP-1(7-36); Thr$^8$Asp$^{17}$Arg$^{26,34}$Lys$^{18}$-(GAB-GTet)-GLP-1(7-36); Thr$^8$Asp$^{19}$Arg$^{26,34}$Lys$^{18}$-(GAB-GTet)-GLP-1(7-36)amide; Thr$^8$Asp$^{17}$Arg$^{26,34}$Lys$^{18}$-(GAB-GTet)-GLP-1(7-36)amide; Thr$^8$Asp$^{19}$Arg$^{26,34}$Lys$^{18}$-(GAB-GTet)-GLP-1(7-37); Thr$^8$Asp$^{19}$Arg$^{26,34}$Lys$^{18}$-(GAB-GTet)-GLP-1(7-38); Thr$^8$Asp$^{17}$Arg$^{26,34}$Lys$^{18}$-(GAB-GTet)-GLP-1(7-38); Arg$^{26,34}$Lys$^{23}$-(GAB-GTet)-GLP-1(7-36); Arg$^{26,34}$Lys$^{23}$-(GAB-GTet)-GLP-1(7-36)amide; Arg$^{26,34}$Lys$^{23}$-(GAB-GTet)-GLP-1(7-37); Arg$^{26,34}$Lys$^{23}$-(GAB-GTet)-GLP-1(7-38); Thr$^8$Asp$^{19}$Arg$^{26,34}$Lys$^{23}$-(GAB-GTet)-GLP-1(7-36); Thr$^8$Asp$^{17}$Arg$^{26,34}$Lys$^{23}$-(GAB-GTet)-GLP-1(7-36); Thr$^8$Asp$^{19}$Arg$^{26,34}$Lys$^{23}$-(GAB-GTet)-GLP-1(7-36)amide; Thr$^8$Asp$^{17}$Arg$^{26,34}$Lys$^{23}$-(GAB-GTet)-GLP-1(7-36)amide; Thr$^8$Asp$^{19}$Arg$^{26,34}$Lys$^{23}$-(GAB-GTet)-GLP-1(7-37); Thr$^8$Asp$^{19}$Arg$^{26,34}$Lys$^{23}$-(GAB-GTet)-GLP-1(7-38); Thr$^8$Asp$^{17}$Arg$^{26,34}$Lys$^{23}$-(GAB-GTet)-GLP-1(7-38); Arg$^{26,34}$Lys$^{27}$-(GAB-GTet)-GLP-1(7-36); Arg$^{26,34}$Lys$^{27}$-(GAB-GTet)-GLP-1(7-36)amide; Arg$^{26,34}$Lys$^{27}$-(GAB-GTet)-GLP-1(7-37); Arg$^{26,34}$Lys$^{27}$-(GAB-GTet)-GLP-1(7-38); Thr$^8$Asp$^{19}$Arg$^{26,34}$Lys$^{27}$-(GAB-GTet)-GLP-1(7-36); Thr$^8$Asp$^{17}$Arg$^{26,34}$Lys$^{27}$-(GAB-GTet)-GLP-1(7-36); Thr$^8$Asp$^{19}$Arg$^{26,34}$Lys$^{27}$-(GAB-GTet)-GLP-1(7-36)amide; Thr$^8$Asp$^{17}$Arg$^{26,34}$Lys$^{27}$-(GAB-GTet)-GLP-1(7-36)amide; Thr$^8$Asp$^{19}$Arg$^{26,34}$Lys$^{27}$-(GAB-GTet)-GLP-1(7-37); Thr$^8$Asp$^{19}$Arg$^{26,34}$Lys$^{27}$-(GAB-GTet)-GLP-1(7-38); Thr$^8$Asp$^{17}$Arg$^{26,34}$Lys$^{27}$-(GAB-GTet)-GLP-1(7-38); Arg$^{26}$Lys$^{34}$-(GAB-GHex)-GLP-1(7-36); Arg$^{34}$Lys$^{26}$-(GAB-GHex)-GLP-1(7-36); Arg$^{26,34}$Lys$^{36}$-(GAB-GHex)-GLP-1(7-36); Arg$^{26}$Lys$^{34}$-(GAB-GHex)-GLP-1(7-36)amide; Arg$^{34}$Lys$^{26}$-(GAB-GHex)-GLP-1(7-36)amide; Arg$^{26,34}$Lys$^{36}$-(GAB-GHex)-GLP-1(7-36)amide; Arg$^{26}$Lys$^{34}$-(GAB-GHex)-GLP-1(7-37); Arg$^{34}$Lys$^{26}$-(GAB-GHex)-GLP-1(7-37); Arg$^{26,34}$Lys$^{36}$-(GAB-GHex)-GLP-1(7-37); Arg$^{26}$Lys$^{34}$-(GAB-GHex)-GLP-1(7-38); Arg$^{34}$Lys$^{26}$-(GAB-GHex)-GLP-1(7-38); Arg$^{26,34}$Lys$^{38}$-(GAB-GHex)-GLP-1(7-38); Arg$^{26}$Lys$^{34}$-(GAB-GHex)-GLP-1(7-39); Arg$^{34}$Lys$^{26}$-(GAB-GHex)-GLP-1(7-39); Arg$^{26,34}$Lys$^{39}$-(GAB-GHex)-GLP-1(7-39); Gly$^8$Arg$^{26}$Lys$^{34}$-(GAB-GHex)-GLP-1(7-36); Gly$^8$Arg$^{34}$Lys$^{26}$-(GAB-GHex)-GLP-1(7-36); Gly$^8$Arg$^{26,34}$Lys$^{36}$-(GAB-GHex)-GLP-1(7-36); Gly$^8$Arg$^{26}$Lys$^{34}$-(GAB-GHex)-GLP-1(7-36)amide; Gly$^8$Arg$^{34}$Lys$^{26}$-(GAB-GHex)-GLP-1(7-36)amide; Gly$^8$Arg$^{26,34}$Lys$^{36}$-(GAB-GHex)-GLP-1(7-36)amide; Gly$^8$Arg$^{26}$Lys$^{34}$-(GAB-GHex)-GLP-1(7-37); Gly$^8$Arg$^{34}$Lys$^{26}$-(GAB-GHex)-GLP-1(7-37); Gly$^8$Arg$^{26,34}$Lys$^{36}$-(GAB-GHex)-GLP-1(7-37); Gly$^8$Arg$^{26}$Lys$^{34}$-(GAB-GHex)-GLP-1(7-38); Gly$^8$Arg$^{34}$Lys$^{26}$-(GAB-GHex)-GLP-1(7-38); Gly$^8$Arg$^{26,34}$Lys$^{38}$-(GAB-GHex)-GLP-1(7-38); Gly$^8$Arg$^{26}$Lys$^{34}$-(GAB-GHex)-GLP-1(7-39); Gly$^1$Arg$^{34}$Lys$^{26}$-(GAB-GHex)-GLP-1(7-39); Gly$^8$Arg$^{26,34}$Lys$^{39}$-(GAB-GHex)-GLP-1(7-39); Val$^8$Arg$^{26}$Lys$^{34}$-(GAB-GHex)-GLP-1(7-36); Val$^8$Arg$^{34}$Lys$^{26}$-(GAB-GHex)-GLP-1(7-36); Val$^8$Arg$^{26,34}$Lys$^{36}$-(GAB-GHex)-GLP-1(7-36); Val$^8$Arg$^{26}$Lys$^{34}$-(GAB-GHex)-GLP-1(7-36)amide; Val$^8$Arg$^{34}$Lys$^{26}$-(GAB-GHex)-GLP-1(7-36)amide; Val$^8$Arg$^{26,34}$Lys$^{36}$-(GAB-GHex)-GLP-1(7-36)amide; Val$^8$Arg$^{26}$Lys$^{34}$-(GAB-GHex)-GLP-1(7-37); Val$^8$Arg$^{34}$Lys$^{26}$-(GAB-GHex)-GLP-1(7-37); Val$^8$Arg$^{26,34}$Lys$^{36}$-(GAB-GHex)-GLP-1(7-37); Val$^8$Arg$^{26}$Lys$^{34}$-(GAB-GHex)-GLP-1(7-38); Val$^8$Arg$^{34}$Lys$^{26}$-(GAB-GHex)-GLP-1(7-38); Val$^8$Arg$^{26,34}$Lys$^{38}$-(GAB-GHex)-GLP-1(7-38); Val$^8$Arg$^{26}$Lys$^{34}$-(GAB-GHex)-GLP-1(7-39); Val$^8$Arg$^{34}$Lys$^{26}$-(GAB-GHex)-GLP-1(7-39); Val$^8$Arg$^{26,34}$Lys$^{39}$-(GAB-GHex)-GLP-1(7-39); Ser$^8$Arg$^{26}$Lys$^{34}$-(GAB-GHex)-GLP-1(7-36); Ser$^8$Arg$^{34}$Lys$^{26}$-(GAB-GHex)-GLP-1(7-36); Ser$^8$Arg$^{26,34}$Lys$^{36}$-(GAB-GHex)-GLP-1(7-36); Ser$^8$Arg$^{26}$Lys$^{34}$-(GAB-GHex)-GLP-1(7-36)amide; Ser$^8$Arg$^{34}$Lys$^{26}$-(GAB-GHex)-GLP-1(7-36)amide; Ser$^8$Arg$^{26,34}$Lys$^{36}$-(GAB-GHex)-GLP-1(7-36)amide; Ser$^8$Arg$^{26}$Lys$^{34}$-(GAB-GHex)-GLP-1(7-37); Ser$^8$Arg$^{34}$Lys$^{26}$-(GAB-GHex)-GLP-1(7-37); Ser$^8$Arg$^{26,34}$Lys$^{36}$-(GAB-GHex)-GLP-1(7-37); Ser$^8$Arg$^{26}$Lys$^{34}$-(GAB-GHex)-GLP-1(7-38); Ser$^8$Arg$^{34}$Lys$^{26}$-(GAB-GHex)-GLP-1(7-38); Ser$^8$Arg$^{26,34}$Lys$^{38}$-(GAB-GHex)-GLP-1(7-38); Ser$^8$Arg$^{26}$Lys$^{34}$-(GAB-GHex)-GLP-1(7-39); Ser$^8$Arg$^{34}$Lys$^{26}$-(GAB-GHex)-GLP-1(7-39); Ser$^8$Arg$^{26,34}$Lys$^{39}$-(GAB-GHex)-GLP-1(7-39); Thr$^8$Arg$^{26}$Lys$^{34}$-(GAB-GHex)-GLP-1(7-36); Thr$^8$Arg$^{34}$Lys$^{26}$-(GAB-GHex)-GLP-1(7-36); Thr$^8$Arg$^{26,34}$Lys$^{36}$-(GAB-GHex)-GLP-1(7-36); Thr$^8$Arg$^{26}$Lys$^{34}$-(GAB-GHex)-GLP-1(7-36)amide; Thr$^8$Arg$^{34}$Lys$^{26}$-(GAB-GHex)-GLP-1(7-36)amide; Thr$^8$Arg$^{26,34}$Lys$^{36}$-(GAB-GHex)-GLP-1(7-36)amide; Thr$^8$Arg$^{26}$Lys$^{34}$-(GAB-GHex)-GLP-1(7-37); Thr$^8$Arg$^{34}$Lys$^{26}$-(GAB-GHex)-GLP-1(7-37); Thr$^8$Arg$^{26,34}$Lys$^{36}$-(GAB-GHex)-GLP-1(7-37); Thr$^8$Arg$^{26}$Lys$^{34}$-(GAB-GHex)-GLP-1(7-38); Thr$^8$Arg$^{34}$Lys$^{26}$-(GAB-GHex)-GLP-1(7-38); Thr$^8$Arg$^{26,34}$Lys$^{38}$-(GAB-GHex)-GLP-1(7-38); Thr$^8$Arg$^{26}$Lys$^{34}$-(GAB-GHex)-GLP-1(7-39); Thr$^8$Arg$^{34}$Lys$^{26}$-(GAB-GHex)-GLP-1(7-39); Thr$^8$Arg$^{26,34}$Lys$^{39}$-(GAB-GHex)-GLP-1(7-39); Gly$^8$Glu$^{35}$Arg$^{26,34}$Lys$^{36}$-(GAB-GHex)-GLP-1(7-36); Gly$^8$Glu$^{35}$Arg$^{26,34}$Lys$^{36}$-(GAB-GHex)-GLP-1(7-36)amide; Gly$^8$Glu$^{36}$Arg$^{26,34}$Lys$^{37}$-(GAB-GHex)-GLP-1(7-37); Gly$^8$Glu$^{37}$Arg$^{26,34}$Lys$^{38}$-(GAB-GHex)-GLP-1(7-38); Gly$^8$Glu$^{38}$Arg$^{26,34}$Lys$^{39}$-(GAB-GHex)-GLP-1(7-39); Gly$^8$Glu$^{35}$Arg$^{26,34}$Lys$^{36}$-(GAB-GHex)-GLP-1(7-36); Gly$^8$Glu$^{35}$Arg$^{26,34}$Lys$^{36}$-(GAB-GHex)-GLP-1(7-36)amide; Gly$^8$Glu$^{36}$Arg$^{26,34}$Lys$^{37}$-(GAB-GHex)-GLP-1(7-37); Gly$^8$Glu$^{37}$Arg$^{26,34}$Lys$^{38}$-(GAB-GHex)-GLP-1(7-38); Gly$^8$Glu$^{38}$Arg$^{26,34}$Lys$^{39}$-(GAB-GHex)-GLP-1(7-39); Gly$^8$Asp$^{35}$Arg$^{26,34}$Lys$^{36}$-(GAB-GHex)-GLP-1(7-36); Gly$^8$Asp$^{35}$Arg$^{26,34}$Lys$^{36}$-(GAB-GHex)-GLP-1(7-36)amide; Gly$^8$Asp$^{36}$Arg$^{26,34}$Lys$^{37}$-(GAB-GHex)-GLP-1(7-37); Gly$^8$Asp$^{37}$Arg$^{26,34}$Lys$^{38}$-(GAB-GHex)-GLP-1(7-38); Gly$^8$Asp$^{38}$Arg$^{26,34}$Lys$^{39}$-(GAB-GHex)-GLP-1(7-39); Gly$^8$Asp$^{35}$Arg$^{26,34}$Lys$^{36}$-(GAB-GHex)-GLP-1(7-36); Gly$^8$Asp$^{35}$Arg$^{26,34}$Lys$^{36}$-(GAB-GHex)-GLP-1(7-36)amide; Gly$^8$Asp$^{36}$Arg$^{26,34}$Lys$^{37}$-(GAB-GHex)-GLP-1(7-37); Gly$^8$Asp$^{37}$Arg$^{26,34}$Lys$^{38}$-(GAB-GHex)-GLP-1(7-38); Gly$^8$Asp$^{38}$Arg$^{26,34}$Lys$^{39}$-(GAB-GHex)-GLP-1(7-39); Val$^8$Glu$^{35}$Arg$^{26,34}$Lys$^{36}$-(GAB-GHex)-GLP-1(7-36); Val$^8$Glu$^{35}$Arg$^{26,34}$Lys$^{36}$-(GAB-GHex)-GLP-1(7-36)amide; Val$^8$Glu$^{36}$Arg$^{26,34}$Lys$^{37}$-(GAB-GHex)-GLP-1(7-37); Val$^8$Glu$^{37}$Arg$^{26,34}$Lys$^{38}$-(GAB-GHex)-GLP-1(7-38); Val$^8$Glu$^{38}$Arg$^{26,34}$Lys$^{39}$-(GAB-GHex)-GLP-1(7-39);

Val⁸Glu³⁵Arg²⁶,³⁴Lys³⁶-(GAB-GHex)-GLP-1(7-36);
Val⁸Glu³⁵Arg²⁶,³⁴Lys³⁶-(GAB-GHex)-GLP-1(7-36)amide;
Val⁸Glu³⁶Arg²⁶,³⁴Lys³⁷-(GAB-GHex)-GLP-1(7-37);
Val⁸Glu³⁷Arg²⁶,³⁴Lys³⁸-(GAB-GHex)-GLP-1(7-38);
Val⁸Glu³⁸Arg²⁶,³⁴Lys³⁹-(GAB-GHex)-GLP-1(7-39);
Val⁸Asp³⁵Arg²⁶,³⁴Lys³⁶-(GAB-GHex)-GLP-1(7-36);
Val⁸Asp³⁵Arg²⁶,³⁴Lys³⁶-(GAB-GHex)-GLP-1(7-36)amide;
Val⁸Asp³⁶Arg²⁶,³⁴Lys³⁷-(GAB-GHex)-GLP-1(7-37);
Val⁸Asp³⁷Arg²⁶,³⁴Lys³⁸-(GAB-GHex)-GLP-1(7-38);
Val⁸Asp³⁸Arg²⁶,³⁴Lys³⁹-(GAB-GHex)-GLP-1(7-39);
Val⁸Asp³⁵Arg²⁶,³⁴Lys³⁶-(GAB-GHex)-GLP-1(7-36);
Val⁸Asp³⁵Arg²⁶,³⁴Lys³⁶-(GAB-GHex)-GLP-1(7-36)amide;
Val⁸Asp³⁶Arg²⁶,³⁴Lys³⁷-(GAB-GHex)-GLP-1(7-37);
Val⁸Asp³⁷Arg²⁶,³⁴Lys³⁸-(GAB-GHex)-GLP-1(7-38);
Val⁸Asp³⁸Arg²⁶,³⁴Lys³⁹-(GAB-GHex)-GLP-1(7-39);
Ser⁸Glu³⁵Arg²⁶,³⁴Lys³⁶-(GAB-GHex)-GLP-1(7-36);
Ser⁸Glu³⁵Arg²⁶,³⁴Lys³⁶-(GAB-GHex)-GLP-1(7-36)amide;
Ser⁸Glu³⁶Arg²⁶,³⁴Lys³⁷-(GAB-GHex)-GLP-1(7-37);
Ser⁸Glu³⁷Arg²⁶,³⁴Lys³⁸ (GAB-GHex)-GLP-1(7-38);
Ser⁸Glu³⁸Arg²⁶,³⁴Lys³⁹-(GAB-GHex)-GLP-1(7-39);
Ser⁸Glu³⁵Arg²⁶,³⁴Lys³⁶-(GAB-GHex)-GLP-1(7-36);
Ser⁸Glu³⁵Arg²⁶,³⁴Lys³⁶-(GAB-GHex)-GLP-1(7-36)amide;
Ser⁸Glu³⁶Arg²⁶,³⁴Lys³⁷-(GAB-GHex)-GLP-1(7-37);
Ser⁸Glu³⁷Arg²⁶,³⁴Lys³⁸-(GAB-GHex)-GLP-1(7-38);
Ser⁸Glu³⁸Arg²⁶,³⁴Lys³⁹-(GAB-GHex)-GLP-1(7-39);
Ser⁸Asp³⁵Arg²⁶,³⁴Lys³⁶-(GAB-GHex)-GLP-1(7-36);
Ser⁸Asp³⁵Arg²⁶,³⁴Lys³⁶-(GAB-GHex)-GLP-1(7-36)amide;
Ser⁸Asp³⁶Arg²⁶,³⁴Lys³⁷-(GAB-GHex)-GLP-1(7-37);
Ser⁸Asp³⁷Arg²⁶,³⁴Lys³⁸-(GAB-GHex)-GLP-1(7-38);
Ser⁸Asp³⁸Arg²⁶,³⁴Lys³⁹-(GAB-GHex)-GLP-1(7-39);
Ser⁸Asp³⁵Arg²⁶,³⁴Lys³⁶-(GAB-GHex)-GLP-1(7-36);
Ser⁸Asp³⁵Arg²⁶,³⁴Lys³⁶-(GAB-GHex)-GLP-1(7-36)amide;
Ser⁸Asp³⁶Arg²⁶,³⁴Lys³⁷ (GAB-GHex)-GLP-1(7-37);
Ser⁸Asp³⁷Arg²⁶,³⁴Lys³⁸-(GAB-GHex)-GLP-1(7-38);
Ser⁸Asp³⁸Arg²⁶,³⁴Lys³⁹-(GAB-GHex)-GLP-1(7-39);
Thr⁸Glu³⁵Arg²⁶,³⁴Lys³⁶-(GAB-GHex)-GLP-1(7-36);
Thr⁸Glu³⁵Arg²⁶,³⁴Lys³⁶-(GAB-GHex)-GLP-1(7-36)amide;
Thr⁸Glu³⁶Arg²⁶,³⁴Lys³⁷-(GAB-GHex)-GLP-1(7-37);
Thr⁸Glu³⁷Arg²⁶,³⁴Lys³⁸-(GAB-GHex)-GLP-1(7-38);
Thr⁸Glu³⁸Arg²⁶,³⁴Lys³⁹-(GAB-GHex)-GLP-1(7-39);
Thr⁸Glu³⁵Arg²⁶,³⁴Lys³⁶-(GAB-GHex)-GLP-1(7-36);
Thr⁸Glu³⁵Arg²⁶,³⁴Lys³⁶-(GAB-GHex)-GLP-1(7-36)amide;
Thr⁸Glu³⁶Arg²⁶,³⁴Lys³⁷-(GAB-GHex)-GLP-1(7-37);
Thr⁸Glu³⁷Arg²⁶,³⁴Lys³⁸-(GAB-GHex)-GLP-1(7-38);
Thr⁸Glu³⁸Arg²⁶,³⁴Lys³⁹-(GAB-GHex)-GLP-1(7-39);
Thr⁸Asp³⁵Arg²⁶,³⁴Lys³⁶-(GAB-GHex)-GLP-1(7-36);
Thr⁸Asp³⁵Arg²⁶,³⁴Lys³⁶-(GAB-GHex)-GLP-1(7-36)amide;
Thr⁸Asp³⁶Arg²⁶,³⁴Lys³⁷-(GAB-GHex)-GLP-1(7-37);
Thr⁸Asp³⁷Arg²⁶,³⁴Lys³⁸-(GAB-GHex)-GLP-1(7-38);
Thr⁸Asp³⁸Arg²⁶,³⁴Lys³⁹-(GAB-GHex)-GLP-1(7-39);
Thr⁸Asp³⁵Arg²⁶,³⁴Lys³⁶-(GAB-GHex)-GLP-1(7-36);
Thr⁸Asp³⁵Arg²⁶,³⁴Lys³⁶-(GAB-GHex)-GLP-1(7-36)amide;
Thr⁸Asp³⁶Arg²⁶,³⁴Lys³⁷-(GAB-GHex)-GLP-1(7-37);
Thr⁸Asp³⁷Arg²⁶,³⁴Lys³⁸-(GAB-GHex)-GLP-1(7-38);
Thr⁸Asp³⁸Arg²⁶,³⁴Lys³⁹-(GAB-GHex)-GLP-1(7-39);
Arg²⁶,³⁴Lys¹⁸-(GAB-GHex)-GLP-1(7-36); Arg²⁶,³⁴Lys¹⁸-(GAB-GHex)-GLP-1(7-36)amide; Arg²⁶,³⁴Lys¹⁸-(GAB-GHex)-GLP-1(7-37); Arg²⁶,³⁴Lys¹⁸-(GAB-GHex)-GLP-1(7-38); Gly⁸Asp¹⁹Arg²⁶,³⁴Lys¹⁸-(GAB-GHex)-GLP-1(7-36); Gly⁸Asp¹⁷Arg²⁶,³⁴Lys¹⁸-(GAB-GHex)-GLP-1(7-36); Gly⁸Asp¹⁹Arg²⁶,³⁴Lys¹⁸-(GAB-GHex)-GLP-1(7-36)amide; Gly⁸Asp¹⁷Arg²⁶,³⁴Lys¹⁸-(GAB-GHex)-GLP-1(7-36)amide; Gly⁸Asp¹⁹Arg²⁶,³⁴Lys¹⁸-(GAB-GHex)-GLP-1(7-37); Gly⁸Asp¹⁷Arg²⁶,³⁴Lys¹⁸-(GAB-GHex)-GLP-1(7-38); Arg²⁶,³⁴Lys²³-(GAB-GHex)-GLP-1(7-36); Arg²⁶,³⁴Lys²³-(GAB-GHex)-GLP-1(7-36)amide; Arg²⁶,³⁴Lys²³-(GAB-GHex)-GLP-1(7-37); Arg²⁶,³⁴Lys²³-(GAB-GHex)-GLP-1(7-38); Gly⁸Asp¹⁹Arg²⁶,³⁴Lys²³-(GAB-GHex)-GLP-1(7-36); Gly⁸Asp¹⁷Arg²⁶,³⁴Lys²³-(GAB-GHex)-GLP-1(7-36); Gly⁸Asp¹⁹Arg²⁶,³⁴Lys²³-(GAB-GHex)-GLP-1(7-36)amide; Gly⁸Asp¹⁷Arg²⁶,³⁴Lys²³-(GAB-GHex)-GLP-1(7-36)amide; Gly⁸Asp¹⁹Arg²⁶,³⁴Lys²³-(GAB-GHex)-GLP-1(7-37); Gly⁸Asp¹⁹Arg²⁶,³⁴Lys²³-(GAB-GHex)-GLP-1(7-38); Gly⁸Asp¹⁷Arg²⁶,³⁴Lys²³-(GAB-GHex)-GLP-1(7-38); Arg²⁶,³⁴Lys²⁷-(GAB-GHex)-GLP-1(7-36); Arg²⁶,³⁴Lys²⁷-(GAB-GHex)-GLP-1(7-36)amide; Arg²⁶,³⁴Lys²⁷-(GAB-GHex)-GLP-1(7-37); Arg²⁶,³⁴Lys²⁷-(GAB-GHex)-GLP-1(7-38); Gly⁸Asp¹⁹Arg²⁶,³⁴Lys²⁷-(GAB-GHex)-GLP-1(7-36); Gly⁸Asp¹⁷Arg²⁶,³⁴Lys²⁷-(GAB-GHex)-GLP-1(7-36); Gly⁸Asp¹⁹Arg²⁶,³⁴Lys²⁷-(GAB-GHex)-GLP-1(7-36)amide; Gly⁸Asp¹⁷Arg²⁶,³⁴Lys²⁷-(GAB-GHex)-GLP-1(7-36)amide; Gly⁸Asp¹⁹Arg²⁶,³⁴Lys²⁷-(GAB-GHex)-GLP-1(7-37); Gly⁸Asp¹⁹Arg²⁶,³⁴Lys²⁷-(GAB-GHex)-GLP-1(7-38); Gly⁸Asp¹⁷Arg²⁶,³⁴Lys²⁷-(GAB-GHex)-GLP-1(7-38); Arg²⁶,³⁴Lys¹⁸-(GAB-GHex)-GLP-1(7-36); Arg²⁶,³⁴Lys¹⁸-(GAB-GHex)-GLP-1(7-36)amide; Arg²⁶,³⁴Lys¹⁸-(GAB-GHex)-GLP-1(7-37); Arg²⁶,³⁴Lys¹⁸-(GAB-GHex)-GLP-1(7-38); Val⁸Asp¹⁹Arg²⁶,³⁴Lys¹⁸-(GAB-GHex)-GLP-1(7-36); Val⁸Asp¹⁷Arg²⁶,³⁴Lys¹⁸-(GAB-GHex)-GLP-1(7-36); Val⁸Asp¹⁹Arg²⁶,³⁴Lys¹⁸-(GAB-GHex)-GLP-1(7-36)amide; Val⁸Asp¹⁷Arg²⁶,³⁴Lys¹⁸-(GAB-GHex)-GLP-1(7-36)amide; Val⁸Asp¹⁹Arg²⁶,³⁴Lys¹⁸-(GAB-GHex)-GLP-1(7-37); Val⁸Asp¹⁹Arg²⁶,³⁴Lys¹⁸-(GAB-GHex)-GLP-1(7-38); Val⁸Asp¹⁷Arg²⁶,³⁴Lys¹⁸-(GAB-GHex)-GLP-1(7-38); Arg²⁶,³⁴Lys²³-(GAB-GHex)-GLP-1(7-36); Arg²⁶,³⁴Lys²³-(GAB-GHex)-GLP-1(7-36)amide; Arg²⁶,³⁴Lys²³-(GAB-GHex)-GLP-1(7-37); Arg²⁶,³⁴Lys²³-(GAB-GHex)-GLP-1(7-38); Val⁸Asp¹⁹Arg²⁶,³⁴Lys²³-(GAB-GHex)-GLP-1(7-36); Val⁸Asp¹⁷Arg²⁶,³⁴Lys²³-(GAB-GHex)-GLP-1(7-36); Val⁸Asp¹⁹Arg²⁶,³⁴Lys²³-(GAB-GHex)-GLP-1(7-36)amide; Val⁸Asp¹⁷Arg²⁶,³⁴Lys²³-(GAB-GHex)-GLP-1(7-36)amide; Val⁸Asp¹⁹Arg²⁶,³⁴Lys²³-(GAB-GHex)-GLP-1(7-37); Val⁸Asp¹⁹Arg²⁶,³⁴Lys²³-(GAB-GHex)-GLP-1(7-38); Val⁸Asp¹⁷Arg²⁶,³⁴Lys²³-(GAB-GHex)-GLP-1(7-38); Arg²⁶,³⁴Lys²⁷-(GAB-GHex)-GLP-1(7-36); Arg²⁶,³⁴Lys²⁷-(GAB-GHex)-GLP-1(7-36)amide; Arg²⁶,³⁴Lys²⁷-(GAB-GHex)-GLP-1(7-37); Arg²⁶,³⁴Lys²⁷-(GAB-GHex)-GLP-1(7-38); Val⁸Asp¹⁹Arg²⁶,³⁴Lys²⁷-(GAB-GHex)-GLP-1(7-36); Val⁸Asp¹⁷Arg²⁶,³⁴Lys²⁷-(GAB-GHex)-GLP-1(7-36); Val⁸Asp¹⁹Arg²⁶,³⁴Lys²⁷-(GAB-GHex)-GLP-1(7-36)amide; Val⁸Asp¹⁷Arg²⁶,³⁴Lys²⁷-(GAB-GHex)-GLP-1(7-36)amide; Val⁸Asp¹⁹Arg²⁶,³⁴Lys²⁷-(GAB-GHex)-GLP-1(7-37); Val⁸Asp¹⁹Arg²⁶,³⁴Lys²⁷-(GAB-GHex)-GLP-1(7-38); Val⁸Asp¹⁷Arg²⁶,³⁴Lys²⁷-(GAB-GHex)-GLP-1(7-38); Arg²⁶,³⁴Lys¹⁸-(GAB-GHex)-GLP-1(7-36); Arg²⁶,³⁴Lys¹⁸-(GAB-GHex)-GLP-1(7-36)amide; Arg²⁶,³⁴Lys¹⁸-(GAB-GHex)-GLP-1(7-37); Arg²⁶,³⁴Lys¹⁸-(GAB-GHex)-GLP-1(7-38); Ser⁸Asp⁹Arg²⁶,³⁴Lysˢ-(GAB-GHex)-GLP-1(7-36); Ser⁸Asp¹⁷Arg²⁶,³⁴Lys¹⁸-(GAB-GHex)-GLP-1(7-36); Ser⁸Asp¹⁹Arg²⁶,³⁴Lys¹⁸-(GAB-GHex)-GLP-1(7-36)amide; Ser⁸Asp¹⁷Arg²⁶,³⁴Lys¹⁸-(GAB-GHex)-GLP-1(7-36)amide; Ser⁸Asp¹⁹Arg²⁶,³⁴Lys¹⁸-(GAB-GHex)-GLP-1(7-37); Ser⁸Asp¹⁹Arg²⁶,³⁴Lys¹⁸-(GAB-GHex)-GLP-1(7-38); Ser⁸Asp¹⁷Arg²⁶,³⁴Lys¹⁸-(GAB-GHex)-GLP-1(7-38); Arg²⁶,³⁴Lys²³-(GAB-GHex)-GLP-1(7-36); Arg²⁶,³⁴Lys²³-(GAB-GHex)-GLP-1(7-36)amide; Arg²⁶,³⁴Lys²³-(GAB-GHex)-GLP-1(7-37); Arg²⁶,³⁴Lys²³-(GAB-GHex)-GLP-1(7-38); Ser⁸Asp¹⁹Arg²⁶,³⁴Lys²³-(GAB-GHex)-GLP-1(7-36); Ser⁸Asp¹⁷Arg²⁶,³⁴Lys²³-(GAB-GHex)-GLP-1(7-36); Ser⁸Asp¹⁹Arg²⁶,³⁴Lys²³-(GAB-GHex)-GLP-1(7-36)amide; Ser⁸Asp¹⁷Arg²⁶,³⁴Lys²³-(GAB-GHex)-GLP-1(7-36)amide; Ser⁸Asp¹⁹Arg²⁶,³⁴Lys²³ (GAB-GHex)-GLP-1(7-37);

Ser⁸Asp¹⁹Arg²⁶,³⁴Lys²³-(GAB-GHex)-GLP-1(7-38);
Ser⁸Asp¹⁷Arg²⁶,³⁴Lys²³-(GAB-GHex)-GLP-1(7-38);
Arg²⁶,³⁴Lys²⁷-(GAB-GHex)-GLP-1(7-36); Arg²⁶,³⁴Lys²⁷-(GAB-GHex)-GLP-1(7-36)amide; Arg²⁶,³⁴Lys²⁷-(GAB-GHex)-GLP-1(7-37); Arg²⁶,³⁴Lys²⁷-(GAB-GHex)-GLP-1(7-38); Ser⁸Asp¹⁹Arg²⁶,³⁴Lys²⁷-(GAB-GHex)-GLP-1(7-36); Ser⁸Asp¹⁷Arg²⁶,³⁴Lys²⁷-(GAB-GHex)-GLP-1(7-36); Ser⁸Asp¹⁹Arg²⁶,³⁴Lys²⁷-(GAB-GHex)-GLP-1(7-36)amide; Ser⁸Asp¹⁷Arg²⁶,³⁴Lys²⁷-(GAB-GHex)-GLP-1(7-36)amide; Ser⁸Asp¹⁹Arg²⁶,³⁴Lys²⁷-(GAB-GHex)-GLP-1(7-37); Ser⁸Asp¹⁹Arg²⁶,³⁴Lys²⁷-(GAB-GHex)-GLP-1(7-38); Ser⁸Asp¹⁷Arg²⁶,³⁴Lys²⁷-(GAB-GHex)-GLP-1(7-38); Arg²⁶,³⁴Lys¹⁸-(GAB-GHex)-GLP-1(7-36); Arg²⁶,³⁴Lys¹⁸-(GAB-GHex)-GLP-1(7-36)amide; Arg²⁶,³⁴Lys¹⁸-(GAB-GHex)-GLP-1(7-37); Arg²⁶,³⁴Lys¹⁸-(GAB-GHex)-GLP-1(7-38); Thr⁸Asp¹⁹Arg²⁶,³⁴Lys¹⁸-(GAB-GHex)-GLP-1(7-36); Thr⁸Asp¹⁷Arg²⁶,³⁴Lys¹⁸-(GAB-GHex)-GLP-1(7-36); Thr⁸Asp¹⁹Arg²⁶,³⁴Lys¹⁸-(GAB-GHex)-GLP-1(7-36)amide; Thr⁸Asp¹⁷Arg²⁶,³⁴Lys¹⁸-(GAB-GHex)-GLP-1(7-36)amide; Thr⁸Asp¹⁹Arg²⁶,³⁴Lys¹⁸-(GAB-GHex)-GLP-1(7-37); Thr⁸Asp¹⁹Arg²⁶,³⁴Lys¹⁸-(GAB-GHex)-GLP-1(7-38); Thr⁸Asp¹⁷Arg²⁶,³⁴Lys¹⁸-(GAB-GHex)-GLP-1(7-38); Arg²⁶,³⁴Lys²³-(GAB-GHex)-GLP-1(7-36); Arg²⁶,³⁴Lys²³-(GAB-GHex)-GLP-1(7-36)amide; Arg²⁶,³⁴Lys²³-(GAB-GHex)-GLP-1(7-37); Arg²⁶,³⁴Lys²³-(GAB-GHex)-GLP-1(7-38); Thr⁸Asp¹⁹Arg²⁶,³⁴Lys²³-(GAB-GHex)-GLP-1(7-36); Thr⁸Asp¹⁷Arg²⁶,³⁴Lys²³-(GAB-GHex)-GLP-1(7-36); Thr⁸Asp¹⁹Arg²⁶,³⁴Lys²³-(GAB-GHex)-GLP-1(7-36)amide; Thr⁸Asp¹⁷Arg²⁶,³⁴Lys²³-(GAB-GHex)-GLP-1(7-36)amide; Thr⁸Asp¹⁹Arg²⁶,³⁴Lys²³-(GAB-GHex)-GLP-1(7-37); Thr⁸Asp¹⁹Arg²⁶,³⁴Lys²³-(GAB-GHex)-GLP-1(7-38); Thr⁸Asp¹⁷Arg²⁶,³⁴Lys²³-(GAB-GHex)-GLP-1(7-38); Arg²⁶,³⁴Lys²⁷-(GAB-GHex)-GLP-1(7-36); Arg²⁶,³⁴Lys²⁷-(GAB-GHex)-GLP-1(7-36)amide; Arg²⁶,³⁴Lys²⁷-(GAB-GHex)-GLP-1(7-37); Arg²⁶,³⁴Lys²⁷-(GAB-GHex)-GLP-1(7-38); Thr⁸Asp¹⁹Arg²⁶,³⁴Lys²⁷-(GAB-GHex)-GLP-1(7-36); Thr⁸Asp¹⁷Arg²⁶,³⁴Lys²⁷-(GAB-GHex)-GLP-1(7-36); Thr⁸Asp¹⁹Arg²⁶,³⁴Lys²⁷-(GAB-GHex)-GLP-1(7-36)amide; Thr⁸Asp¹⁷Arg²⁶,³⁴Lys²⁷-(GAB-GHex)-GLP-1(7-36)amide; Thr⁸Asp¹⁹Arg²⁶,³⁴Lys²⁷-(GAB-GHex)-GLP-1(7-37); Thr⁸Asp¹⁹Arg²⁶,³⁴Lys²⁷-(GAB-GHex)-GLP-1(7-38); Thr⁸Asp¹⁷Arg²⁶,³⁴Lys²⁷-(GAB-GHex)-GLP-1(7-38); Arg²⁶Lys³⁴-(GAB-GOct)-GLP-1(7-36); Arg³⁴Lys²⁶-(GAB-GOct)-GLP-1(7-36); Arg²⁶,³⁴Lys³⁶-(GAB-GOct)-GLP-1(7-36); Arg²⁶Lys³⁴-(GAB-GOct)-GLP-1(7-36)amide; Arg³⁴Lys²⁶-(GAB-GOct)-GLP-1(7-36)amide; Arg²⁶,³⁴Lys³⁶-(GAB-GOct)-GLP-1(7-36)amide; Arg²⁶Lys³⁴-(GAB-GOct)-GLP-1(7-37); Arg³⁴Lys²⁶-(GAB-GOct)-GLP-1(7-37); Arg²⁶,³⁴Lys³⁶-(GAB-GOct)-GLP-1(7-37); Arg²⁶Lys³⁴-(GAB-GOct)-GLP-1(7-38); Arg³⁴Lys²⁶-(GAB-GOct)-GLP-1(7-38); Arg²⁶,³⁴Lys³⁸-(GAB-GOct)-GLP-1(7-38); Arg²⁶Lys³⁴-(GAB-GOct)-GLP-1(7-39); Arg³⁴Lys²⁶-(GAB-GOct)-GLP-1(7-39); Arg²⁶,³⁴Lys³⁹-(GAB-GOct)-GLP-1(7-39);
Gly⁸Arg²⁶Lys³⁴-(GAB-GOct)-GLP-1(7-36);
Gly⁸Arg³⁴Lys²⁶-(GAB-GOct)-GLP-1(7-36); Gly⁸Arg²⁶,³⁴Lys³⁶-(GAB-GOct)-GLP-1(7-36); Gly⁸Arg²⁶Lys³⁴-(GAB-GOct)-GLP-1(7-36)amide; Gly⁸Arg³⁴Lys²⁶-(GAB-GOct)-GLP-1(7-36)amide; Gly⁸Arg²⁶,³⁴Lys³⁶-(GAB-GOct)-GLP-1(7-36)amide; Gly⁸Arg²⁶Lys³⁴-(GAB-GOct)-GLP-1(7-37); Gly⁸Arg³⁴Lys²⁶-(GAB-GOct)-GLP-1(7-37); Gly⁸Arg²⁶,³⁴Lys³⁶-(GAB-GOct)-GLP-1(7-37); Gly⁸Arg²⁶Lys³⁴-(GAB-GOct)-GLP-1(7-38); Gly⁸Arg³⁴Lys²⁶-(GAB-GOct)-GLP-1(7-38); Gly⁸Arg²⁶,³⁴Lys³⁸-(GAB-GOct)-GLP-1(7-38); Gly⁸Arg²⁶Lys³⁴-(GAB-GOct)-GLP-1(7-39); Gly⁸Arg³⁴Lys²⁶-(GAB-GOct)-GLP-1(7-39); Gly⁸Arg²⁶,³⁴Lys³⁹-(GAB-GOct)-GLP-1(7-39);
Val⁸Arg²⁶Lys³⁴-(GAB-GOct)-GLP-1(7-36);
Val⁸Arg³⁴Lys²⁶-(GAB-GOct)-GLP-1(7-36); Val⁸Arg²⁶,³⁴Lys³⁶-(GAB-GOct)-GLP-1(7-36); Val⁸Arg²⁶Lys³⁴-(GAB-GOct)-GLP-1(7-36)amide; Val⁸Arg³⁴Lys²⁶-(GAB-GOct)-GLP-1(7-36)amide; Val⁸Arg²⁶,³⁴Lys³⁶-(GAB-GOct)-GLP-1(7-36)amide; Val⁸Arg²⁶Lys³⁴-(GAB-GOct)-GLP-1(7-37); Val⁸Arg³⁴Lys²⁶-(GAB-GOct)-GLP-1(7-37); Val⁸Arg²⁶,³⁴Lys³⁶-(GAB-GOct)-GLP-1(7-37); Val⁸Arg²⁶Lys³⁴-(GAB-GOct)-GLP-1(7-38); Val⁸Arg³⁴Lys²⁶-(GAB-GOct)-GLP-1(7-38); Val⁸Arg²⁶,³⁴Lys³⁸-(GAB-GOct)-GLP-1(7-38); Val⁸Arg²⁶Lys³⁴-(GAB-GOct)-GLP-1(7-39); Val⁸Arg³⁴Lys²⁶-(GAB-GOct)-GLP-1(7-39); Val⁸Arg²⁶,³⁴Lys³⁹-(GAB-GOct)-GLP-1(7-39);
Ser⁸Arg²⁶Lys³⁴-(GAB-GOct)-GLP-1(7-36);
Ser⁸Arg³⁴Lys²⁶-(GAB-GOct)-GLP-1(7-36); Ser⁸Arg²⁶,³⁴Lys³⁶-(GAB-GOct)-GLP-1(7-36); Ser⁸Arg²⁶Lys³⁴-(GAB-GOct)-GLP-1(7-36)amide; Ser⁸Arg³⁴Lys²⁶-(GAB-GOct)-GLP-1(7-36)amide; Ser⁸Arg²⁶,³⁴Lys³⁶-(GAB-GOct)-GLP-1(7-36)amide; Ser⁸Arg²⁶Lys³⁴-(GAB-GOct)-GLP-1(7-37); Ser⁸Arg³⁴Lys²⁶-(GAB-GOct)-GLP-1(7-37); Ser⁸Arg²⁶,³⁴Lys³⁶-(GAB-GOct)-GLP-1(7-37); Ser⁸Arg²⁶Lys³⁴-(GAB-GOct)-GLP-1(7-38); Ser⁸Arg³⁴Lys²⁶-(GAB-GOct)-GLP-1(7-38); Ser⁸Arg²⁶,³⁴Lys³⁸-(GAB-GOct)-GLP-1(7-38); Ser⁸Arg²⁶Lys³⁴-(GAB-GOct)-GLP-1(7-39); Ser⁸Arg³⁴Lys²⁶-(GAB-GOct)-GLP-1(7-39); Ser⁸Arg²⁶,³⁴Lys³⁹-(GAB-GOct)-GLP-1(7-39);
Thr⁸Arg²⁶Lys³⁴-(GAB-GOct)-GLP-1(7-36);
Thr⁸Arg³⁴Lys²⁶-(GAB-GOct)-GLP-1(7-36); Thr⁸Arg²⁶,³⁴Lys³⁶-(GAB-GOct)-GLP-1(7-36); Thr⁸Arg²⁶Lys³⁴-(GAB-GOct)-GLP-1(7-36)amide; Thr⁸Arg³⁴Lys²⁶-(GAB-GOct)-GLP-1(7-36)amide; Thr⁸Arg²⁶,³⁴Lys³⁶-(GAB-GOct)-GLP-1(7-36)amide; Thr⁸Arg²⁶Lys³⁴-(GAB-GOct)-GLP-1(7-37); Thr⁸Arg³⁴Lys²⁶-(GAB-GOct)-GLP-1(7-37); Thr⁸Arg²⁶,³⁴Lys³⁶-(GAB-GOct)-GLP-1(7-37);
Thr⁸Arg²⁶Lys³⁴-(GAB-GOct)-GLP-1(7-38);
Thr⁸Arg³⁴Lys²⁶-(GAB-GOct)-GLP-1(7-38); Thr⁸Arg²⁶,³⁴Lys³⁸-(GAB-GOct)-GLP-1(7-38); Thr⁸Arg²⁶Lys³⁴-(GAB-GOct)-GLP-1(7-39); Thr⁸Arg³⁴Lys²⁶-(GAB-GOct)-GLP-1(7-39); Thr⁸Arg²⁶,³⁴Lys³⁹-(GAB-GOct)-GLP-1(7-39);
Gly⁸Glu³⁵Arg²⁶,³⁴Lys³⁶-(GAB-GOct)-GLP-1(7-36);
Gly⁸Glu³⁵Arg²⁶,³⁴Lys³⁶-(GAB-GOct)-GLP-1(7-36)amide;
Gly⁸Glu³⁶Arg²⁶,³⁴Lys³⁷-(GAB-GOct)-GLP-1(7-37);
Gly⁸Glu³⁷Arg²⁶,³⁴Lys³⁸-(GAB-GOct)-GLP-1(7-38);
Gly⁸Glu³⁸Arg²⁶,³⁴Lys³⁹-(GAB-GOct)-GLP-1(7-39);
Gly⁸Glu³⁵Arg²⁶,³⁴Lys³⁶-(GAB-GOct)-GLP-1(7-36);
Gly⁸Glu³⁵Arg²⁶,³⁴Lys³⁶-(GAB-GOct)-GLP-1(7-36)amide;
Gly⁸Glu³⁶Arg²⁶,³⁴Lys³⁷-(GAB-GOct)-GLP-1(7-37);
Gly⁸Glu³⁷Arg²⁶,³⁴Lys³⁸-(GAB-GOct)-GLP-1(7-38);
Gly⁸Glu³⁸Arg²⁶,³⁴Lys³⁹-(GAB-GOct)-GLP-1(7-39);
Gly⁸Asp³⁵Arg²⁶,³⁴Lys³⁶-(GAB-GOct)-GLP-1(7-36);
Gly⁸Asp³⁵Arg²⁶,³⁴Lys³⁶-(GAB-GOct)-GLP-1(7-36)amide;
Gly⁸Asp³⁶Arg²⁶,³⁴Lys³⁷-(GAB-GOct)-GLP-1(7-37);
Gly⁸Asp³⁷Arg²⁶,³⁴Lys³⁸-(GAB-GOct)-GLP-1(7-38);
Gly⁸Asp³⁸Arg²⁶,³⁴Lys³⁹-(GAB-GOct)-GLP-1(7-39);
Gly⁸Asp³⁵Arg²⁶,³⁴Lys³⁶-(GAB-GOct)-GLP-1(7-36);
Gly⁸Asp³⁵Arg²⁶,³⁴Lys³⁶-(GAB-GOct)-GLP-1(7-36)amide;
Gly⁸Asp³⁶Arg²⁶,³⁴Lys³⁷-(GAB-GOct)-GLP-1(7-37);
Gly⁸Asp³⁷Arg²⁶,³⁴Lys³⁸-(GAB-GOct)-GLP-1(7-38);
Gly⁸Asp³⁸Arg²⁶,³⁴Lys³⁹-(GAB-GOct)-GLP-1(7-39);
Val⁸Glu³⁵Arg²⁶,³⁴Lys³⁶-(GAB-GOct)-GLP-1(7-36);
Val⁸Glu³⁵Arg²⁶,³⁴Lys³⁶-(GAB-GOct)-GLP-1(7-36)amide;

Val$^8$Glu$^{36}$Arg$^{26,34}$Lys$^{37}$-(GAB-GOct)-GLP-1(7-37);
Val$^8$Glu$^{37}$Arg$^{26,34}$Lys$^{37}$-(GAB-GOct)-GLP-1(7-38);
Val$^8$Glu$^{38}$Arg$^{26,34}$Lys$^{39}$-(GAB-GOct)-GLP-1(7-39);
Val$^8$Glu$^{35}$Arg$^{26,34}$Lys$^{36}$-(GAB-GOct)-GLP-1(7-36);
Val$^8$Glu$^{35}$Arg$^{26,34}$Lys$^{36}$-(GAB-GOct)-GLP-1(7-36)amide;
Val$^8$Glu$^{36}$Arg$^{26,34}$Lys$^{37}$-(GAB-GOct)-GLP-1(7-37);
Val$^8$Glu$^{37}$Arg$^{26,34}$Lys$^{38}$-(GAB-GOct)-GLP-1(7-38);
Val$^8$Glu$^{38}$Arg$^{26,34}$Lys$^{39}$-(GAB-GOct)-GLP-1(7-39);
Val$^8$Asp$^{35}$Arg$^{26,34}$Lys$^{36}$-(GAB-GOct)GLP-1(7-36);
Val$^8$Asp$^{35}$ Arg$^{26,34}$Lys$^{36}$-(GAB-GOct)-GLP-1(7-36)amide;
Val$^8$Asp$^{36}$Arg$^{26,34}$Lys$^{37}$-(GAB-GOct)-GLP-1(7-37);
Val$^8$Asp$^{37}$Arg$^{26,34}$Lys$^{38}$-(GAB-GOct)-GLP-1(7-38);
Val$^8$Asp$^{38}$Arg$^{26,34}$Lys$^{39}$-(GAB-GOct)-GLP-1(7-39);
Val$^8$Asp$^{35}$Arg$^{26,34}$Lys$^{36}$-(GAB-GOct)-GLP-1(7-36);
Val$^8$Asp$^{35}$Arg$^{26,34}$Lys$^{36}$(GAB-GOct)-GLP-1(7-36)amide;
Val$^8$Asp$^{36}$Arg$^{26,34}$Lys$^{37}$-(GAB-GOct)-GLP-1(7-37);
Val$^8$Asp$^{37}$Arg$^{26,34}$Lys$^{38}$-(GAB-GOct)-GLP-1(7-38);
Val$^8$Asp$^{38}$Arg$^{26,34}$Lys$^{39}$-(GAB-GOct)-GLP-1(7-39);
Ser$^8$Glu$^{35}$Arg$^{26,34}$Lys$^{36}$-(GAB-GOct)-GLP-1(7-36);
Ser$^8$Glu$^{35}$Arg$^{26,34}$Lys$^{36}$-(GAB-GOct)-GLP-1(7-36)amide;
Ser$^8$Glu$^{36}$Arg$^{26,34}$Lys$^{37}$-(GAB-GOct)-GLP-1(7-37);
Ser$^8$Glu$^{37}$Arg$^{26,34}$Lys$^{38}$-(GAB-GOct)-GLP-1(7-38);
Ser$^8$Glu$^{38}$Arg$^{26,34}$Lys$^{39}$-(GAB-GOct)-GLP-1(7-39);
Ser$^8$Glu$^{35}$Arg$^{26,34}$Lys$^{36}$-(GAB-GOct)-GLP-1(7-36);
Ser$^8$Glu$^{35}$Arg$^{26,34}$Lys$^{36}$-(GAB-GOct)-GLP-1(7-36)amide;
Ser$^8$Glu$^{36}$Arg$^{26,34}$Lys$^{37}$-(GAB-GOct)-GLP-1(7-37);
Ser$^8$Glu$^{37}$Arg$^{26,34}$Lys$^{38}$-(GAB-GOct)-GLP-1(7-38);
Ser$^8$Glu$^{38}$Arg$^{26,34}$Lys$^{39}$-(GAB-GOct)-GLP-1(7-39);
Ser$^8$Asp$^{35}$Arg$^{26,34}$Lys$^{36}$-(GAB-GOct)-GLP-1(7-36);
Ser$^8$Asp$^{35}$Arg$^{26,34}$Lys$^{36}$-(GAB-GOct)-GLP-1(7-36)amide;
Ser$^8$Asp$^{36}$Arg$^{26,34}$Lys$^{37}$-(GAB-GOct)-GLP-1(7-37);
Ser$^8$Asp$^{37}$Arg$^{26,34}$Lys$^{38}$(GAB-GOct)-GLP-1(7-38);
Ser$^8$Asp$^{38}$Arg$^{26,34}$Lys$^{39}$-(GAB-GOct)-GLP-1(7-39);
Ser$^8$Asp$^{35}$Arg$^{26,34}$Lys$^{36}$-(GAB-GOct)-GLP-1(7-36);
Ser$^8$Asp$^{35}$Arg$^{26,34}$Lys$^{36}$(GAB-GOct)-GLP-1(7-36)amide;
Ser$^8$Asp$^{36}$Arg$^{26,34}$Lys$^{37}$-(GAB-GOct)-GLP-1(7-37);
Ser$^8$Asp$^{37}$Arg$^{26,34}$Lys$^{38}$-(GAB-GOct)-GLP-1(7-38);
Ser$^8$Asp$^{38}$Arg$^{26,34}$Lys$^{39}$-(GAB-GOct)-GLP-1(7-39);
Thr$^8$Glu$^{35}$Arg$^{26,34}$Lys$^{36}$-(GAB-GOct)-GLP-1(7-36);
Thr$^8$Glu$^{35}$Arg$^{26,34}$Lys$^{36}$-(GAB-GOct)-GLP-1(7-36)amide;
Thr$^8$Glu$^{36}$Arg$^{26,34}$Lys$^{37}$-(GAB-GOct)-GLP-1(7-37);
Thr$^8$Glu$^{37}$Arg$^{26,34}$Lys$^{38}$-(GAB-GOct)-GLP-1(7-38);
Thr$^8$Glu$^{38}$Arg$^{26,34}$Lys$^{39}$-(GAB-GOct)-GLP-1(7-39);
Thr$^8$Glu$^{35}$Arg$^{26,34}$Lys$^{36}$-(GAB-GOct)-GLP-1(7-36);
Thr$^8$Glu$^{35}$Arg$^{26,34}$Lys$^{36}$-(GAB-GOct)-GLP-1(7-36)amide;
Thr$^8$Glu$^{36}$Arg$^{26,34}$Lys$^{37}$-(GAB-GOct)-GLP-1(7-37);
Thr$^8$Glu$^{37}$Arg$^{26,34}$Lys$^{38}$-(GAB-GOct)-GLP-1(7-38);
Thr$^8$Glu$^{38}$Arg$^{26,34}$Lys$^{39}$-(GAB-GOct)-GLP-1(7-39);
Thr$^8$Asp$^{35}$Arg$^{26,34}$Lys$^{36}$-(GAB-GOct)-GLP-1(7-36);
Thr$^8$Asp$^{35}$Arg$^{26,34}$Lys$^{36}$-(GAB-GOct)-GLP-1(7-36)amide;
Thr$^8$Asp$^{36}$Arg$^{26,34}$Lys$^{37}$-(GAB-GOct)-GLP-1(7-37);
Thr$^8$Asp$^{37}$Arg$^{26,34}$Lys$^{38}$-(GAB-GOct)-GLP-1(7-38);
Thr$^8$Asp$^{38}$Arg$^{26,34}$Lys$^{39}$-(GAB-GOct)GLP-1(7-39);
Thr$^8$Asp$^{35}$Arg$^{26,34}$Lys$^{36}$-(GAB-GOct)-GLP-1(7-36);
Thr$^8$Asp$^{35}$Arg$^{26,34}$Lys$^{36}$-(GAB-GOct)-GLP-1(7-36)amide;
Thr$^8$Asp$^{36}$Arg$^{26,34}$Lys$^{37}$-(GAB-GOct)-GLP-1(7-37);
Thr$^8$Asp$^{37}$Arg$^{26,34}$Lys$^{38}$-(GAB-GOct)-GLP-1(7-38);
Thr$^8$Asp$^{38}$Arg$^{26,34}$Lys$^{39}$-(GAB-GOct)-GLP-1(7-39);
Arg$^{26,34}$Lys$^{18}$-(GAB-GOct)-GLP-1(7-36); Arg$^{26,34}$Lys$^{18}$-(GAB-GOct)-GLP-1(7-36)amide; Arg$^{26,34}$Lys$^{18}$-(GAB-GOct)-GLP-1(7-37); Arg$^{26,34}$Lys$^{18}$-(GAB-GOct)-GLP-1(7-38); Gly$^8$Asp$^{19}$Arg$^{26,34}$Lys$^{18}$(GAB-GOct)$^{-GLP-}$1(7-36);
Gly$^8$Asp$^{17}$Arg$^{26,34}$Lys$^{18}$-(GAB-GOct)-GLP-1(7-36);
Gly$^8$Asp$^{19}$Arg$^{26,34}$Lys$^{18}$-(GAB-GOct)-GLP-1(7-36)amide;
Gly$^8$Asp$^{17}$Arg$^{26,34}$Lys$^{18}$-(GAB-GOct)-GLP-1(7-36)amide;
Gly$^8$Asp$^{19}$Arg$^{26,34}$Lys$^{18}$-(GAB-GOct)-GLP-1(7-37);
Gly$^8$Asp$^{19}$Arg$^{26,34}$Lys$^{18}$-(GAB-GOct)-GLP-1(7-38);
Gly$^8$Asp$^{17}$Arg$^{26,34}$Lys$^{18}$-(GAB-GOct)-GLP-1(7-38);
Arg$^{26,34}$Lys$^{23}$-(GAB-GOct)-GLP-1(7-36); Arg$^{26,34}$Lys$^{23}$-(GAB-GOct)-GLP-1(7-36)amide; Arg$^{26,34}$Lys$^{23}$-(GAB-GOct)-GLP-1(7-37); Arg$^{26,34}$Lys$^{23}$-(GAB-GOct)-GLP-1(7-38); Gly$^8$Asp$^{19}$Arg$^{26,34}$Lys$^{23}$-(GAB-GOct)-GLP-1(7-36);
Gly$^8$Asp$^{17}$Arg$^{26,34}$Lys$^{23}$-(GAB-GOct)-GLP-1(7-36);
Gly$^8$Asp$^{19}$Arg$^{26,34}$Lys$^{23}$-(GAB-GOct)-GLP-1(7-36)amide;
Gly$^8$Asp$^{17}$Arg$^{26,34}$Lys$^{23}$-(GAB-GOct)-GLP-1(7-36)amide;
Gly$^8$Asp$^{19}$Arg$^{26,34}$Lys$^{23}$ (GAB-GOct)-GLP-1(7-37);
Gly$^8$Asp$^{19}$Arg$^{26,34}$Lys$^{23}$-(GAB-GOct)-GLP-1(7-38);
Gly$^8$Asp$^{17}$Arg$^{26,34}$Lys$^{23}$-(GAB-GOct)-GLP-1(7-38);
Arg$^{26,34}$Lys$^{27}$-(GAB-GOct)-GLP-1(7-36); Arg$^{26,34}$Lys$^{27}$-(GAB-GOct)-GLP-1(7-36)amide; Arg$^{26,34}$Lys$^{27}$-(GAB-GOct)-GLP-1(7-37); Arg$^{26,34}$Lys$^{27}$-(GAB-GOct)-GLP-1(7-38); Gly$^8$Asp$^{19}$Arg$^{26,34}$Lys$^{27}$-(GAB-GOct)-GLP-1(7-36);
Gly$^8$Asp$^{17}$Arg$^{26,34}$Lys$^{27}$-(GAB-GOct)-GLP-1(7-36);
Gly$^8$Asp$^{19}$Arg$^{26,34}$Lys$^{27}$-(GAB-GOct)-GLP-1(7-36)amide;
Gly$^8$Asp$^{17}$Arg$^{26,34}$Lys$^{27}$-(GAB-GOct)-GLP-1(7-36)amide;
Gly$^8$Asp$^{19}$Arg$^{26,34}$Lys$^{27}$-(GAB-GOct)-GLP-1(7-37);
Gly$^8$Asp$^{19}$Arg$^{26,34}$Lys$^{27}$-(GAB-GOct)-GLP-1(7-38);
Gly$^8$Asp$^{17}$Arg$^{26,34}$Lys$^{27}$-(GAB-GOct)-GLP-1(7-38);
Arg$^{26,34}$Lys$^{18}$-(GAB-GOct)-GLP-1(7-36); Arg$^{26,34}$Lys$^{18}$-(GAB-GOct)-GLP-1(7-36)amide; Arg$^{26,34}$Lys$^{18}$-(GAB-GOct)-GLP-1(7-37); Arg$^{26,34}$Lys$^{18}$-(GAB-GOct)-GLP-1(7-38); Val$^8$Asp$^{19}$Arg$^{26,34}$Lys$^{18}$-(GAB-GOct)-GLP-1(7-36);
Val$^8$Asp$^{17}$Arg$^{26,34}$Lys$^{18}$-(GAB-GOct)-GLP-1(7-36);
Val$^8$Asp$^{19}$Arg$^{26,34}$Lys$^{18}$-(GAB-GOct)-GLP-1(7-36)amide;
Val$^8$Asp$^{17}$Arg$^{26,34}$Lys$^{18}$-(GAB-GOct)-GLP-1(7-36)amide;
Val$^8$Asp$^{19}$Arg$^{26,34}$Lys$^{18}$-(GAB-GOct)-GLP-1(7-37);
Val$^8$Asp$^{19}$Arg$^{26,34}$Lys$^{18}$-(GAB-GOct)-GLP-1(7-38);
Val$^8$Asp$^{17}$Arg$^{26,34}$Lys$^{18}$-(GAB-GOct)-GLP-1(7-38);
Arg$^{26,34}$Lys$^{23}$-(GAB-GOct)-GLP-1(7-36); Arg$^{26,34}$Lys$^{23}$-(GAB-GOct)-GLP-1(7-36)amide; Arg$^{26,34}$Lys$^{23}$-(GAB-GOct)-GLP-1(7-37); Arg$^{26,34}$Lys$^{23}$-(GAB-GOct)-GLP-1(7-38); Val$^8$Asp$^{19}$Arg$^{26,34}$Lys$^{23}$-(GAB-GOct)-GLP-1(7-36);
Val$^8$Asp$^{17}$Arg$^{26,34}$Lys$^{23}$-(GAB-GOct)-GLP-1(7-36);
Val$^8$Asp$^{19}$Arg$^{26,34}$Lys$^{23}$-(GAB-GOct)-GLP-1(7-36)amide;
Val$^8$Asp$^{17}$Arg$^{26,34}$Lys$^{23}$-(GAB-GOct)-GLP-1(7-36)amide;
Val$^8$Asp$^{19}$Arg$^{26,34}$Lys$^{23}$ (GAB-GOct)-GLP-1(7-37);
Val$^8$Asp$^{19}$Arg$^{26,34}$Lys$^{23}$-(GAB-GOct)-GLP-1(7-38);
Val$^8$Asp$^{17}$Arg$^{26,34}$Lys$^{23}$-(GAB-GOct)-GLP-1(7-38);
Arg$^{26,34}$Lys$^{27}$-(GAB-GOct)-GLP-1(7-36); Arg$^{26,34}$Lys$^{27}$-(GAB-GOct)-GLP-1(7-36)amide; Arg$^{26,34}$Lys$^{27}$-(GAB-GOct)-GLP-1(7-37); Arg$^{26,34}$Lys$^{27}$-(GAB-GOct)-GLP-1(7-38); Val$^8$Asp$^{19}$Arg$^{26,34}$Lys$^{27}$-(GAB-GOct)-GLP-1(7-36);
Val$^8$Asp$^{17}$Arg$^{26,34}$Lys$^{27}$-(GAB-GOct)-GLP-1(7-36);
Val$^8$Asp$^{19}$Arg$^{26,34}$Lys$^{27}$-(GAB-GOct)-GLP-1(7-36)amide;
Val$^8$Asp$^{17}$Arg$^{26,34}$Lys$^{27}$-(GAB-GOct)-GLP-1(7-36)amide;
Val$^8$Asp$^{19}$Arg$^{26,34}$Lys$^{27}$-(GAB-GOct)-GLP-1(7-37);
Val$^8$Asp$^{19}$Arg$^{26,34}$Lys$^{27}$-(GAB-GOct)-GLP-1(7-38);
Val$^8$Asp$^{17}$Arg$^{26,34}$Lys$^{27}$-(GAB-GOct)-GLP-1(7-38);
Arg$^{26,34}$Lys$^{18}$-(GAB-GOct)-GLP-1(7-36); Arg$^{26,34}$Lys$^{18}$-(GAB-GOct)-GLP-1(7-36)amide; Arg$^{26,34}$Lys$^{18}$-(GAB-GOct)-GLP-1(7-37); Arg$^{26,34}$Lys$^{18}$-(GAB-GOct)-GLP-1(7-38); Ser$^8$Asp$^{19}$Arg$^{26,34}$Lys$^{18}$-(GAB-GOct)-GLP-1(7-36);
Ser$^8$Asp$^{17}$Arg$^{26,34}$Lys$^{18}$-(GAB-GOct)-GLP-1(7-36);
Ser$^8$Asp$^{19}$Arg$^{26,34}$Lys$^{18}$-(GAB-GOct)-GLP-1(7-36)amide;
Ser$^8$Asp$^{17}$Arg$^{26,34}$Lys$^{18}$-(GAB-GOct)-GLP-1(7-36)amide;
Ser$^8$Asp$^{19}$Arg$^{26,34}$Lys$^{18}$-(GAB-GOct)-GLP-1(7-37);
Ser$^8$Asp$^{19}$Arg$^{26,34}$Lys$^{18}$-(GAB-GOct)-GLP-1(7-38);
Ser$^8$Asp$^{17}$Arg$^{26,34}$Lys$^{18}$-(GAB-GOct)-GLP-1(7-38);
Arg$^{26,34}$Lys$^{23}$-(GAB-GOct)-GLP-1(7-36); Arg$^{26,34}$Lys$^{23}$-(GAB-GOct)-GLP-1(7-36)amide; Arg$^{26,34}$Lys$^{23}$-(GAB-GOct)-GLP-1(7-37); Arg$^{26,34}$Lys$^{23}$-(GAB-GOct)-GLP-1(7-38); Ser$^8$Asp$^{19}$Arg$^{26,34}$Lys$^{23}$-(GAB-GOct)-GLP-1(7-36);
Ser$^8$Asp$^{17}$Arg$^{26,34}$Lys$^{23}$-(GAB-GOct)-GLP-1(7-36);

Ser⁸Asp¹⁹Arg²⁶,³⁴Lys²³-(GAB-GOct)-GLP-1(7-36)amide;
Ser⁸Asp¹⁷Arg²⁶,³⁴Lys²³-(GAB-GOct)-GLP-1(7-36)amide;
Ser⁸Asp¹⁹Arg²⁶,³⁴Lys²³-(GAB-GOct)-GLP-1(7-37);
Ser⁸Asp¹⁹Arg²⁶,³⁴Lys²³-(GAB-GOct)-GLP-1(7-38);
Ser⁸Asp¹⁷Arg²⁶,³⁴Lys²³-(GAB-GOct)-GLP-1(7-38);
Arg²⁶,³⁴Lys²⁷-(GAB-GOct)-GLP-1(7-36); Arg²⁶,³⁴Lys²⁷-(GAB-GOct)-GLP-1(7-36)amide; Arg²⁶,³⁴Lys²⁷-(GAB-GOct)-GLP-1(7-37); Arg²⁶,³⁴Lys²⁷-(GAB-GOct)-GLP-1(7-38); Ser⁸Asp¹⁹Arg²⁶,³⁴Lys²⁷-(GAB-GOct)-GLP-1(7-36);
Ser⁸Asp¹⁷Arg²⁶,³⁴Lys²⁷-(GAB-GOct)-GLP-1(7-36);
Ser⁸Asp¹⁹Arg²⁶,³⁴Lys²⁷-(GAB-GOct)-GLP-1(7-36)amide;
Ser⁸Asp¹⁷Arg²⁶,³⁴Lys²⁷-(GAB-GOct)-GLP-1(7-36)amide;
Ser⁸Asp¹⁹Arg²⁶,³⁴Lys²⁷-(GAB-GOct)-GLP-1(7-37);
Ser⁸Asp¹⁹Arg²⁶,³⁴Lys²⁷-(GAB-GOct)-GLP-1(7-38);
Ser⁸Asp¹⁷Arg²⁶,³⁴Lys²⁷-(GAB-GOct)-GLP-1(7-38);
Arg²⁶,³⁴Lys¹⁸-(GAB-GOct)-GLP-1(7-36); Arg²⁶,³⁴Lys¹⁸-(GAB-GOct)-GLP-1(7-36)amide; Arg²⁶,³⁴Lys¹⁸-(GAB-GOct)-GLP-1(7-37); Arg²⁶,³⁴Lys¹⁸-(GAB-GOct)-GLP-1(7-38); Thr⁸Asp¹⁹Arg²⁶,³⁴Lys¹⁸-(GAB-GOct)-GLP-1(7-36);
Thr⁸Asp¹⁷Arg²⁶,³⁴Lys¹⁸-(GAB-GOct)-GLP-1(7-36);
Thr⁸Asp¹⁹Arg²⁶,³⁴Lys¹⁸-(GAB-GOct)-GLP-1(7-36)amide;
Thr⁸Asp¹⁷Arg²⁶,³⁴Lys¹⁸-(GAB-GOct)-GLP-1(7-36)amide;
Thr⁸Asp¹⁹Arg²⁶,³⁴Lys¹⁸-(GAB-GOct)-GLP-1(7-37);
Thr⁸Asp¹⁹Arg²⁶,³⁴Lys¹⁸-(GAB-GOct)-GLP-1(7-38);
Thr⁸Asp¹⁷Arg²⁶,³⁴Lys¹⁸-(GAB-GOct)-GLP-1(7-38);
Arg²⁶,³⁴Lys²³-(GAB-GOct)-GLP-1(7-36); Arg²⁶,³⁴Lys²³-(GAB-GOct)-GLP-1(7-36)amide; Arg²⁶,³⁴Lys²³-(GAB-GOct)-GLP-1(7-37); Arg²⁶,³⁴Lys²³-(GAB-GOct)-GLP-1(7-38); Thr⁸Asp¹⁹Arg²⁶,³⁴Lys²³-(GAB-GOct)-GLP-1(7-36);
Thr⁸Asp¹⁷Arg²⁶,³⁴Lys²³-(GAB-GOct)-GLP-1(7-36);
Thr⁸Asp¹⁹Arg²⁶,³⁴Lys²³-(GAB-GOct)-GLP-1(7-36)amide;
Thr⁸Asp¹⁷Arg²⁶,³⁴Lys²³-(GAB-GOct)-GLP-1(7-36)amide;
Thr⁸Asp¹⁹Arg²⁶,³⁴Lys²³ (GAB-GOct)-GLP-1(7-37);
Thr⁸Asp¹⁹Arg²⁶,³⁴Lys²³-(GAB-GOct)-GLP-1(7-38);
Thr⁸Asp¹⁷Arg²⁶,³⁴Lys²³-(GAB-GOct)-GLP-1(7-38);
Arg²⁶,³⁴Lys²⁷-(GAB-GOct)-GLP-1(7-36); Arg²⁶,³⁴Lys²⁷-(GAB-GOct)-GLP-1(7-36)amide; Arg²⁶,³⁴Lys²⁷-(GAB-GOct)-GLP-1(7-37); Arg²⁶,³⁴Lys²⁷-(GAB-GOct)-GLP-1(7-38); Thr⁸Asp¹⁹Arg²⁶,³⁴Lys²⁷-(GAB-GOct)-GLP-1(7-36);
Thr⁸Asp¹⁷Arg²⁶,³⁴Lys²⁷-(GAB-GOct)-GLP-1(7-36);
Thr⁸Asp¹⁹Arg²⁶,³⁴Lys²⁷-(GAB-GOct)-GLP-1(7-36)amide;
Thr⁸Asp¹⁷Arg²⁶,³⁴Lys²⁷-(GAB-GOct)-GLP-1(7-36)amide;
Thr⁸Asp¹⁹Arg²⁶,³⁴Lys²⁷-(GAB-GOct)-GLP-1(7-37);
Thr⁸Asp¹⁹Arg²⁶,³⁴Lys²⁷-(GAB-GOct)-GLP-1(7-38);
Thr⁸Asp¹⁷Arg²⁶,³⁴Lys²⁷-(GAB-GOct)-GLP-1(7-38);
Arg²⁶Lys³⁴-(GAB-GLit)-GLP-1(7-36); Arg³⁴Lys²⁶-(GAB-GLit)-GLP-1(7-36); Arg²⁶,³⁴Lys³⁶-(GAB-GLit)-GLP-1(7-36); Arg²⁶Lys³⁴-(GAB-GLit)-GLP-1(7-36)amide;
Arg³⁴Lys²⁶-(GAB-GLit)-GLP-1(7-36)amide;
Arg²⁶,³⁴Lys³⁶-(GAB-GLit)-GLP-1(7-36)amide;
Arg²⁶Lys³⁴-(GAB-GLit)-GLP-1(7-37); Arg³⁴Lys²⁶-(GAB-GLit)-GLP-1(7-37); Arg²⁶,³⁴Lys³⁶-(GAB-GLit)-GLP-1(7-37); Arg²⁶Lys³⁴-(GAB-GLit)-GLP-1(7-38); Arg³⁴Lys²⁶-(GAB-GLit)-GLP-1(7-38); Arg²⁶,³⁴Lys³⁸-(GAB-GLit)-GLP-1(7-38); Arg²⁶Lys³⁴-(GAB-GLit)-GLP-1(7-39); Arg³⁴Lys²⁶-(GAB-GLit)-GLP-1(7-39); Arg²⁶,³⁴Lys³⁹-(GAB-GLit)-GLP-1(7-39);
Gly⁸Arg²⁶Lys³⁴-(GAB-GLit)-GLP-1(7-36);
Gly⁸Arg³⁴Lys²⁶-(GAB-GLit)-GLP-1(7-36); Gly⁸Arg²⁶,³⁴Lys³⁶-(GAB-GLit)-GLP-1(7-36); Gly⁸Arg²⁶Lys³⁴-(GAB-GLit)-GLP-1(7-36)amide; Gly⁸Arg³⁴Lys²⁶-(GAB-GLit)-GLP-1(7-36)amide; Gly⁸Arg²⁶,³⁴Lys³⁶-(GAB-GLit)-GLP-1(7-36)amide; Gly⁸Arg²⁶Lys³⁴-(GAB-GLit)-GLP-1(7-37); Gly⁸Arg³⁴Lys²⁶-(GAB-GLit)-GLP-1(7-37); Gly⁸Arg²⁶,³⁴Lys³⁶-(GAB-GLit)-GLP-1(7-37); Gly⁸Arg²⁶Lys³⁴-(GAB-GLit)-GLP-1(7-38); Gly⁸Arg³⁴Lys²⁶-(GAB-GLit)-GLP-1(7-38); Gly⁸Arg²⁶,³⁴Lys³⁸-(GAB-GLit)-GLP-1(7-38); Gly⁸Arg²⁶Lys³⁴-(GAB-GLit)-GLP-1(7-39); Gly⁸Arg³⁴Lys²⁶-(GAB-GLit)-GLP-1(7-39); Gly⁸Arg²⁶,³⁴Lys³⁹-(GAB-GLit)-GLP-1(7-39);
Val⁸Arg²⁶Lys³⁴-(GAB-GLit)-GLP-1(7-36); Val⁸Arg³⁴Lys²⁶-(GAB-GLit)-GLP-1(7-36); Val⁸Arg²⁶,³⁴Lys³⁶-(GAB-GLit)-GLP-1(7-36); Val⁸Arg²⁶Lys³⁴-(GAB-GLit)-GLP-1(7-36)amide; Val⁸Arg³⁴Lys²⁶-(GAB-GLit)-GLP-1(7-36)amide; Val⁸Arg²⁶,³⁴Lys³⁶-(GAB-GLit)-GLP-1(7-36)amide; Val⁸Arg²⁶Lys³⁴-(GAB-GLit)-GLP-1(7-37); Val⁸Arg³⁴Lys²⁶-(GAB-GLit)-GLP-1(7-37); Val⁸Arg²⁶,³⁴Lys³⁶-(GAB-GLit)-GLP-1(7-37); Val⁸Arg²⁶Lys³⁴-(GAB-GLit)-GLP-1(7-38); Val⁸Arg³⁴Lys²⁶-(GAB-GLit)-GLP-1(7-38); Val⁸Arg²⁶,³⁴Lys³⁸-(GAB-GLit)-GLP-1(7-38); Val⁸Arg²⁶Lys³⁴-(GAB-GLit)-GLP-1(7-39); Val⁸Arg³⁴Lys²⁶-(GAB-GLit)-GLP-1(7-39); Val⁸Arg²⁶,³⁴Lys³⁹-(GAB-GLit)-GLP-1(7-39);
Ser⁸Arg²⁶Lys³⁴-(GAB-GLit)-GLP-1(7-36);
Ser⁸Arg³⁴Lys²⁶-(GAB-GLit)-GLP-1(7-36); Ser⁸Arg²⁶,³⁴Lys³⁶-(GAB-GLit)-GLP-1(7-36); Ser⁸Arg²⁶Lys³⁴-(GAB-GLit)-GLP-1(7-36)amide; Ser⁸Arg³⁴Lys²⁶-(GAB-GLit)-GLP-1(7-36)amide; Ser⁸Arg²⁶,³⁴Lys³⁶-(GAB-GLit)-GLP-1(7-36)amide; Ser⁸Arg²⁶Lys³⁴-(GAB-GLit)-GLP-1(7-37); Ser⁸Arg³⁴Lys²⁶-(GAB-GLit)-GLP-1(7-37); Ser⁸Arg²⁶,³⁴Lys³⁶-(GAB-GLit)-GLP-1(7-37); Ser⁸Arg²⁶Lys³⁴-(GAB-GLit)-GLP-1(7-38); Ser⁸Arg³⁴Lys²⁶-(GAB-GLit)-GLP-1(7-38); Ser⁸Arg²⁶,³⁴Lys³⁸-(GAB-GLit)-GLP-1(7-38); Ser⁸Arg²⁶Lys³⁴-(GAB-GLit)-GLP-1(7-39); Ser⁸Arg³⁴Lys²⁶-(GAB-GLit)-GLP-1(7-39); Ser⁸Arg²⁶,³⁴Lys³⁹-(GAB-GLit)-GLP-1(7-39);
Thr⁸Arg²⁶Lys³⁴-(GAB-GLit)-GLP-1(7-36);
Thr⁸Arg³⁴Lys²⁶-(GAB-GLit)-GLP-1(7-36); Thr⁸Arg²⁶,³⁴Lys³⁶-(GAB-GLit)-GLP-1(7-36); Thr⁸Arg²⁶Lys³⁴-(GAB-GLit)-GLP-1(7-36)amide; Thr⁸Arg³⁴Lys²⁶-(GAB-GLit)-GLP-1(7-36)amide; Thr⁸Arg²⁶,³⁴Lys³⁶-(GAB-GLit)-GLP-1(7-36)amide; Thr⁸Arg²⁶Lys³⁴-(GAB-GLit)-GLP-1(7-37); Thr⁸Arg³⁴Lys²⁶-(GAB-GLit)-GLP-1(7-37); Thr⁸Arg²⁶,³⁴Lys³⁶-(GAB-GLit)-GLP-1(7-37); Thr⁸Arg²⁶Lys³⁴-(GAB-GLit)-GLP-1(7-38); Thr⁸Arg³⁴Lys²⁶-(GAB-GLit)-GLP-1(7-38); Thr⁸Arg²⁶,³⁴Lys³⁸-(GAB-GLit)-GLP-1(7-38); Thr⁸Arg²⁶Lys³⁴-(GAB-GLit)-GLP-1(7-39); Thr⁸Arg³⁴Lys²⁶-(GAB-GLit)-GLP-1(7-39); Thr⁸Arg²⁶,³⁴Lys³⁹-(GAB-GLit)-GLP-1(7-39);
Gly⁸Glu³⁵Arg²⁶,³⁴Lys³⁶-(GAB-GLit)-GLP-1(7-36);
Gly⁸Glu³⁵Arg²⁶,³⁴Lys³⁶-(GAB-GLit)-GLP-1(7-36)amide;
Gly⁸Glu³⁶Arg²⁶,³⁴Lys³⁷-(GAB-GLit)-GLP-1(7-37);
Gly⁸Glu³⁷Arg²⁶,³⁴Lys³⁸-(GAB-GLit)-GLP-1(7-38);
Gly⁸Glu³⁸Arg²⁶,³⁴Lys³⁹-(GAB-GLit)-GLP-1(7-39);
Gly⁸Glu³⁵Arg²⁶,³⁴Lys³⁶-(GAB-GLit)-GLP-1(7-36);
Gly⁸Glu³⁵Arg²⁶,³⁴Lys³⁶-(GAB-GLit)-GLP-1(7-36)amide;
Gly⁸Glu³⁶Arg²⁶,³⁴Lys³⁷-(GAB-GLit)-GLP-1(7-37);
Gly⁸Glu³⁷Arg²⁶,³⁴Lys³⁸-(GAB-GLit)-GLP-1(7-38);
Gly⁸Glu³⁸Arg²⁶,³⁴Lys³⁹-(GAB-GLit)-GLP-1(7-39);
Gly⁸Asp³⁵Arg²⁶,³⁴Lys³⁶-(GAB-GLit)-GLP-1(7-36);
Gly⁸Asp³⁵Arg²⁶,³⁴Lys³⁶-(GAB-GLit)-GLP-1(7-36)amide;
Gly⁸Asp³⁶Arg²⁶,³⁴Lys³⁷-(GAB-GLit)-GLP-1(7-37);
Gly⁸Asp³⁷Arg²⁶,³⁴Lys³⁸-(GAB-GLit)-GLP-1(7-38);
Gly⁸Asp³⁸Arg²⁶,³⁴Lys³⁹-(GAB-GLit)-GLP-1(7-39);
Gly⁸Asp³⁵Arg²⁶,³⁴Lys³⁶-(GAB-GLit)-GLP-1(7-36);
Gly⁸Asp³⁵Arg²⁶,³⁴Lys³⁶-(GAB-GLit)-GLP-1(7-36)amide;
Gly⁸Asp³⁶Arg²⁶,³⁴Lys³⁷-(GAB-GLit)-GLP-1(7-37);
Gly⁸Asp³⁷Arg²⁶,³⁴Lys³⁸-(GAB-GLit)-GLP-1(7-38);
Gly⁸Asp³⁸Arg²⁶,³⁴Lys³⁹-(GAB-GLit)-GLP-1(7-39);
Val⁸Glu³⁵Arg²⁶,³⁴Lys¹⁸-3-(GAB-GLit)-GLP-1(7-36);
Val⁸Glu³⁵Arg²⁶,³⁴Lys³⁶-(GAB-GLit)-GLP-1(7-36)amide;
Val⁸Glu³⁶Arg²⁶,³⁴Lys³⁷-(GAB-GLit)-GLP-1(7-37);
Val⁸Glu³⁷Arg²⁶,³⁴Lys³⁸-(GAB-GLit)-GLP-1(7-38);
Val⁸Glu³⁸Arg²⁶,³⁴Lys³⁹-(GAB-GLit)-GLP-1(7-39);

Val⁸Glu³⁵Arg²⁶,³⁴Lys³⁶-(GAB-GLit)-GLP-1(7-36);
Val⁸Glu³⁵Arg²⁶,³⁴Lys³⁶-(GAB-GLit)-GLP-1(7-36)amide;
Val⁸Glu³⁶Arg²⁶,³⁴Lys³⁷-(GAB-GLit)-GLP-1(7-37);
Val⁸Glu³⁷Arg²⁶,³⁴Lys³⁸-(GAB-GLit)-GLP-1(7-38);
Val⁸Glu³⁸Arg²⁶,³⁴Lys³⁹-(GAB-GLit)-GLP-1(7-39);
Val⁸Asp³⁵Arg²⁶,³⁴Lys³⁶-(GAB-GLit)-GLP-1(7-36);
Val⁸Asp³⁵Arg²⁶,³⁴Lys³⁶-(GAB-GLit)-GLP-1(7-36)amide;
Val⁸Asp³⁶Arg²⁶,³⁴Lys³⁷-(GAB-GLit)-GLP-1(7-37);
Val⁸Asp³⁷Arg²⁶,³⁴Lys³⁸-(GAB-GLit)-GLP-1(7-38);
Val⁸Asp³⁸Arg²⁶,³⁴Lys³⁹-(GAB-GLit)-GLP-1(7-39);
Val⁸Asp³⁵Arg²⁶,³⁴Lys³⁶-(GAB-GLit)-GLP-1(7-36);
Val⁸Asp³⁵Arg²⁶,³⁴Lys³⁶-(GAB-GLit)-GLP-1(7-36)amide;
Val⁸Asp³⁶Arg²⁶,³⁴Lys³⁷-(GAB-GLit)-GLP-1(7-37);
Val⁸Asp³⁷Arg²⁶,³⁴Lys³⁸-(GAB-GLit)-GLP-1(7-38);
Val⁸Asp³⁸Arg²⁶,³⁴Lys³⁹-(GAB-GLit)-GLP-1(7-39);
Ser⁸Glu³⁵Arg²⁶,³⁴Lys³⁶-(GAB-GLit)-GLP-1(7-36);
Ser⁸Glu³⁵Arg²⁶,³⁴Lys³⁶-(GAB-GLit)-GLP-1(7-36)amide;
Ser⁸Glu³⁶Arg²⁶,³⁴Lys³⁷-(GAB-GLit)-GLP-1(7-37);
Ser⁸Glu³⁷Arg²⁶,³⁴Lys³⁸-(GAB-GLit)-GLP-1(7-38);
Ser⁸Glu³⁸Arg²⁶,³⁴Lys³⁹-(GAB-GLit)-GLP-1(7-39);
Ser⁸Glu³⁵Arg²⁶,³⁴Lys³⁶-(GAB-GLit)-GLP-1(7-36);
Ser⁸Glu³⁵Arg²⁶,³⁴Lys³⁶-(GAB-GLit)-GLP-1(7-36)amide;
Ser⁸Glu³⁶Arg²⁶,³⁴Lys³⁷-(GAB-GLit)-GLP-1(7-37);
Ser⁸Glu³⁷Arg²⁶,³⁴Lys³⁸-(GAB-GLit)-GLP-1(7-38);
Ser⁸Glu³⁸Arg²⁶,³⁴Lys³⁹-(GAB-GLit)-GLP-1(7-39);
Ser⁸Asp³⁵Arg²⁶,³⁴Lys³⁶-(GAB-GLit)-GLP-1(7-36);
Ser⁸Asp³⁵Arg²⁶,³⁴Lys³⁶-(GAB-GLit)-GLP-1(7-36)amide;
Ser⁸Asp³⁶Arg²⁶,³⁴Lys³⁷-(GAB-GLit)-GLP-1(7-37);
Ser⁸Asp³⁷Arg²⁶,³⁴Lys³⁸-(GAB-GLit)-GLP-1(7-38);
Ser⁸Asp³⁸Arg²⁶,³⁴Lys³⁹-(GAB-GLit)-GLP-1(7-39);
Ser⁸Asp³⁵Arg²⁶,³⁴Lys³⁶-(GAB-GLit)-GLP-1(7-36);
Ser⁸Asp³⁵Arg²⁶,³⁴Lys³⁶-(GAB-GLit)-GLP-1(7-36)amide;
Ser⁸Asp³⁶Arg²⁶,³⁴Lys³⁷-(GAB-GLit)-GLP-1(7-37);
Ser⁸Asp³⁷Arg²⁶,³⁴Lys³⁸-(GAB-GLit)-GLP-1(7-38);
Ser⁸Asp³⁸Arg²⁶,³⁴Lys³⁹-(GAB-GLit)-GLP-1(7-39);
Thr⁸Glu³⁵Arg²⁶,³⁴Lys³⁶-(GAB-GLit)-GLP-1(7-36);
Thr⁸Glu³⁵Arg²⁶,³⁴Lys³⁶-(GAB-GLit)-GLP-1(7-36)amide;
Thr⁸Glu³⁶Arg²⁶,³⁴Lys³⁷-(GAB-GLit)-GLP-1(7-37);
Thr⁸Glu³⁷Arg²⁶,³⁴Lys³⁸-(GAB-G Lit)-GLP-1(7-38);
Thr⁸Glu³Arg²⁶,³⁴Lys³⁹-(GAB-GLit)-GLP-1(7-39);
Thr⁸Glu³⁵Arg²⁶,³⁴Lys³⁶-(GAB-G Lit)-GLP-1(7-36);
Thr⁸Glu³⁵Arg²⁶,³⁴Lys³⁶-(GAB-GLit)-GLP-1(7-36)amide;
Thr⁸Glu³⁶Arg²⁶,³⁴Lys³⁷-(GAB-GLit)-GLP-1(7-37);
Thr⁸Glu³⁷Arg²⁶,³⁴Lys³⁸-(GAB-GLit)-GLP-1(7-38);
Thr⁸Glu³⁸Arg²⁶,³⁴Lys³⁹-(GAB-GLit)-GLP-1(7-39);
Thr⁸Asp³⁵Arg²⁶,³⁴Lys³⁶-(GAB-GLit)-GLP-1(7-36);
Thr⁸Asp³⁵Arg²⁶,³⁴Lys³⁶-(GAB-GLit)-GLP-1(7-36)amide;
Thr⁸Asp³⁶Arg²⁶,³⁴Lys³⁷-(GAB-GLit)-GLP-1(7-37);
Thr⁸Asp³⁷Arg²⁶,³⁴Lys³⁸-(GAB-GLit)-GLP-1(7-38);
Thr⁸Asp³⁸Arg²⁶,³⁴Lys³⁹-(GAB-GLit)-GLP-1(7-39);
Thr⁸Asp³⁵Arg²⁶,³⁴Lys³⁶-(GAB-GLit)-GLP-1(7-36);
Thr⁸Asp³⁵Arg²⁶,³⁴Lys³⁶-(GAB-GLit)-GLP-1(7-36)amide;
Thr⁸Asp³⁶Arg²⁶,³⁴Lys³⁷-(GAB-GLit)-GLP-1(7-37);
Thr⁸Asp³⁷Arg²⁶,³⁴Lys³⁸-(GAB-GLit)-GLP-1(7-38);
Thr⁸Asp³Arg²⁶,³⁴Lys³⁹-(GAB-GLit)-GLP-1(7-39);
Arg²⁶,³⁴Lys¹⁸-(GAB-GLit)-GLP-1(7-36); Arg²⁶,³⁴Lys¹⁸-(GAB-GLit)-GLP-1(7-36)amide; Arg²⁶,³⁴Lys¹⁸-(GAB-GLit)-GLP-1(7-37); Arg²⁶,³⁴Lys¹⁸-(GAB-GLit)-GLP-1(7-38); Gly⁸Asp¹⁹Arg²⁶,³⁴Lys¹⁸-(GAB-GLit)-GLP-1(7-36);
Gly⁸Asp¹⁷Arg²⁶,³⁴Lys¹⁸-(GAB-GLit)-GLP-1(7-36);
Gly⁸Asp¹⁹Arg²⁶,³⁴Lys¹⁸-(GAB-GLit)-GLP-1(7-36)amide;
Gly⁸Asp¹⁷Arg²⁶,³⁴Lys¹⁸-(GAB-GLit)-GLP-1(7-36)amide;
Gly⁸Asp¹⁹Arg²⁶,³⁴Lys¹⁸-(GAB-GLit)-GLP-1(7-37);
Gly⁸Asp¹⁹Arg²⁶,³⁴Lys¹⁸-(GAB-GLit)-GLP-1(7-38);
Gly⁸Asp¹⁷Arg²⁶,³⁴Lys¹⁸-(GAB-GLit)-GLP-1(7-38);
Arg²⁶,³⁴Lys²³-(GAB-GLit)-GLP-1(7-36); Arg²⁶,³⁴Lys²³-(GAB-GLit)-GLP-1(7-36)amide; Arg²⁶,³⁴Lys²³-(GAB-GLit)-GLP-1(7-37); Arg²⁶,³⁴Lys²³-(GAB-GLit)-GLP-1(7-38); Gly⁸Asp¹⁹Arg²⁶,³⁴Lys²³-(GAB-GLit)-GLP-1(7-36);
Gly⁸Asp¹⁷Arg²⁶,³⁴Lys²³-(GAB-GLit)-GLP-1(7-36);
Gly⁸Asp¹⁹Arg²⁶,³⁴Lys²³-(GAB-GLit)-GLP-1(7-36)amide;
Gly⁸Asp¹⁷Arg²⁶,³⁴Lys²³-(GAB-GLit)-GLP-1(7-36)amide;
Gly⁸Asp¹⁹Arg²⁶,³⁴Lys²³-(GAB-GLit)-GLP-1(7-37);
Gly⁸Asp¹⁹Arg²⁶,³⁴Lys²³-(GAB-GLit)-GLP-1(7-38);
Gly⁸Asp¹⁷Arg²⁶,³⁴Lys²³-(GAB-GLit)-GLP-1(7-38);
Arg²⁶,³⁴Lys²⁷-(GAB-GLit)-GLP-1(7-36); Arg²⁶,³⁴Lys²⁷-(GAB-GLit)-GLP-1(7-36)amide; Arg²⁶,³⁴Lys²⁷-(GAB-GLit)-GLP-1(7-37); Arg²⁶,³⁴Lys²⁷-(GAB-GLit)-GLP-1(7-38); Gly⁸Asp¹⁹Arg²⁶,³⁴Lys²⁷-(GAB-GLit)-GLP-1(7-36);
Gly⁸Asp¹⁷Arg²⁶,³⁴Lys²⁷-(GAB-GLit)-GLP-1(7-36);
Gly⁸Asp¹⁹Arg²⁶,³⁴Lys²⁷-(GAB-GLit)-GLP-1(7-36)amide;
Gly⁸Asp¹⁷Arg²⁶,³⁴Lys²⁷-(GAB-GLit)-GLP-1(7-36)amide;
Gly⁸Asp¹⁹Arg²⁶,³⁴Lys²⁷-(GAB-GLit)-GLP-1(7-37);
Gly⁸Asp¹⁹Arg²⁶,³⁴Lys²⁷-(GAB-GLit)-GLP-1(7-38);
Gly⁸Asp¹⁷Arg²⁶,³⁴Lys²⁷-(GAB-GLit)-GLP-1(7-38);
Arg²⁶,³⁴Lys¹⁸-(GAB-GLit)-GLP-1(7-36); Arg²⁶,³⁴Lys¹⁸-(GAB-GLit)-GLP-1(7-36)amide; Arg²⁶,³⁴Lys¹⁸-(GAB-GLit)-GLP-1(7-37); Arg²⁶,³⁴Lys¹⁸-(GAB-GLit)-GLP-1(7-38); Val⁸Asp¹⁹Arg²⁶,³⁴Lys¹⁸-(GAB-GLit)-GLP-1(7-36);
Val⁸Asp¹⁷Arg²⁶,³⁴Lys¹⁸-(GAB-GLit)-GLP-1(7-36);
Val⁸Asp¹⁹Arg²⁶,³⁴Lys¹⁸-(GAB-GLit)-GLP-1(7-36)amide;
Val⁸Asp¹⁷Arg²⁶,³⁴Lys¹⁸-(GAB-GLit)-GLP-1(7-36)amide;
Val⁸Asp¹⁹Arg²⁶,³⁴Lys¹⁸-(GAB-GLit)-GLP-1(7-37);
Val⁸Asp¹⁹Arg²⁶,³⁴Lys¹⁸-(GAB-GLit)-GLP-1(7-38);
Val⁸Asp¹⁷Arg²⁶,³⁴Lys¹⁸-(GAB-GLit)-GLP-1(7-38);
Arg²⁶,³⁴Lys²³-(GAB-GLit)-GLP-1(7-36); Arg²⁶,³⁴Lys²³-(GAB-GLit)-GLP-1(7-36)amide; Arg²⁶,³⁴Lys²³-(GAB-GLit)-GLP-1(7-37); Arg²⁶,³⁴Lys²³-(GAB-GLit)-GLP-1(7-38); Val⁸Asp¹⁹Arg²⁶,³⁴Lys²³-(GAB-GLit)-GLP-1(7-36);
Val⁸Asp¹⁷Arg²⁶,³⁴Lys²³-(GAB-GLit)-GLP-1(7-36);
Val⁸Asp¹⁹Arg²⁶,³⁴Lys²³-(GAB-GLit)-GLP-1(7-36)amide;
Val⁸Asp¹⁷Arg²⁶,³⁴Lys²³-(GAB-GLit)-GLP-1(7-36)amide;
Val⁸Asp¹⁹Arg²⁶,³⁴Lys²³-(GAB-GLit)-GLP-1(7-37);
Val⁸Asp¹⁹Arg²⁶,³⁴Lys²³-(GAB-GLit)-GLP-1(7-38);
Val⁸Asp¹⁷Arg²⁶,³⁴Lys²³-(GAB-GLit)-GLP-1(7-38);
Arg²⁶,³⁴Lys²⁷-(GAB-GLit)-GLP-1(7-36); Arg²⁶,³⁴Lys²⁷-(GAB-GLit)-GLP-1(7-36)amide; Arg²⁶,³⁴Lys²⁷-(GAB-GLit)-GLP-1(7-37); Arg²⁶,³⁴Lys²⁷-(GAB-GLit)-GLP-1(7-38); Val⁸Asp¹⁹Arg²⁶,³⁴Lys²⁷-(GAB-GLit)-GLP-1(7-36);
Val⁸Asp¹⁷Arg²⁶,³⁴Lys²⁷-(GAB-GLit)-GLP-1(7-36);
Val⁸Asp¹⁹Arg²⁶,³⁴Lys²⁷-(GAB-GLit)-GLP-1(7-36)amide;
Val⁸Asp¹⁷Arg²⁶,³⁴Lys²⁷-(GAB-GLit)-GLP-1(7-36)amide;
Val⁸Asp¹⁹Arg²⁶,³⁴Lys²⁷-(GAB-GLit)-GLP-1(7-37);
Val⁸Asp¹⁹Arg²⁶,³⁴Lys²⁷-(GAB-GLit)-GLP-1(7-38);
Val⁸Asp¹⁷Arg²⁶,³⁴Lys²⁷-(GAB-GLit)-GLP-1(7-38);
Arg²⁶,³⁴Lys¹⁸-(GAB-GLit)-GLP-1(7-36); Arg²⁶,³⁴Lys¹⁸-(GAB-GLit)-GLP-1(7-36)amide; Arg²⁶,³⁴Lys¹⁸-(GAB-GLit)-GLP-1(7-37); Arg²⁶,³⁴Lys¹⁸-(GAB-GLit)-GLP-1(7-38); Ser⁸Asp¹⁹Arg²⁶,³⁴Lys¹⁸-(GAB-GLit)-GLP-1(7-36);
Ser⁸Asp¹⁷Arg²⁶,³⁴Lys¹⁸-(GAB-GLit)-GLP-1(7-36);
Ser⁸Asp¹⁹Arg²⁶,³⁴Lys¹⁸-(GAB-GLit)-GLP-1(7-36)amide;
Ser⁸Asp¹⁷Arg²⁶,³⁴Lys¹⁸-(GAB-GLit)-GLP-1(7-36)amide;
Ser⁸Asp¹⁹Arg²⁶,³⁴Lys¹⁸-(GAB-GLit)-GLP-1(7-37);
Ser⁸Asp¹⁹Arg²⁶,³⁴Lys¹⁸-(GAB-GLit)-GLP-1(7-38);
Ser⁸Asp¹⁷Arg²⁶,³⁴Lys¹⁸-(GAB-GLit)-GLP-1(7-38);
Arg²⁶,³⁴Lys²³-(GAB-GLit)-GLP-1(7-36); Arg²⁶,³⁴Lys²³-(GAB-GLit)-GLP-1(7-36)amide; Arg²⁶,³⁴Lys²³-(GAB-GLit)-GLP-1(7-37); Arg²⁶,³⁴Lys²³-(GAB-GLit)-GLP-1(7-38); Ser⁸Asp¹⁹Arg²⁶,³⁴Lys²³-(GAB-GLit)-GLP-1(7-36);
Ser⁸Asp¹⁷Arg²⁶,³⁴Lys²³-(GAB-GLit)-GLP-1(7-36);
Ser⁸Asp¹⁹Arg²⁶,³⁴Lys²³-(GAB-GLit)-GLP-1(7-36)amide;
Ser⁸Asp¹⁷Arg²⁶,³⁴Lys²³-(GAB-GLit)-GLP-1(7-36)amide;
Ser⁸Asp¹⁹Arg²⁶,³⁴Lys²³-(GAB-GLit)-GLP-1(7-37);
Ser⁸Asp¹⁹Arg²⁶,³⁴Lys²³-(GAB-GLit)-GLP-1(7-38);

Ser⁸Asp¹⁷Arg²⁶,³⁴Lys²³-(GAB-GLit)-GLP-1(7-38);
Arg²⁶,³⁴Lys²⁷-(GAB-GLit)-GLP-1(7-36); Arg²⁶,³⁴Lys²⁷-(GAB-GLit)-GLP-1(7-36)amide; Arg²⁶,³⁴Lys²⁷-(GAB-GLit)-GLP-1(7-37); Arg²⁶,³⁴Lys²⁷-(GAB-GLit)-GLP-1(7-38); Ser⁸Asp¹⁹Arg²⁶,³⁴Lys²⁷-(GAB-GLit)-GLP-1(7-36);
Ser⁸Asp¹⁷Arg²⁶,³⁴Lys²⁷-(GAB-GLit)-GLP-1(7-36);
Ser⁸Asp¹⁹Arg²⁶,³⁴Lys²⁷-(GAB-GLit)-GLP-1(7-36)amide;
Ser⁸Asp¹⁷Arg²⁶,³⁴Lys²⁷-(GAB-GLit)-GLP-1(7-36)amide;
Ser⁸Asp¹⁹Arg²⁶,³⁴Lys²⁷-(GAB-GLit)-GLP-1(7-37);
Ser⁸Asp¹⁹Arg²⁶,³⁴Lys²⁷-(GAB-GLit)-GLP-1(7-38);
Ser⁸Asp¹⁷Arg²⁶,³⁴Lys²⁷-(GAB-GLit)-GLP-1(7-38);
Arg²⁶,³⁴Lys¹⁸-(GAB-GLit)-GLP-1(7-36); Arg²⁶,³⁴Lys¹⁸-(GAB-GLit)-GLP-1(7-36)amide; Arg²⁶,³⁴Lys¹⁸-(GAB-GLit)-GLP-1(7-37); Arg²⁶,³⁴Lys¹⁸-(GAB-GLit)-GLP-1(7-38); Thr⁸Asp¹⁹Arg²⁶,³⁴Lys¹⁸-(GAB-GLit)-GLP-1(7-36);
Thr⁸Asp¹⁷Arg²⁶,³⁴Lys¹⁸-(GAB-GLit)-GLP-1(7-36);
Thr⁸Asp¹⁹Arg²⁶,³⁴Lys¹⁸-(GAB-GLit)-GLP-1(7-36)amide;
Thr⁸Asp¹⁷Arg²⁶,³⁴Lys¹⁸-(GAB-GLit)-GLP-1(7-36)amide;
Thr⁸Asp¹⁹Arg²⁶,³⁴Lys¹⁸-(GAB-GLit)-GLP-1(7-37);
Thr⁸Asp¹⁹Arg²⁶,³⁴Lys¹⁸-(GAB-GLit)-GLP-1(7-38);
Thr⁸Asp¹⁷Arg²⁶,³⁴Lys¹⁸-(GAB-GLit)-GLP-1(7-38);
Arg²⁶,³⁴Lys²³-(GAB-GLit)-GLP-1(7-36); Arg²⁶,³⁴Lys²³-(GAB-GLit)-GLP-1(7-36)amide; Arg²⁶,³⁴Lys²³-(GAB-GLit)-GLP-1(7-37); Arg²⁶,³⁴Lys²³-(GAB-GLit)-GLP-1(7-38); Thr⁸Asp¹⁹Arg²⁶,³⁴Lys²³-(GAB-GLit)-GLP-1(7-36);
Thr⁸Asp¹⁷Arg²⁶,³⁴Lys²³-(GAB-GLit)-GLP-1(7-36);
Thr⁸Asp¹⁹Arg²⁶,³⁴Lys²³-(GAB-GLit)-GLP-1(7-36)amide;
Thr⁸Asp¹⁷Arg²⁶,³⁴Lys²³-(GAB-GLit)-GLP-1(7-36)amide;
Thr⁸Asp¹⁹Arg²⁶,³⁴Lys²³-(GAB-GLit)-GLP-1(7-37);
Thr⁸Asp¹⁹Arg²⁶,³⁴Lys²³-(GAB-GLit)-GLP-1(7-38);
Thr⁸Asp¹⁷Arg²⁶,³⁴Lys²³-(GAB-GLit)-GLP-1(7-38);
Arg²⁶,³⁴Lys²⁷-(GAB-GLit)-GLP-1(7-36); Arg²⁶,³⁴Lys²⁷-(GAB-GLit)-GLP-1(7-36)amide; Arg²⁶,³⁴Lys²⁷-(GAB-GLit)-GLP-1(7-37); Arg²⁶,³⁴Lys²⁷-(GAB-GLit)-GLP-1(7-38); Thr⁸Asp¹⁹Arg²⁶,³⁴Lys²⁷-(GAB-GLit)-GLP-1(7-36);
Thr⁸Asp¹⁷Arg²⁶,³⁴Lys²⁷-(GAB-GLit)-GLP-1(7-36);
Thr⁸Asp¹⁹Arg²⁶,³⁴Lys²⁷-(GAB-GLit)-GLP-1(7-36)amide;
Thr⁸Asp¹⁷Arg²⁶,³⁴Lys²⁷-(GAB-GLit)-GLP-1(7-36)amide;
Thr⁸Asp¹⁹Arg²⁶,³⁴Lys²⁷-(GAB-GLit)-GLP-1(7-37);
Thr⁸Asp¹⁹Arg²⁶,³⁴Lys²⁷-(GAB-GLit)-GLP-1(7-38);
Thr⁸Asp¹⁷Arg²⁶,³⁴Lys²⁷-(GAB-GLit)-GLP-1(7-38);

Other preferred derivatives of GLP-1 analogs of the present invention are:
Lys²⁶,³⁴-bis-(Glut-ADod)-GLP-1(7-36); Lys²⁶,³⁴-bis-(Glut-ADod)-GLP-1(7-37); Lys²⁶,³⁴-bis-(Glut-ADod)-GLP-1(7-38); Lys²⁶,³⁴-bis-(Glut-ADod)-GLP-1(7-39)
Arg²⁶Lys³⁴,³⁶-bis-(Glut-ADod)-GLP-1(7-36); Arg³⁴Lys²⁶,³⁶-bis-(Glut-ADod)-GLP-1(7-36); Arg²⁶Lys³⁴,³⁶-bis-(Glut-ADod)-GLP-1(7-37); Arg³⁴Lys²⁶,³⁶-bis-(Glut-ADod)-GLP-1(7-37); Arg²⁶Lys³⁴,³⁷-bis(Glut-ADod)-GLP-1(7-37); Arg³⁴Lys²⁶,³⁷-bis-(Glut-ADod)-GLP-1(7-37); Arg²⁶Lys³⁴,³⁹-bis-(Glut-ADod)-GLP-1(7-39); Arg³⁴Lys²⁶,³⁹-bis-(Glut-ADod)-GLP-1(7-39); Arg²⁶,³⁴Lys³⁶,³⁹-bis-(Glut-ADod)-GLP-1(7-39);
Arg²⁶Lys¹⁸,³⁴-bis-(Glut-ADod)-GLP-1(7-36); Arg³⁴Lys¹⁸,²⁶-bis-(Glut-ADod)-GLP-1(7-36); Arg²⁶Lys¹⁸,³⁴-bis-(Glut-ADod)-GLP-1(7-37); Arg³⁴Lys¹⁸,²⁶-bis-(Glut-ADod)-GLP-1(7-37); Arg²⁶Lys¹⁸,³⁴-bis-(Glut-ADod)-GLP-1(7-38); Arg³⁴Lys¹⁸,²⁶-bis-(Glut-ADod)-GLP-1(7-38); Arg²⁶Lys¹⁸,³⁴-bis-(Glut-ADod)-GLP-1(7-39); Arg³⁴Lys¹⁸,²⁶-bis-(Glut-ADod)-GLP-1(7-39);
Arg²⁶Lys²³,³⁴-bis-(Glut-ADod)-GLP-1(7-36); Arg³⁴Lys²³,²⁶-bis-(Glut-ADod)-GLP-1(7-36); Arg²⁶Lys²³,³⁴-bis-(Glut-ADod)-GLP-1(7-37); Arg³⁴Lys²³,²⁶-bis-(Glut-ADod)-GLP-1(7-37); Arg²⁶Lys²³,³⁴-bis-(Glut-ADod)-GLP-1(7-38); Arg³⁴Lys²³,²⁶-bis-(Glut-ADod)-GLP-1(7-38); Arg²⁶Lys²³,³⁴-bis-(Glut-ADod)-GLP-1(7-39); Arg³⁴Lys²³,²⁶-bis-(Glut-ADod)-GLP-1(7-39);
Arg²⁶Lys²⁷,³⁴-bis-(Glut-ADod)-GLP-1(7-36); Arg³⁴Lys²⁷,²⁶-bis-(Glut-ADod)-GLP-1(7-36); Arg²⁶Lys²⁷,³⁴-bis-(Glut-ADod)-GLP-1(7-37); Arg³⁴Lys²⁷,²⁶-bis-(Glut-ADod)-GLP-1(7-37); Arg²⁶Lys²⁷,³⁴-bis-(Glut-ADod)-GLP-1(7-38); Arg³⁴Lys²⁷,²⁶-bis-(Glut-ADod)-GLP-1(7-38); Arg²⁶Lys²⁷,³⁴-bis-(Glut-ADod)-GLP-1(7-39); Arg³⁴Lys²⁷,²⁶-bis-(Glut-ADod)-GLP-1(7-39);
Gly⁸Lys²⁶,³⁴-bis-(Glut-ADod)-GLP-1(7-36); Gly⁸Lys²⁶,³⁴-bis-(Glut-ADod)-GLP-1(7-37); Gly⁸Lys²⁶,³⁴-bis-(Glut-ADod)-GLP-1(7-38); Gly⁸Lys²⁶,³⁴-bis-(Glut-ADod)-GLP-1(7-39)
Gly⁸Arg²⁶Lys³⁴,³⁶-bis-(Glut-ADod)-GLP-1(7-36);
Gly⁸Arg³⁴Lys²⁶,³⁶-bis-(Glut-ADod)-GLP-1(7-36);
Gly⁸Arg²⁶Lys³⁴,³⁶-bis-(Glut-ADod)-GLP-1(7-37);
Gly⁸Arg³⁴Lys²⁶,³⁶-bis-(Glut-ADod)-GLP-1(7-37);
Gly⁸Arg²⁶Lys³⁴,³⁷-bis-(Glut-ADod)-GLP-1(7-37);
Gly⁸Arg³⁴Lys²⁶,³⁷-bis-(Glut-ADod)-GLP-1(7-37);
Gly⁸Arg²⁶Lys³⁴,³⁸-bis-(Glut-ADod)-GLP-1(7-38);
Gly⁸Arg³⁴Lys²⁶,³⁸-bis-(Glut-ADod)-GLP-1(7-38);
Gly⁸Arg²⁶,³⁴Lys³⁶,³⁸-bis-(Glut-ADod)-GLP-1(7-38);
Gly⁸Arg²⁶Lys³⁴,³⁹-bis-(Glut-ADod)-GLP-1(7-39);
Gly⁸Arg³⁴Lys²⁶,³⁹-bis-(Glut-ADod)-GLP-1(7-39);
Gly⁸Arg²⁶,³⁴Lys³⁶,³⁹-bis-(Glut-ADod)-GLP-1(7-39);
Val⁸Lys²⁶,³⁴-bis-(Glut-ADod)-GLP-1(7-36); Val⁸Lys²⁶,³⁴-bis-(Glut-ADod)-GLP-1(7-37); Val⁸Lys²⁶,³⁴-bis-(Glut-ADod)-GLP-1(7-38); Val⁸Lys²⁶,³⁴-bis-(Glut-ADod)-GLP-1(7-39)
Val⁸Arg²⁶Lys³⁴,³⁶-bis-(Glut-ADod)-GLP-1(7-36);
Val⁸Arg³⁴Lys²⁶,³⁶-bis-(Glut-ADod)-GLP-1(7-36);
Val⁸Arg²⁶Lys³⁴,³⁶-bis-(Glut-ADod)-GLP-1(7-37);
Val⁸Arg³⁴Lys²⁶,³⁶-bis-(Glut-ADod)-GLP-1(7-37);
Val⁸Arg²⁶Lys³⁴,³⁷-bis-(Glut-ADod)-GLP-1(7-37);
Val⁸Arg³⁴Lys²⁶,³⁷-bis-(Glut-ADod)-GLP-1(7-37);
Val⁸Arg²⁶Lys³⁴,³⁸-bis-(Glut-ADod)-GLP-1(7-38);
Val⁸Arg³⁴Lys²⁶,³⁸-bis-(Glut-ADod)-GLP-1(7-38);
Val⁸Arg²⁶,³⁴Lys³⁶,³⁸-bis-(Glut-ADod)-GLP-1(7-38);
Val⁸Arg²⁶Lys³⁴,³⁹-bis-(Glut-ADod)-GLP-1(7-39);
Val⁸Arg³⁴Lys²⁶,³⁹-bis-(Glut-ADod)-GLP-1(7-39);
Val⁸Arg²⁶,³⁴Lys³⁶,³⁹-bis-(Glut-ADod)-GLP-1(7-39);
Ser⁸Lys²⁶,³⁴-bis-(Glut-ADod)-GLP-1(7-36); Ser⁸Lys²⁶,³⁴-bis-(Glut-ADod)-GLP-1(7-37); Ser⁸Lys²⁶,³⁴-bis-(Glut-ADod)-GLP-1(7-38); Ser⁸Lys²⁶,³⁴-bis-(Glut-ADod)-GLP-1(7-39)
Ser⁸Arg²⁶Lys³⁴,³⁶-bis-(Glut-ADod)-GLP-1(7-36);
Ser⁸Arg³⁴Lys²⁶,³⁶-bis-(Glut-ADod)-GLP-1(7-36);
Ser⁸Arg²⁶Lys³⁴,³⁶-bis-(Glut-ADod)-GLP-1(7-37);
Ser⁸Arg³⁴Lys²⁶,³⁶-bis-(Glut-ADod)-GLP-1(7-37);
Ser⁸Arg²⁶Lys³⁴,³⁷-bis-(Glut-ADod)-GLP-1(7-37);
Ser⁸Arg³⁴Lys²⁶,³⁷-bis-(Glut-ADod)-GLP-1(7-37);
Ser⁸Arg²⁶Lys³⁴,³⁸-bis-(Glut-ADod)-GLP-1(7-38);
Ser⁸Arg³⁴Lys²⁶,³⁸-bis-(Glut-ADod)-GLP-1(7-38);
Ser⁸Arg²⁶,³⁴Lys³⁶,³⁸-bis-(Glut-ADod)-GLP-1(7-38);
Ser⁸Arg²⁶Lys³⁴,³⁹-bis-(Glut-ADod)-GLP-1(7-39);
Ser⁸Arg³⁴Lys²⁶,³⁹-bis-(Glut-ADod)-GLP-1(7-39);
Ser⁸Arg²⁶,³⁴Lys³⁶,³⁹-bis-(Glut-ADod)-GLP-1(7-39);
Thr⁸Lys²⁶,³⁴-bis-(Glut-ADod)-GLP-1(7-36); Thr⁸Lys²⁶,³⁴-bis-(Glut-ADod)-GLP-1(7-37); Thr⁸Lys²⁶,³⁴-bis-(Glut-ADod)-GLP-1(7-38); Thr⁸Lys²⁶,³⁴-bis-(Glut-ADod)-GLP-1(7-39)
Thr⁸Arg²⁶Lys³⁴,³⁶-bis-(Glut-ADod)-GLP-1(7-36);
Thr⁸Arg³⁴Lys²⁶,³⁶-bis-(Glut-ADod)-GLP-1(7-36);
Thr⁸Arg²⁶Lys³⁴,³⁶-bis-(Glut-ADod)-GLP-1(7-37);
Thr⁸Arg³⁴Lys²⁶,³⁶-bis-(Glut-ADod)-GLP-1(7-37);
Thr⁸Arg²⁶Lys³⁴,³⁷-bis-(Glut-ADod)-GLP-1(7-37);

Thr⁸Arg³⁴Lys²⁶,³⁷-bis-(Glut-ADod)-GLP-1(7-37);
Thr⁸Arg²⁶Lys³⁴,³⁸-bis-(Glut-ADod)-GLP-1(7-38);
Thr⁸Arg³⁴Lys²⁶,³⁸-bis-(Glut-ADod)-GLP-1(7-38);
Thr⁸Arg²⁶,³⁴Lys³⁶,³⁸-bis-(Glut-ADod)-GLP-1(7-38);
Thr⁸Arg²⁶Lys³⁴,³⁹-bis-(Glut-ADod)-GLP-1(7-39);
Thr⁸Arg³⁴Lys²⁶,³⁹-bis-(Glut-ADod)-GLP-1(7-39);
Thr⁸Arg²⁶,³⁴Lys³⁶,³⁹-bis-(Glut-ADod-GLP-1(7-39);
Lys²⁶,³⁴-bis-(Glut-ATet)-GLP-1(7-36); Lys²⁶,³⁴-bis-(Glut-ATet)-GLP-1(7-37); Lys²⁶,³⁴-bis-(Glut-ATet)-GLP-1(7-38); Lys²⁶,³⁴-bis-(Glut-ATet)-GLP-1(7-39)
Arg²⁶Lys³⁴,³⁶-bis-(Glut-ATet)-GLP-1(7-36); Arg³⁴Lys²⁶,³⁶-bis-(Glut-ATet)-GLP-1(7-36); Arg²⁶Lys³⁴,³⁶-bis-(Glut-ATet)-GLP-1(7-37); Arg³⁴Lys²⁶,³⁶-bis-(Glut-ATet)-GLP-1(7-37); Arg²⁶Lys³⁴,³⁷-bis-(Glut-ATet)-GLP-1(7-37); Arg³⁴Lys²⁶,³⁷-bis-(Glut-ATet)-GLP-1(7-37); Arg²⁶Lys³⁴,³⁹-bis-(Glut-ATet)-GLP-1(7-39); Arg³⁴Lys²⁶,³⁹-bis-(Glut-ATet)-GLP-1(7-39); Arg²⁶,³⁴Lys³⁶,³⁹-bis-(Glut-ATet)-GLP-1(7-39);
Arg²⁶Lys¹⁸,³⁴-bis-(Glut-ATet)-GLP-1(7-36); Arg³⁴Lys¹⁸,²⁶-bis-(Glut-ATet)-GLP-1(7-36); Arg²⁶Lys¹⁸,³⁴-bis-(Glut-ATet)-GLP-1(7-37); Arg³⁴Lys¹⁸,²⁶-bis-(Glut-ATet)-GLP-1(7-37); Arg²⁶Lys¹⁸,³⁴-bis-(Glut-ATet)-GLP-1(7-38); Arg³⁴Lys¹⁸,²⁶-bis-(Glut-ATet)-GLP-1(7-38); Arg²⁶Lys¹⁸,³⁴-bis-(Glut-ATet)-GLP-1(7-39); Arg³⁴Lys¹⁸,²⁶-bis-(Glut-ATet)-GLP-1(7-39);
Arg²⁶Lys²³,³⁴-bis-(Glut-ATet)-GLP-1(7-36); Arg³⁴Lys²³,²⁶-bis-(Glut-ATet)-GLP-1(7-36); Arg²⁶Lys²³,³⁴-bis-(Glut-ATet)-GLP-1(7-37); Arg³⁴Lys²³,²⁶-bis-(Glut-ATet)-GLP-1(7-37); Arg²⁶Lys²³,³⁴-bis-(Glut-ATet)-GLP-1(7-38); Arg³⁴Lys²³,²⁶-bis-(Glut-ATet)-GLP-1(7-38); Arg²⁶Lys²³,³⁴-bis-(Glut-ATet)-GLP-1(7-39); Arg³⁴Lys²³,²⁶-bis-(Glut-ATet)-GLP-1(7-39);
Arg²⁶Lys²⁷,³⁴-bis-(Glut-ATet)-GLP-1(7-36); Arg³⁴Lys²⁷,²⁶-bis-(Glut-ATet)-GLP-1(7-36); Arg²⁶Lys²⁷,³⁴-bis-(Glut-ATet)-GLP-1(7-37); Arg³⁴Lys²⁷,²⁶-bis-(Glut-ATet)-GLP-1(7-37); Arg²⁶Lys²⁷,³⁴-bis-(Glut-ATet)-GLP-1(7-38); Arg³⁴Lys²⁷,²⁶-bis-(Glut-ATet)-GLP-1(7-38); Arg²⁶Lys²⁷,³⁴-bis-(Glut-ATet)-GLP-1(7-39); Arg³⁴Lys²⁷,²⁶-bis-(Glut-ATet)-GLP-1(7-39);
Gly⁸Lys²⁶,³⁴-bis-(Glut-ATet)-GLP-1(7-36); Gly⁸Lys²⁶,³⁴-bis-(Glut-ATet)-GLP-1(7-37); Gly⁸Lys²⁶,³⁴-bis-(Glut-ATet)-GLP-1(7-38); Gly⁸Lys²⁶,³⁴-bis-(Glut-ATet)-GLP-1(7-39)
Gly⁸Arg²⁶Lys³⁴,³⁶-bis-(Glut-ATet)-GLP-1(7-36);
Gly⁸Arg³⁴Lys²⁶,³⁶-bis-(Glut-ATet)-GLP-1(7-36);
Gly⁸Arg²⁶Lys³⁴,³⁶-bis-(Glut-ATet)-GLP-1(7-37);
Gly⁸Arg³⁴Lys²⁶,³⁶-bis-(Glut-ATet)-GLP-1(7-37);
Gly⁸Arg²⁶Lys³⁴,³⁷-bis-(Glut-ATet)-GLP-1(7-37);
Gly⁸Arg³⁴Lys²⁶,³⁷-bis-(Glut-ATet)-GLP-1(7-37);
Gly⁸Arg²⁶Lys³⁴,³⁸-bis-(Glut-ATet)-GLP-1(7-38);
Gly⁸Arg³⁴Lys²⁶,³⁸-bis-(Glut-ATet)-GLP-1(7-38);
Gly⁸Arg²⁶,³⁴Lys³⁶,³⁸-bis-(Glut-ATet)-GLP-1(7-38);
Gly⁸Arg²⁶Lys³⁴,³⁹-bis-(Glut-ATet)-GLP-1(7-39);
Gly⁸Arg³⁴Lys²⁶,³⁹-bis-(Glut-ATet)-GLP-1(7-39);
Gly⁸Arg²⁶,³⁴Lys³⁶,³⁹-bis-(Glut-ATet)-GLP-1(7-39);
Val⁸Lys²⁶,³⁴-bis-(Glut-ATet)-GLP-1(7-36); Val⁸Lys²⁶,³⁴-bis-(Glut-ATet)-GLP-1(7-37); Val⁸Lys²⁶,³⁴-bis-(Glut-ATet)-GLP-1(7-38); Val⁸Lys²⁶,³⁴-bis-(Glut-ATet)-GLP-1(7-39)
Val⁸Arg²⁶Lys³⁴,³⁶-bis-(Glut-ATet)-GLP-1(7-36);
Val⁸Arg³⁴Lys²⁶,³⁶-bis-(Glut-ATet)-GLP-1(7-36);
Val⁸Arg²⁶Lys³⁴,³⁶-bis-(Glut-ATet)-GLP-1(7-37);
Val⁸Arg³⁴Lys²⁶,³⁶-bis-(Glut-ATet)-GLP-1(7-37);
Val⁸Arg²⁶Lys³⁴,³⁷-bis-(Glut-ATet)-GLP-1(7-37);
Val⁸Arg³⁴Lys²⁶,³⁷-bis-(Glut-ATet)-GLP-1(7-37);
Val⁸Arg²⁶Lys³⁴,³⁸-bis-(Glut-ATet)-GLP-1(7-38);
Val⁸Arg³⁴Lys²⁶,³⁸-bis-(Glut-ATet)-GLP-1(7-38); Val⁸Arg²⁶,³⁴Lys³⁶,³⁸-bis-(Glut-ATet)-GLP-1(7-38);
Val⁸Arg²⁶Lys³⁴,³⁹-bis-(Glut-ATet)-GLP-1(7-39);
Val⁸Arg³⁴Lys²⁶,³⁹-bis-(Glut-ATet)-GLP-1(7-39); Val⁸Arg²⁶,³⁴Lys³⁶,³⁹-bis-(Glut-ATet)-GLP-1(7-39);
Ser⁸Lys²⁶,³⁴-bis-(Glut-ATet)-GLP-1(7-36); Ser⁸Lys²⁶,³⁴-bis-(Glut-ATet)-GLP-1(7-37); Ser⁸Lys²⁶,³⁴-bis-(Glut-ATet)-GLP-1(7-38); Ser⁸Lys²⁶,³⁴-bis-(Glut-ATet)-GLP-1(7-39)
Ser⁸Arg²⁶Lys³⁴,³⁶-bis-(Glut-ATet)-GLP-1(7-36);
Ser⁸Arg³⁴Lys²⁶,³⁶-bis-(Glut-ATet)-GLP-1(7-36);
Ser⁸Arg²⁶Lys³⁴,³⁶-bis-(Glut-ATet)-GLP-1(7-37);
Ser⁸Arg³⁴Lys²⁶,³⁶-bis-(Glut-ATet)-GLP-1(7-37);
Ser⁸Arg²⁶Lys³⁴,³⁷-bis-(Glut-ATet)-GLP-1(7-37);
Ser⁸Arg³⁴Lys²⁶,³⁷-bis-(Glut-ATet)-GLP-1(7-37);
Ser⁸Arg²⁶Lys³⁴,³⁸-bis-(Glut-ATet)-GLP-1(7-38);
Ser⁸Arg³⁴Lys²⁶,³⁸-bis-(Glut-ATet)-GLP-1(7-38); Ser⁸Arg²⁶,³⁴Lys³⁶,³⁸-bis-(Glut-ATet)-GLP-1(7-38);
Ser⁸Arg²⁶Lys³⁴,³⁹-bis-(Glut-ATet)-GLP-1(7-39);
Ser⁸Arg³⁴Lys²⁶,³⁹-bis-(Glut-ATet)-GLP-1(7-39); Ser⁸Arg²⁶,³⁴Lys³⁶,³⁹-bis-(Glut-ATet)-GLP-1(7-39);
Thr⁸Lys²⁶,³⁴-bis-(Glut-ATet)-GLP-1(7-36); Thr⁸Lys²⁶,³⁴-bis-(Glut-ATet)-GLP-1(7-37); Thr⁸Lys²⁶,³⁴-bis-(Gut-ATet)-GLP-1(7-38); Thr⁸Lys²⁶,³⁴-bis-(Gut-ATet)-GLP-1(7-39)
Thr⁸Arg²⁶Lys³⁴,³⁶-bis-(Glut-ATet)-GLP-1(7-36);
Thr⁸Arg³⁴Lys²⁶,³⁶-bis-(Glut-ATet)-GLP-1(7-36);
Thr⁸Arg²⁶Lys³⁴,³⁶-bis-(Glut-ATet)-GLP-1(7-37);
Thr⁸Arg³⁴Lys²⁶,³⁶-bis-(Glut-ATet)-GLP-1(7-37);
Thr⁸Arg²⁶Lys³⁴,³⁷-bis-(Glut-ATet)-GLP-1(7-37);
Thr⁸Arg³⁴Lys²⁶,³⁷-bis-(Glut-ATet)-GLP-1(7-37);
Thr⁸Arg²⁶Lys³⁴,³⁸-bis-(Glut-ATet)-GLP-1(7-38);
Thr⁸Arg³⁴Lys²⁶,³⁸-bis-(Glut-ATet)-GLP-1(7-38);
Thr⁸Arg²⁶,³⁴Lys³⁶,³⁸-bis-(Glut-ATet)-GLP-1(7-38);
Thr⁸Arg²⁶Lys³⁴,³⁹-bis-(Glut-ATet)-GLP-1(7-39);
Thr⁸Arg³⁴Lys²⁶,³⁹-bis-(Glut-ATet)-GLP-1(7-39);
Thr⁸Arg²⁶,³⁴Lys³⁶,³⁹-bis-(Glut-ATet)-GLP-1(7-39);
Lys²⁶,³⁴-bis-(Glut-AHex)-GLP-1(7-36); Lys²⁶,³⁴-bis-(Glut-AHex)-GLP-1(7-37); Lys²⁶,³⁴-bis-(Glut-AHex)-GLP-1(7-38); Lys²⁶,³⁴-bis-(Gut-AHex)-GLP-1(7-39)
Arg²⁶Lys³⁴,³⁶-bis-(Glut-AHex)-GLP-1(7-36); Arg³⁴Lys²⁶,³⁶-bis-(Glut-AHex)-GLP-1(7-36); Arg²⁶Lys³⁴,³⁶-bis-(Glut-AHex)-GLP-1(7-37); Arg³⁴Lys²⁶,³⁶-bis-(Glut-AHex)-GLP-1(7-37); Arg²⁶Lys³⁴,³⁷-bis-(Glut-AHex)-GLP-1(7-37); Arg³⁴Lys²⁶,³⁷-bis-(Glut-AHex)-GLP-1(7-37); Arg²⁶Lys³⁴,³⁹-bis-(Glut-AHex)-GLP-1(7-39); Arg³⁴Lys²⁶,³⁹-bis-(Glut-AHex)-GLP-1(7-39); Arg²⁶,³⁴Lys³⁶,³⁹-bis-(Glut-AHex)-GLP-1(7-39);
Arg²⁶Lys¹⁸,³⁴-bis-(Glut-AHex)-GLP-1(7-36); Arg³⁴Lys¹⁸,²⁶-bis-(Glut-AHex)-GLP-1(7-36); Arg²⁶Lys¹⁸,³⁴-bis-(Glut-AHex)-GLP-1(7-37); Arg³⁴Lys¹⁸,²⁶-bis-(Glut-AHex)-GLP-1(7-37); Arg²⁶Lys¹⁸,³⁴-bis-(Glut-AHex)-GLP-1(7-38); Arg³⁴Lys¹⁸,²⁶-bis-(Glut-AHex)-GLP-1(7-38); Arg²⁶Lys¹⁸,³⁴-bis-(Glut-AHex)-GLP-1(7-39); Arg³⁴Lys¹⁸,²⁶-bis-(Glut-AHex)-GLP-1(7-39);
Arg²⁶Lys²³,³⁴-bis-(Glut-AHex)-GLP-1(7-36); Arg³⁴Lys²³,²⁶-bis-(Glut-AHex)-GLP-1(7-36); Arg²⁶Lys²³,³⁴-bis-(Glut-AHex)-GLP-1(7-37); Arg³⁴Lys²³,²⁶-bis-(Glut-AHex)-GLP-1(7-37); Arg²⁶Lys²³,³⁴-bis-(Glut-AHex)-GLP-1(7-38); Arg³⁴Lys²³,²⁶-bis-(Glut-AHex)-GLP-1(7-38); Arg²⁶Lys²³,³⁴-bis-(Glut-AHex)-GLP-1(7-39); Arg³⁴Lys²³,²⁶-bis-(Glut-AHex)-GLP-1(7-39);
Arg²⁶Lys²⁷,³⁴-bis-(Glut-AHex)-GLP-1(7-36); Arg³⁴Lys²⁷,²⁶-bis-(Glut-AHex)-GLP-1(7-36); Arg²⁶Lys²⁷,³⁴-bis-(Glut-AHex)-GLP-1(7-37); Arg³⁴Lys²⁷,²⁶-bis-(Glut-AHex)-GLP-1(7-37); Arg²⁶Lys²⁷,³⁴-bis-(Glut-AHex)-GLP-1(7-38); Arg³⁴Lys²⁷,²⁶-bis-(Glut-AHex)-GLP-1(7-38); Arg²⁶Lys²⁷,³⁴-bis-(Glut-AHex)-GLP-1(7-39); Arg³⁴Lys²⁷,²⁶-bis-(Glut-AHex)-GLP-1(7-39);

Gly$^8$Lys$^{26,34}$-bis-(Glut-AHex)-GLP-1(7-36); Gly$^8$Lys$^{26,34}$-bis-(Glut-AHex)-GLP-1(7-37); Gly$^8$Lys$^{26,34}$-bis-(Glut-AHex)-GLP-1(7-38); Gly$^8$Lys$^{26,34}$-bis-(Glut-AHex)-GLP-1(7-39)

Gly$^8$Arg$^{26}$Lys$^{34,36}$-bis-(Glut-AHex)-GLP-1(7-36);
Gly$^8$Arg$^{34}$Lys$^{26,36}$-bis-(Glut-AHex)-GLP-1(7-36);
Gly$^8$Arg$^{26}$Lys$^{34,36}$-bis-(Glut-AHex)-GLP-1(7-37);
Gly$^8$Arg$^{34}$Lys$^{26,36}$-bis-(Glut-AHex)-GLP-1(7-37);
Gly$^8$Arg$^{26}$Lys$^{34,37}$-bis-(Glut-AHex)-GLP-1(7-37);
Gly$^8$Arg$^{34}$Lys$^{26,37}$-bis-(Glut-AHex)-GLP-1(7-37);
Gly$^8$Arg$^{26}$Lys$^{34,38}$-bis-(Glut-AHex)-GLP-1(7-38);
Gly$^8$Arg$^{34}$Lys$^{26,38}$-bis-(Glut-AHex)-GLP-1(7-38);
Gly$^8$Arg$^{26,34}$Lys$^{36,38}$-bis-(Glut-AHex)-GLP-1(7-38);
Gly$^8$Arg$^{26}$Lys$^{34,39}$-bis-(Glut-AHex)-GLP-1(7-39);
Gly$^8$Arg$^{34}$Lys$^{26,39}$-bis-(Glut-AHex)-GLP-1(7-39);
Gly$^8$Arg$^{26,34}$Lys$^{36,39}$-bis-(Glut-AHex)-GLP-1(7-39);
Val$^8$Lys$^{26,34}$-bis-(Glut-AHex)-GLP-1(7-36); Val$^8$Lys$^{26,34}$-bis-(Glut-AHex)-GLP-1(7-37); Val$^8$Lys$^{26,34}$-bis-(Glut-AHex)-GLP-1(7-38); Val$^8$Lys$^{26,34}$-bis-(Glut-AHex)-GLP-1(7-39)

Val$^8$Arg$^{26}$Lys$^{34,36}$-bis-(Glut-AHex)-GLP-1(7-36);
Val$^8$Arg$^{34}$Lys$^{26,36}$-bis-(Glut-AHex)-GLP-1(7-36);
Val$^8$Arg$^{26}$Lys$^{34,36}$-bis-(Glut-AHex)-GLP-1(7-37);
Val$^8$Arg$^{34}$Lys$^{26,36}$-bis-(Glut-AHex)-GLP-1(7-37);
Val$^8$Arg$^{26}$Lys$^{34,37}$-bis-(Glut-AHex)-GLP-1(7-37);
Val$^8$Arg$^{34}$Lys$^{26,37}$-bis-(Glut-AHex)-GLP-1(7-37);
Val$^8$Arg$^{26}$Lys$^{34,38}$-bis-(Glut-AHex)-GLP-1(7-38);
Val$^8$Arg$^{34}$Lys$^{26,38}$-bis-(Glut-AHex)-GLP-1(7-38);
Val$^8$Arg$^{26,34}$Lys$^{36,38}$-bis-(Glut-AHex)-GLP-1(7-38);
Val$^8$Arg$^{26}$Lys$^{34,39}$-bis-(Glut-AHex)-GLP-1(7-39);
Val$^8$Arg$^{34}$Lys$^{26,39}$-bis-(Glut-AHex)-GLP-1(7-39);
Val$^8$Arg$^{26,34}$Lys$^{36,39}$-bis-(Glut-AHex)-GLP-1(7-39);
Ser$^8$Lys$^{26,34}$-bis-(Glut-AHex)-GLP-1(7-36); Ser$^8$Lys$^{26,34}$-bis-(Glut-AHex)-GLP-1(7-37); Ser$^8$Lys$^{26,34}$-bis-(Glut-AHex)-GLP-1(7-38); Ser$^8$Lys$^{26,34}$-bis-(Glut-AHex)-GLP-1(7-39)

Ser$^8$Arg$^{26}$Lys$^{34,36}$-bis-(Glut-AHex)-GLP-1(7-36);
Ser$^8$Arg$^{34}$Lys$^{26,36}$-bis-(Glut-AHex)-GLP-1(7-36);
Ser$^8$Arg$^{26}$Lys$^{34,36}$-bis-(Glut-AHex)-GLP-1(7-37);
Ser$^8$Arg$^{34}$Lys$^{26,36}$-bis-(Glut-AHex)-GLP-1(7-37);
Ser$^8$Arg$^{26}$Lys$^{34,37}$-bis-(Glut-AHex)-GLP-1(7-37);
Ser$^8$Arg$^{34}$Lys$^{26,37}$-bis-(Glut-AHex)-GLP-1(7-37);
Ser$^8$Arg$^{26}$Lys$^{34,38}$-bis-(Glut-AHex)-GLP-1(7-38);
Ser$^8$Arg$^{34}$Lys$^{26,38}$-bis-(Glut-AHex)-GLP-1(7-38);
Ser$^8$Arg$^{26,34}$Lys$^{36,38}$-bis-(Glut-AHex)-GLP-1(7-38);
Ser$^8$Arg$^{26}$Lys$^{34,39}$-bis-(Glut-AHex)-GLP-1(7-39);
Ser$^8$Arg$^{34}$Lys$^{26,39}$-bis-(Glut-AHex)-GLP-1(7-39);
Ser$^8$Arg$^{26,34}$Lys$^{36,39}$-bis-(Glut-AHex)-GLP-1(7-39);
Thr$^8$Lys$^{26,34}$-bis-(Glut-AHex)-GLP-1(7-36); Thr$^8$Lys$^{26,34}$-bis-(Glut-AHex)-GLP-1(7-37); Thr$^8$Lys$^{26,34}$-bis-(Glut-AHex)-GLP-1(7-38); Thr$^8$Lys$^{26,34}$-bis-(Glut-AHex)-GLP-1(7-39)

Thr$^8$Arg$^{26}$Lys$^{34,36}$-bis-(Glut-AHex)-GLP-1(7-36);
Thr$^8$Arg$^{34}$Lys$^{26,36}$-bis-(Glut-AHex)-GLP-1(7-36);
Thr$^8$Arg$^{26}$Lys$^{34,36}$-bis-(Glut-AHex)-GLP-1(7-37);
Thr$^8$Arg$^{34}$Lys$^{26,36}$-bis-(Glut-AHex)-GLP-1(7-37);
Thr$^8$Arg$^{26}$Lys$^{34,37}$-bis-(Glut-AHex)-GLP-1(7-37);
Thr$^8$Arg$^{34}$Lys$^{26,37}$-bis-(Glut-AHex)-GLP-1(7-37);
Thr$^8$Arg$^{26}$Lys$^{34,38}$-bis-(Glut-AHex)-GLP-1(7-38);
Thr$^8$Arg$^{34}$Lys$^{26,38}$-bis-(Glut-AHex)-GLP-1(7-38);
Thr$^8$Arg$^{26,34}$Lys$^{36,38}$-bis-(Glut-AHex)-GLP-1(7-38);
Thr$^8$Arg$^{26}$Lys$^{34,39}$-bis-(Glut-AHex)-GLP-1(7-39);
Thr$^8$Arg$^{34}$Lys$^{26,39}$-bis-(Glut-AHex)-GLP-1(7-39);
Thr$^8$Arg$^{26,34}$Lys$^{36,39}$-bis-(Glut-AHex)-GLP-1(7-39);
Lys$^{26,34}$-bis-(Glut-AOct)-GLP-1(7-36); Lys$^{26,34}$-bis-(Glut-AOct)-GLP-1(7-37); Lys$^{26,34}$-bis-(Glut-AOct)-GLP-1(7-38); Lys$^{26,34}$-bis-(Glut-AOct)-GLP-1(7-39)

Arg$^{26}$Lys$^{34,36}$-bis-(Glut-AOct)-GLP-1(7-36); Arg$^{34}$Lys$^{26,36}$-bis-(Glut-AOct)-GLP-1(7-36); Arg$^{26}$Lys$^{34,36}$-bis-(Glut-AOct)-GLP-1(7-37); Arg$^{34}$Lys$^{26,36}$-bis-(Glut-AOct)-GLP-1(7-37); Arg$^{26}$Lys$^{34,37}$-bis-(Glut-AOct)-GLP-1(7-37); Arg$^{34}$Lys$^{26,37}$-bis-(Glut-AOct)-GLP-1(7-37); Arg$^{26}$Lys$^{34,39}$-bis-(Glut-AOct)-GLP-1(7-39); Arg$^{34}$Lys$^{26,39}$-bis-(Glut-AOct)-GLP-1(7-39); Arg$^{26,34}$Lys$^{36,39}$-bis-(Glut-AOct)-GLP-1(7-39);

Arg$^{26}$Lys$^{18,34}$-bis-(Glut-AOct)-GLP-1(7-36); Arg$^{34}$Lys$^{18,26}$-bis-(Glut-AOct)-GLP-1(7-36); Arg$^{26}$Lys$^{18,34}$-bis-(Glut-AOct)-GLP-1(7-37); Arg$^{34}$Lys$^{18,26}$-bis-(Glut-AOct)-GLP-1(7-37); Arg$^{26}$Lys$^{18,34}$-bis-(Glut-AOct)-GLP-1(7-38); Arg$^{34}$Lys$^{18,26}$-bis-(Glut-AOct)-GLP-1(7-38); Arg$^{26}$Lys$^{18,34}$-bis-(Glut-AOct)-GLP-1(7-39); Arg$^{34}$Lys$^{18,26}$-bis-(Glut-AOct)-GLP-1(7-39);

Arg$^{26}$Lys$^{23,34}$-bis-(Glut-AOct)-GLP-1(7-36); Arg$^{34}$Lys$^{23,26}$-bis-(Glut-AOct)-GLP-1(7-36); Arg$^{26}$Lys$^{23,34}$-bis-(Glut-AOct)-GLP-1(7-37); Arg$^{34}$Lys$^{23,26}$-bis-(Glut-AOct)-GLP-1(7-37); Arg$^{26}$Lys$^{23,34}$-bis-(Glut-AOct)-GLP-1(7-38); Arg$^{34}$Lys$^{23,26}$-bis-(Glut-AOct)-GLP-1(7-38); Arg$^{26}$Lys$^{23,34}$-bis-(Glut-AOct)-GLP-1(7-39); Arg$^{34}$Lys$^{23,26}$-bis-(Glut-AOct)-GLP-1(7-39);

Arg$^{26}$Lys$^{27,34}$-bis-(Glut-AOct)-GLP-1(7-36); Arg$^{34}$Lys$^{27,26}$-bis-(Glut-AOct)-GLP-1(7-36); Arg$^{26}$Lys$^{27,34}$-bis-(Glut-AOct)-GLP-1(7-37); Arg$^{34}$Lys$^{27,26}$-bis-(Glut-AOct)-GLP-1(7-37); Arg$^{26}$Lys$^{27,34}$-bis-(Glut-AOct)-GLP-1(7-38); Arg$^{34}$Lys$^{27,26}$-bis-(Glut-AOct)-GLP-1(7-38); Arg$^{26}$Lys$^{27,34}$-bis-(Glut-AOct)-GLP-1(7-39); Arg$^{34}$Lys$^{27,26}$-bis-(Glut-AOct)-GLP-1(7-39);

Gly$^8$Lys$^{26,34}$-bis-(Glut-AOct)-GLP-1(7-36); Gly$^8$Lys$^{26,34}$-bis-(Glut-AOct)-GLP-1(7-37); Gly$^8$Lys$^{26,34}$-bis-(Glut-AOct)-GLP-1(7-38); Gly$^8$Lys$^{26,34}$-bis-(Glut-AOct)-GLP-1(7-39)

Gly$^8$Arg$^{26}$Lys$^{34,36}$-bis-(Glut-AOct)-GLP-1(7-36);
Gly$^8$Arg$^{34}$Lys$^{26,36}$-bis-(Glut-AOct)-GLP-1(7-36);
Gly$^8$Arg$^{26}$Lys$^{34,36}$-bis-(Glut-AOct)-GLP-1(7-37);
Gly$^8$Arg$^{34}$Lys$^{26,36}$-bis-(Glut-AOct)-GLP-1(7-37);
Gly$^8$Arg$^{26}$Lys$^{34,37}$-bis-(Glut-AOct)-GLP-1(7-37);
Gly$^8$Arg$^{34}$Lys$^{26,37}$-bis-(Glut-AOct)-GLP-1(7-37);
Gly$^8$Arg$^{26}$Lys$^{34,38}$-bis-(Glut-AOct)-GLP-1(7-38);
Gly$^8$Arg$^{34}$Lys$^{26,38}$-bis-(Glut-AOct)-GLP-1(7-38);
Gly$^8$Arg$^{26,34}$Lys$^{36,38}$-bis-(Glut-AOct)-GLP-1(7-38);
Gly$^8$Arg$^{26}$Lys$^{34,39}$-bis-(Glut-AOct)-GLP-1(7-39);
Gly$^8$Arg$^{34}$Lys$^{26,39}$-bis-(Glut-AOct)-GLP-1(7-39);
Gly$^8$Arg$^{26,34}$Lys$^{36,39}$-bis-(Glut-AOct)-GLP-1(7-39);
Val$^8$Lys$^{26,34}$-bis-(Glut-AOct)-GLP-1(7-36); Val$^8$Lys$^{26,34}$-bis-(Glut-AOct)-GLP-1(7-37); Val$^8$Lys$^{26,34}$-bis-(Glut-AOct)-GLP-1(7-38); Val$^8$Lys$^{26,34}$-bis-(Glut-AOct)-GLP-1(7-39)

Val$^8$Arg$^{26}$Lys$^{34,36}$-bis-(Glut-AOct)-GLP-1(7-36);
Val$^8$Arg$^{34}$Lys$^{26,36}$-bis-(Glut-AOct)-GLP-1(7-36);
Val$^8$Arg$^{26}$Lys$^{34,36}$-bis-(Glut-AOct)-GLP-1(7-37);
Val$^8$Arg$^{34}$Lys$^{26,36}$-bis-(Glut-AOct)-GLP-1(7-37);
Val$^8$Arg$^{26}$Lys$^{34,37}$-bis-(Glut-AOct)-GLP-1(7-37);
Val$^8$Arg$^{34}$Lys$^{26,37}$-bis-(Glut-AOct)-GLP-1(7-37);
Val$^8$Arg$^{26}$Lys$^{34,38}$-bis-(Glut-AOct)-GLP-1(7-38);
Val$^8$Arg$^{34}$Lys$^{26,38}$-bis-(Glut-AOct)-GLP-1(7-38);
Val$^8$Arg$^{26,34}$Lys$^{36,38}$-bis-(Glut-AOct)-GLP-1(7-38);
Val$^8$Arg$^{26}$Lys$^{34,39}$-bis-(Glut-AOct)-GLP-1(7-39);
Val$^8$Arg$^{34}$Lys$^{26,39}$-bis-(Glut-AOct)-GLP-1(7-39);
Val$^8$Arg$^{26,34}$Lys$^{36,39}$-bis-(Glut-AOct)-GLP-1(7-39);
Ser$^8$Lys$^{26,34}$-bis-(Glut-AOct)-GLP-1(7-36); Ser$^8$Lys$^{26,34}$-bis-(Glut-AOct)-GLP-1(7-37); Ser$^8$Lys$^{26,34}$-bis-(Glut-AOct)-GLP-1(7-38); Ser$^8$Lys$^{26,34}$-bis-(Glut-AOct)-GLP-1(7-39)

Ser$^8$Arg$^{26}$Lys$^{34,36}$-bis-(Glut-AOct)-GLP-1(7-36);
Ser$^8$Arg$^{34}$Lys$^{26,36}$-bis-(Glut-AOct)-GLP-1(7-36);

Ser$^8$Arg$^{26}$Lys$^{34,36}$-bis-(Glut-AOct)-GLP-1(7-37);
Ser$^8$Arg$^{34}$Lys$^{26,36}$-bis-(Glut-AOct)-GLP-1(7-37);
Ser$^8$Arg$^{26}$Lys$^{34,37}$-bis-(Glut-AOct)-GLP-1(7-37);
Ser$^8$Arg$^{34}$Lys$^{26,37}$-bis-(Glut-AOct)-GLP-1(7-37);
Ser$^8$Arg$^{26}$Lys$^{34,38}$-bis-(Glut-AOct)-GLP-1(7-38);
Ser$^8$Arg$^{34}$Lys$^{26,38}$-bis-(Glut-AOct)-GLP-1(7-38);
Ser$^8$Arg$^{26,34}$Lys$^{36,38}$-bis-(Glut-AOct)-GLP-1(7-38);
Ser$^8$Arg$^{26}$Lys$^{34,39}$-bis-(Glut-AOct)-GLP-1(7-39);
Ser$^8$Arg$^{34}$Lys$^{26,39}$-bis-(Glut-AOct)-GLP-1(7-39);
Ser$^8$Arg$^{26,34}$Lys$^{36,39}$-bis-(Glut-AOct)-GLP-1(7-39);
Thr$^8$Lys$^{26,34}$-bis-(Glut-AOct)-GLP-1(7-36); Thr$^8$Lys$^{26,34}$-bis-(Glut-AOct)-GLP-1(7-37); Thr$^8$Lys$^{26,34}$-bis-(Glut-AOct)-GLP-1(7-38); Thr$^8$Lys$^{26,34}$-bis-(Glut-AOct)-GLP-1(7-39)
Thr$^8$Arg$^{26}$Lys$^{34,36}$-bis-(Glut-AOct)-GLP-1(7-36);
Thr$^8$Arg$^{34}$Lys$^{26,36}$-bis-(Glut-AOct)-GLP-1(7-36);
Thr$^8$Arg$^{26}$Lys$^{34,36}$-bis-(Glut-AOct)-GLP-1(7-37);
Thr$^8$Arg$^{34}$Lys$^{26,36}$-bis-(Glut-AOct)-GLP-1(7-37);
Thr$^8$Arg$^{26}$Lys$^{34,37}$-bis-(Glut-AOct)-GLP-1(7-37);
Thr$^8$Arg$^{34}$Lys$^{26,37}$-bis-(Glut-AOct)-GLP-1(7-37);
Thr$^8$Arg$^{26}$Lys$^{34,38}$-bis-(Glut-AOct)-GLP-1(7-38);
Thr$^8$Arg$^{34}$Lys$^{26,38}$-bis-(Glut-AOct)-GLP-1(7-38);
Thr$^8$Arg$^{26,34}$Lys$^{36,38}$-bis-(Glut-AOct)-GLP-1(7-38);
Thr$^8$Arg$^{26}$Lys$^{34,39}$-bis-(Glut-AOct)-GLP-1(7-39);
Thr$^8$Arg$^{34}$Lys$^{26,39}$-bis-(Glut-AOct)-GLP-1(7-39);
Thr$^8$Arg$^{26,34}$Lys$^{36,39}$-bis-(Glut-AOct)-GLP-1(7-39);
Lys$^{26,34}$-bis-(Glut-ALit)-GLP-1(7-36); Lys$^{26,34}$-bis-(Glut-ALit)-GLP-1(7-37); Lys$^{26,34}$-bis-(Glut-ALit)-GLP-1(7-38); Lys$^{26,34}$-bis-(Glut-ALit)-GLP-1(7-39)
Arg$^{26}$Lys$^{34,36}$-bis-(Glut-ALit)-GLP-1(7-36); Arg$^{34}$Lys$^{26,36}$-bis-(Glut-ALit)-GLP-1(7-36); Arg$^{26}$Lys$^{34,36}$-bis-(Glut-ALit)-GLP-1(7-37); Arg$^{34}$Lys$^{26,36}$-bis-(Glut-ALit)-GLP-1(7-37); Arg$^{26}$Lys$^{34,37}$-bis-(Glut-ALit)-GLP-1(7-37); Arg$^{34}$Lys$^{26,37}$-bis-(Glut-ALit)-GLP-1(7-37); Arg$^{26}$Lys$^{34,39}$-bis-(Glut-ALit)-GLP-1(7-39); Arg$^{34}$Lys$^{26,39}$-bis-(Glut-ALit)-GLP-1(7-39); Arg$^{26,34}$Lys$^{36,39}$-bis-(Glut-ALit)-GLP-1(7-39);
Arg$^{26}$Lys$^{18,34}$-bis-(Glut-ALit)-GLP-1(7-36); Arg$^{34}$Lys$^{18,26}$-bis-(Glut-ALit)-GLP-1(7-36); Arg$^{26}$Lys$^{18,34}$-bis-(Glut-ALit)-GLP-1(7-37); Arg$^{34}$Lys$^{18,26}$-bis-(Glut-ALit)-GLP-1(7-37); Arg$^{26}$Lys$^{18,34}$-bis-(Glut-ALit)-GLP-1(7-38); Arg$^{34}$Lys$^{8,26}$-bis-(Glut-ALit)-GLP-1(7-38); Arg$^{26}$Lys$^{18,34}$-bis-(Glut-ALit)-GLP-1(7-39); Arg$^{34}$Lys$^{18,26}$-bis-(Glut-ALit)-GLP-1(7-39);
Arg$^{26}$Lys$^{23,34}$-bis-(Glut-ALit)-GLP-1(7-36); Arg$^{34}$Lys$^{23,26}$-bis-(Glut-ALit)-GLP-1(7-36); Arg$^{26}$Lys$^{23,34}$-bis-(Glut-ALit)-GLP-1(7-37); Arg$^{34}$Lys$^{23,26}$-bis-(Glut-ALit)-GLP-1(7-37); Arg$^{26}$Lys$^{23,34}$-bis-(Glut-ALit)-GLP-1(7-38); Arg$^{34}$Lys$^{23,26}$-bis-(Glut-ALit)-GLP-1(7-38); Arg$^{26}$Lys$^{23,34}$-bis-(Glut-ALit)-GLP-1(7-39); Arg$^{34}$Lys$^{23,26}$-bis-(Glut-ALit)-GLP-1(7-39);
Arg$^{26}$Lys$^{27,34}$-bis-(Glut-ALit)-GLP-1(7-36); Arg$^{34}$Lys$^{27,26}$-bis-(Glut-ALit)-GLP-1(7-36); Arg$^{26}$Lys$^{27,34}$-bis-(Glut-ALit)-GLP-1(7-37); Arg$^{34}$Lys$^{27,26}$-bis-(Glut-ALit)-GLP-1(7-37); Arg$^{26}$Lys$^{27,34}$-bis-(Glut-ALit)-GLP-1(7-38); Arg$^{34}$Lys$^{27,26}$-bis-(Glut-ALit)-GLP-1(7-38); Arg$^{26}$Lys$^{27,34}$-bis-(Glut-ALit)-GLP-1(7-39); Arg$^{34}$Lys$^{27,26}$-bis-(Glut-ALit)-GLP-1(7-39);
Gly$^8$Lys$^{26,34}$-bis-(Glut-ALit)-GLP-1(7-36); Gly$^8$Lys$^{26,34}$-bis-(Glut-ALit)-GLP-1(7-37); Gly$^8$Lys$^{26,34}$-bis-(Glut-ALit)-GLP-1(7-38); Gly$^8$Lys$^{26,34}$-bis-(Glut-ALit)-GLP-1(7-39)
Gly$^8$Arg$^{26}$Lys$^{34,36}$-bis-(Glut-ALit)-GLP-1(7-36);
Gly$^8$Arg$^{34}$Lys$^{26,36}$-bis-(Glut-ALit)-GLP-1(7-36);
Gly$^8$Arg$^{26}$Lys$^{34,36}$-bis-(Glut-ALit)-GLP-1(7-37);
Gly$^8$Arg$^{34}$Lys$^{26,36}$-bis-(Glut-ALit)-GLP-1(7-37);
Gly$^8$Arg$^{26}$Lys$^{34,37}$-bis-(Glut-ALit)-GLP-1(7-37);
Gly$^8$Arg$^{34}$Lys$^{26,37}$-bis-(Glut-ALit)-GLP-1(7-37);
Gly$^8$Arg$^{26}$Lys$^{34,38}$-bis-(Glut-ALit)-GLP-1(7-38);
Gly$^8$Arg$^{34}$Lys$^{26,38}$-bis-(Glut-ALit)-GLP-1(7-38);
Gly$^8$Arg$^{26,34}$Lys$^{36,38}$-bis-(Glut-ALit)-GLP-1(7-38);
Gly$^8$Arg$^{26}$Lys$^{34,39}$-bis-(Glut-ALit)-GLP-1(7-39);
Gly$^8$Arg$^{34}$Lys$^{26,39}$-bis-(Glut-ALit)-GLP-1(7-39);
Gly$^8$Arg$^{26,34}$Lys$^{36,39}$-bis-(Glut-ALit)-GLP-1(7-39);
Val$^8$Lys$^{26,34}$-bis-(Glut-ALit)-GLP-1(7-36); Val$^8$Lys$^{26,34}$-bis-(Glut-ALit)-GLP-1(7-37); Val$^8$Lys$^{26,34}$-bis-(Glut-ALit)-GLP-1(7-38); Val$^8$Lys$^{26,34}$-bis-(Glut-ALit)-GLP-1(7-39)
Val$^8$Arg$^{26}$Lys$^{34,36}$-bis-(Glut-ALit)-GLP-1(7-36);
Val$^8$Arg$^{34}$Lys$^{26,36}$-bis-(Glut-ALit)-GLP-1(7-36);
Val$^8$Arg$^{26}$Lys$^{34,36}$-bis-(Glut-ALit)-GLP-1(7-37);
Val$^8$Arg$^{34}$Lys$^{26,36}$-bis-(Glut-ALit)-GLP-1(7-37);
Val$^8$Arg$^{26}$Lys$^{34,37}$-bis-(Glut-ALit)-GLP-1(7-37);
Val$^8$Arg$^{34}$Lys$^{26,37}$-bis-(Glut-ALit)-GLP-1(7-37);
Val$^8$Arg$^{26}$Lys$^{34,38}$-bis-(Glut-ALit)-GLP-1(7-38);
Val$^8$Arg$^{34}$Lys$^{26,38}$-bis-(Glut-ALit)-GLP-1(7-38); Val$^8$Arg$^{26,34}$Lys$^{36,38}$-bis-(Glut-ALit)-GLP-1(7-38);
Val$^8$Arg$^{26}$Lys$^{34,39}$-bis-(Glut-ALit)-GLP-1(7-39);
Val$^8$Arg$^{34}$Lys$^{26,39}$-bis-(Glut-ALit)-GLP-1(7-39); Val$^8$Arg$^{26,34}$Lys$^{36,39}$-bis-(Glut-ALit)-GLP-1(7-39);
Ser$^8$Lys$^{26,34}$-bis-(Glut-ALit)-GLP-1(7-36); Ser$^8$Lys$^{26,34}$-bis-(Glut-ALit)-GLP-1(7-37); Ser$^8$Lys$^{26,34}$-bis-(Glut-ALit)-GLP-1(7-38); Ser$^8$Lys$^{26,34}$-bis-(Glut-ALit)-GLP-1(7-39)
Ser$^8$Arg$^{26}$Lys$^{34,36}$-bis-(Glut-ALit)-GLP-1(7-36);
Ser$^8$Arg$^{34}$Lys$^{26,36}$-bis-(Glut-ALit)-GLP-1(7-36);
Ser$^8$Arg$^{26}$Lys$^{34,36}$-bis-(Glut-ALit)-GLP-1(7-37);
Ser$^8$Arg$^{34}$Lys$^{26,36}$-bis-(Glut-ALit)-GLP-1(7-37);
Ser$^8$Arg$^{26}$Lys$^{34,37}$-bis-(Glut-ALit)-GLP-1(7-37);
Ser$^8$Arg$^{34}$Lys$^{26,37}$-bis-(Glut-ALit)-GLP-1(7-37);
Ser$^8$Arg$^{26}$Lys$^{34,38}$-bis-(Glut-ALit)-GLP-1(7-38);
Ser$^8$Arg$^{34}$Lys$^{26,38}$-bis-(Glut-ALit)-GLP-1(7-38); Ser$^8$Arg$^{26,34}$Lys$^{36,38}$-bis-(Glut-ALit)-GLP-1(7-38);
Ser$^8$Arg$^{26}$Lys$^{34,39}$-bis-(Glut-ALit)-GLP-1(7-39);
Ser$^8$Arg$^{34}$Lys$^{26,39}$-bis-(Glut-ALit)-GLP-1(7-39); Ser$^8$Arg$^{26,34}$Lys$^{36,39}$-bis-(Glut-ALit)-GLP-1(7-39);
Thr$^8$Lys$^{26,34}$-bis-(Glut-ALit)-GLP-1(7-36); Thr$^8$Lys$^{26,34}$-bis-(Glut-ALit)-GLP-1(7-37); Thr$^8$Lys$^{26,34}$-bis-(Glut-ALit)-GLP-1(7-38); Thr$^8$Lys$^{26,34}$-bis-(Glut-ALit)-GLP-1(7-39)
Thr$^8$Arg$^{26}$Lys$^{34,36}$-bis-(Glut-ALit)-GLP-1(7-36);
Thr$^8$Arg$^{34}$Lys$^{26,36}$-bis-(Glut-ALit)-GLP-1(7-36);
Thr$^8$Arg$^{26}$Lys$^{34,36}$-bis-(Glut-ALit)-GLP-1(7-37);
Thr$^8$Arg$^{34}$Lys$^{26,36}$-bis-(Glut-ALit)-GLP-1(7-37);
Thr$^8$Arg$^{26}$Lys$^{34,37}$-bis-(Glut-ALit)-GLP-1(7-37);
Thr$^8$Arg$^{34}$Lys$^{26,37}$-bis-(Glut-ALit)-GLP-1(7-37);
Thr$^8$Arg$^{26}$Lys$^{34,38}$-bis-(Glut-ALit)-GLP-1(7-38);
Thr$^8$Arg$^{34}$Lys$^{26,38}$-bis-(Glut-ALit)-GLP-1(7-38);
Thr$^8$Arg$^{26,34}$Lys$^{36,38}$-bis-(Glut-ALit)-GLP-1(7-38);
Thr$^8$Arg$^{26}$Lys$^{34,39}$-bis-(Glut-ALit)-GLP-1(7-39);
Thr$^8$Arg$^{34}$Lys$^{26,39}$-bis-(Glut-ALit)-GLP-1(7-39);
Thr$^8$Arg$^{26,34}$Lys$^{36,39}$-bis-(Glut-ALit)-GLP-1(7-39);
Lys$^{26,34}$-bis-(Aspa-ADod)-GLP-1(7-36); Lys$^{26,34}$-bis-(Aspa-ADod)-GLP-1(7-37); Lys$^{26,34}$-bis-(Aspa-ADod)-GLP-1(7-38); Lys$^{26,34}$-bis-(Aspa-ADod)-GLP-1(7-39)
Arg$^{26}$Lys$^{34,36}$-bis-(Aspa-ADod)-GLP-1(7-36); Arg$^{34}$Lys$^{26,36}$-bis-(Aspa-ADod)-GLP-1(7-36); Arg$^{26}$Lys$^{34,36}$-bis-(Aspa-ADod)-GLP-1(7-37); Arg$^{34}$Lys$^{26,36}$-bis-(Aspa-ADod)-GLP-1(7-37); Arg$^{26}$Lys$^{34,37}$-bis-(Aspa-ADod)-GLP-1(7-37); Arg$^{34}$Lys$^{26,37}$-bis-(Aspa-ADod)-GLP-1(7-37); Arg$^{26}$Lys$^{34,39}$-bis-(Aspa-ADod)-GLP-1(7-39); Arg$^{34}$Lys$^{26,39}$-bis-(Aspa-ADod)-GLP-1(7-39); Arg$^{26,34}$Lys$^{36,39}$-bis-(Aspa-ADod)-GLP-1(7-39);
Arg$^{26}$Lys$^{18,34}$-bis-(Aspa-ADod)-GLP-1(7-36); Arg$^{34}$Lys$^{18,26}$-bis-(Aspa-ADod)-GLP-1(7-37); Arg$^{34}$Lys$^{18,26}$-bis-(Aspa-ADod)-GLP-1(7-37); Arg$^{26}$Lys$^{18,34}$-bis-(Aspa-ADod)-

GLP-1(7-38); Arg$^{34}$Lys$^{18,26}$-bis-(Aspa-ADod)-GLP-1(7-38); Arg$^{26}$Lys$^{18,34}$-bis-(Aspa-ADod)-GLP-1(7-39); Arg$^{34}$Lys$^{18,26}$-bis-(Aspa-ADod)-GLP-1(7-39);
Arg$^{26}$Lys$^{23,34}$-bis-(Aspa-ADod)-GLP-1(7-36); Arg$^{34}$Lys$^{23,26}$-bis-(Aspa-ADod)-GLP-1(7-36); Arg$^{26}$Lys$^{23,34}$-bis-(Aspa-ADod)-GLP-1(7-37); Arg$^{34}$Lys$^{23,26}$-bis-(Aspa-ADod)-GLP-1(7-37); Arg$^{26}$Lys$^{23,34}$-bis-(Aspa-ADod)-GLP-1(7-38); Arg$^{34}$Lys$^{23,26}$-bis-(Aspa-ADod)-GLP-1(7-38); Arg$^{26}$Lys$^{23,34}$-bis-(Aspa-ADod)-GLP-1(7-39); Arg$^{34}$Lys$^{23,26}$-bis-(Aspa-ADod)-GLP-1(7-39);
Arg$^{26}$Lys$^{27,34}$-bis-(Aspa-ADod)-GLP-1(7-36); Arg$^{34}$Lys$^{27,26}$-bis-(Aspa-ADod)-GLP-1(7-36); Arg$^{26}$Lys$^{27,34}$-bis-(Aspa-ADod)-GLP-1(7-37); Arg$^{34}$Lys$^{27,26}$-bis-(Aspa-ADod)-GLP-1(7-37); Arg$^{26}$Lys$^{27,34}$-bis-(Aspa-ADod)-GLP-1(7-38); Arg$^{34}$Lys$^{27,26}$-bis-(Aspa-ADod)-GLP-1(7-38); Arg$^{26}$Lys$^{27,34}$-bis-(Aspa-ADod)-GLP-1(7-39); Arg$^{34}$Lys$^{27,26}$-bis-(Aspa-ADod)-GLP-1(7-39);
Gly$^8$Lys$^{26,34}$-bis-(Aspa-ADod)-GLP-1(7-36); Gly$^8$Lys$^{26,34}$-bis-(Aspa-ADod)-GLP-1(7-37); Gly$^8$Lys$^{26,34}$-bis-(Aspa-ADod)-GLP-1(7-38); Gly$^8$Lys$^{26,34}$-bis-(Aspa-ADod)-GLP-1(7-39)

Gly$^8$Arg$^{26}$Lys$^{34,36}$-bis-(Aspa-ADod)-GLP-1(7-36); Gly$^8$Arg$^{34}$Lys$^{26,36}$-bis-(Aspa-ADod)-GLP-1(7-36); Gly$^8$Arg$^{26}$Lys$^{34,36}$-bis-(Aspa-ADod)-GLP-1(7-37); Gly$^8$Arg$^{34}$Lys$^{26,36}$-bis-(Aspa-ADod)-GLP-1(7-37); Gly$^8$Arg$^{26}$Lys$^{34,37}$-bis-(Aspa-ADod)-GLP-1(7-37); Gly$^8$Arg$^{34}$Lys$^{26,37}$-bis-(Aspa-ADod)-GLP-1(7-37); Gly$^8$Arg$^{26}$Lys$^{34,38}$-bis-(Aspa-ADod)-GLP-1(7-38); Gly$^8$Arg$^{34}$Lys$^{26,38}$-bis-(Aspa-ADod)-GLP-1(7-38); Gly$^8$Arg$^{26,34}$Lys$^{36,38}$-bis-(Aspa-ADod)-GLP-1(7-38); Gly$^8$Arg$^{26}$Lys$^{34,39}$-bis-(Aspa-ADod)-GLP-1(7-39); Gly$^8$Arg$^{34}$Lys$^{26,39}$-bis-(Aspa-ADod)GLP-1(7-39); Gly$^8$Arg$^{26,34}$Lys$^{36,39}$-bis-(Aspa-ADod)-GLP-1(7-39);
Val$^8$Lys$^{26,34}$-bis-(Aspa-ADod)-GLP-1(7-36); Val$^8$Lys$^{26,34}$-bis-(Aspa-ADod)-GLP-1(7-37); Val$^8$Lys$^{26,34}$-bis-(Aspa-ADod)-GLP-1(7-38); Val$^8$Lys$^{26,34}$-bis-(Aspa-ADod)-GLP-1(7-39)

Val$^8$Arg$^{26}$Lys$^{34,36}$-bis-(Aspa-ADod)-GLP-1(7-36); Val$^8$Arg$^{34}$Lys$^{26,36}$-bis-(Aspa-ADod)-GLP-1(7-36); Val$^8$Arg$^{26}$Lys$^{34,36}$-bis-(Aspa-ADod)-GLP-1(7-37); Val$^8$Arg$^{34}$Lys$^{26,36}$-bis-(Aspa-ADod)-GLP-1(7-37); Val$^8$Arg$^{26}$Lys$^{34,37}$-bis-(Aspa-ADod)-GLP-1(7-37); Val$^8$Arg$^{34}$Lys$^{26,37}$-bis-(Aspa-ADod)-GLP-1(7-37); Val$^8$Arg$^{26}$Lys$^{34,38}$-bis-(Aspa-ADod)-GLP-1(7-38); Val$^8$Arg$^{34}$Lys$^{26,38}$-bis-(Aspa-ADod)-GLP-1(7-38); Val$^8$Arg$^{26,34}$Lys$^{36,38}$-bis-(Aspa-ADod)-GLP-1(7-38); Val$^8$Arg$^{26}$Lys$^{34,39}$-bis-(Aspa-ADod)-GLP-1(7-39); Val$^8$Arg$^{34}$Lys$^{26,39}$-bis-(Aspa-ADod)-GLP-1(7-39); Val$^8$Arg$^{26,34}$Lys$^{36,39}$-bis-(Aspa-ADod)-GLP-1(7-39);
Ser$^8$Lys$^{26,34}$-bis-(Aspa-ADod)-GLP-1(7-36); Ser$^8$Lys$^{26,34}$-bis-(Aspa-ADod)-GLP-1(7-37); Ser$^8$Lys$^{26,34}$-bis-(Aspa-ADod)-GLP-1(7-38); Ser$^8$Lys$^{26,34}$-bis-(Aspa-ADod)-GLP-1(7-39)

Ser$^8$Arg$^{26}$Lys$^{34,36}$-bis-(Aspa-ADod)-GLP-1(7-36); Ser$^8$Arg$^{34}$Lys$^{26,36}$-bis-(Aspa-ADod)-GLP-1(7-36); Ser$^8$Arg$^{26}$Lys$^{34,36}$-bis-(Aspa-ADod)-GLP-1(7-37); Ser$^8$Arg$^{34}$Lys$^{26,36}$-bis-(Aspa-ADod)-GLP-1(7-37); Ser$^8$Arg$^{26}$Lys$^{34,37}$-bis-(Aspa-ADod)-GLP-1(7-37); Ser$^8$Arg$^{34}$Lys$^{26,37}$-bis-(Aspa-ADod)-GLP-1(7-37); Ser$^8$Arg$^{26}$Lys$^{34,38}$-bis-(Aspa-ADod)-GLP-1(7-38); Ser$^8$Arg$^{34}$Lys$^{26,38}$-bis-(Aspa-ADod)-GLP-1(7-38); Ser$^8$Arg$^{26,34}$Lys$^{36,38}$-bis-(Aspa-ADod)-GLP-1(7-38); Ser$^8$Arg$^{26}$Lys$^{34,39}$-bis-(Aspa-ADod)-GLP-1(7-39); Ser$^8$Arg$^{34}$Lys$^{26,39}$-bis-(Aspa-ADod)-GLP-1(7-39); Ser$^8$Arg$^{26,34}$Lys$^{36,39}$-bis-(Aspa-ADod)-GLP-1(7-39);

Thr$^8$Lys$^{26,34}$-bis-(Aspa-ADod)-GLP-1(7-36); Thr$^8$Lys$^{26,34}$-bis-(Aspa-ADod)-GLP-1(7-37); Thr$^8$Lys$^{26,34}$-bis-(Aspa-ADod)-GLP-1(7-38); Thr$^8$Lys$^{26,34}$-bis-(Aspa-ADod)-GLP-1(7-39)

Thr$^8$Arg$^{26}$Lys$^{34,36}$-bis-(Aspa-ADod)-GLP-1(7-36); Thr$^8$Arg$^{34}$Lys$^{26,36}$-bis-(Aspa-ADod)-GLP-1(7-36); Thr$^8$Arg$^{26}$Lys$^{34,36}$-bis-(Aspa-ADod)-GLP-1(7-37); Thr$^8$Arg$^{34}$Lys$^{26,36}$-bis-(Aspa-ADod)-GLP-1(7-37); Thr$^8$Arg$^{26}$Lys$^{34,37}$-bis-(Aspa-ADod)-GLP-1(7-37); Thr$^8$Arg$^{34}$Lys$^{26,37}$-bis-(Aspa-ADod)-GLP-1(7-37); Thr$^8$Arg$^{26}$Lys$^{34,38}$-bis-(Aspa-ADod)-GLP-1(7-38); Thr$^8$Arg$^{34}$Lys$^{26,38}$-bis-(Aspa-ADod)-GLP-1(7-38); Thr$^8$Arg$^{26,34}$Lys$^{36,38}$-bis-(Aspa-ADod)-GLP-1(7-38); Thr$^8$Arg$^{26}$Lys$^{34,39}$-bis-(Aspa-ADod)-GLP-1(7-39); Thr$^8$Arg$^{34}$Lys$^{26,39}$-bis-(Aspa-ADod)-GLP-1(7-39); Thr$^8$Arg$^{26,34}$Lys$^{36,39}$-bis-(Aspa-ADod)-GLP-1(7-39);
Lys$^{26,34}$-bis-(Aspa-ATet)-GLP-1(7-36); Lys$^{26,34}$-bis-(Aspa-ATet)-GLP-1(7-37); Lys$^{26,34}$-bis-(Aspa-ATet)-GLP-1(7-38); Lys$^{26,34}$-bis-(Aspa-ATet)-GLP-1(7-39)

Arg$^{26}$Lys$^{34,36}$-bis-(Aspa-ATet)-GLP-1(7-36); Arg$^{34}$Lys$^{26,36}$-bis-(Aspa-ATet)-GLP-1(7-36); Arg$^{26}$Lys$^{34,36}$-bis-(Aspa-ATet)-GLP-1(7-37); Arg$^{34}$Lys$^{26,36}$-bis-(Aspa-ATet)-GLP-1(7-37); Arg$^{26}$Lys$^{34,37}$-bis-(Aspa-ATet)-GLP-1(7-37); Arg$^{34}$Lys$^{26,37}$-bis-(Aspa-ATet)-GLP-1(7-37); Arg$^{26}$Lys$^{34,39}$-bis-(Aspa-ATet)-GLP-1(7-39); Arg$^{34}$Lys$^{26,39}$-bis-(Aspa-ATet)-GLP-1(7-39); Arg$^{26,34}$Lys$^{36,39}$-bis-(Aspa-ATet)-GLP-1(7-39);

Arg$^{26}$Lys$^{18,34}$-bis-(Aspa-ATet)-GLP-1(7-36); Arg$^{34}$Lys$^{18,26}$-bis-(Aspa-ATet)-GLP-1(7-36); Arg$^{26}$Lys$^{18,34}$-bis-(Aspa-ATet)-GLP-1(7-37); Arg$^{34}$Lys$^{18,26}$-bis-(Aspa-ATet)-GLP-1(7-37); Arg$^{26}$Lys$^{18,34}$-bis-(Aspa-ATet)-GLP-1(7-38); Arg$^{34}$Lys$^{18,26}$-bis-(Aspa-ATet)-GLP-1(7-38); Arg$^{26}$Lys$^{18,34}$-bis-(Aspa-ATet)-GLP-1(7-39); Arg$^{34}$Lys$^{18,26}$-bis-(Aspa-ATet)-GLP-1(7-39);

Arg$^{26}$Lys$^{23,34}$-bis-(Aspa-ATet)-GLP-1(7-36); Arg$^{34}$Lys$^{23,26}$-bis-(Aspa-ATet)-GLP-1(7-36); Arg$^{26}$Lys$^{23,34}$-bis-(Aspa-ATet)-GLP-1(7-37); Arg$^{34}$Lys$^{23,26}$-bis-(Aspa-ATet)-GLP-1(7-37); Arg$^{26}$Lys$^{23,34}$-bis-(Aspa-ATet)-GLP-1(7-38); Arg$^{34}$Lys$^{23,26}$-bis-(Aspa-ATet)-GLP-1(7-38); Arg$^{26}$Lys$^{23,34}$-bis-(Aspa-ATet)-GLP-1(7-39); Arg$^{34}$Lys$^{23,26}$-bis-(Aspa-ATet)-GLP-1(7-39);

Arg$^{26}$Lys$^{27,34}$-bis(Aspa-ATet)-GLP-1(7-36); Arg$^{34}$Lys$^{27,26}$-bis-(Aspa-ATet)-GLP-1(7-36); Arg$^{26}$Lys$^{27,34}$-bis-(Aspa-ATet)-GLP-1(7-37); Arg$^{34}$Lys$^{27,26}$-bis-(Aspa-ATet)-GLP-1(7-37); Arg$^{26}$Lys$^{27,34}$-bis-(Aspa-ATet)-GLP-1(7-38); Arg$^{34}$Lys$^{27,26}$-bis-(Aspa-ATet)-GLP-1(7-38); Arg$^{26}$Lys$^{27,34}$-bis-(Aspa-ATet)-GLP-1(7-39); Arg$^{34}$Lys$^{27,26}$-bis-(Aspa-ATet)-GLP-1(7-39);
Gly$^8$Lys$^{26,34}$-bis-(Aspa-ATet)-GLP-1(7-36); Gly$^8$Lys$^{26,34}$-bis-(Aspa-ATet)-GLP-1(7-37); Gly$^8$Lys$^{26,34}$-bis-(Aspa-ATet)-GLP-1(7-38); Gly$^8$Lys$^{26,34}$-bis-(Aspa-ATet)-GLP-1(7-39)

Gly$^8$Arg$^{26}$Lys$^{34,36}$-bis-(Aspa-ATet)-GLP-1(7-36); Gly$^8$Arg$^{34}$Lys$^{26,36}$-bis-(Aspa-ATet)-GLP-1(7-36); Gly$^8$Arg$^{26}$Lys$^{34,36}$-bis-(Aspa-ATet)-GLP-1(7-37); Gly$^8$Arg$^{34}$Lys$^{26,36}$-bis-(Aspa-ATet)-GLP-1(7-37); Gly$^8$Arg$^{26}$Lys$^{34,37}$-bis-(Aspa-ATet)-GLP-1(7-37); Gly$^8$Arg$^{34}$Lys$^{26,37}$-bis-(Aspa-ATet)-GLP-1(7-37); Gly$^8$Arg$^{26}$Lys$^{34,38}$-bis-(Aspa-ATet)-GLP-1(7-38); Gly$^8$Arg$^{34}$Lys$^{26,38}$-bis-(Aspa-ATet)-GLP-1(7-38); Gly$^8$Arg$^{26,34}$Lys$^{36,38}$-bis-(Aspa-ATet)-GLP-1(7-38); Gly$^8$Arg$^{26}$Lys$^{34,39}$-bis-(Aspa-ATet)-GLP-1(7-39); Gly$^8$Arg$^{34}$Lys$^{26,39}$-bis-(Aspa-ATet)-GLP-1(7-39); Gly$^8$Arg$^{26,34}$Lys$^{36,39}$-bis-(Aspa-ATet)-GLP-1(7-39);

Val$^8$Lys$^{26,34}$-bis-(Aspa-ATet)-GLP-1(7-36); Val$^8$Lys$^{26,34}$-bis-(Aspa-ATet)-GLP-1(7-37); Val$^8$Lys$^{26,34}$-bis-(Aspa-ATet)-GLP-1(7-38); Val$^8$Lys$^{26,34}$-bis-(Aspa-ATet)-GLP-1(7-39)

Val$^8$Arg$^{26}$Lys$^{34,36}$-bis-(Aspa-ATet)-GLP-1(7-36);
Val$^8$Arg$^{34}$Lys$^{26,36}$-bis-(Aspa-ATet)-GLP-1(7-36);
Val$^8$Arg$^{26}$Lys$^{34,36}$-bis-(Aspa-ATet)-GLP-1(7-37);
Val$^8$Arg$^{34}$Lys$^{26,36}$-bis-(Aspa-ATet)-GLP-1(7-37);
Val$^8$Arg$^{26}$Lys$^{34,37}$-bis-(Aspa-ATet)-GLP-1(7-37);
Val$^8$Arg$^{34}$Lys$^{26,37}$-bis-(Aspa-ATet)-GLP-1(7-37);
Val$^8$Arg$^{26}$Lys$^{34,38}$-bis-(Aspa-ATet)-GLP-1(7-38);
Val$^8$Arg$^{34}$Lys$^{26,38}$-bis-(Aspa-ATet)-GLP-1(7-38);
Val$^8$Arg$^{26,34}$Lys$^{36,38}$-bis-(Aspa-ATet)-GLP-1(7-38);
Val$^8$Arg$^{26}$Lys$^{34,39}$-bis-(Aspa-ATet)-GLP-1(7-39);
Val$^8$Arg$^{34}$Lys$^{26,39}$-bis-(Aspa-ATet)-GLP-1(7-39);
Val$^8$Arg$^{26,34}$Lys$^{36,39}$-bis-(Aspa-ATet)-GLP-1(7-39);
Ser$^8$Lys$^{26,34}$-bis-(Aspa-ATet)-GLP-1(7-36); Ser$^8$Lys$^{26,34}$-bis-(Aspa-ATet)-GLP-1(7-37); Ser$^8$Lys$^{26,34}$-bis-(Aspa-ATet)-GLP-1(7-38); Ser$^8$Lys$^{26,34}$-bis-(Aspa-ATet)-GLP-1(7-39)

Ser$^8$Arg$^{26}$Lys$^{34,36}$-bis-(Aspa-ATet)-GLP-1(7-36);
Ser$^8$Arg$^{34}$Lys$^{26,36}$-bis-(Aspa-ATet)-GLP-1(7-36);
Ser$^8$Arg$^{26}$Lys$^{34,36}$-bis-(Aspa-ATet)-GLP-1(7-37);
Ser$^8$Arg$^{34}$Lys$^{26,36}$-bis-(Aspa-ATet)-GLP-1(7-37);
Ser$^8$Arg$^{26}$Lys$^{34,37}$-bis-(Aspa-ATet)-GLP-1(7-37);
Ser$^8$Arg$^{34}$Lys$^{26,37}$-bis-(Aspa-ATet)-GLP-1(7-37);
Ser$^8$Arg$^{26}$Lys$^{34,38}$-bis-(Aspa-ATet)-GLP-1(7-38);
Ser$^8$Arg$^{34}$Lys$^{26,38}$-bis-(Aspa-ATet)-GLP-1(7-38);
Ser$^8$Arg$^{26,34}$Lys$^{36,38}$-bis-(Aspa-ATet)-GLP-1(7-38);
Ser$^8$Arg$^{26}$Lys$^{34,39}$-bis-(Aspa-ATet)-GLP-1(7-39);
Ser$^8$Arg$^{34}$Lys$^{26,39}$-bis-(Aspa-ATet)-GLP-1(7-39);
Ser$^8$Arg$^{26,34}$Lys$^{36,39}$-bis-(Aspa-ATet)-GLP-1(7-39);
Thr$^8$Lys$^{26,34}$-bis-(Aspa-ATet)-GLP-1(7-36); Thr$^8$Lys$^{26,34}$-bis-(Aspa-ATet)-GLP-1(7-37); Thr$^8$Lys$^{26,34}$-bis-(Aspa-ATet)-GLP-1(7-38); Thr$^8$Lys$^{26,34}$-bis-(Aspa-ATet)-GLP-1(7-39)

Thr$^8$Arg$^{26}$Lys$^{34,36}$-bis-(Aspa-ATet)-GLP-1(7-36);
Thr$^8$Arg$^{34}$Lys$^{26,36}$-bis-(Aspa-ATet)-GLP-1(7-36);
Thr$^8$Arg$^{26}$Lys$^{34,36}$-bis-(Aspa-ATet)-GLP-1(7-37);
Thr$^8$Arg$^{34}$Lys$^{26,36}$-bis-(Aspa-ATet)-GLP-1(7-37);
Thr$^8$Arg$^{26}$Lys$^{34,37}$-bis-(Aspa-ATet)-GLP-1(7-37);
Thr$^8$Arg$^{34}$Lys$^{26,37}$-bis-(Aspa-ATet)-GLP-1(7-37);
Thr$^8$Arg$^{26}$Lys$^{34,38}$-bis-(Aspa-ATet)-GLP-1(7-38);
Thr$^8$Arg$^{34}$Lys$^{26,38}$-bis-(Aspa-ATet)-GLP-1(7-38);
Thr$^8$Arg$^{26,34}$Lys$^{36,38}$-bis-(Aspa-ATet)-GLP-1(7-38);
Thr$^8$Arg$^{26}$Lys$^{34,39}$-bis-(Aspa-ATet)-GLP-1(7-39);
Thr$^8$Arg$^{34}$Lys$^{26,39}$-bis-(Aspa-ATet)-GLP-1(7-39);
Thr$^8$Arg$^{26,34}$Lys$^{36,39}$-bis-(Aspa-ATet)-GLP-1(7-39);
Lys$^{26,34}$-bis-(Aspa-AHex)-GLP-1(7-36); Lys$^{26,34}$-bis-(Aspa-AHex)-GLP-1(7-37); Lys$^{26,34}$-bis-(Aspa-AHex)-GLP-1(7-38); Lys$^{26,34}$-bis-(Aspa-AHex)-GLP-1(7-39)

Arg$^{26}$Lys$^{34,36}$-bis-(Aspa-AHex)-GLP-1(7-36); Arg$^{34}$Lys$^{26,36}$-bis-(Aspa-AHex)-GLP-1(7-36); Arg$^{26}$Lys$^{34,36}$-bis-(Aspa-AHex)-GLP-1(7-37); Arg$^{34}$Lys$^{26,36}$-bis-(Aspa-AHex)-GLP-1(7-37); Arg$^{26}$Lys$^{34,37}$-bis-(Aspa-AHex)-GLP-1(7-37); Arg$^{34}$Lys$^{26,37}$-bis-(Aspa-AHex)-GLP-1(7-37); Arg$^{26}$Lys$^{34,39}$-bis-(Aspa-AHex)-GLP-1(7-39); Arg$^{34}$Lys$^{26,39}$-bis-(Aspa-AHex)-GLP-1(7-39); Arg$^{26,34}$Lys$^{36,39}$-bis-(Aspa-AHex)-GLP-1(7-39);

Arg$^{26}$Lys$^{18,34}$-bis-(Aspa-AHex)-GLP-1(7-36); Arg$^{34}$Lys$^{18,26}$-bis-(Aspa-AHex)-GLP-1(7-36); Arg$^{26}$Lys$^{18,34}$-bis-(Aspa-AHex)-GLP-1(7-37); Arg$^{34}$Lys$^{18,26}$-bis-(Aspa-AHex)-GLP-1(7-37); Arg$^{26}$Lys$^{18,34}$-bis-(Aspa-AHex)-GLP-1(7-38); Arg$^{34}$Lys$^{18,26}$-bis-(Aspa-AHex)-GLP-1(7-38); Arg$^{26}$Lys$^{18,34}$-bis-(Aspa-AHex)-GLP-1(7-39); Arg$^{34}$Lys$^{18,26}$-bis-(Aspa-AHex)-GLP-1(7-39);

Arg$^{26}$Lys$^{23,34}$-bis-(Aspa-AHex)-GLP-1(7-36); Arg$^{34}$Lys$^{23,26}$-bis-(Aspa-AHex)-GLP-1(7-36); Arg$^{26}$Lys$^{23,34}$-bis-(Aspa-AHex)-GLP-1(7-37); Arg$^{34}$Lys$^{23,26}$-bis-(Aspa-AHex)-GLP-1(7-37); Arg$^{26}$Lys$^{23,34}$-bis-(Aspa-AHex)-GLP-1(7-38); Arg$^{34}$Lys$^{23,26}$-bis-(Aspa-AHex)-GLP-1(7-38); Arg$^{26}$Lys$^{23,34}$-bis-(Aspa-AHex)-GLP-1(7-39); Arg$^{34}$Lys$^{23,26}$-bis-(Aspa-AHex)-GLP-1(7-39);

Arg$^{26}$Lys$^{27,34}$-bis-(Aspa-AHex)-GLP-1(7-36); Arg$^{34}$Lys$^{27,26}$-bis-(Aspa-AHex)-GLP-1(7-36); Arg$^{26}$Lys$^{27,34}$-bis-(Aspa-AHex)-GLP-1(7-37); Arg$^{34}$Lys$^{27,26}$-bis-(Aspa-AHex)-GLP-1(7-37); Arg$^{26}$Lys$^{27,34}$-bis-(Aspa-AHex)-GLP-1(7-38); Arg$^{34}$Lys$^{27,26}$-bis-(Aspa-AHex)-GLP-1(7-38); Arg$^{26}$Lys$^{27,34}$-bis-(Aspa-AHex)-GLP-1(7-39); Arg$^{34}$Lys$^{27,26}$-bis-(Aspa-AHex)-GLP-1(7-39);

Gly$^8$Lys$^{26,34}$-bis-(Aspa-AHex)-GLP-1(7-36); Gly$^8$Lys$^{26,34}$-bis-(Aspa-AHex)-GLP-1(7-37); Gly$^8$Lys$^{26,34}$-bis-(Aspa-AHex)-GLP-1(7-38); Gly$^8$Lys$^{26,34}$-bis-(Aspa-AHex)-GLP-1(7-39)

Gly$^8$Arg$^{26}$Lys$^{34,36}$-bis-(Aspa-AHex)-GLP-1(7-36);
Gly$^8$Arg$^{34}$Lys$^{26,36}$-bis-(Aspa-AHex)-GLP-1(7-36);
Gly$^8$Arg$^{26}$Lys$^{34,36}$-bis-(Aspa-AHex)-GLP-1(7-37);
Gly$^8$Arg$^{34}$Lys$^{26,36}$-bis-(Aspa-AHex)-GLP-1(7-37);
Gly$^8$Arg$^{26}$Lys$^{34,37}$-bis-(Aspa-AHex)-GLP-1(7-37);
Gly$^8$Arg$^{34}$Lys$^{26,37}$-bis-(Aspa-AHex)-GLP-1(7-37);
Gly$^8$Arg$^{26}$Lys$^{34,38}$-bis-(Aspa-AHex)-GLP-1(7-38);
Gly$^8$Arg$^{34}$Lys$^{26,38}$-bis-(Aspa-AHex)-GLP-1(7-38);
Gly$^8$Arg$^{26,34}$Lys$^{36,38}$-bis-(Aspa-AHex)GLP-1(7-38);
Gly$^8$Arg$^{26}$Lys$^{34,39}$-bis-(Aspa-AHex)-GLP-1(7-39);
Gly$^8$Arg$^{34}$Lys$^{26,39}$-bis-(Aspa-AHex)-GLP-1(7-39);
Gly$^8$Arg$^{26,34}$Lys$^{36,39}$-bis-(Aspa-AHex)-GLP-1(7-39);
Val$^8$Lys$^{26,34}$-bis-(Aspa-AHex)-GLP-1(7-36); Val$^8$Lys$^{26,34}$-bis-(Aspa-AHex)-GLP-1(7-37); Val$^8$Lys$^{26,34}$-bis-(Aspa-AHex)-GLP-1(7-38); Val$^8$Lys$^{26,34}$-bis-(Aspa-AHex)-GLP-1(7-39)

Val$^8$Arg$^{26}$Lys$^{34,36}$-bis-(Aspa-AHex)-GLP-1(7-36);
Val$^8$Arg$^{34}$Lys$^{26,36}$-bis-(Aspa-AHex)-GLP-1(7-36);
Val$^8$Arg$^{26}$Lys$^{34,36}$-bis-(Aspa-AHex)-GLP-1(7-37);
Val$^8$Arg$^{34}$Lys$^{26,36}$-bis-(Aspa-AHex)-GLP-1(7-37);
Val$^8$Arg$^{26}$Lys$^{34,37}$-bis-(Aspa-AHex)-GLP-1(7-37);
Val$^8$Arg$^{34}$Lys$^{26,37}$-bis-(Aspa-AHex)-GLP-1(7-37);
Val$^8$Arg$^{26}$Lys$^{34,38}$-bis-(Aspa-AHex)-GLP-1(7-38);
Val$^8$Arg$^{34}$Lys$^{26,38}$-bis-(Aspa-AHex)-GLP-1(7-38);
Val$^8$Arg$^{26,34}$Lys$^{36,38}$-bis-(Aspa-AHex)-GLP-1(7-38);
Val$^8$Arg$^{26}$Lys$^{34,39}$-bis-(Aspa-AHex)-GLP-1(7-39);
Val$^8$Arg$^{34}$Lys$^{26,39}$-bis-(Aspa-AHex)-GLP-1(7-39);
Val$^8$Arg$^{26,34}$Lys$^{36,39}$-bis-(Aspa-AHex)-GLP-1(7-39);
Ser$^8$Lys$^{26,34}$-bis-(Aspa-AHex)-GLP-1(7-36); Ser$^8$Lys$^{26,34}$-bis-(Aspa-AHex)-GLP-1(7-37); Ser$^8$Lys$^{26,34}$-bis-(Aspa-AHex)-GLP-1(7-38); Ser$^8$Lys$^{26,34}$-bis-(Aspa-AHex)-GLP-1(7-39)

Ser$^8$Arg$^{26}$Lys$^{34,36}$-bis-(Aspa-AHex)-GLP-1(7-36);
Ser$^8$Arg$^{34}$Lys$^{26,36}$-bis-(Aspa-AHex)-GLP-1(7-36);
Ser$^8$Arg$^{26}$Lys$^{34,36}$-bis-(Aspa-AHex)-GLP-1(7-37);
Ser$^8$Arg$^{34}$Lys$^{26,36}$-bis-(Aspa-AHex)-GLP-1(7-37);
Ser$^8$Arg$^{26}$Lys$^{34,37}$-bis-(Aspa-AHex)-GLP-1(7-37);
Ser$^8$Arg$^{34}$Lys$^{26,37}$-bis-(Aspa-AHex)-GLP-1(7-37);
Ser$^8$Arg$^{26}$Lys$^{34,38}$-bis-(Aspa-AHex)-GLP-1(7-38);
Ser$^8$Arg$^{34}$Lys$^{26,38}$-bis-(Aspa-AHex)-GLP-1(7-38);
Ser$^8$Arg$^{26,34}$Lys$^{36,38}$-bis-(Aspa-AHex)-GLP-1(7-38);
Ser$^8$Arg$^{26}$Lys$^{34,39}$-bis-(Aspa-AHex)-GLP-1(7-39);
Ser$^8$Arg$^{34}$Lys$^{26,39}$-bis-(Aspa-AHex)-GLP-1(7-39);
Ser$^8$Arg$^{26,34}$Lys$^{36,39}$-bis-(Aspa-AHex)-GLP-1(7-39);
Thr$^8$Lys$^{26,34}$-bis-(Aspa-AHex)-GLP-1(7-36); Thr$^8$Lys$^{26,34}$-bis-(Aspa-AHex)-GLP-1(7-37); Thr$^8$Lys$^{26,34}$-bis-(Aspa-AHex)-GLP-1(7-38); Thr$^8$Lys$^{26,34}$-bis-(Aspa-AHex)-GLP-1(7-39)

Thr⁸Arg²⁶Lys³⁴,³⁶-bis-(Aspa-AHex)-GLP-1(7-36);
Thr⁸Arg³⁴Lys²⁶,³⁶-bis-(Aspa-AHex)-GLP-1(7-36);
Thr⁸Arg²⁶Lys³⁴,³⁶-bis-(Aspa-AHex)-GLP-1(7-37);
Thr⁸Arg³⁴Lys²⁶,³⁶-bis-(Aspa-AHex)-GLP-1(7-37);
Thr⁸Arg²⁶Lys³⁴,³⁷-bis-(Aspa-AHex)-GLP-1(7-37);
Thr⁸Arg³⁴Lys²⁶,³⁷-bis-(Aspa-AHex)-GLP-1(7-37);
Thr⁸Arg²⁶Lys³⁴,³⁸-bis-(Aspa-AHex)-GLP-1(7-38);
Thr⁸Arg³⁴Lys²⁶,³⁸-bis-(Aspa-AHex)-GLP-1(7-38);
Thr⁸Arg²⁶,³⁴Lys³⁶,³⁸-bis-(Aspa-AHex)-GLP-1(7-38);
Thr⁸Arg²⁶Lys³⁴,³⁹-bis-(Aspa-AHex)-GLP-1(7-39);
Thr⁸Arg³⁴Lys²⁶,³⁹-bis-(Aspa-AHex)-GLP-1(7-39);
Thr⁸Arg²⁶,³⁴Lys³⁶,³⁹-bis-(Aspa-AHex)-GLP-1(7-39);
Lys²⁶,³⁴-bis-(Aspa-AOct)-GLP-1(7-36); Lys²⁶,³⁴-bis-(Aspa-AOct)-GLP-1(7-37); Lys²⁶,³⁴-bis-(Aspa-AOct)-GLP-1(7-38); Lys²⁶,³⁴-bis-(Aspa-AOct)-GLP-1(7-39)
Arg²⁶Lys³⁴,³⁶-bis-(Aspa-AOct)-GLP-1(7-36); Arg³⁴Lys²⁶,³⁶-bis-(Aspa-AOct)-GLP-1(7-36); Arg²⁶Lys³⁴,³⁶-bis-(Aspa-AOct)-GLP-1(7-37); Arg³⁴Lys²⁶,³⁶-bis-(Aspa-AOct)-GLP-1(7-37); Arg²⁶Lys³⁴,³⁷-bis-(Aspa-AOct)-GLP-1(7-37); Arg³⁴Lys²⁶,³⁷-bis-(Aspa-AOct)-GLP-1(7-37); Arg²⁶Lys³⁴,³⁹-bis-(Aspa-AOct)-GLP-1(7-39); Arg³⁴Lys²⁶,³⁹-bis-(Aspa-AOct)-GLP-1(7-39); Arg²⁶,³⁴Lys³⁶,³⁹-bis-(Aspa-AOct)-GLP-1(7-39);
Arg²⁶Lys¹⁸,³⁴-bis-(Aspa-AOct)-GLP-1(7-36); Arg³⁴Lys¹⁸,²⁶-bis-(Aspa-AOct)-GLP-1(7-36); Arg²⁶Lys¹⁸,³⁴-bis-(Aspa-AOct)-GLP-1(7-37); Arg³⁴Lys¹⁸,²⁶-bis-(Aspa-AOct)-GLP-1(7-37); Arg²⁶Lys¹⁸,³⁴-bis-(Aspa-AOct)-GLP-1(7-38); Arg³⁴Lys¹⁸,²⁶-bis-(Aspa-AOct)-GLP-1(7-38); Arg²⁶Lys¹⁸,³⁴-bis-(Aspa-AOct)-GLP-1(7-39); Arg³⁴Lys¹⁸,²⁶-bis-(Aspa-AOct)-GLP-1(7-39);
Arg²⁶Lys²³,³⁴-bis-(Aspa-AOct)-GLP-1(7-36); Arg³⁴Lys²³,²⁶-bis-(Aspa-AOct)-GLP-1(7-36); Arg²⁶Lys²³,³⁴-bis-(Aspa-AOct)-GLP-1(7-37); Arg³⁴Lys²³,²⁶-bis-(Aspa-AOct)-GLP-1(7-37); Arg²⁶Lys²³,³⁴-bis-(Aspa-AOct)-GLP-1(7-38); Arg³⁴Lys²³,²⁶-bis-(Aspa-AOct)-GLP-1(7-38); Arg²⁶Lys²³,³⁴-bis-(Aspa-AOct)-GLP-1(7-39); Arg³⁴Lys²³,²⁶-bis-(Aspa-AOct)-GLP-1(7-39);
Arg²⁶Lys²⁷,³⁴-bis-(Aspa-AOct)-GLP-1(7-36); Arg³⁴Lys²⁷,²⁶-bis-(Aspa-AOct)-GLP-1(7-36); Arg²⁶Lys²⁷,³⁴-bis-(Aspa-AOct)-GLP-1(7-37); Arg³⁴Lys²⁷,²⁶-bis-(Aspa-AOct)-GLP-1(7-37); Arg²⁶Lys²⁷,³⁴-bis-(Aspa-AOct)-GLP-1(7-38); Arg³⁴Lys²⁷,²⁶-bis-(Aspa-AOct)-GLP-1(7-38); Arg²⁶Lys²⁷,³⁴-bis-(Aspa-AOct)-GLP-1(7-39); Arg³⁴Lys²⁷,²⁶-bis-(Aspa-AOct)-GLP-1(7-39);
Gly⁸Lys²⁶,³⁴-bis-(Aspa-AOct)-GLP-1(7-36); Gly⁸Lys²⁶,³⁴-bis-(Aspa-AOct)-GLP-1(7-37); Gly⁸Lys²⁶,³⁴-bis-(Aspa-AOct)-GLP-1(7-38); Gly⁸Lys²⁶,³⁴-bis-(Aspa-AOct)-GLP-1(7-39)
Gly⁸Arg²⁶Lys³⁴,³⁶-bis-(Aspa-AOct)-GLP-1(7-36);
Gly⁸Arg³⁴Lys²⁶,³⁶-bis-(Aspa-AOct)-GLP-1(7-36);
Gly⁸Arg²⁶Lys³⁴,³⁶-bis-(Aspa-AOct)-GLP-1(7-37);
Gly⁸Arg³⁴Lys²⁶,³⁶-bis-(Aspa-AOct)-GLP-1(7-37);
Gly⁸Arg²⁶Lys³⁴,³⁷-bis-(Aspa-AOct)-GLP-1(7-37);
Gly⁸Arg³⁴Lys²⁶,³⁷-bis-(Aspa-AOct)-GLP-1(7-37);
Gly⁸Arg²⁶Lys³⁴,³⁸-bis-(Aspa-AOct)-GLP-1(7-38);
Gly⁸Arg³⁴Lys²⁶,³⁸-bis-(Aspa-AOct)-GLP-1(7-38);
Gly⁸Arg²⁶,³⁴Lys³⁶,³⁸-bis-(Aspa-AOct)-GLP-1(7-38);
Gly⁸Arg²⁶Lys³⁴,³⁹-bis-(Aspa-AOct)-GLP-1(7-39);
Gly⁸Arg³⁴Lys²⁶,³⁹-bis-(Aspa-AOct)-GLP-1(7-39);
Gly⁸Arg²⁶,³⁴Lys³⁶,³⁹-bis-(Aspa-AOct)-GLP-1(7-39);
Val⁸Lys²⁶,³⁴-bis-(Aspa-AOct)-GLP-1(7-36); Val⁸Lys²⁶,³⁴-bis-(Aspa-AOct)-GLP-1(7-37); Val⁸Lys²⁶,³⁴-bis-(Aspa-AOct)-GLP-1(7-38); Val⁸Lys²⁶,³⁴-bis-(Aspa-AOct)-GLP-1(7-39)
Val⁸Arg²⁶Lys³⁴,³⁶-bis-(Aspa-AOct)-GLP-1(7-36);
Val⁸Arg³⁴Lys²⁶,³⁶-bis-(Aspa-AOct)-GLP-1(7-36);
Val⁸Arg²⁶Lys³⁴,³⁶-bis-(Aspa-AOct)-GLP-1(7-37);
Val⁸Arg³⁴Lys²⁶,³⁶-bis-(Aspa-AOct)-GLP-1(7-37);
Val⁸Arg²⁶Lys³⁴,³⁷-bis-(Aspa-AOct)-GLP-1(7-37);
Val⁸Arg³⁴Lys²⁶,³⁷-bis-(Aspa-AOct)-GLP-1(7-37);
Val⁸Arg²⁶Lys³⁴,³⁸-bis-(Aspa-AOct)-GLP-1(7-38);
Val⁸Arg³⁴Lys²⁶,³⁸-bis-(Aspa-AOct)-GLP-1(7-38);
Val⁸Arg²⁶,³⁴Lys³⁶,³⁸-bis-(Aspa-AOct)-GLP-1(7-38);
Val⁸Arg²⁶Lys³⁴,³⁹-bis-(Aspa-AOct)-GLP-1(7-39);
Val⁸Arg³⁴Lys²⁶,³⁹-bis-(Aspa-AOct)-GLP-1(7-39);
Val⁸Arg²⁶,³⁴Lys³⁶,³⁹-bis-(Aspa-AOct)-GLP-1(7-39);
Ser⁸Lys²⁶,³⁴-bis-(Aspa-AOct)-GLP-1(7-36); Ser⁸Lys²⁶,³⁴-bis-(Aspa-AOct)-GLP-1(7-37); Ser⁸Lys²⁶,³⁴-bis-(Aspa-AOct)-GLP-1(7-38); Ser⁸Lys²⁶,³⁴-bis-(Aspa-AOct)-GLP-1(7-39)
Ser⁸Arg²⁶Lys³⁴,³⁶-bis-(Aspa-AOct)-GLP-1(7-36);
Ser⁸Arg³⁴Lys²⁶,³⁶-bis-(Aspa-AOct)-GLP-1(7-36);
Ser⁸Arg²⁶Lys³⁴,³⁶-bis-(Aspa-AOct)-GLP-1(7-37);
Ser⁸Arg³⁴Lys²⁶,³⁶-bis-(Aspa-AOct)-GLP-1(7-37);
Ser⁸Arg²⁶Lys³⁴,³⁷-bis-(Aspa-AOct)-GLP-1(7-37);
Ser⁸Arg³⁴Lys²⁶,³⁷-bis-(Aspa-AOct)-GLP-1(7-37);
Ser⁸Arg²⁶Lys³⁴,³⁸-bis-(Aspa-AOct)-GLP-1(7-38);
Ser⁸Arg³⁴Lys²⁶,³⁸-bis-(Aspa-AOct)-GLP-1(7-38);
Ser⁸Arg²⁶,³⁴Lys³⁶,³⁸-bis-(Aspa-AOct)-GLP-1(7-38);
Ser⁸Arg²⁶Lys³⁴,³⁹-bis-(Aspa-AOct)-GLP-1(7-39);
Ser⁸Arg³⁴Lys²⁶,³⁹-bis-(Aspa-AOct)-GLP-1(7-39);
Ser⁸Arg²⁶,³⁴Lys³⁶,³⁹-bis-(Aspa-AOct)-GLP-1(7-39);
Thr⁸Lys²⁶,³⁴-bis-(Aspa-AOct)-GLP-1(7-36); Thr⁸Lys²⁶,³⁴-bis-(Aspa-AOct)-GLP-1(7-37); Thr⁸Lys²⁶,³⁴-bis-(Aspa-AOct)-GLP-1(7-38); Thr⁸Lys²⁶,³⁴-bis-(Aspa-AOct)-GLP-1(7-39)
Thr⁸Arg²⁶Lys³⁴,³⁶-bis-(Aspa-AOct)-GLP-1(7-36);
Thr⁸Arg³⁴Lys²⁶,³⁶-bis-(Aspa-AOct)-GLP-1(7-36);
Thr⁸Arg²⁶Lys³⁴,³⁶-bis-(Aspa-AOct)-GLP-1(7-37);
Thr⁸Arg³⁴Lys²⁶,³⁶-bis-(Aspa-AOct)-GLP-1(7-37);
Thr⁸Arg²⁶Lys³⁴,³⁷-bis-(Aspa-AOct)-GLP-1(7-37);
Thr⁸Arg³⁴Lys²⁶,³⁷-bis-(Aspa-AOct)-GLP-1(7-37);
Thr⁸Arg²⁶Lys³⁴,³⁸-bis-(Aspa-AOct)-GLP-1(7-38);
Thr⁸Arg³⁴Lys²⁶,³⁸-bis-(Aspa-AOct)-GLP-1(7-38);
Thr⁸Arg²⁶,³⁴Lys³⁶,³⁸-bis-(Aspa-AOct)-GLP-1(7-38);
Thr⁸Arg²⁶Lys³⁴,³⁹-bis-(Aspa-AOct)-GLP-1(7-39);
Thr⁸Arg³⁴Lys²⁶,³⁹-bis-(Aspa-AOct)-GLP-1(7-39);
Thr⁸Arg²⁶,³⁴Lys³⁶,³⁹-bis-(Aspa-AOct)-GLP-1(7-39);
Lys²⁶,³⁴-bis-(Aspa-ALit)-GLP-1(7-36); Lys²⁶,³⁴-bis-(Aspa-ALit)-GLP-1(7-37); Lys²⁶,³⁴-bis-(Aspa-ALit)-GLP-1(7-38); Lys²⁶,³⁴-bis-(Aspa-ALit)-GLP-1(7-39)
Arg²⁶Lys³⁴,³⁶-bis-(Aspa-ALit)-GLP-1(7-36); Arg³⁴Lys²⁶,³⁶-bis-(Aspa-ALit)-GLP-1(7-36); Arg²⁶Lys³⁴,³⁶-bis-(Aspa-ALit)-GLP-1(7-37); Arg³⁴Lys²⁶,³⁶-bis-(Aspa-ALit)-GLP-1(7-37); Arg²⁶Lys³⁴,³⁷-bis-(Aspa-ALit)-GLP-1(7-37); Arg³⁴Lys²⁶,³⁷-bis-(Aspa-ALit)-GLP-1(7-37); Arg²⁶Lys³⁴,³⁹-bis-(Aspa-ALit)-GLP-1(7-39); Arg³⁴Lys²⁶,³⁹-bis-(Aspa-ALit)-GLP-1(7-39); Arg²⁶,³⁴Lys³⁶,³⁹-bis-(Aspa-ALit)-GLP-1(7-39);
Arg²⁶Lys¹⁸,³⁴-bis-(Aspa-ALit)-GLP-1(7-36); Arg³⁴Lys¹⁸,²⁶-bis-(Aspa-ALit)-GLP-1(7-36); Arg²⁶Lys¹⁸,³⁴-bis-(Aspa-ALit)-GLP-1(7-37); Arg³⁴Lys¹⁸,²⁶-bis-(Aspa-ALit)-GLP-1(7-37); Arg²⁶Lys¹⁸,³⁴-bis-(Aspa-ALit)-GLP-1(7-38); Arg³⁴Lys¹⁸,²⁶-bis-(Aspa-ALit)-GLP-1(7-38); Arg²⁶Lys¹⁸,³⁴-bis-(Aspa-ALit)-GLP-1(7-39); Arg³⁴Lys¹⁸,²⁶-bis-(Aspa-ALit)-GLP-1(7-39);
Arg²⁶Lys²³,³⁴-bis-(Aspa-ALit)-GLP-1(7-36); Arg³⁴Lys²³,²⁶-bis-(Aspa-ALit)-GLP-1(7-36); Arg²⁶Lys²³,³⁴-bis-(Aspa-ALit)-GLP-1(7-37); Arg³⁴Lys²³,²⁶-bis-(Aspa-ALit)-GLP-1(7-37); Arg²⁶Lys²³,³⁴-bis-(Aspa-ALit)-GLP-1(7-38); Arg³⁴Lys²³,²⁶-bis-(Aspa-ALit)-GLP-1(7-38); Arg²⁶Lys²³,³⁴-bis-(Aspa-ALit)-GLP-1(7-39); Arg³⁴Lys²³,²⁶-bis-(Aspa-ALit)-GLP-1(7-39);

Arg$^{26}$Lys$^{27,34}$-bis-(Aspa-ALit)-GLP-1(7-36); Arg$^{34}$Lys$^{27,26}$-bis-(Aspa-ALit)-GLP-1(7-36); Arg$^{26}$Lys$^{27,34}$-bis-(Aspa-ALit)-GLP-1(7-37); Arg$^{34}$Lys$^{27,26}$-bis-(Aspa-ALit)-GLP-1(7-37); Arg$^{26}$Lys$^{27,34}$-bis-(Aspa-ALit)-GLP-1(7-38); Arg$^{34}$Lys$^{27,26}$-bis-(Aspa-ALit)-GLP-1(7-38); Arg$^{26}$Lys$^{27,34}$-bis-(Aspa-ALit)-GLP-1(7-39); Arg$^{34}$Lys$^{27,26}$-bis-(Aspa-ALit)-GLP-1(7-39);
Gly$^8$Lys$^{26,34}$-bis-(Aspa-ALit)-GLP-1(7-36); Gly$^8$Lys$^{26,34}$-bis-(Aspa-ALit)-GLP-1(7-37); Gly$^8$Lys$^{26,34}$-bis-(Aspa-ALit)-GLP-1(7-38); Gly$^8$Lys$^{26,34}$-bis-(Aspa-ALit)-GLP-1(7-39)
Gly$^8$Arg$^{26}$Lys$^{34,36}$-bis-(Aspa-ALit)-GLP-1(7-36);
Gly$^8$Arg$^{34}$Lys$^{26,36}$-bis-(Aspa-ALit)-GLP-1(7-36);
Gly$^8$Arg$^{26}$Lys$^{34,36}$-bis-(Aspa-ALit)-GLP-1(7-37);
Gly$^8$Arg$^{34}$Lys$^{26,36}$-bis-(Aspa-ALit)-GLP-1(7-37);
Gly$^8$Arg$^{26}$Lys$^{34,37}$-bis-(Aspa-ALit)-GLP-1(7-37);
Gly$^8$Arg$^{34}$Lys$^{26,37}$-bis-(Aspa-ALit)-GLP-1(7-37);
Gly$^8$Arg$^{26}$Lys$^{34,38}$-bis-(Aspa-ALit)-GLP-1(7-38);
Gly$^8$Arg$^{34}$Lys$^{26,38}$-bis-(Aspa-ALit)-GLP-1(7-38);
Gly$^8$Arg$^{26,34}$Lys$^{36,38}$-bis-(Aspa-ALit)-GLP-1(7-38);
Gly$^8$Arg$^{26}$Lys$^{34,39}$-bis-(Aspa-ALit)-GLP-1(7-39);
Gly$^8$Arg$^{34}$Lys$^{26,39}$-bis(Aspa-ALit)-GLP-1(7-39);
Gly$^8$Arg$^{26,34}$Lys$^{36,39}$-bis-(Aspa-ALit)-GLP-1(7-39);
Val$^8$Lys$^{26,34}$-bis-(Aspa-ALit)-GLP-1(7-36); Val$^3$Lys$^{26,34}$-bis-(Aspa-ALit)-GLP-1(7-37); Val$^8$Lys$^{26,34}$-bis-(Aspa-ALit)-GLP-1(7-38); Val$^8$Lys$^{26,34}$-bis-(Aspa-ALit)-GLP-1(7-39)
Val$^8$Arg$^{26}$Lys$^{34,36}$-bis-(Aspa-ALit-GLP-1(7-36);
Val$^8$Arg$^{34}$Lys$^{26,36}$-bis-(Aspa-ALit)-GLP-1(7-36);
Val$^8$Arg$^{26}$Lys$^{34,36}$-bis-(Aspa-ALit)-GLP-1(7-37);
Val$^8$Arg$^{34}$Lys$^{26,36}$-bis-(Aspa-ALit)-GLP-1(7-37);
Val$^8$Arg$^{26}$Lys$^{34,37}$-bis-(Aspa-ALit)-GLP-1(7-37);
Val$^8$Arg$^{34}$Lys$^{26,37}$-bis-(Aspa-ALit)-GLP-1(7-37);
Val$^8$Arg$^{26}$Lys$^{34,38}$-bis-(Aspa-ALit)-GLP-1(7-38);
Val$^8$Arg$^{34}$Lys$^{26,38}$-bis-(Aspa-ALit)-GLP-1(7-38);
Val$^8$Arg$^{26,34}$Lys$^{36,38}$-bis-(Aspa-ALit)-GLP-1(7-38);
Val$^8$Arg$^{26}$Lys$^{34,39}$-bis-(Aspa-ALit)-GLP-1(7-39);
Val$^8$Arg$^{34}$Lys$^{26,39}$-bis-(Aspa-ALit)-GLP-1(7-39);
Val$^8$Arg$^{26,34}$Lys$^{36,39}$-bis-(Aspa-ALit)-GLP-1(7-39);
Ser$^8$Lys$^{26,34}$-bis-(Aspa-ALit)-GLP-1(7-36); Ser$^8$Lys$^{26,34}$-bis-(Aspa-ALit)-GLP-1(7-37); Ser$^7$Lys$^{26,34}$-bis-(Aspa-ALit)-GLP-1(7-38); Ser$^8$Lys$^{26,34}$-bis-(Aspa-ALit)-GLP-1(7-39)
Ser$^8$Arg$^{26}$Lys$^{34,36}$-bis-(Aspa-ALit)-GLP-1(7-36);
Ser$^8$Arg$^{34}$Lys$^{26,36}$-bis-(Aspa-ALit)-GLP-1(7-36);
Ser$^8$Arg$^{26}$Lys$^{34,36}$-bis-(Aspa-ALit)-GLP-1(7-37);
Ser$^8$Arg$^{34}$Lys$^{26,36}$-bis-(Aspa-ALit)-GLP-1(7-37);
Ser$^8$Arg$^{26}$Lys$^{34,37}$-bis-(Aspa-ALit)-GLP-1(7-37);
Ser$^8$Arg$^{34}$Lys$^{26,37}$-bis-(Aspa-ALit)-GLP-1(7-37);
Ser$^8$Arg$^{26}$Lys$^{34,38}$-bis-(Aspa-ALit)-GLP-1(7-38);
Ser$^8$Arg$^{34}$Lys$^{26,38}$-bis-(Aspa-ALit)-GLP-1(7-38);
Ser$^8$Arg$^{26,34}$Lys$^{36,38}$-bis-(Aspa-ALit)-GLP-1(7-38);
Ser$^8$Arg$^{26}$Lys$^{34,39}$-bis-(Aspa-ALit)-GLP-1(7-39);
Ser$^8$Arg$^{34}$Lys$^{26,39}$-bis-(Aspa-ALit)-GLP-1(7-39);
Ser$^8$Arg$^{26,34}$Lys$^{36,39}$-bis-(Aspa-ALit)-GLP-1(7-39);
Thr$^8$Lys$^{26,34}$-bis-(Aspa-ALit)-GLP-1(7-36); Thr$^8$Lys$^{26,34}$-bis-(Aspa-ALit)-GLP-1(7-37); Thr$^8$Lys$^{26,34}$-bis-(Aspa-ALit)-GLP-1(7-38); Thr$^8$Lys$^{26,34}$-bis-(Aspa-ALit)-GLP-1(7-39)
Thr$^8$Arg$^{26}$Lys$^{34,36}$-bis-(Aspa-ALit)-GLP-1(7-36);
Thr$^8$Arg$^{34}$Lys$^{26,36}$-bis-(Aspa-ALit)-GLP-1(7-36);
Thr$^8$Arg$^{26}$Lys$^{34,36}$-bis-(Aspa-ALit)-GLP-1(7-37);
Thr$^8$Arg$^{34}$Lys$^{26,36}$-bis-(Aspa-ALit)-GLP-1(7-37);
Thr$^8$Arg$^{26}$Lys$^{34,37}$-bis-(Aspa-ALit)-GLP-1(7-37);
Thr$^8$Arg$^{34}$Lys$^{26,37}$-bis-(Aspa-ALit)-GLP-1(7-37);
Thr$^8$Arg$^{26}$Lys$^{34,38}$-bis-(Aspa-ALit)-GLP-1(7-38);
Thr$^8$Arg$^{34}$Lys$^{26,38}$-bis-(A  sa-ALit)-GLP-1(7-38); Thr$^8$Arg$^{26,34}$Lys$^{36,38}$-bis-(Aspa-ALit)-GLP-1(7-38);
Thr$^8$Arg$^{26}$Lys$^{34,39}$-bis-(Aspa-ALit)-GLP-1(7-39);
Thr$^8$Arg$^{34}$Lys$^{26,39}$-bis-(Aspa-ALit)-GLP-1(7-39);
Thr$^8$Arg$^{26,34}$Lys$^{36,39}$-bis-(Aspa-ALit)-GLP-1(7-39);
Lys$^{26,34}$-bis-(Glyc-ADod)-GLP-1(7-36); Lys$^{26,34}$-bis-(Glyc-ADod)-GLP-1(7-37); Lys$^{26,34}$-bis-(Glyc-ADod)-GLP-1(7-38); Lys$^{26,34}$-bis-(Glyc-ADod)-GLP-1(7-39)
Arg$^{26}$Lys$^{34,36}$-bis-(Glyc-ADod)-GLP-1(7-36); Arg$^{34}$Lys$^{26,36}$-bis-(Glyc-ADod)-GLP-1(7-36); Arg$^{26}$Lys$^{34,36}$-bis-(Glyc-ADod)-GLP-1(7-37); Arg$^{34}$Lys$^{26,36}$-bis-(Glyc-ADod)-GLP-1(7-37); Arg$^{26}$Lys$^{34,37}$-bis-(Glyc-ADod)-GLP-1(7-37); Arg$^{34}$Lys$^{26,37}$-bis-(Glyc-ADod)-GLP-1(7-37); Arg$^{26}$Lys$^{34,39}$-bis-(Glyc-ADod)-GLP-1(7-39); Arg$^{34}$Lys$^{26,39}$-bis-(Glyc-ADod)-GLP-1(7-39); Arg$^{26,34}$Lys$^{36,39}$-bis-(Glyc-ADod)-GLP-1(7-39);
Arg$^{26}$Lys$^{18,34}$-bis-(Glyc-ADod)-GLP-1(7-36); Arg$^{34}$Lys$^{18,26}$-bis-(Glyc-ADod)-GLP-1(7-36); Arg$^{26}$Lys$^{18,34}$-bis-(Glyc-ADod)-GLP-1(7-37); Arg$^{34}$Lys$^{18,26}$-bis-(Glyc-ADod)-GLP-1(7-37); Arg$^{26}$Lys$^{18,34}$-bis-(Glyc-ADod)-GLP-1(7-38); Arg$^{34}$Lys$^{826}$-bis-(Glyc-ADod)-GLP-1(7-38); Arg$^{26}$Lys$^{18,34}$-bis-(Glyc-ADod)-GLP-1(7-39); Arg$^{34}$Lys$^{18,26}$-bis-(Glyc-ADod)-GLP-1(7-39);
Arg$^{26}$Lys$^{23,34}$-bis-(Glyc-ADod)-GLP-1(7-36); Arg$^{34}$Lys$^{23,26}$-bis-(Glyc-ADod)-GLP-1(7-36); Arg$^{26}$Lys$^{23,34}$-bis-(Glyc-ADod)-GLP-1(7-37); Arg$^{34}$Lys$^{23,26}$-bis-(Glyc-ADod)-GLP-1(7-37); Arg$^{26}$Lys$^{23,34}$-bis-(Glyc-ADod)-GLP-1(7-38); Arg$^{34}$Lys$^{23,26}$-bis-(Glyc-ADod)-GLP-1(7-38); Arg$^{26}$Lys$^{23,34}$-bis-(Glyc-ADod)-GLP-1(7-39); Arg$^{34}$Lys$^{23,26}$-bis-(Glyc-ADod)-GLP-1(7-39);
Arg$^{26}$Lys$^{27,34}$-bis-(Glyc-ADod)-GLP-1(7-36); Arg$^{34}$Lys$^{27,26}$-bis-(Glyc-ADod)-GLP-1(7-36); Arg$^{26}$Lys$^{27,34}$-bis-(Glyc-ADod)-GLP-1(7-37); Arg$^{34}$Lys$^{27,26}$-bis-(Glyc-ADod)-GLP-1(7-37); Arg$^{26}$Lys$^{27,34}$-bis-(Glyc-ADod)-GLP-1(7-38); Arg$^{34}$Lys$^{27,26}$-bis-(Glyc-ADod)-GLP-1(7-38); Arg$^{26}$Lys$^{27,34}$-bis-(Glyc-ADod)-GLP-1(7-39); Arg$^{34}$Lys$^{27,26}$-bis-(Glyc-ADod)-GLP-1(7-39);
Gly$^8$Lys$^{26,34}$-bis-(Glyc-ADod)-GLP-1(7-36); Gly$^8$Lys$^{26,34}$-bis-(Glyc-ADod)-GLP-1(7-37); Gly$^8$Lys$^{26,34}$-bis-(Glyc-ADod)-GLP-1(7-38); Gly$^8$Lys$^{26,34}$-bis-(Glyc-ADod)-GLP-1(7-39)
Gly$^8$Arg$^{26}$Lys$^{34,36}$-bis-(Glyc-ADod)-GLP-1(7-36);
Gly$^8$Arg$^{34}$Lys$^{26,36}$-bis-(Glyc-ADod)-GLP-1(7-36);
Gly$^8$Arg$^{26}$Lys$^{34,36}$-bis-(Glyc-ADod)-GLP-1(7-37);
Gly$^8$Arg$^{34}$Lys$^{26,36}$-bis-(Glyc-ADod)-GLP-1(7-37);
Gly$^8$Arg$^{26}$Lys$^{34,37}$-bis-(Glyc-ADod)-GLP-1(7-37);
Gly$^8$Arg$^{34}$Lys$^{26,37}$-bis-(Glyc-ADod)-GLP-1(7-37);
Gly$^8$Arg$^{26}$Lys$^{34,38}$-bis-(Glyc-ADod)-GLP-1(7-38);
Gly$^8$Arg$^{34}$Lys$^{26,38}$-bis-(Glyc-ADod)-GLP-1(7-38);
Gly$^8$Arg$^{26,34}$Lys$^{36,38}$-bis-(Glyc-ADod)-GLP-1(7-38);
Gly$^8$Arg$^{26}$Lys$^{34,39}$-bis-(Glyc-ADod)-GLP-1(7-39);
Gly$^8$Arg$^{34}$Lys$^{26,39}$-bis-(Glyc-ADod)-GLP-1(7-39);
Gly$^8$Arg$^{26,34}$Lys$^{36,39}$-bis-(Glyc-ADod)-GLP-1(7-39);
Val$^8$Lys$^{26,34}$-bis-(Glyc-ADod)-GLP-1(7-36); Val$^8$Lys$^{26,34}$-bis-(Glyc-ADod)-GLP-1(7-37); Val$^8$Lys$^{26,34}$-bis-(Glyc-ADod)-GLP-1(7-38); Val$^8$Lys$^{26,34}$-bis-(Glyc-ADod)-GLP-1(7-39)
Val$^8$Arg$^{26}$Lys$^{34,36}$-bis-(Glyc-ADod)-GLP-1(7-36);
Val$^8$Arg$^{34}$Lys$^{26,36}$-bis-(Glyc-ADod)-GLP-1(7-36);
Val$^8$Arg$^{26}$Lys$^{34,36}$-bis-(Glyc-ADod)-GLP-1(7-37);
Val$^8$Arg$^{34}$Lys$^{26,36}$-bis-(Glyc-ADod)-GLP-1(7-37);
Val$^8$Arg$^{26}$Lys$^{34,37}$-bis-(Glyc-ADod)-GLP-1(7-37);
Val$^8$Arg$^{34}$Lys$^{26,37}$-bis-(Glyc-ADod)-GLP-1(7-37);
Val$^8$Arg$^{26}$Lys$^{34,38}$-bis-(Glyc-ADod)-GLP-1(7-38);
Val$^8$Arg$^{34}$Lys$^{26,38}$-bis-(Glyc-ADod)-GLP-1(7-38);
Val$^8$Arg$^{26,34}$Lys$^{36,38}$-bis-(Glyc-ADod)-GLP-1(7-38);
Val$^8$Arg$^{26}$Lys$^{34,39}$-bis-(Glyc-ADod)-GLP-1(7-39);

Val⁸Arg³⁴Lys²⁶,³⁹-bis-(Glyc-ADod)-GLP-1(7-39);
Val⁸Arg²⁶,³⁴Lys³⁶,³⁹-bis-(Glyc-ADod)-GLP-1(7-39);
Ser⁸Lys²⁶,³⁴-bis-(Glyc-ADod)-GLP-1(7-36); Ser⁸Lys²⁶,³⁴-bis-(Glyc-ADod)-GLP-1(7-37); Ser⁸Lys²⁶,³⁴-bis-(Glyc-ADod)-GLP-1(7-38); Ser⁸Lys²⁶,³⁴-bis-(Glyc-ADod)-GLP-1(7-39)
Ser⁸Arg²⁶Lys³⁴,³⁶-bis-(Glyc-ADod)-GLP-1(7-36);
Ser⁸Arg³⁴Lys²⁶,³⁶-bis-(Glyc-ADod)-GLP-1(7-36);
Ser⁸Arg²⁶Lys³⁴,³⁶-bis-(Glyc-ADod)-GLP-1(7-37);
Ser⁸Arg³⁴Lys²⁶,³⁶-bis-(Glyc-ADod)-GLP-1(7-37);
Ser⁸Arg²⁶Lys³⁴,³⁷-bis-(Glyc-ADod)-GLP-1(7-37);
Ser⁸Arg³⁴Lys²⁶,³⁷-bis-(Glyc-ADod)-GLP-1(7-37);
Ser⁸Arg²⁶Lys³⁴,³⁸-bis-(Glyc-ADod)-GLP-1(7-38);
Ser⁸Arg³⁴Lys²⁶,³⁸-bis-(Glyc-ADod)-GLP-1(7-38);
Ser⁸Arg²⁶,³⁴Lys³⁶,³⁸-bis-(Glyc-ADod)-GLP-1(7-38);
Ser⁸Arg²⁶Lys³⁴,³⁹-bis-(Glyc-ADod)-GLP-1(7-39);
Ser⁸Arg³⁴Lys²⁶,³⁹-bis-(Glyc-ADod)-GLP-1(7-39);
Ser⁸Arg²⁶,³⁴Lys³⁶,³⁹-bis-(Glyc-ADod)-GLP-1(7-39);
Thr⁸Lys²⁶,³⁴-bis-(Glyc-ADod)-GLP-1(7-36); Thr⁸Lys²⁶,³⁴-bis-(Glyc-ADod)-GLP-1(7-37); Thr⁸Lys²⁶,³⁴-bis-(Glyc-ADod)-GLP-1(7-38); Thr⁸Lys²⁶,³⁴-bis-(Glyc-ADod)-GLP-1(7-39)
Thr⁸Arg²⁶Lys³⁴,³⁶-bis-(Glyc-ADod)-GLP-1(7-36);
Thr⁸Arg³⁴Lys²⁶,³⁶-bis-(Glyc-ADod)-GLP-1(7-36);
Thr⁸Arg²⁶Lys³⁴,³⁶-bis-(Glyc-ADod)-GLP-1(7-37);
Thr⁸Arg³⁴Lys²⁶,³⁶-bis-(Glyc-ADod)-GLP-1(7-37);
Thr⁸Arg²⁶Lys³⁴,³⁷-bis-(Glyc-ADod)-GLP-1(7-37);
Thr⁸Arg³⁴Lys²⁶,³⁷-bis-(Glyc-ADod)-GLP-1(7-37);
Thr⁸Arg²⁶Lys³⁴,³⁸-bis-(Glyc-ADod)-GLP-1(7-38);
Thr⁸Arg³⁴Lys²⁶,³⁸-bis-(Glyc-ADod)-GLP-1(7-38);
Thr⁸Arg²⁶,³⁴Lys³⁶,³⁸-bis-(Glyc-ADod)-GLP-1(7-38);
Thr⁸Arg²⁶Lys³⁴,³⁹-bis-(Glyc-ADod)-GLP-1(7-39);
Thr⁸Arg³⁴Lys²⁶,³⁹-bis-(Glyc-ADod)-GLP-1(7-39);
Thr⁸Arg²⁶,³⁴Lys³⁶,³⁹-bis-(Glyc-ADod)-GLP-1(7-39);
Lys²⁶,³⁴-bis-(Glyc-ATet)-GLP-1(7-36); Lys²⁶,³⁴-bis-(Glyc-ATet)-GLP-1(7-37); Lys²⁶,³⁴-bis-(Glyc-ATet)-GLP-1(7-38); Lys²⁶,³⁴-bis-(Glyc-ATet)-GLP-1(7-39)
Arg²⁶Lys³⁴,³⁶-bis-(Glyc-ATet)-GLP-1(7-36); Arg³⁴Lys²⁶,³⁶-bis-(Glyc-ATet)-GLP-1(7-36); Arg²⁶Lys³⁴,³⁶-bis-(Glyc-ATet)-GLP-1(7-37); Arg³⁴Lys²⁶,³⁶-bis-(Glyc-ATet)-GLP-1(7-37); Arg²⁶Lys³⁴,³⁷-bis-(Glyc-ATet)-GLP-1(7-37); Arg³⁴Lys²⁶,³⁷-bis-(Glyc-ATet)-GLP-1(7-37); Arg²⁶Lys³⁴,³⁹-bis-(Glyc-ATet)-GLP-1(7-39); Arg³⁴Lys²⁶,³⁹-bis-(Glyc-ATet)-GLP-1(7-39); Arg²⁶,³⁴Lys³⁶,³⁹-bis-(Glyc-ATet)-GLP-1(7-39);
Arg²⁶Lys¹⁸,³⁴-bis-(Glyc-ATet)-GLP-1(7-36); Arg³⁴Lys¹⁸,²⁶-bis-(Glyc-ATet)-GLP-1(7-36); Arg²⁶Lys¹⁸,³⁴-bis (Glyc-ATet)-GLP-1(7-37); Arg³⁴Lys¹⁸,²⁶-bis-(Glyc-ATet)-GLP-1(7-37); Arg²⁶Lys¹⁸,³⁴-bis-(Glyc-ATet)-GLP-1(7-38); Arg³⁴Lys¹⁸,²⁶-bis-(Glyc-ATet)-GLP-1(7-38); Arg²⁶Lys¹⁸,³⁴-bis-(Glyc-ATet)-GLP-1(7-39); Arg³⁴Lys¹⁸,²⁶-bis-(Glyc-ATet)-GLP-1(7-39);
Arg²⁶Lys²³,³⁴-bis-(Glyc-ATet)-GLP-1(7-36); Arg³⁴Lys²³,²⁶-bis-(Glyc-ATet)-GLP-1(7-36); Arg²⁶Lys²³,³⁴-bis-(Glyc-ATet)-GLP-1(7-37); Arg³⁴Lys²³,²⁶-bis-(Glyc-ATet)-GLP-1(7-37); Arg²⁶Lys²³,³⁴-bis-(Glyc-ATet)-GLP-1(7-38); Arg³⁴Lys²³,²⁶-bis-(Glyc-ATet)-GLP-1(7-38); Arg²⁶Lys²³,³⁴-bis-(Glyc-ATet)-GLP-1(7-39); Arg³⁴Lys²³,²⁶-bis-(Glyc-ATet)-GLP-1(7-39);
Arg²⁶Lys²⁷,³⁴-bis-(Glyc-ATet)-GLP-1(7-36); Arg³⁴Lys²⁷,²⁶-bis-(Glyc-ATet)-GLP-1(7-36); Arg²⁶Lys²⁷,³⁴-bis-(Glyc-ATet)-GLP-1(7-37); Arg³⁴Lys²⁷,²⁶-bis-(Glyc-ATet)-GLP-1(7-37); Arg²⁶Lys²⁷,³⁴-bis-(Glyc-ATet)-GLP-1(7-38); Arg³⁴Lys²⁷,²⁶-bis-(Glyc-ATet)-GLP-1(7-38); Arg²⁶Lys²⁷,³⁴-bis-(Glyc-ATet)-GLP-1(7-39); Arg³⁴Lys²⁷,²⁶-bis-(Glyc-ATet)-GLP-1(7-39);

Gly⁸Lys²⁶,³⁴-bis-(Glyc-ATet)-GLP-1(7-36); Gly³Lys²⁶,³⁴-bis-(Glyc-ATet)-GLP-1(7-37); Gly⁸Lys²⁶,³⁴-bis-(Glyc-ATet)-GLP-1(7-38); Gly⁸Lys²⁶,³⁴-bis-(Glyc-ATet)-GLP-1(7-39)
Gly⁸Arg²⁶Lys³⁴,³⁶-bis-(Glyc-ATet)-GLP-1(7-36);
Gly⁸Arg³⁴Lys²⁶,³⁶-bis-(Glyc-ATet)-GLP-1(7-36);
Gly⁸Arg²⁶Lys³⁴,³⁶-bis-(Glyc-ATet)-GLP-1(7-37);
Gly⁸Arg³⁴Lys²⁶,³⁶-bis-(Glyc-ATet)-GLP-1(7-37);
Gly⁸Arg²⁶Lys³⁴,³⁷-bis-(Glyc-ATet)-GLP-1(7-37);
Gly⁸Arg³⁴Lys²⁶,³⁷-bis-(Glyc-ATet)-GLP-1(7-37);
Gly⁸Arg²⁶Lys³⁴,³⁸-bis-(Glyc-ATet)-GLP-1(7-38);
Gly⁸Arg³⁴Lys²⁶,³⁸-bis-(Glyc-ATet)-GLP-1(7-38);
Gly⁸Arg²⁶,³⁴Lys³⁶,³⁸-bis-(Glyc-ATet)-GLP-1(7-38);
Gly⁸Arg²⁶Lys³⁴,³⁹-bis-(Glyc-ATet)-GLP-1(7-39);
Gly⁸Arg³⁴Lys²⁶,³⁹-bis-(Glyc-ATet)-GLP-1(7-39);
Gly⁸Arg²⁶,³⁴Lys³⁶,³⁹-bis-(Glyc-ATet)-GLP-1(7-39);
Val⁸Lys²⁶,³⁴-bis-(Glyc-ATet)-GLP-1(7-36); Val⁸Lys²⁶,³⁴-bis-(Glyc-ATet) GLP-1(7-37); Val⁸Lys²⁶,³⁴-bis-(Glyc-ATet)-GLP-1(7-38); Val⁸Lys²⁶,³⁴-bis-(Glyc-ATet)-GLP-1(7-39)
Val⁸Arg²⁶Lys³⁴,³⁶-bis-(Glyc-ATet)-GLP-1(7-36);
Val⁸Arg³⁴Lys²⁶,³⁶-bis-(Glyc-ATet)-GLP-1(7-36);
Val⁸Arg²⁶Lys³⁴,³⁶-bis-(Glyc-ATet)-GLP-1(7-37);
Val⁸Arg³⁴Lys²⁶,³⁶-bis-(Glyc-ATet)-GLP-1(7-37);
Val⁸Arg²⁶Lys³⁴,³⁷-bis-(Glyc-ATet)-GLP-1(7-37);
Val⁸Arg³⁴Lys²⁶,³⁷-bis-(Glyc-ATet)-GLP-1(7-37);
Val⁸Arg²⁶Lys³⁴,³⁸-bis-(Glyc-ATet)-GLP-1(7-38);
Val⁸Arg³⁴Lys²⁶,³⁸-bis-(Glyc-ATet)-GLP-1(7-38);
Val⁸Arg²⁶,³⁴Lys³⁶,³⁸-bis-(Glyc-ATet)-GLP-1(7-38);
Val⁸Arg²⁶Lys³⁴,³⁹-bis-(Glyc-ATet)-GLP-1(7-39);
Val⁸Arg³⁴Lys²⁶,³⁹-bis-(Glyc-ATet)-GLP-1(7-39);
Val⁸Arg²⁶,³⁴Lys³⁶,³⁹-bis-(Glyc-ATet)-GLP-11(7-3(7-39);
Ser⁸Lys²⁶,³⁴-bis-(Glyc-ATet)-GLP-1(7-36); Ser⁸Lys²⁶,³⁴-bis-(Glyc-ATet)-GLP-1(7-37); Ser⁸Lys²⁶,³⁴-bis-(Glyc-ATet)-GLP-1(7-38); Ser⁸Lys²⁶,³⁴-bis-(Glyc-ATet)-GLP-1(7-39)
Ser⁸Arg²⁶Lys³⁴,³⁶-bis-(Glyc-ATet)-GLP-1(7-36);
Ser⁸Arg³⁴Lys²⁶,³⁶-bis-(Glyc-ATet)-GLP-1(7-36);
Ser⁸Arg²⁶Lys³⁴,³⁶-bis-(Glyc-ATet)-GLP-1(7-37);
Ser⁸Arg³⁴Lys²⁶,³⁶-bis-(Glyc-ATet)-GLP-1(7-37);
Ser⁸Arg²⁶Lys³⁴,³⁷-bis-(Glyc-ATet)-GLP-1(7-37);
Ser⁸Arg³⁴Lys²⁶,³⁷-bis-(Glyc-ATet)-GLP-1(7-37);
Ser⁸Arg²⁶Lys³⁴,³⁸-bis-(Glyc-ATet)-GLP-1(7-38);
Ser⁸Arg³⁴Lys²⁶,³⁸-bis-(Glyc-ATet)-GLP-1(7-38);
Ser⁸Arg²⁶,³⁴Lys³⁶,³⁸-bis-(Glyc-ATet)-GLP-1(7-38);
Ser⁸Arg²⁶Lys³⁴,³⁹-bis-(Glyc-ATet)-GLP-1(7-39);
Ser⁸Arg³⁴Lys²⁶,³⁹-bis-(Glyc-ATet)-GLP-1(7-39);
Ser⁸Arg²⁶,³⁴Lys³⁶,³⁹-bis-(Glyc-ATet)-GLP-1(7-39);
Thr⁸Lys²⁶,³⁴-bis-(Glyc-ATet)-GLP-1(7-36); Thr⁸Lys²⁶,³⁴-bis-(Glyc-ATet)-GLP-1(7-37); Thr⁸Lys²⁶,³⁴-bis-(Glyc-ATet)-GLP-1(7-38); Thr⁸Lys²⁶,³⁴-bis-(Glyc-ATet)-GLP-1(7-39)
Thr⁸Arg²⁶Lys³⁴,³⁶-bis-(Glyc-ATet)-GLP-1(7-36);
Thr⁸Arg³⁴Lys²⁶,³⁶-bis-(Glyc-ATet)-GLP-1(7-36);
Thr⁸Arg²⁶Lys³⁴,³⁶-bis-(Glyc-ATet)-GLP-1(7-37);
Thr⁸Arg³⁴Lys²⁶,³⁶-bis-(Glyc-ATet)-GLP-1(7-37);
Thr⁸Arg²⁶Lys³⁴,³⁷-bis-(Glyc-ATet)-GLP-1(7-37);
Thr⁸Arg³⁴Lys²⁶,³⁷-bis-(Glyc-ATet)-GLP-1(7-37);
Thr⁸Arg²⁶Lys³⁴,³⁸-bis-(Glyc-ATet)-GLP-1(7-38);
Thr⁸Arg³⁴Lys²⁶,³⁸-bis-(Glyc-ATet)-GLP-1(7-38);
Thr⁸Arg²⁶,³⁴Lys³⁶,³⁸-bis-(Glyc-ATet)-GLP-1(7-38);
Thr⁸Arg²⁶Lys³⁴,³⁹-bis-(Glyc-ATet)-GLP-1(7-39);
Thr⁸Arg³⁴Lys²⁶,³⁹-bis-(Glyc-ATet)-GLP-1(7-39);
Thr⁸Arg²⁶,³⁴Lys³⁶,³⁹-bis-(Glyc-ATet)-GLP-1(7-39);
Lys²⁶,³⁴-bis-(Glyc-AHex)-GLP-1(7-36); Lys²⁶,³⁴-bis-(Glyc-AHex)-GLP-1(7-37); Lys²⁶,³⁴-bis-(Glyc-AHex)-GLP-1(7-38); Lys²⁶,³⁴-bis-(Glyc-AHex)-GLP-1(7-39)

Arg²⁶Lys³⁴,³⁶-bis-(Glyc-AHex)-GLP-1(7-36); Arg³⁴Lys²⁶,³⁶-bis-(Glyc-AHex)-GLP-1(7-36); Arg²⁶Lys³⁴,³⁶-bis-(Glyc-AHex)-GLP-1(7-37); Arg³⁴Lys²⁶,³⁶-bis-(Glyc-AHex)-GLP-1(7-37); Arg²⁶Lys³⁴,³⁷-bis-(Glyc-AHex)-GLP-1(7-37); Arg³⁴Lys²⁶,³⁷-bis-(Glyc-AHex)-GLP-1(7-37); Arg²⁶Lys³⁴,³⁹-bis-(Glyc-AHex)-GLP-1(7-39); Arg³⁴Lys²⁶,³⁹-bis-(Glyc-AHex)-GLP-1(7-39); Arg²⁶,³⁴Lys³⁶,³⁹-bis-(Glyc-AHex)-GLP-1(7-39);

Arg²⁶Lys¹⁸,³⁴-bis-(Glyc-AHex)-GLP-1(7-36); Arg³⁴Lys¹⁸,²⁶-bis-(Glyc-AHex)-GLP-1(7-36); Arg²⁶Lys¹⁸,³⁴-bis-(Glyc-AHex)-GLP-1(7-37); Arg³⁴Lys¹⁸,²⁶-bis-(Glyc-AHex)-GLP-1(7-37); Arg²⁶Lys¹⁸,³⁴-bis-(Glyc-AHex)-GLP-1(7-38); Arg³⁴Lys¹⁸,²⁶-bis-(Glyc-AHex)-GLP-1(7-38); Arg²⁶Lys¹⁸,³⁴-bis-(Glyc-AHex)-GLP-1(7-39); Arg³⁴Lys¹⁸,²⁶-bis-(Glyc-AHex)-GLP-1(7-39);

Arg²⁶Lys²³,³⁴-bis-(Glyc-AHex)-GLP-1(7-36); Arg³⁴Lys²³,²⁶-bis-(Glyc-AHex)-GLP-1(7-36); Arg²⁶Lys²³,³⁴-bis-(Glyc-AHex)-GLP-1(7-37); Arg³⁴Lys²³,²⁶-bis-(Glyc-AHex)-GLP-1(7-37); Arg²⁶Lys²³,³⁴-bis-(Glyc-AHex)-GLP-1(7-38); Arg³⁴Lys²³,²⁶-bis-(Glyc-AHex)-GLP-1(7-38); Arg²⁶Lys²³,³⁴-bis-(Glyc-AHex)-GLP-1(7-39); Arg³⁴Lys²³,²⁶-bis-(Glyc-AHex)-GLP-1(7-39);

Arg²⁶Lys²⁷,³⁴-bis-(Glyc-AHex)-GLP-1(7-36); Arg³⁴Lys²⁷,²⁶-bis-(Glyc-AHex)-GLP-1(7-36); Arg²⁶Lys²⁷,³⁴-bis-(Glyc-AHex)-GLP-1(7-37); Arg³⁴Lys²⁷,²⁶-bis-(Glyc-AHex)-GLP-1(7-37); Arg²⁶Lys²⁷,³⁴-bis-(Glyc-AHex)-GLP-1(7-38); Arg³⁴Lys²⁷,²⁶-bis-(Glyc-AHex)-GLP-1(7-38); Arg²⁶Lys²⁷,³⁴-bis-(Glyc-AHex)-GLP-1(7-39); Arg³⁴Lys²⁷,²⁶-bis-(Glyc-AHex)-GLP-1(7-39);

Gly⁸Lys²⁶,³⁴-bis-(Glyc-AHex)-GLP-1(7-36); Gly²Lys²⁶,³⁴-bis-(Glyc-AHex)-GLP-1(7-37); Gly⁸Lys²⁶,³⁴-bis-(Glyc-AHex)-GLP-1(7-38); Gly⁸Lys²⁶,³⁴-bis-(Glyc-AHex)-GLP-1(7-39)

Gly⁸Arg²⁶Lys³⁴,³⁶-bis-(Glyc-AHex)-GLP-1(7-36); Gly⁸Arg³⁴Lys²⁶,³⁶-bis-(Glyc-AHex)-GLP-1(7-36); Gly⁸Arg²⁶Lys³⁴,³⁶-bis-(Glyc-AHex)-GLP-1(7-37); Gly⁸Arg³⁴Lys²⁶,³⁶-bis-(Glyc-AHex)-GLP-1(7-37); Gly⁸Arg²⁶Lys³⁴,³⁷-bis-(Glyc-AHex)-GLP-1(7-37); Gly⁸Arg³⁴Lys²⁶,³⁷-bis-(Glyc-AHex)-GLP-1(7-37); Gly⁸Arg²⁶Lys³⁴,³⁸-bis-(Glyc-AHex)GLP-1(7-38); Gly⁸Arg³⁴Lys²⁶,³⁸-bis-(Glyc-AHex)-GLP-1(7-38); Gly⁸Arg²⁶,³⁴Lys³⁶,³⁸-bis-(Glyc-AHex)-GLP-1(7-38); Gly⁸Arg²⁶Lys³⁴,³⁹-bis-(Glyc-AHex)-GLP-1(7-39); Gly⁸Arg³⁴Lys²⁶,³⁹-bis-(Glyc-AHex)-GLP-1(7-39); Gly⁸Arg²⁶,³⁴Lys³⁶,³⁹-bis-(Glyc-AHex)-GLP-1(7-39);

Val⁸Lys²⁶,³⁴-bis-(Glyc-AHex)-GLP-1(7-36); Val⁸Lys²⁶,³⁴-bis-(Glyc-AHex)-GLP-1(7-37); Val⁸Lys²⁶,³⁴-bis-(Glyc-AHex)-GLP-1(7-38); Val⁸Lys²⁶,³⁴-bis-(Glyc-AHex)-GLP-1(7-39)

Val⁸Arg²⁶Lys³⁴,³⁶-bis-(Glyc-AHex)-GLP-1(7-36); Val⁸Arg³⁴Lys²⁶,³⁶-bis-(Glyc-AHex)-GLP-1(7-36); Val⁸Arg²⁶Lys³⁴,³⁶-bis-(Glyc-AHex)-GLP-1(7-37); Val⁸Arg³⁴Lys²⁶,³⁶-bis-(Glyc-AHex)-GLP-1(7-37); Val⁸Arg²⁶Lys³⁴,³⁷-bis-(Glyc-AHex)-GLP-1(7-37); Val⁸Arg³⁴Lys²⁶,³⁷-bis-(Glyc-AHex)-GLP-1(7-37); Val⁸Arg²⁶Lys³⁴,³⁸-bis-(Glyc-AHex)-GLP-1(7-38); Val⁸Arg³⁴Lys²⁶,³⁸-bis-(Glyc-AHex)-GLP-1(7-38); Val⁸Arg²⁶,³⁴Lys³⁶,³⁸-bis-(Glyc-AHex)-GLP-1(7-38); Val⁸Arg²⁶Lys³⁴,³⁹-bis-(Glyc-AHex)-GLP-1(7-39); Val⁸Arg³⁴Lys²⁶,³⁹-bis-(Glyc-AHex)-GLP-1(7-39); Val⁸Arg²⁶,³⁴Lys³⁶,³⁹-bis-(Glyc-AHex)-GLP-1(7-39);

Ser⁸Lys²⁶,³⁴-bis-(Glyc-AHex)-GLP-1(7-36); Ser⁸Lys²⁶,³⁴-bis-(Glyc-AHex)-GLP-1(7-37); Ser⁸Lys²⁶,³⁴-bis-(Glyc-AHex)-GLP-1(7-38); Ser⁸Lys²⁶,³⁴-bis-(Glyc-AHex)-GLP-1(7-39)

Ser⁸Arg²⁶Lys³⁴,³⁶-bis-(Glyc-AHex)-GLP-1(7-36); Ser⁸Arg³⁴Lys²⁶,³⁶-bis-(Glyc-AHex)-GLP-1(7-36); Ser⁸Arg²⁶Lys³⁴,³⁶-bis-(Glyc-AHex)-GLP-1(7-37); Ser⁸Arg³⁴Lys²⁶,³⁶-bis-(Glyc-AHex)-GLP-1(7-37); Ser⁸Arg²⁶Lys³⁴,³⁷-bis-(Glyc-AHex)-GLP-1(7-37); Ser⁸Arg³⁴Lys²⁶,³⁷-bis-(Glyc-AHex)-GLP-1(7-37); Ser⁸Arg²⁶Lys³⁴,³⁸-bis-(Glyc-AHex)-GLP-1(7-38); Ser⁸Arg³⁴Lys²⁶,³⁸-bis-(Glyc-AHex)-GLP-1(7-38); Ser⁸Arg²⁶,³⁴Lys³⁶,³⁸-bis-(Glyc-AHex)-GLP-1(7-38); Ser⁸Arg²⁶Lys³⁴,³⁹-bis-(Glyc-AHex)-GLP-1(7-39); Ser⁸Arg³⁴Lys²⁶,³⁹-bis-(Glyc-AHex)-GLP-1(7-39); Ser⁸Arg²⁶,³⁴Lys³⁶,³⁹-bis-(Glyc-AHex)-GLP-1(7-39);

Thr⁸Lys²⁶,³⁴-bis-(Glyc-AHex)-GLP-1(7-36); Thr⁸Lys²⁶,³⁴-bis-(Glyc-AHex)-GLP-1(7-37); Thr⁸Lys²⁶,³⁴-bis-(Glyc-AHex)-GLP-1(7-38); Thr⁸Lys²⁶,³⁴-bis-(Glyc-AHex)-GLP-1(7-39)

Thr⁸Arg²⁶Lys³⁴,³⁶-bis-(Glyc-AHex)-GLP-1(7-36); Thr⁸Arg³⁴Lys²⁶,³⁶-bis-(Glyc-AHex)-GLP-1(7-36); Thr⁸Arg²⁶Lys³⁴,³⁶-bis-(Glyc-AHex)-GLP-1(7-37); Thr⁸Arg³⁴Lys²⁶,³⁶-bis-(Glyc-AHex)-GLP-1(7-37); Thr⁸Arg²⁶Lys³⁴,³⁷-bis-(Glyc-AHex)-GLP-1(7-37); Thr⁸Arg³⁴Lys²⁶,³⁷-bis-(Glyc-AHex)-GLP-1(7-37); Thr⁸Arg²⁶Lys³⁴,³⁷-bis-(Glyc-AHex)-GLP-1(7-38); Thr⁸Arg³⁴Lys²⁶,³⁸-bis-(Glyc-AHex)-GLP-1(7-38); Thr⁸Arg²⁶,³⁴Lys³⁶,³⁸-bis-(Glyc-AHex)-GLP-1(7-38); Thr⁸Arg²⁶Lys³⁴,³⁹-bis-(Glyc-AHex)-GLP-1(7-39); Thr⁸Arg³⁴Lys²⁶,³⁹-bis-(Glyc-AHex)-GLP-1(7-39); Thr⁸Arg²⁶,³⁴Lys³⁶,³⁹-bis-(Glyc-AHex)-GLP-1(7-3(7-39);

Lys²⁶,³⁴-bis-(Glyc-AOct)-GLP-1(7-36); Lys²⁶,³⁴-bis-(Glyc-AOct)-GLP-1(7-37); Lys²⁶,³⁴-bis-(Glyc-AOct)-GLP-1(7-38); Lys²⁶,³⁴-bis-(Glyc-AOct)-GLP-1(7-39)

Arg²⁶Lys³⁴,³⁶-bis-(Glyc-AOct)-GLP-1(7-36); Arg³⁴Lys²⁶,³⁶-bis-(Glyc-AOct)-GLP-1(7-36); Arg²⁶Lys³⁴,³⁶-bis-(Glyc-AOct)-GLP-1(7-37); Arg³⁴Lys²⁶,³⁶-bis-(Glyc-AOct)-GLP-1(7-37); Arg²⁶Lys³⁴,³⁷-bis-(Glyc-AOct)-GLP-1(7-37); Arg³⁴Lys²⁶,³⁷-bis-(Glyc-AOct)-GLP-1(7-37); Arg²⁶Lys³⁴,³⁹-bis-(Glyc-AOct)-GLP-1(7-39); Arg³⁴Lys²⁶,³⁹-bis-(Glyc-AOct)-GLP-1(7-39); Arg²⁶,³⁴Lys³⁶,³⁹-bis-(Glyc-AOct)-GLP-1(7-39);

Arg²⁶Lys¹⁸,³⁴-bis-(Glyc-AOct)-GLP-1(7-36); Arg³⁴Lys¹⁸,²⁶-bis-(Glyc-AOct)-GLP-1(7-36); Arg²⁶Lys¹⁸,³⁴-bis-(Glyc-AOct)-GLP-1(7-37); Arg³⁴Lys¹⁸,²⁶-bis-(Glyc-AOct)-GLP-1(7-37); Arg²⁶Lys¹⁸,³⁴-bis-(Glyc-AOct)-GLP-1(7-38); Arg³⁴Lys¹⁸,²⁶-bis-(Glyc-AOct)-GLP-1(7-38); Arg²⁶Lys¹⁸,³⁴-bis-(Glyc-AOct)-GLP-1(7-39); Arg³⁴Lys¹⁸,²⁶-bis-(Glyc-AOct)-GLP-1(7-39);

Arg²⁶Lys²³,³⁴-bis-(Glyc-AOct)-GLP-1(7-36); Arg³⁴Lys²³,²⁶-bis-(Glyc-AOct)-GLP-1(7-36); Arg²⁶Lys²³,³⁴-bis-(Glyc-AOct)-GLP-1(7-37); Arg³⁴Lys²³,²⁶-bis-(Glyc-AOct)-GLP-1(7-37); Arg²⁶Lys²³,³⁴-bis-(Glyc-AOct)-GLP-1(7-38); Arg³⁴Lys²³,²⁶-bis-(Glyc-AOct)-GLP-1(7-38); Arg²⁶Lys²³,³⁴-bis-(Glyc-AOct)-GLP-1(7-39); Arg³⁴Lys²³,²⁶-bis-(Glyc-AOct)-GLP-1(7-39);

Arg²⁶Lys²⁷,³⁴-bis-(Glyc-AOct)-GLP-1(7-36); Arg³⁴Lys²⁷,²⁶-bis-(Glyc-AOct)-GLP-1(7-36); Arg²⁶Lys²⁷,³⁴-bis-(Glyc-AOct)-GLP-1(7-37); Arg³⁴Lys²⁷,²⁶-bis-(Glyc-AOct)-GLP-1(7-37); Arg²⁶Lys²⁷,³⁴-bis-(Glyc-AOct)-GLP-1(7-38); Arg³⁴Lys²⁷,²⁶-bis-(Glyc-AOct)-GLP-1(7-38); Arg²⁶Lys²⁷,³⁴-bis-(Glyc-AOct)-GLP-1(7-39); Arg³⁴Lys²⁷,²⁶-bis-(Glyc-AOct)-GLP-1(7-39);

Gly⁸Lys²⁶,³⁴-bis-(Glyc-AOct)-GLP-1(7-36); Gly⁸Lys²⁶,³⁴-bis-(Glyc-AOct)-GLP-1(7-37); Gly⁸Lys²⁶,³⁴-bis-(Glyc-AOct)-GLP-1(7-38); Gly⁸Lys²⁶,³⁴-bis-(Glyc-AOct)-GLP-1(7-39)

Gly⁸Arg²⁶Lys³⁴,³⁶-bis-(Glyc-AOct)-GLP-1(7-36); Gly⁸Arg³⁴Lys²⁶,³⁶-bis-(Glyc-AOct)-GLP-1(7-36); Gly⁸Arg²⁶Lys³⁴,³⁶-bis-(Glyc-AOct)-GLP-1(7-37); Gly⁸Arg³⁴Lys²⁶,³⁶-bis-(Glyc-AOct)-GLP-1(7-37); Gly⁸Arg²⁶Lys³⁴,³⁷-bis-(Glyc-AOct)-GLP-1(7-37);

Gly$^8$Arg$^{34}$Lys$^{26,37}$-bis-(Glyc-AOct)-GLP-1(7-37);
Gly$^8$Arg$^{26}$Lys$^{34,38}$-bis-(Glyc-AOct)-GLP-1(7-38);
Gly$^8$Arg$^{34}$Lys$^{26,38}$-bis-(Glyc-AOct)-GLP-1(7-38);
Gly$^8$Arg$^{26,34}$Lys$^{36,38}$-bis-(Glyc-AOct)-GLP-1(7-38);
Gly$^8$Arg$^{26}$Lys$^{34,39}$-bis-(Glyc-AOct)-GLP-1(7-39);
Gly$^8$Arg$^{34}$Lys$^{26,39}$-bis-(Glyc-AOct)-GLP-1(7-39);
Gly$^8$Arg$^{26,34}$Lys$^{36,39}$-bis-(Glyc-AOct)-GLP-1(7-39);
Val$^8$Lys$^{26,34}$-bis-(Glyc-AOct-GLP-1(7-36); Val$^8$Lys$^{26,34}$-bis-(Glyc-AOct)-GLP-1(7-37); Val$^8$Lys$^{26,34}$-bis-(Glyc-AOct)-GLP-1(7-38); Val$^8$Lys$^{26,34}$-bis-(Glyc-AOct)-GLP-1(7-39)
Val$^8$Arg$^{26}$Lys$^{34,36}$-bis-(Glyc-AOct)-GLP-1(7-36);
Val$^8$Arg$^{34}$Lys$^{26,36}$-bis-(Glyc-AOct)-GLP-1(7-36);
Val$^8$Arg$^{26}$Lys$^{34,36}$-bis-(Glyc-AOct)-GLP-1(7-37);
Val$^8$Arg$^{34}$Lys$^{26,36}$-bis-(Glyc-AOct)-GLP-1(7-37);
Val$^8$Arg$^{26}$Lys$^{34,37}$-bis-(Glyc-AOct)-GLP-1(7-37);
Val$^8$Arg$^{34}$Lys$^{26,37}$-bis-(Glyc-AOct)-GLP-1(7-37);
Val$^8$Arg$^{26}$Lys$^{34,38}$-bis-(Glyc-AOct)-GLP-1(7-38);
Val$^8$Arg$^{34}$Lys$^{26,38}$-bis-(Glyc-AOct)-GLP-1(7-38);
Val$^8$Arg$^{26,34}$Lys$^{36,38}$-bis-(Glyc-AOct)-GLP-1(7-38);
Val$^8$Arg$^{26}$Lys$^{34,39}$-bis-(Glyc-AOct)-GLP-1(7-39);
Val$^8$Arg$^{34}$Lys$^{26,39}$-bis-(Glyc-AOct)-GLP-1(7-39);
Val$^8$Arg$^{26,34}$Lys$^{36,39}$-bis-(Glyc-AOct)-GLP-1(7-39);
Ser$^8$Lys$^{26,34}$-bis-(Glyc-AOct)-GLP-1(7-36); Ser$^8$Lys$^{26,34}$-bis-(Glyc-AOct)-GLP-1(7-37); Ser$^8$Lys$^{26,34}$-bis-(Glyc-AOct)-GLP-1(7-38); Ser$^8$Lys$^{26,34}$-bis-(Glyc-AOct)-GLP-1(7-39)
Ser$^8$Arg$^{26}$Lys$^{34,36}$-bis-(Glyc-AOct)-GLP-1(7-36);
Ser$^8$Arg$^{34}$Lys$^{26,36}$-bis-(Glyc-AOct)-GLP-1(7-36);
Ser$^8$Arg$^{26}$Lys$^{34,36}$-bis-(Glyc-AOct)-GLP-1(7-37);
Ser$^8$Arg$^{34}$Lys$^{26,36}$-bis-(Glyc-AOct)-GLP-1(7-37);
Ser$^8$Arg$^{26}$Lys$^{34,37}$-bis-(Glyc-AOct)-GLP-1(7-37);
Ser$^8$Arg$^{34}$Lys$^{26,37}$-bis-(Glyc-AOct)-GLP-1(7-37);
Ser$^8$Arg$^{26}$Lys$^{34,38}$-bis-(Glyc-AOct)-GLP-1(7-38);
Ser$^8$Arg$^{34}$Lys$^{26,38}$-bis-(Glyc-AOct)-GLP-1(7-38);
Ser$^8$Arg$^{26,34}$Lys$^{36,38}$-bis-(Glyc-AOct)-GLP-1(7-38);
Ser$^8$Arg$^{26}$Lys$^{34,39}$-bis-(Glyc-AOct)-GLP-1(7-39);
Ser$^8$Arg$^{34}$Lys$^{26,39}$-bis-(Glyc-AOct)-GLP-1(7-39);
Ser$^8$Arg$^{26,34}$Lys$^{36,39}$-bis-(Glyc-AOct)-GLP-1(7-39);
Thr$^8$Lys$^{26,34}$-bis-(Glyc-AOct)-GLP-1(7-36); Thr$^8$Lys$^{26,34}$-bis-(Glyc-AOct)-GLP-1(7-37); Thr$^8$Lys$^{26,34}$-bis-(Glyc-AOct)-GLP-1(7-38); Thr$^8$Lys$^{26,34}$-bis-(Glyc-AOct)-GLP-1(7-39)
Thr$^8$Arg$^{26}$Lys$^{34,36}$-bis-(Glyc-AOct)-GLP-1(7-36);
Thr$^8$Arg$^{34}$Lys$^{26,36}$-bis-(Glyc-AOct)-GLP-1(7-36);
Thr$^8$Arg$^{26}$Lys$^{34,36}$-bis-(Glyc-AOct)-GLP-1(7-37);
Thr$^8$Arg$^{34}$Lys$^{26,36}$-bis-(Glyc-AOct)-GLP-1(7-37);
Thr$^8$Arg$^{26}$Lys$^{34,37}$-bis-(Glyc-AOct)-GLP-1(7-37);
Thr$^8$Arg$^{34}$Lys$^{26,37}$-bis-(Glyc-AOct)-GLP-1(7-37);
Thr$^8$Arg$^{26}$Lys$^{34,38}$-bis-(Glyc-AOct)-GLP-1(7-38);
Thr$^8$Arg$^{34}$Lys$^{26,38}$-bis-(Glyc-AOct)-GLP-1(7-38);
Thr$^8$Arg$^{26,34}$Lys$^{36,38}$-bis-(Glyc-AOct)-GLP-1(7-38);
Thr$^8$Arg$^{26}$Lys$^{34,39}$-bis-(Glyc-AOct)-GLP-1(7-39);
Thr$^8$Arg$^{34}$Lys$^{26,39}$-bis-(Glyc-AOct)-GLP-1(7-39);
Thr$^8$Arg$^{26,34}$Lys$^{36,39}$-bis-(Glyc-AOct)-GLP-1(7-39);
Lys$^{26,34}$-bis-(Glyc-ALit)-GLP-1(7-36); Lys$^{26,34}$-bis-(Glyc-ALit)-GLP-1(7-37); Lys$^{26,34}$-bis-(Glyc-ALit)-GLP-1(7-38); Lys$^{26,34}$-bis-(Glyc-ALit)-GLP-1(7-39)
Arg$^{26}$Lys$^{34,36}$-bis-(Glyc-ALit)-GLP-1(7-36); Arg$^{34}$Lys$^{26,36}$-bis-(Glyc-ALit)-GLP-1(7-36); Arg$^{26}$Lys$^{34,36}$-bis-(Glyc-ALit)-GLP-1(7-37); Arg$^{34}$Lys$^{26,36}$-bis-(Glyc-ALit)-GLP-1(7-37); Arg$^{26}$Lys$^{34,37}$-bis-(Glyc-ALit)-GLP-1(7-37); Arg$^{34}$Lys$^{26,37}$-bis-(Glyc-ALit)-GLP-1(7-37); Arg$^{26}$Lys$^{34,39}$-bis-(Glyc-ALit)-GLP-1(7-39); Arg$^{34}$Lys$^{26,39}$-bis-(Glyc-ALit)-GLP-1(7-39); Arg$^{26,34}$Lys$^{36,39}$-bis-(Glyc-ALit)-GLP-1(7-39);
Arg$^{26}$Lys$^{18,34}$-bis-(Glyc-ALit)-GLP-1(7-36); Arg$^{34}$Lys$^{18,26}$-bis-(Glyc-ALit)-GLP-1(7-36); Arg$^{26}$Lys$^{18,34}$-bis-(Glyc-ALit)-GLP-1(7-37); Arg$^{34}$Lys$^{18,26}$-bis(Glyc-ALit)-GLP-1(7-37); Arg$^{26}$Lys$^{18,34}$-bis-(Glyc-ALit)-GLP-1(7-37); Arg$^{34}$Lys$^{18,26}$-bis-(Glyc-ALit)-GLP-1(7-38); Arg$^{26}$Lys$^{18,34}$-bis-(Glyc-ALit)-GLP-1(7-39); Arg$^{34}$Lys$^{18,26}$-bis-(Glyc-ALit)-GLP-1(7-39);
Arg$^{26}$Lys$^{23,34}$-bis-(Glyc-ALit)-GLP-1(7-36); Arg$^{34}$Lys$^{23,26}$-bis-(Glyc-ALit)-GLP-1(7-36); Arg$^{26}$Lys$^{23,34}$-bis-(Glyc-ALit)-GLP-1(7-37); Arg$^{34}$Lys$^{23,26}$-bis-(Glyc-ALit)-GLP-1(7-37); Arg$^{26}$Lys$^{23,34}$-bis-(Glyc-ALit)-GLP-1(7-38); Arg$^{34}$Lys$^{23,26}$-bis-(Glyc-ALit)-GLP-1(7-38); Arg$^{26}$Lys$^{23,34}$-bis-(Glyc-ALit)-GLP-1(7-39); Arg$^{34}$Lys$^{23,26}$-bis-(Glyc-ALit)-GLP-1(7-39);
Arg$^{26}$Lys$^{27,34}$-bis-(Glyc-ALit)-GLP-1(7-36); Arg$^{34}$Lys$^{27,26}$-bis-(Glyc-ALit)-GLP-1(7-36); Arg$^{26}$Lys$^{27,34}$-bis-(Glyc-ALit)-GLP-1(7-37); Arg$^{34}$Lys$^{27,26}$-bis-(Glyc-ALit)-GLP-1(7-37); Arg$^{26}$Lys$^{27,34}$-bis-(Glyc-ALit)-GLP-1(7-38); Arg$^{34}$Lys$^{27,26}$-bis-(Glyc-ALit)-GLP-1(7-38); Arg$^{26}$Lys$^{27,34}$-bis-(Glyc-ALit)-GLP-1(7-39); Arg$^{34}$Lys$^{27,26}$-bis-(Glyc-ALit)-GLP-1(7-39);
Gly$^8$Lys$^{26,34}$-bis-(Glyc-ALit)-GLP-1(7-36); Gly$^8$Lys$^{26,34}$-bis-(Glyc-ALit)-GLP-1(7-37); Gly$^8$Lys$^{26,34}$-bis-(Glyc-ALit)-GLP-1(7-38); Gly$^8$Lys$^{26,34}$-bis-(Glyc-ALit)-GLP-1(7-39)
Gly$^8$Arg$^{26}$Lys$^{34,36}$-bis-(Glyc-ALit)-GLP-1(7-36);
Gly$^8$Arg$^{34}$Lys$^{26,36}$-bis-(Glyc-ALit)-GLP-1(7-36);
Gly$^8$Arg$^{26}$Lys$^{34,36}$-bis-(Glyc-ALit)-GLP-1(7-37);
Gly$^8$Arg$^{34}$Lys$^{26,36}$-bis-(Glyc-ALit)-GLP-1(7-37);
Gly$^8$Arg$^{26}$Lys$^{34,37}$-bis-(Glyc-ALit)-GLP-1(7-37);
Gly$^8$Arg$^{34}$Lys$^{26,37}$-bis-(Glyc-ALit)-GLP-1(7-37);
Gly$^8$Arg$^{26}$Lys$^{34,38}$-bis-(Glyc-ALit)-GLP-1(7-38);
Gly$^8$Arg$^{34}$Lys$^{26,38}$-bis-(Glyc-ALit)-GLP-1(7-38);
Gly$^8$Arg$^{26,34}$Lys$^{36,38}$-bis-(Glyc-ALit)-GLP-1(7-38);
Gly$^8$Arg$^{26}$Lys$^{34,39}$-bis-(Glyc-ALit)-GLP-1(7-39);
Gly$^8$Arg$^{34}$Lys$^{26,39}$-bis-(Glyc-ALit)-GLP-1(7-39);
Gly$^8$Arg$^{26,34}$Lys$^{36,39}$-bis-(Glyc-ALit)-GLP-1(7-39);
Val$^8$Lys$^{26,34}$-bis-(Glyc-ALit)-GLP-1(7-36); Val$^8$Lys$^{26,34}$-bis-(Glyc-ALit)-GLP-1(7-37); Val$^8$Lys$^{26,34}$-bis-(Glyc-ALit)-GLP-1(7-38); Val$^8$Lys$^{26,34}$-bis-(Glyc-ALit)-GLP-1(7-39)
Val$^8$Arg$^{26}$Lys$^{34,36}$-bis-(Glyc-ALit)-GLP-1(7-36);
Val$^8$Arg$^{34}$Lys$^{26,36}$-bis-(Glyc-ALit)-GLP-1(7-36);
Val$^8$Arg$^{26}$Lys$^{34,36}$-bis-(Glyc-ALit)-GLP-1(7-37);
Val$^8$Arg$^{34}$Lys$^{26,36}$-bis-(Glyc-ALit)-GLP-1(7-37);
Val$^8$Arg$^{26}$Lys$^{34,37}$-bis-(Glyc-ALit)-GLP-1(7-37);
Val$^8$Arg$^{34}$Lys$^{26,37}$-bis-(Glyc-ALit)-GLP-1(7-37);
Val$^8$Arg$^{26}$Lys$^{34,38}$-bis-(Glyc-ALit)-GLP-1(7-38);
Val$^8$Arg$^{34}$Lys$^{26,38}$-bis-(Glyc-ALit)-GLP-1(7-38);
Val$^8$Arg$^{26,34}$Lys$^{36,38}$-bis-(Glyc-ALit)-GLP-1(7-38);
Val$^8$Arg$^{26}$Lys$^{34,39}$-bis-(Glyc-ALit)-GLP-1(7-39);
Val$^8$Arg$^{34}$Lys$^{26,39}$-bis-(Glyc-ALit)-GLP-1(7-39);
Val$^8$Arg$^{26,34}$Lys$^{36,39}$-bis-(Glyc-ALit)-GLP-1(7-39);
Ser$^8$Lys$^{26,34}$-bis-(Glyc-ALit)-GLP-1(7-36); Ser$^8$Lys$^{26,34}$-bis-(Glyc-ALit)-GLP-1(7-37); Ser$^8$Lys$^{26,34}$-bis-(Glyc-ALit)-GLP-1(7-38); Ser$^8$Lys$^{26,34}$-bis-(Glyc-ALit)-GLP-1(7-39)
Ser$^8$Arg$^{26}$Lys$^{34,36}$-bis-(Glyc-ALit)-GLP-1(7-36);
Ser$^8$Arg$^{34}$Lys$^{26,36}$-bis-(Glyc-ALit)-GLP-1(7-36);
Ser$^8$Arg$^{26}$Lys$^{34,36}$-bis-(Glyc-ALit)-GLP-1(7-37);
Ser$^8$Arg$^{34}$Lys$^{26,36}$-bis-(Glyc-ALit)-GLP-1(7-37);
Ser$^8$Arg$^{26}$Lys$^{34,37}$-bis-(Glyc-ALit)-GLP-1(7-37);
Ser$^8$Arg$^{34}$Lys$^{26,37}$-bis-(Glyc-ALit)-GLP-1(7-37);
Ser$^8$Arg$^{26}$Lys$^{34,38}$-bis-(Glyc-ALit)-GLP-1(7-38);
Ser$^8$Arg$^{34}$Lys$^{26,38}$-bis-(Glyc-ALit)-GLP-1(7-38);
Ser$^8$Arg$^{26,34}$Lys$^{36,38}$-bis-(Glyc-ALit)-GLP-1(7-38);
Ser$^8$Arg$^{34}$Lys$^{26,39}$-bis-(Glyc-ALit)-GLP-1(7-39);

Ser$^8$Arg$^{34}$Lys$^{26,39}$-bis-(Glyc-ALit)-GLP-1(7-39);
Ser$^8$Arg$^{26,34}$Lys$^{36,39}$-bis-(Glyc-ALit)-GLP-1(7-39);
Thr$^8$Lys$^{26,34}$-bis-(Glyc-ALit)-GLP-1(7-36); Thr$^8$Lys$^{26,34}$-bis-(Glyc-ALit)-GLP-1(7-37); Thr$^8$Lys$^{26,34}$-bis-(Glyc-ALit)-GLP-1(7-38); Thr$^8$Lys$^{26,34}$-bis-(Glyc-ALit)-GLP-1(7-39)
Thr$^8$Arg$^{26}$Lys$^{34,36}$-bis-(Glyc-ALit)-GLP-1(7-36);
Thr$^8$Arg$^{34}$Lys$^{26,36}$-bis-(Glyc-ALit)-GLP-1(7-36);
Thr$^8$Arg$^{26}$Lys$^{34,36}$-bis-(Glyc-ALit)-GLP-1(7-37);
Thr$^8$Arg$^{34}$Lys$^{26,36}$-bis-(Glyc-ALit)-GLP-1(7-37);
Thr$^8$Arg$^{26}$Lys$^{34,37}$-bis-(Glyc-ALit)-GLP-1(7-37);
Thr$^8$Arg$^{34}$Lys$^{26,37}$-bis-(Glyc-ALit)-GLP-1(7-37);
Thr$^8$Arg$^{26}$Lys$^{34,38}$-bis-(Glyc-ALit)-GLP-1(7-38);
Thr$^8$Arg$^{34}$Lys$^{26,38}$-bis-(Glyc-ALit)-GLP-1(7-38);
Thr$^8$Arg$^{26,34}$Lys$^{36,38}$-bis-(Glyc-ALit)-GLP-1(7-38);
Thr$^8$Arg$^{26}$Lys$^{34,39}$-bis-(Glyc-ALit)-GLP-1(7-39);
Thr$^8$Arg$^{34}$Lys$^{26,39}$-bis-(Glyc-ALit)-GLP-1(7-39);
Thr$^8$Arg$^{26,34}$Lys$^{36,39}$-bis-(Glyc-ALit)-GLP-1(7-39);
Lys$^{26,34}$-bis-(GAB-GDod)-GLP-1(7-36); Lys$^{26,34}$-bis-(GAB-GDod)-GLP-1(7-37); Lys$^{26,34}$-bis-(GAB-GDod)-GLP-1(7-38); Lys$^{26,34}$-bis-(GAB-GDod)-GLP-1(7-39)
Arg$^{26}$Lys$^{34,36}$-bis-(GAB-GDod)-GLP-1(7-36); Arg$^{34}$Lys$^{26,36}$-bis-(GAB-GDod)-GLP-1(7-36); Arg$^{26}$Lys$^{34,36}$-bis-(GAB-GDod)-GLP-1(7-37); Arg$^{34}$Lys$^{26,36}$-bis-(GAB-GDod)-GLP-1(7-37); Arg$^{26}$Lys$^{34,37}$-bis-(GAB-GDod)-GLP-1(7-37); Arg$^{34}$Lys$^{26,37}$-bis-(GAB-GDod)-GLP-1(7-37); Arg$^{26}$Lys$^{34,39}$-bis-(GAB-GDod)-GLP-1(7-39); Arg$^{34}$Lys$^{26,39}$-bis-(GAB-GDod)-GLP-1(7-39); Arg$^{26,34}$Lys$^{36,39}$-bis-(GAB-GDod)-GLP-1(7-39);
Arg$^{26}$Lys$^{18,34}$-bis-(GAB-GDod)-GLP-1(7-36); Arg$^{34}$Lys$^{18,26}$-bis-(GAB-GDod)-GLP-1(7-36); Arg$^{26}$Lys$^{18,34}$-bis-(GAB-GDod))-GLP-1(7-37); Arg$^{34}$Lys$^{18,26}$-bis-(GAB-GDod)-GLP-1(7-37); Arg$^{26}$Lys$^{18,34}$-bis-(GAB-GDod)-GLP-1(7-38); Arg$^{34}$Lys$^{18,26}$-bis-(GAB-GDod)-GLP-1(7-38); Arg$^{26}$Lys$^{18,34}$-bis-(GAB-GDod)-GLP-1(7-39); Arg$^{34}$Lys$^{18,26}$-bis-(GAB-GDod)-GLP-1(7-39);
Arg$^{26}$Lys$^{23,34}$-bis-(GAB-GDod)-GLP-1(7-36); Arg$^{34}$Lys$^{23,26}$-bis-(GAB-GDod)-GLP-1(7-36); Arg$^{26}$Lys$^{23,34}$-bis-(GAB-GDod)-GLP-1(7-37); Arg$^{34}$Lys$^{23,26}$-bis-(GAB-GDod)-GLP-1(7-37);Arg$^{26}$Lys$^{23,34}$ bis-(GAB-GDod)-GLP-1(7-38); Arg$^{34}$Lys$^{23,26}$-bis-(GAB-GDod)-GLP-1(7-38); Arg$^{26}$Lys$^{23,34}$-bis-(GAB-GDod)-GLP-1(7-39); Arg$^{34}$Lys$^{23,26}$-bis-(GAB-GDod)-GLP-1(7-39);
Arg$^{26}$Lys$^{27,34}$-bis-(GAB-GDod)-GLP-1(7-36); Arg$^{34}$Lys$^{27,26}$-bis-(GAB-GDod)-GLP-1(7-36); Arg$^{26}$Lys$^{27,34}$-bis-(GAB-GDod)-GLP-1(7-37); Arg$^{34}$Lys$^{27,26}$-bis-(GAB-GDod)-GLP-1(7-37); Arg$^{26}$Lys$^{27,34}$-bis-(GAB-GDod)-GLP-1(7-38); Arg$^{34}$Lys$^{27,26}$-bis-(GAB-GDod)-GLP-1(7-38); Arg$^{26}$Lys$^{27,34}$-bis-(GAB-GDod)-GLP-1(7-39); Arg$^{34}$Lys$^{27,26}$-bis-(GAB-GDod)-GLP-1(7-39);
Gly$^8$Lys$^{26,34}$-bis-(GAB-GDod)-GLP-1(7-36); Gly$^8$Lys$^{26,34}$-bis-(GAB-GDod)-GLP-1(7-37); Gly$^8$Lys$^{26,34}$-bis-(GAB-GDod)-GLP-1(7-38); Gly$^8$Lys$^{26,34}$-bis-(GAB-GDod)-GLP-1(7-39)
Gly$^8$Arg$^{26}$Lys$^{34,36}$-bis-(GAB-GDod)-GLP-1(7-36);
Gly$^8$Arg$^{34}$Lys$^{26,36}$-bis-(GAB-GDod)-GLP-1(7-36);
Gly$^8$Arg$^{26}$Lys$^{34,36}$-bis-(GAB-GDod)-GLP-1(7-37);
Gly$^8$Arg$^{34}$Lys$^{26,36}$-bis-(GAB-GDod)-GLP-1(7-37);
Gly$^8$Arg$^{26}$Lys$^{34,37}$-bis-(GAB-GDod)-GLP-1(7-37);
Gly$^8$Arg$^{34}$Lys$^{26,37}$-bis-(GAB-GDod)-GLP-1(7-37);
Gly$^8$Arg$^{26}$Lys$^{34,38}$-bis-(GAB-GDod)-GLP-1(7-38);
Gly$^8$Arg$^{34}$Lys$^{26,38}$-bis-(GAB-GDod)-GLP-1(7-38);
Gly$^8$Arg$^{26,34}$Lys$^{36,38}$-bis-(GAB-GDod)GLP-1(7-38);
Gly$^8$Arg$^{26}$Lys$^{34,39}$-bis-(GAB-GDod)-GLP-1(7-39);
Gly$^8$Arg$^{34}$Lys$^{26,39}$-bis-(GAB-GDod)-GLP-1(7-39);
Gly$^8$Arg$^{26,34}$Lys$^{36,39}$-bis-(GAB-GDod)-GLP-1(7-39);
Val$^8$Lys$^{26,34}$-bis-(GAB-GDod)-GLP-1(7-36); Val$^8$Lys$^{26,34}$-bis-(GAB-GDod)-GLP-1(7-37); Val$^8$Lys$^{26,34}$-bis-(GAB-GDod)-GLP-1(7-38); Val$^8$Lys$^{26,34}$-bis-(GAB-GDod)-GLP-1(7-39)
Val$^8$Arg$^{26}$Lys$^{34,36}$-bis-(GAB-GDod)-GLP-1(7-36);
Val$^8$Arg$^{34}$Lys$^{26,36}$-bis-(GAB-GDod)-GLP-1(7-36);
Val$^8$Arg$^{26}$Lys$^{34,36}$-bis-(GAB-GDod)-GLP-1(7-37);
Val$^8$Arg$^{34}$Lys$^{26,36}$-bis-(GAB-GDod)-GLP-1(7-37);
Val$^8$Arg$^{26}$Lys$^{34,37}$-bis-(GAB-GDod)-GLP-1(7-37);
Val$^8$Arg$^{34}$Lys$^{26,37}$-bis-(GAB-GDod)-GLP-1(7-37);
Val$^8$Arg$^{26}$Lys$^{34,38}$-bis-(GAB-GDod)-GLP-1(7-38);
Val$^8$Arg$^{34}$Lys$^{26,38}$-bis-(GAB-GDod)-GLP-1(7-38);
Val$^8$Arg$^{26,34}$Lys$^{36,38}$-bis-(GAB-GDod)-GLP-1(7-38);
Val$^8$Arg$^{26}$Lys$^{34,39}$-bis-(GAB-GDod)-GLP-1(7-39);
Val$^8$Arg$^{34}$Lys$^{26,39}$-bis-(GAB-GDod)-GLP-1(7-39);
Val$^8$Arg$^{26,34}$Lys$^{36,39}$-bis-(GAB-GDod)-GLP-1(7-39);
Ser$^8$Lys$^{26,34}$-bis-(GAB-GDod)-GLP-1(7-36); Ser$^8$Lys$^{26,34}$-bis-(GAB-GDod)-GLP-1(7-37); Ser$^8$Lys$^{26,34}$-bis-(GAB-GDod)-GLP-1(7-38); Ser$^8$Lys$^{26,34}$-bis-(GAB-GDod)-GLP-1(7-39)
Ser$^8$Arg$^{26}$Lys$^{34,36}$-bis-(GAB-GDod)-GLP-1(7-36);
Ser$^8$Arg$^{34}$Lys$^{26,36}$-bis-(GAB-GDod)-GLP-1(7-36);
Ser$^8$Arg$^{26}$Lys$^{34,36}$-bis-(GAB-GDod)-GLP-1(7-37);
Ser$^8$Arg$^{34}$Lys$^{26,36}$-bis-(GAB-GDod)-GLP-1(7-37);
Ser$^8$Arg$^{26}$Lys$^{34,37}$-bis-(GAB-GDod)-GLP-1(7-37);
Ser$^8$Arg$^{34}$Lys$^{26,37}$-bis-(GAB-GDod)-GLP-1(7-37);
Ser$^8$Arg$^{26}$Lys$^{34,38}$-bis-(GAB-GDod)-GLP-1(7-38);
Ser$^8$Arg$^{34}$Lys$^{26,38}$-bis-(GAB-GDod)-GLP-1(7-38);
Ser$^8$Arg$^{26,34}$Lys$^{36,38}$-bis-(GAB-GDod)-GLP-1(7-38);
Ser$^8$Arg$^{26}$Lys$^{34,39}$-bis-(GAB-GDod)-GLP-1(7-39);
Ser$^8$Arg$^{34}$Lys$^{26,39}$-bis-(GAB-GDod)-GLP-1(7-39);
Ser$^8$Arg$^{26,34}$Lys$^{36,39}$-bis-(GAB-GDod)-GLP-1(7-39);
Thr$^8$Lys$^{26,34}$-bis-(GAB-GDod)-GLP-1(7-36); Thr$^8$Lys$^{26,34}$-bis-(GAB-GDod)-GLP-1(7-37); Thr$^8$Lys$^{26,34}$-bis-(GAB-GDod)-GLP-1(7-38); Thr$^8$Lys$^{26,34}$-bis-(GAB-GDod)-GLP-1(7-39)
Thr$^8$Arg$^{26}$Lys$^{34,36}$-bis-(GAB-GDod)-GLP-1(7-36);
Thr$^8$Arg$^{34}$Lys$^{26,36}$-bis-(GAB-GDod)-GLP-1(7-36);
Thr$^8$Arg$^{26}$Lys$^{34,36}$-bis-(GAB-GDod)-GLP-1(7-37);
Thr$^8$Arg$^{34}$Lys$^{26,36}$-bis-(GAB-GDod)-GLP-1(7-37);
Thr$^8$Arg$^{26}$Lys$^{34,37}$-bis-(GAB-GDod)-GLP-1(7-37);
Thr$^8$Arg$^{34}$Lys$^{26,37}$-bis-(GAB-GDod)-GLP-1(7-37);
Thr$^8$Arg$^{26}$Lys$^{34,38}$-bis-(GAB-GDod)-GLP-1(7-38);
Thr$^8$Arg$^{34}$Lys$^{26,38}$-bis-(GAB-GDod)-GLP-1(7-38);
Thr$^8$Arg$^{26,34}$Lys$^{36,38}$-bis-(GAB-GDod)-GLP-1(7-38);
Thr$^8$Arg$^{26}$Lys$^{34,39}$-bis-(GAB-GDod)-GLP-1(7-39);
Thr$^8$Arg$^{34}$Lys$^{26,39}$-bis-(GAB-GDod)-GLP-1(7-39);
Thr$^8$Arg$^{26,34}$Lys$^{36,39}$-bis-(GAB-GDod)-GLP-1(7-39);
Lys$^{26,34}$-bis-(GAB-GTet)-GLP-1(7-36); Lys$^{26,34}$-bis-(GAB-GTet)-GLP-1(7-37); Lys$^{26,34}$-bis-(GAB-GTet)-GLP-1(7-38); Lys$^{26,34}$-bis-(GAB-GTet)-GLP-1(7-39)
Arg$^{26}$Lys$^{34,36}$-bis-(GAB-GTet)-GLP-1(7-36); Arg$^{34}$Lys$^{26,36}$-bis-(GAB-GTet)-GLP-1(7-36); Arg$^{26}$Lys$^{34,36}$-bis-(GAB-GTet)-GLP-1(7-37); Arg$^{34}$Lys$^{26,36}$-bis-(GAB-GTet)-GLP-1(7-37); Arg$^{26}$Lys$^{34,37}$-bis-(GAB-GTet)-GLP-1(7-37); Arg$^{34}$Lys$^{26,37}$-bis-(GAB-GTet)-GLP-1(7-37); Arg$^{26}$Lys$^{34,39}$-bis-(GAB-GTet)-GLP-1(7-39); Arg$^{34}$Lys$^{26,39}$-bis-(GAB-GTet)-GLP-1(7-39); Arg$^{26,34}$Lys$^{36,39}$-bis-(GAB-GTet)-GLP-1(7-39);
Arg$^{26}$Lys$^{18,34}$-bis-(GAB-GTet)-GLP-1(7-36); Arg$^{34}$Lys$^{18,26}$-bis-(GAB-GTet)-GLP-1(7-36); Arg$^{26}$Lys$^{18,34}$-bis-(GAB-GTet)-GLP-1(7-37); Arg$^{34}$Lys$^{18,26}$-bis-(GAB-GTet)-GLP-1(7-37); Arg$^{26}$Lys$^{18,34}$-bis-(GAB-GTet)-GLP-1(7-38); Arg$^{34}$Lys$^{18,26}$-bis-(GAB-GTet)-GLP-1(7-38); Arg$^{26}$Lys$^{18,34}$-bis-(GAB-GTet)-GLP-1(7-39); Arg$^{34}$Lys$^{8,26}$-bis-(GAB-GTet)-GLP-1(7-39);

Arg$^{26}$Lys$^{23,34}$-bis-(GAB-GTet)-GLP-1(7-36); Arg$^{34}$Lys$^{23,26}$-bis-(GAB-GTet)-GLP-1(7-36); Arg$^{26}$Lys$^{23,34}$-bis-(GAB-GTet)-GLP-1(7-37); Arg$^{34}$Lys$^{23,26}$-bis-(GAB-GTet)-GLP-1(7-37); Arg$^{26}$Lys$^{23,34}$-bis-(GAB-GTet)-GLP-1(7-38); Arg$^{34}$Lys$^{23,26}$-bis-(GAB-GTet)-GLP-1(7-38); Arg$^{26}$Lys$^{23,34}$-bis-(GAB-GTet)-GLP-1(7-39); Arg$^{34}$Lys$^{23,26}$-bis-(GAB-GTet)-GLP-1(7-39);

Arg$^{26}$Lys$^{27,34}$-bis-(GAB-GTet)-GLP-1(7-36); Arg$^{34}$Lys$^{27,26}$-bis-(GAB-GTet)-GLP-1(7-36); Arg$^{26}$Lys$^{27,34}$-bis-(GAB-GTet)-GLP-1(7-37); Arg$^{34}$Lys$^{27,26}$-bis-(GAB-GTet)-GLP-1(7-37); Arg$^{26}$Lys$^{27,34}$-bis-(GAB-GTet)-GLP-1(7-38); Arg$^{34}$Lys$^{27,26}$-bis-(GAB-GTet)-GLP-1(7-38); Arg$^{26}$Lys$^{27,34}$-bis-(GAB-GTet)-GLP-1(7-39); Arg$^{34}$Lys$^{27,26}$-bis-(GAB-GTet)-GLP-1(7-39);

Gly$^8$Lys$^{26,34}$-bis-(GAB-GTet)-GLP-1(7-36); Gly$^8$Lys$^{26,34}$-bis-(GAB-GTet)-GLP-1(7-37); Gly$^8$Lys$^{26,34}$-bis-(GAB-GTet)-GLP-1(7-38); Gly$^8$Lys$^{26,34}$-bis-(GAB-GTet)-GLP-1(7-39)

Gly$^8$Arg$^{26}$Lys$^{34,36}$-bis-(GAB-GTet)-GLP-1(7-36); Gly$^8$Arg$^{34}$Lys$^{26,36}$-bis-(GAB-GTet)-GLP-1(7-36); Gly$^8$Arg$^{26}$Lys$^{34,36}$-bis-(GAB-GTet)-GLP-1(7-37); Gly$^8$Arg$^{34}$Lys$^{26,36}$-bis-(GAB-GTet)-GLP-1(7-37); Gly$^8$Arg$^{26}$Lys$^{34,37}$-bis-(GAB-GTet)-GLP-1(7-37); Gly$^8$Arg$^{34}$Lys$^{26,37}$-bis-(GAB-GTet)-GLP-1(7-37); Gly$^8$Arg$^{26}$Lys$^{34,38}$-bis-(GAB-GTet)-GLP-1(7-38); Gly$^8$Arg$^{34}$Lys$^{26,38}$-bis-(GAB-GTet)-GLP-1(7-38); Gly$^8$Arg$^{26,34}$Lys$^{36,38}$-bis-(GAB-GTet)-GTet)-GLP-1(7-38); Gly$^8$Arg$^{26}$Lys$^{34,39}$-bis-(GAB-GTet)-GLP-1(7-39); Gly$^8$Arg$^{34}$Lys$^{26,39}$-bis-(GAB-GTet)-GLP-1(7-39); Gly$^8$Arg$^{26,34}$Lys$^{36,39}$-bis-(GAB-GTet)-GLP-1(7-39);

Val$^8$Lys$^{26,34}$-bis-(GAB-GTet)-GLP-1(7-36); Val$^8$Lys$^{26,34}$-bis-(GAB-GTet)-GLP-1(7-37); Val$^8$Lys$^{26,34}$-bis-(GAB-GTet)-GLP-1(7-38); Val$^8$Lys$^{26,34}$-bis-(GAB-GTet)-GLP-1(7-39)

Val$^8$Arg$^{26}$Lys$^{34,36}$-bis-(GAB-GTet)-GLP-1(7-36); Val$^8$Arg$^{34}$Lys$^{26,36}$-bis-(GAB-GTet)-GLP-1(7-36); Val$^8$Arg$^{26}$Lys$^{34,36}$-bis-(GAB-GTet)-GLP-1(7-37); Val$^8$Arg$^{34}$Lys$^{26,36}$-bis-(GAB-GTet)-GLP-1(7-37); Val$^8$Arg$^{26}$Lys$^{34,37}$-bis-(GAB-GTet)-GLP-1(7-37); Val$^8$Arg$^{34}$Lys$^{26,37}$-bis-(GAB-GTet)-GLP-1(7-37); Val$^8$Arg$^{26}$Lys$^{34,38}$-bis-(GAB-GTet)-GLP-1(7-38); Val$^8$Arg$^{34}$Lys$^{26,38}$-bis-(GAB-GTet)-GLP-1(7-38); Val$^8$Arg$^{26,34}$Lys$^{36,38}$-bis-(GAB-GTet)-GLP-1(7-38); Val$^8$Arg$^{26}$Lys$^{34,39}$-bis-(GAB-GTet)-GLP-1(7-39); Val$^8$Arg$^{34}$Lys$^{26,39}$-bis-(GAB-GTet)-GLP-1(7-39); Val$^8$Arg$^{26,34}$Lys$^{36,39}$-bis-(GAB-GTet)-GLP-1(7-39);

Ser$^8$Lys$^{26,34}$-bis-(GAB-GTet)-GLP-1(7-36); Ser$^8$Lys$^{26,34}$-bis-(GAB-GTet)-GLP-1(7-37); Ser$^8$Lys$^{26,34}$-bis-(GAB-GTet)-GLP-1(7-38); Ser$^8$Lys$^{26,34}$-bis-(GAB-GTet)-GLP-1(7-39)

Ser$^8$Arg$^{26}$Lys$^{34,36}$-bis-(GAB-GTet)-GLP-1(7-36); Ser$^8$Arg$^{34}$Lys$^{26,36}$-bis-(GAB-GTet)-GLP-1(7-36); Ser$^8$Arg$^{26}$Lys$^{34,36}$-bis-(GAB-GTet)-GLP-1(7-37); Ser$^8$Arg$^{34}$Lys$^{26,36}$-bis-(GAB-GTet)-GLP-1(7-37); Ser$^8$Arg$^{26}$Lys$^{34,37}$-bis-(GAB-GTet)-GLP-1(7-37); Ser$^8$Arg$^{34}$Lys$^{26,37}$-bis-(GAB-GTet)-GLP-1(7-37); Ser$^8$Arg$^{26}$Lys$^{34,38}$-bis-(GAB-GTet)-GLP-1(7-38); Ser$^8$Arg$^{34}$Lys$^{26,38}$-bis-(GAB-GTet)-GLP-1(7-38); Ser$^8$Arg$^{26,34}$Lys$^{36,38}$-bis-(GAB-GTet)-GLP-1(7-38); Ser$^8$Arg$^{26}$Lys$^{34,39}$-bis-(GAB-GTet)-GLP-1(7-39); Ser$^8$Arg$^{34}$Lys$^{26,39}$-bis-(GAB-GTet)-GLP-1(7-39); Ser$^8$Arg$^{26,34}$Lys$^{36,39}$-bis-(GAB-GTet)-GLP-1(7-39);

Thr$^8$Lys$^{26,34}$-bis-(GAB-GTet)-GLP-1(7-36); Thr$^8$Lys$^{26,34}$-bis-(GAB-GTet)-GLP-1(7-37); Thr$^8$Lys$^{26,34}$-bis-(GAB-GTet)-GLP-1(7-38); Thr$^8$Lys$^{26,34}$-bis-(GAB-GTet)-GLP-1(7-39)

Thr$^8$Arg$^{26}$Lys$^{34,36}$-bis-(GAB-GTet)-GLP-1(7-36); Thr$^8$Arg$^{34}$Lys$^{26,36}$-bis-(GAB-GTet)-GLP-1(7-36); Thr$^8$Arg$^{26}$Lys$^{34,36}$-bis-(GAB-GTet)-GLP-1(7-37); Thr$^8$Arg$^{34}$Lys$^{26,36}$-bis-(GAB-GTet)-GLP-1(7-37); Thr$^8$Arg$^{26}$Lys$^{34,37}$-bis-(GAB-GTet)-GLP-1(7-37); Thr$^8$Arg$^{34}$Lys$^{26,37}$-bis-(GAB-GTet)-GLP-1(7-37); Thr$^8$Arg$^{26}$Lys$^{34,38}$-bis-(GAB-GTet)-GLP-1(7-38); Thr$^8$Arg$^{34}$Lys$^{26,38}$-bis-(GAB-GTet)-GLP-1(7-38); Thr$^8$Arg$^{26,34}$Lys$^{36,38}$-bis-(GAB-GTet)-GLP-1(7-38); Thr$^8$Arg$^{26}$Lys$^{34,39}$-bis-(GAB-GTet)-GLP-1(7-39); Thr$^8$Arg$^{34}$Lys$^{26,39}$-bis-(GAB-GTet)-GLP-1(7-39); Thr$^8$Arg$^{26,34}$Lys$^{36,39}$-bis-(GAB-GTet)-GLP-1(7-39);

Lys$^{26,34}$-bis-(GAB-GHex)-GLP-1(7-36); Lys$^{26,34}$-bis-(GAB-GHex)-GLP-1(7-37); Lys$^{26,34}$-bis-(GAB-GHex)-GLP-1(7-38); Lys$^{26,34}$-bis-(GAB-GHex)-GLP-1(7-39)

Arg$^{26}$Lys$^{34,36}$-bis-(GAB-GHex)-GLP-1(7-36); Arg$^{34}$Lys$^{26,36}$-bis-(GAB-GHex)-GLP-1(7-36); Arg$^{26}$Lys$^{34,36}$-bis-(GAB-GHex)-GLP-1(7-37); Arg$^{34}$Lys$^{26,36}$-bis-(GAB-GHex)-GLP-1(7-37); Arg$^{26}$Lys$^{34,37}$-bis-(GAB-GHex)-GLP-1(7-37); Arg$^{34}$Lys$^{26,37}$-bis-(GAB-GHex)-GLP-1(7-37); Arg$^{26}$Lys$^{34,39}$-bis-(GAB-GHex)-GLP-1(7-39); Arg$^{34}$Lys$^{26,39}$-bis-(GAB-GHex)-GLP-1(7-39); Arg$^{26,34}$Lys$^{36,39}$-bis-(GAB-GHex)-GLP-1(7-39);

Arg$^{26}$Lys$^{18,34}$-bis-(GAB-GHex)-GLP-1(7-36); Arg$^{34}$Lys$^{18,26}$-bis-(GAB-GHex)-GLP-1(7-36); Arg$^{26}$Lys$^{18,34}$-bis-(GAB-GHex))-GLP-1(7-37); Arg$^{34}$Lys$^{18,26}$-bis-(GAB-GHex)-GLP-1(7-37); Arg$^{26}$Lys$^{18,34}$-bis-(GAB-GHex)-GLP-1(7-38); Arg$^{34}$Lys$^{18,26}$-bis-(GAB-GHex)-GLP-1(7-38); Arg$^{26}$Lys$^{18,34}$-bis-(GAB-GHex)-GLP-1(7-39); Arg$^{34}$Lys$^{18,26}$-bis-(GAB-GHex)-GLP-1(7-39);

Arg$^{26}$Lys$^{23,34}$-bis-(GAB-GHex)-GLP-1(7-36); Arg$^{34}$Lys$^{23,26}$-bis-(GAB-GHex)-GLP-1(7-36); Arg$^{26}$Lys$^{23,34}$-bis-(GAB-GHex)-GLP-1(7-37); Arg$^{34}$Lys$^{23,26}$-bis-(GAB-GHex)-GLP-1(7-37); Arg$^{26}$Lys$^{23,34}$-bis-(GAB-GHex)-GLP-1(7-38); Arg$^{34}$Lys$^{23,26}$-bis-(GAB-GHex)-GLP-1(7-38); Arg$^{26}$Lys$^{23,34}$-bis-(GAB-GHex)-GLP-1(7-39); Arg$^{34}$Lys$^{23,26}$-bis-(GAB-GHex)-GLP-1(7-39);

Arg$^{26}$Lys$^{27,34}$-bis-(GAB-GHex)-GLP-1(7-36); Arg$^{34}$Lys$^{27,26}$-bis-(GAB-GHex)-GLP-1(7-36); Arg$^{26}$Lys$^{27,34}$-bis-(GAB-GHex)-GLP-1(7-37); Arg$^{34}$Lys$^{27,26}$-bis-(GAB-GHex)-GLP-1(7-37); Arg$^{26}$Lys$^{27,34}$-bis-(GAB-GHex)-GLP-1(7-38); Arg$^{34}$Lys$^{27,26}$-bis-(GAB-GHex)-GLP-1(7-38); Arg$^{26}$Lys$^{27,34}$-bis-(GAB-GHex)-GLP-1(7-39); Arg$^{34}$Lys$^{27,26}$-bis-(GAB-GHex)-GLP-1(7-39);

Gly$^8$Lys$^{26,34}$-bis-(GAB-GHex)-GLP-1(7-36); Gly$^8$Lys$^{26,34}$-bis-(GAB-GHex)-GLP-1(7-37); Gly$^8$Lys$^{26,34}$-bis-(GAB-GHex)-GLP-1(7-38); Gly$^8$Lys$^{26,34}$-bis-(GAB-GHex)-GLP-1(7-39)

Gly$^8$Arg$^{26}$Lys$^{34,36}$-bis-(GAB-GHex)-GLP-1(7-36); Gly$^8$Arg$^{34}$Lys$^{26,36}$-bis-(GAB-GHex)-GLP-1(7-36); Gly$^8$Arg$^{26}$Lys$^{34,36}$-bis-(GAB-GHex)-GLP-1(7-37); Gly$^8$Arg$^{34}$Lys$^{26,36}$-bis-(GAB-GHex)-GLP-1(7-37); Gly$^8$Arg$^{26}$Lys$^{34,37}$-bis-(GAB-GHex)-GLP-1(7-37); Gly$^8$Arg$^{34}$Lys$^{26,37}$-bis-(GAB-GHex)-GLP-1(7-37); Gly$^8$Arg$^{26}$Lys$^{34,38}$-bis-(GAB-GHex)-GLP-1(7-38); Gly$^8$Arg$^{34}$Lys$^{26,38}$-bis-(GAB-GHex)-GLP-1(7-38); Gly$^8$Arg$^{26,34}$Lys$^{36,38}$-bis-(GAB-GHex)-GLP-1(7-38); Gly$^8$Arg$^{26}$Lys$^{34,39}$-bis-(GAB-GHex)-GLP-1(7-39); Gly$^8$Arg$^{34}$Lys$^{26,39}$-bis-(GAB-GHex)-GLP-1(7-39); Gly$^8$Arg$^{26,34}$Lys$^{36,39}$-bis-(GAB-GHex)-GLP-1(7-39);

Val$^8$Lys$^{26,34}$-bis-(GAB-GHex)-GLP-1(7-36); Val$^8$Lys$^{26,34}$-bis-(GAB-GHex)-GLP-1(7-37); Val$^8$Lys$^{26,34}$-bis-(GAB-GHex)-GLP-1(7-38); Val$^8$Lys$^{26,34}$-bis-(GAB-GHex)-GLP-1(7-39)

Val$^8$Arg$^{26}$Lys$^{34,36}$-bis-(GAB-GHex)-GLP-1(7-36); Val$^8$Arg$^{34}$Lys$^{26,36}$-bis-(GAB-GHex)-GLP-1(7-36); Val$^8$Arg$^{26}$Lys$^{34,36}$-bis-(GAB-GHex)-GLP-1(7-37);

Val$^8$Arg$^{34}$Lys$^{26,36}$-bis-(GAB-GHex)-GLP-1(7-37);
Val$^8$Arg$^{26}$Lys$^{34,37}$-bis-(GAB-GHex)-GLP-1(7-37);
Val$^8$Arg$^{34}$Lys$^{26,37}$-bis-(GAB-GHex)-GLP-1(7-37);
Val$^8$Arg$^{26}$Lys$^{34,38}$-bis-(GAB-GHex)-GLP-1(7-38);
Val$^8$Arg$^{34}$Lys$^{26,38}$-bis-(GAB-GHex)-GLP-1(7-38);
Val$^8$Arg$^{26,34}$Lys$^{36,38}$-bis-(GAB-GHex)-GLP-1(7-38);
Val$^8$Arg$^{26}$Lys$^{34,39}$-bis-(GAB-GHex)-GLP-1(7-39);
Val$^8$Arg$^{34}$Lys$^{26,39}$-bis-(GAB-GHex)-GLP-1(7-39);
Val$^8$Arg$^{26,34}$Lys$^{36,39}$-bis-(GAB-GHex)-GLP-1(7-39);
Ser$^8$Lys$^{26,34}$-bis-(GAB-GHex)-GLP-1(7-36); Ser$^8$Lys$^{26,34}$-bis-(GAB-GHex)-GLP-1(7-37); Ser$^8$Lys$^{26,34}$-bis-(GAB-GHex)-GLP-1(7-38); Ser$^8$Lys$^{26,34}$-bis-(GAB-GHex)-GLP-1(7-39)
Ser$^8$Arg$^{26}$Lys$^{34,36}$-bis-(GAB-GHex)-GLP-1(7-36);
Ser$^8$Arg$^{34}$Lys$^{26,36}$-bis-(GAB-GHex)-GLP-1(7-36);
Ser$^8$Arg$^{26}$Lys$^{34,36}$-bis-(GAB-GHex)-GLP-1(7-37);
Ser$^8$Arg$^{34}$Lys$^{26,36}$-bis-(GAB-GHex)-GLP-1(7-37);
Ser$^8$Arg$^{26}$Lys$^{34,37}$-bis-(GAB-GHex)-GLP-1(7-37);
Ser$^8$Arg$^{34}$Lys$^{26,37}$-bis-(GAB-GHex)-GLP-1(7-37);
Ser$^8$Arg$^{26}$Lys$^{34,38}$-bis-(GAB-GHex)-GLP-1(7-38);
Ser$^8$Arg$^{34}$Lys$^{26,38}$-bis-(GAB-GHex)-GLP-1(7-38);
Ser$^8$Arg$^{26,34}$Lys$^{36,38}$-bis-(GAB-GHex)-GLP-1(7-38);
Ser$^8$Arg$^{26}$Lys$^{34,39}$-bis-(GAB-GHex)-GLP-1(7-39);
Ser$^8$Arg$^{34}$Lys$^{26,39}$-bis-(GAB-GHex)-GLP-1(7-39);
Ser$^8$Arg$^{26,34}$Lys$^{36,39}$-bis-(GAB-GHex)-GLP-1(7-39);
Thr$^8$Lys$^{26,34}$-bis-(GAB-GHex)-GLP-1(7-36); Thr$^8$Lys$^{26,34}$-bis-(GAB-GHex)-GLP-1(7-37); Thr$^8$Lys$^{26,34}$-bis-(GAB-GHex)-GLP-1(7-38); Thr$^8$Lys$^{26,34}$-bis-(GAB-GHex)-GLP-1(7-39)
Thr$^8$Arg$^{26}$Lys$^{34,36}$-bis-(GAB-GHex)-GLP-1(7-36);
Thr$^8$Arg$^{34}$Lys$^{26,36}$-bis-(GAB-GHex)-GLP-1(7-36);
Thr$^8$Arg$^{26}$Lys$^{34,36}$-bis-(GAB-GHex)-GLP-1(7-37);
Thr$^8$Arg$^{34}$Lys$^{26,36}$-bis-(GAB-GHex)-GLP-1(7-37);
Thr$^8$Arg$^{26}$Lys$^{34,37}$-bis-(GAB-GHex)-GLP-1(7-37);
Thr$^8$Arg$^{34}$Lys$^{26,37}$-bis-(GAB-GHex)-GLP-1(7-37);
Thr$^8$Arg$^{26}$Lys$^{34,38}$-bis-(GAB-GHex)-GLP-1(7-38);
Thr$^8$Arg$^{34}$Lys$^{26,38}$-bis-(GAB-GHex)-GLP-1(7-38);
Thr$^8$Arg$^{26,34}$Lys$^{36,38}$-bis-(GAB-GHex)-GLP-1(7-38);
Thr$^8$Arg$^{26}$Lys$^{34,39}$-bis-(GAB-GHex)-GLP-1(7-39);
Thr$^8$Arg$^{34}$Lys$^{26,39}$-bis-(GAB-GHex)-GLP-1(7-39);
Thr$^8$Arg$^{26,34}$Lys$^{36,39}$-bis-(GAB-GHex)-GLP-1(7-39);
Lys$^{26,34}$-bis-(GAB-GOct)-GLP-1(7-36); Lys$^{26,34}$-bis-(GAB-GOct)-GLP-1(7-37); Lys$^{26,34}$-bis-(GAB-GOct)-GLP-1(7-38); Lys$^{26,34}$-bis-(GAB-GOct)-GLP-1(7-39)
Arg$^{26}$Lys$^{34,36}$-bis-(GAB-GOct)-GLP-1(7-36); Arg$^{34}$Lys$^{26,36}$-bis-(GAB-GOct)-GLP-1(7-36); Arg$^{26}$Lys$^{34,36}$-bis-(GAB-GOct)-GLP-1(7-37); Arg$^{34}$Lys$^{26,36}$-bis-(GAB-GOct)-GLP-1(7-37); Arg$^{26}$Lys$^{34,37}$-bis-(GAB-GOct)-GLP-1(7-37); Arg$^{34}$Lys$^{26,37}$-bis-(GAB-GOct)-GLP-1(7-37); Arg$^{26}$Lys$^{34,39}$-bis-(GAB-GOct)-GLP-1(7-39); Arg$^{34}$Lys$^{26,39}$-bis-(GAB-GOct)-GLP-1(7-39); Arg$^{26,34}$Lys$^{36,39}$-bis-(GAB-GOct)-GLP-1(7-39);
Arg$^{26}$Lys$^{18,34}$-bis-(GAB-GOct)-GLP-1(7-36); Arg$^{34}$Lys$^{18,26}$-bis-(GAB-GOct)-GLP-1(7-36); Arg$^{26}$Lys$^{18,34}$-bis-(GAB-GOct)-GLP-1(7-37); Arg$^{34}$Lys$^{18,26}$-bis-(GAB-GOct)-GLP-1(7-37); Arg$^{26}$Lys$^{18,34}$-bis-(GAB-GOct)-GLP-1(7-38); Arg$^{34}$Lys$^{18,26}$-bis-(GAB-GOct)-GLP-1(7-38); Arg$^{26}$Lys$^{18,34}$-bis-(GAB-GOct)-GLP-1(7-39); Arg$^{34}$Lys$^{18,26}$-bis-(GAB-GOct)-GLP-1(7-39);
Arg$^{26}$Lys$^{23,34}$-bis-(GAB-GOct)-GLP-1(7-36); Arg$^{34}$Lys$^{23,26}$-bis-(GAB-GOct)-GLP-1(7-36); Arg$^{26}$Lys$^{23,34}$-bis-(GAB-GOct)-GLP-1(7-37); Arg$^{34}$Lys$^{23,26}$-bis-(GAB-GOct)-GLP-1(7-37); Arg$^{26}$Lys$^{23,34}$-bis-(GAB-GOct)-GLP-1(7-38); Arg$^{34}$Lys$^{23,26}$-bis-(GAB-GOct)-GLP-1(7-38); Arg$^{26}$Lys$^{23,34}$-bis-(GAB-GOct)-GLP-1(7-39); Arg$^{34}$Lys$^{23,26}$-bis-(GAB-GOct)-GLP-1(7-39);

Arg$^{26}$Lys$^{27,34}$-bis-(GAB-GOct)-GLP-1(7-36); Arg$^{34}$Lys$^{27,26}$-bis-(GAB-GOct)-GLP-1(7-36); Arg$^{26}$Lys$^{27,34}$-bis-(GAB-GOct)-GLP-1(7-37); Arg$^{34}$Lys$^{27,26}$-bis-(GAB-GOct)-GLP-1(7-37); Arg$^{26}$Lys$^{27,34}$-bis-(GAB-GOct)-GLP-1(7-38); Arg$^{34}$Lys$^{27,26}$-bis-(GAB-GOct)-GLP-1(7-38); Arg$^{26}$Lys$^{27,34}$-bis-(GAB-GOct)-GLP-1(7-39); Arg$^{34}$Lys$^{27,26}$-bis-(GAB-GOct)-GLP-1(7-39);
Gly$^8$Lys$^{26,34}$-bis-(GAB-GOct)-GLP-1(7-36); Gly$^8$Lys$^{26,34}$-bis-(GAB-GOct)-GLP-1(7-37); Gly$^8$Lys$^{26,34}$-bis-(GAB-GOct)-GLP-1(7-38); Gly$^8$Lys$^{26,34}$-bis-(GAB-GOct)-GLP-1(7-39)
Gly$^8$Arg$^{26}$Lys$^{34,36}$-bis-(GAB-GOct)-GLP-1(7-36);
Gly$^8$Arg$^{34}$Lys$^{26,36}$-bis-(GAB-GOct)-GLP-1(7-36);
Gly$^8$Arg$^{26}$Lys$^{34,36}$-bis-(GAB-GOct)-GLP-1(7-37);
Gly$^8$Arg$^{34}$Lys$^{26,36}$-bis-(GAB-GOct)-GLP-1(7-37);
Gly$^8$Arg$^{26}$Lys$^{34,37}$-bis-(GAB-GOct)-GLP-1(7-37);
Gly$^8$Arg$^{34}$Lys$^{26,37}$-bis-(GAB-GOct)-GLP-1(7-37);
Gly$^8$Arg$^{26}$Lys$^{34,38}$-bis-(GAB-GOct)-GLP-1(7-38);
Gly$^8$Arg$^{34}$Lys$^{26,38}$-bis-(GAB-GOct)-GLP-1(7-38);
Gly$^8$Arg$^{26,34}$Lys$^{36,38}$-bis-(GAB-GOct)-GLP-1(7-38);
Gly$^8$Arg$^{26}$Lys$^{34,39}$-bis-(GAB-GOct)-GLP-1(7-39);
Gly$^8$Arg$^{34}$Lys$^{26,39}$-bis-(GAB-GOct)-GLP-1(7-39);
Gly$^8$Arg$^{26,34}$Lys$^{36,39}$-bis-(GAB-GOct)-GLP-1(7-39);
Val$^8$Lys$^{26,34}$-bis-(GAB-GOct)-GLP-1(7-36); Val$^8$Lys$^{26,34}$-bis-(GAB-GOct)-GLP-1(7-37); Val$^8$Lys$^{26,34}$-bis-(GAB-GOct)-GLP-1(7-38); Val$^8$Lys$^{26,34}$-bis-(GAB-GOct)-GLP-1(7-39)
Val$^8$Arg$^{26}$Lys$^{34,36}$-bis-(GAB-GOct)-GLP-1(7-36);
Val$^8$Arg$^{34}$Lys$^{26,36}$-bis-(GAB-GOct)-GLP-1(7-36);
Val$^8$Arg$^{26}$Lys$^{34,36}$-bis-(GAB-GOct)-GLP-1(7-37);
Val$^8$Arg$^{34}$Lys$^{26,36}$-bis-(GAB-GOct)-GLP-1(7-37);
Val$^8$Arg$^{26}$Lys$^{34,37}$-bis-(GAB-GOct)-GLP-1(7-37);
Val$^8$Arg$^{34}$Lys$^{26,37}$-bis-(GAB-GOct)-GLP-1(7-37);
Val$^8$Arg$^{26}$Lys$^{34,38}$-bis-(GAB-GOct)-GLP-1(7-38);
Val$^8$Arg$^{34}$Lys$^{26,38}$-bis-(GAB-GOct)-GLP-1(7-38);
Val$^8$Arg$^{26,34}$Lys$^{36,38}$-bis-(GAB-GOct)-GLP-1(7-38);
Val$^8$Arg$^{26}$Lys$^{34,39}$-bis-(GAB-GOct)-GLP-1(7-39);
Val$^8$Arg$^{34}$Lys$^{26,39}$-bis-(GAB-GOct)-GLP-1(7-39);
Val$^8$Arg$^{26,34}$Lys$^{36,39}$-bis-(GAB-GOct)-GLP-1(7-39);
Ser$^8$Lys$^{26,34}$-bis-(GAB-GOct)-GLP-1(7-36); Ser$^8$Lys$^{26,34}$-bis-(GAB-GOct)-GLP-1(7-37); Ser$^8$Lys$^{26,34}$-bis-(GAB-GOct)-GLP-1(7-38); Ser$^8$Lys$^{26,34}$-bis-(GAB-GOct)-GLP-1(7-39)
Ser$^8$Arg$^{26}$Lys$^{34,36}$-bis-(GAB-GOct)-GLP-1(7-36);
Ser$^8$Arg$^{34}$Lys$^{26,36}$-bis-(GAB-GOct)-GLP-1(7-36);
Ser$^8$Arg$^{26}$Lys$^{34,36}$-bis-(GAB-GOct)-GLP-1(7-37);
Ser$^8$Arg$^{34}$Lys$^{26,36}$-bis-(GAB-GOct)-GLP-1(7-37);
Ser$^8$Arg$^{26}$Lys$^{34,37}$-bis-(GAB-GOct)-GLP-1(7-37);
Ser$^8$Arg$^{34}$Lys$^{26,37}$-bis-(GAB-GOct)-GLP-1(7-37);
Ser$^8$Arg$^{26}$Lys$^{34,38}$-bis-(GAB-GOct)-GLP-1(7-38);
Ser$^8$Arg$^{34}$Lys$^{26,38}$-bis-(GAB-GOct)-GLP-1(7-38);
Ser$^8$Arg$^{26,34}$Lys$^{36,38}$-bis-(GAB-GOct)-GLP-1(7-38);
Ser$^8$Arg$^{26}$Lys$^{34,39}$-bis-(GAB-GOct)-GLP-1(7-39);
Ser$^8$Arg$^{34}$Lys$^{26,39}$-bis-(GAB-GOct)-GLP-1(7-39);
Ser$^8$Arg$^{26,34}$Lys$^{36,39}$-bis-(GAB-GOct)-GLP-1(7-39);
Thr$^8$Lys$^{26,34}$-bis-(GAB-GOct)-GLP-1(7-36); Thr$^8$Lys$^{26,34}$-bis-(GAB-GOct)-GLP-1(7-37); Thr$^8$Lys$^{26,34}$-bis-(GAB-GOct)-GLP-1(7-38); Thr$^8$Lys$^{26,34}$-bis-(GAB-GOct)-GLP-1(7-39)
Thr$^8$Arg$^{26}$Lys$^{34,36}$-bis-(GAB-GOct)-GLP-1(7-36);
Thr$^8$Arg$^{34}$Lys$^{26,36}$-bis-(GAB-GOct)-GLP-1(7-36);
Thr$^8$Arg$^{26}$Lys$^{34,36}$-bis-(GAB-GOct)-GLP-1(7-37);
Thr$^8$Arg$^{34}$Lys$^{26,36}$-bis-(GAB-GOct)-GLP-1(7-37);
Thr$^8$Arg$^{26}$Lys$^{34,37}$-bis-(GAB-GOct)-GLP-1(7-37);
Thr$^8$Arg$^{34}$Lys$^{26,37}$-bis-(GAB-GOct)-GLP-1(7-37);
Thr$^8$Arg$^{26}$Lys$^{34,38}$-bis-(GAB-GOct)-GLP-1(7-38);
Thr$^8$Arg$^{34}$Lys$^{26,38}$-bis-(GAB-GOct)-GLP-1(7-38);

Thr$^8$Arg$^{26,34}$Lys$^{36,38}$-bis-(GAB-GOct)-GLP-1(7-38);
Thr$^8$Arg$^{26}$Lys$^{34,39}$-bis-(GAB-GOct)-GLP-1(7-39);
Thr$^8$Arg$^{34}$Lys$^{26,39}$-bis-(GAB-GOct)-GLP-1(7-39);
Thr$^8$Arg$^{26,34}$Lys$^{36,39}$-bis-(GAB-GOct)-GLP-1(7-39);
Lys$^{26,34}$-bis-(GAB-GLit)-GLP-1(7-36); Lys$^{26,34}$-bis-(GAB-GLit)-GLP-1(7-37); Lys$^{26,34}$-bis-(GAB-GLit)-GLP-1(7-38); Lys$^{26,34}$-bis-(GAB-GLit)-GLP-1(7-39)
Arg$^{26}$Lys$^{34,36}$-bis-(GAB-GLit)-GLP-1(7-36); Arg$^{34}$Lys$^{26,36}$-bis-(GAB-GLit)-GLP-1(7-36); Arg$^{26}$Lys$^{34,36}$-bis-(GAB-GLit)-GLP-1(7-37); Arg$^{34}$Lys$^{26,36}$-bis-(GAB-GLit)-GLP-1(7-37); Arg$^{26}$Lys$^{34,37}$-bis-(GAB-GLit)-GLP-1(7-37); Arg$^{34}$Lys$^{26,37}$-bis-(GAB-GLit)-GLP-1(7-37); Arg$^{26}$Lys$^{34,39}$-bis-(GAB-GLit)-GLP-1(7-39); Arg$^{34}$Lys$^{26,39}$-bis-(GAB-GLit)-GLP-1(7-39); Arg$^{26,34}$Lys$^{36,39}$-bis-(GAB-GLit)-GLP-1(7-39);
Arg$^{26}$Lys$^{18,34}$-bis-(GAB-GLit)-GLP-1(7-36); Arg$^{34}$Lys$^{18,26}$-bis-(GAB-GLit)-GLP-1(7-36); Arg$^{26}$Lys$^{18,34}$-bis-(GAB-GLit)-GLP-1(7-37); Arg$^{34}$Lys$^{18,26}$-bis-(GAB-GLit)-GLP-1(7-37); Arg$^{26}$Lys$^{18,34}$-bis-(GAB-GLit)-GLP-1(7-38); Arg$^{34}$Lys$^{18,26}$-bis-(GAB-GLit)-GLP-1(7-38); Arg$^{26}$Lys$^{18,34}$-bis-(GAB-GLit)-GLP-1(7-39); Arg$^{34}$Lys$^{18,26}$-bis-(GAB-GLit)-GLP-1(7-39);
Arg$^{26}$Lys$^{23,34}$-bis-(GAB-GLit)-GLP-1(7-36); Arg$^{34}$Lys$^{23,26}$-bis-(GAB-GLit)-GLP-1(7-36); Arg$^{26}$Lys$^{23,34}$-bis-(GAB-GLit)-GLP-1(7-37); Arg$^{34}$Lys$^{23,26}$-bis-(GAB-GLit)-GLP-1(7-37); Arg$^{26}$Lys$^{23,34}$-bis-(GAB-GLit)-GLP-1(7-38); Arg$^{34}$Lys$^{23,26}$-bis-(GAB-GLit)-GLP-1(7-38); Arg$^{26}$Lys$^{23,34}$-bis-(GAB-GLit)-GLP-1(7-39); Arg$^{34}$Lys$^{23,26}$-bis-(GAB-GLit)-GLP-1(7-39);
Arg$^{26}$Lys$^{27,34}$-bis-(GAB-GLit)-GLP-1(7-36); Arg$^{34}$Lys$^{27,26}$-bis-(GAB-GLit)-GLP-1(7-36); Arg$^{26}$Lys$^{27,34}$-bis-(GAB-GLit)-GLP-1(7-37); Arg$^{34}$Lys$^{27,26}$-bis-(GAB-GLit)-GLP-1(7-37); Arg$^{26}$Lys$^{27,34}$-bis-(GAB-GLit)-GLP-1(7-38); Arg$^{34}$Lys$^{27,26}$-bis-(GAB-GLit)-GLP-1(7-38); Arg$^{26}$Lys$^{27,34}$-bis-(GAB-GLit)-GLP-1(7-39); Arg$^{34}$Lys$^{27,26}$-bis-(GAB-GLit)-GLP-1(7-39);
Gly$^8$Lys$^{26,34}$-bis-(GAB-GLit)-GLP-1(7-36); Gly$^8$Lys$^{26,34}$-bis-(GAB-GLit)-GLP-1(7-37); Gly$^8$Lys$^{26,34}$-bis-(GAB-GLit)-GLP-1(7-38); Gly$^8$Lys$^{26,34}$-bis-(GAB-GLit)-GLP-1(7-39)
Gly$^8$Arg$^{26}$Lys$^{34,36}$-bis-(GAB-GLit)-GLP-1(7-36);
Gly$^8$Arg$^{34}$Lys$^{26,36}$-bis-(GAB-GLit)-GLP-1(7-36);
Gly$^8$Arg$^{26}$Lys$^{34,36}$-bis-(GAB-GLit)-GLP-1(7-37);
Gly$^8$Arg$^{34}$Lys$^{26,36}$-bis-(GAB-GLit)-GLP-1(7-37);
Gly$^8$Arg$^{26}$Lys$^{34,37}$-bis-(GAB-GLit)-GLP-1(7-37);
Gly$^8$Arg$^{34}$Lys$^{26,37}$-bis-(GAB-GLit)-GLP-1(7-37);
Gly$^8$Arg$^{26}$Lys$^{34,38}$-bis-(GAB-GLit)-GLP-1(7-38);
Gly$^8$Arg$^{34}$Lys$^{26,38}$-bis-(GAB-GLit)-GLP-1(7-38);
Gly$^8$Arg$^{26,34}$Lys$^{36,38}$-bis-(GAB-GLit)-GLP-1(7-38);
Gly$^8$Arg$^{26}$Lys$^{34,39}$-bis-(GAB-GLit)-GLP-1(7-39);
Gly$^8$Arg$^{34}$Lys$^{26,39}$-bis-(GAB-GLit)-GLP-1(7-39);
Gly$^8$Arg$^{26,34}$Lys$^{36,39}$-bis-(GAB-GLit)-GLP-1(7-39);
Val$^8$Lys$^{26,34}$-bis-(GAB-GLit)-GLP-1(7-36); Val$^8$Lys$^{26,34}$-bis-(GAB-GLit)-GLP-1(7-37); Val$^8$Lys$^{26,34}$-bis-(GAB-GLit)-GLP-1(7-38); Val$^8$Lys$^{26,34}$-bis-(GAB-GLit)-GLP-1(7-39)
Val$^8$Arg$^{26}$Lys$^{34,36}$-bis-(GAB-GLit)-GLP-1(7-36);
Val$^8$Arg$^{34}$Lys$^{26,36}$-bis-(GAB-GLit)-GLP-1(7-36);
Val$^8$Arg$^{26}$Lys$^{34,36}$-bis-(GAB-GLit)-GLP-1(7-37);
Val$^8$Arg$^{34}$Lys$^{26,36}$-bis-(GAB-GLit)-GLP-1(7-37);
Val$^8$Arg$^{26}$Lys$^{34,37}$-bis-(GAB-GLit)-GLP-1(7-37);
Val$^8$Arg$^{34}$Lys$^{26,37}$-bis-(GAB-GLit)-GLP-1(7-37);
Val$^8$Arg$^{26}$Lys$^{34,38}$-bis-(GAB-GLit)-GLP-1(7-38);
Val$^8$Arg$^{34}$Lys$^{26,38}$-bis-(GAB-GLit)-GLP-1(7-38);
Val$^8$Arg$^{26,34}$Lys$^{36,38}$-bis-(GAB-GLit)-GLP-1(7-38);
Val$^8$Arg$^{26}$Lys$^{34,39}$-bis-(GAB-GLit)-GLP-1(7-39);
Val$^8$Arg$^{34}$Lys$^{26,39}$-bis-(GAB-GLit)-GLP-1(7-39);
Val$^8$Arg$^{26,34}$Lys$^{36,39}$-bis-(GAB-GLit)-GLP-1(7-39);
Ser$^8$Lys$^{26,34}$-bis-(GAB-GLit)-GLP-1(7-36); Ser$^8$Lys$^{26,34}$-bis-(GAB-GLit)-GLP-1(7-37); Ser$^8$Lys$^{26,34}$-bis-(GAB-GLit)-GLP-1(7-38); Ser$^8$Lys$^{26,34}$-bis-(GAB-GLit)-GLP-1(7-39)
Ser$^8$Arg$^{26}$Lys$^{34,36}$-bis-(GAB-GLit)-GLP-1(7-36);
Ser$^8$Arg$^{34}$Lys$^{26,36}$-bis-(GAB-GLit)-GLP-1(7-36);
Ser$^8$Arg$^{26}$Lys$^{34,36}$-bis-(GAB-GLit)-GLP-1(7-37);
Ser$^8$Arg$^{34}$Lys$^{26,36}$-bis-(GAB-GLit)-GLP-1(7-37);
Ser$^8$Arg$^{26}$Lys$^{34,37}$-bis-(GAB-GLit)-GLP-1(7-37);
Ser$^8$Arg$^{34}$Lys$^{26,37}$-bis-(GAB-GLit)-GLP-1(7-37);
Ser$^8$Arg$^{26}$Lys$^{34,38}$-bis-(GAB-GLit)-GLP-1(7-38);
Ser$^8$Arg$^{34}$Lys$^{26,38}$-bis-(GAB-GLit)-GLP-1(7-38);
Ser$^8$Arg$^{26,34}$Lys$^{36,38}$-bis-(GAB-GLit)-GLP-1(7-38);
Ser$^8$Arg$^{26}$Lys$^{34,39}$-bis-(GAB-GLit)-GLP-1(7-39);
Ser$^8$Arg$^{34}$Lys$^{26,39}$-bis-(GAB-GLit)-GLP-1(7-39);
Ser$^8$Arg$^{26,34}$Lys$^{36,39}$-bis-(GAB-GLit)-GLP-1(7-39);
Thr$^8$Lys$^{26,34}$-bis-(GAB-GLit)-GLP-1(7-36); Thr$^8$Lys$^{26,34}$-bis-(GAB-GLit)-GLP-1(7-37); Thr$^8$Lys$^{26,34}$-bis-(GAB-GLit)-GLP-1(7-38); Thr$^8$Lys$^{26,34}$-bis-(GAB-GLit)-GLP-1(7-39)
Thr$^8$Arg$^{26}$Lys$^{34,36}$-bis-(GAB-GLit)-GLP-1(7-36);
Thr$^8$Arg$^{34}$Lys$^{26,36}$-bis-(GAB-GLit)-GLP-1(7-36);
Thr$^8$Arg$^{26}$Lys$^{34,36}$-bis-(GAB-GLit)-GLP-1(7-37);
Thr$^8$Arg$^{34}$Lys$^{26,36}$-bis-(GAB-GLit)-GLP-1(7-37);
Thr$^8$Arg$^{26}$Lys$^{34,37}$-bis-(GAB-GLit)-GLP-1(7-37);
Thr$^8$Arg$^{34}$Lys$^{26,37}$-bis-(GAB-GLit)-GLP-1(7-37);
Thr$^8$Arg$^{26}$Lys$^{34,38}$-bis-(GAB-GLit)-GLP-1(7-38);
Thr$^8$Arg$^{34}$Lys$^{26,38}$-bis-(GAB-GLit)-GLP-1(7-38);
Thr$^8$Arg$^{26,34}$Lys$^{36,38}$-bis-(GAB-GLit)-GLP-1(7-38);
Thr$^8$Arg$^{26}$Lys$^{34,39}$-bis-(GAB-GLit)-GLP-1(7-39);
Thr$^8$Arg$^{34}$Lys$^{26,39}$-bis-(GAB-GLit)-GLP-1(7-39);
Thr$^8$Arg$^{26,34}$Lys$^{36,39}$-bis-(GAB-GLit)-GLP-1(7-39).

Pharmaceutical Compositions

The present invention also relates to pharmaceutical compositions comprising a GLP-1 derivative of the present invention and a pharmaceutically acceptable vehicle or carrier.

Preferably, the pharmaceutical compositions comprise an isotonic agent, a preservative and a buffer. Examples of isotonic agents are sodium chloride, mannitol and glycerol. Examples of preservatives are phenol, m-cresol, methyl p-hydroxybenzoate and benzyl alcohol. Suitable buffers include sodium acetate and sodium phosphate.

The pharmaceutical compositions preferably further comprise a surfactant in order to improve the solubility and/or the stability of the GLP-1 derivative.

Individual embodiments of the surfactant, such as a detergent, for use in the pharmaceutical composition of the invention include ethoxylated castor oil, polyglycolized glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35). Other preferred surfactants include fusidic acid derivatives—(e.g. sodium tauro-dihydrofusidate etc.), long-chain fatty acids and salts thereof C6-C12 (eg. oleic acid and caprylic acid), acylcamitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives.

One group of preferred surfactants consists of zwitterionic surfactants, cationic surfactants, non-ionic surfactants and polymeric surfactants.

Another group of preferred surfactants consists of SDS, sodium caprylate, sodium cholate, sodium deoxycholate, sodium taurocholate and sodium glycocholate.

A further group of preferred surfactants consists of lauroyl lysophosphatidylcholine, palmitoyl lysophosphatidyl-L-serine, myristoyl lysophosphatidylcholine and N-Hexadecyl-N,N-dimethyl-3-ammonio-1-propanesulfonate.

The pharmaceutical compositions preferably also comprise zinc.

The pharmaceutical compositions preferably further comprise another antidiabetic agent. The term "antidiabetic agent" includes compounds for the treatment and/or prophylaxis of insulin resistance and diseases wherein insulin resistance is the pathophysiological mechanism.

In one embodiment of this invention, the antidiabetic agent is an insulin, more preferably human insulin.

In another embodiment the antidiabetic agent is a hypoglycaemic agent, preferably an oral hypoglycaemic agent. Oral hypoglycaemic agents are preferably selected from the group consisting of sulfonylureas, biguanides, thiazolidinediones, glucosidase inhibitors, glucagon antagonists, GLP-1 agonists, potassium channel openers, insulin sensitizers, hepatic enzyme inhibitors, glucose uptake modulators, compounds modifying the lipid metabolism, compounds lowering food intake, and agents acting on the ATP-dependent potassium channel of the β-cells. Preferred sulfonylureas are tolbutamide, glibenclamide, glipizide and gliclazide. A preferred biguanide is metformin. Preferred thiazolidinediones are troglitazone and ciglitazone. A preferred glucosidase inhibitors is acarbose. Preferred agents acting on the ATP-dependent potassium channel of the β-cells are: glibenclamide, glipizide, gliclazide, and repaglinide.

The pharmaceutical compositions of the present invention may further comprise another antiobesity agent.

In one embodiment of this invention, the antiobesity agent is leptin.

In another embodiment the antiobesity agent is amphetamine

In another embodiment the antiobesity agent is dexfenfluramine.

In another embodiment the antiobesity agent is sibutramine.

In another embodiment the antiobesity agent is orlistat.

In another embodiment the antiobesity agent is selected from a group of CART agonists, NPY antagonists, orexin antagonists, H3-antagonists, TNF agonists, CRF agonists, CRF BP antagonists, urocortin agonists, β3 agonists, MSH agonists, CCK agonists, serotonin re-uptake inhibitors, mixed serotonin and noradrenergic compounds, 5HT agonists, bombesin agonists, galanin antagonists, growth hormone, growth hormone releasing compounds, glucagon, TRH agonists, uncoupling protein 2 or 3 modulators, leptin agonists, DA agonists (Bromocriptin, Doprexin), lipase/amylase inhibitors, PPAR modulators, PXR modulators or TR β agonists.

The present invention also relates to pharmaceutical compositions comprising water and a GLP-1 derivative which has a helix content as measured by CD at 222 nm in $H_2O$ at 22±2° C. exceeding 25%, preferably in the range of 25% to 50%, at a peptide concentration of about 10 μM. The size of the partially helical, micelle-like aggregates may be estimated by size-exclusion chromatography. Similarly, the apparent (critical micelle concentrations) CMC's of the peptides may be estimated from the concentration dependent fluorescence in the presence of appropriate dyes (e.g. Brito, R. & Vaz, W. (1986) Anal. Biochem. 152, 250-255).

That the derivatives have a partially structured micellar-like aggregate conformation in aqueous solutions makes them more soluble and stable in solution as compared to the native peptide. The increased solubility and stability can be seen by comparing the solubility after 9 days of standing for a derivative and native GLP-1(7-37) in a pharmaceutical formulation, e.g. 5 mM phosphate buffer, pH 6.9 added 0.1 M NaCl.

Circular Dichroism (CD) can be used to show that the GLP-1 derivatives have a certain partially structured conformation independent of their concentration. In contrast, for native GLP-1(7-37) an increase in the helix content is seen with increasing concentration, from 10-15% to 30-35% (at 500 μM concentration) in parallel with peptide self-association. For the GLP-1 derivatives forming partially structured micellar-like aggregates in aqueous solution the helix content remains constant above 30% at concentrations of 10 μM. The aggregated structured conformation is an inherent property of the derivative present in water or dilute aqueous buffer without the need for any additional structure-inducing components.

The pharmaceutical compositions of the present invention may be prepared by conventional techniques, eg. as described in Remington's *Pharmaceutical Sciences,* 1985 or in Remington: *The Science and Practice of Pharmacy,* 19th edition, 1995.

For example, injectable compositions of the GLP-1 derivative of the invention can be prepared using the conventional techniques of the pharmaceutical industry which involves dissolving and mixing the ingredients as appropriate to give the desired end product.

A composition for nasal administration of certain peptides may, for example, be prepared as described in European Patent No. 272097 (to Novo Nordisk A/S) or in WO 93/18785.

In a preferred embodiment of the present invention, the GLP-1 derivative is provided in the form of a composition suitable for administration by injection. Such a composition can either be an injectable solution ready for use or it can be an amount of a solid composition, eg. a lyophilised product, which has to be dissolved in a solvent before it can be injected. The injectable solution preferably contains not less than about 2 mg/ml, preferably not less than about 5 mg/ml, more preferred not less than about 10 mg/ml of the GLP-1 derivative and, preferably, not more than about 100 mg/ml of the GLP-1 derivative.

Uses

The present invention also relates to the use of a GLP-1 derivative of the invention for the preparation of a medicament which has a protracted profile of action relative to GLP-1(7-37).

The present invention relates also to the use of a GLP-1 derivative of the invention for the preparation of a medicament with protracted effect for the treatment of non-insulin dependent diabetes mellitus.

The present invention also relates to the use of a GLP-1 derivative of the invention for the preparation of a medicament with protracted effect for the treatment of insulin dependent diabetes mellitus.

The present invention also relates to the use of a GLP-1 derivative of the invention for the preparation of a medicament with protracted effect for the treatment of obesity.

The present invention also relates to the use of a GLP-1 derivative of the present invention for treating insulin resistance.

The present invention also relates to the use of a GLP-1 derivative of the present invention for the preparation of a medicament with protracted effect for the treatment of obesity.

The present invention relates to a method of treating insulin dependent or non-insulin dependent diabetes mellitus in a patient in need of such a treatment, comprising administering to the patient a therapeutically effective amount of a GLP-1 derivative of the present invention together with a pharmaceutically acceptable carrier.

The present invention relates to a method of treating obesity in a patient in need of such a treatment, comprising administering to the patient a therapeutically effective amount of a GLP-1 derivative of the present invention together with a pharmaceutically acceptable carrier.

The particular GLP-1 derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case.

The pharmaceutical compositions of the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-1 derivative in the form of a nasal or pulmonal spray. As a still further option, the GLP-1 derivatives of the invention can also be administered transdermally, e.g. from a patch, optionally a iontophoretic patch, or transmucosally, e.g. bucally.

Methods of Production

The parent peptide can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared of published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859-1869, or the method described by Matthes et al, *EMBO Journal* 3 (1984), 801-805. The DNA sequence may also be prepared by polymerase chain reaction using specific primers, for instance as described in U.S. Pat. No. 4,683,202 or Saiki et al, *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf, for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The GLP-1 derivatives of this invention can be used in the treatment of various diseases. The particular GLP-1 derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the GLP-1 derivative of this invention be determined for each individual patient by those skilled in the art.

In particular, it is envisaged that the GLP-1 derivative will be useful for the preparation of a medicament with a protracted profile of action for the treatment of non-insulin dependent diabetes mellitus and/or for the treatment of obesity.

The present invention is further illustrated by the following examples which, however, are not to be construed as limiting the scope of protection. The features disclosed in the foregoing description and in the following examples may, both separately and in any combination thereof, be material for realising the invention in diverse forms thereof

EXAMPLES

The following acronyms for commercially available chemicals are used:
DMF: N,N-Dimethylformamide
DCC: N,N-Dicyclohexylcarbodiimide
NMP: N-Methyl-2-pyrrolidone
EDPA: N-Ethyl-N,N-diisopropylamine
EGTA: Ethylene glycol-bis(β-aminoethyl ether)-N,N,N',N'-tetraacetic acid
GTP Guanosine 5'-triphosphate
TFA: Trifluoroacetic acid
THF: Tetrahydrofuran H-Glu(OH)—OBu$^t$: L-Glutamic acid α-tert-butyl ester
Cac-ONSu: Decanoic acid 2,5-dioxopyrrolidin-1-yl ester
Cap-ONSu: Octanoic acid 2,5-dioxopyrrolidin-1-yl ester
Lau-ONSu: Dodecanoic acid 2,5-dioxopyrrolidin-1-yl ester
Myr-ONSu: Tetradecanoic acid 2,5-dioxopyrrolidin-1-yl ester
Pal-ONSu: Hexadecanoic acid 2,5-dioxopyrrolidin-1-yl ester
Ste-ONSu Octadecanoic acid 2,5-dioxopyrrolidin-1-yl ester

ABBREVIATIONS

PDMS: Plasma Desorption Mass Spectrometry
MALDI-MS: Matrix Assisted Laser Desorption/Ionisation Mass Spectrometry
HPLC: High Performance Liquid Chromatography
amu: atomic mass units
Lit-Glu(ONSu)-OBu$^t$: N$^\alpha$-Lithochoyl-L-glutamic acid α-t-butyl ester γ-2,5-dioxopyrrolidin-1-yl ester
Cap-Glu(ONSu)-OBu$^t$: N$^\alpha$-Octanoyl-L-glutamic acid α-t-butyl ester γ-2,5-dioxopyrrolidin-1-yl ester
Cac-Glu(ONSu)-OBu$^t$: N$^\alpha$-Decanoyl-L-glutamic acid α-t-butyl ester γ-2,5-dioxopyrrolidin-1-yl ester
Lau-Glu(ONSu)-OBu$^t$: N$^\alpha$-Dodecanoyl-L-glutamic acid α-t-butyl ester γ-2,5-dioxopyrrolidin-1-yl ester
Myr-Glu(ONSu)-OBu$^t$: N$^\alpha$-Tetradecanoyl-L-glutamic acid α-t-butyl ester γ-2,5-dioxopyrrolidin-1-yl ester
Pal-Glu(ONSu)-OBu$^t$: N$^\alpha$-Hexadecanoyl-(L)-glutamic acid α-t-butyl-γ-2,5-dioxopyrrolidin-1-yl diester
Ste-Glu(ONSu)-OBu$^t$: N$^\alpha$-Octadecanoyl-(L)-glutamic acid α-t-butyl-γ-2,5-dioxopyrrolidin-1-yl diester
Lau-β-Ala-ONSu: N$^\alpha$-Dodecanoyl-β-alanine 2,5-dioxopyrrolidin-1-yl ester
Pal-β-Ala-ONSu: N$^\beta$-Hexadecanoyl-β-alanine 2,5-dioxopyrrolidin-1-yl ester
Lau-GABA-ONSu: N$^\gamma$-Dodecanoyl-γ-aminobutyric acid 2,5-dioxopyrrolidin-1-yl ester
Myr-GABA-ONSu: N$^\gamma$-Tetradecanoyl-γ-aminobutyric acid 2,5-dioxopyrrolidin-1-yl ester
Pal-GABA-ONSu: N$^\gamma$-Hexadecanoyl-γ-aminobutyric acid 2,5-dioxopyrrolidin-1-yl ester
Ste-GABA-ONSu: N$^\gamma$-Octadecanoyl-γ-aminobutyric acid 2,5-dioxopyrrolidin-1-yl ester
Pal-Isonip-ONSu: N-Hexadecanoyl-piperidine-4-carboxylic acid 2,5-dioxopyrrolidin-1-yl ester
Pal-Glu(OBu$^t$)-ONSu: N$^\alpha$-Hexadecanoyl-L-glutamic acid α-2,5-dioxopyrrolidin-1-yl ester γ-t-butyl ester
HOOC—(CH$_2$)$_6$—COONSu: ω-Carboxyheptanoic acid 2,5-dioxopyrrolidin-1-yl ester
HOOC—(CH$_2$)$_{10}$—COONSu: ω-Carboxyundecanoic acid 2,5-dioxopyrrolidin-1-yl ester
HOOC—(CH$_2$)$_{12}$—COONSu: ω-Carboxytridecanoic acid 2,5-dioxopyrrolidin-1-yl ester
HOOC—(CH$_2$)$_{14}$—COONSu: ω-Carboxypentadecanoic acid 2,5-dioxopyrrolidin-1-yl ester
HOOC—(CH$_2$)$_{16}$—COONSu: ω-Carboxyheptadecanoic acid 2,5-dioxopyrrolidin-1-yl ester
HOOC—(CH$_2$)$_{18}$—COONSu: ω-Carboxynonadecanoic acid 2,5-dioxopyrrolidin-1-yl ester
N$^\alpha$-alkanoyl-Glu(ONSu)-OBu$^t$: N$^\alpha$-Alkanoyl-(L)-glutamic acid α-t-butyl-γ-2,5-dioxopyrrolidin-1-yl diester
Analytical
Plasma Desorption Mass Spectrometry
Sample Preparation:
The sample is dissolved in 0.1% TFA/EtOH (1:1) at a concentration of 1 μg/μl. The sample solution (5-10 μl) is placed on a nitrocellulose target (Bio-ion AB, Uppsala, Sweden) and allowed to adsorb to the target surface for 2 minutes.

The target is subsequently rinsed with 2×25 µl 0.1% TFA and spin-dried. Finally, the nitrocellulose target is placed in a target carrousel and introduced into the mass spectrometer.
MS Analysis:

PDMS analysis was carried out using a Bio-ion 20 time-of flight instrument (Bio-ion Nordic AB, Uppsala, Sweden). An acceleration voltage of 15 kV was applied and molecular ions formed by bombardment of the nitrocellulose surface with 252-Cf fission fragments were accelerated towards a stop detector. The resulting time-of-flight spectrum was calibrated into a true mass spectrum using the $H^+$ and $NO^+$ ions at m/z 1 and 30, respectively. Mass spectra were generally accumulated for $1.0 \times 10^6$ fission events corresponding to 15-20 minutes. Resulting assigned masses all correspond to isotopically averaged molecular masses. The accuracy of mass assignment is generally better than 0.1%.
MALDI-MS MALDI-TOF MS analysis was carried out using a Voyager RP instrument (PerSeptive Biosystems Inc., Framingham, Mass.) equipped with delayed extraction and operated in linear mode. Alpha-cyano-4-hydroxy-cinnamic acid was used as matrix, and mass assignments were based on external calibration.

Example 1

Synthesis of $Lys^{26}(N^\epsilon\text{-tetradecanoyl})\text{-GLP-1(7-37)}$

The title compound was synthesised from GLP-1(7-37). A mixture of GLP-1(7-37) (25 mg, 7.45 µm), EDPA (26.7 mg, 208 µm), NMP (520 µl) and water (260 µl) was gently shaken for 5 min. at room temperature. To the resulting mixture was added a solution of Myr-ONSu (2.5 mg, 7.67 µm) in NMP (62.5 µl), the reaction mixture was gently shaken for 5 min. at room temperature and then allowed to stand for 20 min. An additional amount of Myr-ONSu (2.5 mg, 7.67 µm) in NMP (62.5 µl) was added and the resulting mixture gently shaken for 5 min. After a total reaction time of 40 min. the reaction was quenched by the addition of a solution of glycine (12.5 mg, 166 µmol) in 50% aqueous ethanol (12.5 ml). The title compound was isolated from the reaction mixture by HPLC using a cyanopropyl column (Zorbax 300SB-CN) and a standard acetonitrile/TFA system, yield: 1.3 mg (corresponding to 4.9% of the theoretical yield). The column was heated to 65° C. and the acetonitrile gradient was 0-100% in 60 minutes. The isolated product was analysed by PDMS and the m/z value for the protonated molecular ion was found to be 3567.9±3. The resulting molecular weight was thus 3566.9±3 amu (theoretical value: 3565.9 amu). The position of acylation (Lys26) was verified by enzymatic cleavage of the title compound with *Staphylococcus aureus* V8 protease and subsequent mass determination of the peptide fragments by PDMS.

In addition to the title compound two other GLP-1 derivatives were isolated from the reaction mixture by using the same chromatographic column and a more shallow gradient (35-38% acetonitrile in 60 minutes), see Examples 2 and 3.

Example 2

Synthesis of $Lys^{34}(N^\epsilon\text{-tetradecanoyl})\text{-GLP-1(7-37)}$

The title compound was isolated by HPLC from the reaction mixture described in Example 1. PDMS analysis yielded a protonated molecular ion at m/z 3567.7±3. The molecular weight was found to be 3566.7±3 amu (theoretical value: 3565.9 amu). The acylation site was determined on the basis of the fragmentation pattern.

Example 3

Synthesis of $Lys^{26,34}\text{-bis}(N^\epsilon\text{-tetradecanoyl})\text{-GLP-1} (7\text{-}37)$ The title compound was isolated by HPLC from the reaction mixture described in Example 1. PDMS analysis yielded a protonated molecular ion at m/z 3778.4±3. The molecular weight was found to be 3777.4±3 amu (theoretical value: 3776.1 amu).

Example 4

Synthesis of $Lys^{26}(N^\epsilon\text{-tetradecanoyl})Arg^{34}\text{-GLP-1} (7\text{-}37)$ The title compound was synthesised from $Arg^{34}$-GLP-1(7-37). A mixture of $Arg^{34}$-GLP-1(7-37) (5 mg, 1.47 µm), EDPA (5.3 mg, 41.1 µm), NMP (105 µl) and water (50 µl) was gently shaken for 5 min. at room temperature. To the resulting mixture was added a solution of Myr-ONSu (0.71 mg, 2.2 µm) in NMP (17.8 µl), the reaction mixture was gently shaken for 5 min. at room temperature and then allowed to stand for 20 min. After a total reaction time of 30 min. the reaction was quenched by the addition of a solution of glycine (25 mg, 33.3 µm) in 50% aqueous ethanol (2.5 ml). The reaction mixture was purified by HPLC as described in Example 1. PDMS analysis yielded a protonated molecular ion at m/z 3594.9±3. The molecular weight was found to be 3593.9±3 amu (theoretical value: 3593.9 amu).

Example 5

Synthesis of $Gly^8 Arg^{26,34} Lys^{36}(N^\epsilon\text{-tetradecanoyl})\text{-} GLP\text{-}1(7\text{-}37)$ The title compound was synthesised from $Gly^8 Arg^{26,34} Lys^{36}$-GLP-1(7-37) which was purchased from QCB. A mixture of $Gly^8 Arg^{26,34} Lys^{36}$-GLP-1(7-37) (1.3 mg, 0.39 µm), EDPA (1.3 mg, 10 µm), NMP (125 µl) and water (30 µl) was gently shaken for 5 min. at room temperature. To the resulting mixture was added a solution of Myr-ONSu (0.14 mg, 0.44 µm) in NMP (3.6 ml), the reaction mixture was gently shaken for 15 min. at room temperature. The reaction was quenched by the addition of a solution of glycine (0.1 mg, 1.33 µm) in 50% aqueous ethanol (10 µl). The reaction mixture was purified by HPLC, and the title compound (60 µg, 4%) was isolated.

Example 6

Synthesis of $Arg^{26,34} Lys^{36}(N^\epsilon\text{-tetradecanoyl})\text{-GLP-1} (7\text{-}37)\text{-OH}$ A mixture of $Arg^{26,34} Lys^{36}$-GLP-1(7-37)-OH (5.0 mg, 1.477 µmol), EDPA (5.4 mg, 41.78 µmol), NMP (105 µl) and water (50 µl) was gently shaken for 5 min. at room temperature. To the resulting mixture was added a solution of Myr-ONSu (0.721 mg, 2.215 µmol) in NMP (18 µl). The reaction mixture was gently shaken for 5 min. at room temperature, and then allowed to stand for an additional 45 min. at room temperature. The reaction was quenched by the addition of a solution of glycine (2.5 mg, 33.3 µmol) in 50% aqueous ethanol (250 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (1.49 mg, 28%) was isolated, and the product was analysed by PDMS. The m/z value for the protonated molecular ion was found to be 3595±3. The resulting molecular weight was thus 3594±3 amu (theoretical value 3594 amu).

Example 7

Synthesis of Lys$^{26,34}$bis(N$^\epsilon$-(ω-carboxynonadecanoyl))-GLP-1(7-37)-OH A mixture of GLP-1(7-37)-OH (70 mg, 20.85 µmol), EDPA (75.71 mg, 585.8 µmol), NMP (1.47 ml) and water (700 µl) was gently shaken for 10 min. at room temperature. To the resulting mixture was added a solution of HOOC—(CH$_2$)$_{18}$—COONSu (27.44 mg, 62.42 µmol) in NMP (686 µl), the reaction mixture was gently shaken for 5 min. at room temperature, and then allowed to stand for an additional 50 min. at room temperature. The reaction was quenched by the addition of a solution of glycine (34.43 mg, 458.7 µmol) in 50% aqueous ethanol (3.44 ml). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (8.6 mg, 10%) was isolated, and the product was analysed by PDMS. The m/z value for the protonated molecular ion was found to be 4006±3. The resulting molecular weight was thus 4005±3 amu (theoretical value 4005 amu).

Example 8

Synthesis of Arg$^{26,34}$Lys$^{36}$(N$^\epsilon$-(ω-carboxynonadecanoyl))-GLP-1(7-36)-OH A mixture of Arg$^{26,34}$Lys$^{36}$-GLP-1(7-36)-OH (5.06 mg, 1.52 µmol), EDPA (5.5 mg, 42.58 µmol), NMP (106 µl) and water (100 µl) was gently shaken for 5 min. at room temperature. To the resulting mixture was added a solution of HOOC—(CH$_2$)$_{18}$—COONSu (1.33 mg, 3.04 µmol) in NMP (33.2 µl), the reaction mixture was gently shaken for 5 min. at room temperature, and then allowed to stand for an additional 2.5 h at room temperature. The reaction was quenched by the addition of a solution of glycine (2.50 mg, 33.34 µmol) in 50% aqueous ethanol (250 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.46 mg, 8%) was isolated, and the product was analysed by PDMS. The m/z value for the protonated molecular ion was found to be 3652±3. The resulting molecular weight was thus 3651±3 amu (theoretical value 3651 amu).

Example 9

Synthesis of Arg$^{26,34}$Lys$^{38}$(N$^\epsilon$-(ω-carboxynonadecanoyl))-GLP-1(7-38)-OH A mixture of Arg$^{26,34}$Lys$^{38}$-GLP-1(7-38)-OH (5.556 mg, 1.57 µmol), EDPA (5.68 mg, 43.96 µmol), NMP (116.6 µl) and water (50 µl) was gently shaken for 10 min. at room temperature. To the resulting mixture was added a solution HOOC—(CH$_2$)$_{18}$—COONSu (1.38 mg, 3.14 µmol) in NMP (34.5 µl), the reaction mixture was gently shaken for 5 min. at room temperature, and then allowed to stand for an additional 2.5 h at room temperature. The reaction was quenched by the addition of a solution of glycine (2.5 mg, 33.3 µmol) in 50% aqueous ethanol (250 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.7 mg, 12%) was isolated, and the product was analysed by PDMS. The m/z value for the protonated molecular ion was found to be 3866±3. The resulting molecular weight was thus 3865±3 amu (theoretical value 3865 amu).

Example 10

Synthesis of Arg$^{34}$Lys$^{26}$(N$^\epsilon$-(ω-carboxynonadecanoyl))-GLP-1(7-37)-OH A mixture of Arg$^{34}$-GLP-1(7-37)-OH (5.04 mg, 1.489 µmol), EDPA (5.39 mg, 41.70 µmol), NMP (105 µl) and water (50 µl) was gently shaken for 10 min. at room temperature. To the resulting mixture was added a solution HOOC—(CH$_2$)$_{18}$—COONSu (1.31 mg, 2.97 µmol) in NMP (32.8 µl), the reaction mixture was gently shaken for 5 min. at room temperature, and then allowed to stand for an additional 30 min. at room temperature. The reaction was quenched by the addition of a solution of glycine (2.46 mg, 32.75 µmol) in 50% aqueous ethanol (246 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (1.2 mg, 22%) was isolated, and the product was analysed by PDMS. The m/z value for the protonated molecular ion was found to be 3709±3. The resulting molecular weight was thus 3708±3 amu (theoretical value 3708 amu).

Example 11

Synthesis of Arg$^{34}$Lys$^{26}$(N$^\epsilon$-(ω-carboxyheptadecanoyl))-GLP-1(7-37)-OH A mixture of Arg$^{34}$-GLP-1(7-37)-OH (5.8 mg, 1.714 µmol), EDPA (6.20 mg, 47.99 µmol), NMP (121.8 µl) and water (58 µl) was gently shaken for 10 min. at room temperature. To the resulting mixture was added a solution HOOC—(CH$_2$)$_{16}$—COONSu (2.11 mg, 5.142 µmol) in NMP (52.8 µl), the reaction mixture was gently shaken for 5 min. at room temperature, and then allowed to stand for an additional 2 h at room temperature. The reaction was quenched by the addition of a solution of glycine (2.83 mg, 37.70 µmol) in 50% aqueous ethanol (283 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.81 mg, 13%) was isolated, and the product was analysed by PDMS. The m/z value for the protonated molecular ion was found to be 3681±3. The resulting molecular weight was thus 3680±3 amu (theoretical value 3680 amu).

Example 12

Synthesis of Arg$^{26,34}$Lys$^{36}$(N$^\epsilon$-(ω-carboxyheptadecanoyl))-GLP-1(7-37)-OH A mixture of Arg$^{26,34}$Lys$^{36}$-GLP-1(7-37)-OH (3.51 mg, 1.036 µmol), EDPA (3.75 mg, 29.03 µmol), NMP (73.8 µl)

and water (35 µl) was gently shaken for 10 min. at room temperature. To the resulting mixture was added a solution HOOC—$(CH_2)_{16}$—COONSu (1.27 mg, 3.10 µmol) in NMP (31.8 µl), the reaction mixture was gently shaken for 5 min. at room temperature, and then allowed to stand for an additional 2 h and 10 min. at room temperature. The reaction was quenched by the addition of a solution of glycine (1.71 mg, 22.79 µmol) in 50% aqueous ethanol (171 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.8 mg, 21%) was isolated, and the product was analysed by PDMS. The m/z value for the protonated molecular ion was found to be 3682±3. The resulting molecular weight was thus 3681±3 amu (theoretical value 3681 amu).

Example 13

Synthesis of $Arg^{26,34}Lys^{38}(N^\epsilon$-(c)-carboxyheptadecanoyl))-GLP-1(7-38)-OH A mixture of $Arg^{26,34}Lys^{38}$-GLP-1(7-38)-OH (5.168 mg, 1.459 µmol), EDPA (5.28 mg, 40.85 µmol), NMP (108.6 µl) and water (51.8 µl) was gently shaken for 10 min. at room temperature. To the resulting mixture was added a solution HOOC—$(CH_2)_{16}$—COONSu (1.80 mg, 4.37 µmol) in NMP (45 µl), the reaction mixture was gently shaken for 10 min. at room temperature, and then allowed to stand for an additional 2 h and 15 min. at room temperature. The reaction was quenched by the addition of a solution of glycine (2.41 mg, 32.09 µmol) in 50% aqueous ethanol (241 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.8 mg, 14%) was isolated, and the product was analysed by PDMS. The m/z value for the protonated molecular ion was found to be 3838±3. The resulting molecular weight was thus 3837±3 amu (theoretical value 3837 amu).

Example 14

Synthesis of $Arg^{26,34}Lys^{36}(N^\epsilon$-(ω-carboxyheptadecanoyl))-GLP-1(7-36)-OH A mixture of $Arg^{26,34}Lys^{63}$-GLP-1(7-36)-OH (24.44 mg, 7.34 µmol), EDPA (26.56 mg, 205.52 µmol), NMP (513 µl) and water (244.4 µl) was gently shaken for 5 min. at room temperature. To the resulting mixture was added a solution HOOC—$(CH_2)_{16}$—COONSu (9.06 mg, 22.02 µmol) in NMP (1.21 ml), the reaction mixture was gently shaken for 5 min. at room temperature, and then allowed to stand for an additional 30 min. at room temperature. The reaction was quenched by the addition of a solution of glycine (12.12 mg, 161.48 µmol) in 50% aqueous ethanol (1.21 ml). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (7.5 mg, 28%) was isolated, and the product was analysed by PDMS. The m/z value for the protonated molecular ion was found to be 3625±3. The resulting molecular weight was thus 3624±3 amu (theoretical value 3624 amu).

Example 15

Synthesis of $Arg^{26,34}Lys^{36}(N^\epsilon$-(ω-carboxyundecanoyl))-GLP-1(7-37)-OH A mixture of $Arg^{26,34}Lys^{36}$-GLP-1(7-37)-OH (4.2 mg, 1.24 µmol), EDPA (4.49 mg, 34.72 µmol), NMP (88.2 µl) and water (42 µl) was gently shaken for 10 min. at room temperature. To the resulting mixture was added a solution HOOC—$(CH_2)_{10}$—COONSu (1.21 mg, 3.72 µmol) in NMP (30.25 µl), the reaction mixture was gently shaken for 5 min. at room temperature, and then allowed to stand for an additional 40 min. at room temperature. The reaction was quenched by the addition of a solution of glycine (2.04 mg, 27.28 µmol) in 50% aqueous ethanol (204 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.8 mg, 18%) was isolated, and the product was analysed by PDMS. The m/z value for the protonated molecular ion was found to be 3598±3. The resulting molecular weight was thus 3597±3 amu (theoretical value 3597 amu).

Example 16

Synthesis of $Arg^{26,34}Lys^{38}(N^\epsilon$-(ω-carboxyundecanoyl))-GLP-1(7-38)-OH A mixture of $Arg^{26,34}Lys^{38}$-GLP-1(7-38)-OH (5.168 mg, 1.46 µmol), EDPA (5.28 mg, 40.88 µmol), NMP (108.6 µl) and water (51.7 µl) was gently shaken for 10 min. at room temperature. To the resulting mixture was added a solution HOOC—$(CH_2)_{10}$—COONSu (1.43 mg, 4.38 µmol) in NMP (35.8 µl), the reaction mixture was gently shaken for 5 min. at room temperature, and then allowed to stand for an additional 50 min. at room temperature. The reaction was quenched by the addition of a solution of glycine (2.41 mg, 32.12 µmol) in 50% aqueous ethanol (241 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.85 mg, 16%) was isolated, and the product was analysed by PDMS. The m/z value for the protonated molecular ion was found to be 3753±3. The resulting molecular weight was thus 3752±3 amu (theoretical value 3752 amu).

Example 17

Synthesis of $Lys^{26,34}bis(N^\epsilon$-(ω-carboxyundecanoyl))-GLP-1(7-37)-OH

A mixture of GLP-1(7-37)-OH (10.0 mg, 2.98 µmol), EDPA (10.8 mg, 83.43 µmol), NMP (210 µl) and water (100 µl) was gently shaken for 10 min. at room temperature. To the resulting mixture was added a solution HOOC—$(CH_2)_{10}$—COONSu (2.92 mg, 8.94 µmol) in NMP (73 µl), the reaction mixture was gently shaken for 5 min. at room temperature, and then allowed to stand for an additional 50 min. at room temperature. The reaction was quenched by the addition of a solution of glycine (4.92 mg, 65.56 µmol) in 50% aqueous ethanol (492 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (1.0 mg, 9%) was isolated, and the product was analysed by PDMS. The m/z value for the protonated molecular ion was found to be 3781±3. The resulting molecular weight was thus 3780±3 amu (theoretical value 3780 amu).

Example 18

Synthesis of Arg$^{26,34}$Lys$^{36}$(N$^\epsilon$-(ω-carboxyundecanoyl))-GLP-1(7-36)-OH A mixture of Arg$^{26,34}$Lys$^{36}$-GLP-1(7-36)-OH (15.04 mg, 4.52 μmol), EDPA (16.35 mg, 126.56 μmol), NMP (315.8 μl) and water (150.4 μl) was gently shaken for 10 min. at room temperature. To the resulting mixture was added a solution HOOC—(CH$_2$)$_{10}$—COONSu (4.44 mg, 13.56 μmol) in NMP (111 μl), the reaction mixture was gently shaken for 5 min. at room temperature, and then allowed to stand for an additional 40 min. at room temperature. The reaction was quenched by the addition of a solution of glycine (7.5 mg, 99.44 μmol) in 50% aqueous ethanol (750 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (3.45 mg, 22%) was isolated, and the product was analysed by PDMS. The m/z value for the protonated molecular ion was found to be 3540±3. The resulting molecular weight was thus 3539±3 amu (theoretical value 3539 amu).

Example 19

Synthesis of Arg$^{34}$Lys$^{26}$(N$^\epsilon$-(ω-carboxyundecanoyl))-GLP-1(7-37)-OH A mixture of Arg$^{34}$-GLP-1(7-37)-OH (5.87 mg, 1.73 μmol), EDPA (6.27 mg, 48.57 μmol), NMP (123.3 μl) and water (58.7 μl) was gently shaken for 10 min. at room temperature. To the resulting mixture was added a solution HOOC—(CH$_2$)$_{10}$—COONSu (1.70 mg, 5.20 μmol) in NMP (42.5 μl), the reaction mixture was gently shaken for 5 min. at room temperature, and then allowed to stand for an additional 40 min. at room temperature. The reaction was quenched by the addition of a solution of glycine (2.86 mg, 286 μmol) in 50% aqueous ethanol (286 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (1.27 mg, 20%) was isolated, and the product was analysed by PDMS. The m/z value for the protonated molecular ion was found to be 3597±3. The resulting molecular weight was thus 3596±3 amu (theoretical value 3596 amu).

Example 20

Synthesis of Arg$^{34}$Lys$^{26}$(N$^\epsilon$-(ω-carboxyheptanoyl))-GLP-1(7-37)-OH A mixture of Arg$^{34}$-GLP-1(7-37)-OH (4.472 mg, 1.32 μmol), EDPA (4.78 mg, 36.96 μmol), NMP (94 μl) and water (44.8 μl) was gently shaken for 5 min. at room temperature. To the resulting mixture was added a solution HOOC—(CH$_2$)$_6$—COONSu (1.07 mg, 3.96 μmol) in NMP (26.8 μl), the reaction mixture was gently shaken for 5 min. at room temperature, and then allowed to stand for an additional 1 h and 50 min. at room temperature. The reaction was quenched by the addition of a solution of glycine (2.18 mg, 29.04 μmol) in 50% aqueous ethanol (218 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.5 mg, 11%) was isolated, and the product was analysed by PDMS. The m/z value for the protonated molecular ion was found to be 3540±3. The resulting molecular weight was thus 3539±3 amu (theoretical value 3539 amu).

Example 21

Synthesis of Arg$^{26,34}$Lys$^{38}$(N$^\epsilon$-(ω-carboxyheptanoyl))-GLP-1(7-38)-OH A mixture of Arg$^{26,34}$Lys$^{38}$-GLP-1(7-38)-OH (5.168 mg, 1.459 μmol), EDPA (5.28 mg, 40.85 μmol), NMP (108.6 μl) and water (51.6 μl) was gently shaken for 10 min. at room temperature. To the resulting mixture was added a solution HOOC—(CH$_2$)$_6$—COONSu (1.18 mg, 4.37 μmol) in NMP (29.5 μl), the reaction mixture was gently shaken for 5 min. at room temperature, and then allowed to stand for an additional 1 h and 50 min. at room temperature. The reaction was quenched by the addition of a solution of glycine (2.40 mg, 32.09 μmol) in 50% aqueous ethanol (240 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.5 mg, 9%) was isolated, and the product was analysed by PDMS. The m/z value for the protonated molecular ion was found to be 3697±3. The resulting molecular weight was thus 3695±3 amu (theoretical value 3695 amu).

Example 22

Synthesis of Arg$^{26,34}$Lys$^{36}$(N$^\epsilon$-(ω-carboxyheptanoyl))-GLP-1(7-37)-OH A mixture of Arg$^{26,34}$Lys$^{36}$-GLP-1(7-37)-OH (5.00 mg, 1.47 μmol), EDPA (5.32 mg, 41.16 μmol), NMP (105 μl) and water (50 μl) was gently shaken for 5 min. at room temperature. To the resulting mixture was added a solution HOOC—(CH$_2$)$_6$—COONSu (1.19 mg, 4.41 μmol) in NMP (29.8 μl), the reaction mixture was gently shaken for 5 min. at room temperature, and then allowed to stand for an additional 2 h at room temperature. The reaction was quenched by the addition of a solution of glycine (2.42 mg, 32.34 μmol) in 50% aqueous ethanol (242 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.78 mg, 15%) was isolated, and the product was analysed by PDMS. The m/z value for the protonated molecular ion was found to be 3542±3. The resulting molecular weight was thus 3541±3 amu (theoretical value 3541 amu).

Example 23

Synthesis of Arg$^{26,34}$Lys$^{36}$(N$^\epsilon$-(ω-carboxyheptanoyl))-GLP-1(7-36)-OH A mixture of Arg$^{26,34}$Lys$^{36}$-GLP-1(7-36)-OH (5.00 mg, 1.50 μmol), EDPA (5.44 mg, 42.08 μmol), NMP (210 μl) and water (50 µl) was gently shaken for 5 min. at room temperature. To the resulting mixture was added a solution HOOC—(CH$_2$)$_6$—COONSu (1.22 mg, 4.5 µmol) in NMP (30.5 µl), the reaction mixture was gently shaken for 5 min. at room temperature, and then allowed to stand for an additional 2 h at room temperature. The reaction was quenched by the addition of a solution of glycine (2.47 mg, 33.0 µmol) in 50% aqueous ethanol (247 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.71 mg, 14%) was isolated, and the product was analysed by PDMS. The m/z value for the protonated molecular ion was found to be 3484±3. The resulting molecular weight was thus 3483±3 amu (theoretical value 3483 amu).

Example 24

Synthesis of Lys$^{26,34}$bis(N$^\epsilon$-(ω-carboxyheptanoyl))-GLP-1(7-37)-OH

A mixture of GLP-1(7-37)-OH (10 mg, 2.5 µmol), EDPA (10.8 mg, 83.56 µmol), NMP (210 µl) and water (100 µl) was gently shaken for 10 min. at room temperature. To the resulting mixture was added a solution HOOC—(CH$_2$)$_6$—COONSu (2.42 mg, 8.92 µmol) in NMP (60.5 µl), the reaction mixture was gently shaken for 5 min. at room temperature, and then allowed to stand for an additional 2 h and 35 min. at room temperature. The reaction was quenched by the addition of a solution of glycine (4.92 mg, 65.54 µmol) in 50% aqueous ethanol (492 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (2.16 mg, 24%) was isolated, and the product was analysed by PDMS. The m/z value for the protonated molecular ion was found to be 3669±3. The resulting molecular weight was thus 3668±3 amu (theoretical value 3668 amu).

Example 25

Synthesis of Arg$^{34}$Lys$^{26}$(N$^\epsilon$-(ω-carboxypentadecanoyl))-GLP-1(7-37)-OH A mixture of Arg$^{34}$-GLP-1(7-37)-OH (4.472 mg, 1.321 µmol), EDPA (4.78 mg, 36.99 µmol), NMP (93.9 µl) and water (44.7 µl) was gently shaken for 10 min. at room temperature. To the resulting mixture was added a solution HOOC—(CH$_2$)$_{14}$—COONSu (1.519 mg, 3.963 µmol) in NMP (38 µl), the reaction mixture was gently shaken for 5 min. at room temperature, and then allowed to stand for an additional 1 h at room temperature. The reaction was quenched by the addition of a solution of glycine (2.18 mg, 29.06 µmol) in 50% aqueous ethanol (218 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.58 mg, 12%) was isolated, and the product was analysed by PDMS. The m/z value for the protonated molecular ion was found to be 3654±3. The resulting molecular weight was thus 3653±3 amu (theoretical value 3653 amu).

Example 26

Synthesis of Arg$^{26,34}$Lys$^{36}$(N$^\epsilon$-(ω-carboxyheptanoyl))-GLP-1(7-36)-OH A mixture of Arg$^{26,34}$Lys$^{36}$-GLP-1(7-36)-OH (5.00 mg, 1.50 µmol), EDPA (5.44 mg, 42.08 µmol), NMP (210 µl) and water (50 µl) was gently shaken for 5 min. at room temperature. To the resulting mixture was added a solution HOOC—(CH$_2$)$_{14}$—COONSu (1.72 mg, 4.5 µmol) in NMP (43 µl), the reaction mixture was gently shaken for 5 min. at room temperature, and then allowed to stand for an additional 1 h at room temperature. The reaction was quenched by the addition of a solution of glycine (2.48 mg, 33 µmol) in 50% aqueous ethanol (248 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.58 mg, 11%) was isolated, and the product was analysed by PDMS. The m/z value for the protonated molecular ion was found to be 3596±3. The resulting molecular weight was thus 3595±3 amu (theoretical value 3595 amu).

Example 27

Synthesis of Lithocholic Acid 2,5-dioxo-pyrrolidin-1-yl Ester

To a mixture of lithocholic acid (5.44 g, 14.34 mmol), N-hydroxysuccinimide (1.78 g, 15.0 mmol), anhydrous THF (120 ml) and anhydrous acetonitrile (30 ml), kept at to 10° C., was added a solution of N,N'-dicyclohexylcarbodiimide (3.44 g, 16.67 mmol) in anhydrous THF. The reaction mixture was stirred at ambient temperature for 16 h, filtered and concentrated in vacuo. The residue was dissolved in dichloromethane (450 ml), washed with a 10% aqueous Na$_2$CO$_3$ solution (2×150 ml) and water (2×150 ml), and dried (MgSO$_4$). Filtered and the filtrate concentrated in vacuo to give a crystalline residue. The residue was recrystallised from a mixture of dichloromethane (30 ml) and n-heptane (30 ml to give the title compound (3.46 g, 51%) as a crystalline solid.

Example 28

Synthesis of Arg$^{34}$Lys$^{26}$ (N$^\epsilon$-lithocholyl)-GLP-1(7-37)-OH

A mixture of Arg$^{34}$-GLP-1(7-37)-OH (4.472 mg, 1.32 µmol), EDPA (4.78 mg, 36.96 µmol), NMP (94 µl) and water (44.8 µl) was gently shaken for 10 min. at room temperature. To the resulting mixture was added a solution of lithocholic acid 2,5-dioxo-pyrrolidin-1-yl ester (1.87 mg, 3.96 µmol) in NMP (46.8 µl), the reaction mixture was gently shaken for 5 min. at room temperature, and then allowed to stand for an additional 1 h at room temperature. The reaction was quenched by the addition of a solution of glycine (2.18 mg, 29.04 µmol) in 50% aqueous ethanol (218 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (1.25 mg, 25%) was isolated, and the product was analysed by PDMS. The m/z value for the protonated molecular ion was found to be 3744±3. The resulting molecular weight was thus 3743±3 amu (theoretical value 3743 amu).

Example 29

Synthesis of N$^\alpha$-tetradecanoyl-Glu(ONSu)-OBu$^t$

To a suspension of H-Glu(OH)—OBu$^t$ (2.5 g, 12.3 mmol), DMF (283 ml) and EDPA (1.58 g, 12.3 mmol) was added drop by drop a solution of Myr-ONSu (4.0 g, 12.3 mmol) in DMF (59 ml). The reaction mixture was stirred for 16 h at room temperature and then concentrated in vacuo to a total volume of 20 ml. The residue was partitioned between 5% aqueous citric acid (250 ml) and ethyl acetate (150 ml), and the phases were separated. The organic phase was concentrated in vacuo and the residue dissolved in DMF (40 ml). The resulting solution was added drop by drop to a 10% aqueous solution of citric acid (300 ml) kept at 0° C. The precipitated compound was collected and washed with iced water and dried in a vacuum drying oven. The dried compound was dissolved in DMF (23 ml) and HONSu (1.5 g, 13 mmol) was added. To the resulting mixture was added a solution of N,N'-dicyclohexylcarbodiimide (2.44 g, 11.9 mmol) in dichloromethane (47 ml). The reaction mixture was stirred for 16 h at room temperature, and the precipitated compound was filtered off. The precipitate was recrystallised from n-heptane/2-propanol to give the title compound (3.03 g, 50%).

Example 30

Synthesis of Glu$^{22,23,30}$Arg$^{26,34}$Lys$^{38}$(N$^\epsilon$-($\gamma$-glutamyl (N$^\alpha$-tetradecanoyl)))-GLP-1(7-38)-OH A mixture of Glu$^{22,23,30}$Arg$^{26,34}$Lys$^{38}$-GLP-1(7-38)-OH (1.0 mg, 0.272 µmol), EDPA (0.98 mg, 7.62 µmol), NMP (70 µl) and water (70 µl) was gently shaken for 5 min. at room temperature. To the resulting mixture was added a solution of N$^\alpha$-tetradecanoyl-Glu(ONSu)-OBu$^t$, prepared as described in Example 29, (0.41 mg, 0.816 µmol) in NMP (10.4 µl), the reaction mixture was gently shaken for 5 min. at room temperature, and then allowed to stand for an additional 45 min. at room temperature. The reaction was quenched by the addition of a solution of glycine (0.448 mg, 5.98 µmol) in 50% aqueous ethanol (45 µl). A 0.5% aqueous solution of ammonium acetate (0.9 ml) was added, and the resulting mixture was immobilised on a Varian 500 mg C8 Mega Bond Elut® cartridge, the immobilised compound washed with 5% aqueous acetonitrile (10 ml), and finally liberated from the cartridge by elution with TFA (10 ml). The eluate was concentrated in vacuo, and the reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.35 mg, 32%) was isolated, and the product was analysed by PDMS. The m/z value for the protonated molecular ion was found to be 4012±3. The resulting molecular weight was thus 4011±3 amu (theoretical value 4011 amu).

Example 31

Synthesis of Glu$^{23,26}$Arg$^{34}$Lys$^{38}$(N$^\epsilon$-($\gamma$-glutamyl(N$^\alpha$-tetradecanoyl)))-GLP-1(7-38)-OH A mixture of Glu$^{23,26}$Arg$^{34}$Lys$^{38}$-GLP-1(7-38)-OH (6.07 mg, 1.727 µmol), EDPA (6.25 mg, 48.36 µmol), NMP (425 µl) and water (425 µl) was gently shaken for 5 min. at room temperature. To the resulting mixture was added a solution of N$^\alpha$-tetradecanoyl-Glu(ONSu)-OBu$^t$, prepared as described in example 29, (2.65 mg, 5.18 µmol) in NMP (66.3 µl), the reaction mixture was gently shaken for 5 min. at room temperature, and then allowed to stand for an additional 45 min. at room temperature. The reaction was quenched by the addition of a solution of glycine (2.85 mg, 38.0 µmol) in 50% aqueous ethanol (285 µl). A 0.5% aqueous solution of ammonium acetate (5.4 ml) was added, and the resulting mixture was immobilised on a Varian 500 mg C8 Mega Bond Elut® cartridge, the immobilised compound washed with 5% aqueous acetonitrile (10 ml), and finally liberated from the cartridge by elution with TFA (10 ml). The eluate was concentrated in vacuo, and the reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.78 mg, 12%) was isolated, and the product was analysed by PDMS. The m/z value for the protonated molecular ion was found to be 3854±3. The resulting molecular weight was thus 3853±3 amu (theoretical value 3853 amu).

Example 32

Synthesis of Lys$^{26,34}$-bis(N$^\epsilon$-($\omega$-carboxytridecanoyl))-GLP-1(7-37)-OH A mixture of GLP-1(7-37)-OH (30 mg, 8.9 µmol), EDPA (32.3 mg, 250 µmol), NMP (2.1 ml) and water (2.1 ml) was gently shaken for 5 min. at room temperature. To the resulting mixture was added a solution HOOC—(CH$_2$)$_{12}$—COONSu (12.7 mg, 35.8 µmol) in NMP (318 µl), the reaction mixture was gently shaken for 1 h and 40 min. at room temperature. The reaction was quenched by the addition of a solution of glycine (3.4 mg, 44.7 µmol) in 50% aqueous ethanol (335 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (10 mg, 29%) was isolated, and the product was analysed by PDMS. The m/z value for the protonated molecular ion was found to be 3840±3. The resulting molecular weight was thus 3839±3 amu (theoretical value 3839 amu).

Example 33

Synthesis of Lys$^{26,34}$-bis(N$^\epsilon$-($\gamma$-glutamyl(N$^\alpha$-tetradecanoyl)))-GLP-1(7-37)-OH A mixture of GLP-1(7-37)-OH (300 mg, 79.8 µmol), EDPA (288.9 mg, 2.24 mmol), NMP (21 ml) and water (21 ml) was gently shaken for 5 min. at room temperature. To the resulting mixture was added a solution of N$^\alpha$-tetradecanoyl-Glu(ONSu)-OBu$^t$, prepared as described in Example 29, (163 mg, 319.3 µmol) in NMP (4.08 ml), the reaction mixture was gently shaken for 5 min. at room temperature, and then allowed to stand for an additional 1 h at room temperature. The reaction was quenched by the addition of a solution of glycine (131.8 mg, 1.76 mmol) in 50% aqueous ethanol (13.2 ml). A 0.5% aqueous solution of ammonium-acetate (250 ml) was added, and the resulting mixture was divided into four equal portions. Each portion was eluted onto a Varian 500 mg C8 Mega Bond Elut® cartridge, the immobilised compound washed with 0.1% aqueous TFA (3.5 ml), and finally liberated from the cartridge by elution with 70% aqueous acetonitrile (4 ml). The combined eluates were diluted with 0.1% aqueous TFA (300 ml). The precipitated compound was collected by centrifugation, washed with 0.1% aqueous TFA (50 ml), and finally isolated by centrifugation. To the precipitate was added TFA (60 ml), and the resulting reaction mixture was stirred for 1 h and 30 min. at room temperature. Excess TFA was removed in vacuo, and the residue was poured into water (50 ml). The precipitated compound was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (27.3 mg, 8%) was isolated, and the product was analysed by PDMS. The m/z value for the protonated molecular ion was found to be 4036±3. The resulting molecular weight was thus 4035±3 amu (theoretical value 4035 amu).

Example 34

Synthesis of Arg$^{26,34}$Lys$^{38}$(N$^\epsilon$-(ω-carboxypentadecanoyl))-GLP-1(7-38)-OH A mixture of Arg$^{26,34}$Lys$^{38}$-GLP-1(7-38)-OH (30 mg, 8.9 µmol), EDPA (32.3 mg, 250 µmol), NMP (2.1 ml) and water (2.1 ml) was gently shaken for 5 min. at room temperature. To the resulting mixture was added a solution HOOC—(CH$_2$)$_{14}$—COONSu (13.7 mg, 35.8 µmol) in NMP (343 µl), the reaction mixture was gently shaken for 1 h at room temperature. The reaction was quenched by the addition of a solution of glycine (3.4 mg, 44.7 µmol) in 50% aqueous ethanol (335 µl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (4.8 mg, 14%) was isolated, and the product was analysed by PDMS. The m/z value for the protonated molecular ion was found to be 3894±3. The resulting molecular weight was thus 3893±3 amu (theoretical value 3893 amu).

Example 35

Synthesis of N$^\alpha$-hexadecanoyl-Glu(ONSu)-OBu$^t$

To a suspension of H-Glu(OH)—OBu$^t$ (4.2 g, 20.6 mmol), DMF (500 ml) and EDPA (2.65 g, 20.6 mmol) was added drop by drop a solution of Pal-ONSu (7.3 g, 20.6 mmol) in DMF (100 ml). The reaction mixture was stirred for 64 h at room temperature and then concentrated in vacuo to a total volume of 20 ml. The residue was partitioned between 10% aqueous citric acid (300 ml) and ethyl acetate (250 ml), and the phases were separated. The organic phase was concentrated in vacuo and the residue dissolved in DMF (50 ml). The resulting solution was added drop by drop to a 10% aqueous solution of citric acid (500 ml) kept at 0° C. The precipitated compound was collected and washed with iced water and dried in a vacuum drying oven. The dried compound was dissolved in DMF (45 ml) and HONSu (2.15 g, 18.7 mmol) was added. To the resulting mixture was added a solution of N,N'-dicyclohexylcarbodiimide (3.5 g, 17 mmol) in dichloromethane (67 ml). The reaction mixture was stirred for 16 h at room temperature, and the precipitated compound was filtered off. The precipitate was recrystallised from n-heptane/2-propanol to give the title compound (6.6 g, 72%).

Example 36

Synthesis of Lys$^{26,34}$-bis(N$^\epsilon$-(γ-glutamyl(N$^\alpha$-hexadecanoyl)))-GLP-1(7-37)-OH A mixture of GLP-1(7-37)-OH (10 mg, 2.9 µmol), EDPA (10.8 mg, 83.4 µmol), NMP (0.7 ml) and water (0.7 ml) was gently shaken for 5 min. at room temperature. To the resulting mixture was added a solution of N$^\alpha$-hexadecanoyl-Glu (ONSu)-OBu$^t$, prepared as described in Example 33, (163 mg, 319.3 µmol) in NMP (4.08 ml), the reaction mixture was gently shaken 1 h and 20 min. at room temperature. The reaction was quenched by the addition of a solution of glycine (4.9 mg, 65.6 µmol) in 50% aqueous ethanol (492 µl). A 0.5% aqueous solution of ammonium-acetate (9 ml) was added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (10 ml). The eluate was concentrated in vacuo, and the residue purified by column chromatography using a cyanopropyl column (Zorbax 300SB-CN) and a standard acetonitrile/TFA system. The column was heated to 65° C. and the acetonitrile gradient was 0-100% in 60 minutes. The title compound (2.4 mg, 20%) was isolated, and the product was analysed by PDMS. The m/z value for the protonated molecular ion was found to be 4092±3. The resulting molecular weight was thus 4091±3 amu (theoretical value 4091 amu).

Example 37

Synthesis of Arg$^{34}$Lys$^{26}$(N$^\epsilon$-(γ-glutamyl(N$^\alpha$-hexadecanoyl)))-GLP-1(7-37)-OH A mixture of Arg$^{34}$-GLP-1(7-37)-OH (3.7 mg, 1.1 µmol), EDPA (4.0 mg, 30.8 µmol), acetonitrile (260 µl) and water (260 µl) was gently shaken for 5 min. at room temperature. To the resulting mixture was added a solution of N$^\alpha$-hexadecanoyl-Glu(ONSu)-OBu$^t$, prepared as described in Example 35, (1.8 mg, 3.3 µmol) in acetonitrile (44.2 µl), and the reaction mixture was gently shaken for 1 h and 20 min. at room temperature. The reaction was quenched by the addition of a solution of glycine (1.8 mg, 24.2 µmol) in 50% aqueous ethanol (181 µl). A 0.5% aqueous solution of ammonium-acetate (12 ml) and NMP (300 µl) were added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (6 ml). The eluate was allowed to stand for 2 h at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.23 mg, 6%) was isolated, and the product was analysed by PDMS. The m/z value for the protonated molecular ion was found to be 3752±3. The resulting molecular weight was thus 3751±3 amu (theoretical value 3751 amu).

Example 38

Synthesis of Arg$^{26,34}$Lys$^{38}$(N$^\epsilon$-(γ-glutamyl(N$^\alpha$-tetradecanoyl)))-GLP-1(7-38)-OH A mixture of Arg$^{26,34}$Lys$^{38}$-GLP-1(7-38)-OH (14 mg, 4.0 µmol), EDPA (14.3 mg, 110.6 µmol), NMP (980 µl) and water (980 µl) was gently shaken for 5 min. at room temperature. To the resulting mixture was added a solution of N$^\alpha$-tetradecanoyl-Glu(ONSu)-OBu$^t$, prepared as described in Example 29, (12.1 mg, 23.7 µmol) in NMP (303 µl), and the reaction mixture was gently shaken for 2 h at room temperature. The reaction was quenched by the addition of a solution of glycine (6.5 mg, 86.9 mmol) in 50% aqueous ethanol (652 µl). A 0.5% aqueous solution of ammonium-acetate (50 ml) was added, and the resulting mixture eluted onto a Varian 1 g C8 Mega Bond Elut® cartridge, the immobilised compound washed with 5% aqueous acetonitrile (15 ml), and finally liberated from the cartridge by elution with TFA (6 ml). The eluate was allowed to stand for 1 h and 45 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (3.9 mg, 26%) was isolated, and the product was analysed by PDMS. The m/z value for the protonated molecular ion was found to be 3881±3. The resulting molecular weight was thus 3880±3 amu (theoretical value 3880 amu).

Example 39

Synthesis of $Arg^{26,34}Lys^{38}(N^\epsilon$-($\omega$-carboxypentadecanoyl))-GLP-1(7-38)-OH A mixture of $Arg^{26,34}Lys^{38}$-GLP-1(7-38)-OH (14 mg, 4.0 μmol), EDPA (14.3 mg, 111 μmol), NMP (980 μl) and water (980 μl) was gently shaken for 5 min. at room temperature. To the resulting mixture was added a solution of HOOC—$(CH_2)_{14}$—COONSu (4.5 mg, 11.9 μmol) in NMP (114 μl), the reaction mixture was gently shaken for 1 h and 45 min. at room temperature. An additional solution of HOOC—$(CH_2)_{14}$—COONSu (4.0 mg, 10.4 μmol) in NMP (100 μl) was added, and the resulting mixture was gently shaken for an additional 1 h and 30 min. at room temperature. The reaction was quenched by the addition of a solution of glycine (1.5 mg, 19.8 μmol) in 50% aqueous ethanol (148 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (3.9 mg, 26%) was isolated, and the product was analysed by PDMS. The m/z value for the protonated molecular ion was found to be 3809±3. The resulting molecular weight was thus 3808±3 amu (theoretical value 3808 amu).

Example 40

Synthesis of $Arg^{26,34}Lys^{38}(N^\epsilon$-($\gamma$-glutamyl($N^\alpha$-hexadecanoyl)))-GLP-1(7-38)-OH A mixture of $Arg^{26,34}Lys^{38}$-GLP-1(7-38)-OH (14 mg, 4.0 μmol), EDPA (14.3 mg, 110.6 μmol), NMP (980 μl) and water (980 μl) was gently shaken for 5 min. at room temperature. To the resulting mixture was added a solution of $N^\alpha$-hexadecanoyl-Glu(ONSu)-OBu$^t$, prepared as described in Example 35, (6.4 mg, 11.9 μmol) in NMP (160 μl), and the reaction mixture was gently shaken for 1 h and 20 min. at room temperature. The reaction was quenched by the addition of a solution of glycine (6.5 mg, 87 mmol) in 50% aqueous ethanol (653 μl). A 0.5% aqueous solution of ammonium-acetate (50 ml) was added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (6 ml). The eluate was allowed to stand for 1 h and 30 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (7.2 mg, 47%) was isolated, and the product was analysed by PDMS. The m/z value for the protonated molecular ion was found to be 3881±3. The resulting molecular weight was thus 3880±3 amu (theoretical value 3880 amu).

Example 41

Synthesis of $Arg^{18,21,26,30,34}Lys^{38}(N^\epsilon$-hexadecanoyl)-GLP-1(7-38)-OH A mixture of $Arg^{18,23,26,30,34}Lys^{38}$-GLP-1(7-38)-OH (1.0 mg, 0.27 μmol), EDPA (0.34 mg, 2.7 μmol) and DMSO (600 μl) was gently shaken for 5 min. at room temperature. To the resulting mixture was added a solution of Pal-ONSu (0.28 mg, 0.8 μmol) in NMP (7 μl). The reaction mixture was gently shaken for 5 min. at room temperature, and then allowed to stand for an additional 6 h at room temperature. The reaction was quenched by the addition of a solution of glycine (1.6 mg, 21.7 μmol) in 50% aqueous ethanol (163 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (0.17 mg, 16%) was isolated, and the product was analysed by MALDI-MS. The m/z value for the protonated molecular ion was found to be 3961±3. The resulting molecular weight was thus 3960±3 amu (theoretical value 3960 amu).

Example 42

Synthesis of $Arg^{26,34}Lys^{38}(N^\epsilon$-($\omega$-carboxytridecanoyl))-GLP-1(7-38)-OH A mixture of $Arg^{26,34}Lys^{38}$-GLP-1(7-38)-OH (14 mg, 4.0 μmol), EDPA (14.3 mg, 111 μmol), NMP (980 μl) and water (980 μl) was gently shaken for 5 min. at room temperature. To the resulting mixture was added a solution of HOOC—$(CH_2)_{12}$—COONSu (4.2 mg, 11.9 μmol) in NMP (105 μl), the reaction mixture was gently shaken for 1 h and 50 min. at room temperature. The reaction was quenched by the addition of a solution of glycine (6.5 mg, 87 μmol) in 50% aqueous ethanol (652 μl). The reaction mixture was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (5.8 mg, 39%) was isolated, and the product was analysed by MALDI-MS. The m/z value for the protonated molecular ion was found to be 3780±3. The resulting molecular weight was thus 3779±3 amu (theoretical value 3781 amu).

Example 43

Synthesis of $Arg^{34}Lys^{26}(N^\epsilon$-($\gamma$-glutamyl($N^\alpha$-tetradecanoyl)))-GLP-1(7-37)-OH A mixture of $Arg^{34}$-GLP-1(7-37)-OH (15 mg, 4.4 μmol), EDPA (16 mg, 124 μmol), NMP (2 ml) and water (4.8 ml) was gently shaken for 5 min. at room temperature. To the resulting mixture was added a solution of $N^\alpha$-tetradecanoyl-Glu(ONSu)-OBu$^t$, prepared as described in Example 29, (12.1 mg, 23.7 μmol) in NMP (303 μl), and the reaction mixture was gently shaken for 2 h at room temperature. The reaction was quenched by the addition of a solution of glycine (6.5 mg, 86.9 μmol) in 50% aqueous ethanol (652 μl). A 0.5% aqueous solution of ammonium-acetate (50 ml) was added, and the resulting mixture eluted onto a Varian 1 g C8 Mega Bond Elut® cartridge, the immobilised compound washed with 5% aqueous acetonitrile (15 ml), and finally liberated from the cartridge by elution with TFA (6 ml). The eluate was allowed to stand for 1 h and 45 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (3.9 mg, 26%) was isolated, and the product was analysed by MALDI-MS. The m/z value for the protonated molecular ion was found to be 3723±3. The resulting molecular weight was thus 3722±3 amu (theoretical value 3723 amu).

Example 44

Synthesis of $N^\alpha$-octadecanoyl-Glu(ONSu)-OBu$^t$

To a suspension of H-Glu(OH)—OBu$^t$ (2.82 g, 13.9 mmol), DMF (370 ml) and EDPA (1.79 g, 13.9 mmol) was added drop by drop a solution of Ste-ONSu (5.3 g, 13.9 mmol) in DMF (60 ml). Dichloromethane (35 ml) was added, and the reaction mixture was stirred for 24 h at room temperature and then concentrated in vacuo. The residue was partitioned between 10% aqueous citric acid (330 ml) and ethyl acetate (200 ml), and the phases were separated. The organic phase was concentrated in vacuo and the residue dissolved in DMF (60 ml). The resulting solution was added drop by drop to a 10% aqueous solution of citric acid (400 ml) kept at 0° C. The precipitated compound was collected and washed with iced water and dried in a vacuum drying oven. The dried compound was dissolved in DMF (40 ml) and HONSu (1.63 g, 14.2 mmol) was added. To the resulting mixture was added a solution of DCC (2.66 g, 12.9 mmol) in dichloromethane (51 ml). The reaction mixture was stirred for 64 h at room temperature, and the precipitated compound was filtered off. The precipitate was recrystallised from n-heptane/2-propanol to give the title compound (4.96 g, 68%).

Example 45

Synthesis of Arg$^{26,34}$Lys$^{38}$($N^\epsilon$-($\gamma$-glutamyl($N^\alpha$-octadecanoyl)))-GLP-1(7-38)-OH A mixture of Arg$^{26,34}$-GLP-1(7-38)-OH (28 mg, 7.9 μmol), EDPA (28.6 mg, 221.5 μmol), NMP (1.96 ml) and water (1.96 ml) was gently shaken for 5 min. at room temperature. To the resulting mixture was added a solution of $N^{\alpha HH}$-octadecanoyl-Glu(ONSu)-OBu$^t$ (17.93 g, 31.6 μmol), prepared as described in Example 44, in NMP (448 μl), and the reaction mixture was gently shaken for 2 h at room temperature. The reaction was quenched by the addition of a solution of glycine (13.1 mg, 174 μmol) in 50% aqueous ethanol (1.3 ml). A 0.5% aqueous solution of ammonium-acetate (120 ml) was added, and the resulting mixture was divided into two equal portions. Each portion was eluted onto a Varian 5 g C8 Mega Bond Elut® cartridge, the immobilised compound washed with 5% aqueous acetonitrile (25 ml), and finally liberated from the cartridge by elution TFA (25 ml). The combined eluates were allowed to stand for 1 h and 25 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0-100% in 60 minutes. The title compound (3.6 mg, 11%) was isolated, and the product was analysed by MALDI-MS. The m/z value for the protonated molecular ion was found to be 3940±3. The resulting molecular weight was thus 3939±3 amu (theoretical value 3937 amu).

Biological Findings

Protraction of GLP-1 Derivatives after s.c. Administration

The protraction of a number GLP-1 derivatives of the invention was determined by monitoring the concentration thereof in plasma after sc administration to healthy pigs, using the method described below. For comparison also the concentration in plasma of GLP-1(7-37) after sc. administration was followed. The results are given in Table 1. The protraction of other GLP-1 derivatives of the invention can be determined in the same way.

Pigs (50% Duroc, 25% Yorkshire, 25% Danish Landrace, app 40 kg) were fasted from the beginning of the experiment. To each pig 0.5 nmol of test compound per kg body weight was administered in a 50 μM isotonic solution (5 mM phosphate, pH 7.4, 0.02% Tween®-20 (Merck), 45 mg/ml mannitol (pyrogen free, Novo Nordisk). Blood samples were drawn from a catheter in vena jugularis at the hours indicated in Table 1. 5 ml of the blood samples were poured into chilled glasses containing 175 μl of the following solution: 0.18 M EDTA, 1500 KIE/ml aprotinin (Novo Nordisk) and 3% bacitracin (Sigma), pH 7.4. Within 30 min, the samples were centrifuged for 10 min at 5-6000*g. Temperature was kept at 4° C. The supernatant was pipetted into different glasses and kept at minus 20° C. until use.

The plasma concentrations of the peptides were determined by RIA using a monoclonal antibody specific for the N-terminal region of GLP-1(7-37). The cross reactivities were less than 1% with GLP-1(1-37) and GLP-1(8-36)amide and <0.1% with GLP-1(9-37), GLP-1(10-36)amide and GLP-1(11-36)amide. The entire procedure was carried out at 4° C.

The assay was carried out as follows: 100 μl plasma was mixed with 271 μl 96% ethanol, mixed using a vortex mixer and centrifuged at 2600*g for 30 min. The supernatant was decanted into Minisorp tubes and evaporated completely (Savant Speedvac AS290). The evaporation residue was reconstituted in the assay buffer consisting of 80 mM NaH$_2$PO$_4$Na$_2$HPO$_4$, 0.1% HSA (Orpha 20/21, Behring), 10 mM EDTA, 0.6 mM thiomersal (Sigma), pH 7.5. Samples were reconstituted in volumes suitable for their expected concentrations, and were allowed to reconstitute for 30 min. To 300 μl sample, 100 μl antibody solution in dilution buffer containing 40 mM NaH$_2$PO$_4$/Na$_2$HPO$_4$, 0.1% HSA, 0.6 mM thiomersal, pH 7.5, was added. A non-specific sample was prepared by mixing 300 μl buffer with 100 μl dilution buffer. Individual standards were prepared from freeze dried stocks, dissolved in 300 μl assay buffer. All samples were pre-incubated in Minisorp tubes with antibody as described above for 72 h. 200 μl tracer in dilution buffer containing 6-7000 CPM was added, samples were mixed and incubated for 48 h. 1.5 ml of a suspension of 200 ml per liter of heparin-stabilised bovine plasma and 18 g per liter of activated carbon (Merck) in 40 mM NaH$_2$PO$_4$/Na$_2$HPO$_4$, 0.6 mM thiomersal, pH 7.5, was added to each tube. Before use, the suspension was mixed and allowed to stand for 2 h at 4° C. All samples were incubated for 1 h at 4° C. and then centrifuged at 3400*g for 25 min. Immediately after the centrifugation, the supernatant was decanted and counted in a γ-counter. The concentration in the samples was calculated from individual standard curves. The following plasma concentrations were found, calculated as % of the maximum concentration for the individual compounds (n=2):

TABLE 1

| Test compound*) | Hours after sc. Administration | | | | | | | | |
|---|---|---|---|---|---|---|---|---|---|
| | 0.75 | 1 | 2 | 4 | 6 | 8 | 10 | 12 | 24 |
| GLP-1(7-37) | | 100 | 9 | 1 | | | | | |
| Example 25 | 73 | 92 | 100 | 98 | 82 | 24 | 16 | 16 | 16 |
| Example 17 | 76 | 71 | 91 | 100 | 84 | 68 | 30 | | 9 |
| Example 43 | | 39 | 71 | 93 | 100 | 91 | 59 | 50 | 17 |
| Example 37 | | 26 | 38 | 97 | 100 | 71 | 81 | 80 | 45 |
| Example 11 | 24 | 47 | 59 | 71 | 100 | 94 | 100 | | 94 |
| Example 12 | 36 | 54 | 65 | 94 | 80 | 100 | 85 | | 93 |
| Example 32 | 55 | 53 | 90 | 83 | 88 | 70 | 98 | 100 | 100 |
| Example 14 | 18 | 25 | 32 | 47 | 98 | 83 | 97 | | 100 |
| Example 13 | 15 | 22 | 38 | 59 | 97 | 85 | 100 | | 76 |
| Example 38 | 60 | 53 | 100 | 66 | 48 | 39 | 25 | 29 | 0 |
| Example 39 | 38 | 100 | 70 | 47 | 33 | 33 | 18 | 27 | 14 |
| Example 40 | 47 | 19 | 50 | 100 | 51 | 56 | 34 | 14 | 0 |
| Example 34 | 19 | 32 | 44 | 84 | 59 | 66 | 83 | 84 | 100 |

*)The test compounds are the title compounds of the examples with the numbers given Table 1 shows that the GLP-1 derivatives of the invention have a protracted profile of action relative to GLP-1(7-37) and are much more persistent in plasma than GLP-1(7-37). It also appears from Table 1 that the time at which the peak concentration in plasma is achieved varies within wide limits, depending on the particular GLP-1 derivative selected.

Stimulation of cAMP Formation in a Cell Line Expressing the Cloned Human GLP-1 Receptor In order to demonstrate efficacy of the GLP-1 derivatives, their ability to stimulate formation of cAMP in a cell line expressing the cloned human GLP-1 receptor was tested. An $EC_{50}$ was calculated from the dose-response curve.

Baby hamster kidney (BHK) cells expressing the human pancreatic GLP-1 receptor were used (Knudsen and Pridal, 1996, Eur. J. Pharm. 318, 429-435). Plasma membranes were prepared (Adelhorst et al, 1994, J. Biol. Chem. 269, 6275) by homogenisation in buffer (10 mmol/l Tris-HCl and 30 mmol/l NaCl pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk A/S, Bagsvaerd, Denmark)). The homogenate was centrifuged on top of a layer of 41 w/v % sucrose. The white band between the two layers was diluted in buffer and centrifuged. Plasma membranes were stored at −80° C. until used.

The assay was carried out in 96-well microtiter plates in a total volume of 140 µl. The buffer used was 50 mmol/l Tris-HCl, pH 7.4 with the addition of 1 mmol/l EGTA, 1.5 mmol/l $MgSO_4$, 1.7 mmol/l ATP, 20 mM GTP, 2 mmol/l 3-isobutyl-1-methylxanthine, 0.01% Tween-20 and 0.1% human serum albumin (Reinst, Behringwerke AG, Marburg, Germany). Compounds to be tested for agonist activity were dissolved and diluted in buffer, added to the membrane preparation and the mixture was incubated for 2 h at 37° C. The reaction was stopped by the addition of 25 µl of 0.05 mol/l HCl. Samples were diluted 10 fold before analysis for cAMP by a scintillation proximity assay (RPA 538, Amersham, UK). The following results were obtained:

| Test Compound*) | $EC_{50}$, pM | Test Compound*) | $EC_{50}$, pM |
|---|---|---|---|
| GLP-1(7-37) | 61 | Example 31 | 96 |
| Example 45 | 120 | Example 30 | 41 |
| Example 43 | 24 | Example 26 | 8.8 |
| Example 40 | 55 | Example 25 | 99 |
| Example 39 | 5.1 | Example 19 | 79 |
| Example 38 | 54 | Example 16 | 3.5 |
| Example 37 | 60 | | |

*)The test compounds are the title compounds of the examples with the numbers given.

Example 46

Synthesis of $Arg^{26,34}$, $Lys^{36}(N^{\epsilon}\text{-}(\gamma\text{-glutamyl}(N^{\alpha}\text{-hexadecanoyl})))$ GLP-1(7-36)-OH To a mixture of $Arg^{26,34}$, $Lys^{36}$GLP-1(7-36)-OH (12.2 mg, 3.67 µmol), EDPA (13.3 mg, 103 µmol), NMP (1.71 ml) and water (855 µl) was added a solution of Pal-Glu(ONSu)-OBu$^t$ (5.94 mg, 11 µmol), prepared as described in PCT application no. PCT/DK97/00340, in NMP (148 µl). The reaction mixture was gently shaken for 5 min. at room temperature, and then allowed to stand for an additional 90 min. at room temperature. The reaction was quenched by the addition of a solution of glycine (6 mg, 81 µmol) in water (0.6 ml). A 0.5% aqueous solution of ammonium-acetate (38 ml) was added, and the resulting mixture eluted onto a Varian 5 g C8 Mega Bond Elut®, the immobilised compound washed with 5% aqueous acetonitrile (20 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (3.1 mg, 23%) was isolated, and the product was analysed by PDMS. The m/z value for the protonated molecular ion was found to be 3695±3. The resulting molecular weight was thus 3694±3 amu (theoretical value 3694 amu).

Example 47

Synthesis of $Arg^{26,34}$,$Lys^{36}(N^{\epsilon}\text{-}(\gamma\text{-glutamyl}(N^{\alpha}\text{-octadecanoyl})))$ GLP-1(7-36)-OH To a mixture of $Arg^{26,34}$,$Lys^{36}$GLP-1(7-36)-OH (12.2 mg, 3.7 µmol), EDPA (13.3 mg, 103 µmol), NMP (1.71 ml) and water (855 µl) was added a solution of Ste-Glu(ONSu)-OBu$^t$ (6.25 mg, 11 µmol), prepared as described in PCT application no. PCT/DK97/00340, in NMP (1 ml). The reaction mixture was gently shaken for 5 min. at room temperature, and then allowed to stand for an additional 90 min. at room temperature. The reaction was quenched by the addition of a solution of glycine (6 mg, 81 µmol) in water (0.6 ml). A 0.5% aqueous solution of ammonium acetate (54 ml) was added, and the resulting mixture eluted onto a Varian 5 g C8 Mega Bond Elut®, the immobilised compound washed with 5% aqueous acetonitril (20 ml), and finally liberated from the cartridge by elution with TFA (25 ml). The eluate was concentrated in vacuo, and the residue purified by column chromatography using a cyanopropyl column (Zorbax 300SB-CN) and a standard acetonitril TFA system. The column was heated to 65° C. and the acetonitril gradient was 0-100% in 60 minutes. The title compound (3.7 mg, 27%) was isolated, and the product was analysed by PDMS. The m/z value for the protonated molecular ion was found to be 3723±3. The resulting molecular weight was thus 3722±3 amu (theoretical value 3722 amu).

Example 48

Synthesis of Lithocholic Acid 2,5-dioxopyrrolidin-1-yl Ester

To a solution of lithocholic acid (5.44 g, 14.3 mmol) in a mixture of anhydrous THF (120 ml) and anhydrous acetonitril (30 ml) was added N-hydroxysuccinimide (1.78 g, 15 mmol). The mixture was cooled to 10° C., a solution of DCC (3.44 g, 16.7 mmol) in anhydrous THF (30 ml) was added drop wise, and the resulting reaction mixture stirred for 16 h at room temperature. The reaction mixture was filtered and partitioned between dichloromethane (450 ml) and 10% aqueous $Na_2CO_3$ (150 ml). The phases were separated, and the organic phase washed with 10% aqueous $Na_2CO_3$ (150 ml), water (2×150 ml), and dried ($MgSO_4$). The solvent was concentrated in vacuo. The residue was crystallised from a mixture of dichloromethane (30 ml) and n-heptane (30 ml). The precipitate was dried in a vacuum drying oven for 36 h to give the title compound (3.46 g, 51%).

Example 49

Synthesis of Lit-Glu(ONSu)-OBu$^t$

A suspension of H-Glu(OH)—OBu$^t$ (1.28 g, 6.33 mmol), DMF (88 ml) and EDPA (0.82 g, 6.33 mmol) and lithocholic acid 2,5-dioxopyrrolidin-1-yl ester, prepared as described in example 48, was stirred for 16 h at room temperature. The reaction mixture was concentrated in vacuo and the residue dissolved in ethyl acetate (40 ml). The resulting solution was washed with 5% aqueous citric acid (2×25 ml), brine (10 ml), and filtered). The solvent was concentrated in vacuo and the residue dissolved in DMF (12 ml). The resulting solution was added drop wise to a 10% aqueous solution of citric acid whereby the product precipitates. The precipitate was collected and washed with iced water, and dried in vacuo. The crude product was recrystallised from a mixture of n-heptane (40 ml) and 2-propanol (17 ml). The precipitate was dried in a vacuum drying oven for 4 h to give the free acid intermediate.

To a solution of the free acid intermediate in DMF (18 ml) was added hydroxysuccinimide (0.45 g, 3.91 mmol), followed by a solution of DCC (0.73 g, 3.56 mmol) in dichloromethane (18 ml). The resulting mixture was stirred at ambient temperature for 18 h, and then filtered. The filtrate was concentrated in vacuo to a solid, and the residue was dissolved in dichloromethane (25 ml), and the filtration repeated, the solvent removed in vacuo to give a foam. The residue was dissolved in refluxing n-heptane (35 ml), and the product crystallised b addition of 2-propanol. The precipitate was collected, washed with cold n-heptane, dried at 35° C. in vacuo to give the title compound (1.34 g, 57%).

Example 50

Synthesis of $Arg^{34}Lys^{26}(N^\epsilon$-(γ-glutamyl($N^\alpha$-lithocholyl))) GLP-1(7-37)-OH To a mixture of $Arg^{34},Lys^{26}$GLP-1(7-37)-OH (41.1 mg, 12.2 µmol), EDPA (44 mg, 340 µmol), NMP (5.76 ml) and water (2.88 ml) was added a solution of Lit-Glu(ONSu)-OBu$^t$ (24 mg, 37 µmol), prepared as described in example 49, in NMP (600 µl). The reaction mixture was gently shaken for 5 min. at room temperature, and then allowed to stand for an additional 75 min. at room temperature. The reaction was quenched by the addition of a solution of glycine (20 mg, 268 µmol) in water (2 ml). A 0.5% aqueous solution of ammonium acetate (128 ml) was added, and the resulting mixture divided into two equal portions, and each portion eluted onto a Varian 5 g C8 Mega Bond Elut®, the immobilised compound washed with 5% aqueous acetonitril (2×25 ml), and finally liberated from the cartridge by elution with TFA (2×25 ml). The combined eluates were concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (5 mg, 11%) was isolated, and the product was analysed by PDMS. The m/z value for the protonated molecular ion was found to be 3872±3. The resulting molecular weight was thus 3871±3 amu (theoretical value 3871 amu).

Example 51

Synthesis of $Arg^{26},Lys^{34}(N^\epsilon$-(γ-glutamyl($N^\alpha$-hexadecanoyl))) GLP-1(7-37)-OH To a mixture of $Arg^{26},Lys^{34}$GLP-1(7-37)-OH (18 mg, 5.3 µmol), EDPA (19.3 mg, 149 µmol), NMP (2.52 ml) and water (1.26 ml) was added a solution of Pal-Glu(ONSu)-OBu$^t$ (8.6 mg, 16 µmol) in NMP (215 µl). The reaction mixture was gently shaken for 5 min. at room temperature, and then allowed to stand for an additional 90 min. at room temperature. The reaction was quenched by the addition of a solution of glycine (8.8 mg, 117 µmol) in water (0.88 ml). A 0.5% aqueous solution of ammonium acetate (50 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (6 mg, 30%) was isolated, and the product was analysed by PDMS. The m/z value for the protonated molecular ion was found to be 3752±3. The resulting molecular weight was thus 3751±3 amu (theoretical value 3751 amu).

Example 52

Synthesis of desamino-$His^7,Arg^{26},Lys^{34}(N^\epsilon$-(γ-glutamyl($N^\alpha$-hexadecanoyl))) GLP-1(7-37)-OH To a mixture of desamino-$His^7,Arg^{26},Lys^{34}$GLP-1(7-37)-OH (14.3 mg, 4.2 µmol), EDPA (15.3 mg, 119 µmol), NMP (2 ml) and water (1 ml) was added a solution of Pal-Glu(ONSu)-OBu$^t$ (6.84 mg, 12.7 µmol) in NMP (171 µl). The reaction mixture was gently shaken for 5 min. at room temperature, and then allowed to stand for an additional 50 min. at room temperature. The reaction was quenched by the addition of a solution of glycine (7 mg, 99 µmol) in water (700 µl). A 0.5% aqueous solution of ammonium acetate (42 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (5.6 mg, 35%) was isolated, and the product was analysed by PDMS. The m/z value for the protonated molecular ion was found to be 3738±3. The resulting molecular weight was thus 3737±3 amu (theoretical value 3737 amu).

Example 53

Synthesis of Gly$^8$,Arg$^{26,34}$Lys$^{38}$(N$^\epsilon$-(γ-glutamyl(N$^\alpha$-hexadecanoyl))) GLP-1(7-38)-OH To a mixture of Gly$^8$,Arg$^{26,34}$,Lys$^{38}$GLP-1(7-38)-OH (11.8 mg, 3.4 µmol), EDPA (12.1 mg, 94 µmol), NMP (1.65 ml) and water (0.83 ml) was added a solution of Pal-Glu(ONSu)-OBu$^t$ (5.4 mg, 10 µmol) in NMP (135 µl). The reaction mixture was gently shaken for 5 min. at room temperature, and then allowed to stand for an additional 75 min. at room temperature. The reaction was quenched by the addition of a solution of glycine (5.5 mg, 73.7 µmol) in water (553 µl). A 0.5% aqueous solution of ammonium acetate (36 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (5 mg, 38%) was isolated, and the product was analysed by PDMS. The m/z value for the protonated molecular ion was found to be 3895±3. The resulting molecular weight was thus 3894±3 amu (theoretical value 3894 amu).

Example 54

Synthesis of Gly$^8$,Glu$^{37}$,Arg$^{26,34}$,Lys$^{38}$(N$^\epsilon$-(γ-glutamyl(N$^\alpha$-hexadecanoyl))) GLP-1(7-38)-OH To a mixture of Gly$^8$,Glu$^{37}$Arg$^{26,34}$,Lys$^{38}$GLP-1(7-38)-OH (9 mg, 2.48 µmol), EDPA (9 mg, 69.4 µmol), NMP (1.25 ml) and water (0.63 ml) was added a solution of Pal-Glu(ONSu)-OBu$^t$ (4 mg, 7.4 µmol) in NMP (100 µl). The reaction mixture was gently shaken for 5 min. at room temperature, and then allowed to stand for an additional 105 min. at room temperature. The reaction was quenched by the addition of a solution of glycine (4.1 mg, 54.6 µmol) in water (410 µl). A 0.5% aqueous solution of ammonium acetate (27 ml) was added, and the resulting mixture eluted onto a Varian 5 g C8 Mega Bond Elut®, the immobilised compound washed with 5% aqueous acetonitril (15 ml), and finally liberated from the cartridge by elution with TFA (15 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (2.9 mg, 29%) was isolated, and the product was analysed by PDMS. The m/z value for the protonated molecular ion was found to be 3967±3. The resulting molecular weight was thus 3966±3 amu (theoretical value 3967 amu).

Example 55

Synthesis of Gly$^8$,Glu$^{37}$,Arg$^{26,34}$Lys$^{38}$(N$^\epsilon$-(γ-glutamyl(N$^\alpha$-octadecanoyl))) GLP-1(7-38)-OH To a mixture of Gly$^8$,Glu$^{37}$Arg$^{26,34}$Lys$^3$GLP-1(7-38)-OH (9 mg, 2.5 µmol), EDPA (9 mg, 69.4 µmol), NMP (1.25 ml) and water (0.63 ml) was added a solution of Ste-Glu(ONSu)-OBu$^t$ (4.2 mg, 7.4 µmol in NMP (105 µl). The reaction mixture was gently shaken for 5 min. at room temperature, and then allowed to stand for an additional 105 min. at room temperature. The reaction was quenched by the addition of a solution of glycine (4.1 mg, 54.6 µmol) in water (409 µl). A 0.5% aqueous solution of ammonium acetate (27 ml) was added, and the resulting mixture eluted onto a Varian 5 g C8 Mega Bond Elut®, the immobilised compound washed with 5% aqueous acetonitril (15 ml), and finally liberated from the cartridge by elution with TFA (15 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (3.2 mg, 32%) was isolated, and the product was analysed by PDMS. The m/z value for the protonated molecular ion was found to be 3995±3. The resulting molecular weight was thus 3994±3 amu (theoretical value 3995 amu).

Example 56

Synthesis of Cap-Glu(ONSu)-OBu$^t$

To a solution of octanoic acid (5 g, 34.7 mmol) and N-hydroxysuccinimide (4 g, 34.7 mmol) in anhydrous acetonitril (10 ml) was added a solution of DCC (7.15 g, 34.7 mmol) in anhydrous dichloromethane (15 ml), and the resulting reaction mixture stirred for 16 h at room temperature. The precipitated solid was filtered off and recrystallised from a mixture of n-heptane (40 ml) and 2-propanol (2 ml). The precipitate was dried in a vacuum drying oven for 16 h to give the intermediate Cap-ONSu. A suspension of the crude ester intermediate (3.9 g, 16.2 mmol), (L)-H-Glu(OH)—OBu$^t$ (3.28 g, 16.2 mmol), DMF (268 ml) and EDPA (2.1 g, 16.2 mmol) was stirred for 64 h at room temperature. The reaction mixture was concentrated in vacuo and the residue dissolved in ethyl acetate (50 ml). The resulting solution was washed with 5% aqueous citric acid (2×25 ml). The solvent was concentrated in vacuo and the residue dissolved in DMF (36 ml). The resulting solution was added drop wise to a 10% aqueous solution of citric acid (357 ml) and extracted with ethyl acetate (200 ml), and dried (MgSO$_4$). The solvent was concentrated in vacuo to give the crude glutamic acid intermediate. To a mixture of the crude glutamic acid intermediate, N-hydroxysuccinimide (1.85 g, 16.1 mmol) and DMF (25 ml) was added a solution of DCC (3.32 g, 16.1 mmol) in dichloromethane (15 ml). The resulting mixture was stirred at ambient temperature for 20 h. The reaction mixture was filtered and the solvent concentrated in vacuo. The residue was purified on a silica gel column (40-63μ), eluted with a mixture of dichloromethane and acetonitril (1:1) to give the title compound (0.63 g, 6% over all).

Example 57

Synthesis of desamino-His$^7$,Arg$^{26}$,Lys$^{34}$(N$^\epsilon$-(γ-glutamyl(N$^\alpha$-octanoyl))) GLP-1(7-37)-OH To a mixture of desamino-His$^7$,Arg$^{26}$,Lys$^{34}$GLP-1(7-37)-OH (14.3 mg, 4.2 μmol), EDPA (15.3 mg, 119 μmol), NMP (2 ml) and water (1 ml) was added a solution of Cap-Glu (ONSu)-OBu$^t$ (6.8 mg, 12.7 μmol), prepared as described in example 56, in NMP (135 μl). The reaction mixture was gently shaken for 5 min. at room temperature, and then allowed to stand for an additional 2 h at room temperature. The reaction was quenched by the addition of a solution of glycine (7 mg, 93 μmol) in water (698 μl). A 0.5% aqueous solution of ammonium acetate (42 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (4.1 mg, 27%) was isolated, and the product was analysed by PDMS. The m/z value for the protonated molecular ion was found to be 3626±3. The resulting molecular weight was thus 3625±3 amu (theoretical value 3625 amu).

Example 58

Synthesis of Glu$^{37}$,Arg$^{26,34}$,Lys$^{38}$(N$^\epsilon$-(γ-glutamyl (N$^\alpha$-hexadecanoyl))) GLP-1(7-38)-OH To a mixture of Glu$^{37}$,Arg$^{26,34}$Lys$^{38}$GLP-1(7-38)-OH (17.6 mg, 4.9 μmol), EDPA (17.6 mg, 136 μmol), NMP (1.23 ml) and water (2.46 ml) was added a solution of Pal-Glu (ONSu)-OBu$^t$ (7.9 mg, 14.6 μmol) in NMP (197 μl). The reaction mixture was gently shaken for 5 min. at room temperature, and then allowed to stand for an additional 2 h at room temperature. The reaction was quenched by the addition of a solution of glycine (8 mg, 107 μmol) in water (804 μl). A 0.5% aqueous solution of ammonium acetate (49 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (5.1 mg, 26%) was isolated, and the product was analysed by PDMS. The m/z value for the protonated molecular ion was found to be 3981±3. The resulting molecular weight was thus 3980±3 amu (theoretical value 3981 amu).

Example 59

Synthesis of Arg$^{34}$,Lys$^{26}$(N$^\epsilon$-(γ-glutamyl(N$^\alpha$-octadecanoyl))) GLP-1(7-37)-OH To a mixture of Arg$^{34}$GLP-1(7-37)-OH (41.1 mg, 12.2 μmol), EDPA (44 mg, 341 μmol), NMP (5.76 ml) and water (2.88 ml) was added a solution of Ste-Glu(ONSu)-OBu$^t$ (20.7 mg, 36.5 μmol in NMP (517 μl). The reaction mixture was gently shaken for 5 min. at room temperature, and then allowed to stand for an additional 2 h at room temperature. The reaction was quenched by the addition of a solution of glycine (20.1 mg, 268 μmol) in water (2.01 ml). A 0.5% aqueous solution of ammonium-acetate (120 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (15.4 mg, 34%) was isolated, and the product was analysed by PDMS. The m/z value for the protonated molecular ion was found to be 3781±3. The resulting molecular weight was thus 3780±3 amu (theoretical value 3779 amu).

Example 60

Synthesis of Arg$^{34}$,Lys$^{26}$(N$^\epsilon$-decanoyl) GLP-1(7-37)

To a mixture of Arg$^{34}$GLP-1(7-37)-OH (20 mg, 5.9 μmol), EDPA (21.4 mg, 165 μmol), NMP (2.8 ml) and water (1.4 ml) was added a solution of Cac-ONSu (4.8 mg, 17.7 μmol) in NMP (119 μl). The reaction mixture was gently shaken for 5 min., and then allowed to stand for an additional 2 h at room temperature. The reaction was quenched by the addition of a solution of glycine (9.8 mg, 130 μmol) in water (98 μl). The resulting mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (7.4 mg, 35%) was isolated, and the product was analysed by PDMS. The m/z value for the protonated molecular ion was found to be 3539.6±3. The resulting molecular weight was thus 3538.6±3 amu (theoretical value 3538 amu).

Example 61

Synthesis of Arg$^{34}$,Lys$^{26}$(N$^\epsilon$-(hexadecanoyl)) GLP-1 (7-37)-OH

To a mixture of Arg$^{34}$GLP-1(7-37)-OH (41.1 mg, 12.2 μmol), EDPA (44 mg, 340 μmol), NMP (2.88 ml) and water (2.88 ml) was added a solution of Pal-ONSu (12.9 mg, 36.5 μmol) in NMP (3.3 ml). The reaction mixture was gently shaken for 5 min. at room temperature, and then allowed to stand for an additional 110 min. at room temperature. The reaction was quenched by the addition of a solution of glycine (20.1 mg, 268 μmol) in water (201 μl). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (15 mg, 34%) was isolated, and the product was analysed by PDMS.

Example 62

Synthesis of Arg$^{26,34}$,Lys$^{27}$(N$^\epsilon$-(γ-glutamyl(N$^\alpha$-hexadecanoyl))) GLP-1 (7-37)-OH To a mixture of Arg$^{26,34}$,Lys$^{27}$GLP-1(7-37)-OH (11.6 mg, 3.4 μmol), EDPA (12.3 mg, 94.9 μmol), NMP (1.6 ml) and water (0.8 ml) was added a solution of Pal-Glu(ONSu)-OBu$^t$ (5.5 mg, 10.2 µmol) in NMP (137 µl). The reaction mixture was gently shaken for 5 min. at room temperature, and then allowed to stand for an additional 90 min. at room temperature. The reaction was quenched by the addition of a solution of glycine (5.6 mg, 74.6 µmol) in water (560 µl). A 0.5% aqueous solution of ammonium acetate (34 ml) was added, and the resulting mixture eluted onto a Varian 5 g C8 Mega Bond Elut®, the immobilised compound washed with 5% aqueous acetonitril (15 ml), and finally liberated from the cartridge by elution with TFA (25 ml). The solvent was concentrated in vacuo, and the residue purified by column chromatography using a cyanopropyl column (Zorbax 300SB-CN) and a standard acetonitril TFA system. The column was heated to 65° C. and the acetonitril gradient was 0-100% in 60 minutes. The title compound (2.1 mg, 16%) was isolated, and the product was analysed by PDMS.

Example 63

Synthesis of Arg$^{26,34}$,Lys$^{23}$(N$^\epsilon$-(γ-glutamyl(N$^\alpha$-hexadecanoyl))) GLP-1(7-37)-OH To a mixture of Arg$^{26,34}$,Lys$^{23}$GLP-1(7-37)-OH (11.6 mg, 3.4 µmol), EDPA (12.3 mg, 94.9 µmol), NMP (1.6 ml) and water (0.8 ml) was added a solution of Pal-Glu(ONSu)-OBu$^t$ (5.5 mg, 10.2 µmol) in NMP (137 µl). The reaction mixture was gently shaken for 5 min. at room temperature, and then allowed to stand for an additional 90 min. at room temperature. The reaction was quenched by the addition of a solution of glycine (5.6 mg, 74.6 µmol) in water (560 µl). A 0.5% aqueous solution of ammonium acetate (34 ml) was added, and the resulting mixture eluted onto a Varian 5 g C8 Mega Bond Elut®, the immobilised compound washed with 5% aqueous acetonitril (15 ml), and finally liberated from the cartridge by elution with TFA (25 ml). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (3.1 mg, 24%) was isolated, and the product was analysed by PDMS.

Example 64

Synthesis of Arg$^{26,34}$,Lys$^{18}$(N$^\epsilon$-(γ-glutamyl(N$^\alpha$-hexadecanoyl))) GLP-1(7-37)-OH To a mixture of Arg$^{26,34}$, Lys$^{18}$GLP-1(7-37)-OH (11.7 mg, 3.4 µmol), EDPA (12.2 mg, 94.6 µmol), NMP (1.6 ml) and water (0.8 ml) was added a solution of Pal-Glu(ONSu)-OBu$^t$ (5.5 mg, 10.2 µmol) in NMP (137 µl). The reaction mixture was gently shaken for 5 min. at room temperature, and then allowed to stand for an additional 90 min. at room temperature. The reaction was quenched by the addition of a solution of glycine (5.6 mg, 74.6 µmol) in water (560 µl). A 0.5% aqueous solution of ammonium acetate (34 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (1.9 mg, 15%) was isolated, and the product was analysed by PDMS.

Example 65

Synthesis of Arg$^{34}$,Lys$^{26}$(N$^\epsilon$-(octanoyl)) GLP-1(7-37)-OH

To a mixture of Arg$^{34}$GLP-1(7-37)-OH (41.1 mg, 12.2 µmol), EDPA (44 mg, 341 µmol), NMP (5.76 ml) and water (2.88 ml) was added a solution of Cap-ONSu (8.8 mg, 36.5 µmol), prepared as described in example 56, in NMP (106 µl). The reaction mixture was gently shaken for 5 min. at room temperature, and then allowed to stand for an additional 115 min. at room temperature. The reaction was quenched by the addition of a solution of glycine (20 mg, 268 µmol) in water (200 µl). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (18.8 mg, 44%) was isolated, and the product was analysed by PDMS.

Example 66

Synthesis of Arg$^{34}$,Lys$^{26}$(N$^\epsilon$-(dodecanoyl)) GLP-1(7-37)-OH

To a mixture of Arg$^{34}$GLP-1(7-37)-OH (41.1 mg, 12.2 µmol), EDPA (44 mg, 341 µmol), NMP (5.76 ml) and water (2.88 ml) was added a solution of Lau-ONSu (8.8 mg, 36.5 µmol), prepared in a similar manner as described for Cap-ONSu in example 56), in NMP (271 µl). The reaction mixture was gently shaken for 5 min. at room temperature, and then allowed to stand for an additional 100 min. at room temperature. The reaction was quenched by the addition of a solution of glycine (20.1 mg, 268 µmol) in water (200 µl). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (18 mg, 42%) was isolated, and the product was analysed by PDMS.

Example 67

Synthesis of Pal-GABA-ONSu

A mixture of Pal-ONSu (3 g, 8.48 mmol), γ-aminobutyric acid (0.87 g, 8.48 mmol) in DMF (200 ml) was stirred at room temperature for 60 h. The reaction mixture was filtered and the filtrate was added drop wise to 10% aqueous citric acid (500 ml). The precipitated N-acylated intermediate was collected and dried in vacuo. To a suspension of the dried intermediate in DMF (35 ml) was added a solution of DCC (1.45 g, 7.0 mmol) in dichloromethane (20 ml). The resulting mixture was stirred at room temperature for 20 h, and then filtered. The solvent was removed in vacuo to give a solid residue. The residue was recrystallised from a mixture of n-heptane (50 ml) and 2-propanol (2.5 ml) to give the title compound (2.5 g, 75%).

Example 68

Synthesis of Arg$^{34}$,Lys$^{26}$(N$^\epsilon$-(γ-aminobutyroyl(N$^\gamma$-hexadecanoyl))) GLP-1(7-37)-OH To a mixture of Arg$^{34}$,Lys$^{26}$GLP-1(7-37)-OH (41.1 mg, 12.2 µmol), EDPA (44 mg, 341 µmol), NMP (5.76 ml) and water (2.88 ml) was added a solution of Pal-GABA-ONSu (16 mg, 36.5 μmol), prepared as described in example 67) in NMP (400 μl). The reaction mixture was gently shaken for 5 min. at room temperature, and then allowed to stand for an additional 100 min. at room temperature. The reaction was quenched by the addition of a solution of glycine (20 mg, 268 μmol) in water (200 μl). The solvent was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (15.8 mg, 35%) was isolated, and the product was analysed by PDMS.

Example 69

Synthesis of $N^\alpha$-hexadecanoyl-D-glutamic Acid α-t-butyl ester-γ-2,5-dioxopyrrolidin-1-yl ester A mixture of Pal-ONSu (6.64 g, 18.8 mmol), D-glutamic acid α-tert-butyl ester (4.5 g, 18.8 mmol) and EDPA (4.85 g, 37.5 mmol) in DMF (538 ml) was stirred at room temperature for 60 h. The solvent was removed and the residue dissolved in ethyl acetate (175 ml). The resulting solution was extracted with 10% aqueous citric acid (2×125 ml), and the organic phase concentrated in vacuo. The residue was dissolved in DMF (60 ml), and the resulting mixture slowly added to 10% aqueous citric acid (500 ml). The precipitated compound was collected and dried in vacuo, to give the crude N-acylated glutamic acid intermediate. The crude intermediate was dissolved in DMF (35 ml), and a solution of DCC (3.5 g, 17 mmol) in dichloromethane (70 ml) was added. The resulting mixture was stirred at room temperature for 20 h, and then filtered. The filtrate was concentrated in vacuo, and the solid residue recrystallised from a mixture of n-heptane (75 ml) and 2-propanol (5 ml), to give the title compound (5.2 g, 50%)

Example 70

Synthesis of $Arg^{34}$,$Lys^{26}$($N^\epsilon$-(γ-D-glutamyl($N^\alpha$-hexadecanoyl))) GLP-1(7-37)-OH To a mixture of $Arg^+$,$Lys^{26}$GLP-1(7-37)-OH (41.1 mg, 12.2 μmol), EDPA (44 mg, 341 μmol), NMP (5.76 ml) and water (2.88 ml) was added a solution of $N^\alpha$-hexadecanoyl-D-glutamic acid α-t-butyl ester-γ-2,5-dioxopyrrolidin-1-yl ester (19.7 mg, 36.5 μmol) in NMP (491 μl). The reaction mixture was gently shaken for 5 min. at room temperature, and then allowed to stand for an additional 95 min. at room temperature. The reaction was quenched by the addition of a solution of glycine (20 mg, 268 μmol) in water (2 ml). A 0.5% aqueous solution of ammonium acetate (120 ml) was added, and the resulting mixture divided into to equal portions, and each portion eluted onto a Varian 5 g C8 Mega Bond Elut®, the immobilised compound washed with 5% aqueous acetonitril (25 ml), and finally liberated from the cartridge by elution with TFA (25 ml). The combined eluates were concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (10.5 mg, 23%) was isolated, and the product was analysed by PDMS.

Example 71

Synthesis of $Lys^{34}$($N^\epsilon$-(γ-glutamyl($N^\alpha$-tetradecanoyl))) GLP-1(7-37)

To a mixture of GLP-1(7-37)-OH (33.6 mg, 8.9 μmol), EDPA (32.4 mg, 250 μmol), NMP (2.1 ml) and water (2.1 ml) was added a solution of Myr-Glu(ONSu)-OBu$^t$ (9.1 mg, 17.9 μmol), prepared as described above, in NMP (228 μl). The reaction mixture was gently shaken for 5 min., and then allowed to stand for an additional 80 min. at room temperature. The reaction was quenched by the addition of a solution of glycine (14.8 mg, 197 μmol) in water (1.47 ml). A 0.5% aqueous solution of ammonium acetate (100 ml) was added, and the resulting mixture divided into two equal portions, and each portion eluted onto a Varian 5 g C8 Mega Bond Elut®, the immobilised compound washed with 5% aqueous acetonitril (2×25 ml), and finally liberated from the cartridge by elution with TFA (2×25 ml). The combined eluates were concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (0.19 mg, 0.6%) was isolated, and the product was analysed by PDMS. The m/z value for the protonated molecular ion was found to be 3693±3. The resulting molecular weight was thus 3692±3 amu (theoretical value 3695 amu).

Example 72

Synthesis of $Arg^{26,34}Lys^8$($N^\epsilon$-(γ-glutamyl($N^\alpha$-hexadecanoyl))) GLP-1(7-37)

To a mixture of $Arg^{26,34}$, $Lys^8$-GLP-1(7-37)-OH (10.3 mg, 3 μmol), EDPA (10.8 mg, 83 μmol), NMP (1.44 ml) and water (0.72 ml) was added a solution of Pal-Glu(ONSu)-OBu$^t$ (4.8 mg, 8.9 μmol), prepared as described above, in NMP (120 μl). The reaction mixture was gently shaken for 5 min., and then allowed to stand for an additional 70 min. at room temperature. The reaction was quenched by the addition of a solution of glycine (4.9 mg, 65.3 μmol) in water (490 μl). A 0.5% aqueous solution of ammonium acetate (30 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (3.2 mg, 28%) was isolated, and the product was analysed by PDMS. The m/z value for the protonated molecular ion was found to be 3836±3. The resulting molecular weight was thus 3835±3 AMU (theoretical value 3836 AMU).

Example 73

Synthesis of Lau-Glu(ONSu)-OBu$^t$

To a solution of H-Glu-OBu$^t$ (3 g, 15 mmol) in DMF (344 ml) was added EDPA (2.58 ml, 15 mmol) and a solution of Lau-ONSu (4.5 g, 15 mmol), prepared in a similar manner as described for Cap-ONSu in example 56, in DMF (74 ml). The resulting mixture was stirred at ambient temperature for 18 h, and the solvent removed in vacuo. The oily residue was partitioned between ethyl acetate (150 ml) and 5% aqueous citric acid (250 ml). The organic phase was concentrated in vacuo. The residue was dissolved in DMF (40 ml) and the solution added drop by drop to a 10% aqueous citric acid solution (350 ml). The precipitated product was collected, washed with water and dried in vacuo for 18 h to give the intermediate free acid. To solution of the free acid intermediate in DMF (25 ml)

was added N-hydroxysuccinimide (1.7 g, 14.8 mmol) and a solution of N-(3-dimethylaminopropyl)-N'-ethylcarbodiimide (2.58 g, 13.5 mmol) in dichloromethane (52 ml). The resulting mixture was stirred at room temperature for 18 h, and the solvents removed in vacuo. The oily residue was partitioned between dichloromethane (80 ml) and water (80 ml). The organic phase was washed with 5% aqueous citric acid, dried (MgSO$_4$), and concentrated in vacuo to a solid. The solid residue was crystallised from a mixture of n-heptane (77 ml) and 2-propanol (50 ml), and finally recrystallised from n-heptane (76 ml) to give the title compound (2.96 g, 46%).

Example 74

Synthesis of Arg$^{34}$,Lys$^{26}$(N$^\epsilon$-(γ-glutamyl(N$^\alpha$-dodecanoyl))) GLP-1(7-37)

To a mixture of Arg$^{34}$-GLP-1(7-37)-OH (20.6 mg, 6.1 μmol), EDPA (22 mg, 171 μmol), NMP (2.88 ml) and water (1.44 ml) was added a solution Lau-Glu(ONSu)-OBu$^t$ (10.2 mg, 21.2 μmol), prepared as described in example 73, in NMP (255 μl). The reaction mixture was gently shaken for 5 min., and then allowed to stand for an additional 75 min. at room temperature. The reaction was quenched by the addition of a solution of glycine (10 mg, 134 μmol) in water (100 μl). A 0.5% aqueous solution of ammonium acetate (61 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (8.2 mg, 36%) was isolated, and the product was analysed by PDMS. The m/z value for the protonated molecular ion was found to be 3693±3. The resulting molecular weight is 3692±3 AMU (theoretical value 3693 AMU).

Example 75

Synthesis of Lau-β-Ala-ONSu

To a solution of Lau-ONSu (4.25 g, 14.3 mmol), prepared in a similar manner to in DMF (400 ml) was added EDPA (1.84 g, 14.3 mmol) and β-alanine (1.27 g, 14.3 mmol). The resulting mixture was stirred at ambient temperature for 18 h. Water (250 ml) and DMF (50 ml) were added and the solution stirred for 1 h at room temperature. The solvents were removed in vacuo to give a solid. The solid residue was dissolved in DMF (50 ml) and the solution added drop by drop to a 5% aqueous solution of citric acid (200 ml). The precipitate collected, washed with water (50 ml) and dried in vacuo to give the title compound (3.6 g, 93%).

Example 76

Synthesis of Pal-β-Ala-ONSu

To a solution of Pal-ONSu (4.25 g, 14.3 mmol) in DMF (400 ml) was added EDPA (1.84 g, 14.3 mmol) and β-alanine (1.27 g, 14.3 mmol). The resulting mixture was stirred at ambient temperature for 18 h. Water (250 ml) and DMF (50 ml) were added and the solution stirred for 1 h at room temperature. The solvents were removed in vacuo to give a solid. The solid residue was dissolved in DMF (50 ml) and the solution added drop by drop to a 5% aqueous solution of citric acid (200 ml). The precipitate collected, washed with water (50 ml) and dried in vacuo to give the title compound (3.6 g, 93%).

Example 77

Synthesis of Myr-GABA-ONSu

To a solution of Myr-ONSu (4 g, 12.3 mmol) in DMF (350 ml) was added EDPA (1.58 g, 12.3 mmol) and γ-aminobutyric acid (1.26 g, 12.3 mmol). The resulting mixture was stirred at ambient temperature for 18 h. Water (50 ml) was added and the solution stirred for 1 h at room temperature. The solvents were removed in vacuo to give a solid. The solid residue was dissolved in DMF (75 ml) and the solution added drop by drop to a 5% aqueous solution of citric acid (250 ml). The precipitate collected, washed with water (100 ml) and dried in vacuo to give the free acid intermediate (3.65 g, 95%). To a solution of the free acid intermediate (3 g, 9.6 mmol), N-hydroxysuccinimide (1.65 g, 14.4 mmol) and N-(3-dimethylaminopropyl)-N'-ethylcarbodiimide hydrochloride (3.67 g, 19.1 mmol) in DMF (330 ml) was stirred for 18 h at room temperature, and the solvent removed in vacuo to give a solid. The solid residue was dissolved in dichloromethane (100 ml) and washed with brine (100 ml). The organic phase was dried (MgSO$_4$) and concentrated in vacuo to give a solid. The solid residue was recrystallised from n-heptane (75 ml) to give the title compound (2.8 g, 71%).

Example 78

Synthesis of Pal-β-Ala-ONSu

To a solution of Pal-ONSu (0.9 g, 2.8 mmol) in DMF (100 ml) were added N-hydroxysuccinimide (0.35 g, 3 mmol) and N-(3-dimethylaminopropyl)-N'-ethylcarbodiimide (0.79 g, 4.1 mmol). The resulting mixture was stirred at ambient temperature for 40 h, and the solvent removed in vacuo. The solid residue was partitioned between water (50 ml) and dichloromethane (50 ml). The organic phase was separated, dried (MgSO$_4$) and the solvent removed in vacuo to give the title compound (1.1 g, 94%).

Example 79

Synthesis of Arg$^{34}$,Lys$^{26}$(N$^\gamma$-(β-alanyl(N$^\alpha$-hexadecanoyl))) GLP-1(7-37)

To a mixture of Arg$^{34}$-GLP-1(7-37)-OH (19.2 mg, 5.7 μmol), EDPA (20.5 mg, 159 μmol), NMP (2.7 ml) and water (1.35 ml) was added a solution Pal-β-Ala-ONSu (7.2 mg, 17 μmol), prepared as described in example 79, in NMP (181 μl). The reaction mixture was gently shaken for 5 min., and then allowed to stand for an additional 90 min. at room temperature. The reaction was quenched by the addition of a solution of glycine (9.3 mg, 125 μmol) in water (93 μl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (11.6 mg, 55%) was isolated, and the product was analysed by PDMS. The m/z value for the protonated molecular ion was found to be 3694±3. The resulting molecular weight was thus 3693±3 AMU (theoretical value 3693 AMU).

Example 80

Synthesis of Pal-Glu(OBu$^t$)-ONSu

To a solution of H-Glu(OH)—OBu$^t$ (2.7 g, 11.3 mmol) and Pal-ONSu (3.98 g, 11.3 mmol) in DMF (300 ml) was added EDPA (3.2 g, 24.8 mmol). The resulting mixture was stirred at ambient temperature for 18 h, and the solvent concentrated in vacuo to give an oil. The oily residue was dissolved in DMF (60 ml) and the solution added drop by drop to a 10% aqueous solution of citric acid (300 ml) whereby a precipitate was formed. The precipitate was collected, washed with cold water (25 ml), and dried in vacuo to give free acid intermediate (4.44 g, 89%). The free acid intermediate (4 g, 9.1 mmol) was dissolved in DMF (50 ml) and N-hydroxysuccinimide (1.15 g, 10 mmol) and N-(3-dimethylaminopropyl)-N'-ethylcarbodiimide hydrochloride (2.6 g, 13.6 mmol) were added. The resulting mixture was stirred at room temperature for 60 h, the solvent concentrated in vacuo to give the crude title compound (8.2 g)

Example 81

Synthesis of Arg$^{34}$,Lys$^{26}$(N$^\epsilon$-($\alpha$-glutamyl(N$^\alpha$-hexadecanoyl))) GLP-1(7-37)

To a mixture of Arg$^{34}$-GLP-1 (7-37)-OH (25.6 mg, 7.6 µmol), EDPA (27.4 mg, 212 µmol), NMP (3.5 ml) and water (1.75 ml) was added a solution of Pal-Glu(OBu$^t$)-ONSu (12.2 mg, 22.7 µmol), prepared as described in example 80, in NMP (305 µl). The reaction mixture was gently shaken for 5 min., and then allowed to stand for an additional 100 min. at room temperature. The reaction was quenched by the addition of a solution of glycine (12.5 mg, 168 µmol) in water (125 µl). A 0.5% aqueous solution of ammonium acetate (72.5 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (30 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (6.1 mg, 22%) was isolated, and the product was analysed by PDMS. The m/z value for the protonated molecular ion was found to be 3751±3. The resulting molecular weight was thus 3750±3 AMU (theoretical value 3751 AMU).

Example 82

Synthesis of Ste-GABA-ONSu

To a solution of Ste-ONSu (3 g, 7.9 mmol) in DMF (270 ml) was added EDPA (1 g, 7.9 mmol) and a solution of γ-aminobutyric acid (0.81 g, 7.9 mmol) in water (40 ml). The resulting suspension was stirred at ambient temperature for 18 h, and then concentrated in vacuo to a final volume of 50 ml. The resulting suspension was added to a 5% aqueous solution of citric acid (500 ml) whereby a precipitate is formed. The precipitate was collected and washed with water (50 ml), and dried in vacuo for 4 h to give the free acid intermediate (2.8 g, 97%). To a mixture of the free acid intermediate (2.6 g, 7 mmol), N-hydroxysuccinimide (1.21 g, 10.5 mmol) and N-(3-dimethylaminopropyl)-N'-ethylcarbodiimide hydrochloride (2.69 g, 14 mmol) in NMP (300 ml) was stirred for 70 h, and the solvent removed in vacuo to give a solid. The solid residue was dissolved in dichloromethane (100 ml) and washed with brine (2×100 ml). The organic phase was dried (MgSO$_4$) and concentrated in vacuo to give a solid. The solid residue was recrystallised from n-heptane (75 ml) to give the title compound (2.2 g, 67%).

Example 83

Synthesis of Pal-Isonip-ONSu

To a suspension of 1-hexadecanoylbenzotriazole (3 g, 8.4 mmol), prepared as described in the literature (Kreutzberger; van der Goot, Arch. Pharm., 307, 1974), in DMF (350 ml) were added EDPA (1.08 g, 8.4 mmol) and a solution of piperidine-4-carboxylic acid in water (20 ml). The resulting suspension was stirred at room temperature for 12 d, and then concentrated in vacuo to an oil. The oily residue was added drop by drop to a 5% aqueous solution of citric acid (300 ml) whereby a precipitate was formed. The precipitate was collected and washed with water (50 ml), dried in vacuo for 2 h to give the free acid intermediate (3 g, 97%). To a solution of the free acid intermediate (2.8 g, 7.6 mmol), N-hydroxysuccinimide (1.31 g, 11.4 mmol) in DMF (250 ml) was added N-(3-dimethylaminopropyl)-N'-ethylcarbodiimide hydrochloride (2.92 g, 15.2 mmol). The resulting mixture was stirred at ambient temperature for 18 h, and the solvent removed in vacuo to give an oil. The oily residue was dissolved in dichloromethane (100 ml), washed with brine (50 ml), dried (MgSO$_4$) and concentrated in vacuo to give the crude title compound (4.1 g, quant.).

Example 84

Synthesis of Arg$^{34}$,Lys$^{26}$(N$^\epsilon$-(piperidinyl-4-carbonyl (N-hexadecanoyl))) GLP-1(7-37)

To a mixture of Arg$^{34}$-GLP-1(7-37)-OH (25 mg, 7.4 µmol), EDPA (26.7 mg, 207 µmol), NMP (3.5 ml) and water (1.75 ml) was added a solution Pal-Isonip-ONSu (13.7 mg, 30 µmol), prepared as described in example 83 in NMP (343 µl). The reaction mixture was gently shaken for 5 min., and then allowed to stand for an additional 90 min. at room temperature. The reaction was quenched by the addition of a solution of glycine (12.2 mg, 163 µmol) in water (122 µl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (12 mg, 44%) was isolated, and the product was analysed by PDMS. The m/z value for the protonated molecular ion was found to be 3734±3. The resulting molecular weight was thus 3733±3 amu (theoretical value 3733 amu).

Example 85

Synthesis of Arg$^{34}$,Lys$^{26}$(N$^\epsilon$-(γ-glutamyl(N$^\alpha$-decanoyl))) GLP-1(7-37)

To a mixture of Arg$^{34}$-GLP-1(7-37)-OH (25 mg, 7.4 µmol), EDPA (26.7 mg, 207 µmol), NMP (3.5 ml) and water (1.75 ml) was added a solution of Cac-Glu(ONSu)-OBu$^t$ (10 mg, 22.1 µmol) in NMP (252 µl). The reaction mixture was gently shaken for 5 min., and then allowed to stand for an additional 140 min. at room temperature. The reaction was quenched by the addition of a solution of glycine (12.2 mg, 162 µmol) in water (122 µl). A 0.5% aqueous solution of ammonium acetate (73 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (12.2 mg, 45%) was isolated, and the product was analysed by PDMS. The m/z value for the protonated molecular ion was found to be 3669.7±3. The resulting molecular weight was thus 3668.7±3 amu (theoretical value 3667 amu).

Example 86

General Method A

Synthesis of Alkanoic Acid 2,5-dioxopyrrolidin-1-yl Ester:

To a solution of the alkanoic acid (34.7 mmol) and N-hydroxysuccinimide (4 g, 34.7 mmol) in anhydrous acetonitril (10 ml) was added a solution of DCC (7.15 g, 34.7 mmol) in anhydrous dichloromethane (15 ml), and the resulting reaction mixture was stirred for 16 h at room temperature. The precipitated solid was filtered off and recrystallised from a mixture of n-heptane and 2-propanol. The precipitate was dried in vacuo for 16 h to give the title compound.

Synthesis of Lys($N^\epsilon$-alkanoyl)-peptide:

To a mixture of the peptide (5.9 µmol), EDPA (21 mg, 164 µmol), NMP (5.8 ml) and water (2.9 ml) was added a solution of the alkanoic acid 2,5-dioxopyrrolidin-1-yl ester (37 µmol), prepared as described above, in NMP (0.5 ml). The reaction mixture was gently shaken for 5 min at room temperature, and then allowed to stand for an additional 2 h at room temperature. The reaction was quenched by the addition of a solution of glycine (9.7 mg, 129 µmol) in water (97 µl). The solvent was removed in vacuo, and the residue was purified by column chromatography using a cyanopropyl column (Zorbax 300SB-CN) and a standard acetonitril/TFA system. The column was heated to 65° C. and the acetonitril gradient was 0-100% for 60 minutes.

Coupling of a desired group A comprising the 5- or 6-membered ring system Y to the N-terminal end of the peptide may be performed using solid phase protein synthesis techniques as explained above.

Example 87

General Method B

Synthesis of $N^\alpha$-alkanoyl-(L)-glutamic Acid α-tert-butyl-γ-(2,5-dioxopyrrolidin-1-yl) Diester:

A suspension of the alkanoic acid 2,5-dioxopyrrolidin-1-yl ester (16.2 mmol), prepared as described under General method A, (L)-glutamic acid α-tert-butyl ester (3.28 g, 16.2 mmol), DMF (268 ml) and EDPA (2.1 g, 16.2 mmol) was stirred for 64 h at room temperature. The reaction mixture was concentrated in vacuo and the residue was dissolved in ethyl acetate (50 ml). The resulting solution was washed with 5% aqueous citric acid (2×25 ml). The solvent was concentrated removed in vacuo and the residue dissolved in DMF (36 ml). The resulting solution was carefully added to a 10% aqueous solution of citric acid (357 ml) and extracted with ethyl acetate (200 ml) and dried ($MgSO_4$). The solvent was concentrated removed in vacuo to give the crude glutamic diester intermediate. To a mixture of the crude diester, N-hydroxysuccinimide (1.85 g, 16.1 mmol) and anhydrous DMF (25 ml) was added a solution of DCC (3.32 g, 16.1 mmol) in anhydrous dichloromethane (15 ml). The resulting mixture was stirred at ambient temperature for 20 h. The reaction mixture was filtered and the solvent was concentrated removed in vacuo. The residue was purified on a silica gel column (40-63 µM) and eluted with a mixture of dichloromethane and acetonitril (1:1) to give the title compound.

Synthesis of Lys($N^\epsilon$-(γ-glutamyl $N^\alpha$-alkanoyl)))peptide

To a mixture of the peptide (4.2 µmol), EDPA (15.3 mg, 119 µmol), NMP (2 ml) and water (1 ml) was added a solution of N-alkanoyl-(L)-glutamic acid α-tert-butyl-γ-(2,5-dioxopyrrolidin-1-yl) diester (12.7 µmol), prepared as described above, in NMP (135 ml). The reaction mixture was gently shaken for 5 min at room temperature and then allowed to stand for an additional 2 h at room temperature. The reaction was quenched by the addition of a solution of glycine (7 mg, 93 µmol) in water (698 µl). A 0.5% aqueous solution of ammonium acetate (42 ml) was added, and the resulting mixture was eluted onto a Varian 5 g C8 Mega Bond Elut® cartridge, the immobilised compound was washed with 5% aqueous acetonitril (25 ml) and finally liberated from the cartridge by elution with TFA (25 ml). The eluate was concentrated in vacuo, and the residue was purified by column chromatography using a cyanopropyl column (Zorbax 300SB-CN) and a standard acetonitril/TFA system. The column was heated to 65° C. and the acetonitril gradient was 0-100% for 60 minutes.

Coupling of a desired group A comprising the 5- or 6-membered ring system Y to the N-terminal end of the peptide may be performed using solid phase protein synthesis techniques as explained above.

Example 88

Synthesis of N-Terminal Modified Peptides

Peptides were synthesised according to the Fmoc strategy on an Applied Biosystems 431A peptide synthesiser in 0.25 mmol scale using the manufacturer supplied FastMoc UV protocols starting with a Fmoc-Gly-Wang resin (ovaBiochem). The protected amino acid derivatives used were commercially obtained Fmoc amino acids, and Adoc-Imidazolylpropionic acid. The derivatives used where side chain protection was needed were: Fmoc-Arg(Pmc), Fmoc-Trp (Boc), Fmoc-Glu(OBut), Fmoc-Lys(Boc), Fmoc-Gln(Trt), Fmoc-Tyr(But), Fmoc-Ser(But), Fmoc-Thr(But), Fmoc-His (Trt) and Fmoc-Asp(OBut), and Adoc-Imidazolylpropionic acid.

The peptides were cleaved from the resin and side chain deprotected in TFA/phenol/thioanisole/water/ethanedithiol (83.25:6.25:4.25:4.25:2.00) for 180 min. The cleavage mixture was filtered and the filtrate was concentrated by a stream of nitrogen. The crude peptide was precipitated from this oil with diethyl ether and washed twice with diethyl ether. After drying the crude peptide was dissolved in 50% aqueous acetic acid and diluted to 10% acetic acid with water and purified by semipreparative HPLC on a 25 mm×250 mm column packed with 7 µm C-18 silica. The column was eluted with a gradient of acetonitril against 0.05 M $(NH_4)_2SO_4$, pH 2.5 at 10 ml min. at 40° C. The peptide-containing fractions were collected, diluted with 3 volumes of water and applied to a Sep-Pak® C18 cartridge (Waters part. 51910) which was equilibrated with 0.1% TFA. The peptide was eluted from the Sep-Pak® cartridge with 70% acetonitrile/0.1% TFA, water and isolated from the eluate by lyophilization after dilution with water. The final product obtained was characterised by amino acid analysis, analytical RP-HPLC and by PDMS. Amino acid analysis and mass spectrometry agreed with the expected structure within the experimental error of the method (mass spectrometry +/−2 amu, amino acid analysis +/−10%, RP-HPLC showed a peptide purity >95%).

The RP-HPLC analysis was performed using UV detection at 214 nm and a Vydac 218TP54 4.6 mm×250 mm, 5 μm C-18 silica column which was eluted at 1 ml min. at 42° C. Two different elution conditions were used: a gradient of 5-60% acetonitrile/0.1 M ammonium sulfate, water pH 2.5; and a gradient of 5-60% acetonitrile, 0.1% TFA/0.1% TFA, water.

Example 89

Synthesis of Cap-Glu(ONSu)-OBu$^t$

To a solution of octanoic acid (5 g, 34.7 mmol) and N-hydroxysuccinimide (4 g, 34.7 mmol) in anhydrous acetonitril (10 ml) was added a solution of DCC (7.15 g, 34.7 mmol) in anhydrous dichloromethane (15 ml), and the resulting reaction mixture stirred for 16 h at room temperature. The precipitated solid was filtered off and recrystallised from a mixture of n-heptane (40 ml) and 2-propanol (2 ml). The precipitate was dried in a vacuum drying oven for 16 h to give the intermediate Cap-ONSu. A suspension of the crude ester intermediate (3.9 g, 16.2 mmol), (L)-H-Glu(OH)—OBu$^t$ (3.28 g, 16.2 mmol), DMF (268 ml) and EDPA (2.1 g, 16.2 mmol) was stirred for 64 h at room temperature. The reaction mixture was concentrated in vacuo and the residue dissolved in ethyl acetate (50 ml). The resulting solution was washed with 5% aqueous citric acid (2×25 ml). The solvent was concentrated in vacuo and the residue dissolved in DMF (36 ml). The resulting solution was added drop wise to a 10% aqueous solution of citric acid (357 ml) and extracted with ethyl acetate (200 ml), and dried (MgSO$_4$). The solvent was concentrated in vacuo to give the crude glutamic acid intermediate. To a mixture of the crude glutamic acid intermediate, N-hydroxysuccinimide (1.85 g, 16.1 mmol) and DMF (25 ml) was added a solution of DCC (3.32 g, 16.1 mmol) in dichloromethane (15 ml). The resulting mixture was stirred at ambient temperature for 20 h. The reaction mixture was filtered and the solvent concentrated in vacuo. The residue was purified on a silica gel column (40-63 μm), eluted with a mixture of dichloromethane and acetonitril (1:1) to give the title compound (0.63 g, 6% over all).

Example 90

Synthesis of desamino-His$^7$,Arg$^{34}$,Lys$^{26}$(N$^\epsilon$-(γ-glutamyl(N$^\alpha$-hexadecanoyl))) GLP-1(7-37)

To a mixture of desamino-His$^7$,Arg$^{34}$-GLP-1 (7-37)-OH (20 mg, 5.9 μmol), EDPA (21.5 mg, 166 μmol), NMP (2.8 ml) and water (1.4 ml) was added a solution Pal-Glu(ONSu)-OBu$^t$ (9.6 mg, 17.8 μmol in NMP (240 μl). The reaction mixture was gently shaken for 5 min., and then allowed to stand for an additional 75 min. at room temperature. The reaction was quenched by the addition of a solution of glycine (9.8 mg, 130 μmol) in water (979 μl). A 0.5% aqueous solution of ammonium acetate (58 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (9.1 mg, 41%) was isolated, and the product was analysed by PDMS. The m/z value for the protonated molecular ion was found to be 3739±3. The resulting molecular weight was thus 3738±3 amu (theoretical value 3736 amu).

Example 91

Synthesis of Myr-GABA-ONSu

To a solution of Myr-ONSu (4 g, 12.3 mmol) in DMF (350 ml) was added EDPA (1.58 g, 12.3 mmol) and γ-aminobutyric acid (1.26 g, 12.3 mmol). The resulting mixture was stirred at ambient temperature for 18 h. Water (50 ml) was added and the solution stirred for 1 h at room temperature. The solvents were removed in vacuo to give a solid. The solid residue was dissolved in DMF (75 ml) and the solution added drop by drop to a 5% aqueous solution of citric acid (250 ml). The precipitate collected, washed with water (100 ml) and dried in vacuo to give the free acid intermediate (3.65 g, 95%). To a solution of the free acid intermediate (3 g, 9.6 mmol), N-hydroxysuccinimide (1.65 g, 14.4 mmol) and N-(3-dimethylaminopropyl)-N'ethylcarbodiimide hydrochloride (3.67 g, 19.1 mmol) in DMF (330 ml) was stirred for 18 h at room temperature, and the solvent removed in vacuo to give a solid. The solid residue was dissolved in dichloromethane (100 ml) and washed with brine (100 ml). The organic phase was dried (MgSO$_4$) and concentrated in vacuo to give a solid. The solid residue was recrystallised from n-heptane (75 ml) to give the title compound (2.8 g, 71%).

Example 92

Synthesis of desamino-His$^7$,Arg$^{34}$,Lys$^{26}$(N$^\epsilon$-(γ-aminobutyroyl(N$^\alpha$-hexadecanoyl))) GLP-1(7-37)

To a mixture of desamino-His$^7$,Arg$^{34}$-GLP-1(7-37)-OH (20 mg, 8.9 μmol), EDPA (21.5 mg, 166 μmol), NMP (2.8 ml) and water (1.4 ml) was added a solution Pal-GABA-ONSu (7.8 mg, 17.8 μmol) in NMP (181 μl). The reaction mixture was gently shaken for 5 min., and then allowed to stand for an additional 90 min. at room temperature. The reaction was quenched by the addition of a solution of glycine (9.3 mg, 125 μmol) in water (93 μl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (11.6 mg, 55%) was isolated, and the product was analysed by PDMS. The m/z value for the protonated molecular ion was found to be 3692±3. The resulting molecular weight was thus 3691±3 amu (theoretical value 3693 amu).

Example 93

Synthesis of desamino-His$^7$,Arg$^{34}$,Lys$^{26}$(N$^\epsilon$-(β-alanyl(N$^\gamma$-hexadecanoyl))) GLP-1(7-37)

To a mixture of desamino-His$^7$,Arg$^{34}$-GLP-1(7-37)-OH (25 mg, 7.4 μmol), EDPA (26.8 mg, 208 μmol), NMP (3.5 ml) and water (1.75 ml) was added a solution Pal-β-Ala-ONSu (9.4 mg, 22.2 μmol) in NMP (236 μl). The reaction mixture was gently shaken for 5 min., and then allowed to stand for an additional 130 min. at room temperature. The reaction was quenched by the addition of a solution of glycine (12.2 mg, 163 μmol) in water (122 μl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (13.4 mg, 49%) was isolated, and the product was analysed by PDMS. The m/z value for the protonated molecular ion was found to be 3681±3. The resulting molecular weight was thus 3680±3 amu (theoretical value 3678 amu).

Example 94

Synthesis of Ste-GABA-ONSu

To a solution of Ste-ONSu (3 g, 7.9 mmol) in DMF (270 ml) was added EDPA (1 g, 7.9 mmol) and a solution of γ-aminobutyric acid (0.81 g, 7.9 mmol) in water (40 ml). The resulting suspension was stirred at ambient temperature for 18 h, and then concentrated in vacuo to a final volume of 50 ml. The resulting suspension was added to a 5% aqueous solution of citric acid (500 ml) whereby a precipitate is formed. The precipitate was collected and washed with water (50 ml), and dried in vacuo for 4 h to give the free acid intermediate (2.8 g, 97%). To a mixture of the free acid intermediate (2.6 g, 7 mmol), N-hydroxysuccinimide (1.21 g, 10.5 mmol) and N-(3-dimethylaminopropyl)-N'-ethylcarbodiimide hydrochloride (2.69 g, 14 mmol) in NMP (300 ml) was stirred for 70 h, and the solvent removed in vacuo to give a solid. The solid residue was dissolved in dichloromethane (100 ml) and washed with brine (2×100 ml). The organic phase was dried ($MgSO_4$) and concentrated in vacuo to give a solid. The solid residue was recrystallised from n-heptane (75 ml) to give the title compound (2.2 g, 67%).

Example 95

Synthesis of $Arg^{34}$,$Ala^8$($N^\alpha$-(imidazol-4-ylprop-2-enoyl),$Lys^{26}$($N^\epsilon$-(γ-aminobutyroyl($N^\gamma$-hexadecanoyl))) GLP-1 (8-37)

To a mixture of $Arg^{34}$,$Ala^8$($N^\alpha$-(imidazol-4-ylprop-2-enoyl)-GLP-1(8-37)-OH (5.6 mg, 1.7 µmol), EDPA (6 mg, 46.2 µmol), NMP (0.78 ml) and water (0.39 ml) was added a solution Pal-GABA-ONSu (2.2 mg, 5 µmol) in NMP (54 µl). The reaction mixture was gently shaken for 5 min., and then allowed to stand for an additional 80 min. at room temperature. The reaction was quenched by the addition of a solution of glycine (2.7 mg, 36 µmol) in water (27 µl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (1.9 mg, 31%) was isolated, and the product was analysed by PDMS. The m/z value for the protonated molecular ion was found to be 3690±3. The resulting molecular weight was thus 3689±3 amu (theoretical value 3690 amu).

Example 96

Synthesis of $Arg^{34}$,$Ala^8$($N^\alpha$-(imidazol-4-ylacetyl), $Lys^{26}$($N^\epsilon$-(γ-aminobutyroyl($N^\gamma$-hexadecanoyl))) GLP-1 (8-37)

To a mixture of $Arg^{34}$,$Ala^8$($N^\alpha$-(imidazol-4-ylacetyl)-GLP-1 (8-37)-OH (5.3 mg, 1.6 µmol), EDPA (5.7 mg, 43.9 µmol), NMP (0.74 ml) and water (0.37 ml) was added a solution Pal-GABA-ONSu (2 mg, 4.7 µmol) in NMP (52 µl). The reaction mixture was gently shaken for 5 min., and then allowed to stand for an additional 80 min. at room temperature. The reaction was quenched by the addition of a solution of glycine (2.6 mg, 34 µmol) in water (26 µl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (2.2 mg, 38%) was isolated, and the product was analysed by PDMS. The m/z value for the protonated molecular ion was found to be 3676±3. The resulting molecular weight was thus be 3675±3 amu (theoretical value 3678 amu).

Example 97

Synthesis of desamino-$His^7$,$Arg^{34}$,$Lys^{26}$($N^\epsilon$-(γ-aminobutyroyl($N^\gamma$-tetradecanoyl))) GLP-1 (7-37)

To a mixture of desamino-$His^7$,$Arg^{34}$-GLP-1 (7-37)-OH (25 mg, 7.4 µmol), EDPA (26.9 mg, 208 µmol), NMP (3.5 ml) and water (1.75 ml) was added a solution Myr-GABA-ONSu (9.1 mg, 22.2 µmol), prepared as described in example 91, in NMP (228 µl). The reaction mixture was gently shaken for 5 min., and then allowed to stand for an additional 90 min. at room temperature. The reaction was quenched by the addition of a solution of glycine (12.2 mg, 163 µmol) in water (122 µl). The reaction mixture was purified by column chromatography using a cyanopropyl column (Zorbax 300SB-CN) and a standard acetonitril/TFA system. The column was heated to 65° C. and the acetonitril gradient was 0-100% in 60 minutes. The title compound (10.5 mg, 39%) was isolated, and the product was analysed by PDMS. The m/z value for the protonated molecular ion was found to be 3667±3. The resulting molecular weight was thus 3664±3 amu (theoretical value 3662 amu).

Example 98

Synthesis of desamino-$His^7$,$Arg^{34}$,$Lys^{26}$($N^\epsilon$-(γ-aminobutyroyl($N^{\gamma\alpha}$-octadecanoyl))) GLP-1 (7-37)

To a mixture of desamino-$His^7$,$Arg^{34}$-GLP-1(7-37)-OH (25 mg, 7.4 µmol), EDPA (26.8 mg, 207 µmol), NMP (3.5 ml) and water (1.75 ml) was added a solution Ste-GABA-ONSu (10.4 mg, 22.2 µmol), prepared as described in example 94, in NMP (259 µl). The reaction mixture was gently shaken for 5 min., and then allowed to stand for an additional 170 min. at room temperature. The reaction was quenched by the addition of a solution of glycine (12.2 mg, 163 µmol) in water (122 µl) and the reaction mixture purified by column chromatography using a cyanopropyl column (Zorbax 300SB-CN) and a standard acetonitril/TFA system. The column was heated to 65° C. and the acetonitril gradient was 0-100% in 60 minutes. The title compound (7 mg, 25%) was isolated, and the product was analysed by PDMS. The m/z value for the protonated molecular ion was found to be 3719±3. The resulting molecular weight was thus 3718±3 amu (theoretical value 3720 amu).

Example 99

General Method A

Synthesis of alkanoic Acid 2,5-dioxopyrrolidin-1-yl Ester:

To a solution of the alkanoic acid (34.7 mmol) and N-hydroxysuccinimide (4 g, 34.7 mmol) in anhydrous acetonitril (10 ml) was added a solution of DCC (7.15 g, 34.7 mmol) in anhydrous dichloromethane (15 ml), and the resulting reaction mixture was stirred for 16 h at room temperature. The precipitated solid was filtered off and recrystallised from a mixture of n-heptane and 2-propanol. The precipitate was dried in vacuo for 16 h to give the title compound.

Synthesis of Lys$^\epsilon$-alkanoyl)-peptide:

To a mixture of the desired parent peptide (5.9 µmol), EDPA (21 mg, 164 µmol), NMP (5.8 ml) and water (2.9 ml) was added a solution of the alkanoic acid 2,5-dioxopyrrolidin-1-yl ester (37 µmol), prepared as described above, in NMP (0.5 ml). The reaction mixture was gently shaken for 5 min at room temperature, and then allowed to stand for an additional 2 h at room temperature. The reaction was quenched by the addition of a solution of glycine (9.7 mg, 129 µmol) in water (97 µl). The solvent was removed in vacuo, and the residue was purified by column chromatography using a cyanopropyl column (Zorbax 300SB-CN) and a standard acetonitril/TFA system. The column was heated to 65° C. and the acetonitril gradient is 0-100% for 60 minutes.

General Method B

Synthesis of N$^\alpha$-alkanoyl-(L)-glutamic Acid α-tert-butyl-γ-(2,5-dioxopyrrolidin-1-yl) Diester:

A suspension of the alkanoic acid 2,5-dioxopyrrolidin-1-yl ester (16.2 mmol), prepared as described under General method A, (L)-glutamic acid α-tert-butyl ester (3.28 g, 16.2 mmol), DMF (268 ml) and EDPA (2.1 g, 16.2 mmol) was stirred for 64 h at room temperature. The reaction mixture was concentrated in vacuo and the residue was dissolved in ethyl acetate (50 ml). The resulting solution was washed with 5% aqueous citric acid (2×25 ml). The solvent was removed in vacuo and the residue dissolved in DMF (36 ml). The resulting solution was carefully added to a 10% aqueous solution of citric acid (357 ml) and extracted with ethyl acetate (200 ml) and dried (MgSO$_4$). The solvent was removed in vacuo to give the crude glutamic diester intermediate. To a mixture of the crude diester, N-hydroxysuccinimide (1.85 g, 16.1 mmol) and anhydrous DMF (25 ml) was added a solution of DCC (3.32 g, 16.1 mmol) in anhydrous dichloromethane (15 ml). The resulting mixture was stirred at ambient temperature for 20 h. The reaction mixture was filtered and the solvent was removed in vacuo. The residue was purified on a silica gel column (40-63 µm) and eluted with a mixture of dichloromethane and acetonitril (1:1) to give the title compound.

Synthesis of Lys(N$^\epsilon$-(γ-glutamyl(N$^\alpha$-alkanoyl)))peptide

To a mixture of the desired parent peptide (4.2 µmol), EDPA (15.3 mg, 119 µmol), NMP (2 ml) and water (1 ml) was added a solution of N$^\alpha$-alkanoyl-(L)-glutamic acid α-tert-butyl-γ-(2,5-dioxopyrrolidin-1-yl) diester (12.7 µmol), prepared as described above, in NMP (135 ml). The reaction mixture was gently shaken for 5 min at room temperature and then allowed to stand for an additional 2 h at room temperature. The reaction was quenched by the addition of a solution of glycine (7 mg, 93 µmol) in water (698 µl). A 0.5% aqueous solution of ammonium acetate (42 ml) was added, and the resulting mixture was eluted onto a Varian 5 g C8 Mega Bond Elut® cartridge, the immobilised compound was washed with 5% aqueous acetonitril (25 ml) and finally liberated from the cartridge by elution with TFA (25 ml). The eluate was concentrated in vacuo, and the residue was purified by column chromatography using a cyanopropyl column (Zorbax 300SB-CN) and a standard acetonitril/TFA system. The column was heated to 65° C. and the acetonitril gradient is 0-100% for 60 minutes.

Example 100

Synthesis of Arg$^{34}$,Lys$^{26}$(N$^\epsilon$-(γ-glutamyl(N$^\alpha$-tetradecanoyl))) GLP-1 (9-37)

To a mixture of Arg$^{34}$-GLP-1 (9-37)-OH (22.4 mg, 7.1 µmol), EDPA (25.5 mg, 197 µmol), NMP (3.14 ml) and water (1.57 ml) was added a solution of Myr-Glu(ONSu)-OBu$^t$ (10.8 mg, 21.2 µmol) in NMP (270 µl). The reaction mixture was gently shaken for 5 min., and then allowed to stand for an additional 2 h at room temperature. The reaction was quenched by the addition of a solution of glycine (11.6 mg, 155 µmol) in water (116 µl). A 0.5% aqueous solution of ammonium acetate (67 ml) was added, and the resulting mixture eluted onto a Varian 5 g C8 Mega Bond Elut®, the immobilised compound washed with 5% aqueous acetonitril (25 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0-100% in 60 minutes. The title compound (2.3 mg, 9.2%) was isolated, and the product was analysed by PDMS. The m/z value for the protonated molecular ion was found to be 3516.0±3. The resulting molecular weight was thus 3515.0±3 amu (theoretical value 3515 amu).

Example 101

In this example and examples 102 and 103, the phrase "8 mM phosphate buffer of pH 7.4" means 4 mM NaH$_2$PO$_4$, 2H$_2$O and 4 mM Na$_2$HPO$_4$, 2H$_2$O pH adjusted to 7.4 (using Sodium Hydroxide and/or Hydrochloric acid).

the term "Compound 1" means Arg$^{34}$,Lys$^{26}$(N$^\epsilon$-(γ'-Glu(N$^\alpha$-tetradecanoyl))) GLP-1 (7-37).

the term "Compound 2" means Arg$^{34}$,Lys$^{26}$(N$^\epsilon$-(γ'-Glu(N$^\alpha$-hexadecanoyl))) GLP-1 (7-37).

the term "Compound 3" means Arg$^{26,34}$Lys$^{36}$(N$^\epsilon$-(γ'-Glu(N$^\alpha$-hexadecanoyl))) GLP-1 (7-36).

the term "Compound 4" means Arg$^{26}$,Lys$^{34}$(N$^\epsilon$-(γ'-Glu(N$^\alpha$-hexadecanoyl))) GLP-1 (7-37).

the term "Compound 5" means Gly$^8$,Glu$^{37}$,Arg$^{26,34}$Lys$^{38}$(N$^\epsilon$-(γ'-Glu(N$^\alpha$-hexadecanoyl))) GLP-1 (7-38).

General Example 101

Compound 2—7.5 mg/ml

Mannitol 34-50 mg/ml

Phenol 5-7.5 mg/ml 8 mM phosphate buffer of pH 7.4

Mannitol and phenol were dissolved in the phosphate buffer preadjusted to pH 7.4. The compound was then dissolved under slow stirring. The pH was adjusted to 7.4 using sodium hydroxide and/or hydrochloric acid. Finally, the formulation was sterilised by filtration through an appropriate filter.

The following specific formulations were produced using this procedure:

Example 101-A

| | |
|---|---|
| Compound 1 | 2.0 mg/ml |
| Mannitol | 38 mg/ml |
| Phenol | 5 mg/ml |
| 8 mM phosphate buffer of pH 7.4 ad 100 ml | |

Example 101-B

| | |
|---|---|
| Compound 1 | 5 mg/ml |
| Mannitol | 36.9 mg/ml |
| Phenol | 5 mg/ml |
| 8 mM phosphate buffer of pH 7.4 ad 100 ml | |

Example 101-C

| | |
|---|---|
| Compound 1 | 7.5 mg/ml |
| Mannitol | 34 mg/ml |
| Phenol | 7.5 mg/ml |
| 8 mM phosphate buffer of pH 7.4 ad 100 ml | |

Example 101-D

| | |
|---|---|
| Compound 2 | 2.0 mg/ml |
| Mannitol | 38 mg/ml |
| Phenol | 5 mg/ml |
| 8 mM phosphate buffer of pH 7.4 ad 100 ml | |

Example 101-E

| | |
|---|---|
| Compound 2 | 5 mg/ml |
| Mannitol | 36.9 mg/ml |
| Phenol | 5 mg/ml |
| 8 mM phosphate buffer of pH 7.4 ad 100 ml | |

Example 101-F

| | |
|---|---|
| Compound 2 | 7.5 mg/ml |
| Mannitol | 34 mg/ml |
| Phenol | 7.5 mg/ml |
| 8 mM phosphate buffer of pH 7.4 ad 100 ml | |

Example 101-G

| | |
|---|---|
| Compound 3 | 2.0 mg/ml |
| Mannitol | 38 mg/ml |
| Phenol | 5 mg/ml |
| 8 mM phosphate buffer of pH 7.4 ad 100 ml | |

Example 101-H

| | |
|---|---|
| Compound 3 | 5 mg/ml |
| Mannitol | 36.9 mg/ml |
| Phenol | 5 mg/ml |
| 8 mM phosphate buffer of pH 7.4 ad 100 ml | |

Example 101-I

| | |
|---|---|
| Compound 3 | 7.5 mg/ml |
| Mannitol | 34 mg/ml |
| Phenol | 7.5 mg/ml |
| 8 mM phosphate buffer of pH 7.4 ad 100 ml | |

Example 101-J

| | |
|---|---|
| Compound 4 | 2.0 mg/ml |
| Mannitol | 38 mg/ml |
| Phenol | 5 mg/ml |
| 8 mM phosphate buffer of pH 7.4 ad 100 ml | |

Example 101-K

| | |
|---|---|
| Compound 4 | 5 mg/ml |
| Mannitol | 36.9 mg/ml |
| Phenol | 5 mg/ml |
| 8 mM phosphate buffer of pH 7.4 ad 100 ml | |

Example 101-L

| | |
|---|---|
| Compound 4 | 7.5 mg/ml |
| Mannitol | 34 mg/ml |
| Phenol | 7.5 mg/ml |
| 8 mM phosphate buffer of pH 7.4 ad 100 ml | |

Example 102

| | |
|---|---|
| Compound | 2-7.5 mg/ml |
| Mannitol | 19-25 mg/ml |
| Benzyl Alcohol | 14-18 mg/ml |
| 8 mM phosphate buffer of pH 7.4 | |

Mannitol and benzyl alcohol were dissolved in the phosphate buffer preadjusted to pH 7.4. The compound was then dissolved under slow stirring. The pH was adjusted to 7.4 using sodium hydroxide and/or hydrochloric acid. Finally, the formulation was sterilised by filtration through an appropriate filter.

The following specific formulations were produced using this procedure:

Example 102-A

| | |
|---|---|
| Compound 1 | 2.0 mg/ml |
| Mannitol | 25 mg/ml |
| Benzyl alcohol | 14 mg/ml |
| 8 mM phosphate buffer of pH 7.4 ad 100 ml | |

Example 102-B

| | |
|---|---|
| Compound 1 | 7.5 mg/ml |
| Mannitol | 19 mg/ml |
| Benzyl alcohol | 18 mg/ml |
| 8 mM phosphate buffer of pH 7.4 ad 100 ml | |

Example 102-C

| | |
|---|---|
| Compound 2 | 2.0 mg/ml |
| Mannitol | 25 mg/ml |
| Benzyl alcohol | 14 mg/ml |
| 8 mM phosphate buffer of pH 7.4 ad 100 ml | |

Example 102-D

| | |
|---|---|
| Compound 2 | 7.5 mg/ml |
| Mannitol | 19 mg/ml |
| Benzyl alcohol | 18 mg/ml |
| 8 mM phosphate buffer of pH 7.4 ad 100 ml | |

Example 102-E

| | |
|---|---|
| Compound 3 | 2.0 mg/ml |
| Mannitol | 25 mg/ml |
| Benzyl alcohol | 14 mg/ml |
| 8 mM phosphate buffer of pH 7.4 ad 100 ml | |

Example 102-F

| | |
|---|---|
| Compound 3 | 7.5 mg/ml |
| Mannitol | 19 mg/ml |
| Benzyl alcohol | 18 mg/ml |
| 8 mM phosphate buffer of pH 7.4 ad 100 ml | |

Example 102-G

| | |
|---|---|
| Compound 5 | 2.0 mg/ml |
| Mannitol | 25 mg/ml |
| Benzyl alcohol | 14 mg/ml |
| 8 mM phosphate buffer of pH 7.4 ad 100 ml | |

Example 102-H

| | |
|---|---|
| Compound 5 | 7.5 mg/ml |
| Mannitol | 19 mg/ml |
| Benzyl alcohol | 18 mg/ml |
| 8 mM phosphate buffer of pH 7.4 ad 100 ml | |

Example 103

| | |
|---|---|
| Compound | 2-7.5 mg/ml |
| Mannitol | 42-44 mg/ml |
| Metacresol | 2.5-4.0 mg/ml |
| 8 mM phosphate buffer of pH 7.4 | |

Mannitol and metacresol were dissolved in the phosphate buffer preadjusted to pH 7.4. The compound was then dissolved under slow stirring. The pH was adjusted to 7.4 using sodium hydroxide and/or hydrochloric acid. Finally, the formulation was sterilised by filtration through an appropriate filter.

The following specific formulations were produced using this:

Example 103-A

| | |
|---|---|
| Compound 1 | 2.0 mg/ml |
| Mannitol | 44 mg/ml |
| Metacresol | 2.5 mg/ml |
| 8 mM phosphate buffer of pH 7.4 ad 100 ml | |

Example 103-B

| | |
|---|---|
| Compound 1 | 7.5 mg/ml |
| Mannitol | 42 mg/ml |
| Metacresol | 4 mg/ml |
| 8 mM phosphate buffer of pH 7.4 ad 100 ml | |

Example 103-C

| | |
|---|---|
| Compound 2 | 2.0 mg/ml |
| Mannitol | 44 mg/ml |
| Metacresol | 2.5 mg/ml |
| 8 mM phosphate buffer of pH 7.4 ad 100 ml | |

Example 103-D

| | |
|---|---|
| Compound 2 | 7.5 mg/ml |
| Mannitol | 42 mg/ml |
| Metacresol | 4 mg/ml |
| 8 mM phosphate buffer of pH 7.4 ad 100 ml | |

Example 103-E

| | |
|---|---|
| Compound 3 | 2.0 mg/ml |
| Mannitol | 44 mg/ml |
| Metacresol | 2.5 mg/ml |
| 8 mM phosphate buffer of pH 7.4 ad 100 ml | |

Example 103-F

| | |
|---|---|
| Compound 3 | 7.5 mg/ml |
| Mannitol | 42 mg/ml |
| Metacresol | 4 mg/ml |
| 8 mM phosphate buffer of pH 7.4 ad 100 ml | |

Example 103-G

| | |
|---|---|
| Compound 5 | 2.0 mg/ml |
| Mannitol | 44 mg/ml |
| Metacresol | 2.5 mg/ml |
| 8 mM phosphate buffer of pH 7.4 ad 100 ml | |

Example 103-H

| | |
|---|---|
| Compound 5 | 7.5 mg/ml |
| Mannitol | 42 mg/ml |
| Metacresol | 4 mg/ml |
| 8 mM phosphate buffer of pH 7.4 ad 100 ml | |

Example 104

Circular Dichroism (CD) at 222 nm as a function of peptide concentration for peptides dissolved in 10 mM tris buffer, pH 8, and 23° C. was measured for native GLP-1(7-37) and the following eight GLP-1 derivatives of the present invention:
(a) Example 37
(b) Example 50
(c) Example 63
(d) Example 51
(e) Example 55
(f) Example 61
(g) Example 68
(h) Example 64

The results are shown in FIG. 1. Note that the CD signal is proportional to the average content of α-helix in the peptides, i.e., a CD value of −1 corresponds to 10% α-helix content under these conditions. The FIGURE shows that, as the concentration of native GLP-1(7-37) is raised between 25 and 1000 μM, the content of α-helix increases from about 15% to about 30-35% in parallel with the formation of higher oligomers. In contrast with this concentration dependent behaviour, the FIGURE shows that the helix content remains high and essentially independent of the concentration in the 1-200 μM range for the GLP-1 derivatives of the present invention forming partially structured micelle-like aggregates under the same conditions.

Example 105

Equilibrium Solubility

For pH-solubility profiles, solutions containing the peptide and additives (surfactant and, where indicated, other excipients) at the appropriate concentrations were prepared at pH 9-10. The solutions were filtered, samples were withdrawn, and the pH was adjusted to the desired value in the range of 3-8. The samples were left for 24 hours at 23° C. to attain solubility equilibrium. After centrifugation (20,000 g for 20 minutes, 23° C.) of each sample, the pH was measured, and the solubility was determined from measurement of the absorbance at 276 nm of the supernatant.

Long Term Physical Stability acylated GLP-1(7-37) analogue were dissolved at twice the desired final concentration and incubated briefly (<10 minutes) at pH 11.5, 23° C. before filtration and mixing with an equal volume of a filtered solution containing all the excipients in twice the desired final concentration. The pH was then measured and adjusted as needed. The solution was transferred to pen-fill cartridges containing a small glass ball (to allow visual determination of changes in solution viscosity). The containers were sealed and incubated at the desired temperature between 4° C. and 37° C. At appropriate time intervals, the samples were gently turned and visually examined using a light box. When physical changes were apparent (precipitation, crystallization or gelation), the sample was centrifuged and the absorbance was measured in the supernatant to determine whether the component coming out of solution was the peptide or not.

Equilibrium solubility was determined as a function of pH for 1 mg/ml solutions of the acylated GLP-1(7-37) analogue N$^\epsilon$-hexadecanoyl-γ-glutamyl-Lys26,Art34-GLP-1(7-37) in the absence of additives and in the presence of increasing amounts of the surfactant LPCL (lauroyl lysophosphatidyl choline). The results show that 1 mM and 2 mM LPCL enhance solubility relative to the reference composition, while full solubility is obtained in the presence of 5 mM LPCL.

The invention claimed is:

1. A glucagon-like peptide 1 (GLP-1) derivative, said derivative containing a single lipophilic substituent of from 8 to 40 carbon atoms attached, optionally via a spacer, to the C-terminal amino acid residue of a parent polypeptide where i) the parent polypeptide is selected from the group consisting of GLP-1 (7-35), GLP-1 (7-36), GLP-1 (7-37), GLP-1 (7-38), GLP-1 (7-39), GLP-1 (7-40), GLP-1 (7-41) and an analogue of any of GLP-1 (7-35), GLP-1 (7-36), GLP-1 (7-37), GLP-1 (7-38), GLP-1 (7-39), GLP-1 (7-40) and GLP-1 (7-41) where the total number of different amino acids between said analogue and the corresponding native form of GLP-1 does not exceed five, and ii) the lipophilic substituent is selected from the group consisting of an acyl group of a straight-chain alkane $\alpha,\omega$-dicarboxylic acid, an acyl group of an alkyl group, and a straight chain alkyl group.

2. The GLP-1 derivative of claim 1, wherein the lipophilic substituent is an acyl group of a straight-chain alkane $\alpha,\omega$-dicarboxylic acid.

3. The GLP-1 derivative of claim 2, wherein the acyl group is from 8 to 25 carbons in length.

4. The GLP-1 derivative of claim 2, wherein the acyl group is $HOOC(CH_2)_mCO-$, wherein m is 6-38.

5. The GLP-1 derivative of claim 4, wherein the acyl group is selected from the group consisting of $HOOC(CH_2)_{14}CO-$, $HOOC(CH_2)_{16}CO-$, $HOOC(CH_2)_{18}CO-$, $HOOC(CH_2)_{20}CO-$, and $HOOC(CH_2)_{22}CO-$.

6. The GLP-1 derivative of claim 1, wherein the lipophilic substituent is a straight chain alkyl group.

7. The GLP-1 derivative of claim 6, wherein the alkyl group is from 8 to 25 carbon atoms.

8. The GLP-1 derivative of claim 1, wherein the parent polypeptide is selected from the group consisting of $Arg^{26}$-GLP-1 (7-37); $Arg^{34}$-GLP-1 (7-37); $Lys^{36}$-GLP-1 (7-37); $Arg^{26,34}Lys^{36}$-GLP-1 (7-37); $Arg^{26,34}Lys^{39}$-GLP-1 (7-39); $Arg^{26,34}Lys^{40}$-GLP-1 (7-40); $Arg^{26}Lys^{36}$-GLP-1(7-37); $Arg^{34}Lys^{36}$-GLP-1 (7-37); $Arg^{26}Lys^{39}$-GLP-1 (7-39); $Arg^{34}Lys^{40}$-GLP-1 (7-40); $Arg^{26,34}Lys^{36,39}$-GLP-1 (7-39); $Arg^{26,34}Lys^{36,40}$-GLP-1 (7-40); $Gly^8Arg^{26}$-GLP-1(7-37); $Gly^8Arg^{34}$-GLP-1 (7-37); $Gly^8Lys^{36}$-GLP-1 (7-37); $Gly^8Arg^{26,34}Lys^{36}$-GLP-1 (7-37); $Gly^8Arg^{26,34}Lys^{39}$-GLP-1 (7-39); $Gly^8Arg^{26,34}Lys^{40}$-GLP-1 (7-40); $Gly^8Arg^{26}Lys^{36}$-GLP-1(7-37); $Gly^8Arg^{34}Lys^{36}$-GLP-1 (7-37); $Gly^8Arg^{26}Lys^{39}$-GLP-1 (7-39); $Gly^8Arg^{34}Lys^{40}$-GLP-1 (7-40); $Gly^8Arg^{26,34}Lys^{36,39}$-GLP-1 (7-39); and $Gly^8Arg^{26,34}Lys^{36,40}$-GLP-1 (7-40).

9. The GLP-1 derivative of claim 8, wherein the lipophilic substituent is an acyl group of a straight-chain alkane $\alpha,\omega$-dicarboxylic acid.

10. The GLP-1 derivative of claim 9, wherein the acyl group is from 8 to 25 carbons in length.

11. The GLP-1 derivative of claim 9, wherein the acyl group is $HOOC(CH_2)_mCO-$, wherein m is 6-38.

12. The GLP-1 derivative of claim 11, wherein the acyl group is selected from the group consisting of $HOOC(CH_2)_{14}CO-$, $HOOC(CH_2)_{16}CO-$, $HOOC(CH_2)_{18}CO-$, $HOOC(CH_2)_{20}CO-$, and $HOOC(CH_2)_{22}CO-$.

13. The GLP-1 derivative of claim 8, wherein the lipophilic substituent is a straight chain alkyl group.

14. The GLP-1 derivative of claim 13, wherein the alkyl group is from 8 to 25 carbon atoms.

15. A GLP-1 derivative according to claim 1, wherein the spacer is an amino acid residue except Cys or a dipeptide.

* * * * *